(12) United States Patent
Hossbach et al.

(10) Patent No.: US 11,213,541 B2
(45) Date of Patent: Jan. 4, 2022

(54) ANTISENSE-OLIGONUCLEOTIDES AS INHIBITORS OF TGF-R SIGNALING

(71) Applicant: NeuroVision Pharma GmbH, Grünwald (DE)

(72) Inventors: Markus Hossbach, Kulmbach (DE); Monika Krampert, Bamberg (DE); Hans-Lothar Arth, Berlin (DE)

(73) Assignee: NEUROVISION PHARMA GMBH, Grünwald (DE)

( * ) Notice: Subject to any disclaimer, the term of this patent is extended or adjusted under 35 U.S.C. 154(b) by 405 days.

(21) Appl. No.: 15/525,561

(22) PCT Filed: Nov. 16, 2015

(86) PCT No.: PCT/EP2015/076730
§ 371 (c)(1),
(2) Date: May 9, 2017

(87) PCT Pub. No.: WO2016/075339
PCT Pub. Date: May 19, 2016

(65) Prior Publication Data
US 2017/0319614 A1 Nov. 9, 2017

(30) Foreign Application Priority Data
Nov. 16, 2014 (EP) .................................. 14193368

(51) Int. Cl.
| | | |
|---|---|---|
| *C12N 15/113* | (2010.01) | |
| *A61K 9/00* | (2006.01) | |
| *A61P 35/00* | (2006.01) | |
| *A61P 43/00* | (2006.01) | |
| *A61K 31/7125* | (2006.01) | |

(52) U.S. Cl.
CPC ...... *A61K 31/7125* (2013.01); *C12N 15/1136* (2013.01); *C12N 15/1138* (2013.01); *A61K 9/0019* (2013.01); *A61K 9/0085* (2013.01); *C12N 2310/11* (2013.01); *C12N 2310/313* (2013.01); *C12N 2310/315* (2013.01); *C12N 2310/3231* (2013.01);
(Continued)

(58) Field of Classification Search
CPC ............ A61K 31/7125; C12N 15/1136; C12N 15/1138; C12N 2310/11; C12N 2310/315; C12N 2310/3231; C12N 2310/341
See application file for complete search history.

(56) References Cited

FOREIGN PATENT DOCUMENTS

| WO | WO 03/000656 A2 | 1/2003 |
|---|---|---|
| WO | WO 2005/074981 A2 | 8/2005 |
| WO | WO 2008/109546 A2 | 9/2008 |

OTHER PUBLICATIONS

Gupta et al. (PLOS One, 2010 vol. 5:pp. 1-9).*
(Continued)

*Primary Examiner* — Terra C Gibbs
(74) *Attorney, Agent, or Firm* — Knobbe, Martens, Olson & Bear LLP

(57) ABSTRACT

The present invention relates to antisense-oligonucleotides having a length of at least 10 nucleotides, wherein at least two of the nucleotides are LNAs, their use as inhibitors of TGF-R signaling, pharmaceutical compositions containing such antisense-oligonucleotides and the use for prophylaxis and treatment of neurological, neurodegenerative, fibrotic and hyperproliferative diseases.

5 Claims, 24 Drawing Sheets
(14 of 24 Drawing Sheet(s) Filed in Color)
Specification includes a Sequence Listing.

(52) U.S. Cl.
CPC .. *C12N 2310/341* (2013.01); *C12N 2310/346* (2013.01); *C12N 2320/30* (2013.01); *C12Y 207/1103* (2013.01)

(56) References Cited

OTHER PUBLICATIONS

Grünweller et al. (Nucleic Acids Research, 2003 vol. 31:3185-3193).*
Kurreck et al. (Nucleic Acids Research, 2002 vol. 30:1911-1918).*
Scanlon et al. (Current Pharmaceutical Biotechnology, 2004 vol. 5:415-420).*
Elbashir et al. (Genes & Development, 2001 vol. 15: 188-200).*
International Search Report received in PCT Application No. PCT/EP2015/076730 dated Feb. 8, 2016 in 12 pages.
Bertrand, J-R., et al., Comparison of antisense oligonucleotides and siRNAs in cell culture and in vivo, Biochemical and Biophysical Research Communications, vol. 296, pp. 1000-1004, 2002.
Bramsen, J.B., et al., Improved silencing properties using small internally segmented interfering RNAs, Nucleic Acids Research, vol. 35, No. 17, pp. 5886-5897, 2007.
Delavey, G.F., et al., Designing Chemically Modified Oligonucleotides for Targeted Gene Silencing, Chemistry & Biology, vol. 19, pp. 937-954, 2012.
Watts, J.K., et al., Gene silencing by siRNAs and antisense oligonucleotides in the laboratory and the clinic, The Journal of Pathology, vol. 226, No. 2, pp. 365-379, 2012.
Xu, Y., et al., Functional comparison of single- and double-stranded siRNAs in mammalian cells, Biochemical and Biophysical Research Communications, vol. 316, pp. 680-687, 2004.
Ahmadzada et al., Fundamentals of siRNA and miRNA therapeutics and a Review of Targeted Nanoparticle Delivery Systems in Breast Cancer, Biophysical Reviews, vol. 10, pp. 69-86, 2018.

\* cited by examiner

ReNcell CX
DCX mRNA

SEQUENCE LISTING

<160> NUMBER OF SEQ ID NOS: 828

<210> SEQ ID NO 1
<211> LENGTH: 4629
<212> TYPE: DNA
<213> ORGANISM: Artificial Sequence
<220> FEATURE:
<223> OTHER INFORMATION: Homo sapiens transforming growth factor, beta
receptor II (70/80kDa) (TGFBR2), transcript variant 2, antisense
DNA

<400> SEQUENCE: 1

| tttagctact aggaatggga acaggaggca ggatgctcac ctgagtattt tgctttattc | 60 |
|---|---|
| aatctaataa acattttatt tatgtaaaag acaaacaatg catagaataa aaataagtgc | 120 |
| ttgagacttt tgatataaaa agagtatata gcattcacat tcctatttta atacatgagt | 180 |
| acagctgaag tgttccataa aagaataaaa ctttcccttt atgtatagta gtgaaaaaag | 240 |
| tcagtatttt taggaactac agaatgttat tccttggtct tttttcttga ataagaaaaa | 300 |
| aaaacataaa caaacaagc cacagtatcc tctgacacta cattccagtt tatgctgata | 360 |
| acccagaagt gagaatactc ttgaatcttg aatatctcat gaatggacca gtattctaga | 420 |
| aactcaccac tagaggtcaa tgggcaacag ctattgggat ggtatcagca tgccctacgg | 480 |
| tgcaagtgga atttctaggc gcctctatgc tactgcagcc acactgtctt taactctcag | 540 |
| cccacccaca ctgaggaggg tgcctagagg ttctatttcc aaacctttgc atgtatctta | 600 |
| aaaatctcaa taaatgaga ccttccacca tccaaacaga gctgatattc tcactaccag | 660 |
| tccctctcta atattcctat ttggctgaaa ataagtagct tcaaaaagtt ttaaaaaaga | 720 |
| gattacttgc agcattaaca cttctttgtt gattaacaag tttcctatgg agttttaaag | 780 |
| ctcatacttt gttcttgtcc ttgtggacac aaattttcta actgcaaatg ggacctttgt | 840 |
| gtcccacatt caaatcctct ctagtaattt ctgcaaggt tgagaaggct ggcatgatgg | 900 |
| agagaacggt aaccatgagg aaagcttctt ggagtaaagc actcctctct ccaatgcaga | 960 |
| gggtaaaact attaacatat aagcaaaaga aacttgggct aactgagacc cttaaaggag | 1020 |
| ttccccttta gtccaataaa aggccaactt caaatcttaa caccagataa ggtagtcaaa | 1080 |
| atcatattat atacccagag aatgactgct tgaatgaca tttcttacaa gggaccttgg | 1140 |
| ttaggtgcag atttaattcc tagactgggg tccaggtagg cagtggaaag agctaatgtt | 1200 |
| tacagtgaga agtgaggcag ctttgtaagt gtctccacac cttcacattt tgtgaacgtg | 1260 |
| gactggagat aactgaaaac catctgctat ccttacctgg ggatccagat tttcctgcaa | 1320 |
| aatctccaaa tatttataaa gtggcttcac tttttgaaac gctgtgctga ccaaacaaaa | 1380 |
| catatgttta gagtgcctga ggtcatagtc ctgacaatga tagtattgtg tagttgaaat | 1440 |

-continued

```
cctcttcatc aggccaaact gtgcttgagc aatcaggagc ccagaaagat ggaacccatt    1500
ggtgtttgta tagaaaacta gaaaatcaag tcaagtgtaa tgaaaagta aacacgataa     1560 agcctagagt gagaatttgc tcctttttag aaaaggatga aggctgggag cagagaatag    1620
taacataagt gcaggggaaa gatgaaaaaa agaacaattt ttcattagta gatggtgggg    1680
caatcgcatg gatggggaca tctgttctga ttttctgca acccatgaag gtaaaaagtg     1740
gggttcaaaa cattcaaggt attaaagatg gggtagagtt tctaaactag gttgagggag    1800
agtttctaaa ctagccccc agatttgggg cttggagctt aaatgaaaag tccaggagaa     1860
ataagggcac acaggaaccc cgggaacact ggtcctcaaa cagtgccact gtacttagtt    1920
ccatggccag aagagaagtg ctaggcaggg aatgattatt ttgcaaaagc aagtgcaatg    1980
tggtcatagc tggctgtgag acatggagcc tctttcctca tgcaaagttc actgttttac    2040
agtcagagaa ccactgcatg tgtgattgtc aaatgctaat gctgtcatgg gtcccttcct    2100
tctctgcttg gttctggagt tctccaataa aaccaatttc ctgggaatat ttgatgtttt    2160
tccttgtctc ttttcaaggt atggctatat atatagagct atagacatat atagatatat    2220
atatatatat ataaaacata gctattcata tttatataca ggcattaata aagtgcaaat    2280
gttattggct attgtaaaaa tcaatctcat ttcctgagga agtgctaaca cagcttatcc    2340
tatgacaatg tcaaaggcat agaatgctct atgtcaccca ctccctgctg ctgttgtttc    2400
tgcttatccc cacagcttac agggagggga gtgaccccct tggttttcca ggaagcatca    2460
gttcaggggc agcttcctgc tgcctctgtt ctttggtgag aggggcagcc tctttggaca    2520
tggcccagcc tgccccagaa gagctatttg gtagtgttta gggagccgtc ttcaggaatc    2580
ttctcctccg agcagctcct ccccgagagc ctgtccagat gctccagctc actgaagcgt    2640
tctgccacac actgggctgt gagacgggcc tctgggtcgt ggtcccagca ctcagtcaac    2700
gtctcacaca ccatctggat gccctggtgg ttgagccaga agctgggaat ttctggtcgc    2760
cctcgatctc tcaacacgtt gtccttcatg ctttcgacac aggggtgctc ccgcaccttg    2820
gaaccaaatg gaggctcata atcttttact tctcccactg cattacagcg agatgtcatt    2880
tcccagagca ccagagccat ggagtagaca tcggtctgct tgaaggactc aacattctcc    2940
aaattcatcc tggattctag gacttctgga gccatgtatc ttgcagttcc cacctgccca    3000
ctgttagcca ggtcatccac agacagagta gggtccagca gcagggaaag cccaaagtca    3060
cacaggcagc aggttaggtc gttcttcacg aggatattgg agctcttgag gtccctgtgc    3120
acgatgggca tctgggccct cccacatgga gtgtgatcac tgtggaggtg agcaatcccc    3180
cgggcgaggg agctgcccag cttgcgcagg tcctcccagc tgatgacatg ccgcgtcagg    3240
tactcctgta ggttgccctt ggcgtggaag gcggtgatca gccagtattg tttccccaac    3300
tccgtcttcc gctcctcagc cgtcaggaac tggagtatgt tctcatgctt cagattgatg    3360
tctgagaaga tgtccttctc tgtcttccaa gaggcatact cctcataggg aaagatcttg    3420
actgccactg tctcaaactg ctctgaagtg ttctgcttca gcttggcctt atagacctca    3480
gcaaagcgac cttccccac cagggtgtcc agctcaatgg gcagcagctc tgtgttgtgg    3540
ttgatgttgt tggcacacgt ggagctgatg tcagagcggt catcttccag gatgatggca    3600
cagtgctcgc tgaactccat gagcttccgc gtcttgccgg tttcccaggt tgaactcagc    3660
ttctgctgcc ggttaacgcg gtagcagtag aagatgatga tgacagatat ggcaactccc    3720
agtggtggca ggaggctgat gcctgtcact tgaaatatga ctagcaacaa gtcaggattg    3780
```

| | |
|---|---|
| ctggtgttat attcttctga aagatgatg ttgtcattgc actcatcaga gctacaggaa | 3840 |
| cacatgaaga aagtctcacc aggctttttt ttttccttca taatgcactt tggagaagca | 3900 |
| gcatcttcca gaataaagtc atggtagggg agcttgggt catggcaaac tgtctctagt | 3960 |
| gttatgttct cgtcattctt tctccataca gccacacaga cttcctgtgg cttctcacag | 4020 |
| atggaggtga tgctgcagtt gctcatgcag gatttctggt tgtcacaggt ggaaaatctc | 4080 |
| acatcacaaa atttacacag ttgtggaaac ttgactgcac cgttgttgtc agtgactatc | 4140 |
| atgtcgttat taaccgactt ctgaacgtgc ggtgggatcg tgctggcgat acgcgtccac | 4200 |
| aggacgatgt gcagcggcca caggcccctg agcagccccc gacccatggc agaccccgct | 4260 |
| gctcgtcata gaccgagccc ccagcgcagc ggacggcgcc ttcccggacc cctggctgcg | 4320 |
| cctccgcgcc gcgccctctc cggacccgc gccgggccgg cagcgcagat gtgcgggcca | 4380 |
| gatgtggcgc ccgctcgcca gccaggaggg ggcctggagg ccggcgaggc gcggggaggc | 4440 |
| ccccggcggc cgagggaagc tgcacaggag tccggctcct gtcccgagcg ggtgcacgcg | 4500 |
| cggggggtgtc gtcgctccgt gcgcgcgagt gactcactca acttcaactc agcgctgcgg | 4560 |
| gggaaacagg aaactcctcg ccaacagctg ggcaggacct ctctccgccc gagagccttc | 4620 |
| tccctctcc | 4629 |

<210> SEQ ID NO 2
<211> LENGTH: 4629
<212> TYPE: DNA
<213> ORGANISM: Homo sapiens

<400> SEQUENCE: 2

| | |
|---|---|
| ggagagggag aaggctctcg ggcggagaga ggtcctgccc agctgttggc gaggagtttc | 60 |
| ctgtttcccc cgcagcgctg agttgaagtt gagtgagtca ctcgcgcgca cggagcgacg | 120 |
| acacccccgc gcgtgcaccc gctcgggaca ggagccggac tcctgtgcag cttccctcgg | 180 |
| ccgccggggg cctccccgcg cctcgccggc ctccaggccc cctcctggct ggcgagcggg | 240 |
| cgccacatct ggcccgcaca tctgcgctgc cggcccggcg cggggtccgg agagggcgcg | 300 |
| gcgcggaggc gcagccaggg gtccgggaag gcgccgtccg ctgcgctggg ggctcggtct | 360 |
| atgacgagca gcggggtctg ccatgggtcg ggggctgctc aggggcctgt ggccgctgca | 420 |
| catcgtcctg tggacgcgta tcgccagcac gatcccaccg cacgttcaga agtcggttaa | 480 |
| taacgacatg atagtcactg acaacaacgg tgcagtcaag tttccacaac tgtgtaaatt | 540 |
| ttgtgatgtg agattttcca cctgtgacaa ccagaaatcc tgcatgagca actgcagcat | 600 |
| cacctccatc tgtgagaagc cacaggaagt ctgtgtggct gtatggagaa agaatgacga | 660 |
| gaacataaca ctagagacag tttgccatga ccccaagctc ccctaccatg actttattct | 720 |
| ggaagatgct gcttctccaa agtgcattat gaaggaaaaa aaaagcctg gtgagacttt | 780 |
| cttcatgtgt tcctgtagct ctgatgagtg caatgacaac atcatcttct cagaagaata | 840 |
| taacaccagc aatcctgact tgttgctagt catatttcaa gtgacaggca tcagcctcct | 900 |
| gccaccactg ggagttgcca tatctgtcat catcatcttc tactgctacc gcgttaaccg | 960 |
| gcagcagaag ctgagttcaa cctgggaaac cggcaagacg cggaagctca tggagttcag | 1020 |
| cgagcactgt gccatcatcc tggaagatga ccgctctgac atcagctcca cgtgtgccaa | 1080 |
| caacatcaac cacaacacag agctgctgcc cattgagctg gacacctgg tggggaaagg | 1140 |
| tcgctttgct gaggtctata aggccaagct gaagcagaac acttcagagc agtttgagac | 1200 |
| agtggcagtc aagatctttc cctatgagga gtatgcctct tggaagacag agaaggacat | 1260 |

```
cttctcagac atcaatctga agcatgagaa catactccag ttcctgacgg ctgaggagcg    1320
gaagacggag ttggggaaac aatactggct gatcaccgcc ttccacgcca agggcaacct    1380
acaggagtac ctgacgcggc atgtcatcag ctgggaggac ctgcgcaagc tgggcagctc    1440
cctcgcccgg gggattgctc acctccacag tgatcacact ccatgtggga ggcccaagat    1500
gcccatcgtg cacagggacc tcaagagctc caatatcctc gtgaagaacg acctaacctg    1560
ctgcctgtgt gactttgggc tttccctgcg tctggaccct actctgtctg tggatgacct    1620
ggctaacagt gggcaggtgg gaactgcaag atacatggct ccagaagtcc tagaatccag    1680
gatgaatttg gagaatgttg agtccttcaa gcagaccgat gtctactcca tggctctggt    1740
gctctgggaa atgacatctc gctgtaatgc agtgggagaa gtaaaagatt atgagcctcc    1800
atttggttcc aaggtgcggg agcacccctg tgtcgaaagc atgaaggaca acgtgttgag    1860
agatcgaggg cgaccagaaa ttcccagctt ctggctcaac caccagggca tccagatggt    1920
gtgtgagacg ttgactgagt gctgggacca cgacccagag gcccgtctca cagcccagtg    1980
tgtggcagaa cgcttcagtg agctggagca tctggacagg ctctcgggga ggagctgctc    2040
ggaggagaag attcctgaag acggctccct aaacactacc aaatagctct tctggggcag    2100
gctgggccat gtccaaagag gctgcccctc tcaccaaaga acagaggcag caggaagctg    2160
cccctgaact gatgcttcct ggaaaaccaa gggggtcact cccctccctg taagctgtgg    2220
ggataagcag aaacaacagc agcagggagt gggtgacata gagcattcta tgcctttgac    2280
attgtcatag gataagctgt gttagcactt cctcaggaaa tgagattgat ttttacaata    2340
gccaataaca tttgcacttt attaatgcct gtatataaat atgaatagct atgttttata    2400
tatatatata tatatctata tatgtctata gctctatata tatagccata ccttgaaaag    2460
agacaaggaa aaacatcaaa tattcccagg aaattggttt tattggagaa ctccagaacc    2520
aagcagagaa ggaagggacc catgacagca ttagcatttg acaatcacac atgcagtggt    2580
tctctgactg taaaacagtg aactttgcat gaggaaagag gctccatgtc tcacagccag    2640
ctatgaccac attgcacttg cttttgcaaa ataatcattc cctgcctagc acttctcttc    2700
tggccatgga actaagtaca gtggcactgt ttgaggacca gtgttcccgg ggttcctgtg    2760
tgcccttatt tctcctggac ttttcattta agctccaagc cccaaatctg ggggctagt     2820 ttagaaactc tccctcaacc tagtttagaa actctacccc atctttaata ccttgaatgt    2880 tttgaaccce acttttttacc ttcatgggtt gcagaaaaat cagaacagat gtccccatcc    2940
atgcgattgc cccaccatct actaatgaaa aattgttctt tttttcatct ttcccctgca    3000
cttatgttac tattctctgc tcccagcctt catccttttc taaaaggag caaattctca     3060 ctctaggctt tatcgtgttt acttttttcat tacacttgac ttgatttttct agttttctat    3120 acaaacacca atgggttcca tcttttctggg ctcctgattg ctcaagcaca gtttggcctg   3180
atgaagagga tttcaactac acaatactat cattgtcagg actatgacct caggcactct    3240
aaacatatgt tttgtttggt cagcacagcg tttcaaaaag tgaagccact ttataaatat    3300
ttggagattt tgcaggaaaa tctggatccc caggtaagga tagcagatgg ttttcagtta    3360
tctccagtcc acgttcacaa aatgtgaagg tgtggagaca cttacaaagc tgcctcactt    3420
ctcactgtaa acattagctc tttccactgc ctacctggac cccagtctag gaattaaatc    3480
tgcacctaac caaggtccct tgtaagaaat gtccattcaa gcagtcattc tctgggtata    3540
taatatgatt ttgactacct tatctggtgt taagatttga agttggcctt ttattggact    3600
```

```
aaagggggaac tccttttaagg gtctcagtta gcccaagttt cttttgctta tatgttaata    3660
gttttaccct ctgcattgga gagaggagtg ctttactcca agaagctttc tcatggtta      3720
ccgttctctc catcatgcca gccttctcaa cctttgcaga aattactaga gaggatttga    3780
atgtgggaca caaaggtccc atttgcagtt agaaaatttg tgtccacaag gacaagaaca    3840
aagtatgagc tttaaaactc cataggaaac ttgttaatca acaagaagt gttaatgctg      3900
caagtaatct ctttttttaaa acttttgaa gctacttatt ttcagccaaa taggaatatt    3960
agagagggac tggtagtgag aatatcagct ctgtttggat ggtggaaggt ctcattttat    4020
tgagattttt aagatacatg caaaggtttg gaaatagaac ctctaggcac cctcctcagt    4080
gtgggtgggc tgagagttaa agacagtgtg gctgcagtag catagaggcg cctagaaatt    4140
ccacttgcac cgtagggcat gctgatacca tcccaatagc tgttgcccat tgacctctag    4200
tggtgagttt ctagaatact ggtccattca tgagatattc aagattcaag agtattctca    4260
cttctgggtt atcagcataa actgaatgt agtgtcagag gatactgtgg cttgttttgt      4320
ttatgttttt ttttcttatt caagaaaaaa gaccaaggaa taacattctg tagttcctaa    4380
aaatactgac tttttttcact actatacata aagggaaagt tttattcttt tatggaacac    4440
ttcagctgta ctcatgtatt aaaataggaa tgtgaatgct atatactctt tttatatcaa    4500
aagtctcaag cacttatttt tattctatgc attgtttgtc ttttacataa ataaaatgtt    4560
tattagattg aataaagcaa aatactcagg tgagcatcct gcctcctgtt cccattccta    4620
gtagctaaa                                                              4629

<210> SEQ ID NO 3
<211> LENGTH: 4629
<212> TYPE: RNA
<213> ORGANISM: Homo sapiens

<400> SEQUENCE: 3
ggagagggag aaggcucucg ggcggagaga ggucccugccc agcuguuggc gaggaguuuc      60
cuguuucccc cgcagcgcug aguugaaguu gagugaguca cucgcgcgca cggagcgacg    120
acacccccgc gcgugcaccc gcucgggaca ggagccggac uccugugcag cuucccucgg    180
ccgccggggg ccuccccgcg ccucgccggc cuccaggccc cuccugggcu ggcgagcggg    240
cgccacaucu ggcccgcaca ucugcgcugc cggcccggcg cggggucccgg agagggcgcg    300
gcgcggaggc gcagccaggg gucggaaag gcgccguccg cugcgcuggg ggcucggucu      360
augacgagca gcggggucug ccaugggucg ggggcugcuc aggggccugu ggccgcugca    420
caucguccug uggacgcgua ucgccagcac gaucccaccg cacguucaga agucgguuaa    480
uaacgacaug auagucacug acaacaacgg ugcagucaag uuccacaac uguguaaauu      540
uugugaugug agauuuucca ccugugacaa ccagaaauuc ugcaugagca acugcagcau    600
caccuccauc ugugagaagc cacaggaagu cugugugcugcu guaggagaa agaaugacga    660
gaacauaaca cuagagacag uuugccauga ccccaagcuc cccuaccaug acuuauuucu    720
ggaagaugcu gcuucuccaa agugcauuau gaaggaaaaa aaaaagccug gugagacuuu    780
cuucaugugu uccuguagcu cugaugaugu caaugacaac aucaucuucu cagaagaaua    840
uaacaccagc aauccugacu uguugcuagu cauauuucaa gugacaggca ucagccuccu    900
gccaccacug ggaguugcca uacugucau caucaucuuc uacugcuacc gcguuaaccg    960
gcagcagaag cugagucaa ccuggaaaac cgcaagacg cggaagcuca uggagaucag    1020
cgagcacugu gccaucaucc uggaagauga ccgcucugac aucagcucca cgugugccaa    1080
```

-continued

| | |
|---|---|
| caacaucaac cacaacacag agcugcugcc cauugagcug gacacccugg uggggaaagg | 1140 |
| ucgcuuugcu gaggucuaua aggccaagcu gaagcagaac acuucagagc aguuugagac | 1200 |
| aguggcaguc aagaucuuuc ccuaugagga guaugccucu uggaagacag agaaggacau | 1260 |
| cuucucagac aucaaucuga agcaugaaca cauaccag uuccgacgg cugaggagcg | 1320 |
| gaagacggag uuggggaaac aauacuggcu gaucaccgcc uuccacgcca agggcaaccu | 1380 |
| acaggaguac cugacgcggc augcaucag cugggaggac cugcgcaagc ugggcagcuc | 1440 |
| ccucgcccgg gggauugcuc accuccacag ugaucacacu ccauguggga ggcccaagau | 1500 |
| gcccaucgug cacagggacc ucaagagcuc caauauccuc gugaagaacg accuaaccug | 1560 |
| cugccugugu gacuugggc uucccugcg ucuggacccu acucugucug uggaugaccu | 1620 |
| ggcuaacagu gggcaggugg gaacugcaag auacauggcu ccagaagucc uagaauccag | 1680 |
| gaugaauuug gagaauguug agccuucaa gcagaccgau gucuacucca uggcucuggu | 1740 |
| gcucugggaa augacaucuc gcuguaaugc aguggagaa uaaaagauu augagccucc | 1800 |
| auuugguucc aaggugcggg agcaccccug ugucgaaagc augaaggaca acguguugag | 1860 |
| agaucgaggc cgaccagaaa uucccagcuu cuggcucaac caccagggca uccagauggu | 1920 |
| gugugagacg uugacugagu gcugggacca cgacccagag gcccgucuca cagcccagug | 1980 |
| uguggcagaa cgcuucagug agcuggagca ucuggacagg cucucgggga ggagcugcuc | 2040 |
| ggaggagaag auuccugaag acggcucccu aaacacuacc aaauagcucu ucuggggcag | 2100 |
| gcugggccau guccaaagag gcugcccuc ucaccaaaga acagaggcag caggaagcug | 2160 |
| ccccugaacu gaugcuuccu ggaaaaccaa ggggucacu ccccucccug uaagcugugg | 2220 |
| ggauaagcag aaacaacagc agcagggagu gggugacaua gagcauucua ugccuuugac | 2280 |
| auugucauag gauaagcugu guuagcacuu ccucaggaaa ugagauugau uuuuacaaua | 2340 |
| gccaauaaca uuugcacuuu auuaaugccu guauauaaau augaauagcu auguuuaua | 2400 |
| uauauauaua uauaucuaua uaugucuaua gcucuauaua uauagccaua ccugaaaag | 2460 |
| agacaaggaa aaacaucaaa uauucccagg aaauugguuu uauuggagaa cuccagaacc | 2520 |
| aagcagagaa ggaagggacc caugacagca uuagcauuug acaaucacac augcagguggu | 2580 |
| ucucugacug uaaacagug aacuuugcau gaggaaagag gcuccaugguc ucacagccag | 2640 |
| cuaugaccac auugcacuug cuuuugcaaa auaaucauuc ccugccuagc acuucucuuc | 2700 |
| uggccaugga acuaaguaca guggcacugu uugaggacca guguccccgg gguccugug | 2760 |
| ugcccuuauu ucuccggac uuucauuua agcuccaagc cccaaaucug ggggcuagu | 2820 |
| uuagaaacuc ucccucaacc uaguuuagaa acucuacccc aucuuuaaua ccuugaaugu | 2880 |
| uuugaaccc acuuuuacc uucaugggu gcagaaaaau cagaacagau gucccccaucc | 2940 |
| augcgauugc cccaccaucu acuaaugaaa aauuguucuu uuuucaucu uuccccugca | 3000 |
| cuuauguuac uauucucugc ucccagccuu cauccuuuuc uaaaaaggag caaauucuca | 3060 |
| cucuaggcuu uaucguguuu acuuuucau uacacuugac uugauuucu aguuucuau | 3120 |
| acaaacacca augguuucca ucuuucuggg cuccgauug ucaagcaca guuggccug | 3180 |
| augaagagga uuucaacuac acaauacuau cauugucagg acaugaccu caggcacucu | 3240 |
| aaacauaugu uuguuuggu cagcacagcg uucaaaaag ugaagccacu uuauaaauau | 3300 |
| uuggagauuu ugcaggaaaa ucuggauccc cagguaagga uagcagaugg uuuucaguua | 3360 |
| ucuccagucc acguucacaa aaugugaagg uguggagaca cuuacaaagc ugccucacuu | 3420 |

```
cucacuguaa acauuagcuc uuuccacugc cuaccuggac cccagucuag gaauuaaauc    3480
ugcaccuaac caaggucccu uguaagaaau guccauucaa gcagucauuc ucugqguaua    3540 uaauaugauu uugacuaccu uaucuggugu uaagauuuga aguggccuu uuauuggacu     3600 aaaggggaac uccuuuaagg gucucaguua gcccaaguuu cuuuugcuua uauguuaaua    3660
guuuuacccu cugcauugga gagaggagug cuuuacucca agaagcuuuc cucauggua     3720 ccguucucuc caucaugcca gccuucucaa ccuuugcaga aauuacuaga gaggauuuga    3780 auguqgqaca caaaggcccc auuugcaguu agaaaauuug uguccacaag gacaagaaca    3840
aaguaugagc uuuaaaaacuc cauaggaaac uuguuaauca acaaagaagu guuaaugcug   3900
caaguaaucu cuuuuuaaa acuuuugaa gcacuuauu uucagccaaa uaggaauauu       3960
agagagggac ugguagugag aauaucagcu cuguuuggau ggugqaaggu ucauuuuau     4020 ugagauuuuu aagauacaug caaagguuug gaaauagaac cucuaggcac ccuccucagu    4080
gugggugggc ugagaguuaa agacagugug gcugcaguag cauagaggcg ccuagaaauu    4140
ccacuugcac cguagggcau gcugauacca ucccaauagc uguugcccau ugaccucuag    4200
uggugaguuu cuagaauacu gguccauuca ugagauauuc aagauucaag aguauucuca    4260 cuucugqguu aucagcauaa acuqgaaugu agugucagag gauacugugg cuuguuuugu    4320
uuauguuuuu uuuucuuauu caagaaaaaa gaccaaggaa uaacauucug uaguccuaa     4380 aaauacugac uuuuuucacu acauacaua aagggaaagu uuuauucuuu uaqggaacac     4440 uucagcugua cucauguauu aaaauaggaa ugugaaugcu auauacucuu uuuuauaucaa   4500 aagcucaag cacuuauuuu uauucuaugc auuguuugc uuuuacauaa auaaaauguu     4560
uauuagauug aauaaagcaa aauacucagg ugagcauccu gccuccuguu cccauuccua    4620
guagcuaaa                                                            4629

<210> SEQ ID NO 4
<211> LENGTH: 10
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 4
tggtccattc                                                           10

<210> SEQ ID NO 5
<211> LENGTH: 10
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 5
ccctaaacac                                                           10

<210> SEQ ID NO 6
<211> LENGTH: 10
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense
```

-continued

```
<400> SEQUENCE: 6
actaccaaat                                                              10

<210> SEQ ID NO 7
<211> LENGTH: 10
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 7
ggacgcgtat                                                              10

<210> SEQ ID NO 8
<211> LENGTH: 10
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 8
gtctatgacg                                                              10

<210> SEQ ID NO 9
<211> LENGTH: 10
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 9
ttattaatgc                                                              10

<210> SEQ ID NO 10
<211> LENGTH: 10
<212> TYPE: DNA
<213> ORGANISM: Artificial Sequence
<220> FEATURE:
<223> OTHER INFORMATION: General Formula S3
<220> FEATURE:
<221> NAME/KEY: misc_feature
<222> LOCATION: (1)..(1)
<223> OTHER INFORMATION: n may represent 5'TGCCCCAGAAGAGCTATTTGGTAG'3 or
      sequences derived from 5'TGCCCCAGAAGAGCTATTTGGTAG'3, wherein one
      or more nucleotides are eliminated from the 5'-end and wherein n
      is at least G
<220> FEATURE:
<221> NAME/KEY: misc_feature
<222> LOCATION: (10)..(10)
<223> OTHER INFORMATION: n may represent 5'GAGCCGTCTTCAGGAATCTTCTCC'3 or
      sequences derived from 5'GAGCCGTCTTCAGGAATCTTCTCC'3, wherein one
      or more nucleotides are eliminated from the 3'-end and wherein n
      is at least G

<400> SEQUENCE: 10 ntgtttaggn                                                              10

<210> SEQ ID NO 11
<211> LENGTH: 10
<212> TYPE: DNA
<213> ORGANISM: Artificial Sequence
<220> FEATURE:
```

```
<223> OTHER INFORMATION: General Formula S4
<220> FEATURE:
<221> NAME/KEY: misc_feature
<222> LOCATION: (1)..(1)
<223> OTHER INFORMATION: n may represent 5'GCCCAGCCTGCCCCAGAAGAGCTA'3 or
      sequences derived from 5'GCCCAGCCTGCCCCAGAAGAGCTA'3, wherein one
      or more nucleotides are eliminated from the 5'-end and wherein n
      is at least A
<220> FEATURE:
<221> NAME/KEY: misc_feature
<222> LOCATION: (10)..(10)
<223> OTHER INFORMATION: n may represent 5'TGTTTAGGGAGCCGTCTTCAGGAA'3 or
      sequences derived from 5'TGTTTAGGGAGCCGTCTTCAGGAA'3, wherein one
      or more nucleotides are eliminated from the 3'-end and wherein n
      is at least T

<400> SEQUENCE: 11 ntttggtagn                                                                10

<210> SEQ ID NO 12
<211> LENGTH: 10
<212> TYPE: DNA
<213> ORGANISM: Artificial Sequence
<220> FEATURE:
<223> OTHER INFORMATION: General Formula S1
<220> FEATURE:
<221> NAME/KEY: misc_feature
<222> LOCATION: (1)..(1)
<223> OTHER INFORMATION: n may represent 5'CATGGCAGACCCCGCTGCTC'3 or
      sequences derived from 5'CATGGCAGACCCCGCTGCTC'3, wherein one or
      more nucleotides are eliminated from the 5'-end and wherein n is
      at least C
<220> FEATURE:
<221> NAME/KEY: misc_feature
<222> LOCATION: (10)..(10)
<223> OTHER INFORMATION: n may represent 5'CCGAGCCCCCAGCGCAGCGG'3 or
      sequences derived from 5'CCGAGCCCCCAGCGCAGCGG'3, wherein one or
      more nucleotides are eliminated from the 3'-end and wherein n is
      at least C

<400> SEQUENCE: 12 ngtcatagan                                                                10

<210> SEQ ID NO 13
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 13
gctcgtcata gaccga                                                         16

<210> SEQ ID NO 14
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 14
cgatacgcgt ccacag                                                         16

<210> SEQ ID NO 15
<211> LENGTH: 16
<212> TYPE: DNA
<213> ORGANISM: Artificial Sequence
```

```
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 15
gtagtgttta gggagc                                                       16

<210> SEQ ID NO 16
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 16
gctatttggt agtgtt                                                       16

<210> SEQ ID NO 17
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 17
catgaatgga ccagta                                                       16

<210> SEQ ID NO 18
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 18
aggcattaat aaagtg                                                       16

<210> SEQ ID NO 19
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 19
ccgctgctcg tcatagac                                                     18

<210> SEQ ID NO 20
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 20
cgctgctcgt catagacc                                                     18
```

```
<210> SEQ ID NO 21
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 21
gctgctcgtc atagaccg                                                 18

<210> SEQ ID NO 22
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 22
ctgctcgtca tagaccga                                                 18

<210> SEQ ID NO 23
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 23
tgctcgtcat agaccgag                                                 18

<210> SEQ ID NO 24
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 24
gctcgtcata gaccgagc                                                 18

<210> SEQ ID NO 25
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 25
ctcgtcatag accgagcc                                                 18

<210> SEQ ID NO 26
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2
```

-continued

<400> SEQUENCE: 26
tcgtcataga ccgagccc                                          18

<210> SEQ ID NO 27
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 27
cgtcatagac cgagcccc                                          18

<210> SEQ ID NO 28
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 28
cgctgctcgt catagac                                           17

<210> SEQ ID NO 29
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 29
gctgctcgtc atagacc                                           17

<210> SEQ ID NO 30
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 30
ctgctcgtca tagaccg                                           17

<210> SEQ ID NO 31
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 31
tgctcgtcat agaccga                                           17

<210> SEQ ID NO 32
<211> LENGTH: 17
<212> TYPE: DNA

```
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 32
gctcgtcata gaccgag                                                   17

<210> SEQ ID NO 33
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 33
ctcgtcatag accgagc                                                   17

<210> SEQ ID NO 34
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 34
tcgtcataga ccgagcc                                                   17

<210> SEQ ID NO 35
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 35
cgtcatagac cgagccc                                                   17

<210> SEQ ID NO 36
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 36
gctgctcgtc atagac                                                    16

<210> SEQ ID NO 37
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 37
ctgctcgtca tagacc                                                    16
```

<210> SEQ ID NO 38
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 38
tgctcgtcat agaccg                                                       16

<210> SEQ ID NO 39
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 39
gctcgtcata gaccga                                                       16

<210> SEQ ID NO 40
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 40
ctcgtcatag accgag                                                       16

<210> SEQ ID NO 41
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 41
tcgtcataga ccgagc                                                       16

<210> SEQ ID NO 42
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 42
cgtcatagac cgagcc                                                       16

<210> SEQ ID NO 43
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2), transcript variant 2

<400> SEQUENCE: 43
ctgctcgtca tagac                                                              15

<210> SEQ ID NO 44
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 44
tgctcgtcat agacc                                                              15

<210> SEQ ID NO 45
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 45
gctcgtcata gaccg                                                              15

<210> SEQ ID NO 46
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 46
ctcgtcatag accga                                                              15

<210> SEQ ID NO 47
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 47
tcgtcataga ccgag                                                              15

<210> SEQ ID NO 48
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 48
cgtcatagac cgagc                                                              15

<210> SEQ ID NO 49
<211> LENGTH: 14

<210> SEQ ID NO 49
<211> LENGTH: 14
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 49
tgctcgtcat agac                                                       14

<210> SEQ ID NO 50
<211> LENGTH: 14
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 50
gctcgtcata gacc                                                       14

<210> SEQ ID NO 51
<211> LENGTH: 14
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 51
ctcgtcatag accg                                                       14

<210> SEQ ID NO 52
<211> LENGTH: 14
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 52
tcgtcataga ccga                                                       14

<210> SEQ ID NO 53
<211> LENGTH: 14
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 53
cgtcatagac cgag                                                       14

<210> SEQ ID NO 54
<211> LENGTH: 18
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 54
gctggcgata cgcgtcca                                                 18

<210> SEQ ID NO 55
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 55
ctggcgatac gcgtccac                                                 18

<210> SEQ ID NO 56
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 56
tggcgatacg cgtccaca                                                 18

<210> SEQ ID NO 57
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 57
ggcgatacgc gtccacag                                                 18

<210> SEQ ID NO 58
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 58
gcgatacgcg tccacagg                                                 18

<210> SEQ ID NO 59
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 59
cgatacgcgt ccacagga                                                 18

<210> SEQ ID NO 60
<211> LENGTH: 18
<212> TYPE: DNA
<213> ORGANISM: Artificial Sequence
<220> FEATURE:
<223> OTHER INFORMATION: Antisense oligonucleotide against Homo sapiens

```
       transforming growth factor, beta receptor II (70/80kDa) (TGFBR2),
       transcript variant 2

<400> SEQUENCE: 60
gatacgcgtc cacaggac                                                     18

<210> SEQ ID NO 61
<211> LENGTH: 18
<212> TYPE: DNA
<213> ORGANISM: Artificial Sequence
<220> FEATURE:
<223> OTHER INFORMATION: Antisense oligonucleotide against Homo sapiens
       transforming growth factor, beta receptor II (70/80kDa) (TGFBR2),
       transcript variant 2

<400> SEQUENCE: 61
atacgcgtcc acaggacg                                                     18

<210> SEQ ID NO 62
<211> LENGTH: 18
<212> TYPE: DNA
<213> ORGANISM: Artificial Sequence
<220> FEATURE:
<223> OTHER INFORMATION: Antisense oligonucleotide against Homo sapiens
       transforming growth factor, beta receptor II (70/80kDa) (TGFBR2),
       transcript variant 2

<400> SEQUENCE: 62
tacgcgtcca caggacga                                                     18

<210> SEQ ID NO 63
<211> LENGTH: 17
<212> TYPE: DNA
<213> ORGANISM: Artificial Sequence
<220> FEATURE:
<223> OTHER INFORMATION: Antisense oligonucleotide against Homo sapiens
       transforming growth factor, beta receptor II (70/80kDa) (TGFBR2),
       transcript variant 2

<400> SEQUENCE: 63
ctggcgatac gcgtcca                                                      17

<210> SEQ ID NO 64
<211> LENGTH: 17
<212> TYPE: DNA
<213> ORGANISM: Artificial Sequence
<220> FEATURE:
<223> OTHER INFORMATION: Antisense oligonucleotide against Homo sapiens
       transforming growth factor, beta receptor II (70/80kDa) (TGFBR2),
       transcript variant 2

<400> SEQUENCE: 64
tggcgatacg cgtccac                                                      17

<210> SEQ ID NO 65
<211> LENGTH: 17
<212> TYPE: DNA
<213> ORGANISM: Artificial Sequence
<220> FEATURE:
<223> OTHER INFORMATION: Antisense oligonucleotide against Homo sapiens
       transforming growth factor, beta receptor II (70/80kDa) (TGFBR2),
       transcript variant 2

<400> SEQUENCE: 65
ggcgatacgc gtccaca                                                      17

<210> SEQ ID NO 66
```

```
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 66
gcgatacgcg tccacag                                                   17

<210> SEQ ID NO 67
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 67
cgatacgcgt ccacagg                                                   17

<210> SEQ ID NO 68
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 68
gatacgcgtc cacagga                                                   17

<210> SEQ ID NO 69
<211> LENGTH: 12
<212> TYPE: DNA
<213> ORGANISM: Artificial Sequence
<220> FEATURE:
<223> OTHER INFORMATION: General Sequence
<220> FEATURE:
<221> NAME/KEY: misc_feature
<222> LOCATION: (1)..(1)
<223> OTHER INFORMATION: n may represent 5'CATGGCAGACCCCGCTGCT'3 or
      sequences derived from 5'CATGGCAGACCCCGCTGCT'3, wherein one or
      more nucleotides are eliminated from the 5'-end and wherein n is
      at least T
<220> FEATURE:
<221> NAME/KEY: misc_feature
<222> LOCATION: (10)..(10)
<223> OTHER INFORMATION: n may represent 5'CGAGCCCCAGCGCAGCGG'3 or
      sequences derived from 5'CGAGCCCCAGCGCAGCGG'3, wherein one or
      more nucleotides are eliminated from the 3'-end and wherein n is
      at least C
<220> FEATURE:
<221> NAME/KEY: misc_feature
<222> LOCATION: (12)..(12)
<223> OTHER INFORMATION: n is a, c, g, or t

<400> SEQUENCE: 69
ncgtcataga cn                                                        12

<210> SEQ ID NO 70
<211> LENGTH: 12
<212> TYPE: DNA
<213> ORGANISM: Artificial Sequence
<220> FEATURE:
<223> OTHER INFORMATION: General Formula
<220> FEATURE:
<221> NAME/KEY: misc_feature
```

<222> LOCATION: (1)..(1)
<223> OTHER INFORMATION: n may represent 5'GGTGGGATCGTGCTGGCGA'3 or
      sequences derived from 5'GGTGGGATCGTGCTGGCGA'3, wherein one or
      more nucleotides are eliminated from the 5'-end and wherein n is
      at least A
<220> FEATURE:
<221> NAME/KEY: misc_feature
<222> LOCATION: (12)..(12)
<223> OTHER INFORMATION: n may represent 5'CAGGACGATGTGCAGCGGC'3 or
      sequences derived from 5'CAGGACGATGTGCAGCGGC'3, wherein one or
      more nucleotides are eliminated from the 3'-end and wherein n is
      at least C

<400> SEQUENCE: 70
ntacgcgtcc an                                                            12

<210> SEQ ID NO 71
<211> LENGTH: 12
<212> TYPE: DNA
<213> ORGANISM: Artificial Sequence
<220> FEATURE:
<223> OTHER INFORMATION: General Sequence
<220> FEATURE:
<221> NAME/KEY: misc_feature
<222> LOCATION: (1)..(1)
<223> OTHER INFORMATION: n may represent 5'TGCCCCAGAAGAGCTATTTGGTA'3 or
      sequences derived from 5'TGCCCCAGAAGAGCTATTTGGTA'3, wherein one or
      more nucleotides are eliminated from the 5'-end and wherein n is
      at least A
<220> FEATURE:
<221> NAME/KEY: misc_feature
<222> LOCATION: (12)..(12)
<223> OTHER INFORMATION: n may represent 5'AGCCGTCTTCAGGAATCTTCTCC'3 or
      sequences derived from 5'AGCCGTCTTCAGGAATCTTCTCC'3, wherein one or
      more nucleotides are eliminated from the 3'-end and wherein n is
      at least A

<400> SEQUENCE: 71
ngtgtttagg gn                                                            12

<210> SEQ ID NO 72
<211> LENGTH: 12
<212> TYPE: DNA
<213> ORGANISM: Artificial Sequence
<220> FEATURE:
<223> OTHER INFORMATION: General Sequence
<220> FEATURE:
<221> NAME/KEY: misc_feature
<222> LOCATION: (1)..(1)
<223> OTHER INFORMATION: n may represent 5'GCCCAGCCTGCCCCAGAAGAGCT'3 or
      sequences derived from 5'GCCCAGCCTGCCCCAGAAGAGCT'3, wherein one or
      more nucleotides are eliminated from the 5'-end and wherein n is
      at least T
<220> FEATURE:
<221> NAME/KEY: misc_feature
<222> LOCATION: (12)..(12)
<223> OTHER INFORMATION: n may represent 5'GTTTAGGGAGCCGTCTTCAGGAA'3 or
      sequences derived from 5'GTTTAGGGAGCCGTCTTCAGGAA'3, wherein one or
      more nucleotides are eliminated from the 3'-end and wherein n is
      at least G

<400> SEQUENCE: 72
natttggtag tn                                                            12

<210> SEQ ID NO 73
<211> LENGTH: 12
<212> TYPE: DNA
<213> ORGANISM: Artificial Sequence
<220> FEATURE:
<223> OTHER INFORMATION: General Sequence
<220> FEATURE:
<221> NAME/KEY: misc_feature
<222> LOCATION: (1)..(1)

```
<223> OTHER INFORMATION: n may represent 5'TGAATCTTGAATATCTCAT'3 or
      sequences derived from 5'TGAATCTTGAATATCTCAT'3, wherein one or
      more nucleotides are eliminated from the 5'-end and wherein n is
      at least T
<220> FEATURE:
<221> NAME/KEY: misc_feature
<222> LOCATION: (12)..(12)
<223> OTHER INFORMATION: n may represent 5'GTATTCTAGAAACTCACCA'3 or
      sequences derived from 5'GTATTCTAGAAACTCACCA'3, wherein one or
      more nucleotides are eliminated from the 5'-end and wherein n is
      at least G

<400> SEQUENCE: 73
ngaatggacc an                                                              12

<210> SEQ ID NO 74
<211> LENGTH: 12
<212> TYPE: DNA
<213> ORGANISM: Artificial Sequence
<220> FEATURE:
<223> OTHER INFORMATION: General Sequence
<220> FEATURE:
<221> NAME/KEY: misc_feature
<222> LOCATION: (1)..(1)
<223> OTHER INFORMATION: n may represent 5'ATTCATATTTATATACAGG'3 or
      sequences derived from 5'ATTCATATTTATATACAGG'3, wherein one or
      more nucleotides are eliminated from the 5'-end and wherein n is
      at least G
<220> FEATURE:
<221> NAME/KEY: misc_feature
<222> LOCATION: (12)..(12)
<223> OTHER INFORMATION: n may represent 5'GTGCAAATGTTATTGGCTA'3 or
      sequences derived from 5'GTGCAAATGTTATTGGCTA'3, wherein one or
      more nucleotides are eliminated from the 3'-end and wherein n is
      at least G

<400> SEQUENCE: 74
ncattaataa an                                                              12

<210> SEQ ID NO 75
<211> LENGTH: 41
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 75
gaatcttgaa tatctcatga atggaccagt attctagaaa c                              41

<210> SEQ ID NO 76
<211> LENGTH: 15
<212> TYPE: DNA
<213> ORGANISM: Artificial Sequence
<220> FEATURE:
<223> OTHER INFORMATION: Reference Oligonucleotide (scrambled control)

<400> SEQUENCE: 76
aacacgtcta tacgc                                                           15

<210> SEQ ID NO 77
<211> LENGTH: 41
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 77
```
ttcatattta tatacaggca ttaataaagt gcaaatgtta t                    41

<210> SEQ ID NO 78
<211> LENGTH: 42
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 78
tgaggaagtg ctaacacagc ttatcctatg acaatgtcaa ag                  42

<210> SEQ ID NO 79
<211> LENGTH: 49
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 79
gcctgcccca gaagagctat ttggtagtgt tagggagcc gtcttcagg            49

<210> SEQ ID NO 80
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 80
ttgaatatct catgaatgga                                            20

<210> SEQ ID NO 81
<211> LENGTH: 49
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 81
cgcaggtcct cccagctgat gacatgccgc gtcaggtact cctgtaggt           49

<210> SEQ ID NO 82
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 82
cagaagagct atttggtagt                                            20

<210> SEQ ID NO 83
<211> LENGTH: 78
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

-continued

```
<400> SEQUENCE: 83
atgtcgttat taaccgactt ctgaacgtgc ggtgggatcg tgctggcgat acgcgtccac    60
aggacgatgt gcagcggc                                                  78

<210> SEQ ID NO 84
<211> LENGTH: 74
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 84
ggccacaggc ccctgagcag cccccgaccc atggcagacc ccgctgctcg tcatagaccg    60
agcccccagc gcag                                                      74

<210> SEQ ID NO 85
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 85
tggtagtgtt tagggagccg                                                20

<210> SEQ ID NO 86
<211> LENGTH: 149
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 86
atgtcgttat taaccgactt ctgaacgtgc ggtgggatcg tgctggcgat acgcgtccac    60
aggacgatgt gcagcggcca caggcccctg agcagccccc gacccatggc agacccgct    120 gctcgtcata gaccgagccc ccagcgcag                                     149

<210> SEQ ID NO 87
<211> LENGTH: 31
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 87
ttgaatatct catgaatgga ccagtattct a                                   31

<210> SEQ ID NO 88
<211> LENGTH: 33
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 88
caagtggaat ttctaggcgc ctctatgcta ctg                                 33
```

<210> SEQ ID NO 89
<211> LENGTH: 31
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 89
atttatatac aggcattaat aaagtgcaaa t                               31

<210> SEQ ID NO 90
<211> LENGTH: 32
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 90
aagtgctaac acagcttatc ctatgacaat gt                              32

<210> SEQ ID NO 91
<211> LENGTH: 39
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 91
ccccagaaga gctatttggt agtgtttagg gagccgtct                       39

<210> SEQ ID NO 92
<211> LENGTH: 78
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 92
ctggtcgccc tcgatctctc aacacgttgt ccttcatgct ttcgacacag gggtgctccc     60
gcaccttgga accaaatg                                                  78

<210> SEQ ID NO 93
<211> LENGTH: 39
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 93
gtcctcccag ctgatgacat gccgcgtcag gtactcctg                       39

<210> SEQ ID NO 94
<211> LENGTH: 40
<212> TYPE: DNA
<213> ORGANISM: Artificial Sequence
<220> FEATURE:

<223> OTHER INFORMATION: Antisense oligonucleotide against Homo sapiens
      transforming growth factor, beta receptor II (70/80kDa) (TGFBR2),
      transcript variant 2

<400> SEQUENCE: 94
ctcagcttct gctgccggtt aacgcggtag cagtagaaga                               40

<210> SEQ ID NO 95
<211> LENGTH: 68
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 95
gttattaacc gacttctgaa cgtgcggtgg gatcgtgctg gcgatacgcg tccacaggac         60
gatgtgca                                                                 68

<210> SEQ ID NO 96
<211> LENGTH: 64
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 96
caggcccctg agcagccccc gacccatggc agacccgct gctcgtcata gaccgagccc          60
ccag                                                                     64

<210> SEQ ID NO 97
<211> LENGTH: 52
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 97
cacgcgcggg ggtgtcgtcg ctccgtgcgc gcgagtgact cactcaactt ca                 52

<210> SEQ ID NO 98
<211> LENGTH: 10
<212> TYPE: DNA
<213> ORGANISM: Artificial Sequence
<220> FEATURE:
<223> OTHER INFORMATION: General formula S2
<220> FEATURE:
<221> NAME/KEY: misc_feature
<222> LOCATION: (1)..(1)
<223> OTHER INFORMATION: w may represent 5'GGTGGGATCGTGCTGGCGAT'3 or
      sequences derived from 5'GGTGGGATCGTGCTGGCGAT'3, wherein one or
      more nucleotides are eliminated from the 5'-end and wherein w is
      at least T
<220> FEATURE:
<221> NAME/KEY: misc_feature
<222> LOCATION: (10)..(10)
<223> OTHER INFORMATION: r may represent 5'ACAGGACGATGTGCAGCGGC'3 or
      sequences derived from 5'ACAGGACGATGTGCAGCGGC'3, wherein one or
      more nucleotides are eliminated from the 3'-end and wherein w is
      at least A

<400> SEQUENCE: 98 nacgcgtccn                                                               10

<210> SEQ ID NO 99
<211> LENGTH: 10
<212> TYPE: DNA
<213> ORGANISM: Artificial Sequence
<220> FEATURE:
<223> OTHER INFORMATION: General formula S5
<220> FEATURE:
<221> NAME/KEY: misc_feature
<222> LOCATION: (1)..(1)
<223> OTHER INFORMATION: w may represent 5'CCCAGCCTGCCCCAGAAGAGCTATTTG'3
      or sequences derived from 5'CCCAGCCTGCCCCAGAAGAGCTATTTG'3, wherein
      one or more nucleotides are eliminated from the 5'-end and wherein
      w is at least G
<220> FEATURE:
<221> NAME/KEY: misc_feature
<222> LOCATION: (10)..(10)
<223> OTHER INFORMATION: r may represent 5'TAGGGAGCCGTCTTCAGGAATCTTCTC'3
      or sequences derived from 5'TAGGGAGCCGTCTTCAGGAATCTTCTC'3, wherein
      one or more nucleotides are eliminated from the 3'-end and wherein
      w is at least G

<400> SEQUENCE: 99 ngtagtgttn                                                          10

<210> SEQ ID NO 100
<211> LENGTH: 10
<212> TYPE: DNA
<213> ORGANISM: Artificial Sequence
<220> FEATURE:
<223> OTHER INFORMATION: General formula S6
<220> FEATURE:
<221> NAME/KEY: misc_feature
<222> LOCATION: (1)..(1)
<223> OTHER INFORMATION: w may represent 5'TGAATCTTGAATATCTCATG'3 or
      sequences derived from 5'TGAATCTTGAATATCTCATG'3, wherein one or
      more nucleotides are eliminated from the 5'-end and wherein w is
      at least G
<220> FEATURE:
<221> NAME/KEY: misc_feature
<222> LOCATION: (1)..(1)
<223> OTHER INFORMATION: n may represent 5'TGAATCTTGAATATCTCATG'3 or
      sequences derived from 5'TGAATCTTGAATATCTCATG'3, wherein one or
      more nucleotides are eliminated from the 5'-end and wherein n is
      at least G
<220> FEATURE:
<221> NAME/KEY: misc_feature
<222> LOCATION: (10)..(10)
<223> OTHER INFORMATION: r may represent 5'AGTATTCTAGAAACTCACCA'3 or
      sequences derived from 5'AGTATTCTAGAAACTCACCA'3, wherein one or
      more nucleotides are eliminated from the 3'-end and wherein w is
      at least A

<400> SEQUENCE: 100 naatggaccn                                                          10

<210> SEQ ID NO 101
<211> LENGTH: 10
<212> TYPE: DNA
<213> ORGANISM: Artificial Sequence
<220> FEATURE:
<223> OTHER INFORMATION: General formula S7
<220> FEATURE:
<221> NAME/KEY: misc_feature
<222> LOCATION: (1)..(1)
<223> OTHER INFORMATION: w may represent 5'ATTCATATTTATATACAGGC'3 or
      sequences derived from 5'ATTCATATTTATATACAGGC'3, wherein one or
      more nucleotides are eliminated from the 5'-end and wherein w is
      at least C
<220> FEATURE:
<221> NAME/KEY: misc_feature
<222> LOCATION: (10)..(10)
<223> OTHER INFORMATION: r may represent 5'AGTGCAAATGTTATTGGCTA'3 or
      sequences derived from 5'AGTGCAAATGTTATTGGCTA'3, wherein one or more nucleotides are eliminated from the 3'-end and wherein w is
at least A
<220> FEATURE:
<221> NAME/KEY: misc_feature
<222> LOCATION: (10)..(10)
<223> OTHER INFORMATION: n may represent 5'AGTGCAAATGTTATTGGCTA'3 or
sequences derived from 5'AGTGCAAATGTTATTGGCTA'3, wherein one or
more nucleotides are eliminated from the 3'-end and wherein n is
at least A

<400> SEQUENCE: 101 nattaataan                                                              10

<210> SEQ ID NO 102
<211> LENGTH: 17
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 102
gcgagtgact cactcaa                                                      17

<210> SEQ ID NO 103
<211> LENGTH: 15
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 103
cgagtgactc actca                                                        15

<210> SEQ ID NO 104
<211> LENGTH: 16
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 104
gcgagtgact cactca                                                       16

<210> SEQ ID NO 105
<211> LENGTH: 17
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 105
cgcgagtgac tcactca                                                      17

<210> SEQ ID NO 106
<211> LENGTH: 14
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

```
<400> SEQUENCE: 106
cgagtgactc actc                                                    14

<210> SEQ ID NO 107
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 107
cgcgagtgac tcactc                                                  16

<210> SEQ ID NO 108
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 108
gcgcgagtga ctcactc                                                 17

<210> SEQ ID NO 109
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 109
gcgagtgact cact                                                    14

<210> SEQ ID NO 110
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 110
gcgcgagtga ctcact                                                  16

<210> SEQ ID NO 111
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 111
cgcgcgagtg actcact                                                 17

<210> SEQ ID NO 112
<211> LENGTH: 12
<212> TYPE: DNA
```

```
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 112
cgagtgactc ac                                                        12

<210> SEQ ID NO 113
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 113
gcgagtgact cac                                                       13

<210> SEQ ID NO 114
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 114
cgcgagtgac tcac                                                      14

<210> SEQ ID NO 115
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 115
cgcgcgagtg actcac                                                    16

<210> SEQ ID NO 116
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 116
gcgcgcgagt gactcac                                                   17

<210> SEQ ID NO 117
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 117
cgcgagtgac tca                                                       13
```

<210> SEQ ID NO 118
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 118
gcgcgagtga ctca                                                        14

<210> SEQ ID NO 119
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 119
cgcgcgagtg actca                                                       15

<210> SEQ ID NO 120
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 120
gcgcgcgagt gactca                                                      16

<210> SEQ ID NO 121
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 121
tgcgcgcgag tgactca                                                     17

<210> SEQ ID NO 122
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 122
cgcgcgagtg actc                                                        14

<210> SEQ ID NO 123
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2), transcript variant 2

<400> SEQUENCE: 123
tgcgcgcgag tgactc                                                           16

<210> SEQ ID NO 124
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 124
gtgcgcgcga gtgactc                                                          17

<210> SEQ ID NO 125
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 125
cgcgcgagtg act                                                              13

<210> SEQ ID NO 126
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 126
tgcgcgcgag tgac                                                             14

<210> SEQ ID NO 127
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 127
cgtgcgcgcg agtgac                                                           16

<210> SEQ ID NO 128
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 128
tgcgcgcgag tga                                                              13

<210> SEQ ID NO 129
<211> LENGTH: 16

```
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 129
gtcgtcgctc cgtgcg                                                      16

<210> SEQ ID NO 130
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 130
gtcgtcgctc cgtgc                                                       15

<210> SEQ ID NO 131
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 131
gtgtcgtcgc tccgtgc                                                     17

<210> SEQ ID NO 132
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 132
tcgtcgctcc gtg                                                         13

<210> SEQ ID NO 133
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 133
tgtcgtcgct ccgtg                                                       15

<210> SEQ ID NO 134
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 134
```

-continued

```
tcgtcgctcc gt                                                            12

<210> SEQ ID NO 135
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 135
gtcgtcgctc cgt                                                           13

<210> SEQ ID NO 136
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 136
tgtcgtcgct ccgt                                                          14

<210> SEQ ID NO 137
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 137
gtgtcgtcgc tccgt                                                         15

<210> SEQ ID NO 138
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 138
ggtgtcgtcg ctccgt                                                        16

<210> SEQ ID NO 139
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 139
cgtcatagac cgagcc                                                        16

<210> SEQ ID NO 140
<211> LENGTH: 12
<212> TYPE: DNA
<213> ORGANISM: Artificial Sequence
<220> FEATURE:
<223> OTHER INFORMATION: Antisense oligonucleotide against Homo sapiens
``` transforming growth factor, beta receptor II (70/80kDa) (TGFBR2),
      transcript variant 2

<400> SEQUENCE: 140
atagaccgag cc                                                              12

<210> SEQ ID NO 141
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 141
gctcgtcata gaccga                                                          16

<210> SEQ ID NO 142
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 142
cgtcatagac cga                                                             13

<210> SEQ ID NO 143
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 143
ctcgtcatag accg                                                            14

<210> SEQ ID NO 144
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 144
gctcgtcata gaccg                                                           15

<210> SEQ ID NO 145
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 145
gctcgtcata gacc                                                            14

<210> SEQ ID NO 146

```
<210> SEQ ID NO 146
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 146
cagcccccga cccatgg                                                    17

<210> SEQ ID NO 147
<211> LENGTH: 16
<212> TYPE: DNA
<213> ORGANISM: Artificial Sequence
<220> FEATURE:
<223> OTHER INFORMATION: Reference Oligonucleotide

<400> SEQUENCE: 147
cagcccccga cccatg                                                     16

<210> SEQ ID NO 148
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 148
agcccccgac ccat                                                       14

<210> SEQ ID NO 149
<211> LENGTH: 28
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 149
cagcccccga cccaagcccc cgacccat                                        28

<210> SEQ ID NO 150
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 150
cgcgtccaca ggacgat                                                    17

<210> SEQ ID NO 151
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 151
cgcgtccaca ggac                                                       14
```

<210> SEQ ID NO 152
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 152
cgatacgcgt ccaca                                                    15

<210> SEQ ID NO 153
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 153
cgatacgcgt cca                                                      13

<210> SEQ ID NO 154
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 154
tggcgatacg cgtcca                                                   16

<210> SEQ ID NO 155
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 155
cgatacgcgt cc                                                       12

<210> SEQ ID NO 156
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 156
gcgatacgcg tcc                                                      13

<210> SEQ ID NO 157
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2), transcript variant 2

<400> SEQUENCE: 157
gctggcgata cgcgtcc                                                17

<210> SEQ ID NO 158
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 158
ctggcgatac gcgtc                                                  15

<210> SEQ ID NO 159
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 159
gcgatacgcg tc                                                     12

<210> SEQ ID NO 160
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 160
gctggcgata cgcgtc                                                 16

<210> SEQ ID NO 161
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 161
tggcgatacg cgtc                                                   14

<210> SEQ ID NO 162
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 162
tggcgatacg cgt                                                    13

<210> SEQ ID NO 163
<211> LENGTH: 14

```
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 163
ctggcgatac gcgt                                                        14

<210> SEQ ID NO 164
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 164
ggcgatacgc gt                                                          12

<210> SEQ ID NO 165
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 165
ctggcgatac gcg                                                         13

<210> SEQ ID NO 166
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 166
tggcgatacg cg                                                          12

<210> SEQ ID NO 167
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 167
atcgtgctgg cgatacg                                                     17

<210> SEQ ID NO 168
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 168
```

```
cgtgcggtgg gatcgt                                                       16

<210> SEQ ID NO 169
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 169
acgtgcggtg ggatcgt                                                      17

<210> SEQ ID NO 170
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 170
aacgtgcggt gggatcg                                                      17

<210> SEQ ID NO 171
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 171
aacgtgcggt gggat                                                        15

<210> SEQ ID NO 172
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 172
tgaacgtgcg gtgggat                                                      17

<210> SEQ ID NO 173
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 173
cgacttctga acgtgcg                                                      17

<210> SEQ ID NO 174
<211> LENGTH: 17
<212> TYPE: DNA
<213> ORGANISM: Artificial Sequence
<220> FEATURE:
<223> OTHER INFORMATION: Antisense oligonucleotide against Homo sapiens
``` transforming growth factor, beta receptor II (70/80kDa) (TGFBR2),
transcript variant 2

<400> SEQUENCE: 174
ttaacgcggt agcagta                                                     17

<210> SEQ ID NO 175
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 175
taacgcggta gcagta                                                      16

<210> SEQ ID NO 176
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 176
gttaacgcgg tagcagt                                                     17

<210> SEQ ID NO 177
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 177
ttaacgcggt agcag                                                       15

<210> SEQ ID NO 178
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 178
taacgcggta gca                                                         13

<210> SEQ ID NO 179
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 179
taacgcggta gc                                                          12

<210> SEQ ID NO 180

```
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 180
ttaacgcggt agc                                                          13

<210> SEQ ID NO 181
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 181
ttaacgcggt ag                                                           12

<210> SEQ ID NO 182
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 182
gttaacgcgg tag                                                          13

<210> SEQ ID NO 183
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 183
cggttaacgc ggtag                                                        15

<210> SEQ ID NO 184
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 184
ccggttaacg cggtag                                                       16

<210> SEQ ID NO 185
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 185
```
cggttaacgc ggta                                                        14

<210> SEQ ID NO 186
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 186
ggttaacgcg gta                                                         13

<210> SEQ ID NO 187
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 187
ccggttaacg cggta                                                       15

<210> SEQ ID NO 188
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 188
gccggttaac gcggta                                                      16

<210> SEQ ID NO 189
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 189
tgccggttaa cgcggta                                                     17

<210> SEQ ID NO 190
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 190
cggttaacgc ggt                                                         13

<210> SEQ ID NO 191
<211> LENGTH: 13
<212> TYPE: DNA
<213> ORGANISM: Artificial Sequence
<220> FEATURE:

```
<223> OTHER INFORMATION: Antisense oligonucleotide against Homo sapiens
      transforming growth factor, beta receptor II (70/80kDa) (TGFBR2),
      transcript variant 2

<400> SEQUENCE: 191
ccggttaacg cgg                                                          13

<210> SEQ ID NO 192
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 192
gccggttaac gcgg                                                         14

<210> SEQ ID NO 193
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 193
tgccggttaa cgcgg                                                        15

<210> SEQ ID NO 194
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 194
gccggttaac gcg                                                          13

<210> SEQ ID NO 195
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 195
ctgccggtta acgcg                                                        15

<210> SEQ ID NO 196
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 196
gctgccggtt aacgcg                                                       16
```

<210> SEQ ID NO 197
<211> LENGTH: 16
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 197
atgccgcgtc aggtac                                                       16

<210> SEQ ID NO 198
<211> LENGTH: 13
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 198
acatgccgcg tca                                                          13

<210> SEQ ID NO 199
<211> LENGTH: 16
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 199
gatgacatgc cgcgtc                                                       16

<210> SEQ ID NO 200
<211> LENGTH: 12
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 200
gacatgccgc gt                                                           12

<210> SEQ ID NO 201
<211> LENGTH: 15
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 201
gatgacatgc cgcgt                                                        15

<210> SEQ ID NO 202
<211> LENGTH: 13
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

```
<400> SEQUENCE: 202
atgacatgcc gcg                                                        13

<210> SEQ ID NO 203
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 203
tcccgcacct tggaacc                                                    17

<210> SEQ ID NO 204
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 204
cgatctctca acacgt                                                     16

<210> SEQ ID NO 205
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 205
tcgatctctc aacacgt                                                    17

<210> SEQ ID NO 206
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 206
cgatctctca acacg                                                      15

<210> SEQ ID NO 207
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 207
tcgatctctc aacacg                                                     16

<210> SEQ ID NO 208
<211> LENGTH: 17
<212> TYPE: DNA
<213> ORGANISM: Artificial Sequence
```

```
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 208
ctcgatctct caacacg                                                    17

<210> SEQ ID NO 209
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 209
gtagtgttta gggagc                                                     16

<210> SEQ ID NO 210
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 210
gctatttggt agtgtt                                                     16

<210> SEQ ID NO 211
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 211
agcttatcct atgac                                                      15

<210> SEQ ID NO 212
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 212
agcttatcct atga                                                       14

<210> SEQ ID NO 213
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 213
caggcattaa taaagtg                                                    17
```

<210> SEQ ID NO 214
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 214
ctaggcgcct ctatgc                                                       16

<210> SEQ ID NO 215
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 215
taggcgcctc tatg                                                         14

<210> SEQ ID NO 216
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 216
ctaggcgcct ctatg                                                        15

<210> SEQ ID NO 217
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 217
taggcgcctc tat                                                          13

<210> SEQ ID NO 218
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 218
catgaatgga ccagta                                                       16

<210> SEQ ID NO 219
<211> LENGTH: 10
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

-continued

<400> SEQUENCE: 219
gaatggacca                                                                              10

<210> SEQ ID NO 220
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 220
tgaatggacc ag                                                                           12

<210> SEQ ID NO 221
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 221
tgaatggacc agt                                                                          13

<210> SEQ ID NO 222
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 222
atgaatggac cagt                                                                         14

<210> SEQ ID NO 223
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 223
atgaatggac cagta                                                                        15

<210> SEQ ID NO 224
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 224
catgaatgga ccagtat                                                                      17

<210> SEQ ID NO 225
<211> LENGTH: 18
<212> TYPE: DNA

```
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 225
tcatgaatgg accagtat                                                       18

<210> SEQ ID NO 226
<211> LENGTH: 19
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 226
tcatgaatgg accagtatt                                                      19

<210> SEQ ID NO 227
<211> LENGTH: 20
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 227
ctcatgaatg gaccagtatt                                                     20

<210> SEQ ID NO 228
<211> LENGTH: 22
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 228
tctcatgaat ggaccagtat tc                                                  22

<210> SEQ ID NO 229
<211> LENGTH: 24
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 229
atctcatgaa tggaccagta ttct                                                24

<210> SEQ ID NO 230
<211> LENGTH: 26
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 230
tatctcatga atggaccagt attcta                                              26
```

<210> SEQ ID NO 231
<211> LENGTH: 28
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 231
atatctcatg aatggaccag tattctag                                        28

<210> SEQ ID NO 232
<211> LENGTH: 10
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 232
cgtcatagac                                                            10

<210> SEQ ID NO 233
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 233
tcgtcataga cc                                                         12

<210> SEQ ID NO 234
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 234
tcgtcataga ccg                                                        13

<210> SEQ ID NO 235
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 235
ctcgtcatag accga                                                      15

<210> SEQ ID NO 236
<211> LENGTH: 28
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2), transcript variant 2

<400> SEQUENCE: 236
atatacaggc attaataaag tgcaaatg                                          28

<210> SEQ ID NO 237
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 237
tgctcgtcat agaccga                                                      17

<210> SEQ ID NO 238
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 238
tgctcgtcat agaccgag                                                     18

<210> SEQ ID NO 239
<211> LENGTH: 19
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 239
tgctcgtcat agaccgagc                                                    19

<210> SEQ ID NO 240
<211> LENGTH: 20
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 240
ctgctcgtca tagaccgagc                                                   20

<210> SEQ ID NO 241
<211> LENGTH: 22
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 241
gctgctcgtc atagaccgag cc                                                22

<210> SEQ ID NO 242
<211> LENGTH: 24

```
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 242
cgctgctcgt catagaccga gccc                                          24

<210> SEQ ID NO 243
<211> LENGTH: 26
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 243
ccgctgctcg tcatagaccg agcccc                                        26

<210> SEQ ID NO 244
<211> LENGTH: 28
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 244
cccgctgctc gtcatagacc gagccccc                                      28

<210> SEQ ID NO 245
<211> LENGTH: 10
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 245
tacgcgtcca                                                          10

<210> SEQ ID NO 246
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 246
atacgcgtcc ac                                                       12

<210> SEQ ID NO 247
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 247
```

```
gatacgcgtc cac                                                        13

<210> SEQ ID NO 248
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 248
gatacgcgtc caca                                                       14

<210> SEQ ID NO 249
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 249
cgatacgcgt ccacag                                                     16

<210> SEQ ID NO 250
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 250
gcgatacgcg tccacag                                                    17

<210> SEQ ID NO 251
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 251
gcgatacgcg tccacagg                                                   18

<210> SEQ ID NO 252
<211> LENGTH: 19
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 252
gcgatacgcg tccacagga                                                  19

<210> SEQ ID NO 253
<211> LENGTH: 20
<212> TYPE: DNA
<213> ORGANISM: Artificial Sequence
<220> FEATURE:
<223> OTHER INFORMATION: Antisense oligonucleotide against Homo sapiens
``` transforming growth factor, beta receptor II (70/80kDa) (TGFBR2), transcript variant 2

<400> SEQUENCE: 253
ggcgatacgc gtccacagga                                                   20

<210> SEQ ID NO 254
<211> LENGTH: 22
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 254
tggcgatacg cgtccacagg ac                                                22

<210> SEQ ID NO 255
<211> LENGTH: 24
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 255
ctggcgatac gcgtccacag gacg                                              24

<210> SEQ ID NO 256
<211> LENGTH: 26
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 256
gctggcgata cgcgtccaca ggacga                                            26

<210> SEQ ID NO 257
<211> LENGTH: 28
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 257
tgctggcgat acgcgtccac aggacgat                                          28

<210> SEQ ID NO 258
<211> LENGTH: 10
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 258
gtgtttaggg                                                              10

<210> SEQ ID NO 259

-continued

```
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 259
agtgtttagg ga                                                              12

<210> SEQ ID NO 260
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 260
tagtgtttag gga                                                             13

<210> SEQ ID NO 261
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 261
tagtgtttag ggag                                                            14

<210> SEQ ID NO 262
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 262
tagtgtttag ggagc                                                           15

<210> SEQ ID NO 263
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 263
gtagtgttta gggagcc                                                         17

<210> SEQ ID NO 264
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 264
```

```
ggtagtgttt agggagcc                                                    18

<210> SEQ ID NO 265
<211> LENGTH: 19
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 265
ggtagtgttt agggagccg                                                   19

<210> SEQ ID NO 266
<211> LENGTH: 20
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 266
tggtagtgtt tagggagccg                                                  20

<210> SEQ ID NO 267
<211> LENGTH: 22
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 267
ttggtagtgt ttagggagcc gt                                               22

<210> SEQ ID NO 268
<211> LENGTH: 24
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 268
tttggtagtg tttagggagc cgtc                                             24

<210> SEQ ID NO 269
<211> LENGTH: 26
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 269
atttggtagt gtttagggag ccgtct                                           26

<210> SEQ ID NO 270
<211> LENGTH: 28
<212> TYPE: DNA
<213> ORGANISM: Artificial Sequence
<220> FEATURE:
```

<223> OTHER INFORMATION: Antisense oligonucleotide against Homo sapiens
      transforming growth factor, beta receptor II (70/80kDa) (TGFBR2),
      transcript variant 2

<400> SEQUENCE: 270
tatttggtag tgtttaggga gccgtctt                                    28

<210> SEQ ID NO 271
<211> LENGTH: 10
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 271
atttggtagt                                                        10

<210> SEQ ID NO 272
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 272
tatttggtag tg                                                     12

<210> SEQ ID NO 273
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 273
tatttggtag tgt                                                    13

<210> SEQ ID NO 274
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 274
ctatttggta gtgt                                                   14

<210> SEQ ID NO 275
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 275
ctatttggta gtgtt                                                  15

```
<210> SEQ ID NO 276
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 276
gctatttggt agtgttt                                                     17

<210> SEQ ID NO 277
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 277
agctatttgg tagtgttt                                                    18

<210> SEQ ID NO 278
<211> LENGTH: 19
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 278
agctatttgg tagtgttta                                                   19

<210> SEQ ID NO 279
<211> LENGTH: 20
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 279
gagctatttg gtagtgttta                                                  20

<210> SEQ ID NO 280
<211> LENGTH: 22
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 280
agagctattt ggtagtgttt ag                                               22

<210> SEQ ID NO 281
<211> LENGTH: 24
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2
```

```
<400> SEQUENCE: 281
aagagctatt tggtagtgtt tagg                                              24

<210> SEQ ID NO 282
<211> LENGTH: 26
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 282
gaagagctat tggtagtgt ttaggg                                             26

<210> SEQ ID NO 283
<211> LENGTH: 28
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 283
agaagagcta tttggtagtg tttaggga                                          28

<210> SEQ ID NO 284
<211> LENGTH: 10
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 284
cattaataaa                                                              10

<210> SEQ ID NO 285
<211> LENGTH: 12
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 285
gcattaataa ag                                                           12

<210> SEQ ID NO 286
<211> LENGTH: 13
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 286
gcattaataa agt                                                          13

<210> SEQ ID NO 287
<211> LENGTH: 14
<212> TYPE: DNA
<213> ORGANISM: Artificial Sequence
```

```
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 287
ggcattaata aagt                                                           14

<210> SEQ ID NO 288
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 288
ggcattaata aagtg                                                          15

<210> SEQ ID NO 289
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 289
aggcattaat aaagtg                                                         16

<210> SEQ ID NO 290
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 290
caggcattaa taaagtgc                                                       18

<210> SEQ ID NO 291
<211> LENGTH: 19
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 291
acaggcatta ataaagtgc                                                      19

<210> SEQ ID NO 292
<211> LENGTH: 20
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 292
acaggcatta ataaagtgca                                                     20
```

<210> SEQ ID NO 293
<211> LENGTH: 22
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 293
tacaggcatt aataaagtgc aa                                              22

<210> SEQ ID NO 294
<211> LENGTH: 24
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 294
atacaggcat taataaagtg caaa                                            24

<210> SEQ ID NO 295
<211> LENGTH: 26
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2), transcript variant 2

<400> SEQUENCE: 295
tatacaggca ttaataaagt gcaaat                                          26

<210> SEQ ID NO 296
<211> LENGTH: 11
<212> TYPE: DNA
<213> ORGANISM: Artificial Sequence
<220> FEATURE:
<223> OTHER INFORMATION: Target sequence within the homo sapiens transforming growth factor, beta receptor II (70/80kDa) (TGFBR2), transcript variant 2, sense

<400> SEQUENCE: 296
ctggtccatt c                                                          11

<210> SEQ ID NO 297
<211> LENGTH: 11
<212> TYPE: DNA
<213> ORGANISM: Artificial Sequence
<220> FEATURE:
<223> OTHER INFORMATION: Target sequence within the homo sapiens transforming growth factor, beta receptor II (70/80kDa) (TGFBR2), transcript variant 2, sense

<400> SEQUENCE: 297
tggtccattc a                                                          11

<210> SEQ ID NO 298
<211> LENGTH: 12
<212> TYPE: DNA
<213> ORGANISM: Artificial Sequence
<220> FEATURE:
<223> OTHER INFORMATION: Target sequence within the homo sapiens transforming growth factor, beta receptor II (70/80kDa) (TGFBR2), transcript variant 2, sense -continued

<400> SEQUENCE: 298
ctggtccatt ca                                                        12

<210> SEQ ID NO 299
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 299
tccctaaaca c                                                         11

<210> SEQ ID NO 300
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 300
ccctaaacac t                                                         11

<210> SEQ ID NO 301
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 301
tccctaaaca ct                                                        12

<210> SEQ ID NO 302
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 302
cactaccaaa t                                                         11

<210> SEQ ID NO 303
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 303
actaccaaat a                                                         11

<210> SEQ ID NO 304
<211> LENGTH: 12
<212> TYPE: DNA

-continued

<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 304
cactaccaaa ta                                                         12

<210> SEQ ID NO 305
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 305
tggacgcgta t                                                          11

<210> SEQ ID NO 306
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 306
ggacgcgtat c                                                          11

<210> SEQ ID NO 307
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 307
tggacgcgta tc                                                         12

<210> SEQ ID NO 308
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 308
ggtctatgac g                                                          11

<210> SEQ ID NO 309
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 309
gtctatgacg a                                                          11

<210> SEQ ID NO 310
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 310
ggtctatgac ga                                                             12

<210> SEQ ID NO 311
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 311
tttattaatg c                                                              11

<210> SEQ ID NO 312
<211> LENGTH: 11
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 312
ttattaatgc c                                                              11

<210> SEQ ID NO 313
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 313
tttattaatg cc                                                             12

<210> SEQ ID NO 314
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 314
actggtccat tc                                                             12

<210> SEQ ID NO 315
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2), transcript variant 2, sense

<400> SEQUENCE: 315
tggtccattc at                                                          12

<210> SEQ ID NO 316
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 316
ctggtccatt cat                                                         13

<210> SEQ ID NO 317
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 317
actggtccat tca                                                         13

<210> SEQ ID NO 318
<211> LENGTH: 14
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 318
actggtccat tcat                                                        14

<210> SEQ ID NO 319
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 319
ctccctaaac ac                                                          12

<210> SEQ ID NO 320
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 320
ccctaaacac ta                                                          12

<210> SEQ ID NO 321
<211> LENGTH: 13

```
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 321
tccctaaaca cta                                                    13

<210> SEQ ID NO 322
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 322
ctccctaaac act                                                    13

<210> SEQ ID NO 323
<211> LENGTH: 14
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 323
ctccctaaac acta                                                   14

<210> SEQ ID NO 324
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 324
acactaccaa at                                                     12

<210> SEQ ID NO 325
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 325
actaccaaat ag                                                     12

<210> SEQ ID NO 326
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 326
```
cactaccaaa tag                                                          13

<210> SEQ ID NO 327
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 327
acactaccaa ata                                                          13

<210> SEQ ID NO 328
<211> LENGTH: 14
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 328
acactaccaa atag                                                         14

<210> SEQ ID NO 329
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 329
gtggacgcgt at                                                           12

<210> SEQ ID NO 330
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 330
ggacgcgtat cg                                                           12

<210> SEQ ID NO 331
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 331
tggacgcgta tcg                                                          13

<210> SEQ ID NO 332
<211> LENGTH: 13
<212> TYPE: DNA
<213> ORGANISM: Artificial Sequence
<220> FEATURE:
<223> OTHER INFORMATION: Target sequence within the homo sapiens transforming growth factor, beta receptor II (70/80kDa) (TGFBR2),
transcript variant 2, sense

<400> SEQUENCE: 332
gtggacgcgt atc                                                          13

<210> SEQ ID NO 333
<211> LENGTH: 14
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 333
gtggacgcgt atcg                                                         14

<210> SEQ ID NO 334
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 334
cggtctatga cg                                                           12

<210> SEQ ID NO 335
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 335
gtctatgacg ag                                                           12

<210> SEQ ID NO 336
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 336
ggtctatgac gag                                                          13

<210> SEQ ID NO 337
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 337
cggtctatga cga                                                          13

<210> SEQ ID NO 338

```
<211> LENGTH: 14
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 338
cggtctatga cgag                                                         14

<210> SEQ ID NO 339
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 339
ctttattaat gc                                                           12

<210> SEQ ID NO 340
<211> LENGTH: 12
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 340
ttattaatgc ct                                                           12

<210> SEQ ID NO 341
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 341
tttattaatg cct                                                          13

<210> SEQ ID NO 342
<211> LENGTH: 13
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 342
ctttattaat gcc                                                          13

<210> SEQ ID NO 343
<211> LENGTH: 14
<212> TYPE: DNA
<213> ORGANISM: Artificial Sequence
<220> FEATURE:
<223> OTHER INFORMATION: Target sequence within the homo sapiens
      transforming growth factor, beta receptor II (70/80kDa) (TGFBR2),
      transcript variant 2, sense

<400> SEQUENCE: 343
```
ctttattaat gcct					14

<210> SEQ ID NO 344
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 344
gtgcagggga aagatgaaaa					20

<210> SEQ ID NO 345
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 345
gagctcttga ggtccctgtg					20

<210> SEQ ID NO 346
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 346
agcctctttc ctcatgcaaa					20

<210> SEQ ID NO 347
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 347
ccttctctgc ttggttctgg					20

<210> SEQ ID NO 348
<211> LENGTH: 20
<212> TYPE: DNA
<213> ORGANISM: Artificial Sequence
<220> FEATURE:
<223> OTHER INFORMATION: Reference Oligonucleotide

<400> SEQUENCE: 348
gccatggagt agacatcggt					20

<210> SEQ ID NO 349
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 349
atacgcgtcc acaggac					17

<210> SEQ ID NO 350

```
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 350
tacgcgtcca caggacg                                                    17

<210> SEQ ID NO 351
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 351
tggcgatacg cgtcca                                                     16

<210> SEQ ID NO 352
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 352
ggcgatacgc gtccac                                                     16

<210> SEQ ID NO 353
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 353
gcgatacgcg tccaca                                                     16

<210> SEQ ID NO 354
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 354
cgatacgcgt ccacag                                                     16

<210> SEQ ID NO 355
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 355
```

```
gatacgcgtc cacagg                                                    16

<210> SEQ ID NO 356
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 356
atacgcgtcc acagga                                                    16

<210> SEQ ID NO 357
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 357
tacgcgtcca caggac                                                    16

<210> SEQ ID NO 358
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 358
ggcgatacgc gtcca                                                     15

<210> SEQ ID NO 359
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 359
gcgatacgcg tccac                                                     15

<210> SEQ ID NO 360
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 360
cgatacgcgt ccaca                                                     15

<210> SEQ ID NO 361
<211> LENGTH: 15
<212> TYPE: DNA
<213> ORGANISM: Artificial Sequence
<220> FEATURE:
```

<223> OTHER INFORMATION: Antisense oligonucleotide against Homo sapiens
      transforming growth factor, beta receptor II (70/80kDa) (TGFBR2),
      transcript variant 2

<400> SEQUENCE: 361
gatacgcgtc cacag                                                          15

<210> SEQ ID NO 362
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 362
atacgcgtcc acagg                                                          15

<210> SEQ ID NO 363
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 363
tacgcgtcca cagga                                                          15

<210> SEQ ID NO 364
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 364
gcgatacgcg tcca                                                           14

<210> SEQ ID NO 365
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 365
cgatacgcgt ccac                                                           14

<210> SEQ ID NO 366
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 366
gatacgcgtc caca                                                           14

```
<210> SEQ ID NO 367
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 367
atacgcgtcc acag                                                         14

<210> SEQ ID NO 368
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 368
tacgcgtcca cagg                                                         14

<210> SEQ ID NO 369

<400> SEQUENCE: 369

000

<210> SEQ ID NO 370
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 370
tttggtagtg tttaggga                                                     18

<210> SEQ ID NO 371
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 371
ttggtagtgt ttagggag                                                     18

<210> SEQ ID NO 372
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 372
tggtagtgtt tagggagc                                                     18

<210> SEQ ID NO 373
<211> LENGTH: 18
```

```
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 373
ggtagtgttt agggagcc                                                   18

<210> SEQ ID NO 374
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 374
gtagtgttta gggagccg                                                   18

<210> SEQ ID NO 375
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 375
tagtgtttag ggagccgt                                                   18

<210> SEQ ID NO 376
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 376
agtgtttagg gagccgtc                                                   18

<210> SEQ ID NO 377
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 377
gtgtttaggg agccgtct                                                   18

<210> SEQ ID NO 378
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 378
```
tttggtagtg tttaggg                                                17

<210> SEQ ID NO 379
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 379
ttggtagtgt ttaggga                                                17

<210> SEQ ID NO 380
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 380
tggtagtgtt tagggag                                                17

<210> SEQ ID NO 381
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 381
ggtagtgttt agggagc                                                17

<210> SEQ ID NO 382
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 382
gtagtgttta gggagcc                                                17

<210> SEQ ID NO 383
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 383
tagtgtttag ggagccg                                                17

<210> SEQ ID NO 384
<211> LENGTH: 17
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2),
      transcript variant 2

<400> SEQUENCE: 384
agtgtttagg gagccgt                                                     17

<210> SEQ ID NO 385
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 385
gtgtttaggg agccgtc                                                     17

<210> SEQ ID NO 386
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 386
ttggtagtgt ttaggg                                                      16

<210> SEQ ID NO 387
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 387
tggtagtgtt taggga                                                      16

<210> SEQ ID NO 388

<400> SEQUENCE: 388

000

<210> SEQ ID NO 389
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 389
gtagtgttta gggagc                                                      16

<210> SEQ ID NO 390
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

```
<400> SEQUENCE: 390
tagtgtttag ggagcc                                                      16

<210> SEQ ID NO 391
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 391
agtgtttagg gagccg                                                      16

<210> SEQ ID NO 392
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 392
gtgtttaggg agccgt                                                      16

<210> SEQ ID NO 393
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 393
tggtagtgtt taggg                                                       15

<210> SEQ ID NO 394
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 394
ggtagtgttt aggga                                                       15

<210> SEQ ID NO 395
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 395
gtagtgttta gggag                                                       15

<210> SEQ ID NO 396
<211> LENGTH: 15
<212> TYPE: DNA
```

<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 396
tagtgtttag ggagc                                                    15

<210> SEQ ID NO 397
<211> LENGTH: 15
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 397
agtgtttagg gagcc                                                    15

<210> SEQ ID NO 398
<211> LENGTH: 15
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 398
gtgtttaggg agccg                                                    15

<210> SEQ ID NO 399
<211> LENGTH: 14
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 399
ggtagtgttt aggg                                                     14

<210> SEQ ID NO 400
<211> LENGTH: 14
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 400
gtagtgttta ggga                                                     14

<210> SEQ ID NO 401
<211> LENGTH: 14
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 401
tagtgtttag ggag                                                     14

<210> SEQ ID NO 402
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 402
agtgtttagg gagc                                                         14

<210> SEQ ID NO 403
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 403
gtgtttaggg agcc                                                         14

<210> SEQ ID NO 404
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 404
gaagagctat ttggtagt                                                     18

<210> SEQ ID NO 405
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 405
aagagctatt tggtagtg                                                     18

<210> SEQ ID NO 406
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 406
agagctattt ggtagtgt                                                     18

<210> SEQ ID NO 407
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2), transcript variant 2

<400> SEQUENCE: 407
gagctatttg gtagtgtt                                                   18

<210> SEQ ID NO 408
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 408
agctatttgg tagtgttt                                                   18

<210> SEQ ID NO 409
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 409
gctatttggt agtgttta                                                   18

<210> SEQ ID NO 410
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 410
ctatttggta gtgtttag                                                   18

<210> SEQ ID NO 411
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 411
tatttggtag tgtttagg                                                   18

<210> SEQ ID NO 412
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 412
atttggtagt gtttaggg                                                   18

<210> SEQ ID NO 413
<211> LENGTH: 17

<210> SEQ ID NO 413
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 413
aagagctatt tggtagt                                                  17

<210> SEQ ID NO 414
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 414
agagctattt ggtagtg                                                  17

<210> SEQ ID NO 415
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 415
gagctatttg gtagtgt                                                  17

<210> SEQ ID NO 416
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 416
agctatttgg tagtgtt                                                  17

<210> SEQ ID NO 417
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 417
gctatttggt agtgttt                                                  17

<210> SEQ ID NO 418
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 418

-continued ctatttggta gtgttta                                              17

<210> SEQ ID NO 419
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 419
atttggtagt gtttagg                                              17

<210> SEQ ID NO 420
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 420
atttggtagt gtttagg                                              17

<210> SEQ ID NO 421
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 421
agagctattt ggtagt                                               16

<210> SEQ ID NO 422
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 422
gagctatttg gtagtg                                               16

<210> SEQ ID NO 423
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 423
agctatttgg tagtgt                                               16

<210> SEQ ID NO 424
<211> LENGTH: 16
<212> TYPE: DNA
<213> ORGANISM: Artificial Sequence
<220> FEATURE:
<223> OTHER INFORMATION: Antisense oligonucleotide against Homo sapiens transforming growth factor, beta receptor II (70/80kDa) (TGFBR2),
transcript variant 2

<400> SEQUENCE: 424
gctatttggt agtgtt                                              16

<210> SEQ ID NO 425
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 425
ctatttggta gtgttt                                              16

<210> SEQ ID NO 426
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 426
tatttggtag tgttta                                              16

<210> SEQ ID NO 427
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 427
atttggtagt gtttag                                              16

<210> SEQ ID NO 428
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 428
gagctatttg gtagt                                               15

<210> SEQ ID NO 429
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 429
agctatttgg tagtg                                               15

<210> SEQ ID NO 430

```
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 430
gctatttggt agtgt                                                      15

<210> SEQ ID NO 431
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 431
ctatttggta gtgtt                                                      15

<210> SEQ ID NO 432
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 432
tatttggtag tgttt                                                      15

<210> SEQ ID NO 433
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 433
atttggtagt gttta                                                      15

<210> SEQ ID NO 434
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 434
agctatttgg tagt                                                       14

<210> SEQ ID NO 435
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 435
```

```
<210> SEQ ID NO 436
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 436
ctatttggta gtgt                                                        14

<210> SEQ ID NO 437
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 437
tatttggtag tgtt                                                        14

<210> SEQ ID NO 438
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 438
atttggtagt gttt                                                        14

<210> SEQ ID NO 439
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 439
tatctcatga atggacca                                                    18

<210> SEQ ID NO 440
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 440
atctcatgaa tggaccag                                                    18

<210> SEQ ID NO 441
<211> LENGTH: 18
<212> TYPE: DNA
<213> ORGANISM: Artificial Sequence
<220> FEATURE:
```
gctatttggt agtg                                                        14

```
<223> OTHER INFORMATION: Antisense oligonucleotide against Homo sapiens
      transforming growth factor, beta receptor II (70/80kDa) (TGFBR2),
      transcript variant 2

<400> SEQUENCE: 441
tctcatgaat ggaccagt                                                 18

<210> SEQ ID NO 442
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 442
ctcatgaatg gaccagta                                                 18

<210> SEQ ID NO 443
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 443
tcatgaatgg accagtat                                                 18

<210> SEQ ID NO 444
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 444
catgaatgga ccagtatt                                                 18

<210> SEQ ID NO 445
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 445
atgaatggac cagtattc                                                 18

<210> SEQ ID NO 446
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 446
tgaatggacc agtattct                                                 18
```

<210> SEQ ID NO 447
<211> LENGTH: 18
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 447
gaatggacca gtattcta                                                18

<210> SEQ ID NO 448
<211> LENGTH: 17
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 448
atctcatgaa tggacca                                                 17

<210> SEQ ID NO 449
<211> LENGTH: 17
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 449
tctcatgaat ggaccag                                                 17

<210> SEQ ID NO 450
<211> LENGTH: 17
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 450
ctcatgaatg gaccagt                                                 17

<210> SEQ ID NO 451
<211> LENGTH: 17
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

<400> SEQUENCE: 451
tcatgaatgg accagta                                                 17

<210> SEQ ID NO 452
<211> LENGTH: 17
<212> TYPE: DNA
<213> ORGANISM: Artificial Sequence
<220> FEATURE:
<223> OTHER INFORMATION: Antisense oligonucleotide against Homo sapiens
transforming growth factor, beta receptor II (70/80kDa) (TGFBR2),
transcript variant 2

```
<400> SEQUENCE: 452
catgaatgga ccagtat                                                  17

<210> SEQ ID NO 453
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 453
atgaatggac cagtatt                                                  17

<210> SEQ ID NO 454
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 454
tgaatggacc agtattc                                                  17

<210> SEQ ID NO 455
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 455
gaatggacca gtattct                                                  17

<210> SEQ ID NO 456
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 456
tctcatgaat ggacca                                                   16

<210> SEQ ID NO 457
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 457
ctcatgaatg gaccag                                                   16

<210> SEQ ID NO 458
<211> LENGTH: 16
<212> TYPE: DNA
<213> ORGANISM: Artificial Sequence
```

```
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 458
tcatgaatgg accagt                                                     16

<210> SEQ ID NO 459
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 459
catgaatgga ccagta                                                     16

<210> SEQ ID NO 460
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 460
atgaatggac cagtat                                                     16

<210> SEQ ID NO 461
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 461
tgaatggacc agtatt                                                     16

<210> SEQ ID NO 462
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 462
gaatggacca gtattc                                                     16

<210> SEQ ID NO 463
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 463
ctcatgaatg gacca                                                      15
```

-continued

<210> SEQ ID NO 464
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 464
tcatgaatgg accag                                                      15

<210> SEQ ID NO 465
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 465
catgaatgga ccagt                                                      15

<210> SEQ ID NO 466
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 466
atgaatggac cagta                                                      15

<210> SEQ ID NO 467
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 467
tgaatggacc agtat                                                      15

<210> SEQ ID NO 468
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 468
gaatggacca gtatt                                                      15

<210> SEQ ID NO 469
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

```
<400> SEQUENCE: 469
tcatgaatgg acca                                                         14

<210> SEQ ID NO 470
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 470
catgaatgga ccag                                                         14

<210> SEQ ID NO 471
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 471
atgaatggac cagt                                                         14

<210> SEQ ID NO 472
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 472
tgaatggacc agta                                                         14

<210> SEQ ID NO 473
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 473
gaatggacca gtat                                                         14

<210> SEQ ID NO 474
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 474
tatacaggca ttaataaa                                                     18

<210> SEQ ID NO 475
<211> LENGTH: 18
<212> TYPE: DNA
```

```
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 475
atacaggcat taataaag                                                 18

<210> SEQ ID NO 476
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 476
tacaggcatt aataaagt                                                 18

<210> SEQ ID NO 477
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 477
acaggcatta ataaagtg                                                 18

<210> SEQ ID NO 478
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 478
caggcattaa taaagtgc                                                 18

<210> SEQ ID NO 479
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 479
aggcattaat aaagtgca                                                 18

<210> SEQ ID NO 480
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 480
ggcattaata aagtgcaa                                                 18
```

<210> SEQ ID NO 481
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 481
gcattaataa agtgcaaa                                                 18

<210> SEQ ID NO 482
<211> LENGTH: 18
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 482
cattaataaa gtgcaaat                                                 18

<210> SEQ ID NO 483
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 483
atacaggcat taataaa                                                  17

<210> SEQ ID NO 484
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 484
tacaggcatt aataaag                                                  17

<210> SEQ ID NO 485
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 485
acaggcatta ataaagt                                                  17

<210> SEQ ID NO 486
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2), transcript variant 2

<400> SEQUENCE: 486
caggcattaa taaagtg                                                17

<210> SEQ ID NO 487
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 487
aggcattaat aaagtgc                                                17

<210> SEQ ID NO 488
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 488
ggcattaata aagtgca                                                17

<210> SEQ ID NO 489
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 489
gcattaataa agtgcaa                                                17

<210> SEQ ID NO 490
<211> LENGTH: 17
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 490
cattaataaa gtgcaaa                                                17

<210> SEQ ID NO 491
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 491
tacaggcatt aataaa                                                 16

<210> SEQ ID NO 492
<211> LENGTH: 16

```
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 492
acaggcatta ataaag                                                      16

<210> SEQ ID NO 493
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 493
caggcattaa taaagt                                                      16

<210> SEQ ID NO 494
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 494
aggcattaat aaagtg                                                      16

<210> SEQ ID NO 495
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 495
ggcattaata aagtgc                                                      16

<210> SEQ ID NO 496
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 496
gcattaataa agtgca                                                      16

<210> SEQ ID NO 497
<211> LENGTH: 16
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 497
```

-continued cattaataaa gtgcaa                                          16

<210> SEQ ID NO 498
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 498
acaggcatta ataaa                                           15

<210> SEQ ID NO 499
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 499
caggcattaa taaag                                           15

<210> SEQ ID NO 500
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 500
aggcattaat aaagt                                           15

<210> SEQ ID NO 501
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 501
ggcattaata aagtg                                           15

<210> SEQ ID NO 502
<211> LENGTH: 15
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 502
gcattaataa agtgc                                           15

<210> SEQ ID NO 503
<211> LENGTH: 15
<212> TYPE: DNA
<213> ORGANISM: Artificial Sequence
<220> FEATURE:
<223> OTHER INFORMATION: Antisense oligonucleotide against Homo sapiens -continued transforming growth factor, beta receptor II (70/80kDa) (TGFBR2),
transcript variant 2

<400> SEQUENCE: 503
cattaataaa gtgca                                                    15

<210> SEQ ID NO 504
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 504
caggcattaa taaa                                                     14

<210> SEQ ID NO 505
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 505
aggcattaat aaag                                                     14

<210> SEQ ID NO 506
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 506
ggcattaata aagt                                                     14

<210> SEQ ID NO 507
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 507
gcattaataa agtg                                                     14

<210> SEQ ID NO 508
<211> LENGTH: 14
<212> TYPE: DNA
<213> ORGANISM: Artificial Sequence
<220> FEATURE:
<223> OTHER INFORMATION: Antisense oligonucleotide against Homo sapiens
      transforming growth factor, beta receptor II (70/80kDa) (TGFBR2),
      transcript variant 2

<400> SEQUENCE: 508
cattaataaa gtgc                                                     14

<210> SEQ ID NO 509

```
<211> LENGTH: 20
<212> TYPE: DNA
<213> ORGANISM: Artificial Sequence
<220> FEATURE:
<223> OTHER INFORMATION: N1 Sequence

<400> SEQUENCE: 509
catggcagac cccgctgctc                                                    20

<210> SEQ ID NO 510
<211> LENGTH: 19
<212> TYPE: DNA
<213> ORGANISM: Artificial Sequence
<220> FEATURE:
<223> OTHER INFORMATION: N1 Sequence

<400> SEQUENCE: 510
atggcagacc ccgctgctc                                                     19

<210> SEQ ID NO 511
<211> LENGTH: 18
<212> TYPE: DNA
<213> ORGANISM: Artificial Sequence
<220> FEATURE:
<223> OTHER INFORMATION: N1 Sequence

<400> SEQUENCE: 511
tggcagaccc cgctgctc                                                      18

<210> SEQ ID NO 512
<211> LENGTH: 17
<212> TYPE: DNA
<213> ORGANISM: Artificial Sequence
<220> FEATURE:
<223> OTHER INFORMATION: N1 Sequence

<400> SEQUENCE: 512
ggcagacccc gctgctc                                                       17

<210> SEQ ID NO 513
<211> LENGTH: 16
<212> TYPE: DNA
<213> ORGANISM: Artificial Sequence
<220> FEATURE:
<223> OTHER INFORMATION: N1 Sequence

<400> SEQUENCE: 513
gcagaccccg ctgctc                                                        16

<210> SEQ ID NO 514
<211> LENGTH: 15
<212> TYPE: DNA
<213> ORGANISM: Artificial Sequence
<220> FEATURE:
<223> OTHER INFORMATION: N1 Sequence

<400> SEQUENCE: 514
cagaccccgc tgctc                                                         15

<210> SEQ ID NO 515
<211> LENGTH: 14
<212> TYPE: DNA
<213> ORGANISM: Artificial Sequence
<220> FEATURE:
<223> OTHER INFORMATION: N1 Sequence

<400> SEQUENCE: 515
```
agaccccgct gctc								14

<210> SEQ ID NO 516
<211> LENGTH: 13
<212> TYPE: DNA
<213> ORGANISM: Artificial Sequence
<220> FEATURE:
<223> OTHER INFORMATION: N1 Sequence

<400> SEQUENCE: 516
gaccccgctg ctc								13

<210> SEQ ID NO 517
<211> LENGTH: 12
<212> TYPE: DNA
<213> ORGANISM: Artificial Sequence
<220> FEATURE:
<223> OTHER INFORMATION: N1 Sequence

<400> SEQUENCE: 517
accccgctgc tc								12

<210> SEQ ID NO 518
<211> LENGTH: 11
<212> TYPE: DNA
<213> ORGANISM: Artificial Sequence
<220> FEATURE:
<223> OTHER INFORMATION: N1 Sequence

<400> SEQUENCE: 518
ccccgctgct c								11

<210> SEQ ID NO 519
<211> LENGTH: 10
<212> TYPE: DNA
<213> ORGANISM: Artificial Sequence
<220> FEATURE:
<223> OTHER INFORMATION: N1 Sequence

<400> SEQUENCE: 519 cccgctgctc								10

<210> SEQ ID NO 520
<211> LENGTH: 10
<212> TYPE: DNA
<213> ORGANISM: Artificial Sequence
<220> FEATURE:
<223> OTHER INFORMATION: N2 Sequence

<400> SEQUENCE: 520 ccgagccccc								10

<210> SEQ ID NO 521
<211> LENGTH: 11
<212> TYPE: DNA
<213> ORGANISM: Artificial Sequence
<220> FEATURE:
<223> OTHER INFORMATION: N2 Sequence

<400> SEQUENCE: 521
ccgagccccc a								11

<210> SEQ ID NO 522
<211> LENGTH: 12
<212> TYPE: DNA

```
<213> ORGANISM: Artificial Sequence
<220> FEATURE:
<223> OTHER INFORMATION: N2 Sequence

<400> SEQUENCE: 522
ccgagccccc ag                                                          12

<210> SEQ ID NO 523
<211> LENGTH: 13
<212> TYPE: DNA
<213> ORGANISM: Artificial Sequence
<220> FEATURE:
<223> OTHER INFORMATION: N2 Sequence

<400> SEQUENCE: 523
ccgagccccc agc                                                         13

<210> SEQ ID NO 524
<211> LENGTH: 14
<212> TYPE: DNA
<213> ORGANISM: Artificial Sequence
<220> FEATURE:
<223> OTHER INFORMATION: N2 Sequence

<400> SEQUENCE: 524
ccgagccccc agcg                                                        14

<210> SEQ ID NO 525
<211> LENGTH: 15
<212> TYPE: DNA
<213> ORGANISM: Artificial Sequence
<220> FEATURE:
<223> OTHER INFORMATION: N2 Sequence

<400> SEQUENCE: 525
ccgagccccc agcgc                                                       15

<210> SEQ ID NO 526
<211> LENGTH: 16
<212> TYPE: DNA
<213> ORGANISM: Artificial Sequence
<220> FEATURE:
<223> OTHER INFORMATION: N2 Sequence

<400> SEQUENCE: 526
ccgagccccc agcgca                                                      16

<210> SEQ ID NO 527
<211> LENGTH: 17
<212> TYPE: DNA
<213> ORGANISM: Artificial Sequence
<220> FEATURE:
<223> OTHER INFORMATION: N2 Sequence

<400> SEQUENCE: 527
ccgagccccc agcgcag                                                     17

<210> SEQ ID NO 528
<211> LENGTH: 18
<212> TYPE: DNA
<213> ORGANISM: Artificial Sequence
<220> FEATURE:
<223> OTHER INFORMATION: N2 Sequence

<400> SEQUENCE: 528
ccgagccccc agcgcagc                                                    18
```

<210> SEQ ID NO 529
<211> LENGTH: 19
<212> TYPE: DNA
<213> ORGANISM: Artificial Sequence
<220> FEATURE:
<223> OTHER INFORMATION: N2 Sequence

<400> SEQUENCE: 529
ccgagccccc agcgcagcg					19

<210> SEQ ID NO 530
<211> LENGTH: 20
<212> TYPE: DNA
<213> ORGANISM: Artificial Sequence
<220> FEATURE:
<223> OTHER INFORMATION: N2 Sequence

<400> SEQUENCE: 530
ccgagccccc agcgcagcgg					20

<210> SEQ ID NO 531
<211> LENGTH: 20
<212> TYPE: DNA
<213> ORGANISM: Artificial Sequence
<220> FEATURE:
<223> OTHER INFORMATION: N3 Sequence

<400> SEQUENCE: 531
ggtgggatcg tgctggcgat					20

<210> SEQ ID NO 532
<211> LENGTH: 19
<212> TYPE: DNA
<213> ORGANISM: Artificial Sequence
<220> FEATURE:
<223> OTHER INFORMATION: N3 Sequence

<400> SEQUENCE: 532
gtgggatcgt gctggcgat					19

<210> SEQ ID NO 533
<211> LENGTH: 18
<212> TYPE: DNA
<213> ORGANISM: Artificial Sequence
<220> FEATURE:
<223> OTHER INFORMATION: N3 Sequence

<400> SEQUENCE: 533
tgggatcgtg ctggcgat					18

<210> SEQ ID NO 534
<211> LENGTH: 17
<212> TYPE: DNA
<213> ORGANISM: Artificial Sequence
<220> FEATURE:
<223> OTHER INFORMATION: N3 Sequence

<400> SEQUENCE: 534
gggatcgtgc tggcgat					17

<210> SEQ ID NO 535
<211> LENGTH: 16
<212> TYPE: DNA
<213> ORGANISM: Artificial Sequence
<220> FEATURE:

-continued

```
<223> OTHER INFORMATION: N3 Sequence

<400> SEQUENCE: 535
ggatcgtgct ggcgat                                                    16

<210> SEQ ID NO 536
<211> LENGTH: 15
<212> TYPE: DNA
<213> ORGANISM: Artificial Sequence
<220> FEATURE:
<223> OTHER INFORMATION: N3 Sequence

<400> SEQUENCE: 536
gatcgtgctg gcgat                                                     15

<210> SEQ ID NO 537
<211> LENGTH: 14
<212> TYPE: DNA
<213> ORGANISM: Artificial Sequence
<220> FEATURE:
<223> OTHER INFORMATION: N3 Sequence

<400> SEQUENCE: 537
atcgtgctgg cgat                                                      14

<210> SEQ ID NO 538
<211> LENGTH: 13
<212> TYPE: DNA
<213> ORGANISM: Artificial Sequence
<220> FEATURE:
<223> OTHER INFORMATION: N3 Sequence

<400> SEQUENCE: 538
tcgtgctggc gat                                                       13

<210> SEQ ID NO 539
<211> LENGTH: 12
<212> TYPE: DNA
<213> ORGANISM: Artificial Sequence
<220> FEATURE:
<223> OTHER INFORMATION: N3 Sequence

<400> SEQUENCE: 539
cgtgctggcg at                                                        12

<210> SEQ ID NO 540
<211> LENGTH: 11
<212> TYPE: DNA
<213> ORGANISM: Artificial Sequence
<220> FEATURE:
<223> OTHER INFORMATION: N3 Sequence

<400> SEQUENCE: 540
gtgctggcga t                                                         11

<210> SEQ ID NO 541
<211> LENGTH: 10
<212> TYPE: DNA
<213> ORGANISM: Artificial Sequence
<220> FEATURE:
<223> OTHER INFORMATION: N3 Sequence

<400> SEQUENCE: 541
tgctggcgat                                                           10
```

```
<210> SEQ ID NO 542
<211> LENGTH: 20
<212> TYPE: DNA
<213> ORGANISM: Artificial Sequence
<220> FEATURE:
<223> OTHER INFORMATION: N4 Sequence

<400> SEQUENCE: 542
acaggacgat gtgcagcggc                                              20

<210> SEQ ID NO 543
<211> LENGTH: 19
<212> TYPE: DNA
<213> ORGANISM: Artificial Sequence
<220> FEATURE:
<223> OTHER INFORMATION: N4 Sequence

<400> SEQUENCE: 543
acaggacgat gtgcagcgg                                               19

<210> SEQ ID NO 544
<211> LENGTH: 18
<212> TYPE: DNA
<213> ORGANISM: Artificial Sequence
<220> FEATURE:
<223> OTHER INFORMATION: N4 Sequence

<400> SEQUENCE: 544
acaggacgat gtgcagcg                                                18

<210> SEQ ID NO 545
<211> LENGTH: 17
<212> TYPE: DNA
<213> ORGANISM: Artificial Sequence
<220> FEATURE:
<223> OTHER INFORMATION: N4 Sequence

<400> SEQUENCE: 545
acaggacgat gtgcagc                                                 17

<210> SEQ ID NO 546
<211> LENGTH: 16
<212> TYPE: DNA
<213> ORGANISM: Artificial Sequence
<220> FEATURE:
<223> OTHER INFORMATION: N4 Sequence

<400> SEQUENCE: 546
acaggacgat gtgcag                                                  16

<210> SEQ ID NO 547
<211> LENGTH: 15
<212> TYPE: DNA
<213> ORGANISM: Artificial Sequence
<220> FEATURE:
<223> OTHER INFORMATION: N4 Sequence

<400> SEQUENCE: 547
acaggacgat gtgca                                                   15

<210> SEQ ID NO 548
<211> LENGTH: 14
<212> TYPE: DNA
<213> ORGANISM: Artificial Sequence
<220> FEATURE:
<223> OTHER INFORMATION: N4 Sequence
```

```
<400> SEQUENCE: 548
acaggacgat gtgc                                                      14

<210> SEQ ID NO 549
<211> LENGTH: 13
<212> TYPE: DNA
<213> ORGANISM: Artificial Sequence
<220> FEATURE:
<223> OTHER INFORMATION: N4 Sequence

<400> SEQUENCE: 549
acaggacgat gtg                                                       13

<210> SEQ ID NO 550
<211> LENGTH: 12
<212> TYPE: DNA
<213> ORGANISM: Artificial Sequence
<220> FEATURE:
<223> OTHER INFORMATION: N4 Sequence

<400> SEQUENCE: 550
acaggacgat gt                                                        12

<210> SEQ ID NO 551
<211> LENGTH: 11
<212> TYPE: DNA
<213> ORGANISM: Artificial Sequence
<220> FEATURE:
<223> OTHER INFORMATION: N4 Sequence

<400> SEQUENCE: 551
acaggacgat g                                                         11

<210> SEQ ID NO 552
<211> LENGTH: 10
<212> TYPE: DNA
<213> ORGANISM: Artificial Sequence
<220> FEATURE:
<223> OTHER INFORMATION: N4 Sequence

<400> SEQUENCE: 552
acaggacgat                                                           10

<210> SEQ ID NO 553
<211> LENGTH: 24
<212> TYPE: DNA
<213> ORGANISM: Artificial Sequence
<220> FEATURE:
<223> OTHER INFORMATION: N5 Sequence

<400> SEQUENCE: 553
gcccagcctg ccccagaaga gcta                                           24

<210> SEQ ID NO 554
<211> LENGTH: 23
<212> TYPE: DNA
<213> ORGANISM: Artificial Sequence
<220> FEATURE:
<223> OTHER INFORMATION: N5 Sequence

<400> SEQUENCE: 554
cccagcctgc cccagaagag cta                                            23

<210> SEQ ID NO 555
<211> LENGTH: 22
```

-continued

```
<212> TYPE: DNA
<213> ORGANISM: Artificial Sequence
<220> FEATURE:
<223> OTHER INFORMATION: N5 Sequence

<400> SEQUENCE: 555
ccagcctgcc ccagaagagc ta                                      22

<210> SEQ ID NO 556
<211> LENGTH: 21
<212> TYPE: DNA
<213> ORGANISM: Artificial Sequence
<220> FEATURE:
<223> OTHER INFORMATION: N5 Sequence

<400> SEQUENCE: 556
cagcctgccc cagaagagct a                                       21

<210> SEQ ID NO 557
<211> LENGTH: 20
<212> TYPE: DNA
<213> ORGANISM: Artificial Sequence
<220> FEATURE:
<223> OTHER INFORMATION: N5 Sequence

<400> SEQUENCE: 557
agcctgcccc agaagagcta                                         20

<210> SEQ ID NO 558
<211> LENGTH: 19
<212> TYPE: DNA
<213> ORGANISM: Artificial Sequence
<220> FEATURE:
<223> OTHER INFORMATION: N5 Sequence

<400> SEQUENCE: 558
gcctgcccca gaagagcta                                          19

<210> SEQ ID NO 559
<211> LENGTH: 18
<212> TYPE: DNA
<213> ORGANISM: Artificial Sequence
<220> FEATURE:
<223> OTHER INFORMATION: N5 Sequence

<400> SEQUENCE: 559
cctgccccag aagagcta                                           18

<210> SEQ ID NO 560
<211> LENGTH: 17
<212> TYPE: DNA
<213> ORGANISM: Artificial Sequence
<220> FEATURE:
<223> OTHER INFORMATION: N5 Sequence

<400> SEQUENCE: 560
ctgccccaga agagcta                                            17

<210> SEQ ID NO 561
<211> LENGTH: 16
<212> TYPE: DNA
<213> ORGANISM: Artificial Sequence
<220> FEATURE:
<223> OTHER INFORMATION: N5 Sequence

<400> SEQUENCE: 561
```

```
tgccccagaa gagcta                                                    16

<210> SEQ ID NO 562
<211> LENGTH: 15
<212> TYPE: DNA
<213> ORGANISM: Artificial Sequence
<220> FEATURE:
<223> OTHER INFORMATION: N5 Sequence

<400> SEQUENCE: 562
gccccagaag agcta                                                     15

<210> SEQ ID NO 563
<211> LENGTH: 14
<212> TYPE: DNA
<213> ORGANISM: Artificial Sequence
<220> FEATURE:
<223> OTHER INFORMATION: N5 Sequence

<400> SEQUENCE: 563
ccccagaaga gcta                                                      14

<210> SEQ ID NO 564
<211> LENGTH: 13
<212> TYPE: DNA
<213> ORGANISM: Artificial Sequence
<220> FEATURE:
<223> OTHER INFORMATION: N5 Sequence

<400> SEQUENCE: 564
cccagaagag cta                                                       13

<210> SEQ ID NO 565
<211> LENGTH: 12
<212> TYPE: DNA
<213> ORGANISM: Artificial Sequence
<220> FEATURE:
<223> OTHER INFORMATION: N5 Sequence

<400> SEQUENCE: 565
ccagaagagc ta                                                        12

<210> SEQ ID NO 566
<211> LENGTH: 11
<212> TYPE: DNA
<213> ORGANISM: Artificial Sequence
<220> FEATURE:
<223> OTHER INFORMATION: N5 Sequence

<400> SEQUENCE: 566
cagaagagct a                                                         11

<210> SEQ ID NO 567
<211> LENGTH: 10
<212> TYPE: DNA
<213> ORGANISM: Artificial Sequence
<220> FEATURE:
<223> OTHER INFORMATION: N5 Sequence

<400> SEQUENCE: 567
agaagagcta                                                           10

<210> SEQ ID NO 568
<211> LENGTH: 24
<212> TYPE: DNA
<213> ORGANISM: Artificial Sequence
```

```
<220> FEATURE:
<223> OTHER INFORMATION: N6 Sequence

<400> SEQUENCE: 568
tgtttaggga gccgtcttca ggaa                                              24

<210> SEQ ID NO 569
<211> LENGTH: 23
<212> TYPE: DNA
<213> ORGANISM: Artificial Sequence
<220> FEATURE:
<223> OTHER INFORMATION: N6 Sequence

<400> SEQUENCE: 569
tgtttaggga gccgtcttca gga                                               23

<210> SEQ ID NO 570
<211> LENGTH: 22
<212> TYPE: DNA
<213> ORGANISM: Artificial Sequence
<220> FEATURE:
<223> OTHER INFORMATION: N6 Sequence

<400> SEQUENCE: 570
tgtttaggga gccgtcttca gg                                                22

<210> SEQ ID NO 571
<211> LENGTH: 21
<212> TYPE: DNA
<213> ORGANISM: Artificial Sequence
<220> FEATURE:
<223> OTHER INFORMATION: N6 Sequence

<400> SEQUENCE: 571
tgtttaggga gccgtcttca g                                                 21

<210> SEQ ID NO 572
<211> LENGTH: 20
<212> TYPE: DNA
<213> ORGANISM: Artificial Sequence
<220> FEATURE:
<223> OTHER INFORMATION: N6 Sequence

<400> SEQUENCE: 572
tgtttaggga gccgtcttca                                                   20

<210> SEQ ID NO 573
<211> LENGTH: 19
<212> TYPE: DNA
<213> ORGANISM: Artificial Sequence
<220> FEATURE:
<223> OTHER INFORMATION: N6 Sequence

<400> SEQUENCE: 573
tgtttaggga gccgtcttc                                                    19

<210> SEQ ID NO 574
<211> LENGTH: 18
<212> TYPE: DNA
<213> ORGANISM: Artificial Sequence
<220> FEATURE:
<223> OTHER INFORMATION: N6 Sequence

<400> SEQUENCE: 574
tgtttaggga gccgtctt                                                     18
```

```
<210> SEQ ID NO 575
<211> LENGTH: 17
<212> TYPE: DNA
<213> ORGANISM: Artificial Sequence
<220> FEATURE:
<223> OTHER INFORMATION: N6 Sequence

<400> SEQUENCE: 575
tgtttaggga gccgtct                                                  17

<210> SEQ ID NO 576
<211> LENGTH: 16
<212> TYPE: DNA
<213> ORGANISM: Artificial Sequence
<220> FEATURE:
<223> OTHER INFORMATION: N6 Sequence

<400> SEQUENCE: 576
tgtttaggga gccgtc                                                   16

<210> SEQ ID NO 577
<211> LENGTH: 15
<212> TYPE: DNA
<213> ORGANISM: Artificial Sequence
<220> FEATURE:
<223> OTHER INFORMATION: N6 Sequence

<400> SEQUENCE: 577
tgtttaggga gccgt                                                    15

<210> SEQ ID NO 578
<211> LENGTH: 14
<212> TYPE: DNA
<213> ORGANISM: Artificial Sequence
<220> FEATURE:
<223> OTHER INFORMATION: N6 Sequence

<400> SEQUENCE: 578
tgtttaggga gccg                                                     14

<210> SEQ ID NO 579
<211> LENGTH: 13
<212> TYPE: DNA
<213> ORGANISM: Artificial Sequence
<220> FEATURE:
<223> OTHER INFORMATION: N6 Sequence

<400> SEQUENCE: 579
tgtttaggga gcc                                                      13

<210> SEQ ID NO 580
<211> LENGTH: 12
<212> TYPE: DNA
<213> ORGANISM: Artificial Sequence
<220> FEATURE:
<223> OTHER INFORMATION: N6 Sequence

<400> SEQUENCE: 580
tgtttaggga gc                                                       12

<210> SEQ ID NO 581
<211> LENGTH: 11
<212> TYPE: DNA
<213> ORGANISM: Artificial Sequence
<220> FEATURE:
<223> OTHER INFORMATION: N6 Sequence
```

```
<400> SEQUENCE: 581
tgtttaggga g                                                    11

<210> SEQ ID NO 582
<211> LENGTH: 10
<212> TYPE: DNA
<213> ORGANISM: Artificial Sequence
<220> FEATURE:
<223> OTHER INFORMATION: N6 Sequence

<400> SEQUENCE: 582
tgtttaggga                                                      10

<210> SEQ ID NO 583
<211> LENGTH: 20
<212> TYPE: DNA
<213> ORGANISM: Artificial Sequence
<220> FEATURE:
<223> OTHER INFORMATION: N7 Sequence

<400> SEQUENCE: 583
tgaatcttga atatctcatg                                           20

<210> SEQ ID NO 584
<211> LENGTH: 19
<212> TYPE: DNA
<213> ORGANISM: Artificial Sequence
<220> FEATURE:
<223> OTHER INFORMATION: N7 Sequence

<400> SEQUENCE: 584
gaatcttgaa tatctcatg                                            19

<210> SEQ ID NO 585
<211> LENGTH: 18
<212> TYPE: DNA
<213> ORGANISM: Artificial Sequence
<220> FEATURE:
<223> OTHER INFORMATION: N7 Sequence

<400> SEQUENCE: 585
aatcttgaat atctcatg                                             18

<210> SEQ ID NO 586
<211> LENGTH: 17
<212> TYPE: DNA
<213> ORGANISM: Artificial Sequence
<220> FEATURE:
<223> OTHER INFORMATION: N7 Sequence

<400> SEQUENCE: 586
atcttgaata tctcatg                                              17

<210> SEQ ID NO 587
<211> LENGTH: 16
<212> TYPE: DNA
<213> ORGANISM: Artificial Sequence
<220> FEATURE:
<223> OTHER INFORMATION: N7 Sequence

<400> SEQUENCE: 587
tcttgaatat ctcatg                                               16

<210> SEQ ID NO 588
```

```
<211> LENGTH: 15
<212> TYPE: DNA
<213> ORGANISM: Artificial Sequence
<220> FEATURE:
<223> OTHER INFORMATION: N7 Sequence

<400> SEQUENCE: 588
cttgaatatc tcatg                                               15

<210> SEQ ID NO 589
<211> LENGTH: 14
<212> TYPE: DNA
<213> ORGANISM: Artificial Sequence
<220> FEATURE:
<223> OTHER INFORMATION: N7 Sequence

<400> SEQUENCE: 589
ttgaatatct catg                                                14

<210> SEQ ID NO 590
<211> LENGTH: 13
<212> TYPE: DNA
<213> ORGANISM: Artificial Sequence
<220> FEATURE:
<223> OTHER INFORMATION: N7 Sequence

<400> SEQUENCE: 590
tgaatatctc atg                                                 13

<210> SEQ ID NO 591
<211> LENGTH: 12
<212> TYPE: DNA
<213> ORGANISM: Artificial Sequence
<220> FEATURE:
<223> OTHER INFORMATION: N7 Sequence

<400> SEQUENCE: 591
gaatatctca tg                                                  12

<210> SEQ ID NO 592
<211> LENGTH: 11
<212> TYPE: DNA
<213> ORGANISM: Artificial Sequence
<220> FEATURE:
<223> OTHER INFORMATION: N7 Sequence

<400> SEQUENCE: 592
aatatctcat g                                                   11

<210> SEQ ID NO 593
<211> LENGTH: 10
<212> TYPE: DNA
<213> ORGANISM: Artificial Sequence
<220> FEATURE:
<223> OTHER INFORMATION: N7 Sequence

<400> SEQUENCE: 593
atatctcatg                                                     10

<210> SEQ ID NO 594
<211> LENGTH: 20
<212> TYPE: DNA
<213> ORGANISM: Artificial Sequence
<220> FEATURE:
<223> OTHER INFORMATION: N8 Sequence

<400> SEQUENCE: 594
```

-continued agtattctag aaactcacca                                            20

<210> SEQ ID NO 595
<211> LENGTH: 19
<212> TYPE: DNA
<213> ORGANISM: Artificial Sequence
<220> FEATURE:
<223> OTHER INFORMATION: N8 Sequence

<400> SEQUENCE: 595
agtattctag aaactcacc                                             19

<210> SEQ ID NO 596
<211> LENGTH: 18
<212> TYPE: DNA
<213> ORGANISM: Artificial Sequence
<220> FEATURE:
<223> OTHER INFORMATION: N8 Sequence

<400> SEQUENCE: 596
agtattctag aaactcac                                              18

<210> SEQ ID NO 597
<211> LENGTH: 17
<212> TYPE: DNA
<213> ORGANISM: Artificial Sequence
<220> FEATURE:
<223> OTHER INFORMATION: N8 Sequence

<400> SEQUENCE: 597
agtattctag aaactca                                               17

<210> SEQ ID NO 598
<211> LENGTH: 16
<212> TYPE: DNA
<213> ORGANISM: Artificial Sequence
<220> FEATURE:
<223> OTHER INFORMATION: N8 Sequence

<400> SEQUENCE: 598
agtattctag aaactc                                                16

<210> SEQ ID NO 599
<211> LENGTH: 15
<212> TYPE: DNA
<213> ORGANISM: Artificial Sequence
<220> FEATURE:
<223> OTHER INFORMATION: N8 Sequence

<400> SEQUENCE: 599
agtattctag aaact                                                 15

<210> SEQ ID NO 600
<211> LENGTH: 14
<212> TYPE: DNA
<213> ORGANISM: Artificial Sequence
<220> FEATURE:
<223> OTHER INFORMATION: N8 Sequence

<400> SEQUENCE: 600
agtattctag aaac                                                  14

<210> SEQ ID NO 601
<211> LENGTH: 13
<212> TYPE: DNA

```
<213> ORGANISM: Artificial Sequence
<220> FEATURE:
<223> OTHER INFORMATION: N8 Sequence

<400> SEQUENCE: 601
agtattctag aaa                                                          13

<210> SEQ ID NO 602
<211> LENGTH: 12
<212> TYPE: DNA
<213> ORGANISM: Artificial Sequence
<220> FEATURE:
<223> OTHER INFORMATION: N8 Sequence

<400> SEQUENCE: 602
agtattctag aa                                                           12

<210> SEQ ID NO 603
<211> LENGTH: 11
<212> TYPE: DNA
<213> ORGANISM: Artificial Sequence
<220> FEATURE:
<223> OTHER INFORMATION: N8 Sequence

<400> SEQUENCE: 603
agtattctag a                                                            11

<210> SEQ ID NO 604
<211> LENGTH: 10
<212> TYPE: DNA
<213> ORGANISM: Artificial Sequence
<220> FEATURE:
<223> OTHER INFORMATION: N8 Sequence

<400> SEQUENCE: 604
agtattctag                                                              10

<210> SEQ ID NO 605
<211> LENGTH: 20
<212> TYPE: DNA
<213> ORGANISM: Artificial Sequence
<220> FEATURE:
<223> OTHER INFORMATION: N9 Sequence

<400> SEQUENCE: 605
attcatattt atatacaggc                                                   20

<210> SEQ ID NO 606
<211> LENGTH: 19
<212> TYPE: DNA
<213> ORGANISM: Artificial Sequence
<220> FEATURE:
<223> OTHER INFORMATION: N9 Sequence

<400> SEQUENCE: 606
ttcatattta tatacaggc                                                    19

<210> SEQ ID NO 607
<211> LENGTH: 18
<212> TYPE: DNA
<213> ORGANISM: Artificial Sequence
<220> FEATURE:
<223> OTHER INFORMATION: N9 Sequence

<400> SEQUENCE: 607
tcatatttat atacaggc                                                     18
```

<210> SEQ ID NO 608
<211> LENGTH: 17
<212> TYPE: DNA
<213> ORGANISM: Artificial Sequence
<220> FEATURE:
<223> OTHER INFORMATION: N9 Sequence

<400> SEQUENCE: 608
catatttata tacaggc                                                  17

<210> SEQ ID NO 609
<211> LENGTH: 16
<212> TYPE: DNA
<213> ORGANISM: Artificial Sequence
<220> FEATURE:
<223> OTHER INFORMATION: N9 Sequence

<400> SEQUENCE: 609
atatttatat acaggc                                                   16

<210> SEQ ID NO 610
<211> LENGTH: 15
<212> TYPE: DNA
<213> ORGANISM: Artificial Sequence
<220> FEATURE:
<223> OTHER INFORMATION: N9 Sequence

<400> SEQUENCE: 610
tatttatata caggc                                                    15

<210> SEQ ID NO 611
<211> LENGTH: 14
<212> TYPE: DNA
<213> ORGANISM: Artificial Sequence
<220> FEATURE:
<223> OTHER INFORMATION: N9 Sequence

<400> SEQUENCE: 611
atttatatac aggc                                                     14

<210> SEQ ID NO 612
<211> LENGTH: 13
<212> TYPE: DNA
<213> ORGANISM: Artificial Sequence
<220> FEATURE:
<223> OTHER INFORMATION: N9 Sequence

<400> SEQUENCE: 612
tttatataca ggc                                                      13

<210> SEQ ID NO 613
<211> LENGTH: 12
<212> TYPE: DNA
<213> ORGANISM: Artificial Sequence
<220> FEATURE:
<223> OTHER INFORMATION: N9 Sequence

<400> SEQUENCE: 613
ttatatacag gc                                                       12

<210> SEQ ID NO 614
<211> LENGTH: 11
<212> TYPE: DNA
<213> ORGANISM: Artificial Sequence
<220> FEATURE:

<223> OTHER INFORMATION: N9 Sequence

<400> SEQUENCE: 614
tatatacagg c                                              11

<210> SEQ ID NO 615
<211> LENGTH: 10
<212> TYPE: DNA
<213> ORGANISM: Artificial Sequence
<220> FEATURE:
<223> OTHER INFORMATION: N9 Sequence

<400> SEQUENCE: 615
atatacaggc                                                10

<210> SEQ ID NO 616
<211> LENGTH: 20
<212> TYPE: DNA
<213> ORGANISM: Artificial Sequence
<220> FEATURE:
<223> OTHER INFORMATION: N10 Sequence

<400> SEQUENCE: 616
agtgcaaatg ttattggcta                                     20

<210> SEQ ID NO 617
<211> LENGTH: 19
<212> TYPE: DNA
<213> ORGANISM: Artificial Sequence
<220> FEATURE:
<223> OTHER INFORMATION: N10 Sequence

<400> SEQUENCE: 617
agtgcaaatg ttattggct                                      19

<210> SEQ ID NO 618
<211> LENGTH: 18
<212> TYPE: DNA
<213> ORGANISM: Artificial Sequence
<220> FEATURE:
<223> OTHER INFORMATION: N10 Sequence

<400> SEQUENCE: 618
agtgcaaatg ttattggc                                       18

<210> SEQ ID NO 619
<211> LENGTH: 17
<212> TYPE: DNA
<213> ORGANISM: Artificial Sequence
<220> FEATURE:
<223> OTHER INFORMATION: N10 Sequence

<400> SEQUENCE: 619
agtgcaaatg ttattgg                                        17

<210> SEQ ID NO 620
<211> LENGTH: 16
<212> TYPE: DNA
<213> ORGANISM: Artificial Sequence
<220> FEATURE:
<223> OTHER INFORMATION: N10 Sequence

<400> SEQUENCE: 620
agtgcaaatg ttattg                                         16

```
<210> SEQ ID NO 621
<211> LENGTH: 15
<212> TYPE: DNA
<213> ORGANISM: Artificial Sequence
<220> FEATURE:
<223> OTHER INFORMATION: N10 Sequence

<400> SEQUENCE: 621
agtgcaaatg ttatt                                                   15

<210> SEQ ID NO 622
<211> LENGTH: 14
<212> TYPE: DNA
<213> ORGANISM: Artificial Sequence
<220> FEATURE:
<223> OTHER INFORMATION: N10 Sequence

<400> SEQUENCE: 622
agtgcaaatg ttat                                                    14

<210> SEQ ID NO 623
<211> LENGTH: 13
<212> TYPE: DNA
<213> ORGANISM: Artificial Sequence
<220> FEATURE:
<223> OTHER INFORMATION: N10 Sequence

<400> SEQUENCE: 623
agtgcaaatg tta                                                     13

<210> SEQ ID NO 624
<211> LENGTH: 12
<212> TYPE: DNA
<213> ORGANISM: Artificial Sequence
<220> FEATURE:
<223> OTHER INFORMATION: N10 Sequence

<400> SEQUENCE: 624
agtgcaaatg tt                                                      12

<210> SEQ ID NO 625
<211> LENGTH: 11
<212> TYPE: DNA
<213> ORGANISM: Artificial Sequence
<220> FEATURE:
<223> OTHER INFORMATION: N10 Sequence

<400> SEQUENCE: 625
agtgcaaatg t                                                       11

<210> SEQ ID NO 626
<211> LENGTH: 10
<212> TYPE: DNA
<213> ORGANISM: Artificial Sequence
<220> FEATURE:
<223> OTHER INFORMATION: N10 Sequence

<400> SEQUENCE: 626
agtgcaaatg                                                         10

<210> SEQ ID NO 627
<211> LENGTH: 24
<212> TYPE: DNA
<213> ORGANISM: Artificial Sequence
<220> FEATURE:
<223> OTHER INFORMATION: N11 Sequence
```

```
<400> SEQUENCE: 627
tgccccagaa gagctatttg gtag                                          24

<210> SEQ ID NO 628
<211> LENGTH: 23
<212> TYPE: DNA
<213> ORGANISM: Artificial Sequence
<220> FEATURE:
<223> OTHER INFORMATION: N11 Sequence

<400> SEQUENCE: 628
gccccagaag agctatttgg tag                                           23

<210> SEQ ID NO 629
<211> LENGTH: 22
<212> TYPE: DNA
<213> ORGANISM: Artificial Sequence
<220> FEATURE:
<223> OTHER INFORMATION: N11 Sequence

<400> SEQUENCE: 629
ccccagaaga gctatttggt ag                                            22

<210> SEQ ID NO 630
<211> LENGTH: 21
<212> TYPE: DNA
<213> ORGANISM: Artificial Sequence
<220> FEATURE:
<223> OTHER INFORMATION: N11 Sequence

<400> SEQUENCE: 630
cccagaagag ctatttggta g                                             21

<210> SEQ ID NO 631
<211> LENGTH: 20
<212> TYPE: DNA
<213> ORGANISM: Artificial Sequence
<220> FEATURE:
<223> OTHER INFORMATION: N11 Sequence

<400> SEQUENCE: 631
ccagaagagc tatttggtag                                               20

<210> SEQ ID NO 632
<211> LENGTH: 19
<212> TYPE: DNA
<213> ORGANISM: Artificial Sequence
<220> FEATURE:
<223> OTHER INFORMATION: N11 Sequence

<400> SEQUENCE: 632
cagaagagct atttggtag                                                19

<210> SEQ ID NO 633
<211> LENGTH: 18
<212> TYPE: DNA
<213> ORGANISM: Artificial Sequence
<220> FEATURE:
<223> OTHER INFORMATION: N11 Sequence

<400> SEQUENCE: 633
agaagagcta tttggtag                                                 18

<210> SEQ ID NO 634
<211> LENGTH: 17
```

```
<212> TYPE: DNA
<213> ORGANISM: Artificial Sequence
<220> FEATURE:
<223> OTHER INFORMATION: N11 Sequence

<400> SEQUENCE: 634
gaagagctat ttggtag                                                    17

<210> SEQ ID NO 635
<211> LENGTH: 16
<212> TYPE: DNA
<213> ORGANISM: Artificial Sequence
<220> FEATURE:
<223> OTHER INFORMATION: N11 Sequence

<400> SEQUENCE: 635
aagagctatt tggtag                                                     16

<210> SEQ ID NO 636
<211> LENGTH: 15
<212> TYPE: DNA
<213> ORGANISM: Artificial Sequence
<220> FEATURE:
<223> OTHER INFORMATION: N11 Sequence

<400> SEQUENCE: 636
agagctattt ggtag                                                      15

<210> SEQ ID NO 637
<211> LENGTH: 14
<212> TYPE: DNA
<213> ORGANISM: Artificial Sequence
<220> FEATURE:
<223> OTHER INFORMATION: N11 Sequence

<400> SEQUENCE: 637
gagctatttg gtag                                                       14

<210> SEQ ID NO 638
<211> LENGTH: 13
<212> TYPE: DNA
<213> ORGANISM: Artificial Sequence
<220> FEATURE:
<223> OTHER INFORMATION: N11 Sequence

<400> SEQUENCE: 638
agctatttgg tag                                                        13

<210> SEQ ID NO 639
<211> LENGTH: 12
<212> TYPE: DNA
<213> ORGANISM: Artificial Sequence
<220> FEATURE:
<223> OTHER INFORMATION: N11 Sequence

<400> SEQUENCE: 639
gctatttggt ag                                                         12

<210> SEQ ID NO 640
<211> LENGTH: 11
<212> TYPE: DNA
<213> ORGANISM: Artificial Sequence
<220> FEATURE:
<223> OTHER INFORMATION: N11 Sequence

<400> SEQUENCE: 640
```

-continued ctatttggta g                                          11

<210> SEQ ID NO 641
<211> LENGTH: 10
<212> TYPE: DNA
<213> ORGANISM: Artificial Sequence
<220> FEATURE:
<223> OTHER INFORMATION: N11 Sequence

<400> SEQUENCE: 641
tatttggtag                                            10

<210> SEQ ID NO 642
<211> LENGTH: 24
<212> TYPE: DNA
<213> ORGANISM: Artificial Sequence
<220> FEATURE:
<223> OTHER INFORMATION: N12 Sequence

<400> SEQUENCE: 642
gagccgtctt caggaatctt ctcc                            24

<210> SEQ ID NO 643
<211> LENGTH: 23
<212> TYPE: DNA
<213> ORGANISM: Artificial Sequence
<220> FEATURE:
<223> OTHER INFORMATION: N12 Sequence

<400> SEQUENCE: 643
gagccgtctt caggaatctt ctc                             23

<210> SEQ ID NO 644
<211> LENGTH: 22
<212> TYPE: DNA
<213> ORGANISM: Artificial Sequence
<220> FEATURE:
<223> OTHER INFORMATION: N12 Sequence

<400> SEQUENCE: 644
gagccgtctt caggaatctt ct                              22

<210> SEQ ID NO 645
<211> LENGTH: 21
<212> TYPE: DNA
<213> ORGANISM: Artificial Sequence
<220> FEATURE:
<223> OTHER INFORMATION: N12 Sequence

<400> SEQUENCE: 645
gagccgtctt caggaatctt c                               21

<210> SEQ ID NO 646
<211> LENGTH: 20
<212> TYPE: DNA
<213> ORGANISM: Artificial Sequence
<220> FEATURE:
<223> OTHER INFORMATION: N12 Sequence

<400> SEQUENCE: 646
gagccgtctt caggaatctt                                 20

<210> SEQ ID NO 647
<211> LENGTH: 19
<212> TYPE: DNA
<213> ORGANISM: Artificial Sequence

```
<220> FEATURE:
<223> OTHER INFORMATION: N12 Sequence

<400> SEQUENCE: 647
gagccgtctt caggaatct                                              19

<210> SEQ ID NO 648
<211> LENGTH: 18
<212> TYPE: DNA
<213> ORGANISM: Artificial Sequence
<220> FEATURE:
<223> OTHER INFORMATION: N12 Sequence

<400> SEQUENCE: 648
gagccgtctt caggaatc                                               18

<210> SEQ ID NO 649
<211> LENGTH: 17
<212> TYPE: DNA
<213> ORGANISM: Artificial Sequence
<220> FEATURE:
<223> OTHER INFORMATION: N12 Sequence

<400> SEQUENCE: 649
gagccgtctt caggaat                                                17

<210> SEQ ID NO 650
<211> LENGTH: 16
<212> TYPE: DNA
<213> ORGANISM: Artificial Sequence
<220> FEATURE:
<223> OTHER INFORMATION: N12 Sequence

<400> SEQUENCE: 650
gagccgtctt caggaa                                                 16

<210> SEQ ID NO 651
<211> LENGTH: 15
<212> TYPE: DNA
<213> ORGANISM: Artificial Sequence
<220> FEATURE:
<223> OTHER INFORMATION: N12 Sequence

<400> SEQUENCE: 651
gagccgtctt cagga                                                  15

<210> SEQ ID NO 652
<211> LENGTH: 14
<212> TYPE: DNA
<213> ORGANISM: Artificial Sequence
<220> FEATURE:
<223> OTHER INFORMATION: N12 Sequence

<400> SEQUENCE: 652
gagccgtctt cagg                                                   14

<210> SEQ ID NO 653
<211> LENGTH: 13
<212> TYPE: DNA
<213> ORGANISM: Artificial Sequence
<220> FEATURE:
<223> OTHER INFORMATION: N12 Sequence

<400> SEQUENCE: 653
gagccgtctt cag                                                    13
```

<210> SEQ ID NO 654
<211> LENGTH: 12
<212> TYPE: DNA
<213> ORGANISM: Artificial Sequence
<220> FEATURE:
<223> OTHER INFORMATION: N12 Sequence

<400> SEQUENCE: 654
gagccgtctt ca                                                          12

<210> SEQ ID NO 655
<211> LENGTH: 11
<212> TYPE: DNA
<213> ORGANISM: Artificial Sequence
<220> FEATURE:
<223> OTHER INFORMATION: N12 Sequence

<400> SEQUENCE: 655
gagccgtctt c                                                           11

<210> SEQ ID NO 656
<211> LENGTH: 10
<212> TYPE: DNA
<213> ORGANISM: Artificial Sequence
<220> FEATURE:
<223> OTHER INFORMATION: N12 Sequence

<400> SEQUENCE: 656
gagccgtctt                                                             10

<210> SEQ ID NO 657
<211> LENGTH: 19
<212> TYPE: DNA
<213> ORGANISM: Artificial Sequence
<220> FEATURE:
<223> OTHER INFORMATION: N1A Sequence

<400> SEQUENCE: 657
catggcagac cccgctgct                                                   19

<210> SEQ ID NO 658
<211> LENGTH: 18
<212> TYPE: DNA
<213> ORGANISM: Artificial Sequence
<220> FEATURE:
<223> OTHER INFORMATION: N1A Sequence

<400> SEQUENCE: 658
atggcagacc ccgctgct                                                    18

<210> SEQ ID NO 659
<211> LENGTH: 17
<212> TYPE: DNA
<213> ORGANISM: Artificial Sequence
<220> FEATURE:
<223> OTHER INFORMATION: N1A Sequence

<400> SEQUENCE: 659
tggcagaccc cgctgct                                                     17

<210> SEQ ID NO 660
<211> LENGTH: 16
<212> TYPE: DNA
<213> ORGANISM: Artificial Sequence
<220> FEATURE:
<223> OTHER INFORMATION: N1A Sequence

```
<400> SEQUENCE: 660
ggcagacccc gctgct                                                     16

<210> SEQ ID NO 661
<211> LENGTH: 15
<212> TYPE: DNA
<213> ORGANISM: Artificial Sequence
<220> FEATURE:
<223> OTHER INFORMATION: N1A Sequence

<400> SEQUENCE: 661
gcagaccccg ctgct                                                      15

<210> SEQ ID NO 662
<211> LENGTH: 14
<212> TYPE: DNA
<213> ORGANISM: Artificial Sequence
<220> FEATURE:
<223> OTHER INFORMATION: N1A Sequence

<400> SEQUENCE: 662
cagaccccgc tgct                                                       14

<210> SEQ ID NO 663
<211> LENGTH: 13
<212> TYPE: DNA
<213> ORGANISM: Artificial Sequence
<220> FEATURE:
<223> OTHER INFORMATION: N1A Sequence

<400> SEQUENCE: 663
agaccccgct gct                                                        13

<210> SEQ ID NO 664
<211> LENGTH: 12
<212> TYPE: DNA
<213> ORGANISM: Artificial Sequence
<220> FEATURE:
<223> OTHER INFORMATION: N1A Sequence

<400> SEQUENCE: 664
gaccccgctg ct                                                         12

<210> SEQ ID NO 665
<211> LENGTH: 11
<212> TYPE: DNA
<213> ORGANISM: Artificial Sequence
<220> FEATURE:
<223> OTHER INFORMATION: N1A Sequence

<400> SEQUENCE: 665
accccgctgc t                                                          11

<210> SEQ ID NO 666
<211> LENGTH: 10
<212> TYPE: DNA
<213> ORGANISM: Artificial Sequence
<220> FEATURE:
<223> OTHER INFORMATION: N1A Sequence

<400> SEQUENCE: 666
ccccgctgct                                                            10

<210> SEQ ID NO 667
```

```
<211> LENGTH: 10
<212> TYPE: DNA
<213> ORGANISM: Artificial Sequence
<220> FEATURE:
<223> OTHER INFORMATION: N2A Sequence

<400> SEQUENCE: 667
cgagccccca                                                              10

<210> SEQ ID NO 668
<211> LENGTH: 11
<212> TYPE: DNA
<213> ORGANISM: Artificial Sequence
<220> FEATURE:
<223> OTHER INFORMATION: N2A Sequence

<400> SEQUENCE: 668
cgagccccca g                                                            11

<210> SEQ ID NO 669
<211> LENGTH: 12
<212> TYPE: DNA
<213> ORGANISM: Artificial Sequence
<220> FEATURE:
<223> OTHER INFORMATION: N2A Sequence

<400> SEQUENCE: 669
cgagccccca gc                                                           12

<210> SEQ ID NO 670
<211> LENGTH: 13
<212> TYPE: DNA
<213> ORGANISM: Artificial Sequence
<220> FEATURE:
<223> OTHER INFORMATION: N2A Sequence

<400> SEQUENCE: 670
cgagccccca gcg                                                          13

<210> SEQ ID NO 671
<211> LENGTH: 14
<212> TYPE: DNA
<213> ORGANISM: Artificial Sequence
<220> FEATURE:
<223> OTHER INFORMATION: N2A Sequence

<400> SEQUENCE: 671
cgagccccca gcgc                                                         14

<210> SEQ ID NO 672
<211> LENGTH: 15
<212> TYPE: DNA
<213> ORGANISM: Artificial Sequence
<220> FEATURE:
<223> OTHER INFORMATION: N2A Sequence

<400> SEQUENCE: 672
cgagccccca gcgca                                                        15

<210> SEQ ID NO 673
<211> LENGTH: 16
<212> TYPE: DNA
<213> ORGANISM: Artificial Sequence
<220> FEATURE:
<223> OTHER INFORMATION: N2A Sequence

<400> SEQUENCE: 673
```
cgagccccca gcgcag                                                    16

<210> SEQ ID NO 674
<211> LENGTH: 17
<212> TYPE: DNA
<213> ORGANISM: Artificial Sequence
<220> FEATURE:
<223> OTHER INFORMATION: N2A Sequence

<400> SEQUENCE: 674
cgagccccca gcgcagc                                                   17

<210> SEQ ID NO 675
<211> LENGTH: 18
<212> TYPE: DNA
<213> ORGANISM: Artificial Sequence
<220> FEATURE:
<223> OTHER INFORMATION: N2A Sequence

<400> SEQUENCE: 675
cgagccccca gcgcagcg                                                  18

<210> SEQ ID NO 676
<211> LENGTH: 19
<212> TYPE: DNA
<213> ORGANISM: Artificial Sequence
<220> FEATURE:
<223> OTHER INFORMATION: N2A Sequence

<400> SEQUENCE: 676
cgagccccca gcgcagcgg                                                 19

<210> SEQ ID NO 677
<211> LENGTH: 19
<212> TYPE: DNA
<213> ORGANISM: Artificial Sequence
<220> FEATURE:
<223> OTHER INFORMATION: N3A Sequence

<400> SEQUENCE: 677
ggtgggatcg tgctggcga                                                 19

<210> SEQ ID NO 678
<211> LENGTH: 18
<212> TYPE: DNA
<213> ORGANISM: Artificial Sequence
<220> FEATURE:
<223> OTHER INFORMATION: N3A Sequence

<400> SEQUENCE: 678
gtgggatcgt gctggcga                                                  18

<210> SEQ ID NO 679
<211> LENGTH: 17
<212> TYPE: DNA
<213> ORGANISM: Artificial Sequence
<220> FEATURE:
<223> OTHER INFORMATION: N3A Sequence

<400> SEQUENCE: 679
tgggatcgtg ctggcga                                                   17

<210> SEQ ID NO 680
<211> LENGTH: 16
<212> TYPE: DNA

```
<213> ORGANISM: Artificial Sequence
<220> FEATURE:
<223> OTHER INFORMATION: N3A Sequence

<400> SEQUENCE: 680
gggatcgtgc tggcga                                                   16

<210> SEQ ID NO 681
<211> LENGTH: 15
<212> TYPE: DNA
<213> ORGANISM: Artificial Sequence
<220> FEATURE:
<223> OTHER INFORMATION: N3A Sequence

<400> SEQUENCE: 681
ggatcgtgct ggcga                                                    15

<210> SEQ ID NO 682
<211> LENGTH: 14
<212> TYPE: DNA
<213> ORGANISM: Artificial Sequence
<220> FEATURE:
<223> OTHER INFORMATION: N3A Sequence

<400> SEQUENCE: 682
gatcgtgctg gcga                                                     14

<210> SEQ ID NO 683
<211> LENGTH: 13
<212> TYPE: DNA
<213> ORGANISM: Artificial Sequence
<220> FEATURE:
<223> OTHER INFORMATION: N3A Sequence

<400> SEQUENCE: 683
atcgtgctgg cga                                                      13

<210> SEQ ID NO 684
<211> LENGTH: 12
<212> TYPE: DNA
<213> ORGANISM: Artificial Sequence
<220> FEATURE:
<223> OTHER INFORMATION: N3A Sequence

<400> SEQUENCE: 684
tcgtgctggc ga                                                       12

<210> SEQ ID NO 685
<211> LENGTH: 11
<212> TYPE: DNA
<213> ORGANISM: Artificial Sequence
<220> FEATURE:
<223> OTHER INFORMATION: N3A Sequence

<400> SEQUENCE: 685
cgtgctggcg a                                                        11

<210> SEQ ID NO 686
<211> LENGTH: 10
<212> TYPE: DNA
<213> ORGANISM: Artificial Sequence
<220> FEATURE:
<223> OTHER INFORMATION: N3A Sequence

<400> SEQUENCE: 686
gtgctggcga                                                          10
```

-continued

```
<210> SEQ ID NO 687
<211> LENGTH: 19
<212> TYPE: DNA
<213> ORGANISM: Artificial Sequence
<220> FEATURE:
<223> OTHER INFORMATION: N4A Sequence

<400> SEQUENCE: 687
caggacgatg tgcagcggc                                                19

<210> SEQ ID NO 688
<211> LENGTH: 18
<212> TYPE: DNA
<213> ORGANISM: Artificial Sequence
<220> FEATURE:
<223> OTHER INFORMATION: N4A Sequence

<400> SEQUENCE: 688
caggacgatg tgcagcgg                                                 18

<210> SEQ ID NO 689
<211> LENGTH: 17
<212> TYPE: DNA
<213> ORGANISM: Artificial Sequence
<220> FEATURE:
<223> OTHER INFORMATION: N4A Sequence

<400> SEQUENCE: 689
caggacgatg tgcagcg                                                  17

<210> SEQ ID NO 690
<211> LENGTH: 16
<212> TYPE: DNA
<213> ORGANISM: Artificial Sequence
<220> FEATURE:
<223> OTHER INFORMATION: N4A Sequence

<400> SEQUENCE: 690
caggacgatg tgcagc                                                   16

<210> SEQ ID NO 691
<211> LENGTH: 15
<212> TYPE: DNA
<213> ORGANISM: Artificial Sequence
<220> FEATURE:
<223> OTHER INFORMATION: N4A Sequence

<400> SEQUENCE: 691
caggacgatg tgcag                                                    15

<210> SEQ ID NO 692
<211> LENGTH: 14
<212> TYPE: DNA
<213> ORGANISM: Artificial Sequence
<220> FEATURE:
<223> OTHER INFORMATION: N4A Sequence

<400> SEQUENCE: 692
caggacgatg tgca                                                     14

<210> SEQ ID NO 693
<211> LENGTH: 13
<212> TYPE: DNA
<213> ORGANISM: Artificial Sequence
<220> FEATURE:
```

<223> OTHER INFORMATION: N4A Sequence

<400> SEQUENCE: 693
caggacgatg tgc                                                              13

<210> SEQ ID NO 694
<211> LENGTH: 12
<212> TYPE: DNA
<213> ORGANISM: Artificial Sequence
<220> FEATURE:
<223> OTHER INFORMATION: N4A Sequence

<400> SEQUENCE: 694
caggacgatg tg                                                               12

<210> SEQ ID NO 695
<211> LENGTH: 11
<212> TYPE: DNA
<213> ORGANISM: Artificial Sequence
<220> FEATURE:
<223> OTHER INFORMATION: N4A Sequence

<400> SEQUENCE: 695
caggacgatg t                                                                11

<210> SEQ ID NO 696
<211> LENGTH: 10
<212> TYPE: DNA
<213> ORGANISM: Artificial Sequence
<220> FEATURE:
<223> OTHER INFORMATION: N4A Sequence

<400> SEQUENCE: 696
caggacgatg                                                                  10

<210> SEQ ID NO 697
<211> LENGTH: 23
<212> TYPE: DNA
<213> ORGANISM: Artificial Sequence
<220> FEATURE:
<223> OTHER INFORMATION: N5A Sequence

<400> SEQUENCE: 697
gcccagcctg ccccagaaga gct                                                   23

<210> SEQ ID NO 698
<211> LENGTH: 22
<212> TYPE: DNA
<213> ORGANISM: Artificial Sequence
<220> FEATURE:
<223> OTHER INFORMATION: N5A Sequence

<400> SEQUENCE: 698
cccagcctgc cccagaagag ct                                                    22

<210> SEQ ID NO 699
<211> LENGTH: 21
<212> TYPE: DNA
<213> ORGANISM: Artificial Sequence
<220> FEATURE:
<223> OTHER INFORMATION: N5A Sequence

<400> SEQUENCE: 699
ccagcctgcc ccagaagagc t                                                     21

```
<210> SEQ ID NO 700
<211> LENGTH: 20
<212> TYPE: DNA
<213> ORGANISM: Artificial Sequence
<220> FEATURE:
<223> OTHER INFORMATION: N5A Sequence

<400> SEQUENCE: 700
cagcctgccc cagaagagct                                              20

<210> SEQ ID NO 701
<211> LENGTH: 19
<212> TYPE: DNA
<213> ORGANISM: Artificial Sequence
<220> FEATURE:
<223> OTHER INFORMATION: N5A Sequence

<400> SEQUENCE: 701
agcctgcccc agaagagct                                               19

<210> SEQ ID NO 702
<211> LENGTH: 18
<212> TYPE: DNA
<213> ORGANISM: Artificial Sequence
<220> FEATURE:
<223> OTHER INFORMATION: N5A Sequence

<400> SEQUENCE: 702
gcctgcccca gaagagct                                                18

<210> SEQ ID NO 703
<211> LENGTH: 17
<212> TYPE: DNA
<213> ORGANISM: Artificial Sequence
<220> FEATURE:
<223> OTHER INFORMATION: N5A Sequence

<400> SEQUENCE: 703
cctgccccag aagagct                                                 17

<210> SEQ ID NO 704
<211> LENGTH: 16
<212> TYPE: DNA
<213> ORGANISM: Artificial Sequence
<220> FEATURE:
<223> OTHER INFORMATION: N5A Sequence

<400> SEQUENCE: 704
ctgccccaga agagct                                                  16

<210> SEQ ID NO 705
<211> LENGTH: 15
<212> TYPE: DNA
<213> ORGANISM: Artificial Sequence
<220> FEATURE:
<223> OTHER INFORMATION: N5A Sequence

<400> SEQUENCE: 705
tgccccagaa gagct                                                   15

<210> SEQ ID NO 706
<211> LENGTH: 14
<212> TYPE: DNA
<213> ORGANISM: Artificial Sequence
<220> FEATURE:
<223> OTHER INFORMATION: N5A Sequence
```

```
<400> SEQUENCE: 706
gccccagaag agct                                                         14

<210> SEQ ID NO 707
<211> LENGTH: 13
<212> TYPE: DNA
<213> ORGANISM: Artificial Sequence
<220> FEATURE:
<223> OTHER INFORMATION: N5A Sequence

<400> SEQUENCE: 707
ccccagaaga gct                                                          13

<210> SEQ ID NO 708
<211> LENGTH: 12
<212> TYPE: DNA
<213> ORGANISM: Artificial Sequence
<220> FEATURE:
<223> OTHER INFORMATION: N5A Sequence

<400> SEQUENCE: 708
cccagaagag ct                                                           12

<210> SEQ ID NO 709
<211> LENGTH: 11
<212> TYPE: DNA
<213> ORGANISM: Artificial Sequence
<220> FEATURE:
<223> OTHER INFORMATION: N5A Sequence

<400> SEQUENCE: 709
ccagaagagc t                                                            11

<210> SEQ ID NO 710
<211> LENGTH: 10
<212> TYPE: DNA
<213> ORGANISM: Artificial Sequence
<220> FEATURE:
<223> OTHER INFORMATION: N5A Sequence

<400> SEQUENCE: 710
cagaagagct                                                              10

<210> SEQ ID NO 711
<211> LENGTH: 23
<212> TYPE: DNA
<213> ORGANISM: Artificial Sequence
<220> FEATURE:
<223> OTHER INFORMATION: N6A Sequence

<400> SEQUENCE: 711
gtttagggag ccgtcttcag gaa                                               23

<210> SEQ ID NO 712
<211> LENGTH: 22
<212> TYPE: DNA
<213> ORGANISM: Artificial Sequence
<220> FEATURE:
<223> OTHER INFORMATION: N6A Sequence

<400> SEQUENCE: 712
gtttagggag ccgtcttcag ga                                                22

<210> SEQ ID NO 713
<211> LENGTH: 21
```

```
<212> TYPE: DNA
<213> ORGANISM: Artificial Sequence
<220> FEATURE:
<223> OTHER INFORMATION: N6A Sequence

<400> SEQUENCE: 713
gtttagggag ccgtcttcag g                                          21

<210> SEQ ID NO 714
<211> LENGTH: 20
<212> TYPE: DNA
<213> ORGANISM: Artificial Sequence
<220> FEATURE:
<223> OTHER INFORMATION: N6A Sequence

<400> SEQUENCE: 714
gtttagggag ccgtcttcag                                            20

<210> SEQ ID NO 715
<211> LENGTH: 19
<212> TYPE: DNA
<213> ORGANISM: Artificial Sequence
<220> FEATURE:
<223> OTHER INFORMATION: N6A Sequence

<400> SEQUENCE: 715
gtttagggag ccgtcttca                                             19

<210> SEQ ID NO 716
<211> LENGTH: 18
<212> TYPE: DNA
<213> ORGANISM: Artificial Sequence
<220> FEATURE:
<223> OTHER INFORMATION: N6A Sequence

<400> SEQUENCE: 716
gtttagggag ccgtcttc                                              18

<210> SEQ ID NO 717
<211> LENGTH: 17
<212> TYPE: DNA
<213> ORGANISM: Artificial Sequence
<220> FEATURE:
<223> OTHER INFORMATION: N6A Sequence

<400> SEQUENCE: 717
gtttagggag ccgtctt                                               17

<210> SEQ ID NO 718
<211> LENGTH: 16
<212> TYPE: DNA
<213> ORGANISM: Artificial Sequence
<220> FEATURE:
<223> OTHER INFORMATION: N6A Sequence

<400> SEQUENCE: 718
gtttagggag ccgtct                                                16

<210> SEQ ID NO 719
<211> LENGTH: 15
<212> TYPE: DNA
<213> ORGANISM: Artificial Sequence
<220> FEATURE:
<223> OTHER INFORMATION: N6A Sequence

<400> SEQUENCE: 719
```

```
gtttagggag ccgtc                                                     15

<210> SEQ ID NO 720
<211> LENGTH: 14
<212> TYPE: DNA
<213> ORGANISM: Artificial Sequence
<220> FEATURE:
<223> OTHER INFORMATION: N6A Sequence

<400> SEQUENCE: 720
gtttagggag ccgt                                                      14

<210> SEQ ID NO 721
<211> LENGTH: 13
<212> TYPE: DNA
<213> ORGANISM: Artificial Sequence
<220> FEATURE:
<223> OTHER INFORMATION: N6A Sequence

<400> SEQUENCE: 721
gtttagggag ccg                                                       13

<210> SEQ ID NO 722
<211> LENGTH: 12
<212> TYPE: DNA
<213> ORGANISM: Artificial Sequence
<220> FEATURE:
<223> OTHER INFORMATION: N6A Sequence

<400> SEQUENCE: 722
gtttagggag cc                                                        12

<210> SEQ ID NO 723
<211> LENGTH: 11
<212> TYPE: DNA
<213> ORGANISM: Artificial Sequence
<220> FEATURE:
<223> OTHER INFORMATION: N6A Sequence

<400> SEQUENCE: 723
gtttagggag c                                                         11

<210> SEQ ID NO 724
<211> LENGTH: 10
<212> TYPE: DNA
<213> ORGANISM: Artificial Sequence
<220> FEATURE:
<223> OTHER INFORMATION: N6A Sequence

<400> SEQUENCE: 724
gtttagggag                                                           10

<210> SEQ ID NO 725
<211> LENGTH: 19
<212> TYPE: DNA
<213> ORGANISM: Artificial Sequence
<220> FEATURE:
<223> OTHER INFORMATION: N7A Sequence

<400> SEQUENCE: 725
tgaatcttga atatctcat                                                 19

<210> SEQ ID NO 726
<211> LENGTH: 18
<212> TYPE: DNA
<213> ORGANISM: Artificial Sequence
```

```
<220> FEATURE:
<223> OTHER INFORMATION: N7A Sequence

<400> SEQUENCE: 726
gaatcttgaa tatctcat                                                    18

<210> SEQ ID NO 727
<211> LENGTH: 17
<212> TYPE: DNA
<213> ORGANISM: Artificial Sequence
<220> FEATURE:
<223> OTHER INFORMATION: N7A Sequence

<400> SEQUENCE: 727
aatcttgaat atctcat                                                     17

<210> SEQ ID NO 728
<211> LENGTH: 16
<212> TYPE: DNA
<213> ORGANISM: Artificial Sequence
<220> FEATURE:
<223> OTHER INFORMATION: N7A Sequence

<400> SEQUENCE: 728
atcttgaata tctcat                                                      16

<210> SEQ ID NO 729
<211> LENGTH: 15
<212> TYPE: DNA
<213> ORGANISM: Artificial Sequence
<220> FEATURE:
<223> OTHER INFORMATION: N7A Sequence

<400> SEQUENCE: 729
tcttgaatat ctcat                                                       15

<210> SEQ ID NO 730
<211> LENGTH: 14
<212> TYPE: DNA
<213> ORGANISM: Artificial Sequence
<220> FEATURE:
<223> OTHER INFORMATION: N7A Sequence

<400> SEQUENCE: 730
cttgaatatc tcat                                                        14

<210> SEQ ID NO 731
<211> LENGTH: 13
<212> TYPE: DNA
<213> ORGANISM: Artificial Sequence
<220> FEATURE:
<223> OTHER INFORMATION: N7A Sequence

<400> SEQUENCE: 731
ttgaatatct cat                                                         13

<210> SEQ ID NO 732
<211> LENGTH: 12
<212> TYPE: DNA
<213> ORGANISM: Artificial Sequence
<220> FEATURE:
<223> OTHER INFORMATION: N7A Sequence

<400> SEQUENCE: 732
tgaatatctc at                                                          12
```

```
<210> SEQ ID NO 733
<211> LENGTH: 11
<212> TYPE: DNA
<213> ORGANISM: Artificial Sequence
<220> FEATURE:
<223> OTHER INFORMATION: N7A Sequence

<400> SEQUENCE: 733
gaatatctca t                                                          11

<210> SEQ ID NO 734
<211> LENGTH: 10
<212> TYPE: DNA
<213> ORGANISM: Artificial Sequence
<220> FEATURE:
<223> OTHER INFORMATION: N7A Sequence

<400> SEQUENCE: 734
aatatctcat                                                            10

<210> SEQ ID NO 735
<211> LENGTH: 19
<212> TYPE: DNA
<213> ORGANISM: Artificial Sequence
<220> FEATURE:
<223> OTHER INFORMATION: N8A Sequence

<400> SEQUENCE: 735
gtattctaga aactcacca                                                  19

<210> SEQ ID NO 736
<211> LENGTH: 18
<212> TYPE: DNA
<213> ORGANISM: Artificial Sequence
<220> FEATURE:
<223> OTHER INFORMATION: N8A Sequence

<400> SEQUENCE: 736
gtattctaga aactcacc                                                   18

<210> SEQ ID NO 737
<211> LENGTH: 17
<212> TYPE: DNA
<213> ORGANISM: Artificial Sequence
<220> FEATURE:
<223> OTHER INFORMATION: N8A Sequence

<400> SEQUENCE: 737
gtattctaga aactcac                                                    17

<210> SEQ ID NO 738
<211> LENGTH: 16
<212> TYPE: DNA
<213> ORGANISM: Artificial Sequence
<220> FEATURE:
<223> OTHER INFORMATION: N8A Sequence

<400> SEQUENCE: 738
gtattctaga aactca                                                     16

<210> SEQ ID NO 739
<211> LENGTH: 15
<212> TYPE: DNA
<213> ORGANISM: Artificial Sequence
<220> FEATURE:
<223> OTHER INFORMATION: N8A Sequence
```

```
<400> SEQUENCE: 739
gtattctaga aactc                                                    15

<210> SEQ ID NO 740
<211> LENGTH: 14
<212> TYPE: DNA
<213> ORGANISM: Artificial Sequence
<220> FEATURE:
<223> OTHER INFORMATION: N8A Sequence

<400> SEQUENCE: 740
gtattctaga aact                                                     14

<210> SEQ ID NO 741
<211> LENGTH: 13
<212> TYPE: DNA
<213> ORGANISM: Artificial Sequence
<220> FEATURE:
<223> OTHER INFORMATION: N8A Sequence

<400> SEQUENCE: 741
gtattctaga aac                                                      13

<210> SEQ ID NO 742
<211> LENGTH: 12
<212> TYPE: DNA
<213> ORGANISM: Artificial Sequence
<220> FEATURE:
<223> OTHER INFORMATION: N8A Sequence

<400> SEQUENCE: 742
gtattctaga aa                                                       12

<210> SEQ ID NO 743
<211> LENGTH: 11
<212> TYPE: DNA
<213> ORGANISM: Artificial Sequence
<220> FEATURE:
<223> OTHER INFORMATION: N8A Sequence

<400> SEQUENCE: 743
gtattctaga a                                                        11

<210> SEQ ID NO 744
<211> LENGTH: 10
<212> TYPE: DNA
<213> ORGANISM: Artificial Sequence
<220> FEATURE:
<223> OTHER INFORMATION: N8A Sequence

<400> SEQUENCE: 744
gtattctaga                                                          10

<210> SEQ ID NO 745
<211> LENGTH: 19
<212> TYPE: DNA
<213> ORGANISM: Artificial Sequence
<220> FEATURE:
<223> OTHER INFORMATION: N9A Sequence

<400> SEQUENCE: 745
attcatattt atatacagg                                                19

<210> SEQ ID NO 746
```

```
<211> LENGTH: 18
<212> TYPE: DNA
<213> ORGANISM: Artificial Sequence
<220> FEATURE:
<223> OTHER INFORMATION: N9A Sequence

<400> SEQUENCE: 746
ttcatattta tatacagg                                                      18

<210> SEQ ID NO 747
<211> LENGTH: 17
<212> TYPE: DNA
<213> ORGANISM: Artificial Sequence
<220> FEATURE:
<223> OTHER INFORMATION: N9A Sequence

<400> SEQUENCE: 747
tcatatttat atacagg                                                       17

<210> SEQ ID NO 748
<211> LENGTH: 16
<212> TYPE: DNA
<213> ORGANISM: Artificial Sequence
<220> FEATURE:
<223> OTHER INFORMATION: N9A Sequence

<400> SEQUENCE: 748
catatttata tacagg                                                        16

<210> SEQ ID NO 749
<211> LENGTH: 15
<212> TYPE: DNA
<213> ORGANISM: Artificial Sequence
<220> FEATURE:
<223> OTHER INFORMATION: N9A Sequence

<400> SEQUENCE: 749
atatttatat acagg                                                         15

<210> SEQ ID NO 750
<211> LENGTH: 14
<212> TYPE: DNA
<213> ORGANISM: Artificial Sequence
<220> FEATURE:
<223> OTHER INFORMATION: N9A Sequence

<400> SEQUENCE: 750
tatttatata cagg                                                          14

<210> SEQ ID NO 751
<211> LENGTH: 13
<212> TYPE: DNA
<213> ORGANISM: Artificial Sequence
<220> FEATURE:
<223> OTHER INFORMATION: N9A Sequence

<400> SEQUENCE: 751
atttatatac agg                                                           13

<210> SEQ ID NO 752
<211> LENGTH: 12
<212> TYPE: DNA
<213> ORGANISM: Artificial Sequence
<220> FEATURE:
<223> OTHER INFORMATION: N9A Sequence

<400> SEQUENCE: 752
```
tttatataca gg                                                    12

<210> SEQ ID NO 753
<211> LENGTH: 11
<212> TYPE: DNA
<213> ORGANISM: Artificial Sequence
<220> FEATURE:
<223> OTHER INFORMATION: N9A Sequence

<400> SEQUENCE: 753
ttatatacag g                                                     11

<210> SEQ ID NO 754
<211> LENGTH: 10
<212> TYPE: DNA
<213> ORGANISM: Artificial Sequence
<220> FEATURE:
<223> OTHER INFORMATION: N9A Sequence

<400> SEQUENCE: 754
tatatacagg                                                       10

<210> SEQ ID NO 755
<211> LENGTH: 19
<212> TYPE: DNA
<213> ORGANISM: Artificial Sequence
<220> FEATURE:
<223> OTHER INFORMATION: N10A Sequence

<400> SEQUENCE: 755
gtgcaaatgt tattggcta                                             19

<210> SEQ ID NO 756
<211> LENGTH: 18
<212> TYPE: DNA
<213> ORGANISM: Artificial Sequence
<220> FEATURE:
<223> OTHER INFORMATION: N10A Sequence

<400> SEQUENCE: 756
gtgcaaatgt tattggct                                              18

<210> SEQ ID NO 757
<211> LENGTH: 17
<212> TYPE: DNA
<213> ORGANISM: Artificial Sequence
<220> FEATURE:
<223> OTHER INFORMATION: N10A Sequence

<400> SEQUENCE: 757
gtgcaaatgt tattggc                                               17

<210> SEQ ID NO 758
<211> LENGTH: 16
<212> TYPE: DNA
<213> ORGANISM: Artificial Sequence
<220> FEATURE:
<223> OTHER INFORMATION: N10A Sequence

<400> SEQUENCE: 758
gtgcaaatgt tattgg                                                16

<210> SEQ ID NO 759
<211> LENGTH: 15
<212> TYPE: DNA

```
<213> ORGANISM: Artificial Sequence
<220> FEATURE:
<223> OTHER INFORMATION: N10A Sequence

<400> SEQUENCE: 759
gtgcaaatgt tattg                                                    15

<210> SEQ ID NO 760
<211> LENGTH: 14
<212> TYPE: DNA
<213> ORGANISM: Artificial Sequence
<220> FEATURE:
<223> OTHER INFORMATION: N10A Sequence

<400> SEQUENCE: 760
gtgcaaatgt tatt                                                     14

<210> SEQ ID NO 761
<211> LENGTH: 13
<212> TYPE: DNA
<213> ORGANISM: Artificial Sequence
<220> FEATURE:
<223> OTHER INFORMATION: N10A Sequence

<400> SEQUENCE: 761
gtgcaaatgt tat                                                      13

<210> SEQ ID NO 762
<211> LENGTH: 12
<212> TYPE: DNA
<213> ORGANISM: Artificial Sequence
<220> FEATURE:
<223> OTHER INFORMATION: N10A Sequence

<400> SEQUENCE: 762
gtgcaaatgt ta                                                       12

<210> SEQ ID NO 763
<211> LENGTH: 11
<212> TYPE: DNA
<213> ORGANISM: Artificial Sequence
<220> FEATURE:
<223> OTHER INFORMATION: N10A Sequence

<400> SEQUENCE: 763
gtgcaaatgt t                                                        11

<210> SEQ ID NO 764
<211> LENGTH: 10
<212> TYPE: DNA
<213> ORGANISM: Artificial Sequence
<220> FEATURE:
<223> OTHER INFORMATION: N10A Sequence

<400> SEQUENCE: 764
gtgcaaatgt                                                          10

<210> SEQ ID NO 765
<211> LENGTH: 23
<212> TYPE: DNA
<213> ORGANISM: Artificial Sequence
<220> FEATURE:
<223> OTHER INFORMATION: N11A Sequence

<400> SEQUENCE: 765
tgccccagaa gagctatttg gta                                           23
```

```
<210> SEQ ID NO 766
<211> LENGTH: 22
<212> TYPE: DNA
<213> ORGANISM: Artificial Sequence
<220> FEATURE:
<223> OTHER INFORMATION: N11A Sequence

<400> SEQUENCE: 766
gccccagaag agctatttgg ta                                          22

<210> SEQ ID NO 767
<211> LENGTH: 21
<212> TYPE: DNA
<213> ORGANISM: Artificial Sequence
<220> FEATURE:
<223> OTHER INFORMATION: N11A Sequence

<400> SEQUENCE: 767
ccccagaaga gctatttggt a                                           21

<210> SEQ ID NO 768
<211> LENGTH: 20
<212> TYPE: DNA
<213> ORGANISM: Artificial Sequence
<220> FEATURE:
<223> OTHER INFORMATION: N11A Sequence

<400> SEQUENCE: 768
cccagaagag ctatttggta                                             20

<210> SEQ ID NO 769
<211> LENGTH: 19
<212> TYPE: DNA
<213> ORGANISM: Artificial Sequence
<220> FEATURE:
<223> OTHER INFORMATION: N11A Sequence

<400> SEQUENCE: 769
ccagaagagc tatttggta                                              19

<210> SEQ ID NO 770
<211> LENGTH: 18
<212> TYPE: DNA
<213> ORGANISM: Artificial Sequence
<220> FEATURE:
<223> OTHER INFORMATION: N11A Sequence

<400> SEQUENCE: 770
cagaagagct atttggta                                               18

<210> SEQ ID NO 771
<211> LENGTH: 17
<212> TYPE: DNA
<213> ORGANISM: Artificial Sequence
<220> FEATURE:
<223> OTHER INFORMATION: N11A Sequence

<400> SEQUENCE: 771
agaagagcta tttggta                                                17

<210> SEQ ID NO 772
<211> LENGTH: 16
<212> TYPE: DNA
<213> ORGANISM: Artificial Sequence
<220> FEATURE:
```

```
<223> OTHER INFORMATION: N11A Sequence

<400> SEQUENCE: 772
gaagagctat ttggta                                                          16

<210> SEQ ID NO 773
<211> LENGTH: 15
<212> TYPE: DNA
<213> ORGANISM: Artificial Sequence
<220> FEATURE:
<223> OTHER INFORMATION: N11A Sequence

<400> SEQUENCE: 773
aagagctatt tggta                                                           15

<210> SEQ ID NO 774
<211> LENGTH: 14
<212> TYPE: DNA
<213> ORGANISM: Artificial Sequence
<220> FEATURE:
<223> OTHER INFORMATION: N11A Sequence

<400> SEQUENCE: 774
agagctattt ggta                                                            14

<210> SEQ ID NO 775
<211> LENGTH: 13
<212> TYPE: DNA
<213> ORGANISM: Artificial Sequence
<220> FEATURE:
<223> OTHER INFORMATION: N11A Sequence

<400> SEQUENCE: 775
gagctatttg gta                                                             13

<210> SEQ ID NO 776
<211> LENGTH: 12
<212> TYPE: DNA
<213> ORGANISM: Artificial Sequence
<220> FEATURE:
<223> OTHER INFORMATION: N11A Sequence

<400> SEQUENCE: 776
agctatttgg ta                                                              12

<210> SEQ ID NO 777
<211> LENGTH: 11
<212> TYPE: DNA
<213> ORGANISM: Artificial Sequence
<220> FEATURE:
<223> OTHER INFORMATION: N11A Sequence

<400> SEQUENCE: 777
gctatttggt a                                                               11

<210> SEQ ID NO 778
<211> LENGTH: 10
<212> TYPE: DNA
<213> ORGANISM: Artificial Sequence
<220> FEATURE:
<223> OTHER INFORMATION: N11A Sequence

<400> SEQUENCE: 778
ctatttggta                                                                 10
```

```
<210> SEQ ID NO 779
<211> LENGTH: 23
<212> TYPE: DNA
<213> ORGANISM: Artificial Sequence
<220> FEATURE:
<223> OTHER INFORMATION: N12A Sequence

<400> SEQUENCE: 779
agccgtcttc aggaatcttc tcc                                              23

<210> SEQ ID NO 780
<211> LENGTH: 22
<212> TYPE: DNA
<213> ORGANISM: Artificial Sequence
<220> FEATURE:
<223> OTHER INFORMATION: N12A Sequence

<400> SEQUENCE: 780
agccgtcttc aggaatcttc tc                                               22

<210> SEQ ID NO 781
<211> LENGTH: 21
<212> TYPE: DNA
<213> ORGANISM: Artificial Sequence
<220> FEATURE:
<223> OTHER INFORMATION: N12A Sequence

<400> SEQUENCE: 781
agccgtcttc aggaatcttc t                                                21

<210> SEQ ID NO 782
<211> LENGTH: 20
<212> TYPE: DNA
<213> ORGANISM: Artificial Sequence
<220> FEATURE:
<223> OTHER INFORMATION: N12A Sequence

<400> SEQUENCE: 782
agccgtcttc aggaatcttc                                                  20

<210> SEQ ID NO 783
<211> LENGTH: 19
<212> TYPE: DNA
<213> ORGANISM: Artificial Sequence
<220> FEATURE:
<223> OTHER INFORMATION: N12A Sequence

<400> SEQUENCE: 783
agccgtcttc aggaatctt                                                   19

<210> SEQ ID NO 784
<211> LENGTH: 18
<212> TYPE: DNA
<213> ORGANISM: Artificial Sequence
<220> FEATURE:
<223> OTHER INFORMATION: N12A Sequence

<400> SEQUENCE: 784
agccgtcttc aggaatct                                                    18

<210> SEQ ID NO 785
<211> LENGTH: 17
<212> TYPE: DNA
<213> ORGANISM: Artificial Sequence
<220> FEATURE:
<223> OTHER INFORMATION: N12A Sequence
```

```
<400> SEQUENCE: 785
agccgtcttc aggaatc                                                      17

<210> SEQ ID NO 786
<211> LENGTH: 16
<212> TYPE: DNA
<213> ORGANISM: Artificial Sequence
<220> FEATURE:
<223> OTHER INFORMATION: N12A Sequence

<400> SEQUENCE: 786
agccgtcttc aggaat                                                       16

<210> SEQ ID NO 787
<211> LENGTH: 15
<212> TYPE: DNA
<213> ORGANISM: Artificial Sequence
<220> FEATURE:
<223> OTHER INFORMATION: N12A Sequence

<400> SEQUENCE: 787
agccgtcttc aggaa                                                        15

<210> SEQ ID NO 788
<211> LENGTH: 14
<212> TYPE: DNA
<213> ORGANISM: Artificial Sequence
<220> FEATURE:
<223> OTHER INFORMATION: N12A Sequence

<400> SEQUENCE: 788
agccgtcttc agga                                                         14

<210> SEQ ID NO 789
<211> LENGTH: 13
<212> TYPE: DNA
<213> ORGANISM: Artificial Sequence
<220> FEATURE:
<223> OTHER INFORMATION: N12A Sequence

<400> SEQUENCE: 789
agccgtcttc agg                                                          13

<210> SEQ ID NO 790
<211> LENGTH: 12
<212> TYPE: DNA
<213> ORGANISM: Artificial Sequence
<220> FEATURE:
<223> OTHER INFORMATION: N12A Sequence

<400> SEQUENCE: 790
agccgtcttc ag                                                           12

<210> SEQ ID NO 791
<211> LENGTH: 11
<212> TYPE: DNA
<213> ORGANISM: Artificial Sequence
<220> FEATURE:
<223> OTHER INFORMATION: N12A Sequence

<400> SEQUENCE: 791
agccgtcttc a                                                            11

<210> SEQ ID NO 792
<211> LENGTH: 10
```

```
<212> TYPE: DNA
<213> ORGANISM: Artificial Sequence
<220> FEATURE:
<223> OTHER INFORMATION: N12A Sequence

<400> SEQUENCE: 792
agccgtcttc                                                          10

<210> SEQ ID NO 793
<211> LENGTH: 27
<212> TYPE: DNA
<213> ORGANISM: Artificial Sequence
<220> FEATURE:
<223> OTHER INFORMATION: N13 Sequence

<400> SEQUENCE: 793
cccagcctgc cccagaagag ctatttg                                       27

<210> SEQ ID NO 794
<211> LENGTH: 26
<212> TYPE: DNA
<213> ORGANISM: Artificial Sequence
<220> FEATURE:
<223> OTHER INFORMATION: N13 Sequence

<400> SEQUENCE: 794
ccagcctgcc ccagaagagc tatttg                                        26

<210> SEQ ID NO 795
<211> LENGTH: 25
<212> TYPE: DNA
<213> ORGANISM: Artificial Sequence
<220> FEATURE:
<223> OTHER INFORMATION: N13 Sequence

<400> SEQUENCE: 795
cagcctgccc cagaagagct atttg                                         25

<210> SEQ ID NO 796
<211> LENGTH: 24
<212> TYPE: DNA
<213> ORGANISM: Artificial Sequence
<220> FEATURE:
<223> OTHER INFORMATION: N13 Sequence

<400> SEQUENCE: 796
agcctgcccc agaagagcta tttg                                          24

<210> SEQ ID NO 797
<211> LENGTH: 23
<212> TYPE: DNA
<213> ORGANISM: Artificial Sequence
<220> FEATURE:
<223> OTHER INFORMATION: N13 Sequence

<400> SEQUENCE: 797
gcctgcccca gaagagctat ttg                                           23

<210> SEQ ID NO 798
<211> LENGTH: 22
<212> TYPE: DNA
<213> ORGANISM: Artificial Sequence
<220> FEATURE:
<223> OTHER INFORMATION: N13 Sequence

<400> SEQUENCE: 798
```
cctgccccag aagagctatt tg                                          22

<210> SEQ ID NO 799
<211> LENGTH: 21
<212> TYPE: DNA
<213> ORGANISM: Artificial Sequence
<220> FEATURE:
<223> OTHER INFORMATION: N13 Sequence

<400> SEQUENCE: 799
ctgccccaga agagctattt g                                           21

<210> SEQ ID NO 800
<211> LENGTH: 20
<212> TYPE: DNA
<213> ORGANISM: Artificial Sequence
<220> FEATURE:
<223> OTHER INFORMATION: N13 Sequence

<400> SEQUENCE: 800
tgccccagaa gagctatttg                                             20

<210> SEQ ID NO 801
<211> LENGTH: 19
<212> TYPE: DNA
<213> ORGANISM: Artificial Sequence
<220> FEATURE:
<223> OTHER INFORMATION: N13 Sequence

<400> SEQUENCE: 801
gccccagaag agctatttg                                              19

<210> SEQ ID NO 802
<211> LENGTH: 18
<212> TYPE: DNA
<213> ORGANISM: Artificial Sequence
<220> FEATURE:
<223> OTHER INFORMATION: N13 Sequence

<400> SEQUENCE: 802
ccccagaaga gctatttg                                               18

<210> SEQ ID NO 803
<211> LENGTH: 17
<212> TYPE: DNA
<213> ORGANISM: Artificial Sequence
<220> FEATURE:
<223> OTHER INFORMATION: N13 Sequence

<400> SEQUENCE: 803
cccagaagag ctatttg                                                17

<210> SEQ ID NO 804
<211> LENGTH: 16
<212> TYPE: DNA
<213> ORGANISM: Artificial Sequence
<220> FEATURE:
<223> OTHER INFORMATION: N13 Sequence

<400> SEQUENCE: 804
ccagaagagc tatttg                                                 16

<210> SEQ ID NO 805
<211> LENGTH: 15
<212> TYPE: DNA
<213> ORGANISM: Artificial Sequence

```
<220> FEATURE:
<223> OTHER INFORMATION: N13 Sequence

<400> SEQUENCE: 805
cagaagagct atttg                                                        15

<210> SEQ ID NO 806
<211> LENGTH: 14
<212> TYPE: DNA
<213> ORGANISM: Artificial Sequence
<220> FEATURE:
<223> OTHER INFORMATION: N13 Sequence

<400> SEQUENCE: 806
agaagagcta tttg                                                         14

<210> SEQ ID NO 807
<211> LENGTH: 13
<212> TYPE: DNA
<213> ORGANISM: Artificial Sequence
<220> FEATURE:
<223> OTHER INFORMATION: N13 Sequence

<400> SEQUENCE: 807
gaagagctat ttg                                                          13

<210> SEQ ID NO 808
<211> LENGTH: 12
<212> TYPE: DNA
<213> ORGANISM: Artificial Sequence
<220> FEATURE:
<223> OTHER INFORMATION: N13 Sequence

<400> SEQUENCE: 808
aagagctatt tg                                                           12

<210> SEQ ID NO 809
<211> LENGTH: 11
<212> TYPE: DNA
<213> ORGANISM: Artificial Sequence
<220> FEATURE:
<223> OTHER INFORMATION: N13 Sequence

<400> SEQUENCE: 809
agagctattt g                                                            11

<210> SEQ ID NO 810
<211> LENGTH: 10
<212> TYPE: DNA
<213> ORGANISM: Artificial Sequence
<220> FEATURE:
<223> OTHER INFORMATION: N13 Sequence

<400> SEQUENCE: 810
gagctatttg                                                              10

<210> SEQ ID NO 811
<211> LENGTH: 27
<212> TYPE: DNA
<213> ORGANISM: Artificial Sequence
<220> FEATURE:
<223> OTHER INFORMATION: N14 Sequence

<400> SEQUENCE: 811
tagggagccg tcttcaggaa tcttctc                                           27
```

```
<210> SEQ ID NO 812
<211> LENGTH: 26
<212> TYPE: DNA
<213> ORGANISM: Artificial Sequence
<220> FEATURE:
<223> OTHER INFORMATION: N14 Sequence

<400> SEQUENCE: 812
tagggagccg tcttcaggaa tcttct                                           26

<210> SEQ ID NO 813
<211> LENGTH: 25
<212> TYPE: DNA
<213> ORGANISM: Artificial Sequence
<220> FEATURE:
<223> OTHER INFORMATION: N14 Sequence

<400> SEQUENCE: 813
tagggagccg tcttcaggaa tcttc                                            25

<210> SEQ ID NO 814
<211> LENGTH: 24
<212> TYPE: DNA
<213> ORGANISM: Artificial Sequence
<220> FEATURE:
<223> OTHER INFORMATION: N14 Sequence

<400> SEQUENCE: 814
tagggagccg tcttcaggaa tctt                                             24

<210> SEQ ID NO 815
<211> LENGTH: 23
<212> TYPE: DNA
<213> ORGANISM: Artificial Sequence
<220> FEATURE:
<223> OTHER INFORMATION: N14 Sequence

<400> SEQUENCE: 815
tagggagccg tcttcaggaa tct                                              23

<210> SEQ ID NO 816
<211> LENGTH: 22
<212> TYPE: DNA
<213> ORGANISM: Artificial Sequence
<220> FEATURE:
<223> OTHER INFORMATION: N14 Sequence

<400> SEQUENCE: 816
tagggagccg tcttcaggaa tc                                               22

<210> SEQ ID NO 817
<211> LENGTH: 21
<212> TYPE: DNA
<213> ORGANISM: Artificial Sequence
<220> FEATURE:
<223> OTHER INFORMATION: N14 Sequence

<400> SEQUENCE: 817
tagggagccg tcttcaggaa t                                                21

<210> SEQ ID NO 818
<211> LENGTH: 20
<212> TYPE: DNA
<213> ORGANISM: Artificial Sequence
<220> FEATURE:
<223> OTHER INFORMATION: N14 Sequence
```

```
<400> SEQUENCE: 818
tagggagccg tcttcaggaa                                                    20

<210> SEQ ID NO 819
<211> LENGTH: 19
<212> TYPE: DNA
<213> ORGANISM: Artificial Sequence
<220> FEATURE:
<223> OTHER INFORMATION: N14 Sequence

<400> SEQUENCE: 819
tagggagccg tcttcagga                                                     19

<210> SEQ ID NO 820
<211> LENGTH: 18
<212> TYPE: DNA
<213> ORGANISM: Artificial Sequence
<220> FEATURE:
<223> OTHER INFORMATION: N14 Sequence

<400> SEQUENCE: 820
tagggagccg tcttcagg                                                      18

<210> SEQ ID NO 821
<211> LENGTH: 17
<212> TYPE: DNA
<213> ORGANISM: Artificial Sequence
<220> FEATURE:
<223> OTHER INFORMATION: N14 Sequence

<400> SEQUENCE: 821
tagggagccg tcttcag                                                       17

<210> SEQ ID NO 822
<211> LENGTH: 16
<212> TYPE: DNA
<213> ORGANISM: Artificial Sequence
<220> FEATURE:
<223> OTHER INFORMATION: N14 Sequence

<400> SEQUENCE: 822
tagggagccg tcttca                                                        16

<210> SEQ ID NO 823
<211> LENGTH: 15
<212> TYPE: DNA
<213> ORGANISM: Artificial Sequence
<220> FEATURE:
<223> OTHER INFORMATION: N14 Sequence

<400> SEQUENCE: 823
tagggagccg tcttc                                                         15

<210> SEQ ID NO 824
<211> LENGTH: 14
<212> TYPE: DNA
<213> ORGANISM: Artificial Sequence
<220> FEATURE:
<223> OTHER INFORMATION: N14 Sequence

<400> SEQUENCE: 824
tagggagccg tctt                                                          14

<210> SEQ ID NO 825
```

```
<211> LENGTH: 13
<212> TYPE: DNA
<213> ORGANISM: Artificial Sequence
<220> FEATURE:
<223> OTHER INFORMATION: N14 Sequence

<400> SEQUENCE: 825
tagggagccg tct                                              13

<210> SEQ ID NO 826
<211> LENGTH: 12
<212> TYPE: DNA
<213> ORGANISM: Artificial Sequence
<220> FEATURE:
<223> OTHER INFORMATION: N14 Sequence

<400> SEQUENCE: 826
tagggagccg tc                                               12

<210> SEQ ID NO 827
<211> LENGTH: 11
<212> TYPE: DNA
<213> ORGANISM: Artificial Sequence
<220> FEATURE:
<223> OTHER INFORMATION: N14 Sequence

<400> SEQUENCE: 827
tagggagccg t                                                11

<210> SEQ ID NO 828
<211> LENGTH: 10
<212> TYPE: DNA
<213> ORGANISM: Artificial Sequence
<220> FEATURE:
<223> OTHER INFORMATION: N14 Sequence

<400> SEQUENCE: 828
tagggagccg                                                  10
```

ANTISENSE-OLIGONUCLEOTIDES AS INHIBITORS OF TGF-R SIGNALING

SEQUENCE LISTING IN ELECTRONIC FORMAT

The present application is filed with an Electronic Sequence Listing as an ASCII text file via EFS-Web. The Electronic Sequence Listing is provided as a file entitled Sequence_Listing.txt, created on May 9, 2017, which is 187,681 bytes in size, and updated by a file entitled ABK009002APCSEQLISTREPLACEMENT.txt, created on Jul. 15, 2019, which is 247,495 bytes in size. The information in the Electronic Sequence Listing is incorporated herein by reference in its entirety.

The present invention relates to antisense-oligonucleotides, their use as inhibitors of TGF-R signaling, pharmaceutical compositions containing such antisense-oligonucleotides and the use for prophylaxis and treatment of neurological, neurodegenerative and hyperproliferative including oncological diseases.

TGF-β exists in three known subtypes in humans, TGF-β1, TGF-β2, and TGF-β3. These are upregulated in neurodegenerative diseases, such as ALS, and some human cancers, and increased expression of this growth factor in pathological conditions of neurodegenerative diseases, acute trauma, and neuro-inflammation and ageing has been demonstrated. Isoforms of transforming growth factor-beta (TGF-β1) are also thought to be involved in the pathogenesis of pre-eclampsia.

Activated TGF-βs exert their effects on the target cell via three different receptor classes: type I (TGFRI), also termed activin-like kinases (ALK; 53 kDa), type II (TGFRII; 70-100 kDa), and type III (TGFRIII; 200-400 kDa. TGF-β receptors are single pass serine/threonine kinase receptors. Whereas type II receptor kinase is constitutively active, type I receptor needs to be activated. This process is initiated through binding of a ligand to TGFRII; this triggers the transient formation of a complex that includes the ligand and receptor types I and II. Taking into account the dimeric composition of the ligand, the receptor complex most likely consists of a tetrameric structure formed by two pairs of each receptor type.

TGF-β signal transduction takes place through its receptors and downstream through Smad proteins. Smad-dependent cellular signal transduction initiated by binding of the TGF-β isoform to a specific TGFRI/II receptor pair, leads to the phosphorylation of intracellular Smads and subsequently the translocation of an activated Smad complex into the nucleus in order to influence specific target gene expression. Signal divergence into other pathways and convergence from neighboring signaling pathways generate a highly complex network. Depending on the environmental and cellular context, TGF-beta signaling results in a variety of different cellular responses such as cellular proliferation, differentiation, motility, and apoptosis in tumor cells. In cancer, TGF-β can affect tumor growth directly (referred to as intrinsic effect of TGF-β signaling) or indirectly (referred to as extrinsic effect) by promoting tumor growth, inducing epithelial-mesenchymal transition (EMT), blocking antitumor immune responses, increasing tumor-associated fibrosis, modulating extracellular matrix (ECN) and cell migration, and finally enhancing angiogenesis. The factors (e.g. concentration, timing, local exposure) determining whether TGF-β signaling has a tumor promoter or suppressor function are a matter of intense research and discussion. Currently, it is postulated that the tumor suppressor function of TGF-β signaling is lost in early stages of cancer similar to recessive loss-of-function mutations in other tumor suppressors. Therefore there are several pharmacological approaches for treatment of divers cancers by blocking TGF-beta signaling pathways, such as investigation of Galunisertib and TEW-7197, both are small molecule inhibitor of TGFRI and being in clinical investigation, and LY3022859, an antibody against TGFRII.

Signals provided by proteins of the transforming growth factor (TGF-β) family represent a system by which neural stem cells are controlled under physiological conditions but in analogy to other cell types are released from this control after transformation to cancer stem cells. TGF-β is a multifunctional cytokine involved in various physiological and patho-physiological processes of the brain. It is induced in the adult brain after injury or hypoxia and during neurodegeneration when it modulates and dampens inflammatory responses. After injury, although TGF-β is in general neuroprotective, it limits the self-repair of the brain by inhibiting neural stem cell proliferation and inducing fibrosis/gliosis for scar formation. Similar to its effect on neural stem cells, TGF-β reveals anti-proliferative control on most cell types; however, paradoxically, many tumors escape from TGF-β control. Moreover, these tumors develop mechanisms that change the anti-proliferative influence of TGF-β into oncogenic cues, mainly by orchestrating a multitude of TGF-β-mediated effects upon matrix, migration and invasion, angiogenesis, and, most importantly, immune escape mechanisms. Thus, TGF-β is involved in tumor progression (see FIG. 3).

Consequently, the TGF Receptor II (transforming growth factor, beta receptor II; synonymously used symbols: TGF-beta type II receptor, TGFBR2; AAT3; FAA3; LDS1B; LDS2; LDS2B; MFS2; RIIC; TAAD2; TGFR-2; TGFbeta-RII, TGF-RII, TGF-$R_{II}$), and in particular its inhibition, was validated as target for the treatment of neurodegenerative diseases, such as ALS, and hyperproliferative diseases such as cancer and fibrotic diseases.

Thus objective of the present application is to provide pharmaceutically active compounds able inhibit expression of the TGF Receptor III (TGF-$R_{II}$) and therefore, reduce the amount of TGF Receptor II (TGF-$R_{II}$) and decrease the activity of TGF-β downstream signaling.

The objective of the present invention is solved by the teaching of the independent claims. Further advantageous features, aspects and details of the invention are evident from the dependent claims, the description, the figures, and the examples of the present application.

Surprisingly under thousands of candidate substances, such as protein-nucleotide complexes, siRNA, microRNA (miRNA), ribozymes, aptamers, CpG-oligos, DNA-zymes, riboswitches, lipids, peptides, small molecules, modifiers of rafts or caveoli, modifiers of golgi apparatus, antibodies and their derivatives, especially chimeras, Fab-fragments, and Fc-fragments, antisense-oligonucleotides containing LNAs (LNA®: Locked Nucleic Acids) were found the most promising candidates for the uses disclosed herein.

Thus, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence TGGTC-CATTC (Seq. ID No. 4) or the sequence CCCTAAACAC (Seq. ID No. 5) or the sequence ACTACCAAAT (Seq. ID No. 6) or the sequence GGACGCGTAT (Seq. ID No. 7) or the sequence GTCTATGACG (Seq. ID No. 8) or the sequence TTATTAATGC (Seq. ID No. 9), and the antisense-oligonucleotide comprises a sequence capable of hybridizing with said sequence TGGTCCATTC (Seq. ID No. 4) or sequence CCCTAAACAC (Seq. ID No. 5) or sequence ACTACCAAAT (Seq. ID No. 6) or sequence GGACGCGTAT (Seq. ID No. 7) or sequence GTCTATGACG (Seq. ID No. 8) or sequence TTATTAATGC (Seq. ID No. 9) respectively and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence TGGTCCATTC (Seq. ID No. 4) or the sequence CCCTAAACAC (Seq. ID No. 5) or the sequence ACTACCAAAT (Seq. ID No. 6) or the sequence GGACGCGTAT (Seq. ID No. 7) or the sequence GTCTATGACG (Seq. ID No. 8) or sequence TTATTAATGC (Seq. ID No. 9), and the antisense-oligonucleotide comprises a sequence capable of hybridizing with said sequence TGGTCCATTC (Seq. ID No. 4) or sequence CCCTAAACAC (Seq. ID No. 5) or sequence ACTACCAAAT (Seq. ID No. 6) or sequence GGACGCGTAT (Seq. ID No. 7) or sequence GTCTATGACG (Seq. ID No. 8) or sequence TTATTAATGC (Seq. ID No. 9) respectively and salts and optical isomers of said antisense-oligonucleotide.

Alternatively the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence TGGTCCATTC (Seq. ID No. 4) or the sequence CCCTAAACAC (Seq. ID No. 5) or the sequence ACTACCAAAT (Seq. ID No. 6) or the sequence GGACGCGTAT (Seq. ID No. 7) or the sequence GTCTATGACG (Seq. ID No. 8) or the sequence TTATTAATGC (Seq. ID No. 9), and the antisense-oligonucleotide comprises a sequence complementary to the sequence TGGTCCATTC (Seq. ID No. 4) or the sequence CCCTAAACAC (Seq. ID No. 5) or the sequence ACTACCAAAT (Seq. ID No. 6) or the sequence GGACGCGTAT (Seq. ID No. 7) or the sequence GTCTATGACG (Seq. ID No. 8) or the sequence TTATTAATGC (Seq. ID No. 9) respectively and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence TGGTCCATTC (Seq. ID No. 4) or the sequence CCCTAAACAC (Seq. ID No. 5) or the sequence ACTACCAAAT (Seq. ID No. 6) or the sequence GGACGCGTAT (Seq. ID No. 7) or the sequence GTCTATGACG (Seq. ID No. 8) or the sequence TTATTAATGC (Seq. ID No. 9), and the antisense-oligonucleotide comprises a sequence complementary to the sequence TGGTCCATTC (Seq. ID No. 4) or the sequence CCCTAAACAC (Seq. ID No. 5) or the sequence ACTACCAAAT (Seq. ID No. 6) or the sequence GGACGCGTAT (Seq. ID No. 7) or the sequence GTCTATGACG (Seq. ID No. 8) or the sequence TTATTAATGC (Seq. ID No. 9) respectively and salts and optical isomers of said antisense-oligonucleotide.

Preferably the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence TGGTCCATTC (Seq. ID No. 4), and the antisense-oligonucleotide comprises a sequence capable of hybridizing with said sequence TGGTCCATTC (Seq. ID No. 4) and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence TGGTCCATTC (Seq. ID No. 4), and the antisense-oligonucleotide comprises a sequence capable of hybridizing with said sequence TGGTCCATTC (Seq. ID No. 4) and salts and optical isomers of said antisense-oligonucleotide.

Alternatively the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence TGGTCCATTC (Seq. ID No. 4), and the antisense-oligonucleotide comprises a sequence complementary to the sequence TGGTCCATTC (Seq. ID No. 4) and salts and optical isomers of said antisense-oligonucleotide.

Slightly reworded consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence TGGTCCATTC (Seq. ID No. 4), and the antisense-oligonucleotide comprises a sequence complementary to the sequence TGGTCCATTC (Seq. ID No. 4) and salts and optical isomers of said antisense-oligonucleotide.

Preferably the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CCCTAAACAC (Seq. ID No. 5), and the antisense-oligonucleotide comprises a sequence capable of hybridizing with said sequence CCCTAAACAC (Seq. ID No. 5) and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence CCCTAAACAC (Seq. ID No. 5), and the antisense-oligonucleotide comprises a sequence capable of hybridizing with said sequence CCCTAAACAC (Seq. ID No. 5) and salts and optical isomers of said antisense-oligonucleotide.

Alternatively the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CCCTAAACAC (Seq. ID No. 5), and the antisense-oligonucleotide comprises a sequence complementary to the sequence CCCTAAACAC (Seq. ID No. 5) and salts and optical isomers of said antisense-oligonucleotide.

Slightly reworded consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence CCCTAAACAC (Seq. ID No. 5), and the antisense-oligonucleotide comprises a sequence complementary to the sequence CCCTAAACAC (Seq. ID No. 5) and salts and optical isomers of said antisense-oligonucleotide.

Preferably the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence ACTACCAAAT (Seq. ID No. 6), and the antisense-oligonucleotide comprises a sequence capable of hybridizing with said sequence ACTACCAAAT (Seq. ID No. 6) and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence ACTACCAAAT (Seq. ID No. 6), and the antisense-oligonucleotide comprises a sequence capable of hybridizing with said sequence ACTACCAAAT (Seq. ID No. 6) and salts and optical isomers of said antisense-oligonucleotide.

Alternatively the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence ACTACCAAAT (Seq. ID No. 6), and the antisense-oligonucleotide comprises a sequence complementary to the sequence ACTACCAAAT (Seq. ID No. 6) and salts and optical isomers of said antisense-oligonucleotide.

Slightly reworded consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence ACTACCAAAT (Seq. ID No. 6), and the antisense-oligonucleotide comprises a sequence complementary to the sequence ACTACCAAAT (Seq. ID No. 6) and salts and optical isomers of said antisense-oligonucleotide.

Preferably the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence GGACGCGTAT (Seq. ID No. 7), and the antisense-oligonucleotide comprises a sequence capable of hybridizing with said sequence GGACGCGTAT (Seq. ID No. 7) and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence GGACGCGTAT (Seq. ID No. 7), and the antisense-oligonucleotide comprises a sequence capable of hybridizing with said sequence GGACGCGTAT (Seq. ID No. 7) and salts and optical isomers of said antisense-oligonucleotide.

Alternatively the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence GGACGCGTAT (Seq. ID No. 7), and the antisense-oligonucleotide comprises a sequence complementary to the sequence GGACGCGTAT (Seq. ID No. 7) and salts and optical isomers of said antisense-oligonucleotide.

Slightly reworded consisting of 10 to 28 nucleotides and at least two of the 10 to 28 nucleotides are LNAs and the antisense-oligonucleotide is capable of hybridizing with a region of the open reading frame of the gene encoding the TGF-R$_{II}$ or with a region of the mRNA encoding the TGF-R$_{II}$, wherein the region of the open reading frame of the gene encoding the TGF-R$_{II}$ or the region of the mRNA encoding the TGF-R$_{II}$ comprises the sequence GGACGCGTAT (Seq. ID No. 7), and the antisense-oligonucleotide comprises a sequence complementary to the sequence GGACGCGTAT (Seq. ID No. 7) and salts and optical isomers of said antisense-oligonucleotide.

Preferably the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence GTCTATGACG (Seq. ID No. 8), and the antisense-oligonucleotide comprises a sequence capable of hybridizing with said sequence GTCTATGACG (Seq. ID No. 8) and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-$R_{II}$ or with a region of the mRNA encoding the TGF-$R_{II}$, wherein the region of the open reading frame of the gene encoding the TGF-$R_{II}$ or the region of the mRNA encoding the TGF-$R_{II}$ comprises the sequence GTCTATGACG (Seq. ID No. 8), and the antisense-oligonucleotide comprises a sequence capable of hybridizing with said sequence GTCTATGACG (Seq. ID No. 8) and salts and optical isomers of said antisense-oligonucleotide.

Alternatively the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence GTCTATGACG (Seq. ID No. 8), and the antisense-oligonucleotide comprises a sequence complementary to the sequence GTCTATGACG (Seq. ID No. 8) and salts and optical isomers of said antisense-oligonucleotide.

Slightly reworded consisting of 10 to 28 nucleotides and at least two of the 10 to 28 nucleotides are LNAs and the antisense-oligonucleotide is capable of hybridizing with a region of the open reading frame of the gene encoding the TGF-$R_{II}$ or with a region of the mRNA encoding the TGF-$R_{II}$, wherein the region of the open reading frame of the gene encoding the TGF-$R_{II}$ or the region of the mRNA encoding the TGF-$R_{II}$ comprises the sequence GTCTATGACG (Seq. ID No. 8), and the antisense-oligonucleotide comprises a sequence complementary to the sequence GTCTATGACG (Seq. ID No. 8) and salts and optical isomers of said antisense-oligonucleotide.

Preferably the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence TTATTAATGC (Seq. ID No. 9), and the antisense-oligonucleotide comprises a sequence capable of hybridizing with said sequence TTATTAATGC (Seq. ID No. 9) and salts and optical isomers of said antisense-oligonucleotide.

Slightly reworded the present invention is directed to antisense-oligonucleotide(s) consisting of 10 to 28 nucleotides and at least two of the 10 to 28 nucleotides are LNAs and the antisense-oligonucleotide is capable of hybridizing with a region of the open reading frame of the gene encoding the TGF-$R_{II}$ or with a region of the mRNA encoding the TGF-$R_{II}$, wherein the region of the open reading frame of the gene encoding the TGF-$R_{II}$ or the region of the mRNA encoding the TGF-$R_{II}$ comprises the sequence TTATTAATGC (Seq. ID No. 9), and the antisense-oligonucleotide comprises a sequence capable of hybridizing with said sequence TTATTAATGC (Seq. ID No. 9) and salts and optical isomers of said antisense-oligonucleotide.

Alternatively the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence TTATTAATGC (Seq. ID No. 9), and the antisense-oligonucleotide comprises a sequence complementary to the sequence TTATTAATGC (Seq. ID No. 9) and salts and optical isomers of said antisense-oligonucleotide.

Slightly reworded consisting of 10 to 28 nucleotides and at least two of the 10 to 28 nucleotides are LNAs and the antisense-oligonucleotide is capable of hybridizing with a region of the open reading frame of the gene encoding the TGF-$R_{II}$ or with a region of the mRNA encoding the TGF-$R_{II}$, wherein the region of the open reading frame of the gene encoding the TGF-$R_{II}$ or the region of the mRNA encoding the TGF-$R_{II}$ comprises the sequence TTATTAATGC (Seq. ID No. 9), and the antisense-oligonucleotide comprises a sequence complementary to the sequence TTATTAATGC (Seq. ID No. 9) and salts and optical isomers of said antisense-oligonucleotide.

The antisense-oligonucleotides of the present invention preferably comprise 2 to 10 LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention which contain 3 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units.

Moreover, the antisense-oligonucleotides may contain common nucleobases such as adenine, guanine, cytosine, thymine and uracil as well as common derivatives thereof. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide.

Thus, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-R$_{II}$ or the region of the mRNA encoding the TGF-R$_{II}$ comprises the sequence CTGGTCCATTC (Seq. ID No. 296), TGGTCCATTCA (Seq. ID No. 297), CTGGTCCATTCA (Seq. ID No. 298), TCCCTAAACAC (Seq. ID No. 299), CCCTAAACACT (Seq. ID No. 300), TCCCTAAACACT (Seq. ID No. 301), CACTACCAAAT (Seq. ID No. 302), ACTACCAAATA (Seq. ID No. 303), CACTACCAAATA (Seq. ID No. 304), TGGACGCGTAT (Seq. ID No. 305), GGACGCGTATC (Seq. ID No. 306), TGGACGCGTATC (Seq. ID No. 307), GGTCTATGACG (Seq. ID No. 308), GTCTATGACGA (Seq. ID No. 309), GGTCTATGACGA (Seq. ID No. 310), TTTATTAATGC (Seq. ID No. 311), TTATTAATGCC (Seq. ID No. 312), or TTTATTAATGCC (Seq. ID No. 313), and the antisense-oligonucleotide comprises a sequence capable of hybridizing with said sequence CTGGTCCATTC (Seq. ID No. 296), TGGTCCATTCA (Seq. ID No. 297), CTGGTCCATTCA (Seq. ID No. 298), TCCCTAAACAC (Seq. ID No. 299), CCCTAAACACT (Seq. ID No. 300), TCCCTAAACACT (Seq. ID No. 301), CACTACCAAAT (Seq. ID No. 302), ACTACCAAATA (Seq. ID No. 303), CACTACCAAATA (Seq. ID No. 304), TGGACGCGTAT (Seq. ID No. 305), GGACGCGTATC (Seq. ID No. 306), TGGACGCGTATC (Seq. ID No. 307), GGTCTATGACG (Seq. ID No. 308), GTCTATGACGA (Seq. ID No. 309), GGTCTATGACGA (Seq. ID No. 310), TTTATTAATGC (Seq. ID No. 311), TTATTAATGCC (Seq. ID No. 312), or TTTATTAATGCC (Seq. ID No. 313) respectively and salts and optical isomers of said antisense-oligonucleotide.

Alternatively the present invention is directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CTGGTCCATTC (Seq. ID No. 296), TGGTCCATTCA (Seq. ID No. 297), CTGGTCCATTCA (Seq. ID No. 298), TCCCTAAACAC (Seq. ID No. 299), CCCTAAACACT (Seq. ID No. 300), TCCCTAAACACT (Seq. ID No. 301), CACTACCAAAT (Seq. ID No. 302), ACTACCAAATA (Seq. ID No. 303), CACTACCAAATA (Seq. ID No. 304), TGGACGCGTAT (Seq. ID No. 305), GGACGCGTATC (Seq. ID No. 306), TGGACGCGTATC (Seq. ID No. 307), GGTCTATGACG (Seq. ID No. 308), GTCTATGACGA (Seq. ID No. 309), GGTCTATGACGA (Seq. ID No. 310), TTTATTAATGC (Seq. ID No. 311), TTATTAATGCC (Seq. ID No. 312), or TTTATTAATGCC (Seq. ID No. 313), and the antisense-oligonucleotide comprises a sequence complementary to the sequence CTGGTCCATTC (Seq. ID No. 296), TGGTCCATTCA (Seq. ID No. 297), CTGGTCCATTCA (Seq. ID No. 298), TCCCTAAACAC (Seq. ID No. 299), CCCTAAACACT (Seq. ID No. 300), TCCCTAAACACT (Seq. ID No. 301), CACTACCAAAT (Seq. ID No. 302), ACTACCAAATA (Seq. ID No. 303), CACTACCAAATA (Seq. ID No. 304), TGGACGCGTAT (Seq. ID No. 305), GGACGCGTATC (Seq. ID No. 306), TGGACGCGTATC (Seq. ID No. 307), GGTCTATGACG (Seq. ID No. 308), GTCTATGACGA (Seq. ID No. 309), GGTCTATGACGA (Seq. ID No. 310), TTTATTAATGC (Seq. ID No. 311), TTATTAATGCC (Seq. ID No. 312), or TTTATTAATGCC (Seq. ID No. 313) respectively and salts and optical isomers of said antisense-oligonucleotide.

Preferably, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CTGGTCCATTC (Seq. ID No. 296), TGGTCCATTCA (Seq. ID No. 297), or CTGGTCCATTCA (Seq. ID No. 298), and the antisense-oligonucleotide comprises a sequence capable of hybridizing with said sequence CTGGTCCATTC (Seq. ID No. 296), TGGTCCATTCA (Seq. ID No. 297), or CTGGTCCATTCA (Seq. ID No. 298) respectively and salts and optical isomers of said antisense-oligonucleotide.

Slightly reworded, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CTGGTCCATTC (Seq. ID No. 296), TGGTCCATTCA (Seq. ID No. 297), or CTGGTCCATTCA (Seq. ID No. 298), and the antisense-oligonucleotide comprises a sequence complementary to the sequence CTGGTCCATTC (Seq. ID No. 296), TGGTCCATTCA (Seq. ID No. 297), or CTGGTCCATTCA (Seq. ID No. 298) respectively and salts and optical isomers of said antisense-oligonucleotide.

Preferably, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence TCCCTAAACAC (Seq. ID No. 299), CCCTAAACACT (Seq. ID No. 300), or TCCCTAAACACT (Seq. ID No. 301), and the antisense-oligonucleotide comprises a sequence capable of hybridizing with said sequence TCCCTAAACAC (Seq. ID No. 299), CCCTAAACACT (Seq. ID No. 300), or TCCCTAAACACT (Seq. ID No. 301) respectively and salts and optical isomers of said antisense-oligonucleotide.

Slightly reworded, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence TCCCTAAACAC (Seq. ID No. 299), CCCTAAACACT (Seq. ID No. 300), or TCCCTAAACACT (Seq. ID No. 301), and the antisense-oligonucleotide comprises a sequence complementary to the sequence TCCCTAAACAC (Seq. ID No. 299), CCCTAAACACT (Seq. ID No. 300), or TCCCTAAACACT (Seq. ID No. 301) respectively and salts and optical isomers of said antisense-oligonucleotide.

Preferably, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CACTACCAAAT (Seq. ID No. 302), ACTACCAAATA (Seq. ID No.

303), or CACTACCAAATA (Seq. ID No. 304), and the antisense-oligonucleotide comprises a sequence capable of hybridizing with said sequence CACTACCAAAT (Seq. ID No. 302), ACTACCAAATA (Seq. ID No. 303), or CACTACCAAATA (Seq. ID No. 304) respectively and salts and optical isomers of said antisense-oligonucleotide.

Slightly reworded, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence CACTACCAAAT (Seq. ID No. 302), ACTACCAAATA (Seq. ID No. 303), or CACTACCAAATA (Seq. ID No. 304), and the antisense-oligonucleotide comprises a sequence complementary to the sequence CACTACCAAAT (Seq. ID No. 302), ACTACCAAATA (Seq. ID No. 303), or CACTACCAAATA (Seq. ID No. 304) respectively and salts and optical isomers of said antisense-oligonucleotide.

Preferably, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence TGGACGCGTAT (Seq. ID No. 305), GGACGCGTATC (Seq. ID No. 306), or TGGACGCGTATC (Seq. ID No. 307), and the antisense-oligonucleotide comprises a sequence capable of hybridizing with said sequence TGGACGCGTAT (Seq. ID No. 305), GGACGCGTATC (Seq. ID No. 306), or TGGACGCGTATC (Seq. ID No. 307) respectively and salts and optical isomers of said antisense-oligonucleotide.

Slightly reworded, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence TGGACGCGTAT (Seq. ID No. 305), GGACGCGTATC (Seq. ID No. 306), or TGGACGCGTATC (Seq. ID No. 307), and the antisense-oligonucleotide comprises a sequence complementary to the sequence TGGACGCGTAT (Seq. ID No. 305), GGACGCGTATC (Seq. ID No. 306), or TGGACGCGTATC (Seq. ID No. 307) respectively and salts and optical isomers of said antisense-oligonucleotide.

Preferably, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence GGTCTATGACG (Seq. ID No. 308), GTCTATGACGA (Seq. ID No. 309), or GGTCTATGACGA (Seq. ID No. 310), and the antisense-oligonucleotide comprises a sequence capable of hybridizing with said sequence GGTCTATGACG (Seq. ID No. 308), GTCTATGACGA (Seq. ID No. 309), or GGTCTATGACGA (Seq. ID No. 310) respectively and salts and optical isomers of said antisense-oligonucleotide.

Slightly reworded, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence GGTCTATGACG (Seq. ID No. 308), GTCTATGACGA (Seq. ID No. 309), or GGTCTATGACGA (Seq. ID No. 310), and the antisense-oligonucleotide comprises a sequence complementary to the sequence GGTCTATGACG (Seq. ID No. 308), GTCTATGACGA (Seq. ID No. 309), or GGTCTATGACGA (Seq. ID No. 310) respectively and salts and optical isomers of said antisense-oligonucleotide.

Preferably, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence TTTATTAATGC (Seq. ID No. 311), TTATTAATGCC (Seq. ID No. 312), or TTTATTAATGCC (Seq. ID No. 313), and the antisense-oligonucleotide comprises a sequence capable of hybridizing with said sequence TTTATTAATGC (Seq. ID No. 311), TTATTAATGCC (Seq. ID No. 312), or TTTATTAATGCC (Seq. ID No. 313) respectively and salts and optical isomers of said antisense-oligonucleotide.

Slightly reworded, the present invention is also directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence TTTATTAATGC (Seq. ID No. 311), TTATTAATGCC (Seq. ID No. 312), or TTTATTAATGCC (Seq. ID No. 313), and the antisense-oligonucleotide comprises a sequence complementary to the sequence TTTATTAATGC (Seq. ID No. 311), TTATTAATGCC (Seq. ID No. 312), or TTTATTAATGCC (Seq. ID No. 313) respectively and salts and optical isomers of said antisense-oligonucleotide.

The antisense-oligonucleotides of the present invention preferably comprise 3 to 10 LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention which contain 3 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units.

Moreover, the antisense-oligonucleotides may contain common nucleobases such as adenine, guanine, cytosine, thymine and uracil as well as common derivatives thereof. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide.

Thus, the present invention is also directed to antisense-oligonucleotide(s) consisting of 14 to 20 more preferably 14 to 18 nucleotides and at least four of the 14 to 20 more preferably 14 to 18 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence ACTGGTCCATTC (Seq. ID No. 314), TGGTCCATTCAT (Seq. ID No. 315), CTGGTCCATTCAT (Seq. ID No. 316), ACTGGTCCATTCA (Seq. ID No. 317), ACTGGTCCATTCAT (Seq. ID No. 318), CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), CTCCCTAAACACTA (Seq. ID No. 323), ACACTACCAAAT (Seq. ID No. 324), ACTACCAAATAG (Seq. ID No. 325), CACTACCAAATAG (Seq. ID No. 326), ACACTACCAAATA (Seq. ID No. 327), ACACTACCAAATAG (Seq. ID No. 328), GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), GTGGACGCGTATCG (Seq. ID No. 333), CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), CGGTCTATGACGAG (Seq. ID No. 338), CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), and the antisense-oligonucleotide comprises a sequence capable of hybridizing with said sequence ACTGGTCCATTC (Seq. ID No. 314), TGGTCCATTCAT (Seq. ID No. 315), CTGGTCCATTCAT (Seq. ID No. 316), ACTGGTCCATTCA (Seq. ID No. 317), ACTGGTCCATTCAT (Seq. ID No. 318), CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), CTCCCTAAACACTA (Seq. ID No. 323), ACACTACCAAAT (Seq. ID No. 324), ACTACCAAATAG (Seq. ID No. 325), CACTACCAAATAG (Seq. ID No. 326), ACACTACCAAATA (Seq. ID No. 327), ACACTACCAAATAG (Seq. ID No. 328), GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), GTGGACGCGTATCG (Seq. ID No. 333), CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), CGGTCTATGACGAG (Seq. ID No. 338), CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), respectively and salts and optical isomers of said antisense-oligonucleotide.

Alternatively the present invention is directed to antisense-oligonucleotide(s) consisting of 14 to 20 more preferably 14 to 18 nucleotides and at least four of the 14 to 20 more preferably 14 to 18 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence ACTGGTCCATTC (Seq. ID No. 314), TGGTCCATTCAT (Seq. ID No. 315), CTGGTCCATTCAT (Seq. ID No. 316), ACTGGTCCATTCA (Seq. ID No. 317), ACTGGTCCATTCAT (Seq. ID No. 318), CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), CTCCCTAAACACTA (Seq. ID No. 323), ACACTACCAAAT (Seq. ID No. 324), ACTACCAAATAG (Seq. ID No. 325), CACTACCAAATAG (Seq. ID No. 326), ACACTACCAAATA (Seq. ID No. 327), ACACTACCAAATAG (Seq. ID No. 328), GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), GTGGACGCGTATCG (Seq. ID No. 333), CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), CGGTCTATGACGAG (Seq. ID No. 338), CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), and the antisense-oligonucleotide comprises a sequence complementary to the sequence ACTGGTCCATTC (Seq. ID No. 314), TGGTCCATTCAT (Seq. ID No. 315), CTGGTCCATTCAT (Seq. ID No. 316), ACTGGTCCATTCA (Seq. ID No. 317), ACTGGTCCATTCAT (Seq. ID No. 318), CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), CTCCCTAAACACTA (Seq. ID No. 323), ACACTACCAAAT (Seq. ID No. 324), ACTACCAAATAG (Seq. ID No. 325), CACTACCAAATAG (Seq. ID No. 326), ACACTACCAAATA (Seq. ID No. 327), ACACTACCAAATAG (Seq. ID No. 328), GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), GTGGACGCGTATCG (Seq. ID No. 333), CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), CGGTCTATGACGAG (Seq. ID No. 338), CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), respectively and salts and optical isomers of said antisense-oligonucleotide.

Preferably the present invention is also directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence ACTGGTCCATTC (Seq. ID No. 314), TGGTCCATTCAT (Seq. ID No. 315), CTGGTCCATTCAT (Seq. ID No. 316), ACTGGTCCATTCA (Seq. ID No. 317), ACTGGTCCATTCAT (Seq.

ID No. 318), and the antisense-oligonucleotide comprises a sequence capable of hybridizing with said sequence ACTGGTCCATTC (Seq. ID No. 314), TGGTCCATTCAT (Seq. ID No. 315), CTGGTCCATTCAT (Seq. ID No. 316), ACTGGTCCATTCA (Seq. ID No. 317), ACTGGTCCATTCAT (Seq. ID No. 318), respectively and salts and optical isomers of said antisense-oligonucleotide.

Slightly reworded, the present invention is directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence ACTGGTCATTC (Seq. ID No. 314), TGGTCCATTCAT (Seq. ID No. 315), CTGGTCCATTCAT (Seq. ID No. 316), ACTGGTCATTCA (Seq. ID No. 317), or ACTGGTCCATTCAT (Seq. ID No. 318), and the antisense-oligonucleotide comprises a sequence complementary to the sequence ACTGGTCATTC (Seq. ID No. 314), TGGTCCATTCAT (Seq. ID No. 315), CTGGTCCATTCAT (Seq. ID No. 316), ACTGGTCATTCA (Seq. ID No. 317), or ACTGGTCCATTCAT (Seq. ID No. 318), respectively and salts and optical isomers of said antisense-oligonucleotide.

Preferably the present invention is also directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), or CTCCCTAAACACTA (Seq. ID No. 323), and the antisense-oligonucleotide comprises a sequence capable of hybridizing with said sequence CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), or CTCCCTAAACACTA (Seq. ID No. 323), respectively and salts and optical isomers of said antisense-oligonucleotide.

Slightly reworded, the present invention is directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), or CTCCCTAAACACTA (Seq. ID No. 323), and the antisense-oligonucleotide comprises a sequence complementary to the sequence CTCCCTAAACAC (Seq. ID No. 319), CCCTAAACACTA (Seq. ID No. 320), TCCCTAAACACTA (Seq. ID No. 321), CTCCCTAAACACT (Seq. ID No. 322), or CTCCCTAAACACTA (Seq. ID No. 323), respectively and salts and optical isomers of said antisense-oligonucleotide.

Preferably the present invention is also directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence ACACTACCAAAT (Seq. ID No. 324), ACTACCAAATAG (Seq. ID No. 325), CACTACCAAATAG (Seq. ID No. 326), ACACTACCAAATA (Seq. ID No. 327), or ACACTACCAAATAG (Seq. ID No. 328), and the antisense-oligonucleotide comprises a sequence capable of hybridizing with said sequence ACACTACCAAAT (Seq. ID No. 324), ACTACCAAATAG (Seq. ID No. 325), CACTACCAAATAG (Seq. ID No. 326), ACACTACCAAATA (Seq. ID No. 327), or ACACTACCAAATAG (Seq. ID No. 328), respectively and salts and optical isomers of said antisense-oligonucleotide.

Slightly reworded, the present invention is directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence ACACTACCAAAT (Seq. ID No. 324), ACTACCAAATAG (Seq. ID No. 325), CACTACCAAATAG (Seq. ID No. 326), ACACTACCAAATA (Seq. ID No. 327), or ACACTACCAAATAG (Seq. ID No. 328), and the antisense-oligonucleotide comprises a sequence complementary to the sequence ACACTACCAAAT (Seq. ID No. 324), ACTACCAAATAG (Seq. ID No. 325), CACTACCAAATAG (Seq. ID No. 326), ACACTACCAAATA (Seq. ID No. 327), or ACACTACCAAATAG (Seq. ID No. 328), respectively and salts and optical isomers of said antisense-oligonucleotide.

Preferably the present invention is also directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), or GTGGACGCGTATCG (Seq. ID No. 333), and the antisense-oligonucleotide comprises a sequence capable of hybridizing with said sequence GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), or GTGGACGCGTATCG (Seq. ID No. 333), respectively and salts and optical isomers of said antisense-oligonucleotide.

Slightly reworded, the present invention is directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-R$_{II}$ or with a region of the mRNA encoding the TGF-R$_{II}$, wherein the region of the gene encoding the TGF-R$_{II}$ or the region of the mRNA encoding the TGF-R$_{II}$ comprises the sequence GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), or GTGGACGCGTATCG (Seq. ID No. 333), and the antisense-oligonucleotide comprises a sequence complementary to the sequence GTGGACGCGTAT (Seq. ID No. 329), GGACGCGTATCG (Seq. ID No. 330), TGGACGCGTATCG (Seq. ID No. 331), GTGGACGCGTATC (Seq. ID No. 332), or GTGGACGCGTATCG (Seq. ID No. 333), respectively and salts and optical isomers of said antisense-oligonucleotide.

Preferably the present invention is also directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), or CGGTCTATGACGAG (Seq. ID No. 338), and the antisense-oligonucleotide comprises a sequence capable of hybridizing with said sequence CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), or CGGTCTATGACGAG (Seq. ID No. 338), respectively and salts and optical isomers of said antisense-oligonucleotide.

Slightly reworded, the present invention is directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), or CGGTCTATGACGAG (Seq. ID No. 338), and the antisense-oligonucleotide comprises a sequence complementary to the sequence CGGTCTATGACG (Seq. ID No. 334), GTCTATGACGAG (Seq. ID No. 335), GGTCTATGACGAG (Seq. ID No. 336), CGGTCTATGACGA (Seq. ID No. 337), or CGGTCTATGACGAG (Seq. ID No. 338), respectively and salts and optical isomers of said antisense-oligonucleotide.

Preferably the present invention is also directed to antisense-oligonucleotide(s) consisting of 14 to 20 more preferably 14 to 18 nucleotides and at least four of the 14 to more preferably 14 to 18 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), and the antisense-oligonucleotide comprises a sequence capable of hybridizing with said sequence CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), respectively and salts and optical isomers of said antisense-oligonucleotide.

Slightly reworded, the present invention is directed to antisense-oligonucleotide(s) consisting of 14 to 20 more preferably 14 to 18 nucleotides and at least four of the 14 to 20 more preferably 14 to 18 nucleotides are LNAs and the antisense-oligonucleotide is capable of hybridizing with a region of the gene encoding the TGF-$R_{II}$ or with a region of the mRNA encoding the TGF-$R_{II}$, wherein the region of the gene encoding the TGF-$R_{II}$ or the region of the mRNA encoding the TGF-$R_{II}$ comprises the sequence CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), and the antisense-oligonucleotide comprises a sequence complementary to the sequence CTTTATTAATGC (Seq. ID No. 339), TTATTAATGCCT (Seq. ID No. 340), TTTATTAATGCCT (Seq. ID No. 341), CTTTATTAATGCC (Seq. ID No. 342), or CTTTATTAATGCCT (Seq. ID No. 343), respectively and salts and optical isomers of said antisense-oligonucleotide.

The antisense-oligonucleotides of the present invention preferably comprise 4 to 11 LNA units, more preferably 4 to 10 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention which contain 3 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units.

Moreover, the antisense-oligonucleotides may contain common nucleobases such as adenine, guanine, cytosine, thymine and uracil as well as common derivatives thereof. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide.

Thus, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^1$-GTCATAGA-$N^2$-3' (Seq. ID No. 12) or 5'-$N^3$-ACGCGTCC-$N^4$-3' (Seq. ID No. 98) or 5'-$N^{11}$-TGTT-TAGG-$N^{12}$-3' (Seq. ID No. 10) or 5'-$N^5$-TTTGGTAG-$N^6$-3' (Seq. ID No. 11) or 5'-$N^7$-AATGGACC-$N^8$-3' (Seq. ID No. 100) or 5'-$N^9$-ATTAATAA-$N^{10}$-3' (Seq. ID No. 101), wherein $N^1$ represents: CATGGCAGACCCCGCTGCTC- (Seq. ID No. 509), ATGGCAGACCCCGCTGCTC- (Seq. ID No. 510), TGGCAGACCCCGCTGCTC- (Seq. ID No. 511), GGCAGACCCCGCTGCTC- (Seq. ID No. 512), GCAGACCCCGCTGCTC- (Seq. ID No. 513), CAGACCCCGCTGCTC- (Seq. ID No. 514), AGACCCCGCTGCTC- (Seq. ID No. 515), GACCCCGCTGCTC- (Seq. ID No. 516), ACCCCGCTGCTC- (Seq. ID No. 517), CCCCGCTGCTC- (Seq. ID No. 518), CCCGCTGCTC- (Seq. ID No. 519), CCGCTGCTC-, CGCTGCTC-, GCTGCTC-, CTGCTC-, TGCTC-, GCTC-, CTC-, TC-, or C-;

N² represents: -C, -CC, -CCG, -CCGA, -CCGAG, -CCGAGC, -CCGAGCC, -CCGAGCCC, -CCGAGCCCC, -CCGAGCCCCC (Seq. ID No. 520), -CCGAGCCCCCA (Seq. ID No. 521), -CCGAGCCCCCAG (Seq. ID No. 522), -CCGAGCCCCCAGC (Seq. ID No. 523), -CCGAGCCCCCAGCG (Seq. ID No. 524), -CCGAGCCCCCAGCGC (Seq. ID No. 525), -CCGAGCCCCCAGCGCA (Seq. ID No. 526), -CCGAGCCCCCAGCGCAG (Seq. ID No. 527), -CCGAGCCCCCAGCGCAGC (Seq. ID No. 528), -CCGAGCCCCCAGCGCAGCGjeq ID No. 529), or -CCGAGCCCCCAGCGCAGCGG (Seq. ID No. 530);

N³ represents: GGTGGGATCGTGCTGGCGAT- (Seq. ID No. 531), GTGGGATCGTGCTGGCGAT- (Seq. ID No. 532), TGGGATCGTGCTGGCGAT- (Seq. ID No. 533), GGGATCGTGCTGGCGAT- (Seq. ID No. 534), GGATCGTGCTGGCGAT- (Seq. ID No. 535), GATCGTGCTGGCGAT- (Seq. ID No. 536), ATCGTGCTGGCGAT- (Seq. ID No. 537), TCGTGCTGGCGAT- (Seq. ID No. 538), CGTGCTGGCGAT- (Seq. ID No. 539), GTGCTGGCGAT- (Seq. ID No. 540), TGCTGGCGAT- (Seq. ID No. 541), GCTGGCGAT-, CTGGCGAT-, TGGCGAT-, GGCGAT-, GCGAT-, CGAT-, GAT-, AT-, or T-;

N⁴ represents: -ACAGGACGATGTGCAGCGGC (Seq. ID No. 542), -ACAGGACGATGTGCAGCGG (Seq. ID No. 543), -ACAGGACGATGTGCAGCG (Seq. ID No. 544), -ACAGGACGATGTGCAGC (Seq. ID No. 545), -ACAGGACGATGTGCAG (Seq ID No. 546), -ACAGGACGATGTGCA (Seq. ID No. 547), -ACAGGACGATGTGC (Seq. ID No. 548), -ACAGGACGATGTG (Seq. ID No. 549), -ACAGGACGATGT (Seq. ID No. 550), -ACAGGACGATG (Seq. ID No. 551), -ACAGGACGAT (Seq. ID No. 552), -ACAGGACGA, -ACAGGACG, -ACAGGAC, -ACAGGA, -ACAGG, -ACAG, -ACA, -AC, or -A;

N⁵ represents: GCCCAGCCTGCCCCAGAAGAGCTA- (Seq. ID No. 553), CCCAGCCTGCCCCAGAAGAGCTA- (Seq. ID No. 554), CCAGCCTGCCCCAGAAGAGCTA- (Seq. ID No. 555), CAGCCTGCCCCAGAAGAGCTA- (Seq. ID No. 556), AGCCTGCCCCAGAAGAGCTA- (Seq. ID No. 557), GCCTGCCCCAGAAGAGCTA- (Seq. ID No. 558), CCTGCCCCAGAAGAGCTA- (Seq. ID No. 559), CTGCCCCAGAAGAGCTA- (Seq. ID No. 560), TGCCCCAGAAGAGCTA- (Seq. ID No. 561), GCCCCAGAAGAGCTA- (Seq. ID No. 562), CCCCAGAAGAGCTA- (Seq. ID No. 563), CCCAGAAGAGCTA- (Seq. ID No. 564), CCAGAAGAGCTA- (Seq. ID No. 565), CAGAAGAGCTA- (Seq. ID No. 566), AGAAGAGCTA- (Seq. ID No. 567), GAAGAGCTA-, AAGAGCTA-, AGAGCTA-, GAGCTA-, AGCTA-, GCTA-, CTA-, TA-, or A-;

N⁶ represents: -TGTTTAGGGAGCCGTCTTCAGGAA (Seq. ID No. 568), -TGTTTAGGGAGCCGTCTTCAGGA (Seq. ID No. 569), -TGTTTAGGGAGCCGTCTTCAGG (Seq. ID No. 570), -TGTTTAGGGAGCCGTCTTCAG (Seq. ID No. 571), -TGTTTAGGGAGCCGTCTTCA (Seq. ID No. 572), -TGTTTAGGGAGCCGTCTTC (Seq. ID No. 573), -TGTTTAGGGAGCCGTCTT (Seq. ID No. 574). -TGTTTAGGGAGCCGTCT (Seq. ID No. 575), -TGTT-TAGGGAGCCGTC (Seq. ID No. 576), -TGTTTAGG-GAGCCGT (Seq. ID No. 577), -TGTTTAGGGAGCCG (Seq. ID No. 578), -TGTTTAGGGAGCC (Seq. ID No. 579), -TGTTTAGGGAGC (Seq. ID No. 580), -TGTT-TAGGGAG (Seq. ID No. 581), -TGTTTAGGGA (Seq. ID No. 582), -TGTTTAGGG, -TGTTTAGG, -TGTTTAG, -TGTTTA, -TGTTT, -TGTT, -TGT, -TG, or -T;

N⁷ represents: TGAATCTTGAATATCTCATG- (Seq. ID No. 583), GAATCTTGAATATCTCATG- (Seq. ID No. 584), AATCTTGAATATCTCATG- (Seq. ID No. 585), ATCTTGAATATCTCATG- (Seq. ID No. 586), TCTT-GAATATCTCATG- (Seq. ID No. 587), CTTGAATATCT-CATG- (Seq. ID No. 588), TTGAATATCTCATG- (Seq. ID No. 589), TGAATATCTCATG- (Seq. ID No. 590), GAATATCTCATG- (Seq. ID No. 591), AATATCTCATG- (Seq. ID No. 592), ATATCTCATG- (Seq. ID No. 593), TATCTCATG-, ATCTCATG-, TCTCATG-, CTCATG-, TCATG-, CATG-, ATG-, TG-, or G-;

N⁸ represents: -AGTATTCTAGAAACTCACCA (Seq. ID No. 594), -AGTATTCTAGAAACTCACC (Seq. ID No. 595), -AGTATTCTAGAAACTCAC (Seq. ID No. 596), -AGTATTCTAGAAACTCA (Seq. ID No. 597), -AGTAT-TCTAGAAACTC (Seq. ID No. 598), -AGTAT-TCTAGAAACT (Seq. ID No. 599), -AGTATTCTAGAAAC (Seq. ID No. 600), -AGTATTCTAGAAA (Seq. ID No. 601), -AGTATTCTAGAA (Seq. ID No. 602), -AGTATTCTAGA (Seq. ID No. 603), -AGTATTCTAG (Seq. ID No. 604), -AGTATTCTA, -AGTATTCT, -AGTATTC, -AGTATT, -AGTAT, -AGTA, -AGT, -AG, or -A;

N⁹ represents: ATTCATATTTATATACAGGC- (Seq. ID No. 605), TTCATATTTATATACAGGC- (Seq. ID No. 606), TCATATTTATATACAGGC- (Seq. ID No. 607), CATATT-TATATACAGGC- (Seq. ID No. 608), ATATTTATATA-CAGGC- (Seq. ID No. 69, TATTTATATACAGGC- (Seq. ID No. 610), ATTTATATACAGGC- (Seq. ID No. 611), TTTATATACAGGC- (Seq. ID No. 612), TTATATA-CAGGC- (Seq. ID No. 613), TATATACAGGC- (Seq. ID No. 614), ATATACAGGC- (Seq. ID No. 615), TATA-CAGGC-, ATACAGGC-, TACAGGC-, ACAGGC-, CAGGC-, AGGC-, GGC-, GC-, or C-;

N¹⁰ represents: -AGTGCAAATGTTATTGGCTA (Seq. ID No. 616), -AGTGCAAATGTTATTGGCT (Seq. ID No. 617), -AGTGCAAATGTTATTGGC (Seq. ID No. 618), -AGTGCAAATGTTATTGG (Seq. ID No. 619), -AGTGCAAATGTTATTG (Seq. ID No. 620), -AGTGCAAATGTTATT (Seq. ID No. 621), -AGTGCAAATGTTAT (Seq. ID No. 622), -AGTGCAAATGTTA (Seq. ID No. 623), -AGTGCAAATGTT (Seq. ID No. 624), -AGTGCAAATGT (Seq. ID No. 625), -AGTGCAAATG (Seq. ID No. 626), -AGTGCAAAT, -AGTGCAAA, -AGTGCAA, -AGTGCA, -AGTGC, -AGTG, -AGT, -AG, or -A;

N¹¹ represents: TGCCCCAGAAGAGCTATTTGGTAG- (Seq. ID No. 627), GCCCCAGAAGAGCTATTTGGTAG- (Seq. ID No. 628), CCCCAGAAGAGCTATTTGGTAG- (Seq. ID No. 629), CCCAGAAGAGCTATTTGGTAG- (Seq. ID No. 630), CCAGAAGAGCTATTTGGTAG- (Seq. ID No. 631), CAGAAGAGCTATTTGGTAG- (Seq. ID No. 632), AGAAGAGCTATTTGGTAG- (Seq. ID No. 633), GAAGAGCTATTTGGTAG- (Seq. ID No. 634), AAGAGC-TATTTGGTAG- (Seq. ID No. 635), AGAGCTAT-TTGGTAG- (Seq. ID No. 636), GAGCTATTTGGTAG- (Seq. ID No. 637), AGCTATTTGGTAG- (Seq. ID No. 638), GCTATTTGGTAG- (Seq. ID No. 639), CTATTTGGTAG- (Seq. ID No. 640), TATTTGGTAG- (Seq. ID No. 641), ATTTGGTAG-, TTTGGTAG-, TTGGTAG-, TGGTAG-, GGTAG-, GTAG-, TAG-, AG- or G-, N¹² represents: -GAGCCGTCTTCAGGAATCTTCTCC (Seq. ID No. 642), -GAGCCGTCTTCAGGAATCTTCTC (Seq. ID No. 643), -GAGCCGTCTTCAGGAATCTTCT (Seq. ID No. 644), -GAGCCGTCTTCAGGAATCTTC (Seq. ID No. 645), -GAGCCGTCTTCAGGAATCTT (Seq ID No. 646), -GAGCCGTCTTCAGGAATCT (Seq. ID No. 647), -GAGCCGTCTTCAGGAATC (Seq. ID No. 648), -GAGCCGTCTTCAGGAAT (Seq. ID No. 649), -GAGCCGTCTTCAGGAA (Seq. ID No. 650), -GAGCCGTCTTCAGGA (Seq. ID No. 651), -GAGCCGTCTTCAGG (Seq. ID No. 652), -GAGCCGTCTTCAG (Seq. ID No. 653), -GAGCCGTCTTCA (Seq. ID No. 654), -GAGCCGTCTTC (Seq. ID No. 655), -GAGCCGTCTT (Seq. ID No. 656), -GAGCCGTCT, -GAGCCGTC, -GAGCCGT, -GAGCCG, -GAGCC, -GAGC, -GAG, -GA, or -G;

and salts and optical isomers of the antisense-oligonucleotide.

Thus, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-N¹-GTCATAGA-N²-3' (Seq. ID No. 12) or 5'-N³-ACGCGTCC-N⁴-3' (Seq. ID No. 98) or 5'-N¹¹-TGTT-TAGG-N¹²-3' (Seq. ID No. 10) or 5'-N⁵-TTTGGTAG-N⁶-3' (Seq. ID No. 11) or 5'-N⁷-AATGGACC-N⁸-3' (Seq. ID No. 100) or 5'-N⁹-ATTAATAA-N¹⁰-3' (Seq. ID No. 101), wherein the residues N¹ to N¹² have the meanings especially the further limited meanings as disclosed herein and salts and optical isomers of said antisense-oligonucleotide.

Moreover, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-N¹-GTCATAGA-N²-3' (Seq. ID No. 12), wherein N¹ represents: CATGGCAGACCCCGCTGCTC-, ATGGCAGACCCCGCTGCTC-, TGGCAGACCCCGCTGCTC-, GGCAGACCCCGCTGCTC-, GCAGACCCCGCTGCTC-, CAGACCCCGCTGCTC-, AGACCCCGCTGCTC-, GACCCCGCTGCTC-, ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-;

N² represents: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCCCCAG, -CCGAGCCCCCAGC, -CCGAGCCCCCAGCG, -CCGAGCCCCCAGCGC, -CCGAGCCCCCAGCGCA, -CCGAGCCCCCAGCGCAG, -CCGAGCCCCCAGCGCAGC, -CCGAGCCCCCAGCGCAGCG, or -CCGAGCCCCCAGCGCAGCGG;

and salts and optical isomers of the antisense-oligonucleotide.

The antisense-oligonucleotides of formula S1 (Seq. ID No. 12) preferably comprise 2 to LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention designed as GAPmers which contain 2 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units. More preferably the antisense-oligonucleotides comprise 2 to 4 LNA units at the 5' terminal end and 2 to 4 LNA units at the 3' terminal end and still more preferred comprise 3 to 4 LNA units at the 5' terminal end and 3 to 4 LNA units at the 3' terminal end and contain preferably at least 7 non-LNA units and most preferably at least 8 non-LNA units such as DNA units in between both LNA segments.

Moreover, the antisense-oligonucleotides may contain common nucleobases such as adenine, guanine, cytosine, thymine and uracil as well as common derivatives thereof such as 5-methylcytosine or 2-aminoadenine. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide. As LNA units especially the residues $b^1$ to $b^9$ as disclosed herein are preferred.

Thus, preferred are antisense-oligonucleotides of the formula (S1):

$$5'-N^1\text{-}\mathbf{GTCATAGA}\text{-}N^2\text{-}3' \quad \text{(Seq. ID No. 12)}$$

wherein

N¹ represents: CATGGCAGACCCCGCTGCTC-, ATGGCAGACCCCGCTGCTC-, TGGCAGACCCCGCTGCTC-, GGCAGACCCCGCTGCTC-, GCAGACCCCGCTGCTC-, CAGACCCCGCTGCTC-, AGACCCCGCTGCTC-, GACCCCGCTGCTC-, ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-;

and

N² is selected from: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCCCCAG, -CCGAGCCCCCAGC, -CCGAGCCCCCAGCG, -CCGAGCCCCCAGCGC, -CCGAGCCCCCAGCGCA, -CCGAGCCCCCAGCGCAG, -CCGAGCCCCCAGCGCAGC, -CCGAGCCCCCAGCGCAGCG, or -CCGAGCCCCCAGCGCAGCGG.

Preferably the antisense-oligonucleotide of general formula (S1) has between 10 and 28 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S1) has between 11 and 24 nucleotides and at least two LNA nucleotides at the 3' terminus and at least two LNA nucleotides at the 5' terminus.

Still more preferably the antisense-oligonucleotide of general formula (S1) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Further preferred are antisense-oligonucleotides of the formula (S1):

5'-N$^1$-GTCATAGA-N$^2$-3' wherein

N$^1$ represents: TGGCAGACCCCGCTGCTC-, GGCA-GACCCCGCTGCTC-, GCAGACCCCGCTGCTC-, CAGACCCCGCTGCTC-, AGACCCCGCTGCTC-, GACCCCGCTGCTC-, ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-;
and N$^2$ is selected from: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCCCAG, -CCGAGCCCCAGC, -CCGAGCCCCAGCG, -CCGAGCCCCAGCGC, -CCGAGCCCCAGCGCA, -CCGAGCCCCAGCGCAG, or -CCGAGCCCCAGCGCAGC.

Also preferred are antisense-oligonucleotides of the formula (S1):

5'-N$^1$-GTCATAGA-N$^2$-3' wherein

N$^1$ represents: GACCCCGCTGCTC-, ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-;
and N$^2$ is selected from: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCCCAG, or —CCGAGCCCCAGC.

Also preferred are antisense-oligonucleotides of the formula (S1):

5'-N$^1$-GTCATAGA-N$^2$-3' wherein

N$^1$ represents: CGCTGCTC-, GCTGCTC-, CTGCTC-, TGCTC-, GCTC-, CTC-, TC-, or C-;
and N$^2$ is selected from: -C, -CC, -CCG, -CCGA, -CCGAG, -CCGAGC, -CCGAGCC, or -CCGAGCCC.

Preferably, the present invention is directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^{1A}$-CGTCATAGAC-N$^{2A}$-3' (Seq. ID No. 69), wherein N$^{1A}$ represents: CATGGCAGACCCCGCTGCT- (Seq. ID No. 657), ATGGCAGACCCCGCTGCT- (Seq. ID No. 658), TGGCAGACCCCGCTGCT- (Seq. ID No. 659), GGCAGACCCCGCTGCT- (Seq. ID No. 660), GCAGACCCCGCTGCT- (Seq. ID No. 661), CAGACCCCGCTGCT- (Seq. ID No. 662), AGACCCCGCTGCT- (Seq. ID No. 663), GACCCCGCTGCT- (Seq. ID No. 664), ACCCCGCTGCT- (Seq. ID No. 665), CCCCGCTGCT- (Seq. ID No. 666), CCCGCTGCT-, CCGCTGCT-, CGCTGCT-, GCTGCT-, CTGCT-, TGCT-, GCT-, CT-, or T-;

N$^{2A}$ represents: -C, -CG, -CGA, -CGAG, -CGAGC, -CGAGCC, -CGAGCCC, -CGAGCCCC, -CGAGCCCCC, -CGAGCCCCCA (Seq. ID No. 667), -CGAGCCCCAG (Seq. ID No. 668), -CGAGCCCCAGC (Seq. ID No. 669), -CGAGCCCCAGCG (Seq. ID No. 670), -CGAGCCCCAGCGC (Seq. ID No. 671), -CGAGCCCCAGCGCA (Seq. ID No. 672), -CGAGCCCCAGCGCAG (Seq. ID No. 673), -CGAGCCCCAGCGCAGC (Seq. ID No. 674), -CGAGCCCCAGCGCAGCG (Seq. ID No. 675), or -CGAGCCCCAGCGCAGCGG (Seq. ID No. 676);

and salts and optical isomers of the antisense-oligonucleotide.

Preferably N$^{1A}$ represents: TGGCAGACCCCGCTGCT-, GGCAGACCCCGCTGCT-, GCAGACCCCGCTGCT-, CAGACCCCGCTGCT-, AGACCCCGCTGCT-, GACCCCGCTGCT-, ACCCCGCTGCT-, CCCCGCTGCT-, CCCGCTGCT-, CCGCTGCT-, CGCTGCT-, GCTGCT-, CTGCT-, TGCT-, GCT-, CT-, or T-;
and N$^{2A}$ represents: -C, -CG, -CGA, -CGAG, -CGAGC, -CGAGCC, -CGAGCCC, -CGAGCCCC, -CGAGCCCCC, -CGAGCCCCA, -CGAGCCCCAG, -CGAGCCCCAGC, -CGAGCCCCAGCG, -CGAGCCCCAGCGC, -CGAGCCCCAGCGCA, -CGAGCCCCAGCGCAG, or -CGAGCCCCAGCGCAGC.

More preferably N$^{1A}$ represents: GACCCCGCTGCT-, ACCCCGCTGCT-, CCCCGCTGCT-, CCCGCTGCT-, CCGCTGCT-, CGCTGCT-, GCTGCT-, CTGCT-, TGCT-, GCT-, CT-, or T-; and N$^{2A}$ represents: -C, -CG, -CGA, -CGAG, -CGAGC, -CGAGCC, -CGAGCCC, -CGAGCCCC, -CGAGCCCCC, -CGAGCCCCA, -CGAGCCCCAG, or -CGAGCCCCAGC.

Still more preferably N$^{1A}$ represents: CGCTGCT-, GCTGCT-, CTGCT-, TGCT-, GCT-, CT-, or T-; and N$^{2A}$ represents: -C, -CG, -CGA, -CGAG, -CGAGC, -CGAGCC, or -CGAGCCC.

Preferably the antisense-oligonucleotide of general formula (S1A/Seq. ID No. 69) has between 12 and 24 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S1A) has between 12 and 22 nucleotides and at least two LNA nucleotides at the 3' terminus and at least two LNA nucleotides at the 5' terminus.

Still more preferably the antisense-oligonucleotide of general formula (S1A) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Moreover, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^3$-ACGCGTCC-$N^4$-3' (Seq. ID No. 98), wherein $N^3$ represents: GGTGGGATCGTGCTGGCGAT-, GTGGGATCGTGCTGGCGAT-, TGGGATCGTGCTGGC-GAT-, GGGATCGTGCTGGCGAT-, GGATCGTGCTGGC-GAT-, GATCGTGCTGGCGAT-, ATCGTGCTGGCGAT-, TCGTGCTGGCGAT-, CGTGCTGGCGAT-, GTGCTGGC-GAT-, TGCTGGCGAT-, GCTGGCGAT-, CTGGCGAT-, TGGCGAT-, GGCGAT-, GCGAT-, CGAT-, GAT-, AT-, or T-;

$N^4$ represents: -ACAGGACGATGTGCAGCGGC, -ACAGGACGATGTGCAGCGG, -ACAGGAC-GATGTGCAGCG, -ACAGGACGATGTGCAGC, -ACAGGACGATGTGCAG, -ACAGGACGATGTGCA, -ACAGGACGATGTGC, -ACAGGACGATGTG, -ACAGGACGATGT, -ACAGGACGATG, -ACAGGAC-GAT, -ACAGGACGA, -ACAGGACG, -ACAGGAC, -ACAGGA, -ACAGG, -ACAG, -ACA, -AC, or -A;

and salts and optical isomers of the antisense-oligonucleotide.

The antisense-oligonucleotides of formula S2 (Seq. ID No. 98) preferably comprise 2 to LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention designed as GAPmers which contain 2 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units. More preferably the antisense-oligonucleotides comprise 2 to 4 LNA units at the 5' terminal end and 2 to 4 LNA units at the 3' terminal end and still more preferred comprise 3 to 4 LNA units at the 5' terminal end and 3 to 4 LNA units at the 3' terminal end and contain preferably at least 7 non-LNA units and most preferably at least 8 non-LNA units such as DNA units in between both LNA segments.

Moreover the antisense-oligonucleotides may contain common nucleobases such as adenine, guanine, cytosine, thymine and uracil as well as common derivatives thereof such as 5-methylcytosine or 2-aminoadenine. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide. As LNA units especially the residues $b^1$ to $b^9$ as disclosed herein are preferred.

Thus, preferred are antisense-oligonucleotides of the formula (S2):

(Seq. ID No. 98)
5'-$N^3$-ACGCGTCC-$N^4$-3' wherein
$N^3$ represents: GGTGGGATCGTGCTGGCGAT-, GTGGGATCGTGCTGGCGAT-, TGGGATCGTGCTGGC-GAT-, GGGATCGTGCTGGCGAT-, GGATCGTGCTGGC-GAT-, GATCGTGCTGGCGAT-, ATCGTGCTGGCGAT-, TCGTGCTGGCGAT-, CGTGCTGGCGAT-, GTGCTGGC-GAT-, TGCTGGCGAT-, GCTGGCGAT-, CTGGCGAT-, TGGCGAT-, GGCGAT-, GCGAT-, CGAT-, GAT-, AT-, or T-;

and
$N^4$ represents: -ACAGGACGATGTGCAGCGGC, -ACAGGACGATGTGCAGCGG, -ACAGGAC-GATGTGCAGCG, -ACAGGACGATGTGCAGC, -ACAGGACGATGTGCAG, -ACAGGACGATGTGCA, -ACAGGACGATGTGC, -ACAGGACGATGTG, -ACAGGACGATGT, -ACAGGACGATG, -ACAGGAC-GAT, -ACAGGACGA, -ACAGGACG, -ACAGGAC, -ACAGGA, -ACAGG, -ACAG, -ACA, -AC, or -A.

Preferably the antisense-oligonucleotide of general formula (S2) has between 10 and 28 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S2) has between 11 and 24 nucleotides and at least two LNA nucleotides at the 3' terminus and at least two LNA nucleotides at the 5' terminus.

Still more preferably the antisense-oligonucleotide of general formula (S2) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Further preferred are antisense-oligonucleotides of the formula (S2):

5'-$N^3$-ACGCGTCC-$N^4$-3' wherein $N^3$ represents: TGGGATCGTGCTGGCGAT-, GGGATCGTGCTGGCGAT-, GGATCGTGCTGGCGAT-, GATCGTGCTGGCGAT-, ATCGTGCTGGCGAT-, TCGTGCTGGCGAT-, CGTGCTGGCGAT-, GTGCTGGCGAT-, TGCTGGCGAT-, GCTGGCGAT-, CTGGCGAT-, TGGCGAT-, GGCGAT-, GCGAT-, CGAT-, GAT-, AT-, or T-;

and $N^4$ represents: -ACAGGACGATGTGCAGCG, -ACAGGACGATGTGCAGC, -ACAGGACGATGTGCAG, -ACAGGACGATGTGCA, -ACAGGACGATGTGC, -ACAGGACGATGTG, -ACAGGACGATGT, -ACAGGACGATG, -ACAGGACGAT, -ACAGGACGA, -ACAGGACG, -ACAGGAC, -ACAGGA, -ACAGG, -ACAG, -ACA, -AC, or -A.

Also preferred are antisense-oligonucleotides of the formula (S2):

$$5'-N^3\text{-ACGCGTCC-}N^4\text{-}3'$$

wherein $N^3$ represents: TCGTGCTGGCGAT-, CGTGCTGGCGAT-, GTGCTGGCGAT-, TGCTGGCGAT-, GCTGGCGAT-, CTGGCGAT-, TGGCGAT-, GGCGAT-, GCGAT-, CGAT-, GAT-, AT-, or T-;

and $N^4$ represents: -ACAGGACGATGTG, -ACAGGACGATGT, -ACAGGACGATG, -ACAGGACGAT, -ACAGGACGA, -ACAGGACG, -ACAGGAC, -ACAGGA, -ACAGG, -ACAG, -ACA, -AC, or -A.

Also preferred are antisense-oligonucleotides of the formula (S2):

$$5'-N^3\text{-ACGCGTCC-}N^4\text{-}3'$$

wherein $N^3$ represents: CTGGCGAT-, TGGCGAT-, GGCGAT-, GCGAT-, CGAT-, GAT-, AT-, or T-;

and $N^4$ represents: -ACAGGACG, -ACAGGAC, -ACAGGA, -ACAGG, -ACAG, -ACA, -AC, or -A.

Preferably, the present invention is directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^{3,4}$-TACGCGTCCA-$N^{4,4}$-3' (Seq. ID No. 70), wherein $N^{3,4}$ represents: GGTGGGATCGTGCTGGCGA- (Seq. ID No. 677), GTGGGATCGTGCTGGCGA- (Seq. ID No. 678), TGGGATCGTGCTGGCGA- (Seq. ID No. 679), GGGATCGTGCTGGCGA- (Seq. ID No. 680), GGATCGTGCTGGCGA- (Seq. ID No. 68, GATCGTGCTGGCGA- (Seq. ID No. 682), ATCGTGCTGGCGA- (Seq. ID No. 683), TCGTGCTGGCGA- (Seq. ID No. 684), CGTGCTGGCGA- (Seq. ID No. 685), GTGCTGGCGA- (Seq. ID No. 686), TGCTGGCGA-, GCTGGCGA-, CTGGCGA-, TGGCGA-, GGCGA-, GCGA-, CGA-, GA-, or A-;

$N^{4,4}$ represents: -CAGGACGATGTGCAGCGGC (Seq. ID No. 687), -CAGGACGATGTGCAGCGG (Seq. ID No. 688), -CAGGACGATGTGCAGCG (Seq. ID No. 69), -CAGGACGATGTGCAGC (Seq. ID No. 690), -CAGGAC- GATGTGCAG (Seq. ID No. 691), -CAGGACGATGTGCA (Seq. ID No. 692), -CAGGACGATGTGC (Seq. ID No. 693), -CAGGACGATGTG (Seq. ID No. 694), -CAGGAC-GATGT (Seq. ID No. 695), -CAGGACGATG (Seq. ID No. 696), -CAGGACGAT, -CAGGACGA, -CAGGACG, -CAGGAC, -CAGGA, -CAGG, -CAG, -CA, or —C;

and salts and optical isomers of the antisense-oligonucleotide.

Preferably $N^{3,4}$ represents: TGGGATCGTGCTGGCGA-, GGGATCGTGCTGGCGA-, GGATCGTGCTGGCGA-, GATCGTGCTGGCGA-, ATCGTGCTGGCGA-, TCGTGCTGGCGA-, CGTGCTGGCGA-, GTGCTGGCGA-, TGCTGGCGA-, GCTGGCGA-, CTGGCGA-, TGGCGA-, GGCGA-, GCGA-, CGA-, GA-, or A-;

and $N^{4,4}$ represents: -CAGGACGATGTGCAGCG, -CAGGACGATGTGCAGC, -CAGGACGATGTGCAG, -CAGGACGATGTGCA, -CAGGACGATGTGC, -CAGGACGATGTG, -CAGGACGATGT, -CAGGAC-GATG, -CAGGACGAT, -CAGGACGA, -CAGGACG, -CAGGAC, -CAGGA, -CAGG, -CAG, -CA, or —C.

More preferably $N^{3,4}$ represents: TCGTGCTGGCGA-, CGTGCTGGCGA-, GTGCTGGCGA-, TGCTGGCGA-, GCTGGCGA-, CTGGCGA-, TGGCGA-, GGCGA-, GCGA-, CGA-, GA-, or A-; and $N^{4,4}$ represents: -CAGGACGATGTG, -CAGGAC-GATGT, -CAGGACGATG, -CAGGACGAT, -CAGGACGA, -CAGGACG, -CAGGAC, -CAGGA, -CAGG, -CAG, -CA, or —C.

Still more preferably $N^{3,4}$ represents: CTGGCGA-, TGGCGA-, GGCGA-, GCGA-, CGA-, GA-, or A-; and $N^{4,4}$ represents: -CAGGACG, -CAGGAC, -CAGGA, -CAGG, -CAG, -CA, or —C.

Preferably the antisense-oligonucleotide of general formula (S2A/Seq. ID No. 70) has between 12 and 24 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S2A) has between 12 and 22 nucleotides and at least two LNA nucleotides at the 3' terminus and at least two LNA nucleotides at the 5' terminus.

Still more preferably the antisense-oligonucleotide of general formula (S2A) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Moreover, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^{11}$-TGTTTAGG-$N^{12}$-3' (Seq. ID No. 10), wherein $N^{11}$ represents: TGCCCCAGAAGAGCTATTTGGTAG-, GCCCCAGAAGAGCTATTTGGTAG-, CCCCAGAAGAGCTATTTGGTAG-, CCCAGAAGAGCTATTTGGTAG-, CCAGAAGAGCTATTTGGTAG-, CAGAAGAGCTATTTGGTAG-, AGAAGAGCTATTTGGTAG-, GAAGAGCTATTTGGTAG-, AAGAGCTATTTGGTAG-, AGAGCTATTTGGTAG-, GAGCTATTTGGTAG-, AGCTATTTGGTAG-, GCTATTTGGTAG-, CTATTTGGTAG-, TATTTGGTAG-, ATTTGGTAG-, TTTGGTAG-, TTGGTAG-, TGGTAG-, GGTAG-, GTAG-, TAG-, AG- or G-, $N^{12}$ represents: -GAGCCGTCTTCAGGAATCTTCTCC, -GAGCCGTCTTCAGGAATCTTCTC, -GAGCCGTCTTCAGGAATCTTCT, -GAGCCGTCTTCAGGAATCTTC, -GAGCCGTCTTCAGGAATCTT, -GAGCCGTCTTCAGGAATCT, -GAGCCGTCTTCAGGAATC, -GAGCCGTCTTCAGGAAT, -GAGCCGTCTTCAGGAA, -GAGCCGTCTTCAGGA, -GAGCCGTCTTCAGG, -GAGCCGTCTTCAG, -GAGCCGTCTTCA, -GAGCCGTCTTC, -GAGCCGTCTT, -GAGCCGTCT, -GAGCCGTC, -GAGCCGT, -GAGCCG, -GAGCC, -GAGC, -GAG, -GA, or -G;

and salts and optical isomers of the antisense-oligonucleotide.

The antisense-oligonucleotides of formula S3 (Seq. ID No. 10) preferably comprise 2 to LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention designed as GAPmers which contain 2 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units. More preferably the antisense-oligonucleotides comprise 2 to 4 LNA units at the 5' terminal end and 2 to 4 LNA units at the 3' terminal end and still more preferred comprise 3 to 4 LNA units at the 5' terminal end and 3 to 4 LNA units at the 3' terminal end and contain preferably at least 7 non-LNA units and most preferably at least 8 non-LNA units such as DNA units in between both LNA segments.

Moreover the antisense-oligonucleotides may contain common nucleobases such as adenine, guanine, cytosine, thymine and uracil as well as common derivatives thereof such as 5-methylcytosine or 2-aminoadenine. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide. As LNA units especially the residues $b^1$ to $b^9$ as disclosed herein are preferred.

Thus, preferred are antisense-oligonucleotides of the formula (S3):

(Seq. ID No. 10)
5'-$N^{11}$-TGTTTAGG-$N^{12}$-3' wherein
$N^{11}$ represents: TGCCCCAGAAGAGCTATTTGGTAG-, GCCCCAGAAGAGCTATTTGGTAG-, CCCCAGAAGAGCTATTTGGTAG-, CCCAGAAGAGCTATTTGGTAG-, CCAGAAGAGCTATTTGGTAG-, CAGAAGAGCTATTTGGTAG-, AGAAGAGCTATTTGGTAG-, GAAGAGCTATTTGGTAG-, AAGAGCTATTTGGTAG-, AGAGCTATTTGGTAG-, GAGCTATTTGGTAG-, AGCTATTTGGTAG-, GCTATTTGGTAG-, CTATTTGGTAG-, TATTTGGTAG-, ATTTGGTAG-, TTTGGTAG-, TTGGTAG-, TGGTAG-, GGTAG-, GTAG-, TAG-, AG- or G-, and
$N^{12}$ represents: -GAGCCGTCTTCAGGAATCTTCTCC, -GAGCCGTCTTCAGGAATCTTCTC, -GAGCCGTCTTCAGGAATCTTCT, -GAGCCGTCTTCAGGAATCTTC, -GAGCCGTCTTCAGGAATCTT, -GAGCCGTCTTCAGGAATCT, -GAGCCGTCTTCAGGAATC, -GAGCCGTCTTCAGGAAT, -GAGCCGTCTTCAGGAA, -GAGCCGTCTTCAGGA, -GAGCCGTCTTCAGG, -GAGCCGTCTTCAG, -GAGCCGTCTTCA, -GAGCCGTCTTC, -GAGCCGTCTT, -GAGCCGTCT, -GAGCCGTC, -GAGCCGT, -GAGCCG, -GAGCC, -GAGC, -GAG, -GA, or -G.

Preferably the antisense-oligonucleotide of general formula (S3) has between 10 and 28 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S3) has between 11 and 24 nucleotides and at least two LNA nucleotides at the 3' terminus and at least two LNA nucleotides at the 5' terminus.

Still more preferably the antisense-oligonucleotide of general formula (S3) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Further preferred are antisense-oligonucleotides of the formula (S3):

5'-$N^{11}$-TGTTTAGG-$N^{12}$-3' wherein
$N^{11}$ represents: AGAAGAGCTATTTGGTAG-, GAAGAGCTATTTGGTAG-, AAGAGCTATTTGGTAG-, AGAGCTATTTGGTAG-, GAGCTATTTGGTAG-, AGCTATTTGGTAG-, GCTATTTGGTAG-, CTATTTGGTAG-, TATTTGGTAG-, ATTTGGTAG-, TTTGGTAG-, TTCTATGGTAG-, TATGGGGTAG-, TAG-, AG- or G-;

and
$N^{12}$ represents: -GAGCCGTCTTCAGGAATC, -GAGCCGTCTTCAGGAAT, -GAGCCGTCTTCAGGAA, -GAGCCGTCTTCAGGA, -GAGCCGTCTTCAGG, -GAGCCGTCTTCAG, -GAGCCGTCTTCA, -GAGCCG-TCTTC, -GAGCCGTCTT, -GAGCCGTCT, -GAGUGGIC, -GAGCCGT, -GAGCCG, -GAGCC, -GAGC, -GAG, -GA, or -G.

Also preferred are antisense-oligonucleotides of the formula (S3):

$$5'-N^{11}-\text{TGTTTAGG}-N^{12}-3'$$

wherein $N^{11}$ represents: AGCTATTTGGTAG-, GCTATTTGGT-AG-, CTATTTGGTAG-, TATTTGGTAG-, ATTTGGTAG-, TTTGGTAG-, TTGGTAG-, TGGTAG-, GGTAG-, GTAG-, TAG-, AG- or G-;
and $N^{12}$ represents: -GAGCCGTCTTCAG, -GAGCCGTCTTCA, -GAGCCGTCTTC, -GAGCCGTCTT, -GAGCCGTCT, -GAGCCGTC, -GAGCCGT, -GAGCCG, -GAGCC, -GAGC, -GAG, -GA, or -G.

Also preferred are antisense-oligonucleotides of the formula (S3):

$$5'-N^{11}-\text{TGTTTAGG}-N^{12}-3'$$

wherein $N^{11}$ represents: TTTGGTAG-, TTGGTAG-, TGGTAG-, GGTAG-, GTAG-, TAG-, AG- or G-; and $N^{12}$ represents: -GAGCCGTC, -GAGCCGT, -GAGCCG, -GAGCC, -GAGC, -GAG, -GA, or -G.

Preferably, the present invention is directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^{11A}$-GTGTTTAGGG-$N^{12A}$-3' (Seq. ID No. 71), wherein NilA represents: TGCCCCAGAAGAGCTATTTGGTA- (Seq. ID No. 765), GCCCCAGAAGAGCTATTTGGTA- (Seq. ID No. 766), CCCCAGAAGAGCTATTTGGTA- (Seq. ID No. 767), CCCAGAAGAGCTATTTGGTA- (Seq. ID No. 768), CCAGAAGAGCTATTTGGTA- (Seq. ID No. 769), CAGAAGAGCTATTTGGTA- (Seq. ID No. 770), AGAAGAGCTATTTGGTA- (Seq. ID No. 771), GAAGAGCTATTTGGTA- (Seq. ID No. 772), AAGAGCTATTTGGTA- (Seq. ID No. 773), AGAGCTATTTGGTA- (Seq. ID No. 774), GAGCTATTTGGTA- (Seq. ID No. 775), AGCTATTTGGTA- (Seq. ID No. 776), GCTATTTGGTA- (Seq. ID No. 777), CTATTTGGTA- (Seq. ID No. 778), TATTTGGTA-, ATTTGGTA-, TTTGGTA-, TTGGTA-, TGGTA-, GGTA-, GTA-, TA-, or A-, $N^{12A}$ represents: -AGCCGTCTTCAGGAATCTTCTCC (Seq. ID No. 779), -AGCCGTCTTCAGGAATCTTCTC (Seq. ID No. 780), -AGCCGTCTTCAGGAATCTTCT (Seq. ID No. 781), -AGCCGTCTTCAGGAATCTTC (Seq. ID No. 782), -AGCCGTCTTCAGGAATCTT (Seq. ID No. 783), -AGCCGTCTTCAGGAATCT (Seq. ID No. 784), -AGCCGTCTTCAGGAATC (Seq. ID No. 785), -AGCCGTCTTCAGGAAT (Seq. ID No. 786), -AGCCGTCTTCAGGAA (Seq. ID No. 787), -AGCCGTCTTCAGGA (Seq. ID No. 788), -AGCCGTCTTCAGG (Seq. ID No. 789), -AGCCGTCTTCAG (Seq. ID No. 790), -AGCCGTCTTCA (Seq. ID No. 791), -AGCCGTCTTC (Seq. ID No. 792), -AGCCGTCTT, -AGCCGTCT, -AGCCGTC, -AGCCGT, -AGCCG, -AGCC, -AGC, -AG, or -A;

and salts and optical isomers of the antisense-oligonucleotide.

Preferably $N^{11A}$ represents: AGAAGAGCTATTTGGTA-, GAAGAGCTATTTGGTA-, AAGAGCTATTTGGTA-, AGAGCTATTTGGTA-, GAGCTATTTGGTA-, AGCTATTTGGTA-, GCTATTTGGTA-, CTATTTGGTA-, TATTTGGTA-, ATTTGGTA-, TTTGGTA-, TTGGTA-, TGGTA-, GGTA-, GTA-, TA-, or A-; and $N^{12A}$ represents: -AGCCGTCTTCAGGAATC, -AGCCGTCTTCAGGAAT, -AGCCGTCTTCAGGAA, -AGCCGTCTTCAGGA, -AGCCGTCTTCAGG, -AGCCGTCTTCAG, -AGCCGTCTTCA, -AGCCGTCTTC, -AGCCGTCTT, -AGCCGTCT, -AGCCGTC, -AGCCGT, -AGCCG, -AGCC, -AGC, -AG, or -A.

More preferably $N^{11A}$ represents: AGCTATTTGGTA-, GCTATTTGGTA-, CTATTTGGTA-, TATTTGGTA-, ATTTGGTA-, TTTGGTA-, TTGGTA-, TGGTA-, GGTA-, GTA-, TA-, or A-; and $N^{12A}$ represents: -AGCCGTCTTCAG, -AGCCGTCTTCA, -AGCCGTCTTC, -AGCCGTCTT, -AGCCGTCT, -AGCCGTC, -AGCCGT, -AGCCG, -AGCC, -AGC, -AG, or -A.

Still more preferably $N^{11A}$ represents: TTTGGTA-, TTGGTA-, TGGTA-, GGTA-, GTA-, TA-, or A-; and $N^{12A}$ represents: -AGCCGTC, -AGCCGT, -AGCCG, -AGCC, -AGC, -AG, or -A.

Preferably the antisense-oligonucleotide of general formula (S3A/Seq. ID No. 71) has between 12 and 24 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S3A) has between 12 and 22 nucleotides and at least two LNA nucleotides at the 3' terminus and at least two LNA nucleotides at the 5' terminus.

Still more preferably the antisense-oligonucleotide of general formula (S3A) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Moreover, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^5$-TTTGGTAG-$N^6$-3' (Seq. ID No. 11), wherein $N^5$ represents: GCCCAGCCTGCCCCAGAAGAGCTA-, CCCAGCCTGCCCCAGAAGAGCTA-, CCAGCCTGCC-CCAGAAGAGCTA-, CAGCCTGCCCCAGAAGA-GCTA-, AGCCTGCCCCAGAAGAGCTA-, GCCTGCCC-CAGAAGAGCTA-, CCTGCCCCAGAAGAGCTA-, CTGCCCCAGAAGAGCTA-, TGCCCCAGAAGAGCTA-, GCCCCAGAAGAGCTA-, CCCCAGAAGAGCTA-, CCCAGAAGAGCTA-, CCAGAAGAGCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-;

N⁶ represents: -TGTTTAGGGAGCCGTCTTCAGGAA, -TGTTTAGGGAGCCGTCTTCAGGA, -TGTTTAGGGAGCCGTCTTCAGG, -TGTTTAGGGAGCCGTCTTCAG, -TGTTTAGGGAGCCGTCTTCA, -TGTTTAGGGAGCCGTCTTC, -TGTTTAGGGAGCCGTCTT, -TGTTTAGGGAGCCGTCT, -TGTTTAGGGAGCCGTC, -TGTTTAGGGAGCCGT, -TGTTTAGGGAGCCG, -TGTTTAGGGAGCC, -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T;

and salts and optical isomers of the antisense-oligonucleotide.

The antisense-oligonucleotides of formula S4 (Seq. ID No. 11) preferably comprise 2 to LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention designed as GAPmers which contain 2 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units. More preferably the antisense-oligonucleotides comprise 2 to 4 LNA units at the 5' terminal end and 2 to 4 LNA units at the 3' terminal end and still more preferred comprise 3 to 4 LNA units at the 5' terminal end and 3 to 4 LNA units at the 3' terminal end and contain preferably at least 7 non-LNA units and most preferably at least 8 non-LNA units such as DNA units in between both LNA segments.

Moreover the antisense-oligonucleotides may contain common nucleobases such as adenine, guanine, cytosine, thymine and uracil as well as common derivatives thereof such as 5-methylcytosine or 2-aminoadenine. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide. As LNA units especially the residues $b^1$ to $b^9$ as disclosed herein are preferred.

Thus, preferred are antisense-oligonucleotides of the formula (S4):

(Seq. ID No. 11)
5'-N⁵-TTTGGTAG-N⁶-3' wherein

N⁵ represents: GCCCAGCCTGCCCCAGAAGAGCTA-, CCCAGCCTGCCCCAGAAGAGCTA-, CCAGCCTGCCCCAGAAGAGCTA-, CAGCCTGCCCCA- GAAGAGCTA-, AGCCTGCCCCAGAAGAGCTA-, GCCTGCCCCAGAAGAGCTA-, CCTGCCCCAGA- AGAGCTA-, CTGCCCCAGAAGAGCTA-, TGCCCCA- GAAGAGCTA-, GCCCCAGAAGAGCTA-, CCCCAG- AAGAGCTA-, CCCAGAAGAGCTA-, CCAGAAGA- GCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-;

and

N⁶ is selected from: -TGTTTAGGGAGCCGTCTTCAGGAA, -TGTTTAGGGAGCCGTCTTCAGGA, -TGTTTAGGGAGCCGTCTTCAGG, -TGTTTAGGGAGCCGTCTTCAG, -TGTTTAGGGAGCCGTCTTCA, -TGTTTAGGGAGCCGTCTTC, -TGTTTAGGGAGCCGTCTT, -TGTTTAGGGAGCCGTCT, -TGTTTAGGGAGCCGTC, -TGTTTAGGGAGCCGT, -TGTTTAGGGAGCCG, -TGTTTAGGGAGCC, -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T.

Preferably the antisense-oligonucleotide of general formula (S4) has between 10 and 28 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S4) has between 11 and 24 nucleotides and at least two LNA nucleotides at the 3' terminus and at least two LNA nucleotides at the 5' terminus.

Still more preferably the antisense-oligonucleotide of general formula (S4) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Further preferred are antisense-oligonucleotides of the formula (S4):

5'-N⁵-TTTGGTAG-N⁶-3' wherein

N⁵ represents: CCTGCCCCAGAAGAGCTA-, CTGCCCCAGAAGAGCTA-, TGCCCCAGAAGAGCTA-, GCCCCAGAAGAGCTA-, CCCCAGAAGAGCTA-, CCCAGAAGAGCTA-, CCAGAAGAGCTA-, CAGAAG- AGCTA-, AGAAGAGCTA-, GAAGAGCTA-, AAGAGCTA-, AGAGCTA-, GAGCTA-, AGCTA-, GCTA-, CTA-, TA-, or A-; and N⁶ is selected from: -TGTTTAGGGAGCCGTCTT, -TGTTTAGGGAGCCGTCT, -TGTTTAGGGAGCCGTC, -TGTTTAGGGAGCCGT, -TGTTTAGGGAGCCG, -TGTTTAGGGAGCC, -TGTTTAGGGAGC, -TGTT- TAGGGAG, -TGTTTAGGGA, -TGTTTAGGG, -TGTT-TAGG, -TGTTTAG, -TGTTTA, -TGTTT, -TGTT, -TGT, -TG, or -T.

Also preferred are antisense-oligonucleotides of the formula (S4):

$$5'-N^5-\text{TTTGGTAG}-N^6-3'$$

wherein

N$^5$ represents: CCCAGAAGAGCTA-, CCAGAAGAGCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-; and N$^6$ is selected from: -TGTTTAGGGAGCC, -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T.

Also preferred are antisense-oligonucleotides of the formula (S4):

$$5'-N^5-\text{TTTGGTAG}-N^6-3'$$

wherein

N$^5$ represents: AAGAGCTA-, AGAGCTA-, GAGCTA-, AGCTA-, GCTA-, CTA-, TA-, or A-; and N$^6$ is selected from: -TGTTTAGG, -TGTTTAG, -TGTTTA, -TGTTT, -TGTT, -TGT, -TG, or -T.

Preferably, the present invention is directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^{5A}$-ATTTGGTAGT-N$^{6A}$-3' (Seq. ID No. 72), wherein N$^{5A}$ represents: GCCCAGCCTGCCCCAGAAGAGCT- (Seq. ID No. 697), CCCAGCCTGCCCCAGAAGAGCT- (Seq. ID No. 698), CCAGCCTGCCCCAGAAGAGCT- (Seq. ID No. 699), CAGCCTGCCCCAGAAGAGCT- (Seq. ID No. 700), AGCCTGCCCCAGAAGAGCT- (Seq. ID No. 701), GCCTGCCCCAGAAGAGCT- (Seq. ID No. 702), CCTGCCCCAGAAGAGCT- (Seq. ID No. 703), CTGCCCCAGAAGAGCT- (Seq. ID No. 704), TGCCCCAGAAGAGCT- (Seq. ID No. 705), GCCCCAGAAGAGCT- (Seq. ID No. 706), CCCCAGAAGAGCT- (Seq. ID No. 707), CCCAGAAGAGCT- (Seq. ID No. 708), CCAGAAGAGCT- (Seq. ID No. 709), CAGAAGAGCT- (Seq. ID No. 710), AGAAGAGCT-, GAAGAGCT-, AAGAGCT-, AGAGCT-, GAGCT-, AGCT-, GCT-, CT-, or T-;

N$^{6A}$ represents: -GTTTAGGGAGCCGTCTTCAGGAA (Seq. ID No. 711), -GTTTAGGGAGCCGTCTTCAGGA (Seq. ID No. 712), -GTTTAGGGAGCCGTCTTCAGG (Seq. ID No. 713), -GTTTAGGGAGCCGTCTTCAG (Seq. ID No. 714), -GTTTAGGGAGCCGTCTTCA (Seq. ID No. 715), -GTTTAGGGAGCCGTCTTC (Seq. ID No. 716), -GTTTAGGGAGCCGTCTT (Seq. ID No. 717), -GTTTAGGGAGCCGTCT (Seq. ID No. 718), -GTTTAGGGAGCCGTC (Seq. ID No. 719), -GTTTAGGGAGCCGT (Seq. ID No. 720), -GTTTAGGGAGCCG (Seq. ID No. 721), -GTTTAGGGAGCC (Seq. ID No. 722), -GTTTAGGGAGC (Seq. ID No. 723), -GTTTAGGGAG (Seq. ID No. 724), -GTTTAGGGA, -GTTTAGGG, -GTTTAGG, -GTTTAG, -GTTTA, -GTTT, -GTT, -GT, or -G;

and salts and optical isomers of the antisense-oligonucleotide.

Preferably N$^{5A}$ represents: CCTGCCCCAGAAGAGCT-, CTGCCCCAGAAGAGCT-, TGCCCCAGAAGAGCT-, GCCCCAGAAGAGCT-, CCCCAGAAGAGCT-, CCCAGAAGAGCT-, CCAGAAGAGCT-, CAGAAGAGCT-, AGAAGAGCT-, GAAGAGCT-, AAGAGCT-, AGAGCT-, GAGCT-, AGCT-, GCT-, CT-, or T-; and N$^{6A}$ represents: -GTTTAGGGAGCCGTCTT, -GTTTAGGGAGCCGTCT, -GTTTAGGGAGCCGTC, -GTTTAGGGAGCCGT, -GTTTAGGGAGCCG, -GTTTAGGGAGCC, -GTTTAGGGAGC, -GTTTAGGGAG, -GTTTAGGGA, -GTTTAGGG, -GTTTAGG, -GTTTAG, -GTTTA, -GTTT, -GTT, -GT, or -G.

More preferably N$^{5A}$ represents: CCCAGAAGAGCT-, CCAGAAGAGCT-, CAGAAGAGCT-, AGAAGAGCT-, GAAGAGCT-, AAGAGCT-, AGAGCT-, GAGCT-, AGCT-, GCT-, CT-, or T-; and N$^{6A}$ represents: -GTTTAGGGAGCC, -GTTTAGGGAGC, -GTTTAGGGAG, -GTTTAGGGA, -GTTTAGGG, -GTTTAGG, -GTTTAG, -GTTTA, -GTTT, -GTT, -GT, or -G.

Still more preferably N$^{5A}$ represents: AAGAGCT-, AGAGCT-, GAGCT-, AGCT-, GCT-, CT-, or T-; and N$^{6A}$ represents: -GTTTAGG, -GTTTAG, -GTTTA, -GTTT, -GTT, -GT, or -G.

Preferably the antisense-oligonucleotide of general formula (S4A/Seq. ID No. 72) has between 12 and 24 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S4A) has between 12 and 22 nucleotides and at least two LNA nucleotides at the 3' terminus and at least two LNA nucleotides at the 5' terminus.

Still more preferably the antisense-oligonucleotide of general formula (S4A) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Moreover, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^7$-AATGGACC-N$^8$-3' (Seq. ID No. 100), wherein N$^7$ represents: TGAATCTTGAATATCTCATG-, GAATCTTGAATATCTCATG-, AATCTTGAATATCTCATG-, ATCTTGAATATCTCATG-, TCTTGAATATCTCATG-, CTTGAATATCTCATG-, TTGAATATCTCATG-, TGAATATCTCATG-, GAATATCTCATG-, AATATCT-CATG-, ATATCTCATG-, TATCTCATG-, ATCTCATG-, TCTCATG-, CTCATG-, TCATG-, CATG-, ATG-, TG-, or G-;

N⁸ represents: -AGTATTCTAGAAACTCACCA, -AGTATTCTAGAAACTCACC, -AGTATTCTAGAAACTCAC, -AGTATTCTAGAAACTCA, -AGTATTCTAGAAACTC, -AGTATTCTAGAAACT, -AGTATTCTAGAAAC, -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A;

and salts and optical isomers of the antisense-oligonucleotide.

The antisense-oligonucleotides of formula S6 (Seq. ID No. 100) preferably comprise 2 to LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention designed as GAPmers which contain 2 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units. More preferably the antisense-oligonucleotides comprise 2 to 4 LNA units at the 5' terminal end and 2 to 4 LNA units at the 3' terminal end and still more preferred comprise 3 to 4 LNA units at the 5' terminal end and 3 to 4 LNA units at the 3' terminal end and contain preferably at least 7 non-LNA units and most preferably at least 8 non-LNA units such as DNA units in between both LNA segments.

Moreover the antisense-oligonucleotides may contain common nucleobases such as adenine, guanine, cytosine, thymine and uracil as well as common derivatives thereof such as 5-methylcytosine or 2-aminoadenine. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide. As LNA units especially the residues $b^1$ to $b^9$ as disclosed herein are preferred.

Thus, preferred are antisense-oligonucleotides of the formula (S6):

(Seq. ID No. 100)
5'-N⁷-AATGGACC-N⁸-3' wherein
N⁷ represents: TGAATCTTGAATATCTCATG-, GAATCTTGAATATCTCATG-, AATCTTGAATATCTCATG-, ATCTTGAATATCTCATG-, TCTTGAATATCTCATG-, CTTGAATATCTCATG-, TTGAATATCTCATG-, TGAATATCTCATG-, GAATATCTCATG-, AATATCTCATG-, ATATCTCATG-, TATCTCATG-, ATCTCATG-, TCTCATG-, CTCATG-, TCATG-, CATG-, ATG-, TG-, or G-;
and
N⁸ is selected from: -AGTATTCTAGAAACTCACCA, -AGTATTCTAGAAACTCACC, -AGTATTCTAGAAACTCAC, -AGTATTCTAGAAACTCA, -AGTATTCTAGAAACTC, -AGTATTCTAGAAACT, -AGTATTCTAGAAAC, -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A.

Preferably the antisense-oligonucleotide of general formula (S6) has between 10 and 28 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S6) has between 11 and 24 nucleotides and at least two LNA nucleotides at the 3' terminus and at least two LNA nucleotides at the 5' terminus.

Still more preferably the antisense-oligonucleotide of general formula (S6) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Further preferred are antisense-oligonucleotides of the formula (S6):

5'-N⁷-AATGGACC-N⁸-3' wherein
N⁷ represents: AATCTTGAATATCTCATG-, ATCTTGAATATCTCATG-, TCTTGAATATCTCATG-, CTTGAATATCTCATG-, TTGAATATCTCATG-, TGAATATCTCATG-, GAATATCTCATG-, AATATCTCATG-, ATATCTCATG-, TATCTCATG-, ATCTCATG-, TCTCATG-, CTCATG-, TCATG-, CATG-, ATG-, TG-, or G-;
and
N⁸ is selected from: -AGTATTCTAGAAACTCAC, -AGTATTCTAGAAACTCA, -AGTATTCTAGAAACTC, -AGTATTCTAGAAACT, -AGTATTCTAGAAAC, -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A.

Also preferred are antisense-oligonucleotides of the formula (S6):

5'-N⁷-AATGGACC-N⁸-3' wherein
N⁷ represents: TGAATATCTCATG-, GAATATCTCATG-, AATATCTCATG-, ATATCTCATG-, TATCTCATG-, ATCTCATG-, TCTCATG-, CTCATG-, TCATG-, CATG-, ATG-, TG-, or G-; and
N⁸ is selected from: -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A.

Also preferred are antisense-oligonucleotides of the formula (S6):

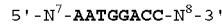

5'-N⁷-AATGGACC-N⁸-3' wherein

N⁷ represents: ATCTCATG-, TCTCATG-, CTCATG-, TCATG-, CATG-, ATG-, TG-, or G-; and N⁸ is selected from: -AGTATTCT, -AGTATTC, -AGTATT, -AGTAT, -AGTA, -AGT, -AG, or -A.

Preferably, the present invention is directed to antisense-oligonucleotide(s) consisting of 12 to 24 nucleotides and at least three of the 12 to 24 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^{7.4}$-GAATGGACCA-$N^{8.4}$-3' (Seq. ID No. 73), wherein $N^{7.4}$ represents: TGAATCTTGAATATCTCAT- (Seq. ID No. 725), GAATCTTGAATATCTCAT- (Seq. ID No. 726), AATCTTGAATATCTCAT- (Seq. ID No. 727], ATCTTGAATATCTCAT- (Seq. ID No. 728), TCTTGAATATCTCAT- (Seq. ID No. 729), CTTGAATATCTCAT- (Seq. ID No. 730), TTGAATATCTCAT- (Seq. ID No. 731), TGAATATCTCAT- (Seq. ID No. 732), GAATATCTCAT- (Seq. ID No. 733), AATATCTCAT- (Seq. ID No. 734), ATATCTCAT-, TATCTCAT-, ATCTCAT-, TCTCAT-, CTCAT-, TCAT-, CAT-, AT-, or T-;

$N^{8.4}$ represents: -GTATTCTAGAAACTCACCA (Seq. ID No. 735), -GTATTCTAGAAACTCACC (Seq. ID No. 736), -GTATTCTAGAAACTCAC (Seq. ID No. 737), -GTATTCTAGAAACTCA (Seq. ID No. 738), -GTATTCTAGAAACTC (Seq. ID No. 739), -GTATTCTAGAAACT (Seq. ID No. 740), -GTATTCTAGAAAC (Seq. ID No. 741), -GTATTCTAGAAA (Seq. ID No. 742), -GTATTCTAGAA (Seq. ID No. 743), -GTATTCTAGA (Seq. ID No. 744), -GTATTCTAG, -GTATTCTA, -GTATTCT, -GTATTC, -GTATT, -GTAT, -GTA, -GT, or -G;

and salts and optical isomers of the antisense-oligonucleotide.

Preferably $N7^4$ represents: AATCTTGAATATCTCAT-, ATCTTGAATATCTCAT-, TCTTGAATATCTCAT-, CTTGAATATCTCAT-, TTGAATATCTCAT-, TGAATATCTCAT-, GAATATCTCAT-, AATATCTCAT-, ATATCTCAT-, TATCTCAT-, ATCTCAT-, TCTCAT-, CTCAT-, TCAT-, CAT-, AT-, or T-;

and $N^{8.4}$ represents: -GTATTCTAGAAACTCAC, -GTATTCTAGAAACTCA, -GTATTCTAGAAACTC, -GTATTCTAGAAACT, -GTATTCTAGAAAC, -GTATTCTAGAAA, -GTATTCTAGAA, -GTATTCTAGA, -GTATTCTAG, -GTATTCTA, -GTATTCT, -GTATTC, -GTATT, -GTAT, -GTA, -GT, or -G.

More preferably $N7^4$ represents: TGAATATCTCAT-, GAATATCTCAT-, AATATCTCAT-, ATATCTCAT-, TATCTCAT-, ATCTCAT-, TCTCAT-, CTCAT-, TCAT-, CAT-, AT-, or T-; and $N^{8.4}$ represents: -GTATTCTAGAAA, -GTATTCTAGAA, -GTATTCTAGA, -GTATTCTAG, -GTATTCTA, -GTATTCT, -GTATTC, -GTATT, -GTAT, -GTA, -GT, or -G.

Still more preferably $N^{7.4}$ represents: ATICAT-, TCTUAT-, CTCAT-, TCAT-, CAT-, AT-, or T-; and $N^{8.4}$ represents: -GTATTCT, -GTATTC, -GTATT, -GTAT, -GTA, -GT, or -G.

Preferably the antisense-oligonucleotide of general formula (S6A/Seq. ID No. 73) has between 12 and 24 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S6A) has between 12 and 22 nucleotides and at least two LNA nucleotides at the 3' terminus and at least two LNA nucleotides at the 5' terminus.

Still more preferably the antisense-oligonucleotide of general formula (S6A) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Moreover, the present invention is directed to antisense-oligonucleotide(s) consisting of 10 to 28 nucleotides and at least two of the 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^9$-ATTAATAA-$N^{10}$-3' (Seq. ID No. 101), wherein N⁹ represents: ATTCATATTTATATACAGGC-, TTCATATTTATATACAGGC-, TCATATTTATATACAGGC-, CATATTTATATACAGGC-, ATATTTATATACAGGC-, TATTTATATACAGGC-, ATTTATATACAGGC-, TTTATATACAGGC-, TTATATACAGGC-, TATATACAGGC-, ATATACAGGC-, TATACAGGC-, ATACAGGC-, TACAGGC-, ACAGGC-, CAGGC-, AGGC-, GGC-, GO—, or C-;

$N^{10}$ represents: -AGTGCAAATGTTATTGGCTA, -AGTGCAAATGTTATTGGCT, -AGTGCAAATGTTATTGGC, -AGTGCAAATGTTATTGG, -AGTGCAAATGTTATTG, -AGTGCAAATGTTATT, -AGTGCAAATGTTAT, -AGTGCAAATGTTA, -AGTGCAAATGTT, -AGTGCAAATGT, -AGTGCAAATG, -AGTGCAAAT, -AGTGCAAA, -AGTGCAA, -AGTGCA, -AGTGC, -AGTG, -AGT, -AG, or -A;

and salts and optical isomers of the antisense-oligonucleotide.

The antisense-oligonucleotides of formula S7 (Seq. ID No. 101) preferably comprise 2 to LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention designed as GAPmers which contain 2 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units. More preferably the antisense-oligonucleotides comprise 2 to 4 LNA units at the 5' terminal end and 2 to 4 LNA units at the 3' terminal end and still more preferred comprise 3 to 4 LNA units at the 5' terminal end and 3 to 4 LNA units at the 3' terminal end and contain preferably at least 7 non-LNA units and most preferably at least 8 non-LNA units such as DNA units in between both LNA segments.

Moreover the antisense-oligonucleotides may contain common nucleobases such as adenine, guanine, cytosine, thymine and uracil as well as common derivatives thereof such as 5-methylcytosine or 2-aminoadenine. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide. As LNA units especially the residues $b^1$ to $b^9$ as disclosed herein are preferred.

Thus, preferred are antisense-oligonucleotides of the formula (S7):

$$5'-N^9-\text{ATTAATAA}-N^{10}-3' \quad (\text{Seq. ID No. 101})$$

wherein $N^9$ represents: ATTCATATTTATATACAGGC-, TTCATATTTATATACAGGC-, TCATATTTATATACAGGC-, CATATTTATATACAGGC-, ATATTTATATACAGGC-, TATT-TATATACAGGC-, ATTTATATACAGGC-, TTTATATAC-AGGC-, TTATATACAGGC-, TATATACAGGC-, ATATA-CAGGC-, TATACAGGC-, ATACAGGC-, TACAGGC-, ACAGGC-, CAGGC-, AGGC-, GGC-, GC-, or C-; and $N^{10}$ is selected from: -AGTGCAAATGTTATTGGCTA, -AGTGCAAATGTTATTGGCT, -AGTGCAAATGTTAT-TGGC, -AGTGCAAATGTTATTGG, -AGTGCAAATGTT-ATTG, -AGTGCAAATGTTATT, -AGTGCAAATGTTAT, -AGTGCAAATGTTA, -AGTGCAAATGTT, -AGTGCAA-ATGT, -AGTGCAAATG, -AGTGCAAAT, -AGTGCAAA, -AGTGCAA, -AGTGCA, -AGTGC, -AGTG, -AGT, -AG, or -A.

Preferably the antisense-oligonucleotide of general formula (S7) has between 10 and 28 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S7) has between 11 and 24 nucleotides and at least two LNA nucleotides at the 3' terminus and at least two LNA nucleotides at the 5' terminus.

Still more preferably the antisense-oligonucleotide of general formula (S7) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Further preferred are antisense-oligonucleotides of the formula (S7):

$$5'-N^9-\text{ATTAATAA}-N^{10}-3'$$

wherein $N^9$ represents: TCATATTTATATACAGGC-, CATATT-TATATACAGGC-, ATATTTATATACAGGC-, TATT-TATATACAGGC-, ATTTATATACAGGC-, TTTATATA-CAGGC-, TTATATACAGGC-, TATATACAGGC-, ATATACAGGC-, TATACAGGC-, ATACAGGC-, TACAGGC-, ACAGGC-, CAGGC-, AGGC-, GGC-, GC-, or C-; and $N^{10}$ is selected from: -AGTGCAAATGTTATTGGC, -AGTGCAAATGTTATTGG, -AGTGCAAATGTTATTG, -AGTGCAAATGTTATT, -AGTGCAAATGTTAT, -AGTG-CAAATGTTA, -AGTGCAAATGTT, -AGTGCAAATGT, -AGTGCAAATG, -AGTGCAAAT, -AGTGCAAA, -AGTGCAA, -AGTGCA, -AGTGC, -AGTG, -AGT, -AG, or -A.

Also preferred are antisense-oligonucleotides of the formula (S7):

$$5'-N^9-\text{ATTAATAA}-N^{10}-3'$$

wherein $N^9$ represents: TTTATATACAGGC-, TTATATA-CAGGC-, TATATACAGGC-, ATATACAGGC-, TATA-CAGGC-, ATACAGGC-, TACAGGC-, ACAGGC-, CAGGC-, AGGC-, GGC-, GC-, or C-; and $N^{10}$ is selected from: -AGTGCAAATGTTA, -AGTGCAAATGTT, -AGTGCAAATGT, -AGTGCAA-ATG, -AGTGCAAAT, -AGTGCAAA, -AGTGCAA, -AGTGCA, -AGTGC, -AGTG, -AGT, -AG, or -A.

Also preferred are antisense-oligonucleotides of the formula (S7):

$$5'-N^9-\text{ATTAATAA}-N^{10}-3'$$

wherein $N^9$ represents: ATACAGGC-, TACAGGC-, ACAGGC-, CAGGC-, AGGC-, GGC-, GC-, or C-; and $N^{10}$ is selected from: -AGTGCAAA, -AGTGCAA, -AGTGCA, -AGTGC, -AGTG, -AGT, -AG, or -A.

Preferably, the present invention is directed to antisense-oligonucleotide(s) consisting of 12 to 24 nucleotides and at least three of the 12 to 24 nucleotides are LNAs and the antisense-oligonucleotide is capable of hybridizing with a region of the gene encoding the $TGF-R_{II}$ or with a region of the mRNA encoding the $TGF-R_{II}$, wherein the antisense-oligonucleotide is represented by the following sequence $5'-N^{9A}$-CATTAATAAA-$N^{10A}$-3' (Seq. ID No. 74), wherein $N^{9A}$ represents: ATTCATATTTATATACAGG- (Seq. ID No. 745), TTCATATTTATATACAGG- (Seq. ID No. 746), TCATATTTATATACAGG- (Seq. ID No. 747), CATATT-TATATACAGG- (Seq. ID No. 748), ATATTTATATA-CAGG- (Seq. ID No. 749), TATTTATATACAGG- (Seq. ID No. 750), ATTTATATACAGG- (Seq. ID No. 751), TTTATATACAGG- (Seq. ID No. 752), TTATATACAGG- (Seq. ID No. 753), TATATACAGG- (Seq. ID No. 754), ATATACAGG-, TATACAGG-, ATACAGG-, TACAGG-, ACAGG-, CAGG-, AGG-, GG-, or G-;

$N^{10A}$ represents: -GTGCAAATGTTATTGGCTA (Seq. ID No. 755), -GTGCAAATGTTATTGGCT (Seq. ID No. 756), -GTGCAAATGTTATTGGC (Seq. ID No. 757), -GTGCAAATGTTATTGG (Seq. ID No. 758), -GTGCAAATGTTATTG (Seq. ID No. 759), -GTGCAAATGTTATT (Seq. ID No. 760), -GTGCAAATGTTAT (Seq. ID No. 761), -GTGCAAATGTTA (Seq. ID No. 762), -GTGCAAATGTT (Seq. ID No. 763), -GTGCAAATGT (Seq. ID No. 764), -GTGCAAATG, -GTGCAAAT, -GTGCAAA, -GTGCAA, -GTGCA, -GTGC, -GTG, -GT, or -G;

and salts and optical isomers of the antisense-oligonucleotide.

Preferably $N^{9A}$ represents: TCATATTTATATACAGG-, CATATTTATATACAGG-, ATATTTATATACAGG-, TATTTATATACAGG-, ATTTATATACAGG-, TTTATATACAGG-, TTATATACAGG-, TATATACAGG-, ATATACAGG-, TATACAGG-, ATACAGG-, TACAGG-, ACAGG-, CAGG-, AGG-, GG-, or G-;
and
$N^{10A}$ represents: -GTGCAAATGTTATTGGC, -GTGCAAATGTTATTGG, -GTGCAAATGTTATTG, -GTGCAAATGTTATT, -GTGCAAATGTTAT, -GTGCAAATGTTA, -GTGCAAATGTT, -GTGCAAATGT, -GTGCAAATG, -GTGCAAAT, -GTGCAAA, -GTGCAA, -GTGCA, -GTGC, -GTG, -GT, or -G.

More preferably $N^{9A}$ represents: TTTATATACAGG-, TTATATACAGG-, TATATACAGG-, ATATACAGG-, TATACAGG-, ATACAGG-, TACAGG-, ACAGG-, CAGG-, AGG-, GG-, or G-; and
$N^{10A}$ represents: -GTGCAAATGTTA, -GTGCAAATGTT, -GTGCAAATGT, -GTGCAAATG, -GTGCAAAT, -GTGCAAA, -GTGCAA, -GTGCA, -GTGC, -GTG, -GT, or -G.

Still more preferably $N^{9A}$ represents: ATACAGG-, TACAGG-, ACAGG-, CAGG-, AGG-, GG-, or G-; and
$N^{10A}$ represents: -GTGCAAA, -GTGCAA, -GTGCA, -GTGC, -GTG, -GT, or -G.

Preferably the antisense-oligonucleotide of general formula (S7A/Seq. ID No. 74) has between 12 and 24 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S7A) has between 12 and 22 nucleotides and at least two LNA nucleotides at the 3' terminus and at least two LNA nucleotides at the 5' terminus.

Still more preferably the antisense-oligonucleotide of general formula (S7A) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Moreover, the present invention is directed to antisense-oligonucleotide(s) consisting of 8 to 18, preferably 10 to 28 nucleotides and at least two of the 8 to 28, preferably 10 to 28 nucleotides are LNAs and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$(N^{13})_m$-GTAGTGTT-$(N^{14})_n$-3' (Seq. ID No. 99), wherein $N^{13}$ represents: CCCAGCCTGCCCCAGAAGAGCTATTTG- (Seq. ID No. 793), CCAGCCTGCCCCAGAAGAGCTATTTG- (Seq. ID No. 794), CAGCCTGCCCCAGAAGAGCTATTTG- (Seq. ID No. 795), AGCCTGCCCCAGAAGAGCTATTTG- (Seq. ID No. 796), GCCTGCCCCAGAAGAGCTATTTG- (Seq. ID No. 797), CCTGCCCCAGAAGAGCTATTTG- (Seq. ID No. 798), CTGCCCCAGAAGAGCTATTTG- (Seq. ID No. 799), TGCCCCAGAAGAGCTATTTG- (Seq. ID No. 800), GCCCCAGAAGAGCTATTTG- (Seq. ID No. 801), CCCCAGAAGAGCTATTTG- (Seq. ID No. 802), CCCAGAAGAGCTATTTG- (Seq. ID No. 803), CCAGAAGAGCTATTTG- (Seq. ID No. 804), CAGAAGAGCTATTTG- (Seq. ID No. 805), AGAAGAGCTATTTG- (Seq. ID No. 86, GAAGAGCTATTTG- (Seq. ID No. 807), AAGAGCTATTTG- (Seq. ID No. 808), AGAGCTATTTG- (Seq. ID No. 809), GAGCTATTTG- (Seq. ID No. 810), AGCTATTTG-, GCTATTTG-, CTATTTG-, TATTTG-, ATTTG-, TTTG-, TTG-, TG-, or G-;
and
$N^{14}$ is selected from: -TAGGGAGCCGTCTTCAGGAATCTTCTC (Seq. ID No. 811), -TAGGGAGCCGTCTTCAGGAATCTTCT (Seq. ID No. 812), -TAGGGAGCCGTCTTCAGGAATCTTC (Seq. ID No. 813), -TAGGGAGCCGTCTTCAGGAATCTT (Seq. ID No. 814), -TAGGGAGCCGTCTTCAGGAATCT (Seq. ID No. 815), -TAGGGAGCCGTCTTCAGGAATC (Seq. ID No. 816), -TAGGGAGCCGTCTTCAGGAAT (Seq. ID No. 817), -TAGGGAGCCGTCTTCAGGAA (Seq. ID No. 818), -TAGGGAGCCGTCTTCAGGA (Seq. ID No. 819), -TAGGGAGCCGTCTTCAGG (Seq. ID No. 820), -TAGGGAGCCGTCTTCAG (Seq. ID No. 821), -TAGGGAGCCGTCTTCA (eq. ID No. 822), -TAGGGAGCCGTCTTC (Seq. ID No. 823), -TAGGGAGCCGTCTT (Seq. ID No. 824), -TAGGGAGCCGTCT (Seq. ID No. 825), -TAGGGAGCCGTC (Seq. ID No. 826), -TAGGGAGCCGT (Seq. ID No. 827), -TAGGGAGCCG (Seq. ID No. 828), -TAGGGAGCC, -TAGGGAGC, -TAGGGAG, -TAGGGA, -TAGGG, -TAGG, -TAG, -TA, or -T;

m represents 0 or 1;
n represents 0 or 1;
and n+m=1 or 2;
and salts and optical isomers of the antisense-oligonucleotide.

The antisense-oligonucleotides of formula S5 (Seq. ID No. 99) preferably comprise 2 to LNA units, more preferably 3 to 9 LNA units and still more preferably 4 to 8 LNA units and also preferably at least 6 non-LNA units, more preferably at least 7 non-LNA units and most preferably at least 8 non-LNA units. The non-LNA units are preferably DNA units. The LNA units are preferably positioned at the 3' terminal end (also named 3' terminus) and the 5' terminal end (also named 5' terminus). Preferably at least one and more preferably at least two LNA units are present at the 3' terminal end and/or at the 5' terminal end.

Thus, preferred are antisense-oligonucleotides of the present invention designed as GAPmers which contain 2 to 10 LNA units and which especially contain 1 to 5 LNA units at the 5' terminal end and 1 to 5 LNA units at the 3' terminal end of the antisense-oligonucleotide and between the LNA units at least 7 and more preferably at least 8 DNA units. More preferably the antisense-oligonucleotides comprise 2 to 4 LNA units at the 5' terminal end and 2 to 4 LNA units at the 3' terminal end and still more preferred comprise 3 to 4 LNA units at the 5' terminal end and 3 to 4 LNA units at the 3' terminal end and contain preferably at least 7 non-LNA units and most preferably at least 8 non-LNA units such as DNA units in between both LNA segments.

Moreover the antisense-oligonucleotides may contain common nucleobases such as adenine, guanine, cytosine, thymine and uracil as well as common derivatives thereof such as 5-methylcytosine or 2-aminoadenine. The antisense-oligonucleotides of the present invention may also contain modified internucleotide bridges such as phosphorothioate or phosphorodithioate instead of phosphate bridges. Such modifications may be present only in the LNA segments or only in the non-LNA segment of the antisense-oligonucleotide. As LNA units especially the residues $b^1$ to $b^9$ as disclosed herein are preferred.

Thus, preferred are antisense-oligonucleotides of the formula (S5):

$$5'-(N^{13})_m\text{-GTAGTGTT-}(N^{14})_n-3'$$

wherein $N^{13}$ represents: GCCTGCCCCAGAAGAGCTATTTG-, CCTGCCCCAGAAGAGCTATTTG-, CTGCCCCAGA-AGAGCTATTTG-, TGCCCCAGAAGAGCTATTTG-, GCCCCAGAAGAGCTATTTG-, CCCCAGAAGAGCTAT-TTG-, CCCAGAAGAGCTATTTG-, CCAGAAGAGCTAT-TTG-, CAGAAGAGCTATTTG-, AGAAGAGCTATTTG-, GAAGAGCTATTTG-, AAGAGCTATTTG-, AGAGCTAT-TTG-, GAGCTATTTG-, AGCTATTTG-, GCTATTTG-, CTATTTG-, TATTTG-, ATTTG-, TTTG-, TTG-, TG-, or G-; and $N^{14}$ is selected from: -TAGGGAGCCGTCTTC, -TAGG-GAGCCGTCTT, -TAGGGAGCCGTCT, -TAGG-GAGCCGTC, -TAGGGAGCCGT, -TAGGGAGCCG, -TAGGGAGCC, -TAGGGAGC, -TAGGGAG, -TAGGGA, -TAGGG, -TAGG, -TAG, -TA, or -T; and m represents 0 or 1; n represents 0 or 1; and n+m=1 or 2.

Preferably the antisense-oligonucleotide of general formula (S5) has between 10 and 28 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S5) has between 11 and 24 nucleotides and at least two LNA nucleotides at the 3' terminus and at least two LNA nucleotides at the 5' terminus.

Still more preferably the antisense-oligonucleotide of general formula (S5) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Further preferred are antisense-oligonucleotides of the formula (S5):

$$5'-(N^{13})_m\text{-GTAGTGTT-}(N^{14})_n-3'$$

wherein $N^{13}$ represents: CCCCAGAAGAGCTATTTG-, CCCAGAAGAGCTATTTG-, CCAGAAGAGCTATTTG-, CAGAAGAGCTATTTG-, AGAAGAGCTATTTG-, GAAGAGCTATTTG-, AAGAGCTATTTG-, AGAGCTAT-TTG-, GAGCTATTTG-, AGCTATTTG-, GCTATTTG-, CTATTTG-, TATTTG-, ATTTG-, TTTG-, TTG-, TG-, or G-; and $N^{14}$ is selected from: -TAGGGAGCCG, -TAGGGAGCC, -TAGGGAGC, -TAGGGAG, -TAGGGA, -TAGGG, -TAGG, -TAG, -TA, or -T; and m represents 0 or 1; n represents 0 or 1; and n+m=1 or 2.

Also preferred are antisense-oligonucleotides of the formula (S5):

$$5'-(N^{13})_m\text{-GTAGTGTT-}(N^{14})_n-3'$$

wherein $N^{13}$ represents: GAAGAGCTATTTG-, AAGAGCTAT-TTG-, AGAGCTATTTG-, GAGCTATTTG-, AGCTAT-TTG-, GCTATTTG-, CTATTTG-, TATTTG-, ATTTG-, TTTG-, TTG-, TG-, or G-; and $N^{14}$ is selected from: -TAGGG, -TAGG, -TAG, -TA, or -T; and m represents 0 or 1; n represents 0 or 1; and n+m=1 or 2.

Also preferred are antisense-oligonucleotides of the formula (S5):

$$5'-(N^{13})_m\text{-GTAGTGTT-}(N^{14})_n-3'$$

wherein $N^{13}$ represents: CAGAAGAGCTATTTG-, AGAAGAGCTATTTG-, GAAGAGCTATTTG-, AAGAG-CTATTTG-, AGAGCTATTTG-, GAGCTATTTG-, AGCT-ATTTG-, GCTATTTG-, CTATTTG-, TATTTG-, ATTTG-, TTTG-, TTG-, TG-, or G-; and $N^{14}$ is selected from: -TAGGGAGCCGTCTTCAG-GAATCT, -TAGGGAGCCGTCTTCAGGAATC, -TAGG-GAGCCGTCTTCAGGAAT, -TAGGGAGCCGTCT-TCAGGAA, -TAGGGAGCCGTCTTCAGGA, -TAGG-GAGCCGTCTTCAGG, -TAGGGAGCCGTCTTCAG, -TAGGGAGCCGTCTTCA, -TAGGGAGCCGTCTTC, -TAGGGAGCCGTCTT, -TAGGGAGCCGTCT, -TAGG-GAGCCGTC, -TAGGGAGCCGT, -TAGGGAGCCG, -TAGGGAGCC, -TAGGGAGC, -TAGGGAG, -TAGGGA, -TAGGG, -TAGG, -TAG, -TA, or -T; and m represents 0 or 1; n represents 0 or 1; and n+m=1 or 2.

Also preferred are antisense-oligonucleotides of the formula (S5):

$$5'-(N^{13})_m\text{-}\mathbf{GTAGTGTT}\text{-}(N^{14})_n\text{-}3'$$

wherein $N^{13}$ represents: GAGCTATTTG-, AGCTATTTG-, GCTATTTG-, CTATTTG-, TATTTG-, ATTTG-, TTTG-, TTG-, TG-, or G-; and $N^{14}$ is selected from: -TAGGGAGCCGTCTTCAGG, -TAGGGAGCCGTCTTCAG, -TAGGGAGCCGTCTTCA, -TAGGGAGCCGTCTTC, -TAGGGAGCCGTCTT, -TAGGGAGCCGTCT, -TAGGGAGCCGTC, -TAGGGAGCCGT, -TAGGGAGCCG, -TAGGGAGCC, -TAGGGAGC, -TAGGGAG, -TAGGGA, -TAGGG, -TAGG, -TAG, -TA, or -T; and m represents 0 or 1; n represents 0 or 1; and n+m=1 or 2.

Also preferred are antisense-oligonucleotides of the formula (S5):

$$5'-(N^{13})_m\text{-}\mathbf{GTAGTGTT}\text{-}(N^{14})_n\text{-}3'$$

wherein $N^{13}$ represents: ATTTG-, TTTG-, TTG-, TG-, or G-; and $N^{14}$ is selected from: -TAGGGAGCCGTCT, -TAGGGAGCCGTC, -TAGGGAGCCGT, -TAGGGAGCCG, -TAGGGAGCC, -TAGGGAGC, -TAGGGAG, -TAGGGA, -TAGGG, -TAGG, -TAG, -TA, or -T; and m represents 0 or 1; n represents 0 or 1; and n+m=1 or 2.

Preferably the antisense-oligonucleotide of general formula (S5/Seq. ID No. 99) has between 12 and 24 nucleotides and at least one LNA nucleotide at the 3' terminus and at least one LNA nucleotide at the 5' terminus. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable.

More preferably the antisense-oligonucleotide of general formula (S5) has between 12 and 22 nucleotides and at least two LNA nucleotides at the 3' terminus and at least two LNA nucleotides at the 5' terminus.

Still more preferably the antisense-oligonucleotide of general formula (S5) has between 12 and 20, more preferably between 13 and 19 and still more preferable between 14 and 18 nucleotides and between 2 and 5, preferably 3 and 5 and more preferably between 3 and 4 LNA units at the 3' terminal end and between 2 and 5, preferably 3 and 5 and more preferably between 3 and 4 LNA units at the 5' terminal end. Preferably the antisense-oligonucleotides are GAPmers of the form LNA segment A—DNA segment—LNA segment B. Preferably the antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases".

Another aspect of the present invention relates to antisense-oligonucleotide(s) having a length of 10 to 28 nucleotides, preferably 10 to 24 nucleotides, more preferably 11 to 22 nucleotides or 12 to 20 nucleotides, still more preferably 13 to 19 nucleotides, and most preferably 14 to 18 nucleotides, wherein at least two of the nucleotides, preferably at least three of the nucleotides, and more preferably at least four of the nucleotides are LNAs and the sequence of the antisense-oligonucleotide of the 10 to 28 nucleotides, preferably 10 to 24 nucleotides, more preferably 11 to 22 nucleotides or 12 to 20 nucleotides, still more preferably 13 to 19 nucleotides, and most preferably 14 to 18 nucleotides is selected from the group of sequences of 10 to 28 nucleotides, preferably 10 to 24 nucleotides, more preferably 11 to 22 nucleotides or 12 to 20 nucleotides, still more preferably 13 to 19 nucleotides, and most preferably 14 to 18 nucleotides contained in a sequence selected from the following group:

(Seq. ID No. 75: 383-423 of Seq. ID No. 1)
GAATCTTGAATATCTCATGAATGGACCAGTATTCTAGAAAC, (Seq. ID No. 77: 2245-2285 of Seq. ID No. 1)
TTCATATTTATATACAGGCATTAATAAAGTGCAAATGTTAT, (Seq. ID No. 78: 2315-2356 of Seq. ID No. 1)
TGAGGAAGTGCTAACACAGCTTATCCTATGACAATGTCAAAG, (Seq. ID No. 79: 2528-2576 of Seq. ID No. 1)
GCCTGCCCCAGAAGAGCTATTTGGTAGTGTTTAGGGAGCCGTCTTCAGG, (Seq. ID No. 81: 3205-3253 of Seq. ID No. 1)
CGCAGGTCCTCCCAGCTGATGACATGCCGCGTCAGGTACTCCTGTAGGT, (Seq. ID No. 83: 4141-4218 of Seq. ID No. 1)
ATGTCGTTATTAACCGACTTCTGAACGTGCGGTGGGATCGTGCTGGCGAT

ACGCGTCCACAGGACGATGTGCAGCGGC, (Seq. ID No. 84: 4216-4289 of Seq. ID No. 1)
GGCCACAGGCCCCTGAGCAGCCCCCGACCCATGGCAGACCCCGCTGCT

CGTCATAGACCGAGCCCCCAGCGCAG, (Seq. ID No. 86: 4141-4289 of Seq. ID No. 1)
ATGTCGTTATTAACCGACTTCTGAACGTGCGGTGGGATCGTGCTGGCGAT

ACGCGTCCACAGGACGATGTGCAGCGGCCACAGGCCCCTGAGCAGCCC

CCGACCCATGGCAGACCCCGCTGCTCGTCATAGACCGAGCCCCCAGCG

CAG, (Seq. ID No. 87: 388-418 of Seq. ID No. 1)
TTGAATATCTCATGAATGGACCAGTATTCTA, (Seq. ID No. 88: 483-515 of Seq. ID No. 1)
CAAGTGGAATTTCTAGGCGCCTCTATGCTACTG, (Seq. ID No. 89: 2250-2280 of Seq. ID No. 1)
ATTTATATACAGGCATTAATAAAGTGCAAAT, (Seq. ID No. 90: 2320-2351 of Seq. ID No. 1)
AAGTGCTAACACAGCTTATCCTATGACAATGT, (Seq. ID No. 91: 2533-2571 of Seq. ID No. 1)
CCCCAGAAGAGCTATTTGGTAGTGTTTAGGGAGCCGTCT, (Seq. ID No. 92: 2753-2830 of Seq. ID No. 1)
CTGGTCGCCCTCGATCTCTCAACACGTTGTCCTTCATGCT

TTCGACACAGGGGTGCTCCCGCACCTTGGAACCAAATG, (Seq. ID No. 93: 3210-3248 of Seq. ID No. 1)
GTCCTCCCAGCTGATGACATGCCGCGTCAGGTACTCCTG, (Seq. ID No. 94: 3655-3694 of Seq. ID No. 1)
CTCAGCTTCTGCTGCCGGTTAACGCGGTAGCAGTAGAAGA, (Seq. ID No. 95: 4146-4213 of Seq. ID No. 1)
GTTATTAACCGACTTCTGAACGTGCGGTGGGATCGTGCTG

GCGATACGCGTCCACAGGACGATGTGCA,

-continued (Seq. ID No. 96: 4221-4284 of Seq. ID No. 1)
CAGGCCCCTGAGCAGCCCCCGACCCATGGCAGACCCCGC

TGCTCGTCATAGACCGAGCCCCAG, (Seq. ID No. 97: 4495-4546 of Seq. ID No. 1)
CACGCGCGGGGGTGTCGTCGCTCCGTGCGCGCGAGTGAC

TCACTCAACTTCA, wherein the antisense-oligonucleotide is capable of selectively hybridizing in regard to the whole human transcriptome only with the gene encoding TGF-$R_{II}$ or with the mRNA encoding TGF-$R_{II}$ and salts and optical isomers of said antisense-oligonucleotide.

Said antisense-oligonucleotide having a sequence contained in the sequences No. 75, 77, 78, 79, 81, 83, 84, 86-97 have between 2 and 5, preferably 3 and 5 and more preferably between 3 and 4 LNA units at the 3' terminal end and between 2 and 5, preferably 3 and 5 and more preferably between 3 and 4 LNA units at the 5' terminal end and have preferably the structure of GAPmers of the form LNA segment A—DNA segment—LNA segment B. As LNA nucleotides (LNA units) especially these disclosed in the chapter "Locked Nucleic Acids (LNA®)" and preferably in the chapter "Preferred LNAs" are suitable and as internucleotides bridges especially these disclosed in the chapter "Internucleotide Linkages (IL)" are suitable. Preferably said antisense-oligonucleotides contain at least 6, more preferably at least 7 and most preferably at least 8 non-LNA units such as DNA units in between the two LNA segments. Suitable nucleobases for the non-LNA units and the LNA units are disclosed in the chapter "Nucleobases". Suitable examples for said antisense-oligonucleotides are represented by the formulae (S1) to (S7), (S1A) to (S4A), (S6A) and (S7A).

The Seq. ID No. 1 represents the antisense strand of the cDNA (cDNA) (5'-3' antisense-sequence) of the *Homo sapiens* transforming growth factor, beta receptor II (TGF-$R_{II}$), transcript variant 2.

The Seq. ID No. 2 represents the sense strand of the cDNA (5'-3' sense-sequence) of the *Homo sapiens* transforming growth factor, beta receptor II (70/80 kDa) (TGF-$R_{II}$), transcript variant 2. Alternatively, one can also regard the sequence of Seq. ID No. 2 to represent the sequence of the mRNA of the *Homo sapiens* transforming growth factor, beta receptor II (TGF-$R_{II}$), transcript variant 2 (Seq. ID No. 3), but written in the DNA code, i.e. represented in G, C, A, T code, and not in the RNA code.

The Seq. ID No. 3 represents the mRNA (5'-3' sense-sequence) of the *Homo sapiens* transforming growth factor, beta receptor II (TGF-$R_{II}$), transcript variant 2. It is evident that the mRNA displayed in Seq. ID No. 3 is written in the RNA code, i.e. represented in G, C, A, U code.

It shall be understood, that "coding DNA strand", as used herein, refers to the DNA strand that is identical to the mRNA (except that is written in the DNA code) and that encompasses the codons that used for protein translation. It is not used as template for the transcription into mRNA. Thus, the terms "coding DNA strand", "sense DNA strand" and "non-template DNA strand" can be used interchangeably. Furthermore, "non-coding DNA strand", as used herein, refers to the DNA strand that is complementary to the "coding DNA strand" and serves as a template for the transcription of mRNA. Thus, the terms "non-coding DNA strand", "antisense DNA strand" and "template DNA strand" can be used interchangeably The term "antisense-oligonucleotide" refers to an oligomer or polymer of ribonucleic acid (RNA) or deoxyribonucleic acid (DNA) or mimetics or variants thereof such as antisense-oligonucleotides having a modified internucleotide linkage like a phosphorothioate linkage and/or one or more modified nucleobases such as 5-methylcytosine and/or one or more modified nucleotide units such as LNAs like s-D-oxy-LNA. The term "antisense-oligonucleotide" includes oligonucleotides composed of naturally-occurring nucleobases, sugars and covalent internucleotide (backbone) linkages as well as oligonucleotides having non-naturally-occurring portions which function similarly. Such modified or substituted oligonucleotides are often preferred over native forms, because of desirable properties such as, for example, enhanced cellular uptake, enhanced affinity for nucleic acid target and increased stability in the presence of nucleases. The antisense-oligonucleotides are short catalytic RNAs or catalytic oligonucleotides which hybridize to the target nucleic acid and inhibit its expression.

The term "nucleoside" is well known to a skilled person and refers to a pentose sugar moiety like ribose, desoxyribose or a modified or locked ribose or a modified or locked desoxyribose like the LNAs which are below disclosed in detail. A nucleobase is linked to the glycosidic carbon atom (position 1' of the pentose) and an internucleotide linkage is formed between the 3' oxygen or sulfur atom and preferably the 3' oxygen atom of a nucleoside and the 5' oxygen or sulfur atom and preferably the 5' oxygen atom of the adjacent nucleoside, while the internucleotide linkage does not belong to the nucleoside (see FIG. 2).

The term "nucleotide" is well known to a skilled person and refers to a pentose sugar moiety like ribose, desoxyribose or a modified or locked ribose or a modified or locked desoxyribose like the LNAs which are below disclosed in detail. A nucleobase is linked to the glycosidic carbon atom (position 1' of the pentose) and an internucleotide linkage is formed between the 3' oxygen or sulfur atom and preferably the 3' oxygen atom of a nucleotide and the 5' oxygen or sulfur atom and preferably the 5' oxygen atom of the adjacent nucleotide, while the internucleotide linkage is a part of the nucleotide (see FIG. 2).

Nucleobases

The term "nucleobase" is herein abbreviated with "B" and refers to the five standard nucleotide bases adenine (A), thymine (T), guanine (G), cytosine (C), and uracil (U) as well as to modifications or analogues thereof or analogues with ability to form Watson-Crick base pair with bases in the complimentary strand. Modified nucleobases include other synthetic and natural nucleobases such as 5-methylcytosine (C*), 5-hydroxymethyl cytosine, $N^4$-methylcytosine, xanthine, hypoxanthine, 7-deazaxanthine, 2-aminoadenine, 6-methyladenine, 6-methylguanine, 6-ethyladenine, 6-ethylguanine, 2-propyladenine, 2-propylguanine, 6-carboxyuracil, 5-halouracil, 5,6-dihydrouracil, 5-halocytosine, 5-propynyl uracil, 5-propynyl cytosine, 6-aza uracil, 6-aza cytosine, 6-aza thymine, 5-uracil (pseudouracil), 4-thiouracil, 8-fluoroadenine, 8-chloroadenine, 8-bromoadenine, 8-iodoadenine, 8-aminoadenine, 8-thioladenine, 8-thioalkyladenine, 8-hydroxyladenine, 8-fluoroguanine, 8-chloroguanine, 8-bromoguanine, 8-iodoguanine, 8-aminoguanine, 8-thiolguanine, 8-thioalkylguanine, 8-hydroxylguanine, 5-fluorouracil, 5-bromouracil, 5-chlorouracil, 5-iodouracil, 5-trifluoromethyluracil, 5-fluorocytosine, 5-bromocytosine, 5-chlorocytosine, 5-iodocytosine, 5-trifluoromethylcytosine, 7-methylguanine, 7-methyladenine, 8-azaguanine, 8-azaadenine, 7-deazaguanine, 7-deazaadenine, 7-deaza-8-azaadenine, 3-deazaguanine, 3-deazaadenine, 2-thiouracil, 2-thiothymine and 2-thiocytosine etc., with 5-methylcytosine and/or 2-aminoadenine substitutions being preferred since these modifications have been shown to increase nucleic acid duplex stability.

Preferred antisense-oligonucleotides of the present invention can comprise analogues of nucleobases. The nucleobase of only one nucleotide unit of the antisense-oligonucleotide could be replaced by an analogue of a nucleobase or two, three, four, five or even all nucleobases in an antisense-oligonucleotide could be replaced by analogues of nucleobases, such as 5-methylcytosine, or $N^6$-methyl-adenine or 2-aminoadenine. Preferably the LNA units might be connected to analogues of nucleobases such as 5-methylcytosine.

It will be recognized that when referring to a sequence of nucleotides or monomers, what is referred to, is the sequence of bases, such as A, T, G, C or U. However, except the specific examples disclosed in Tables 3 to 8 the representation of the antisense-oligonucleotides by the letter code A, T, G, C and U has to be understood that said antisense-oligonucleotide may contain any the nucleobases as disclosed herein, any of the 3' end groups as disclosed herein, any of the 5' end groups as disclosed herein, and any of the internucleotide linkages (also referred to as internucleotide bridges) as disclosed herein. The nucleotides A, T, G, C and U have also to be understood as being LNA nucleotides or non-LNA nucleotides such as preferably DNA nucleotides.

Only in regard to the specific examples as disclosed in Tables 4 to 9 the nucleobases, the LNA units, the non-LNA units, the internucleotide linkages and the end groups are further specified as outlined in the chapter "Legend" before Table 2.

The antisense-oligonucleotides as well as the salts of the antisense-oligonucleotides as disclosed herein have been proven to be complementary to the target which is the gene encoding for the TGF-$R_{II}$ or the mRNA encoding the TGF-$R_{II}$, i.e., hybridize sufficiently well and with sufficient specificity and especially selectivity to give the desired inhibitory effect.

The term "salt" refers to physiologically and/or pharmaceutically acceptable salts of the antisense-oligonucleotides of the present invention. The antisense-oligonucleotides contain nucleobases like adenine, guanine, thymine, cytosine or derivatives thereof which are basic and which form a salt like a chloride or mesylate salt. The internucleotide linkage preferably contains a negatively charged oxygen or sulfur atom which form salts like the sodium, lithium or potassium salt. Thus, pharmaceutically acceptable base addition salts are formed with inorganic bases or organic bases. Examples for suitable organic and inorganic bases are bases derived from metal ions, e.g., aluminum, alkali metal ions, such as sodium or potassium, alkaline earth metal ions such as calcium or magnesium, or an amine salt ion or alkali- or alkaline-earth hydroxides, -carbonates or -bicarbonates. Examples include aqueous LiOH, NaOH, KOH, $NH_4OH$, potassium carbonate, ammonia and sodium bicarbonate, ammonium salts, primary, secondary and tertiary amines, such as, e.g., tetraalkylammonium hydroxide, lower alkylamines such as methylamine, t-butylamine, procaine, ethanolamine, arylalkylamines such as dibenzylamine and N,N-dibenzylethylenediamine, lower alkylpiperidines such as N-ethylpiperidine, cycloalkylamines such as cyclohexylamine or dicyclohexylamine, morpholine, glucamine, N-methyl- and N,N-dimethylglucamine, 1-adamantylamine, benzathine, or salts derived from amino acids like arginine, lysine, ornithine or amides of originally neutral or acidic amino acids, chloroprocaine, choline, procaine or the like.

Since the antisense-oligonucleotides are basic, they form pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyltartaric acid, tartronic acid, □-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

In the context of this invention, "hybridization" means nucleic acid hybridization, wherein a single-stranded nucleic acid (DNA or RNA) interacts with another single-stranded nucleic acid having a very similar or even complementary sequence. Thereby the interaction takes place by hydrogen bonds between specific nucleobases (base pairing).

As used herein, the term "complementarity" (DNA and RNA base pair complementarity) refers to the capacity for precise pairing between two nucleic acids. The nucleotides in a base pair are complementary when their shape allows them to bond together by hydrogen bonds. Thereby forms the pair of adenine and thymidine (or uracil) two hydrogen bonds and the cytosine-guanine pair forms three hydrogen bonds. "Complementary sequences" as used herein means DNA or RNA sequences, being such that when they are aligned antiparallel to each other, the nucleotide bases at each position in the sequences will be complementary, much like looking in the mirror and seeing the reverse of things.

The term "specifically hybridizable" as used herein indicates a sufficient degree of complementarity or precise base pairing of the antisense-oligonucleotide to the target sequence such that stable and specific binding occurs between the antisense-oligonucleotide and the DNA or RNA target. The sequence of an -oligonucleotide according to the invention does not need to be 100% complementary to that of its target nucleic acid to be specifically hybridizable, although a 100% complementarity is preferred. Thereby "100% complementarity" means that the antisense-oligonucleotide hybridizes with the target over its complete or full length without mismatch. In other words, within the present invention it is defined that an antisense compound is specifically hybridizable when binding of the compound to the target DNA or RNA molecule takes place under physiological or pathological conditions but non-specific binding of the antisense-oligonucleotide to non-target sequences is highly unlikely or even impossible.

Therefore, the present invention refers preferably to antisense oligonucleotides, wherein the antisense oligonucleotides bind with 100% complementarity to the mRNA encoding TGF RII and do not bind to any other region in the complete human transcriptome. Further preferred the present invention refers to antisense oligonucleotides, wherein the antisense oligonucleotides have 100% complementarity over their complete length to the mRNA encoding TGF RII and have no off-target effects. Alternatively, the present invention refers preferably to antisense oligonucleotides having 100% complementarity to the mRNA encoding TGF RII but no complementarity to another mRNA of the human transcriptome. Thereby the term "human transcriptome" refers to the total set of transcripts in the human organism, which means transcripts of all cell types and environmental conditions (at any given time).

Specificity

The antisense-oligonucleotides of the present invention have in common that they are specific in regard to the region where they bind to the gene or to the mRNA encoding TGF-$R_{II}$. According to the present invention it is preferred that within the human transcriptome, the antisense-oligonucleotides have 100% complementarity over their full length only with the mRNA encoding TGF-RII. In addition, it was a goal of the present invention to find antisense-oligonucleotides without cross-reactivity within to the transcriptome of mammalian other than monkeys; in particular, the antisense-oligonucleotides have only cross-reactivity with the transcriptome of great apes. This should avoid off-effects. Thus the antisense-oligonucleotides of the present invention are highly specific concerning hybridization with the gene or with the mRNA encoding TGF-RII. The antisense-oligonucleotides of the invention bind preferably over their complete length with 100% complementarity specific to the gene encoding TGF-RII or to the mRNA encoding TGF-RII and do not bind to any other region in the complete human transcriptome. This means, the antisense-oligonucleotides of the present invention hybridize with the target (TGF-RII mRNA) without mismatch.

The term "mRNA", as used herein, may encompass both mRNA containing introns (also referred to as Pre-mRNA) as well as mRNA which does not contain any introns.

The antisense-oligonucleotides of the present invention are able to bind or hybridize with the Pre-mRNA and/or with the mRNA. That means the antisense-oligonucleotides can bind to or hybridize at an intron region or within an intron region of the Pre-mRNA or can bind to or hybridize at an overlapping intron—exon region of the Pre-mRNA or can bind to or hybridize at an exon region or within an exon region of the Pre-mRNA and the exon region of the mRNA (see FIG. 1). Preferred are antisense-oligonucleotides which are able to bind to or hybridize with Pre-mRNA and mRNA. Binding or hybridization of the antisense-oligonucleotides (ASO) to the Pre-mRNA inhibits the 5' cap formation, inhibits splicing of the Pre-mRNA in order to obtain the mRNA and activates RNase H which cleaves the Pre-mRNA. Binding or hybridization of the antisense-oligonucleotides (ASO) to the mRNA activates RNase H which cleaves the mRNA and inhibits binding of the ribosomal subunits.

The antisense-oligonucleotides of the present invention consist of at least 10 and no more than 28, preferably no more than 24 and more preferably no more than 20 nucleotides and consequently consist of 10, 11, 12, 13, 14, 15, 16, 17, 18, 19, or 20 nucleotides, preferably of 11 to 20, or 11 to 19, or 12 to 19, or 13 to 19, or 13 to 18 nucleotides and more preferably of 14 to 18 nucleotides, wherein at least two, preferably three of these nucleotides are locked nucleic acids (LNA). Shorter antisense-oligonucleotides, i.e. antisense-oligonucleotides having less than 10 nucleotides, are also possible but the shorter the antisense-oligonucleotides the higher the risk that the hybridization is not sufficiently strong anymore and that selectivity will decrease or will get lost. Non-selective antisense-oligonucleotides bear the risk to bind to undesired regions in the human transcriptome and to undesired mRNAs coding for other proteins than TGF-$R_{II}$ thereby causing undesired side effects. Longer antisense-oligonucleotides having more than 20 nucleotides are also possible but further increasing the length make the synthesis of such antisense-oligonucleotides even more complicated and expensive without any further benefit in increasing selectivity or strength of hybridization or better stability in regard to degradation.

Thus the present invention is directed to antisense-oligonucleotides consisting of 10 to nucleotides, wherein at least two nucleotides and preferably the 3' and 5' terminal nucleotides are LNAs. Thus, it is preferred that at least the terminal 3' nucleotide is an LNA and also at least the 5' terminal nucleotide is an LNA. In case more than 2 LNAs are present, it is preferred that the further LNAs are linked to the 3' or 5' terminal LNA like it is the case in gapmers as disclosed herein.

One nucleotide building block present in an antisense-oligonucleotide of the present invention can be represented by the following general formula (B1) and (B2):

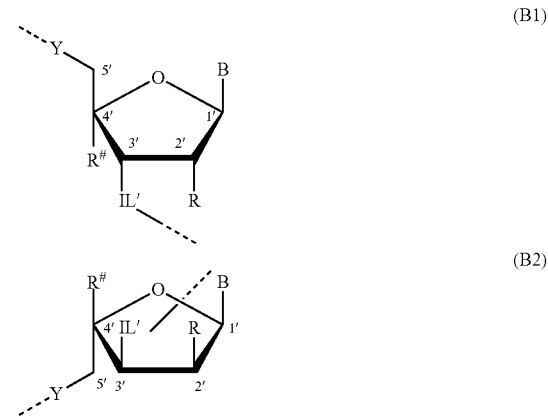

wherein
B represents a nucleobase;
IL' represents —X"—P(=X⁻)(X⁻)—;
R represents —H, —F, —OH, —NH₂, —OCH₃, —OCH₂CH₂OCH₃ and $R^{\#}$ represents —H; or R and $R^{\#}$ form together the bridge —$R^{\#}$—R— which is selected from —CH₂—O—, —CH₂—S—, —CH₂—NH—, —CH₂—N(CH₃)—, —CH₂—N(C₂H₅)—, —CH₂—CH₂—O—, —CH₂—CH₂—S—, —CH₂—CH₂—NH—, —CH₂—CH₂—N(CH₃)—, or —CH₂—CH₂—N(C₂H₅)—;
X' represents =O or =S;
X⁻ represents —O⁻, —OH, —OR$^H$, —NHR$^H$, —N(R$^H$)₂, —OCH₂CH₂OR$^H$, —OCH₂CH₂SR$^H$, -BH₃⁻, —R$^H$, —SH, —SR$^H$, or —S;
X" represents —O—, —NH—, —NR$^H$—, —CH₂—, or —S—;
Y is —O—, —NH—, —NR$^H$—, —CH₂— or —S—;
R$^H$ is selected from hydrogen and C₁₋₄-alkyl and preferably —CH₃ or —C₂H₅ and most preferably —CH₃.
Preferably X⁻ represents —O—, —OH, —OCH₃, —NH (CH₃), —N(CH₃)₂, —OCH₂CH₂OCH₃, —OCH₂CH₂SCH₃, —BH₃⁻, —CH₃, —SH, —SCH₃, or —S⁻; and more preferably —O⁻, —OH, —OCH₃, —N(CH₃)₂, —OCH₂CH₂OCH₃, —BH₃~, —SH, —SCH₃, or —S⁻.
IL' represents preferably —O—P(O)(O⁻)—, —O—P(O) (S⁻)—, —O—P(S)(S⁻)—, —S—P(O)(O⁻)—, —S—P(O) (S⁻)—, —S—P(S)(S⁻)—, —O—P(O)(O⁻)—, —O—P(O) (S⁻)—, —S—P(O)(O⁻)—, —O—P(O)(R$^H$)—, —O—P(O)

(OR$^H$)—, —O—P(O)(NHR$^H$)—, —O—P(O)[N(R$^H$)$_2$]-, —O—P(O)(BH$_3$$^-$)—, —O—P(O)(OCH$_2$CH$_2$OR$^H$)—, —O—P(O)(OCH$_2$CH$_2$SR$^H$)—, —O—P(O)(O$^-$)—, —NR$^H$—P(O)(O$^-$)—, wherein R$^H$ is selected from hydrogen and C$_{1-4}$-alkyl.

The group —O—P(O)(R$^H$)—O— is preferably —O—P(O)(CH$_3$)—O— or —O—P(O)(C$_2$H$_5$)—O— and most preferably —O—P(O)(CH$_3$)—O—.

The group —O—P(O)(OR$^H$)—O— is preferably —O—P(O)(OCH$_3$)—O— or —O—P(O)(OC$_2$H$_5$)—O— and most preferably —O—P(O)(OCH$_3$)—O—.

The group —O—P(O)(NHR$^H$)—O— is preferably —O—P(O)(NHCH$_3$)—O— or —O—P(O)(NHC$_2$H$_5$)—O— and most preferably —O—P(O)(NHCH$_3$)—O—.

The group —O—P(O)[N(R$^H$)$_2$]—O— is preferably —O—P(O)[N(CH$_3$)$_2$]—O— or —O—P(O)[N(C$_2$H$_5$)$_2$]—O— and most preferably —O—P(O)[N(CH$_3$)$_2$]—O—.

The group —O—P(O)(OCH$_2$CH$_2$OR$^H$)—O— is preferably —O—P(O)(OCH$_2$CH$_2$OCH$_3$)—O— or —O—P(O)(OCH$_2$CH$_2$OC$_2$H$_5$)—O— and most preferably —O—P(O)(OCH$_2$CH$_2$OCH$_3$)—O—.

The group —O—P(O)(OCH$_2$CH$_2$SR$^H$)—O— is preferably —O—P(O)(OCH$_2$CH$_2$SCH$_3$)—O— or -O—P(O)(OCH$_2$CH$_2$SC$_2$H$_5$)—O— and most preferably —O—P(O)(OCH$_2$CH$_2$SCH$_3$)—O—.

The group —O—P(O)(O$^-$)—NR$^H$- is preferably —O—P(O)(O$^-$)—NH— or —O—P(O)(O$^-$)—N(CH$_3$)—and most preferably —O—P(O)(O$^-$)—NH—.

The group —NR$^H$—P(O)(O$^-$)—O— is preferably —NH—P(O)(O$^-$)—O— or —N(CH$_3$)—P(O)(O$^-$)—O— and most preferably —NH—P(O)(O$^-$)—O—.

Even more preferably IL' represents —O—P(O)(O$^-$)—, —O—P(O)(S$^-$)—, —O—P(S)(S$^-$)—, —O—P(O)(NHR$^H$)—, or —O—P(O)[N(R$^H$)$_2$]-, and still more preferably IL' represents —O—P(O)(O$^-$)—, —O—P(O)(S$^-$)—, or —O—P(S)(S$^-$)—, and most preferably IL' represents —O—P(O)(S$^-$)—, or —O—P(S)(S$^-$)—.

Preferably Y represents —O—.

Preferably B represents a standard nucleobase selected from A, T, G, C, U.

Preferably IL represents —O—P(=O)(S$^-$)— or —O—P(=S)(S$^-$)—.

The above definitions of B, Y and IL' apply also to the formula b$^1$ to b$^9$.

Thus the following general formula (B3) to (B6) are preferred:

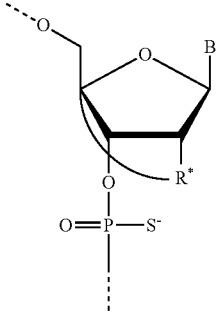
(B3)

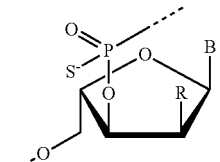
(B4)

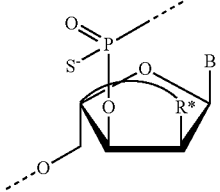
(B5)

(B6)

wherein

B represents a nucleobase and preferably A, T, G, C, U;

R represents —H, —F, —OH, —NH$_2$, —N(CH$_3$)$_2$, —OCH$_3$, —OCH$_2$CH$_2$OCH$_3$, —OCH$_2$CH$_2$OH, —OCH$_2$CH$_2$CH$_2$NH$_2$ and preferably —H;

R* represents the moiety -R$^\#$—R- as defined below and is, for instance, preferably selected from —C(R$^a$R$^b$)—O—, —C(R$^a$R$^b$)—NR$^c$—, —C(R$^a$R$^b$)—S—, and —C(R$^a$R$^b$)—C(R$^a$R$^b$)—O—, wherein the substituents R$^a$, R$^b$ and R$^c$ have the meanings as defined herein. More preferably R* is selected from —CH$_2$—O—, —CH$_2$—S—, —CH$_2$—NH—, —CH$_2$—N(CH$_3$)—, —CH$_2$—CH$_2$—O—, or —CH$_2$—CH$_2$—S—, and more preferably —CH$_2$—O—, —CH$_2$—S—, —CH$_2$—CH$_2$—O—, or —CH$_2$—CH$_2$—S—, and still more preferably —CH$_2$—O—, —CH$_2$—S—, or —CH$_2$—CH$_2$—O—, and still more preferably —CH$_2$—O— or —CH$_2$—S—, and most preferably —CH$_2$—O—.

Examples of preferred nucleotides which are non-LNA units are the following:

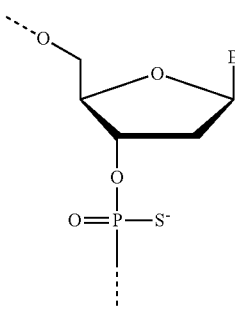
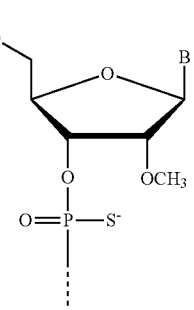

57
-continued
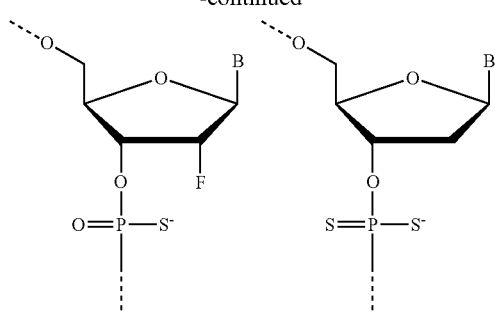
58
-continued
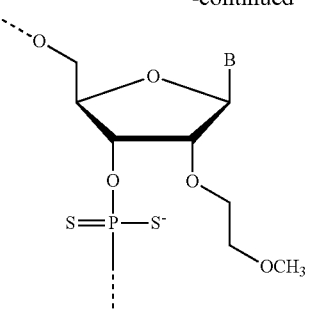
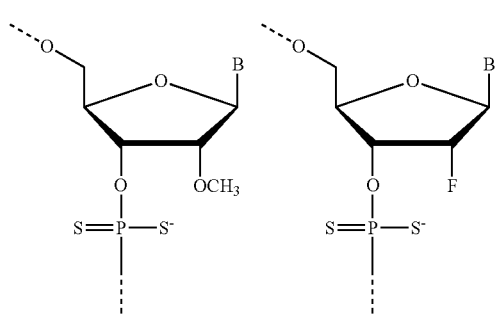
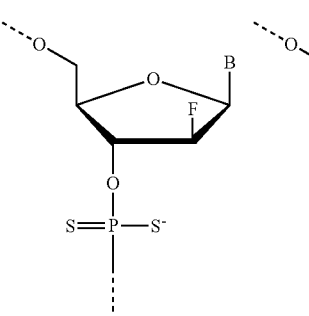
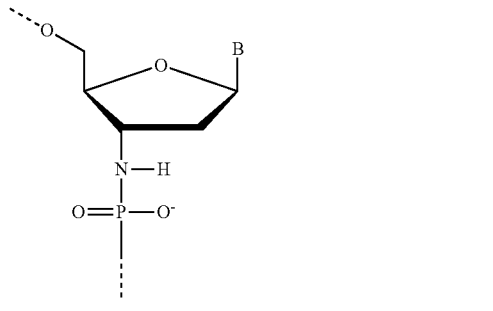
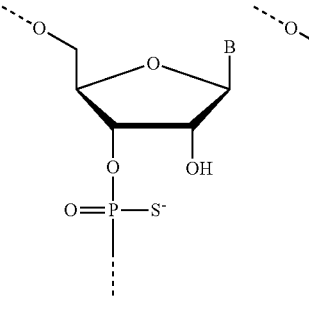
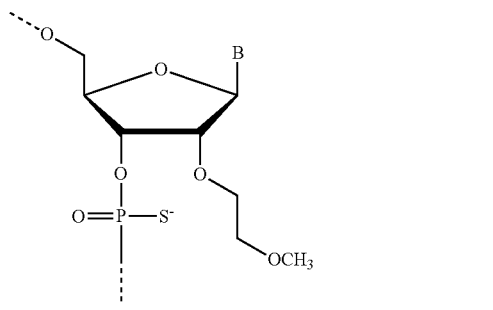
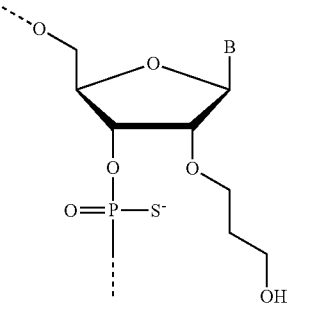
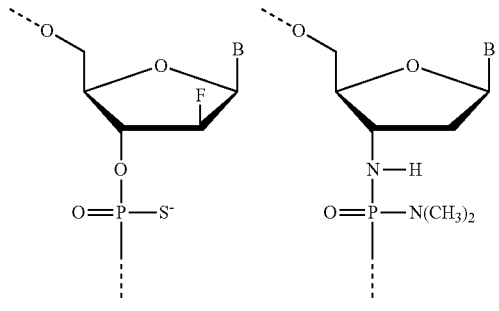
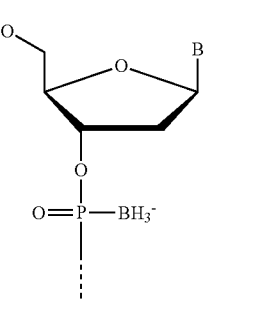

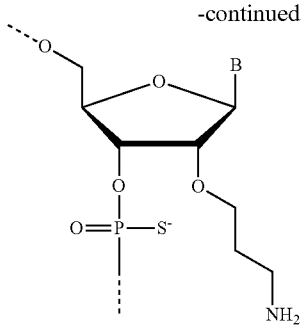

Internucleotide Linkages (IL)

The monomers of the antisense-oligonucleotides described herein are coupled together via an internucleotide linkage. Suitably, each monomer is linked to the 3' adjacent monomer via an internucleotide linkage. The person having ordinary skill in the art would understand that, in the context of the present invention, the 5' monomer at the end of an oligomer does not comprise a 5' internucleotide linkage, although it may or may not comprise a 5' terminal group. The term "internucleotide linkage" is intended to mean a group capable of covalently coupling together two nucleotides, two nucleotide analogues like two LNAs, and a nucleotide and a nucleotide analogue like an LNA. Specific and preferred examples include phosphate groups and phosphorothioate groups.

The nucleotides of the antisense-oligonucleotides of the present invention or contiguous nucleotide sequences thereof are coupled together via internucleotide linkages. Suitably each nucleotide is linked through the 5' position to the 3' adjacent nucleotide via an internucleotide linkage.

The antisense-oligonucleotides can be modified by several different ways. Modifications within the backbone are possible and refer to antisense-oligonucleotides wherein the phosphate groups (also named phosphodiester groups) in their internucleotide backbone are partially or completely replaced by other groups. Preferred modified antisense-oligonucleotide backbones include, for instance, phosphorothioates, chiral phosphorothioates, phosphorodithioates, phosphotriester, aminoalkylphosphotriesters, methyl, ethyl and $C_3$-$C_{10}$-alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters and boranophosphates having normal 3'-5' linkages, 2'-5' linked analogues of these, and those having inverted polarity wherein the adjacent pairs of nucleotide units are linked 3'-5' to 5'-3' or 2'-5' to 5'-2'. Various salts, mixed salts and free acids forms thereof are also included and disclosed herein in further detail.

Suitable internucleotide linkages include those listed within WO2007/031091, for example the internucleotide linkages listed on the first paragraph of page 34 of WO2007/031091 (hereby incorporated by reference). It is, in some embodiments, preferred to modify the internucleotide linkage from its normal phosphodiester to one that is more resistant to nuclease attack, such as phosphorothioate or boranophosphate—these two, accepted by RNase H mediated cleavage, also allow that route of antisense inhibition in reducing the expression of the target gene.

The internucleotide linkage consists of the group IL' which is the group bound to the 3' carbon atom of the ribose moiety and the group Y which is the group bound to the 5' carbon atom of the contiguous ribose moiety as shown in the formula (IL'Y) below

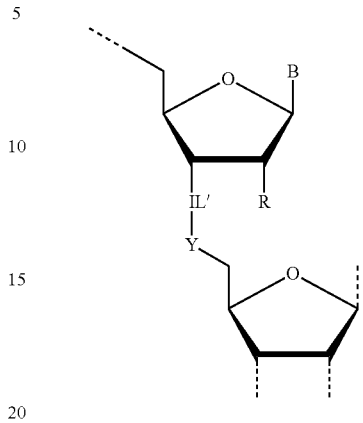

The internucleotide linkage IL is represented by -IL'-Y-. IL' represents —X"—P(=X$^-$)(X$^-$)— so that IL is represented by —X"—P(=X$^-$)(X$^-$)—Y—, wherein the substituents X$^-$, X$^-$, X" and Y have the meanings as disclosed herein.

The internucleotide linkage IL=—X"—P(=X$^-$)(X$^-$)—Y— is preferably selected form the group consisting of:
—O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —S—P(S)(S$^-$)—O—, —O—P(O)(O$^-$)—S—, —O—P(O)(S$^-$)—S—, —S—P(O)(O$^-$)—S—, —O—P(O)(R$^H$)—O—, —O—P(O)(OR$^H$)—O—, —O—P(O)(NHR$^H$)—O—, —O—P(O)[N(R$^H$)$_2$]—O—, —O—P(O)(BH$_3^-$)—O—, —O—P(O)(OCH$_2$CH$_2$OR$^H$)—O—, —O—P(O)(OCH$_2$CH$_2$SR$^H$)—O—, —O—P(O)(O$^-$)—NR$^H$—, —NR$^H$—P(O)(O$^-$)—O—, where R$^H$ is selected from hydrogen and $C_{1-4}$-alkyl.

The group —O—P(O)(R$^H$)—O— is preferably —O—P(O)(CH$_3$)—O— or —O—P(O)(C$_2$H$_5$)—O— and most preferably —O—P(O)(CH$_3$)—O—.

The group —O—P(O)(OR$^H$)—O— is preferably —O—P(O)(OCH$_3$)—O— or —O—P(O)(OC$_2$H$_5$)—O— and most preferably —O—P(O)(OCH$_3$)—O—.

The group —O—P(O)(NHR$^H$)—O— is preferably —O—P(O)(NHCH$_3$)—O— or —O—P(O)(NHC$_2$H$_5$)—O— and most preferably -O—P(O)(NHCH$_3$)—O—.

The group —O—P(O)[N(R$^H$)$_2$]—O— is preferably —O—P(O)[N(CH$_3$)$_2$]—O— or —O—P(O)[N(C$_2$H$_5$)$_2$]—O— and most preferably —O—P(O)[N(CH$_3$)$_2$]—O—.

The group —O—P(O)(OCH$_2$CH$_2$OR$^H$)—O— is preferably —O—P(O)(OCH$_2$CH$_2$OCH$_3$)—O— or —O—P(O)(OCH$_2$CH$_2$OC$_2$H$_5$)—O— and most preferably —O—P(O)(OCH$_2$CH$_2$OCH$_3$)—O—.

The group —O—P(O)(OCH$_2$CH$_2$SR$^H$)—O— is preferably -O—P(O)(OCH$_2$CH$_2$SCH$_3$)—O— or —O—P(O)(OCH$_2$CH$_2$SC$_2$H$_5$)—O— and most preferably —O—P(O)(OCH$_2$CH$_2$SCH$_3$)—O—.

The group —O—P(O)(O$^-$)—NR$^H$- is preferably —O—P(O)(O$^-$)—NH— or —O—P(O)(O$^-$)—N(CH$_3$)—and most preferably —O—P(O)(O$^-$)—NH—.

The group —NR$^H$—P(O)(O$^-$)—O— is preferably —NH—P(O)(O$^-$)—O— or —N(CH$_3$)—P(O)(O$^-$)—O— and most preferably —NH—P(O)(O$^-$)—O—.

Even more preferably IL represents —O—P(O)(O$^-$)—O—, —O—P(O)(S$^-$)—O—, —O—P(S)(S$^-$)—O—, —O—P(O)(NHR$^H$)—O—, or —O—P(O)[N(R$^H$)$_2$]—O—, and still more preferably IL represents —O—P(O)(O⁻)—O—, —O—P(O)(S⁻)—O—, or —O—P(S)(S⁻)—O—, and most preferably IL represents —O—P(O)(S⁻)—O—, or —O—P(O)(O⁻)—O—.

Thus IL is preferably a phosphate group (—O—P(O)(O⁻)—O—), a phosphorothioate group (—O—P(O)(S⁻)—O—) or a phosphorodithioate group (—O—P(S)(S⁻)—O—).

The nucleotide units or the nucleosides of the antisense-oligonucleotides are connected to each other by internucleotide linkages so that within one antisense-oligonucleotide different internucleotide linkages can be present. The LNA units are preferably linked by internucleotide linkages which are not phosphate groups. The LNA units are linked to each other by a group IL which is preferably selected from —O—P(O)(S⁻)—O—, —O—P(S)(S⁻)—O—, —O—P(O)(NHR^H)—O—, and —O—P(O)[N(R^H)₂]—O— and more preferably from —O—P(O)(S⁻)—O— and —O—P(S)(S⁻)—O—.

The non-LNA units are linked to each other by a group IL which is preferably selected from —O—P(O)(O⁻)—O—, —O—P(O)(S⁻)—O—, —O—P(S)(S⁻)—O—, —O—P(O)(NHR^H)—O—, and —O—P(O)[N(R^H)₂]—O— and more preferably from —O—P(O)(O⁻)—O—, —O—P(O)(S⁻)—O— and —O—P(S)(S⁻)—O—.

A non-LNA unit is linked to an LNA unit by a group IL which is preferably selected from —O—P(O)(S⁻)—O—, —O—P(S)(S⁻)—O—, —O—P(O)(NHR^H)—O—, and —O—P(O)[N(R^H)₂]—O— and more preferably from —O—P(O)(S⁻)—O— and —O—P(S)(S⁻)—O—.

The term "LNA unit" as used herein refers to a nucleotide which is locked, i.e. to a nucleotide which has a bicyclic structure and especially a bicyclic ribose structure and more especially a bicyclic ribose structure as shown in general formula (II). The bridge "locks" the ribose in the 3'-endo (North) conformation. The ribose moiety of an LNA nucleotide is modified with an extra bridge connecting the 2' oxygen and 4' carbon. Alternatively used terms for LNA are bicyclic nucleotides or bridged nucleotides, thus, an alternative term for LNA unit is bicyclic nucleotide unit or bridged nucleotide unit.

The term "non-LNA unit" as used herein refers to a nucleotide which is not locked, i.e. to a nucleotide which has no bicyclic sugar moiety and especially no bicyclic ribose structure and more especially no bicyclic ribose structure as shown in general formula (II). The non-LNA units are most preferably DNA units.

The term "DNA unit" as used herein refers to a nucleotide containing a 2-deoxyribose as sugar. Thus, the nucleotide is made of a nucleobase and a 2-deoxyribose.

The term "unit" as used herein refers to a part or a fragment or a moiety of an antisense-oligonucleotide of the present invention. Thus a "unit" is not a complete molecule, it is a part or a fragment or a moiety of an antisense-oligonucleotide which has at least one position for a covalent linkage to another part or fragment or moiety of the antisense-oligonucleotide. For example, the general structures (B1) to (B6) are units, because they can be covalently linked through the group Y and IL' or —O— and —O—P(O)(S⁻)—respectively. Preferably a unit is a moiety consisting of a pentose structure, a nucleobase connected to the pentose structure a 5' radical group and an IL' radical group.

The term "building block" or "monomer" as used herein refers to a molecule and especially to a nucleoside which is used in the synthesis of an antisense-oligonucleotide of the present invention. Examples are the LNA molecules of general formula (I), wherein Y represents a 5'-terminal group and IL' represents a 3'-terminal group.

Furthermore, pure diastereomeric anti-sense-oligonucleotides are preferred. Preferred are Sp- and Rp-diastereomers as shown at hand-right side:

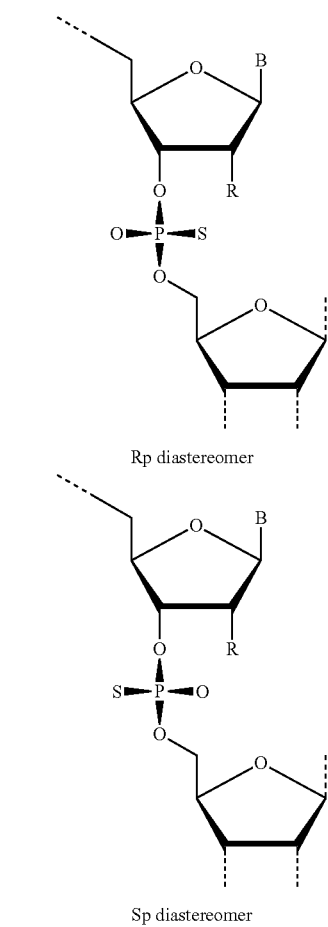

Rp diastereomer

Sp diastereomer

Suitable sulphur (S) containing internucleotide linkages as provided herein are preferred.

Preferred are phosphorothioate moieties in the backbone where at least 50% of the internucleotide linkages are phosphorothioate groups. Also preferred is that the LNA units, if present, are linked through phosphorothioates as internucleotide linkages. Most preferred is a complete phosphorothioate backbone, i.e. most preferred is when all nucleotide units and also the LNA units (if present) are linked to each other through phosphorothioate groups which are defined as follows: —O—P(O)(S⁻)—O— which is synonymous to -O—P(O,S)—O— or to -O—P(O⁻)(S)—O—.

In case the antisense-oligonucleotide is a gapmer, it is preferred that the LNA regions have internucleotide linkages selected from —O—P(O)(S⁻)—O— and —O—P(S)(S⁻)—O— and that the non-LNA region, the middle part, has internucleotide linkages selected from —O—P(O)(O⁻)—O—, —O—P(O)(S⁻)—O— and —O—P(S)(S⁻)—O— and that the LNA regions are connected to the non-LNA region through internucleotide linkages selected from —O—P(O)(O⁻)—O—, —O—P(O)(S⁻)—O— and —O—P(S)(S⁻)—O—.

It is even more preferred if all internucleotide linkages which are 9 in a 10-mer and 19 in a 20-mer are selected from —O—P(O)(S⁻)—O— and —O—P(S)(S⁻)—O—. Still more preferred is that all internucleotide linkages are phosphorothioate groups (—O—P(O)(S⁻)—O—) or are phosphorodithioate groups (—O—P(S)(S⁻)—O—).

Locked Nucleic Acids (LNA*)

It is especially preferred that some of the nucleotides of the general formula (B1) or (B2) in the antisense-oligonucleotides are replaced by so-called LNAs (Locked Nucleic Acids). The abbreviation LNA is a registered trademark, but herein the term "LNA" is solely used in a descriptive manner.

Preferably the terminal nucleotides are replaced by LNAs and more preferred the last 1 to 4 nucleotides at the 3' end and/or the last 1 to 4 nucleotides at the 5' end are replaced by LNAs. It is also preferred to have at least the terminal nucleotide at the 3' end and at the 5' end replaced by an LNA each.

The term "LNA" as used herein, refers to a bicyclic nucleotide analogue, known as "Locked Nucleic Acid". It may refer to an LNA monomer, or, when used in the context of an "LNA antisense-oligonucleotide" or an "antisense-oligonucleotide containing LNAs", LNA refers to an oligonucleotide containing one or more such bicyclic nucleotide analogues. LNA nucleotides are characterized by the presence of a linker group (such as a bridge) between C2' and C4' of the ribose sugar ring—for example as shown as the biradical $R^\#$- R as described below. The LNA used in the antisense-oligonucleotides of the present invention preferably has the structure of the general formula (I)

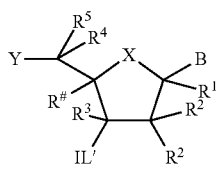

(I)

wherein for all chiral centers, asymmetric groups may be found in either R or S orientation;

wherein X is selected from —O—, —S—, —N($R^N$)—, —C($R^6R^7$)—, and preferably X is —O—; B is selected from hydrogen, optionally substituted $C_{1-4}$-alkoxy, optionally substituted $C_{1-4}$-alkyl, optionally substituted $C_{1-4}$-acyloxy, nucleobases and nucleobase analogues, and preferably B is a nucleobase or a nucleobase analogue and most preferred a standard nucleobase;

Y represents a part of an internucleotide linkage to an adjacent nucleotide in case the moiety of general formula (I) is an LNA unit of an antisense-oligonucleotide of the present invention, or a 5'-terminal group in case the moiety of general formula (I) is a monomer or building block for synthesizing an antisense-oligonucleotide of the present invention. The 5' carbon atom optionally includes the substituent $R^4$ and $R^5$;

IL' represents a part of an internucleotide linkage to an adjacent nucleotide in case the moiety of general formula (I) is an LNA unit of an antisense-oligonucleotide of the present invention, or a 3'-terminal group in case the moiety of general formula (I) is a monomer or building block for synthesizing an antisense-oligonucleotide of the present invention.

$R^\#$ and R together represent a bivalent linker group consisting of 1-4 groups or atoms selected from —C($R^aR^b$)—, —C($R^a$)═C($R^b$)—, —C($R^a$)═N—, —O—, —Si($R^a$)₂—, —S—, —SO₂—, —N($R^c$)—, and >C═Z, wherein Z is selected from —O—, —S—, and —N($R^a$)—, and $R^a$, $R^b$ and $R^c$ are independently of each other selected from hydrogen, optionally substituted $C_{1-12}$-alkyl, optionally substituted $C_{2-6}$-alkenyl, optionally substituted $C_{2-6}$-alkynyl, hydroxy, optionally substituted $C_{1-12}$-alkoxy, $C_{1-6}$-alkoxy-$C_{1-6}$-alkyl, $C_{2-6}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkylenyl-aminocarbonyl, mono- and di($C_{1-6}$-alkyl)amino-$C_{1-6}$-alkylenyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents $R^a$ and $R^b$ together may represent optionally substituted methylene (═CH2), wherein for all chiral centers, asymmetric groups may be found in either R or S orientation, and;

each of the substituents $R^1$, $R^2$, $R^3$, $R^4$, $R^5$, $R^6$ and $R^7$, which are present is independently selected from hydrogen, optionally substituted $C_{1-12}$-alkyl, optionally substituted $C_{2-6}$-alkenyl, optionally substituted $C_{2-6}$-alkynyl, hydroxy, $C_{1-12}$-alkoxy, $C_{1-6}$-alkoxy-$C_{1-6}$-alkyl, $C_{2-6}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted, and where two geminal substituents together may designate oxo, thioxo, imino, or optionally substituted methylene;

wherein $R^N$ is selected from hydrogen and $C_{1-4}$-alkyl, and where two adjacent (non-geminal) substituents may designate an additional bond resulting in a double bond; and $R^N$, when present and not involved in a biradical, is selected from hydrogen and $C_{1-4}$-alkyl; and basic salts and acid addition salts thereof. For all chiral centers, asymmetric groups may be found in either R or S orientation.

In preferred embodiments, $R^\#$ and R together represent a biradical consisting of a groups selected from the group consisting of —C($R^aR^b$)—C($R^aR^b$)—, —C($R^aR^b$)—O—, —C($R^aR^b$)—NR^c—, —C($R^aR^b$)—S—, and —C($R^aR^b$)—C($R^aR^b$)—O—, wherein each $R^a$, $R^b$ and $R^c$ may optionally be independently selected.

In some embodiments, $R^a$ and $R^b$ may be, optionally independently selected from the group consisting of hydrogen and $C_{1-6}$-alkyl, such as methyl, and preferred is hydrogen.

In preferred embodiments, $R^1$, $R^2$, $R^3$, $R^4$, and $R^5$ are independently selected from the group consisting of hydrogen, halogen, $C_{1-6}$-alkyl, substituted $C_{1-6}$-alkyl, $C_{2-6}$-alkenyl, substituted $C_{2-6}$-alkenyl, $C_{2-6}$-alkynyl or substituted $C_{2-6}$-alkynyl, $C_{1-6}$-alkoxyl, substituted $C_{1-6}$-alkoxyl, acyl, substituted acyl, $C_{1-6}$-aminoalkyl or substituted $C_{1-6}$-aminoalkyl. For all chiral centers, asymmetric groups may be found in either R or S orientation.

In preferred embodiments $R^1$, $R^2$, $R^3$, $R^4$, and $R^5$ are hydrogen.

In some embodiments, $R^1$, $R^2$, and $R^3$, are independently selected from the group consisting of hydrogen, halogen, $C_{1-6}$-alkyl, substituted $C_{1-6}$-alkyl, $C_{2-6}$-alkenyl, substituted $C_{2-6}$-alkenyl, $C_{2-6}$-alkynyl or substituted $C_{2-6}$-alkynyl, $C_{1-6}$-alkoxyl, substituted $C_{1-6}$-alkoxyl, acyl, substituted acyl, $C_{1-6}$-aminoalkyl or substituted $C_{1-6}$-aminoalkyl. For all chiral centers, asymmetric groups may be found in either R or S orientation. In preferred embodiments $R^1$, $R^2$, and $R^3$ are hydrogen.

In preferred embodiments, $R^4$ and $R^5$ are each independently selected from the group consisting of —H, —CH$_3$, —CH$_2$—CH$_3$, —CH$_2$—O—CH$_3$, and —CH=CH$_2$. Suitably in some embodiments, either $R^4$ or $R^5$ are hydrogen, whereas the other group ($R^4$ or $R^5$ respectively) is selected from the group consisting of $C_{1-6}$-alkyl, $C_{2-6}$-alkenyl, $C_{2-6}$-alkynyl, substituted $C_{1-6}$-alkyl, substituted $C_{2-6}$-alkenyl, substituted $C_{2-6}$-alkynyl or substituted acyl (—C(=O)—); wherein each substituted group is mono or poly substituted with substituent groups independently selected from halogen, $C_{1-6}$-alkyl, substituted $C_{1-6}$-alkyl, $C_{2-6}$-alkenyl, substituted $C_{2-6}$-alkenyl, $C_{2-6}$-alkynyl, substituted $C_{2-6}$-alkynyl, —OJ$_1$, —SJ$_1$, —NJ$_1$J$_2$, —N$_3$, —COOJ$_1$, —CN, —O—C(=O)NJ$_1$J$_2$, —N(H)C(=NH)NJ$_1$J$_2$ or —N(H)C(=X)N(H)J$_2$, wherein X is O or S; and each J$_1$ and J$_2$ is, independently —H, $C_{1-6}$-alkyl, substituted $C_{1-6}$-alkyl, $C_{2-6}$-alkenyl, substituted $C_{2-6}$-alkenyl, $C_{2-6}$-alkynyl, substituted $C_{2-6}$-alkynyl, $C_{1-6}$-aminoalkyl, substituted $C_{1-6}$-aminoalkyl or a protecting group. In some embodiments either $R^4$ or $R^5$ is substituted $C_{1-6}$-alkyl. In some embodiments either $R^4$ or $R^5$ is substituted methylene, wherein preferred substituent groups include one or more groups independently selected from —F, —NJ$_1$J$_2$, —N$_3$, —CN, —OJ$_1$, —SJ$_1$, —O—C(=O)NJ$_1$J$_2$, —N(H)C(=NH)NJ$_1$J$_2$ or —N(H)C(=O)N(H)J$_2$. In some embodiments each J$_1$ and J$_2$ is, independently —H or $C_{1-6}$-alkyl. In some embodiments either $R^4$ or $R^5$ is methyl, ethyl or methoxymethyl. In some embodiments either $R^4$ or $R^5$ is methyl. In a further embodiment either $R^4$ or $R^5$ is ethylenyl. In some embodiments either $R^4$ or $R^5$ is substituted acyl. In some embodiments either $R^4$ or $R^5$ is -O—C(=O)NJ$_1$J$_2$. For all chiral centers, asymmetric groups may be found in either R or S orientation. Such 5' modified bicyclic nucleotides are disclosed in WO 2007/134181 A, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In preferred embodiments, $R^\#$ and R together represent a biradical selected from —C(R$^a$R$^b$)—O—, —C(R$^a$R$^b$)—C(R$^c$R$^d$)—O—, —C(R$^a$R$^b$)—C(R$^c$R$^d$)—C(R$^e$R$^f$)—O—, —C(R$^a$R$^b$)—O—C(R$^d$R$^e$)—, —C(R$^a$R$^b$)—O—C(R$^d$R$^e$)—O—, —C(R$^a$R$^b$)—C(R$^d$R$^e$)—, —C(R$^a$R$^b$)—C(R$^c$R$^d$)—C(R$^e$R$^f$)—, —C(R$^a$)=C(R$^b$)—C(R$^d$R$^e$)—, —C(R$^a$R$^b$)—N(R$^c$)—, —C(R$^a$R$^b$)—C(R$^d$R$^e$)—N(R$^c$)—, —C(R$^a$R$^b$)—N(R$^c$)—O—, —C(R$^a$R$^b$)—S—, and —C(R$^a$R$^b$)—C(R$^d$R$^e$)—S—, wherein R$^a$, R$^b$, R$^c$, R$^d$, R$^e$, and R$^f$ each is independently selected from hydrogen, optionally substituted $C_{1-12}$-alkyl, optionally substituted $C_{2-6}$-alkenyl, optionally substituted $C_{2-6}$-alkynyl, hydroxy, $C_{1-12}$-alkoxy, $C_{1-6}$-alkoxy-$C_{1-6}$-alkyl, $C_{2-6}$-alkenyloxy, carboxy, $C_{1-12}$-alkoxycarbonyl $C_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents R$^a$ and R$^b$ together may designate optionally substituted methylene (=CH$_2$). For all chiral centers, asymmetric groups may be found in either R or S orientation.

In a further embodiment $R^\#$ and R together designate a biradical (bivalent group) selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH=CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, —CH(CH$_2$—O—CH$_3$)—O—, —CH$_2$—CH$_2$—, and —CH=CH—. For all chiral centers, asymmetric groups may be found in either R or S orientation.

In some embodiments, $R^\#$ and R together designate the biradical —C(R$^a$R$^b$)—N(R$^c$)—O—, wherein R$^a$ and R$^b$ are independently selected from the group consisting of hydrogen, halogen, $C_{1-6}$-alkyl, substituted $C_{1-6}$-alkyl, $C_{2-6}$-alkenyl, substituted $C_{2-6}$-alkenyl, $C_{2-6}$-alkynyl or substituted $C_{2-6}$-alkynyl, $C_{1-6}$-alkoxyl, substituted $C_{1-6}$-alkoxyl, acyl, substituted acyl, $C_{1-6}$-aminoalkyl or substituted $C_{1-6}$-aminoalkyl, such as hydrogen, and; wherein R$^c$ is selected from the group consisting of hydrogen, halogen, $C_{1-6}$-alkyl, substituted $C_{1-6}$-alkyl, $C_{2-6}$-alkenyl, substituted $C_{2-6}$-alkenyl, $C_{2-6}$-alkynyl or substituted $C_{2-6}$-alkynyl, $C_{1-6}$-alkoxyl, substituted $C_{1-6}$-alkoxyl, acyl, substituted acyl, $C_{1-6}$-aminoalkyl or substituted $C_{1-6}$-aminoalkyl, and preferably hydrogen.

In preferred embodiments, $R^\#$ and R together represent the biradical —C(R$^a$R$^b$)—O—C(R$^d$R$^e$)—O—, wherein R$^a$, R$^b$, R$^d$, and R$^e$ are independently selected from the group consisting of hydrogen, halogen, $C_{1-6}$-alkyl, substituted $C_{1-6}$-alkyl, $C_{2-6}$-alkenyl, substituted $C_{2-6}$-alkenyl, $C_{2-6}$-alkynyl or substituted $C_{2-6}$-alkynyl, $C_{1-6}$-alkoxyl, substituted $C_{1-6}$-alkoxyl, acyl, substituted acyl, $C_{1-6}$-aminoalkyl or substituted $C_{1-6}$-aminoalkyl, and preferably hydrogen.

In preferred embodiments, $R^\#$ and R form the biradical —CH(Z)—O—, wherein Z is selected from the group consisting of $C_{1-6}$-alkyl, $C_{2-6}$-alkenyl, $C_{2-6}$-alkynyl, substituted $C_{1-6}$-alkyl, substituted $C_{2-6}$-alkenyl, substituted $C_{2-6}$-alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, —OJ$_1$, —NJ$_1$J$_2$, —SJ$_1$, —N$_3$, —OC(=X)J$_1$, —OC(=X)NJ$_1$J$_2$, —NJ$^3$C(=X)NJ$_1$J$_2$ and —CN, wherein each J$_1$, J$_2$ and J$_3$ is, independently, —H or $C_{1-6}$-alkyl, and X is O, S or NJ$_1$. In preferred embodiments Z is $C_{1-6}$-alkyl or substituted $C_{1-6}$-alkyl. In further preferred embodiments Z is methyl. In preferred embodiments Z is substituted $C_{1-6}$-alkyl. In preferred embodiments said substituent group is $C_{1-6}$-alkoxy. In some embodiments Z is CH$_3$OCH$_2$-. For all chiral centers, asymmetric groups may be found in either R or S orientation. Such bicyclic nucleotides are disclosed in U.S. Pat. No. 7,399,845 which is hereby incorporated by reference in its entirety. In preferred embodiments, $R^1$, $R^2$, $R^3$, $R^4$, and $R^5$ are hydrogen. In preferred embodiments, $R^1$, $R^2$, and $R^3$ are hydrogen, and one or both of $R^4$, $R^5$ may be other than hydrogen as referred to above and in WO 2007/134181.

In preferred embodiments, $R^\#$ and R together represent a biradical which comprise a substituted amino group in the bridge such as the biradical —$CH_2$—$N(R^c)$—, wherein $R^c$ is $C_{1\text{-}12}$-alkyloxy. In preferred embodiments $R^\#$ and R together represent a biradical -$Cq_3q_4$-NOR—, wherein $q_3$ and $q_4$ are independently selected from the group consisting of hydrogen, halogen, $C_{1\text{-}6}$-alkyl, substituted $C_{1\text{-}6}$-alkyl, $C_{2\text{-}6}$-alkenyl, substituted $C_{2\text{-}6}$-alkenyl, $C_{2\text{-}6}$-alkynyl or substituted $C_{2\text{-}6}$-alkynyl, $C_{1\text{-}6}$-alkoxyl, substituted $C_{1\text{-}6}$-alkoxyl, acyl, substituted acyl, $C_{1\text{-}6}$-aminoalkyl or substituted $C_{1\text{-}6}$-aminoalkyl; wherein each substituted group is, independently, mono or poly substituted with substituent groups independently selected from halogen, —$OJ_1$, —$SJ_1$, —$NJ_1J_2$, —$COOJ_1$, —CN, —$OC(=O)NJ_1J_2$, —NH—$C(=NH)$ $NJ_1J_2$ or -NH—$C(=X)NHJ_2$, wherein X is O or S; and each of $J_1$ and $J_2$ is, independently, —H, $C_{1\text{-}6}$-alkyl, $C_{2\text{-}6}$-alkenyl, $C_{2\text{-}6}$-alkynyl, $C_{1\text{-}6}$-aminoalkyl or a protecting group. For all chiral centers, asymmetric groups may be found in either R or S orientation. Such bicyclic nucleotides are disclosed in WO2008/150729 which is hereby incorporated by reference in its entirety. In preferred embodiments, $R^1$, $R^2$, $R^3$, $R^4$, and $R^5$ are independently selected from the group consisting of hydrogen, halogen, $C_{1\text{-}6}$-alkyl, substituted $C_{1\text{-}6}$-alkyl, $C_{2\text{-}6}$-alkenyl, substituted $C_{2\text{-}6}$-alkenyl, $C_{2\text{-}6}$-alkynyl or substituted $C_{2\text{-}6}$-alkynyl, $C_{1\text{-}6}$-alkoxyl, substituted $C_{1\text{-}6}$-alkoxyl, acyl, substituted acyl, $C_{1\text{-}6}$-aminoalkyl or substituted $C_{1\text{-}6}$-aminoalkyl. In preferred embodiments, $R^1$, $R^2$, $R^3$, $R^4$, and $R^5$ are hydrogen. In preferred embodiments, $R^1$, $R^2$, and $R^3$ are hydrogen and one or both of $R^4$, $R^5$ may be other than hydrogen as referred to above and in WO 2007/134181.

In preferred embodiments $R^\#$ and R together represent a biradical (bivalent group) -$C(R^aR^b)$—O—, wherein $R^a$ and $R^b$ are each independently halogen, $C_{1\text{-}12}$-alkyl, substituted $C_{1\text{-}12}$-alkyl, $C_{2\text{-}6}$-alkenyl, substituted $C_{2\text{-}6}$-alkenyl, $C_{2\text{-}6}$-alkynyl, substituted $C_{2\text{-}6}$-alkynyl, $C_{1\text{-}12}$-alkoxy, substituted $C_{1\text{-}12}$-alkoxy, —$OJ_1$, —$SJ_1$, —$S(O)J_1$, —$SO_2$-$J_1$, —$NJ_1J_2$, —$N_3$, —CN, —$C(=O)OJ_1$, —$C(=O)NJ_1J_2$, —$C(=O)J_1$, —$OC(=O)NJ_1J_2$, —NH—$C(=NH)NJ_1J_2$, —NH—$C(=O)$ $NJ_1J_2$, or, —NH—$C(=S)NJ_1J_2$; or $R^a$ and $R^b$ together are =$C(q_3)(q_4)$; $q_3$ and $q_4$ are each, independently, —H, halogen, $C_{1\text{-}12}$-alkyl or substituted $C_{1\text{-}12}$-alkyl; each substituted group is, independently, mono or poly substituted with substituent groups independently selected from halogen, $C_{1\text{-}6}$-alkyl, substituted $C_{1\text{-}6}$-alkyl, $C_{2\text{-}6}$-alkenyl, substituted $C_{2\text{-}6}$-alkenyl, $C_{2\text{-}6}$-alkynyl, substituted $C_{2\text{-}6}$-alkynyl, —$OJ_1$, —$SJ_1$, —$NJ_1J_2$, —$N_3$, —CN, —$C(=O)OJ_1$, —$C(=O)$ $NJ_1J_2$, —$C(=O)J_1$, —$OC(=O)NJ_1J_2$, —NH—$C(=O)$ $NJ_1J_2$, or -NH—$C(=S)NJ_1J_2$ and; each $J_1$ and $J_2$ is independently, —H, $C_{1\text{-}6}$-alkyl, substituted $C_{1\text{-}6}$-alkyl, $C_{2\text{-}6}$-alkenyl, substituted $C_{2\text{-}6}$-alkenyl, $C_{2\text{-}6}$-alkynyl, substituted $C_{2\text{-}6}$-alkynyl, $C_{1\text{-}6}$-aminoalkyl, substituted $C_{1\text{-}6}$-aminoalkyl or a protecting group. Such compounds are disclosed in WO2009006478A, hereby incorporated in its entirety by reference.

In preferred embodiments, $R^\#$ and R form the biradical -Q-, wherein Q is -$C(q_1)(q_2)C(q_3)(q_4)$—, —$C(q_1)=C(q_3)$—, —C[=$C(qi)(q_2)$]-$C(q_3)(q_4)$— or -$C(q_1)(q_2)$—C[=$C(q_3)$ $(q_4)$]-;

$q_1$, $q_2$, $q_3$, $q_4$ are each independently of each other -H, halogen, $C_{1\text{-}12}$-alkyl, substituted $C_{1\text{-}12}$-alkyl, $C_{2\text{-}6}$-alkenyl, substituted $C_{1\text{-}12}$-alkoxy, —$OJ_1$, —$SJ_1$, —$S(O)J_1$, —$SO_2$-$J_1$, -$NJ_1J_2$, —$N_a$, —CN, —$C(=O)OJ_1$, —$C(=O)NJ_1J_2$, —$C(=O)J_1$, —$OC(=O)NJ_1J_2$, —NH—$C(=NH)NJ_1J_2$, —NH—$C(=O)NJ_1J_2$, or, -NH—$C(=S)NJ_1J_2$; each $J_1$ and $J_2$ is independently of each other -H, $C_{1\text{-}6}$-alkyl, $C_{2\text{-}6}$-alkenyl, $C_{2\text{-}6}$-alkynyl, $C_{1\text{-}6}$-aminoalkyl or a protecting group; and optionally when Q is -$C(q_1)(q_2)C(q_3)(q_4)$- and one of $q_3$ or $q_4$ is —$CH_3$, then at least one of the other of $q_3$ or $q_4$ or one of $q_1$ and $q_2$ is other than -H. In preferred embodiments $R^1$, $R^2$, $R^3$, $R^4$, and $R^5$ are hydrogen. For all chiral centers, asymmetric groups may be found in either R or S orientation. Such bicyclic nucleotides are disclosed in WO2008/154401 which is hereby incorporated by reference in its entirety. In preferred embodiments $R^1$, $R^2$, $R^3$, $R^4$, and $R^5$ are independently of each other selected from the group consisting of hydrogen, halogen, $C_{1\text{-}6}$-alkyl, substituted $C_{1\text{-}6}$-alkyl, $C_{2\text{-}6}$-alkenyl, substituted $C_{2\text{-}6}$-alkenyl, $C_{2\text{-}6}$-alkynyl or substituted $C_{2\text{-}6}$-alkynyl, $C_{1\text{-}6}$-alkoxyl, substituted $C_{1\text{-}6}$-alkoxyl, acyl, substituted acyl, $C_{1\text{-}6}$-aminoalkyl or substituted $C_{1\text{-}6}$-aminoalkyl. In preferred embodiments $R^1$, $R^2$, $R^3$, $R^4$, and $R^5$ are hydrogen. In preferred embodiments $R^1$, $R^2$, and $R^3$ are hydrogen and one or both of $R^4$, $R^5$ may be other than hydrogen as referred to above and in WO 2007/134181 or WO2009/067647 (alpha-L-bicyclic nucleic acids analogues).

As used herein, the term "$C_1$-$C_6$-alkyl" refers to —$CH_3$, —$C_2H_5$, —$C_3H_7$, —$CH(CH_3)_2$, —$C_4H_9$, —$CH_2$—CH $(CH_3)_2$, —$CH(CH_3)$—$C_2H_5$, —$C(CH_3)_3$, —$C_5H_{11}$, —CH $(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —CH $(C_2H_5)_2$, —$C_2H_4$—$CH(CH_3)_2$, —$C_6H_{13}$, —$C_3H_6$—CH $(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—CH $(CH_3)_2$, —$CH(CH_3)$—$CH(CH_3)$—$C_2H_5$, —$CH_2$—CH $(CH_3)$—$CH(CH_3)_2$, —$CH_2$—$C(CH_3)_2$—$C_2H_5$, —C $(CH_3)_2$—$C_3H_7$, —$C(CH_3)_2$—$CH(CH_3)_2$, —$C_2H_4$—C $(CH_3)_3$, —$CH_2$—$CH(C_2H_5)_2$, and —$CH(CH_3)$—$C(CH_3)_3$. The term "$C_1$-$C_6$-alkyl" shall also include "$C_1$-$C_6$-cycloalkyl" like cyclo-$C_3H_5$, cyclo-$C_4H_7$, cyclo-$C_5H_9$, and cyclo-$C_6H_{11}$.

Preferred are —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, and —$C_5H_{11}$. Especially preferred are —$CH_3$, —$C_2H_5$, —$C_3H_7$, and —$CH(CH_3)_2$.

The term "$C_1$-$C_6$-alkyl" shall also include "$C_1$-$C_6$-cycloalkyl" like cyclo-$C_3H_5$, cyclo-$C_4H_7$, cyclo-$C_5H_9$, and cyclo-$C_6H_{11}$.

As used herein, the term "$C_1$-$C_{12}$-alkyl" refers to $C_1$-$C_6$-alkyl, —$C_7H_{15}$, —$C_8H_{17}$, —$C_9H_{19}$, —$C_{10}H_{21}$, —$C_{11}H_{23}$, —$C_{12}H_{25}$.

As used herein, the term "$C_1$-$C_6$-alkylenyl" refers to —$CH_2$—, —$C_2H_4$—, —$CH(CH_3)$—, —$C_3H_6$—, —$CH_2$—$CH(CH_3)$—, —$CH(CH_3)$—$CH_2$—, —$C(CH_3)_2$—, —$C_4H_8$—, —$CH_2$—$C(CH_3)_2$—, —$C(CH_3)_2$—$CH_2$—, —$C_2H_4$—$CH(CH_3)$—, —$CH(CH_3)$—$C_2H_4$—, —$CH_2$—$CH(CH_3)$—$CH_2$—, —$CH(CH_3)$—$CH(CH_3)$—, —$C_5H_{10}$—, —$CH(CH_3)$—$C_3H_6$—, —$CH_2$—$CH(CH_3)$—$C_2H_4$—, —$C_2H_4$—$CH(CH_3)$—$CH_2$—, —$C_3H_6$—$CH(CH_3)$—, —$C_2H_4$—$C(CH_3)_2$—, —$C(CH_3)_2$—$C_2H_4$—, —$CH_2$—C $(CH_3)_2$—$CH_2$—, —$CH_2$—$CH(CH_3)$—$CH(CH_3)$—, —CH $(CH_3)$—$CH_2$—$CH(CH_3)$—, —$CH(CH_3)$—$CH(CH_3)$—$CH_2$—, —$CH(CH_3)$—$CH(CH_3)$—$CH(CH_3)$—, —C $(CH_3)_2$—$C_3H_6$—, —$CH_2$—$C(CH_3)_2$—$C_2H_4$—, —$C_2H_4$—$C(CH_3)_2$—$CH_2$—, —$C_3H_6$—$C(CH_3)_2$—, —$CH(CH_3)$—$C_4H_6$—, —$C_6H_{12}$—, —$CH_2$—$CH(CH_3)$—$C_3H_6$—, —$C_2H_4$—$CH(CH_3)$—$C_2H_4$—, —$C_3H_6$—$CH(CH_3)$—$CH_2$—, —$C_4H_8$—$CH(CH_3)$—, —$C_2H_4$—$CH(CH_3)$—CH $(CH_3)$—, —$CH_2$—$CH(CH_3)$—$CH(CH_3)$—$CH_2$—, —$CH_2$—$CH(CH_3)$—$CH_2$—$CH(CH_3)$—, —$CH(CH_3)$—$C_2H_4$—$CH(CH_3)$—, —$CH(CH_3)$—$CH_2$—$CH(CH_3)$—$CH_2$—, and —$CH(CH_3)$—$CH(CH_3)$—$C_2H_4$—.

As used herein, the term "$C_2$-$C_6$-alkenyl" refers to —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$-C(CH$_3$)=CH$_2$, —C$_2$H$_4$—CH(CH$_3$)—CH=CH$_2$, —CH$_2$—CH(CH$_3$)—CH$_2$—CH=CH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, —CH$_2$—CH=CH—CH=CH—CH$_3$, —CH=CH—CH$_2$—CH=CH—CH$_3$, —CH=CH—CH$_2$—CH$_2$—CH=CH$_2$, —CH=CH—CH=CH—C$_2$H$_5$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH=CH—CH=CH$_2$, —CH=CH—CH$_2$—C(CH$_3$)=CH$_2$, —CH=CH—CH(CH$_3$)—CH=CH$_2$, —C(CH$_3$)=CH—CH$_2$—CH=CH$_2$, —CH=C(CH$_3$)—CH$_2$—CH=CH$_2$, —C(CH$_3$)=CH—CH=CH—CH$_3$, —CH=CH—C(CH$_3$)=CH—CH$_3$, —CH=C(CH$_3$)—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, and —CH=CH—CH=CH—CH=CH$_2$.

Preferred are —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$. Especially preferred are —CH=CH$_2$, —CH$_2$—CH=CH$_2$, and —CH=CH—CH$_3$.

As used herein, the term "$C_2$-$C_6$-alkynyl" refers to —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C$_2$H$_4$—CH(CH$_3$)—C≡CH, —CH$_2$—CH(CH$_3$)—C≡CH, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —C≡C—C(CH$_3$)$_3$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH$_3$, —CH$_2$—CH(C≡CH)$_2$, —CH(C≡CH)—C≡C—CH$_3$. Preferred are —C≡CH and —C≡C—CH$_3$.

The term "$C_{1-6}$-alkoxyl" refers to "$C_1$-$C_6$-alkyl-O—".

The term "$C_{1-12}$-alkoxyl" refers to "$C_1$-$C_{12}$-alkyl-O—".

The term "$C_{1-6}$-aminoalkyl" refers to "H$_2$N—$C_1$-$C_6$-alkyl-".

The term "$C_2$-$C_6$-alkenyloxy" refers to "$C_2$-$C_6$-alkenyl-O—".

The term "$C_{1-6}$-alkylcarbonyl" refers to "$C_1$-$C_6$-alkyl-CO—". Also referred to as "acyl".

The term "$C_{1-12}$-alkylcarbonyl" refers to "$C_1$-$C_{12}$-alkyl-CO—". Also referred to as "acyl".

The term "$C_{1-6}$-alkoxycarbonyl" refers to "$C_1$-$C_6$-alkyl-O—CO—".

The term "$C_{1-12}$-alkoxycarbonyl" refers to "$C_1$-$C_{12}$-alkyl-O—CO—".

The term "$C_1$-$C_6$-alkanoyloxy" refers to "$C_1$-$C_6$-alkyl-CO-O—".

The term "$C_{1-6}$-alkylthio" refers to "$C_1$-$C_6$-alkyl-S—".

The term "$C_{1-6}$-alkylsulphonyloxy" refers to "$C_1$-$C_6$-alkyl-SO$_2$—O—".

The term "$C_{1-6}$-alkylcarbonylamino" refers to "$C_1$-$C_6$-alkyl-CO-NH—".

The term "$C_{1-6}$-alkylamino" refers to "$C_1$-$C_6$-alkyl-NH—".

The term "($C_{1-6}$-)$_2$alkylamino" refers to a dialkylamino group like "[$C_1$-$C_6$-alkyl][$C_1$-$C_6$-alkyl]N—".

The term "$C_{1-6}$-alkylaminocarbonyl" refers to "$C_1$-$C_6$-alkyl-NH—CO—"

The term "($C_{1-6}$-)$_2$alkylaminocarbonyl" refers to a dialkylaminocarbonyl group like "[$C_1$-$C_6$-alkyl][$C_1$-$C_6$-alkyl]N—CO—".

The term "amino-$C_{1-6}$-alkylaminocarbonyl" refers to "H$_2$N—[$C_1$-$C_6$-alkylenyl]-NH—CO—".

The term "$C_{1-6}$-alkyl-amino-$C_{1-6}$-alkylaminocarbonyl" refers to "$C_{1-6}$-alkyl-HN—[$C_1$-$C_6$-alkylenyl]-NH—CO—".

The term "($C_{1-6}$-)$_2$alkyl-amino-$C_{1-6}$-alkylaminocarbonyl" refers to "[$C_1$-$C_6$-alkyl][$C_1$-$C_6$-alkyl]N—[$C_1$-$C_6$-alkylenyl]-NH—CO—".

The term "aryl" refers to phenyl, toluyl, substituted phenyl and substituted toluyl.

The term "aryloxy" refers to "aryl-O—".

The term "arylcarbonyl" refers to "aryl-CO—".

The term "aryloxycarbonyl" refers to "aryl-O—CO—".

The term "heteroaryl" refers to substituted or not substituted heteroaromatic groups which have from 4 to 9 ring atoms, from 1 to 4 of which are selected from O, N and/or S. Preferred "heteroaryl" groups have 1 or 2 heteroatoms in a 5- or 6-membered aromatic ring. Mono and bicyclic ring systems are included. Typical "heteroaryl" groups are pyridyl, furyl, thienyl, pyrrolyl, oxazolyl, thiazolyl, imidazolyl, isoxazolyl, isothiazolyl, oxadiazolyl, pyridazinyl, pyrimidyl, pyrazinyl, 1,3,5-triazinyl, 1,2,3-triazolyl, 1,3,4-thiadiazolyl, indolizinyl, indolyl, isoindolyl, benzo[b]furyl, benzo[b]thienyl, indazolyl, benzimidazolyl, benzthiazolyl, purinyl, quinolizinyl, quinolyl, isoquinolyl, quinazolinyl, quinoxalinyl, 1,8-naphthyridinyl, tetrahydroquinolyl, benzooxazolyl, chrom-2-onyl, indazolyl, and the like.

The term "heteroaryloxy" refers to "heteroaryl-O—".

The term "heteroarylcarbonyl" refers to "heteroaryl-CO—".

The term "heteroaryloxycarbonyl" refers to "heteroaryl-O—CO—".

The term "substituted" refers to groups wherein one or more hydrogen atoms are replaced by one or more of the following substituents: —OH, —OCH$_3$, —OC$_2$H$_5$, —OC$_3$H$_7$, —O-cyclo-C$_3$H$_5$, —OCH(CH$_3$)$_2$, —OCH$_2$Ph, —F, —Cl, —COCH$_3$, —COC$_2$H$_5$, —COC$_3$H$_7$, —CO-cyclo-C$_3$H$_5$, —COCH(CH$_3$)$_2$, —COOH, —CONH$_2$, —NH$_2$, —NHCH$_3$, —NHC$_2$H$_5$, —NHC$_3$H$_7$, —NH-cyclo-C$_3$H$_5$, —NHCH(CH$_3$)$_2$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —SO$_3$H, —OCF$_3$, —OC$_2$F$_5$, cyclo-C$_3$H$_5$, —CH$_3$, —C$_2$H$_5$, —C$_3$H$_7$, —CH(CH$_3$)$_2$, —CH=CH$_2$, —CH$_2$—CH=CH$_2$, —C≡CH and/or —C≡C—CH$_3$.

In case the general structure (I) represents monomers or building blocks for synthesizing the antisense-oligonucleotides of the present invention, the terminal groups Y and IL' are selected independently of each other from hydrogen, azido, halogen, cyano, nitro, hydroxy, PG-O—, AG-O—, mercapto, PG-S—, AG-S—, C$_{1-6}$-alkylthio, amino, PG-N(R$^H$)—, AG-N(R$^H$)—, mono- or di(C$_{1-6}$-alkyl)amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate, monothiophosphate, diphosphate, dithiophosphate, triphosphate, trithiophosphate, carboxy, sulphono, hydroxymethyl, PG-O—CH$_2$—, AG-O—CH$_2$—, aminomethyl, PG-N(R$^H$)—CH$_2$—, AG-N(R$^H$)—CH$_2$—, carboxymethyl, sulphonomethyl, where PG is a protection group for —OH, —SH, and —NH(R$^H$), respectively, AG is an activation group for —OH, —SH, and —NH(R$^H$), respectively, and R$^H$ is selected from hydrogen and C$_{1-6}$- alkyl.

The protection groups PG of hydroxy substituents comprise substituted trityl, such as 4,4'-dimethoxytrityl (DMT), 4-monomethoxytrityl (MMT), optionally substituted 9-(9-phenyl)xanthenyl (pixyl), optionally substituted methoxytetrahydropyranyl (mthp), silyl such as trimethylsilyl (TMS), triisopropylsilyl (TIPS), tert-butyldimethylsilyl (TBDMS), triethylsilyl, and phenyldimethylsilyl, tert-butylethers, acetals (including two hydroxy groups), acyl such as acetyl or halogen substituted acetyls, e.g. chloroacetyl or fluoroacetyl, isobutyryl, pivaloyl, benzoyl and substituted benzoyls, methoxymethyl (MOM), benzyl ethers or substituted benzyl ethers such as 2,6-dichlorobenzyl (2,6-Cl$_2$Bzl). Alternatively when Y or IL' is hydroxyl they may be protected by attachment to a solid support optionally through a linker.

When Y or IL' is an amino group, illustrative examples of the amino protection groups are fluorenylmethoxycarbonyl (Fmoc), tert-butyloxycarbonyl (BOC), trifluoroacetyl, allyloxycarbonyl (alloc or AOC), benzyloxycarbonyl (Z or Cbz), substituted benzyloxycarbonyls such as 2-chloro benzyloxycarbonyl (2-CIZ), monomethoxytrityl (MMT), dimethoxytrityl (DMT), phthaloyl, and 9-(9-phenyl)xanthenyl (pixyl).

Act represents an activation group for —OH, —SH, and —NH(R$^H$), respectively. Such activation groups are, for instance, selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P(OR$^x$)—N(R$^y$)$_2$, wherein R$^x$ designates an optionally substituted alkyl group, e.g. methyl, 2-cyanoethyl, or benzyl, and each of R$^y$ designate optionally substituted alkyl groups, e.g. ethyl or isopropyl, or the group —N(R$^y$)$_2$ forms a morpholino group (—N(CH$_2$CH$_2$)$_2$O). R$^x$ preferably designates 2-cyanoethyl and the two R$^y$ are preferably identical and designate isopropyl. Thus, an especially relevant phosphoramidite is N,N-diisopropyl-O-(2-cyanoethyl)-phosphoramidite.

LNA Monomers or LNA Building Blocks

The LNA monomers or LNA building blocks used as starting materials in the synthesis of the antisense-oligonucleotides of the present invention are preferably LNA nucleosides of the following general formulae:

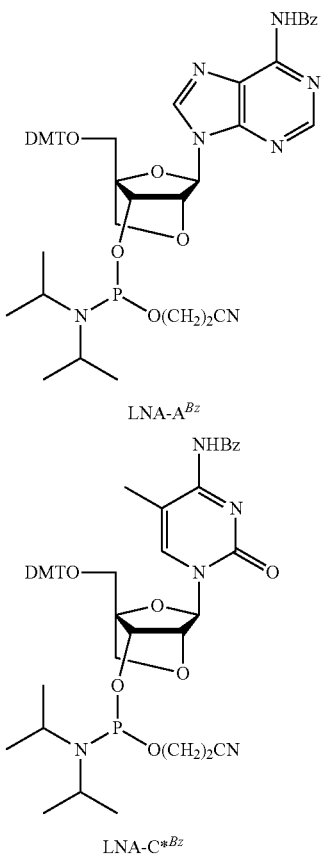

LNA-A$^{Bz}$

LNA-C*$^{Bz}$

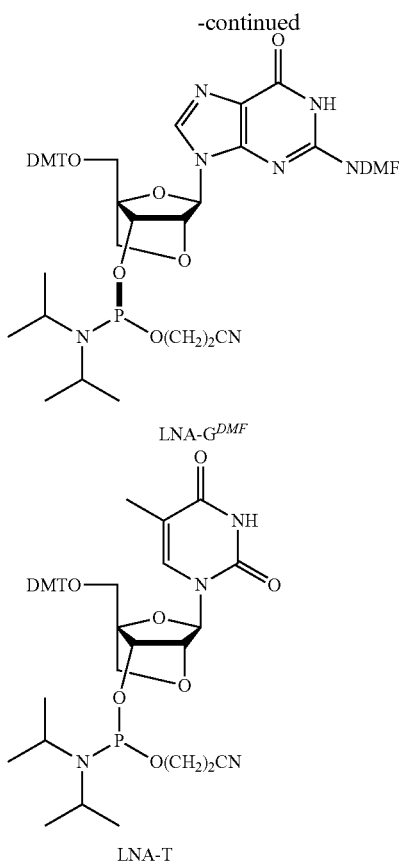

LNA-G$^{DMF}$

LNA-T

The LNA building blocks are normally provided as LNA phosphoramidites with the four different nucleobases: adenine (A), guanine (G), 5-methyl-cytosine (C*) and thymine (T). The antisense-oligonucleotides of the present invention containing LNA units are synthesized by standard phosphoramidite chemistry. In the LNA building blocks the nucleobases are protected. A preferred protecting group for the amino group of the purin base is a benzoyl group (Bz), indicated as A$^{Bz}$. A preferred protecting group for the amino group of the 5-methylpyrimidinone base is a benzoyl group (Bz), indicated as C*$^{Bz}$. A preferred protecting group for the amino group of the purinone base is a dimethylformamidine (DMF) group, a diethylformamidine (DEF), a dipropylformamidine (DPF), a dibutylformamidine (DBF), or a iso-butyryl (—CO—CH(CH$_3$)$_2$) group, indicated as G$^{DMF}$, G$^{DEF}$, G$^{DPF}$, G$^{DBF}$, or G$^{iBu}$. Thus the group -NDMF refers to —N=CH—N(CH$_3$)$_2$. DMT refers to 4,4'-dimethoxytrityl.

Thus, LNA-T refers to 5'-O-(4,4'-dimethoxytrityl)-3'-O-(2-cyanoethyl-N,N-diisopropyl)-phosphoramidite-thymidine LNA. LNA-C*$^{Bz}$ refers to 5'-O-(4,4'-dimethoxytrityl)-3'-0-(2-cyanoethyl-N,N-diisopropyl)phosphoramidite-4-N-benzoyl-5-methyl-2'-cytidine LNA. LNA-A$^{Bz}$ refers to 5'-O-(4,4'-dimethoxytrityl)-3'-O-(2-cyanoethyl-N,N-diisopropyl)phosphoramidite-6-N-benzoyl-2'-adenosine LNA. LNA-G$^{DMF}$ refers to 5'-O-(4,4'-dimethoxytrityl)-3'-O-(2-cyanoethyl-N,N-diisopropyl)-phosphoramidite-2-N-dimethylformamidine-2'-guanosine LNA. LNA-G$^{iBu}$ refers to 5'-O-(4,4'-dimethoxy-trityl)-3'-O-(2-cyanoethyl-N,N-diisopropyl)phosphoramidite-2-N-butyryl-2'-guanosine LNA.

Terminal Groups

In case Y represents the 5'-terminal group of an antisense-oligonucleotide of the present invention, the residue Y is also named Y$^{5'}$ and represents:

—OH, —O—C$_{1-6}$-alkyl, —S-C$_{1-6}$-alkyl, —O—C$_{6-9}$-phenyl, —O—C$_{7-10}$-benzyl, —NH—C$_{1-6}$-alkyl, —N(C$_{1-6}$-alkyl)$_2$, —O—C$_{2-6}$-alkenyl, —S-C$_{2-6}$-alkenyl, —NH—C$_{2-6}$-alkenyl, —N(C$_{2-6}$-alkenyl)$_2$, —O—C$_{2-6}$-alkynyl, —S-C$_{2-6}$-alkynyl, —NH—C$_{2-6}$-alkynyl, —N(C$_{2-6}$-alkynyl)$_2$, —O—C$_{1-6}$-alkylenyl-O—C$_{1-6}$-alkyl, —O—[C$_{1-6}$-alkylenyl-O]$_m$—C$_{1-6}$-alkyl, —O—CO—C$_{1-6}$-alkyl, —O—CO—C$_{2-6}$-alkenyl, —O—CO—C$_{2-6}$-alkynyl, —O—S(O)—C$_{1-6}$-alkyl, —O—SO$_2$-C$_{1-6}$-alkyl, —O—SO$_2$—O—C$_{1-6}$-alkyl, —O—P(O)(O$^-$)$_2$, —O—P(O)(O$^-$)(O—C$_{1-6}$-alkyl), —O—P(O)(O—C$_{1-6}$-alkyl)$_2$, —O—P(O)(S$^-$)$_2$, —O—P(O)(S—C$_{1-6}$-alkyl)$_2$, —O—P(O)(S$^-$)(O—C$_{1-6}$-alkyl), —O—P(O)(O$^-$)(NH—C$_{1-6}$-alkyl), —O—P(O)(O—C$_{1-6}$-alkyl)(NH—C$_{1-6}$-alkyl), —O—P(O)(O$^-$)[N(C$_{1-6}$-alkyl)$_2$], —O—P(O)(O—C$_{1-6}$-alkyl)[N(C$_{1-6}$-alkyl)$_2$], —O—P(O)(O$^-$)(BH$_3$$^-$), —O—P(O)(O—C$_{1-6}$-alkyl)(BH$_3$$^-$), —O—P(O)(O$^-$)(O—C$_{1-6}$-alkylenyl-O—C$_{1-6}$-alkyl), —O—P(O)(O—C$_{1-6}$-alkylenyl-O—C$_{1-6}$-alkyl)$_2$, —O—P(O)(O$^-$)(O—C$_{1-6}$-alkylenyl-S-C$_{1-6}$-alkyl), —O—P(O)(O—CO$_6$-alkylenyl-S-C$_{1-6}$-alkyl)$_2$, —O—P(O)(O$^-$)(OCH$_2$CH$_2$O—C$_{1-6}$-alkyl), —O—P(O)(OCH$_2$CH$_2$O—C$_{1-6}$-alkyl)$_2$, —O—P(O)(O$^-$)(OCH$_2$CH$_2$S-C$_{1-6}$-alkyl), —O—P(O)(OCH$_2$CH$_2$S-C$_{1-6}$-alkyl)$_2$, —O—P(O)(O$^-$)OC$_3$H$_6$OH, —O—P(O)(S$^-$)OC$_3$H$_6$OH, —O—P(S)(S$^-$)OC$_3$H$_6$OH, wherein the C$_{1-6}$-alkyl, C$_{2-6}$-alkenyl, C$_{2-6}$-alkynyl, —O—C$_{6-9}$-phenyl or —O—C$_{7-10}$-benzyl may be further substituted by —F, —OH, C$_{1-4}$-alkyl, C$_{2-4}$-alkenyl and/or C$_{2-4}$-alkynyl where m is selected from 1, 2, 3, 4, 5, 6, 7, 8, 9 or 10.

More preferred are: -OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_5$, —OPh, —OCH$_2$-Ph, —O—COCH$_3$, —O—COC$_2$H$_5$, —O—COC$_3$H$_7$, —O—CO-cycl-C$_3$H$_5$, —O-GOGH(CH$_3$)$_2$, —OCF$_3$, —O—S(O)CH$_3$, —O—S(O)C$_2$H$_5$, —O—S(O)C$_3$H$_7$, —O—S(O)-cycl-C$_3$H$_5$, —O—SO$_2$CH$_3$, —O—SO$_2$C$_2$H$_5$, —O—SO$_2$C$_3$H$_7$, —O—SO$_2$-cyclo-C$_3$H$_5$, —O—SO$_2$—OCH$_3$, —O—SO$_2$—OC$_2$H$_5$, —O—SO$_2$—OC$_3$H$_7$, —O—SO$_2$—O-cyclo-C$_3$H$_5$, —O(CH$_2$)$_n$N[(CH$_2$)$_n$OH], —O(CH$_2$)$_n$N[(CH$_2$)$_n$—H], —O—P(O)(O$^-$)OC$_3$H$_6$OH, —O—P(O)(S$^-$)OC$_3$H$_6$OH, even more preferred are: —OCH$_3$, —OC$_2$H$_5$, —OCH$_2$CH$_2$OCH$_3$ (also known as MOE), —OCH$_2$CH$_2$—N(CH$_3$)$_2$ (also known as DMAOE), —O[(CH$_2$)$_n$O]$_m$CH$_3$, —O(CH$_2$)$_n$OCH$_3$, —O(CH$_2$)$_n$NH$_2$, —O(CH$_2$)$_n$N(CH$_3$)$_2$, —O—P(O)(O$^-$)OC$_3$H$_6$OH, —O—P(O)(S$^-$)OC$_3$H$_6$OH, where n is selected from 1, 2, 3, 4, 5, or 6; and where m is selected from 1, 2, 3, 4, 5, 6, 7, 8, 9 or 10.

In case IL' represents the 3'-terminal group of an antisense-oligonucleotide of the present invention, the residue IL' is also named IL'$^{3'}$ and represents:

—OH, —O—C$_{1-6}$-alkyl, —S-C$_{1-6}$-alkyl, —O—C$_{6-9}$-phenyl, —O—C$_{7-10}$-benzyl, —NH—C$_{1-6}$-alkyl, —N(C$_{1-6}$-alkyl)$_2$, —O—C$_{2-6}$-alkenyl, —S-C$_{2-6}$-alkenyl, —NH—C$_{2-6}$-alkenyl, —N(C$_{2-6}$-alkenyl)$_2$, —O—C$_{2-6}$-alkynyl, —S-C$_{2-6}$-alkynyl, —NH—C$_{2-6}$-alkynyl, —N(C$_{2-6}$-alkynyl)$_2$, —O—C$_{1-6}$-alkylenyl-O—C$_{1-6}$-alkyl, —O—[C$_{1-6}$-alkylenyl-O]$_m$-C$_{1-6}$-alkyl, —O—CO—C$_{1-6}$-alkyl, —O—CO—C$_{2-6}$-alkenyl, —O—CO—C$_{2-6}$-alkynyl, —O—S(O)—C$_{1-6}$-alkyl, —O—SO$_2$-C$_{1-6}$-alkyl, —O—SO$_2$—O—C$_{1-6}$-alkyl, —O—P(O)(O$^-$)$_2$, —O—P(O)(O$^-$)(O—C$_{1-6}$-alkyl), —O—P(O)(O—C$_{1-6}$-alkyl)$_2$, —O—P(O)(S$^-$)$_2$, —O—P(O)(S—C$_{1-6}$-alkyl)$_2$, —O—P(O)(S$^-$)(O—C$_{1-6}$-alkyl), —O—P(O)(O$^-$)(NH—C$_{1-6}$-alkyl), —O—P(O)(O—C$_{1-6}$-alkyl)(NH—C$_{1-6}$-alkyl), —O—P(O)(O$^-$)[N(C$_{1-6}$-alkyl)$_2$], —O—P(O)(O—C$_{1-6}$-alkyl)[N(C$_{1-6}$-alkyl)$_2$], —O—P(O)(O$^-$)(BH$_3$$^-$), —O—P(O)(O—C$_{1-6}$-alkyl)(BH$_3$$^-$), —O—P(O)(O$^-$)(O—C$_{1-6}$-alkylenyl-O—C$_{1-6}$- alkyl), —O—P(O)(O—C$_{1-6}$-alkylenyl-O—C$_{1-6}$-alkyl)$_2$, —O—P(O)(O$^-$)(O—C$_{1-6}$-alkylenyl-S-C$_{1-6}$-alkyl), —O—P(O)(O—C$_{1-6}$-alkylenyl-S-C$_{1-6}$-alkyl)$_2$, —O—P(O)(O$^-$)(OCH$_2$CH$_2$O—C$_{1-6}$-alkyl), —O—P(O)(OCH$_2$CH$_2$O—C$_{1-6}$-alkyl)$_2$, —O—P(O)(O$^-$)(OCH$_2$CH$_2$S-C$_{1-6}$-alkyl), —O—P(O) (OCH$_2$CH$_2$S-C$_{1-6}$-alkyl)$_2$, —O—P(O)(O$^-$)OC$_3$H$_6$OH, —O—P(O)(S$^-$)OC$_3$H$_6$OH, wherein the C$_{1-6}$-alkyl, C$_{2-6}$-alkenyl, C$_{2-6}$-alkynyl, —O—C$_{6-9}$-phenyl or —O—C$_{7-10}$-benzyl may be further substituted by —F, —OH, C$_{1-4}$-alkyl, C$_{2-4}$-alkenyl and/or C$_{2-4}$-alkynyl where m is selected from 1, 2, 3, 4, 5, 6, 7, 8, 9 or 10.

More preferred are: -OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —O—COCH$_3$, —O—COC$_2$H$_5$, —O—COC$_3$H$_7$, —O—CO-cyclo-C$_3$H$_5$, —O—COCH(CH$_3$)$_2$, —OCF$_3$, —O—S(O)CH$_3$, —O—S(O)C$_2$H$_5$, —O—S(O)C$_3$H$_7$, —O—S(O)-cyclo-C$_3$H$_5$, —O—SO$_2$CH$_3$, —O—SO$_2$C$_2$H$_5$, —O—SO$_2$C$_3$H$_7$, —O—SO$_2$-cyclo-C$_3$H$_5$, —O—SO$_2$—OCH$_3$, —O—SO$_2$—OC$_2$H$_5$, —O—SO$_2$—OC$_3$H$_7$, —O—SO$_2$—O-cyclo-C$_3$H$_5$, —O(CH$_2$)$_n$N[(CH$_2$)$_n$OH], —O(CH$_2$)$_n$N[(CH$_2$)$_n$—H], —O—P(O)(O$^-$)OC$_3$H$_6$OH, —O—P(O)(S$^-$)OC$_3$H$_6$OH, even more preferred are: —OCH$_3$, —OC$_2$H$_5$, —OCH$_2$CH$_2$OCH$_3$ (also known as MOE), —OCH$_2$CH$_2$—N(CH$_3$)$_2$ (also known as DMAOE), —O[(CH$_2$)$_n$O]$_m$CH$_3$, —O(CH$_2$)$_n$OCH$_3$, —O(CH$_2$)$_n$NH$_2$, —O(CH$_2$)$_n$N(CH$_3$)$_2$, —O—P(O)(O$^-$)OC$_3$H$_6$OH, —O—P(O)(S$^-$)OC$_3$H$_6$OH, where n is selected from 1, 2, 3, 4, 5, or 6; and where m is selected from 1, 2, 3, 4, 5, 6, 7, 8, 9 or 10.

Preferred LNAs

In preferred embodiments LNA units used in the anti-sense-oligonucleotides of the present invention preferably have the structure of general formula (II):

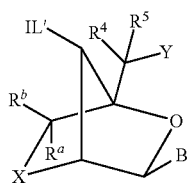

(II)

The moiety —C(R$^a$R$^b$)—X— represents preferably —C(R$^a$R$^b$)—O—, —C(R$^a$R$^b$)—NR$^c$-, —C(R$^a$R$^b$)—S—, and —C(R$^a$R$^b$)—C(R$^a$R$^b$)—O—, wherein the substituents R$^a$, R$^b$ and R$^c$ have the meanings as defined herein and are preferably C$_{1-6}$-alkyl and more preferably C$_{1-4}$-alkyl. More preferably —C(R$^a$R$^b$)—X— is selected from —CH$_2$—O—, —CH$_2$—S—, —CH$_2$—NH—, —CH$_2$—N(CH$_3$)—, —CH$_2$—CH$_2$—O—, or —CH$_2$—CH$_2$—S—, and more preferably —CH$_2$—O—, —CH$_2$—S—, —CH$_2$—CH$_2$—O—, or —CH$_2$—CH$_2$—S—, and still more preferably —CH$_2$—O—, —CH$_2$—S—, or —CH$_2$—CH$_2$—O—, and still more preferably —CH$_2$—O— or —CH$_2$—S—, and most preferably —CH$_2$—O—.

All chiral centers and asymmetric substituents (if any) can be either in R or in S orientation. For example, two exemplary stereochemical isomers are the beta-D and alpha-L isoforms as shown below:

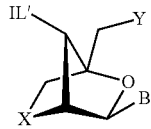

Formula (IIA)

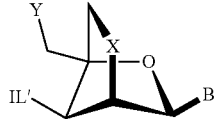

Formula (IIB)

Preferred LNA units are selected from general formula (b$^1$) to (b$^9$):

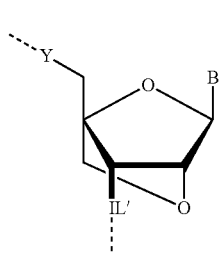

β-D-oxy-LNA (b$^1$)

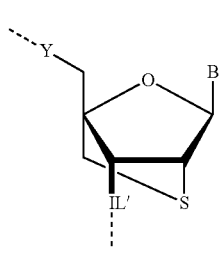

β-D-thio-LNA (b$^2$)

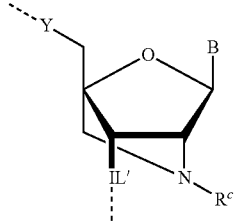

β-D-amino-LNA (b$^3$)

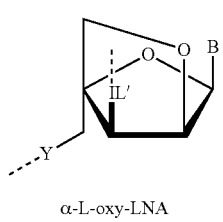

α-L-oxy-LNA (b$^4$)

(b⁵)
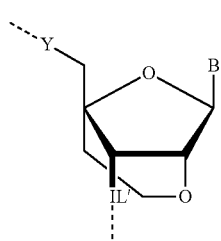
β-D-ENA (b⁶)
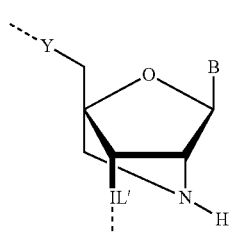
β-D-(NH)-LNA (b⁷)
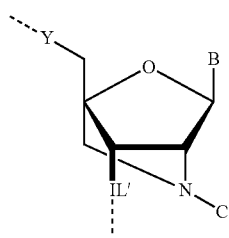
β-D-(NCH₃)-LNA (b⁸)
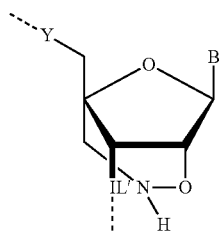
β-D-(ONH)-LNA (b⁹)
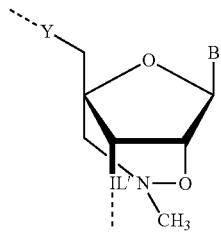
β-D-(ONCH₃)-LNA The term "thio-LNA" comprises a locked nucleotide in which X in the general formula (II) is selected from —S— or —CH₂—S-. Thio-LNA can be in both beta-D and alpha-L-configuration.

The term "amino-LNA" comprises a locked nucleotide in which X in the general formula (II) is selected from —NH—, —N(R)—, —CH₂—NH—, and —CH₂—N(R)-, where R is selected from hydrogen and $C_{1-4}$-alkyl. Amino-LNA can be in both beta-D and alpha-L-configuration.

The term "oxy-LNA" comprises a locked nucleotide in which X in the general formula (II) is -O—. Oxy-LNA can be in both beta-D and alpha-L-configuration.

The term "ENA" comprises a locked nucleotide in which X in the general formula (II) is —CH₂—O— (where the oxygen atom of —CH₂—O— is attached to the 2'-position relative to the base B). $R^a$ and $R^b$ are independently of each other hydrogen or methyl.

In preferred exemplary embodiments LNA is selected from beta-D-oxy-LNA, alpha-L-oxy-LNA, beta-D-amino-LNA and beta-D-thio-LNA, in particular beta-D-oxy-LNA.

Still more preferred are the following antisense-oligonucleotides (Table 1):

| SP | L | Seq ID No. | Sequence, 5'-3' |
|---|---|---|---|
| 89 | 17 | 102a | GCGAGTGACTCACTCAA |
| 90 | 15 | 103a | CGAGTGACTCACTCA |
| 90 | 16 | 104a | GCGAGTGACTCACTCA |
| 90 | 17 | 105a | CGCGAGTGACTCACTCA |
| 91 | 14 | 106a | CGAGTGACTCACTC |
| 91 | 16 | 107a | CGCGAGTGACTCACTC |
| 91 | 17 | 108a | GCGCGAGTGACTCACTC |
| 92 | 14 | 109a | GCGAGTGACTCACT |
| 92 | 16 | 110a | GCGCGAGTGACTCACT |
| 92 | 17 | 111a | CGCGCGAGTGACTCACT |
| 93 | 12 | 112a | CGAGTGACTCAC |
| 93 | 13 | 113a | GCGAGTGACTCAC |
| 93 | 14 | 114a | CGCGAGTGACTCAC |
| 93 | 16 | 115a | CGCGCGAGTGACTCAC |
| 93 | 17 | 116a | GCGCGCGAGTGACTCAC |
| 94 | 13 | 117a | CGCGAGTGACTCA |
| 94 | 14 | 118a | GCGCGAGTGACTCA |
| 94 | 15 | 119a | CGCGCGAGTGACTCA |
| 94 | 16 | 120a | GCGCGCGAGTGACTCA |
| 94 | 17 | 121a | TGCGCGCGAGTGACTCA |
| 95 | 14 | 122a | CGCGCGAGTGACTC |
| 95 | 16 | 123a | TGCGCGCGAGTGACTC |
| 95 | 17 | 124a | GTGCGCGCGAGTGACTC |
| 96 | 13 | 125a | CGCGCGAGTGACT |
| 97 | 14 | 126a | TGCGCGCGAGTGAC |
| 97 | 16 | 127a | CGTGCGCGCGAGTGAC |
| 98 | 13 | 128a | TGCGCGCGAGTGA |
| 107 | 16 | 129a | GTCGTCGCTCCGTGCG |
| 108 | 15 | 130a | GTCGTCGCTCCGTGC |
| 108 | 17 | 131a | GTGTCGTCGCTCCGTGC |
| 109 | 13 | 132a | TCGTCGCTCCGTG |

| SP | L | Seq ID No. | Sequence, 5'-3' |
|---|---|---|---|
| 109 | 15 | 133a | TGTCGTCGCTCCGTG |
| 110 | 12 | 134a | TCGTCGCTCCGT |
| 110 | 13 | 135a | GTCGTCGCTCCGT |
| 110 | 14 | 136a | TGTCGTCGCTCCGT |
| 110 | 15 | 137a | GTGTCGTCGCTCCGT |
| 110 | 16 | 138a | GGTGTCGTCGCTCCGT |
| 351 | 16 | 139a | CGTCATAGACCGAGCC |
| 351 | 12 | 140a | ATAGACCGAGCC |
| 354 | 16 | 141a | GCTCGTCATAGACCGA |
| 354 | 13 | 142a | CGTCATAGACCGA |
| 355 | 14 | 143a | CTCGTCATAGACCG |
| 355 | 15 | 144a | GCTCGTCATAGACCG |
| 356 | 14 | 145a | GCTCGTCATAGACC |
| 381 | 17 | 146a | CAGCCCCGACCCATGG |
| 382 | 16 | 147a | CAGCCCCGACCCATG |
| 383 | 14 | 148a | AGCCCCGACCCAT |
| 384 | 14 | 149a | CAGCCCCGACCCA |
| 422 | 17 | 150a | CGCGTCCACAGGACGAT |
| 425 | 14 | 151a | CGCGTCCACAGGAC |
| 429 | 15 | 152a | CGATACGCGTCCACA |
| 431 | 13 | 153a | CGATACGCGTCCA |
| 431 | 16 | 154a | TGGCGATACGCGTCCA |
| 432 | 12 | 155a | CGATACGCGTCC |
| 432 | 13 | 156a | GCGATACGCGTCC |
| 432 | 17 | 157a | GCTGGCGATACGCGTCC |
| 433 | 15 | 158a | CTGGCGATACGCGTC |
| 433 | 12 | 159a | GCGATACGCGTC |
| 433 | 16 | 160a | GCTGGCGATACGCGTC |
| 433 | 14 | 161a | TGGCGATACGCGTC |
| 434 | 13 | 162a | TGGCGATACGCGT |
| 434 | 14 | 163a | CTGGCGATACGCGT |
| 434 | 12 | 164a | GGCGATACGCGT |
| 435 | 13 | 165a | CTGGCGATACGCG |
| 435 | 12 | 166a | TGGCGATACGCG |
| 437 | 17 | 167a | ATCGTGCTGGCGATACG |
| 449 | 16 | 168a | CGTGCGGTGGGATCGT |
| 449 | 17 | 169a | ACGTGCGGTGGGATCGT |
| 450 | 17 | 170a | AACGTGCGGTGGGATCG |
| 452 | 15 | 171a | AACGTGCGGTGGGAT |
| 452 | 17 | 172a | TGAACGTGCGGTGGGAT |
| 459 | 17 | 173a | CGACTTCTGAACGTGCG |
| 941 | 17 | 174a | TTAACGCGGTAGCAGTA |
| 941 | 16 | 175a | TAACGCGGTAGCAGTA |
| 942 | 17 | 176a | GTTAACGCGGTAGCAGT |
| 943 | 15 | 177a | TTAACGCGGTAGCAG |
| 944 | 13 | 178a | TAACGCGGTAGCA |
| 945 | 12 | 179a | TAACGCGGTAGC |
| 945 | 13 | 180a | TTAACGCGGTAGC |
| 946 | 12 | 181a | TTAACGCGGTAG |
| 946 | 13 | 182a | GTTAACGCGGTAG |
| 946 | 15 | 183a | CGGTTAACGCGGTAG |
| 946 | 16 | 184a | CCGGTTAACGCGGTAG |
| 947 | 14 | 185a | CGGTTAACGCGGTA |
| 947 | 13 | 186a | GGTTAACGCGGTA |
| 947 | 15 | 187a | CCGGTTAACGCGGTA |
| 947 | 16 | 188a | GCCGGTTAACGCGGTA |
| 947 | 17 | 189a | TGCCGGTTAACGCGGTA |
| 948 | 13 | 190a | CGGTTAACGCGGT |
| 949 | 13 | 191a | CCGGTTAACGCGG |
| 949 | 14 | 192a | GCCGGTTAACGCGG |
| 949 | 15 | 193a | TGCCGGTTAACGCGG |
| 950 | 13 | 194a | GCCGGTTAACGCG |
| 950 | 15 | 195a | CTGCCGGTTAACGCG |
| 950 | 16 | 196a | GCTGCCGGTTAACGCG |
| 1387 | 16 | 197a | ATGCCGCGTCAGGTAC |
| 1392 | 13 | 198a | ACATGCCGCGTCA |
| 1393 | 16 | 199a | GATGACATGCCGCGTC |
| 1394 | 12 | 200a | GACATGCCGCGT |
| 1394 | 15 | 201a | GATGACATGCCGCGT |
| 1395 | 13 | 202a | ATGACATGCCGCG |
| 1805 | 17 | 203a | TCCCGCACCTTGGAACC |
| 1851 | 16 | 204a | CGATCTCTCAACACGT |
| 1851 | 17 | 205a | TCGATCTCTCAACACGT |
| 1852 | 15 | 206a | CGATCTCTCAACACG |
| 1852 | 16 | 207a | TCGATCTCTCAACACG |
| 1852 | 17 | 208a | CTCGATCTCTCAACACG |
| 2064 | 16 | 209a | GTAGTGTTTAGGGAGC |

-continued

| SP | L | Seq ID No. | Sequence, 5'-3' |
|---|---|---|---|
| 2072 | 16 | 210a | GCTATTTGGTAGTGTT |
| 2284 | 15 | 211a | AGCTTATCCTATGAC |
| 2285 | 14 | 212a | AGCTTATCCTATGA |
| 2355 | 17 | 213a | CAGGCATTAATAAAGTG |
| 4120 | 16 | 214a | CTAGGCGCCTCTATGC |
| 4121 | 14 | 215a | TAGGCGCCTCTATG |
| 4121 | 15 | 216a | CTAGGCGCCTCTATG |
| 4122 | 13 | 217a | TAGGCGCCTCTAT |
| 4217 | 16 | 218a | CATGAATGGACCAGTA |

SP: start position or start nucleotide on Seq. ID No. 2
L: length of the sequence The antisense-oligonucleotides as disclosed herein such as the antisense-oligonucleotides of Tables 1 to 3 and especially the antisense-oligonucleotides of Tables 4 to 9 consist of nucleotides, preferably DNA nucleotides, which are non-LNA units (also named herein non-LNA nucleotides) as well as LNA units (also named herein LNA nucleotides).

Although not explicitly indicated, the antisense-oligonucleotides of the sequences Seq. ID No.s 102a-218a of Table 1 comprise 2 to 4 LNA nucleotides (LNA units) at the 3' terminus and 2 to 4 LNA nucleotides (LNA units) at the 5' terminus. Although not explicitly indicated, the "C" in Table 2 which refer to LNA units preferably contain 5-methylcytosine (C*) as nucleobase.

That means, as long as not explicitly indicated, the antisense-oligonucleotides of the present invention or as disclosed herein by the letter code A, C, G, T and U may contain any internucleotide linkage, any end group and any nucleobase as disclosed herein. Moreover the antisense-oligonucleotides of the present invention or as disclosed herein are gapmers of any gapmer structure as disclosed herein with at least one LNA unit at the 3' terminus and at least one LNA unit at the 5' terminus. Moreover any LNA unit as disclosed herein can be used within the antisense-oligonucleotides of the present invention or as disclosed herein. Thus, for instance, the antisense-oligonucleotide GCTCGTCATAGACCGA (Seq. ID No. 13) or CGATACGCGTCCACAG (Seq. ID No. 14) or GTAGTGTTTAGGGAGC (Seq. ID No. 15) or GCTATTTGGTAGTGTT (Seq. ID No. 16) or CATGAATGGACCAGTA (Seq. ID No. 17) or AGGCATTAATAAAGTG (Seq. ID No. 18) contains at least one LNA unit at the 5' terminus and at least one LNA unit at the 3' terminus, any nucleobase, any 3' end group, any 5' end group, any gapmer structure, and any internucleotide linkage as disclosed herein and covers also salts and optical isomers of that antisense-oligonucleotide.

The use of LNA units is preferred especially at the 3' terminal and the 5' terminal end. Thus it is preferred if the last 1-5 nucleotides at the 3' terminal end and also the last 1-5 nucleotides at the 5' terminal end especially of the sequences disclosed herein and particularly of Seq. ID No.s 102a-218a of Table 1 are LNA units (also named LNA nucleotides) while in between the 1-5 LNA units at the 3' and 5' end 2-14, preferably 3-12, more preferably 4-10, more preferably 5-9, still more preferably 6-8, non-LNA units (also named non-LNA nucleotides) are present. Such kind of antisense-oligonucleotides are called gapmers and are disclosed in more detail below. More preferred are 2-5 LNA nucleotides at the 3' end and 2-5 LNA nucleotides at the 5' end or 1-4 LNA nucleotides at the 3' end and 1-4 LNA nucleotides at the 5' end and still more preferred are 2-4 LNA nucleotides at the 3' end and 2-4 LNA nucleotides at the 5' end of the antisense-oligonucleotides with a number of preferably 4-10, more preferably 5-9, still more preferably 6-8 non-LNA units in between the LNA units at the 3' and the 5' end.

Moreover as internucleotide linkages between the LNA units and between the LNA units and the non-LNA units, the use of phosphorothioates or phosphorodithioates and preferably phosphorothioates is preferred.

Thus further preferred are antisense-oligonucleotides wherein more than 50%, preferably more than 60%, more preferably more than 70%, still more preferably more than 80%, and most preferably more than 90% of the internucleotide linkages are phosphorothioates or phosphates and more preferably phosphorothioate linkages and wherein the last 1-4 or 2-5 nucleotides at the 3' end are LNA units and the last 1-4 or 2-5 nucleotides at the 5' end are LNA units and between the LNA units at the ends a sequence of 6-14 nucleotides, preferably 7-12, preferably 8-11, more preferably 8-10 are present which are non-LNA units, preferably DNA units. Moreover it is preferred that these antisense-oligonucleotides in form of gapmers consist in total of 12 to 20, preferably 12 to 18 nucleotides.

Gapmers

The antisense-oligonucleotides of the invention may consist of nucleotide sequences which comprise both DNA nucleotides which are non-LNA units as well as LNA nucleotides, and may be arranged in the form of a gapmer.

Thus, the antisense-oligonucleotides of the present invention are preferably gapmers. A gapmer consists of a middle part of DNA nucleotide units which are not locked, thus which are non-LNA units. The DNA nucleotides of this middle part could be linked to each other by the internucleotide linkages (IL) as disclosed herein which preferably may be phosphate groups, phosphorothioate groups or phosphorodithioate groups and which may contain nucleobase analogues such as 5-propynyl cytosine, 7-methylguanine, 7-methyladenine, 2-aminoadenine, 2-thiothymine, 2-thiocytosine, or 5-methylcytosine. That DNA units or DNA nucleotides are not bicyclic pentose structures. The middle part of non-LNA units is flanked at the 3' end and the 5' end by sequences consisting of LNA units. Thus gapmers have the general formula:

LNA sequence 1—non-LNA sequence—LNA sequence 2 or region A—region B—region C

The middle part of the antisense-oligonucleotide which consists of DNA nucleotide units which are non-LNA units is, when formed in a duplex with the complementary target RNA, capable of recruiting RNase. The 3' and 5' terminal nucleotide units are LNA units which are preferably in alpha-L configuration, particularly preferred being beta-D-oxy-LNA and alpha-L-oxy LNAs.

Thus, a gapmer is an antisense-oligonucleotide which comprises a contiguous stretch of DNA nucleotides which is capable of recruiting an RNase, such as RNaseH, such as a region of at least 6 or 7 DNA nucleotides which are non-LNA units, referred to herein as middle part or region B, wherein region B is flanked both 5' and 3' by regions of affinity enhancing nucleotide analogues which are LNA units, such as between 1-6 LNA units 5' and 3' to the contiguous stretch of DNA nucleotides which is capable of recruiting RNase—these flanking regions are referred to as regions A and C respectively.

Preferably the gapmer comprises a (poly)nucleotide sequence of formula (5' to 3'), A-B-C, or optionally A-B-C-D or D-A-B-C, wherein; region A (5' region) consists of at least one nucleotide analogue, such as at least one LNA unit, such as between 1-6 LNA units, and region B consists of at least five consecutive DNA nucleotides which are non-LNA units and which are capable of recruiting RNase (when formed in a duplex with a complementary RNA molecule, such as the mRNA target), and region C (3'region) consists of at least one nucleotide analogue, such as at least one LNA unit, such as between 1-6 LNA units, and region D, when present consists of 1, 2 or 3 DNA nucleotide units which are non-LNA units.

In some embodiments, region A consists of 1, 2, 3, 4, 5 or 6 LNA units, such as between 2-5 LNA units, such as 3 or 4 LNA units; and/or region C consists of 1, 2, 3, 4, 5 or 6 LNA units, such as between 2-5 LNA units, such as 3 or 4 LNA units.

In some embodiments B consists of 5, 6, 7, 8, 9, 10, 11 or 12 consecutive DNA nucleotides which are capable of recruiting RNase, or between 6-10, or between 7-9, such as 8 consecutive nucleotides which are capable of recruiting RNase. In some embodiments region B consists of at least one DNA nucleotide unit, such as 1-12 DNA nucleotide units, preferably between 4-12 DNA nucleotide units, more preferably between 6-10 DNA nucleotide units, still more preferred such as between 7-10 DNA nucleotide units, and most preferably 8, 9 or 10 DNA nucleotide units which are non-LNA units.

In some embodiments region A consist of 3 or 4 LNA, region B consists of 7, 8, 9 or 10 DNA nucleotide units, and region C consists of 3 or 4 LNA units. Such designs include (A-B-C): 1-7-2, 2-7-1, 2-7-2, 3-7-1, 3-7-2, 1-7-3, 2-7-3, 3-7-3, 2-7-4, 3-7-4, 4-7-2, 4-7-3, 4-7-4, 1-8-1, 1-8-2, 2-8-1, 2-8-2, 1-8-3, 3-8-1, 3-8-3, 2-8-3, 3-8-2, 4-8-1, 4-8-2, 1-8-4, 2-8-4, 3-8-4, 4-8-3, 4-8-4, 1-9-1, 1-9-2, 2-9-1, 2-9-2, 2-9-3, 3-9-2, 3-9-3, 1-9-3, 3-9-1, 4-9-1, 1-9-4, 4-9-2, 2-9-4, 4-9-3, 3-9-4, 4-9-4, 3-9-4, 4-9-4, 1-10-1, 1-10-2, 2-10-1, 2-10-2, 1-10-3, 3-10-1, 2-10-2, 2-10-3, 3-10-2, 3-10-3, 2-10-4, 4-10-2, 3-10-4, 4-10-3, 4-10-4, 1-11-1, 1-11-2, 2-11-1, 2-11-2, 1-11-3, 3-11-1, 2-11-2, 2-11-3, 3-11-2, 3-11-3, 2-11-4, 4-11-2, 3-11-4, 4-11-3, 4-11-4, and may further include region D, which may have one or 2 DNA nucleotide units, which are non-LNA units.

Further gapmer designs are disclosed in WO2004/046160A and are hereby incorporated by reference. U.S. provisional application, 60/977,409, hereby incorporated by reference, refers to 'shortmer' gapmer antisense-oligonucleotide, which are also suitable for the present invention.

In some embodiments the antisense-oligonucleotide consists of a contiguous nucleotide sequence of a total of 10, 11, 12, 13 or 14 nucleotide units (LNA units and non-LNA units together), wherein the contiguous nucleotide sequence is of formula (5'-3'), A-B-C, or optionally A-B-C-D or D-A-B-C, wherein A consists of 1, 2 or 3 LNA units, and B consists of 7, 8 or 9 contiguous DNA nucleotide units which are non-LNA units and which are capable of recruiting RNase when formed in a duplex with a complementary RNA molecule (such as a mRNA target), and C consists of 1, 2 or 3 LNA units. When present, D consists of a single DNA nucleotide unit which is a non-LNA unit.

In some embodiments A consists of 1 LNA unit. In some embodiments A consists of 2 LNA units. In some embodiments A consists of 3 LNA units. In some embodiments C consists of 1 LNA unit. In some embodiments C consists of 2 LNA units. In some embodiments C consists of 3 LNA units. In some embodiments B consists of 7 DNA nucleotide units which are non-LNA units. In some embodiments B consists of 8 DNA nucleotide units. In some embodiments B consists of 9 DNA nucleotide units. In some embodiments B consists of 1-9 DNA nucleotide units, such as 2, 3, 4, 5, 6, 7 or 8 DNA nucleotide units. The DNA nucleotide units are always non-LNA units. In some embodiments B comprises 1, 2 or 3 LNA units which are preferably in the alpha-L configuration and which are more preferably alpha-L-oxy LNA units. In some embodiments the number of nucleotides present in A-B-C are selected from the group consisting of (LNA units—region B—LNA units and more preferably alpha-L-oxy LNA units (region A)—region B—(region C) alpha-L-oxy LNA units): 1-8-1, 1-8-2, 2-8-1, 2-8-2, 1-8-3, 3-8-1, 3-8-3, 2-8-3, 3-8-2, 4-8-1, 4-8-2, 1-8-4, 2-8-4, 3-8-4, 4-8-3, 4-8-4, 1-9-1, 1-9-2, 2-9-1, 2-9-2, 2-9-3, 3-9-2, 3-9-3, 1-9-3, 3-9-1, 4-9-1, 1-9-4, 4-9-2, 2-9-4, 4-9-3, 3-9-4, 4-9-4, 1-10-1, 1-10-2, 2-10-1, 2-10-2, 1-10-3, 3-10-1, 2-10-2, 2-10-3, 3-10-2, 3-10-3, 2-10-4, 4-10-2, 3-10-4, 4-10-3, 4-10-4, 1-11-1, 1-11-2, 2-11-1, 2-11-2, 1-11-3, 3-11-1, 2-11-2, 2-11-3, 3-11-2, 3-11-3, 2-11-4, 4-11-2, 3-11-4, 4-11-3, 4-11-4. In further preferred embodiments the number of nucleotides in A-B-C are selected from the group consisting of: 3-8-3, 4-8-2, 2-8-4, 3-8-4, 4-8-3, 4-8-4, 3-9-3, 4-9-2, 2-9-4, 4-9-3, 3-9-4, 4-9-4, 3-10-3, 2-10-4, 4-10-2, 3-10-4, 4-10-3, 4-10-4, 2-11-4, 4-11-2, 3-11-4, 4-11-3 and still more preferred are: 3-8-3, 3-8-4, 4-8-3, 4-8-4, 3-9-3, 4-9-3, 3-9-4, 4-9-4, 3-10-3, 3-10-4, 4-10-3, 4-10-4, 3-11-4, and 4-11-3.

Phosphorothioate, phosphate or phosphorodithioate and especially phosphorothioate internucleotide linkages are also preferred, particularly for the gapmer region B. Phosphorothioate, phosphate or phosphorodithioate linkages and especially phosphorothioate internucleotide linkages may also be used for the flanking regions (A and C, and for linking A or C to D, and within region D, if present).

Regions A, B and C, may however comprise internucleotide linkages other than phosphorothioate or phosphorodithioate, such as phosphodiester linkages, particularly, for instance when the use of nucleotide analogues protects the internucleotide linkages within regions A and C from endonuclease degradation—such as when regions A and C consist of LNA units.

The internucleotide linkages in the antisense-oligonucleotide may be phosphodiester, phosphorothioate, phosphorodithioate or boranophosphate so as to allow RNase H cleavage of targeted RNA. Phosphorothioate or phosphorodithioate is preferred, for improved nuclease resistance and other reasons, such as ease of manufacture. In one aspect of the oligomer of the invention, the LNA units and/or the non-LNA units are linked together by means of phosphorothioate groups.

It is recognized that the inclusion of phosphodiester linkages, such as one or two linkages, into an otherwise phosphorothioate antisense-oligonucleotide, particularly between or adjacent to LNA units (typically in region A and or C) can modify the bioavailability and/or bio-distribution of an antisense-oligonucleotide (see WO2008/053314A which is hereby incorporated by reference).

In some embodiments, such as in the sequences of the antisense-oligonucleotides disclosed herein and where suitable and not specifically indicated, all remaining internucleotide linkage groups are either phosphodiester groups or phosphorothioate groups, or a mixture thereof.

In some embodiments all the internucleotide linkage groups are phosphorothioate groups. When referring to specific gapmer antisense-oligonucleotide sequences, such as those provided herein, it will be understood that, in various embodiments, when the linkages are phosphorothioate linkages, alternative linkages, such as those disclosed herein may be used, for example phosphate (also named phosphodiester) linkages may be used, particularly for linkages between nucleotide analogues, such as LNA units. Likewise, when referring to specific gapmer antisense-oligonucleotide sequences, such as those provided herein, when the C residues are annotated as 5'-methyl modified cytosine, in various embodiments, one or more of the Cs present in the oligomer may be unmodified C residues.

Legend

As used herein the abbreviations b, d, s, ss have the following meaning:

b LNA unit or LNA nucleotide (any one selected from $b^1$-$b^7$)
$b^1$ β-D-oxy-LNA
$b^2$ β-D-thio-LNA
$b^3$ β-D-amino-LNA
$b^4$ α-L-oxy-LNA
$b^5$ β-D-ENA
$b^6$ β-D-(NH)-LNA
$b^7$ β-D-(NCH$_3$)-LNA d 2-deoxy, that means 2-deoxyribose units (e.g. formula B3 or B5 with R=—H)

C* methyl-C(5-methylcytosine); [consequently dC* is 5-methyl-2'-deoxycytidine]

A* 2-aminoadenine [consequently dA* is 2-amino-2'-deoxyadenosine]

s the internucleotide linkage is a phosphorothioate group (—O—P(O)(S$^-$)—O—)

ss the internucleotide linkage is a phosphorodithioate group (—O—P(S)(S$^-$)—O—)

/5SpC3/—O—P(O)(O$^-$)OC$_3$H$_6$OH at 5'-terminal group of an antisense-oligonucleotide /3SpC3/—O—P(O)(O$^-$)OC$_3$H$_6$OH at 3'-terminal group of an antisense-oligonucleotide /5SpC3s/—O—P(O)(S$^-$)OC$_3$H$_6$OH at 5'-terminal group of an antisense-oligonucleotide /3SpC3s/—O—P(O)(S$^-$)OC$_3$H$_6$OH at 3'-terminal group of an antisense-oligonucleotide nucleotides in bold are LNA nucleotides
nucleotides not in bold are non-LNA nucleotides Gapmer Sequences The following antisense-oligonucleotides in form of gapmers as listed in Table 2 to Table 9 and more preferably in Table 4 to 9 are especially preferred.

TABLE 2

| SP | L | Seq ID No. | Sequence, 5'-3' |
|---|---|---|---|
| 89 | 17 | 102b | GbsCbsGbsAbsdGsdTsdGsdAsdCsdTsdCsdAsdCsTbsCbsAbsAb |
| 90 | 15 | 103b | CbsGbsAbsdGsdTsdGsdAsdCsdTsdCsdAsdCsTbsCbsAb |
| 90 | 16 | 104b | GbsCbsGbsdAsdGsdTsdGsdAsdCsdTsdCsdAsdCsTbsCbsAb |
| 90 | 17 | 105b | CbsGbsCbsGbsdAsdGsdTsdGsdAsdCsdTsdCsdAsCbsTbsCbsAb |
| 91 | 14 | 106b | CbsGbsAbsdGsdTsdGsdAsdCsdTsdCsdAsCbsTbsCb |
| 91 | 16 | 107b | CbsGbsCbsdGsdAsdGsdTsdGsdAsdCsdTsdCsdAsCbsTbsCb |
| 91 | 17 | 108b | GbsCbsGbsCbsdGsdAsdGsdTsdGsdAsdCsdTsdCsAsAbsCbsTbsCb |
| 92 | 14 | 109b | GbsCbsGbsdAsdGsdTsdGsdAsdCsdTsdCsAbsCbsTb |
| 92 | 16 | 110b | GbsCbsGbsdCsdGsdAsdGsdTsdGsdAsdCsdTsdCsAbsCbsTb |
| 92 | 17 | 111b | CbsGbsCbsGbsdCsdGsdAsdGsdTsdGsdAsdCsdTsCbsAbsCbsTb |
| 93 | 12 | 112b | CbsGbsdAsdGsdTsdGsdAsdCsdTsdCsAbsCb |
| 93 | 13 | 113b | GbsCbsGbsdAsdGsdTsdGsdAsdCsdTsdCsAbsCb |
| 93 | 14 | 114b | CbsGbsCbsdGsdAsdGsdTsdGsdAsdCsdTsCbsAbsCb |
| 93 | 16 | 115b | CbsGbsCbsdGsdCsdGsdAsdGsdTsdGsdAsdCsdTsCbsAbsCb |
| 93 | 17 | 116b | GbsCbsGbsCbsdGsdCsdGsdAsdGsdTsdGsdAsdCsTbsCbsAbsCb |
| 94 | 13 | 117b | CbsGbsCbsdGsdAsdGsdTsdGsdAsdCsdTsCbsAb |
| 94 | 14 | 118b | GbsCbsGbsdCsdGsdAsdGsdTsdGsdAsdCsTbsCbsAb |
| 94 | 15 | 119b | CbsGbsCbsdCsdGsdCsdGsdAsdGsdTsdGsdAsdCsTbsCbsAb |
| 94 | 16 | 120b | GbsCbsGbsdCsdGsdCsdGsdAsdGsdTsdGsdAsdCsTbsCbsAb |
| 94 | 17 | 121b | TbsGbsCbsGbsdCsdGsdCsdGsdAsdGsdTsdGsdAsCbsTbsCbsAb |
| 95 | 14 | 122b | CbsGbsCbsdCsdGsdCsdGsdAsdGsdTsdGsdAsCbsTbsCb |
| 95 | 16 | 123b | TbsGbsCbsdGsdCsdGsdCsdGsdAsdGsdTsdGsdAsCbsTbsCb |

TABLE 2-continued

| SP | L | Seq ID No. | Sequence, 5'-3' |
|---|---|---|---|
| 95 | 17 | 124b | GbsTbsGbsCbsdGsdCsdGsdCsdGsdAsdGsdTsdGsAbsCbsTbsCb |
| 96 | 13 | 125b | CbsGbsCbsdGsdCsdGsdAsdGsdTsdGsdAsCbsTb |
| 97 | 14 | 126b | TbsGbsCbsdGsdCsdGsdCsdGsdAsdGsdTsGbsAbsCb |
| 97 | 16 | 127b | CbsGbsTbsdGsdCsdGsdCsdGsdCsdGsdAsdGsdTsGbsAbsCb |
| 98 | 13 | 128b | TbsGbsCbsdGsdCsdGsdCsdGsdAsdGsdTsGbsAb |
| 107 | 16 | 129b | GbsTbsCbsdGsdTsdCsdGsdCsdTsdCsdCsdGsdTsGbsCbsGb |
| 108 | 15 | 130b | GbsTbsCbsdGsdTsdCsdGsdCsdTsdCsdCsdGsTbsGbsCb |
| 108 | 17 | 131b | GbsTbsGbsTbsdCsdGsdTsdCsdGsdCsdTsdCsdCsGbsTbsGbsCb |
| 109 | 13 | 132b | TbsCbsGbsdTsdCsdGsdCsdTsdCsdCsdGsTbsGb |
| 109 | 15 | 133b | TbsGbsTbsdCsdGsdTsdCsdGsdCsdTsdCsdCsGbsTbsGb |
| 110 | 12 | 134b | TbsCbsdGsdTsdCsdGsdCsdTsdCsdCsGbsTb |
| 110 | 13 | 135b | GbsTbsCbsdGsdTsdCsdGsdCsdTsdCsdCsGbsTb |
| 110 | 14 | 136b | TbsGbsTbsdCsdGsdTsdCsdGsdCsdTsdCsCbsGbsTb |
| 110 | 15 | 137b | GbsTbsGbsdTsdCsdGsdTsdCsdGsdCsdTsdCsCbsGbsTb |
| 110 | 16 | 138b | GbsGbsTbsdGsdTsdCsdGsdTsdCsdGsdCsdTsdCsCbsGbsTb |
| 351 | 16 | 139b | CbsGbsTbsdCsdAsdTsdAsdGsdAsdCsdCsdGsdAsGbsCbsCb |
| 351 | 12 | 140b | AbsTbsdAsdGsdAsdCsdCsdGsdAsdGsCbsCb |
| 354 | 16 | 141b | GbsCbsTbsdCsdGsdTsdCsdAsdTsdAsdGsdAsdCsCbsGbsAb |
| 354 | 13 | 142b | CbsGbsTbsdCsdAsdTsdAsdGsdAsdCsdCsGbsAb |
| 355 | 14 | 143b | CbsTbsdCsdGsdTsdCsdAsdTsdAsdGsdAsCbsCbsGb |
| 355 | 14 | 143c | CbsTbsCbsdGsdTsdCsdAsdTsdAsdGsdAsdCsCbsGb |
| 355 | 14 | 143d | CbsTbsCbsdGsdTsdCsdAsdTsdAsdGsdAsCbsCbsGb |
| 355 | 15 | 144b | GbsCbsTbsdCsdGsdTsdCsdAsdTsdAsdGsdAsCbsCbsGb |
| 356 | 14 | 145b | GbsCbsTbsdCsdGsdTsdCsdAsdTsdAsdGsAbsCbsCb |
| 381 | 17 | 146b | CbsAbsGbsCbsdCsdCsdCsdCsdGsdAsdCsdCsdCsAbsTbsGbsGb |
| 382 | 16 | 147b | CbsAbsGbsdCsdCsdCsdCsdCsdGsdAsdCsdCsdCsAbsTbsGb |
| 382 | 16 | 147c | CbsAbsGbsdCsdCsdCsdCsdCsdGsdAsdCsdCsdCsAsTsG |
| 382 | 16 | 147d | CbsAbsGbsdCsdCsdCsdCsdCsdGsdAsdCsdCsCbsAbsTbsGb |
| 382 | 16 | 147e | CbsAbsGbsCbsdCsdCsdCsdCsdGsdAsdCsdCsdCsAbsTbsGb |
| 382 | 16 | 147f | CbsAbsGbsCbsdCsdCsdCsdCsdGsdAsdCsdCsCbsAbsTbsGb |
| 383 | 14 | 148b | AbsGbsdCsdCsdCsdCsdCsdGsdAsdCsdCsCbsAbsTb |
| 383 | 14 | 148c | AbsGbsCbsdCsdCsdCsdCsdGsdAsdCsdCsdCsAbsTb |
| 383 | 14 | 148d | AbsGbsCbsdCsdCsdCsdCsdGsdAsdCsdCsCbsAbsTb |
| 384 | 14 | 149 | CbsAbsGbsdCsdCsdCsdCsdCsdGsdAsdCsCbsCbsAb |
| 422 | 17 | 150b | CbsGbsCbsGbsdTsdCsdCsdAsdCsdAsdGsdGsdAsCbsGbsAbsTb |
| 425 | 14 | 151b | CbsGbsCbsdGsdTsdCsdCsdAsdCsdAsdGsGbsAbsCb |
| 429 | 15 | 152b | CbsGbsAbsdTsdAsdCsdGsdCsdGsdTsdCsdCsAbsCbsAb |
| 429 | 15 | 152c | CbsGbsAbsdTsdAsdCsdGsdCsdGsdTsdCsCbsAbsCbsAb |
| 429 | 15 | 152d | CbsGbsAbsTbsdAsdCsdGsdCsdGsdTsdCsdCsAbsCbsAb |

TABLE 2-continued

| SP | L | Seq ID No. | Sequence, 5'-3' |
|---|---|---|---|
| 432 | 12 | 155b | CbsGbsdAsdTsdAsdCsdGsdCsdGsdTsCbsCb |
| 431 | 13 | 153b | CbsGbsAbsdTsdAsdCsdGsdCsdGsdTsdCsCbsAb |
| 431 | 13 | 153c | CbsGbsdAsdTsdAsdCsdGsdCsdGsdTsCbsCbsAb |
| 431 | 16 | 154b | TbsGbsGbsdCsdGsdAsdTsdAsdCsdGsdCsdGsdTsCbsCbsAb |
| 432 | 12 | 155c | CbsGbsdAsdTsdAsdCsdGsdCsdGsdTsdCsCb |
| 432 | 12 | 155d | CbsdGsdAsdTsdAsdCsdGsdCsdGsdTsCbsCb |
| 432 | 13 | 156b | GbsCbsGbsdAsdTsdAsdCsdGsdCsdGsdTsCbsCb |
| 432 | 17 | 157b | GbsCbsTbsGbsdGsdCsdGsdAsdTsdAsdCsdGsdCsGbsTbsCbsCb |
| 433 | 15 | 158b | CbsTbsGbsdCsdCsdGsdAsdTsdAsdCsdGsdCsGbsTbsCb |
| 433 | 12 | 159b | GbsCbsdGsdAsdTsdAsdCsdGsdCsdGsTbsCb |
| 433 | 16 | 160b | GbsCbsTbsdGsdCsdGsdGsdAsdTsdAsdCsdGsdCsGbsTbsCb |
| 433 | 14 | 161b | TbsGbsGbsdCsdGsdAsdTsdAsdCsdGsdCsGbsTbsCb |
| 434 | 12 | 164b | GbsGbsdCsdGsdAsdTsdAsdCsdGsdCsGbsTb |
| 434 | 13 | 162b | TbsGbsGbsdCsdGsdAsdTsdAsdCsdGsdCsGbsTb |
| 434 | 13 | 162c | TbsGbsdCsdGsdAsdTsdAsdCsdGsdGsCbsGbsTb |
| 434 | 14 | 163b | CbsTbsGbsdGsdCsdGsdAsdTsdAsdCsdGsCbsGbsTb |
| 435 | 13 | 165b | CbsTbsGbsdCsdCsdGsdAsdTsdAsdCsdGsCbsGb |
| 435 | 12 | 166b | TbsGbsdGsdCsdGsdAsdTsdAsdCsdGsCbsGb |
| 437 | 17 | 167b | AbsTbsCbsGbsdTsdGsdCsdTsdGsdGsdCsdGsdAsTbsAbsCbsGb |
| 449 | 16 | 168b | CbsGbsTbsdGsdCsdGsdGsdTsdGsdGsdGsdAsdTsCbsGbsTb |
| 449 | 17 | 169b | AbsCbsGbsTbsdGsdCsdGsdGsdTsdGsdGsdGsdAsTbsCbsGbsTb |
| 450 | 17 | 170b | AbsAbsCbsGbsdTsdGsdCsdGsdGsdTsdGsdGsdGsAbsTbsCbsGb |
| 452 | 15 | 171b | AbsAbsCbsdGsdTsdGsdCsdGsdGsdTsdGsdGsGbsAbsTb |
| 452 | 17 | 172b | TbsGbsAbsAbsdCsdGsdTsdGsdCsdGsdGsdTsdGsGbsGbsAbsTb |
| 459 | 17 | 173b | CbsGbsAbsCbsdTsdTsdCsdTsdGsdAsdAsdCsdGsTbsGbsCbsGb |
| 941 | 17 | 174b | TbsTbsAbsAbsdCsdGsdCsdGsdGsdTsdAsdGsdCsAbsGbsTbsAb |
| 941 | 16 | 175b | TbsAbsAbsdCsdGsdCsdGsdGsdTsdAsdGsdCsdAsGbsTbsAb |
| 942 | 17 | 176b | GbsTbsTbsAbsdAsdCsdGsdCsdGsdGsdTsdAsdGsCbsAbsGbsTb |
| 943 | 15 | 177b | TbsTbsAbsdAsdCsdGsdCsdGsdGsdTsdAsdGsCbsAbsGb |
| 944 | 13 | 178b | TbsAbsAbsdCsdGsdCsdGsdGsdTsdAsdGsCbsAb |
| 945 | 12 | 179b | TbsAbsdAsdCsdGsdCsdGsdGsdGsdTsdAsGbsCb |
| 945 | 13 | 180b | TbsTbsAbsdAsdCsdGsdCsdGsdGsdGsdTsdAsGbsCb |
| 946 | 12 | 181b | TbsTbsdAsdAsdCsdGsdCsdGsdGsdGsdTsAbsGb |
| 946 | 13 | 182b | GbsTbsTbsdAsdAsdCsdGsdCsdGsdGsdGsdTsAbsGb |
| 946 | 15 | 183b | CbsGbsGbsdTsdTsdAsdAsdCsdGsdCsdGsdGsdGsTbsAbsGb |
| 946 | 16 | 184b | CbsCbsGbsGbsdTsdTsdAsdAsdCsdGsdCsdGsdGsdGsTbsAbsGb |
| 947 | 14 | 185b | CbsGbsGbsdTsdTsdAsdAsdCsdGsdCsdGsdGsGbsTbsAb |
| 947 | 13 | 186b | GbsGbsTbsdTsdAsdAsdCsdGsdCsdGsdGsdGsTbsAb |
| 947 | 15 | 187b | CbsCbsGbsdGsdTsdTsdAsdAsdCsdGsdCsdGsdGsGbsTbsAb |

TABLE 2-continued

| SP | L | Seq ID No. | Sequence, 5'-3' |
|---|---|---|---|
| 947 | 16 | 188b | GbsCbsCbsdGsdGsdTsdTsdAsdAsdCsdGsdCsdGsGbsTbsAb |
| 947 | 17 | 189b | TbsGbsCbsCbsdGsdGsdTsdTsdAsdAsdCsdGsdCsGbsGbsTbsAb |
| 948 | 13 | 190b | CbsGbsGbsdTsdTsdAsdAsdCsdGsdCsdGsGbsTb |
| 949 | 13 | 191b | CbsCbsGbsdGsdTsdTsdAsdAsdCsdGsdCsGbsGb |
| 949 | 14 | 192b | GbsCbsGbsdGsdGsdTsdTsdAsdAsdCsdGsdCbsGbsGb |
| 949 | 15 | 193b | TbsGbsCbsdCsdGsdGsdTsdTsdAsdAsdCsdGsCbsGbsGb |
| 950 | 13 | 194b | GbsCbsCbsdGsdGsdTsdTsdAsdAsdCsdGsCbsGb |
| 950 | 15 | 195b | CbsTbsGbsdCsdCsdGsdGsdTsdTsdAsdAsdCsGbsCbsGb |
| 950 | 16 | 196b | GbsCbsTbsdGsdCsdCsdGsdGsdTsdTsdAsdAsdCsGbsCbsGb |
| 1387 | 16 | 197b | AbsTbsGbsdCsdCsdGsdCsdGsdTsdCsdAsdGsdGsTbsAbsCb |
| 1392 | 13 | 198b | AbsCbsAbsdTsdGsdCsdCsdGsdCsdGsdTsCbsAb |
| 1393 | 16 | 199b | GbsAbsTbsdGsdAsdCsdAsdTsdGsdCsdCsdGsdCsGbsTbsCb |
| 1393 | 16 | 199c | GbsAbsTbsdGsdAsdCsdAsdTsdGsdCsdCsdGsdCsCbsGbsTbsCb |
| 1393 | 16 | 199d | GbsAbsTbsGbsdAsdCsdAsdTsdGsdCsdCsdGsdCsGbsTbsCb |
| 1393 | 16 | 199e | GbsAbsTbsGbsdAsdCsdAsdTsdGsdCsdCsdGsdCsCbsGbsTbsCb |
| 1394 | 12 | 200b | GbsAbsdCsdAsdTsdGsdCsdCsdGsdCsGbsTb |
| 1394 | 15 | 201b | GbsAbsTbsdGsdAsdCsdAsdTsdGsdCsdCsdGsdCsCbsGbsTb |
| 1395 | 13 | 202b | AbsTbsGbsdAsdCsdAsdTsdGsdCsdCsdGsCbsGb |
| 1805 | 17 | 203b | TbsCbsCbsCbsdGsdCsdAsdCsdCsdTsdTsdGsdGsAbsAbsCbsCb |
| 1851 | 16 | 204b | CbsGbsAbsdTsdCsdTsdCsdTsdCsdAsdAsdCsdAsCbsGbsTb |
| 1851 | 17 | 205b | TbsCbsGbsAbsdTsdCsdTsdCsdTsdCsdAsdAsdCsAbsCbsGbsTb |
| 1852 | 15 | 206b | CbsGbsAbsdTsdCsdTsdCsdTsdCsdAsdAsdCsAbsCbsGb |
| 1852 | 16 | 207b | TbsCbsGbsdAsdTsdCsdTsdCsdTsdCsdAsdAsdCsAbsCbsGb |
| 1852 | 17 | 208b | CbsTbsCbsGbsdAsdTsdCsdTsdCsdTsdCsdAsdAsCbsAbsCbsGb |
| 2064 | 16 | 209b | GbsTbsdAsdGsdTsdGsdTsdTsdAsdGsdGsdGsdGsAbsGbsCb |
| 2064 | 16 | 209c | GbsTbsAbsGbsdTsdGsdTsdTsdAsdGsdGsdGsdGsAbsGbsCb |
| 2064 | 16 | 209d | GbsTbsAbsdGsdTsdGsdTsdTsdAsdGsdGsdGsdGsAbsGbsCb |
| 2064 | 16 | 209e | GbsTbsAbsdGsdTsdGsdTsdTsdAsdGsdGsdGsdGsdAsGbsCb |
| 2064 | 16 | 209f | GbsTbsAbsdGsdTsdGsdTsdTsdAsdGsdGsdGsGbsAbsGbsCb |
| 2064 | 16 | 209g | GbsTbsAbsGbsdTsdGsdTsdTsdAsdGsdGsdGsGbsAbsGbsCb |
| 2064 | 16 | 209h | GbsTbsdAsdGsdTsdGsdTsdTsdAsdGsdGsdGsdGsAbsGbsCb |
| 2064 | 16 | 209i | GbsTbsAbsGbsTbsdGsdTsdTsdAsdGsdGsdGsGbsAbsGbsCb |
| 2064 | 16 | 209j | GbsTbsAbsGbsdTsdGsdTsdTsdAsdGsdGsGbsGbsAbsGbsCb |
| 2064 | 16 | 209k | GbsTbsAbsGbsTbsdGsdTsdTsdAsdGsdGsGbsGbsAbsGbsCb |
| 2072 | 16 | 210b | GbsCbsdTsdAsdTsdTsdTsdGsdGsdTsdAsdGsdTsGbsTbsTb |
| 2072 | 16 | 210c | GbsCbsTbsdAsdTsdTsdTsdGsdGsdTsdAsdGsdTsdGsTbsTb |
| 2072 | 16 | 210d | GbsCbsTbsdAsdTsdTsdTsdGsdGsdTsdAsdGsdTsGbsTbsTb |
| 2072 | 16 | 210e | GbsCbsTbsAbsdTsdTsdTsdGsdGsdTsdAsdGsdTsGbsTbsTb |
| 2072 | 16 | 210f | GbsCbsTbsdAsdTsdTsdTsdGsdGsdTsdAsdGsTbsGbsTbsTb |

TABLE 2-continued

| SP | L | Seq ID No. | Sequence, 5'-3' |
|---|---|---|---|
| 2072 | 16 | 210g | GbsCbsTbsAbsdTsdTsdTsdGsdGsdTsdAsdGsTbsGbsTbsTb |
| 2284 | 15 | 211b | AbsGbsCbsdTsdTsdAsdTsdCsdCsdTsdAsdTsGbsAbsCb |
| 2284 | 15 | 211c | AbsGbsCbsdTsdTsdAsdTsdCsdCsdTsdAsTbsGbsAbsCb |
| 2284 | 15 | 211d | AbsGbsCbsTbsdTsdAsdTsdCsdCsdTsdAsdTsGbsAbsCb |
| 2285 | 14 | 212b | AbsGbCsdCsdTsdTsdAsdTsdCsdCsdTsdAsTbsGbsAb |
| 2285 | 14 | 212c | AbsGbsCbsdTsdTsdAsdTsdCsdCsdTsdAsdTsGbsAb |
| 2285 | 14 | 212d | AbsGbsCbsdTsdTsdAsdTsdCsdCsdTsdAsTbsGbsAb |
| 2355 | 17 | 213b | CbsAbsGbsdGsdCsdAsdTsdTsdAsdAsdTsdAsdAsdAsGbsTbsGb |
| 2355 | 17 | 213c | CbsAbsGbsGbdCsdAsdTsdTsdAsdAsdTsdAsdAsdAsGbsTbsGb |
| 2355 | 17 | 213d | CbsAbsGbsdGsdCsdAsdTsdTsdAsdAsdTsdAsdAsdAsAbsGbsTbsGb |
| 2355 | 17 | 213e | CbsAbsGbsGbdCsdAsdTsdTsdAsdAsdTsdAsdAsdAsAbsGbsTbsGb |
| 4217 | 16 | 218d | CbsAbsTbsdGsdAsdAsdTsdGsdGsdAsdCsdCsdAsGbsTbsAb |
| 4217 | 16 | 218e | CbsAbsTbsdGsdAsdAsdTsdGsdGsdAsdCsdCsAbsGbsTbsAb |
| 4217 | 16 | 218f | CbsAbsTbsGbsdAsdAsdTsdGsdGsdAsdCsdCsdAsGbsTbsAb |
| 4217 | 16 | 218g | CbsAbsTbsGbsdAsdAsdTsdGsdGsdAsdCsdCsAbsGbsTbsAb |
| 4120 | 16 | 214 | CbsTbsAbsdGsdGsdCsdGsdCsdCsdTsdCsdTsdAsTbsGbsCb |
| 4121 | 14 | 215b | TbsAbsGbsdGsdCsdGsdCsdCsdTsdCsdTsAbsTbsGb |
| 4121 | 15 | 216b | CbsTbsAbsdGsdGsdCsdGsdCsdCsdTsdCsdTsAbsTbsGb |
| 4122 | 13 | 217b | TbsAbsGbsdGsdCsdGsdCsdCsdTsdCsdTsAbsTb |

TABLE 3

| SP | L | Seq ID No. | Sequence, 5'-3' |
|---|---|---|---|
| 2064 | 16 | 209m | GbsTbsAbsGbsdTsdGsdTsdTsdTsdAsdGsdGsdGs**AbsGbsC*b** |
| 2064 | 16 | 209n | GbsTbsAbsdGsdTsdGsdTsdTsdTsdAsdGsdGsdGs**AbsGbsC*b** |
| 2064 | 16 | 209o | GbsTbsAbsdGsdTsdGsdTsdTsdTsdAsdGsdGsdGsdAs**GbsC*b** |
| 2064 | 16 | 209p | GbsTbsAbsdGsdTsdGsdTsdTsdTsdAsdGsdGs**GbsAbsGbsC*b** |
| 2064 | 16 | 209q | GbsTbsAbsGbsdTsdGsdTsdTsdTsdAsdGsdGs**GbsAbsGbsC*b** |
| 2064 | 16 | 209r | GbsTbsdAsdGsdTsdGsdTsdTsdTsdAsdGsdGsdGs**AbsGbsC*b** |
| 429 | 15 | 152e | **C*bsGbsAbsTb**sdAsdC*sdGsdC*sdGsdTsdC*sdC*s**AbsC*bsAb** |
| 4217 | 16 | -218j | **C*bsAbsTb**sdGsdAsdAsdTsdGsdGsdAsdC*sdC*sAbsGbsTbsAb |
| 2355 | 17 | 213f | **C*bsAbsGb**sdGsdC*sdAsdTsdTsdAsdAsdTsdAsdAsAbsGbsTbsGb |
| 2355 | 17 | 213g | **C*bsAbsGbsGb**sdC*sdAsdTsdTsdAsdAsdTsdAsdAsdAsGbsTbsGb |
| 432 | 12 | 155e | **C*bsGb**sdAsdTsdAsdC*sdGsdC*sdGsdTsC*bsC*b |
| 4217 | 16 | 218h | **C*bsAbsTbsGb**sdAsdAsdTsdGsdGsdAsdC*sdC*sAbsGbsTbsAb |
| 2072 | 16 | 210h | **GbsC*bsTbsAbsdTsdTsdTsdGsdGsdTsdAsdGsTbsGbsTbsTb** |
| 2072 | 16 | 210i | **GbsC*bsdTsdAsdTsdTsdTsdGsdGsdTsdAsdGsTbsGbsTbsTb** |
| 432 | 12 | 155f | **C*bsGb**sdAsdTsdAsdC*sdGsdC*sdGsdTsdC*sC*b |
| 2072 | 16 | 210j | **GbsC*bsTbsdAsdTsdTsdTsdGsdGsdTsdAsdGsdTsdGsTbsTb** |
| 432 | 12 | 155g | **C*b**sdGsdAsdTsdAsdC*sdGsdC*sdGsdTsC*bsC*b |

TABLE 3-continued

| SP | L | Seq ID No. | Sequence, 5'-3' |
|---|---|---|---|
| 431 | 13 | 153d | C*bsGbsAbsdTsdAsdC*sdGsdC*sdGsdTsdC*sC*bsAb |
| 429 | 15 | 152f | C*bsGbsAbsdTsdAsdC*sdGsdC*sdGsdTsdC*sdC*sAbsC*bsAb |
| 4217 | 16 | 218i | C*bsAbsTbsGbsdAsdAsdTsdGsdGsdAsdC*sdC*sdAsGbsTbsAb |
| 1393 | 16 | 199f | GbsAbsTbsdGsdAsdC*sdAsdTsdGsdC*sdC*sdGsdC*sGbsTbsC*b |
| 2285 | 14 | 212e | AbsGbsC*bsdTsdTsdAsdTsdC*sdC*sdTsdAsdTsGbsAb |
| 355 | 14 | 143e | C*bsTbsdC*sdGsdTsdC*sdAsdTsdAsdGsdAsC*bsC*bsGb |
| 2072 | 16 | 210k | GbsC*bsTbsdAsdTsdTsdTsdGsdGsdTsdAsdGsdTsGbsTbsTb |
| 1393 | 16 | 199g | GbsAbsTbsdGsdAsdC*sdAsdTsdGsdC*sdC*sdGsC*bsGbsTbsC*b |
| 2355 | 17 | 213h | C*bsAbsGbsGbsdC*sdAsdTsdTsdAsdAsdTsdAsdAsAbsGbsTbsGb |
| 429 | 15 | 152g | C*bsGbsAbsdTsdAsdC*sdGsdC*sdGsdTsdC*sC*bsAbsC*bsAb |
| 2285 | 14 | 212f | AbsGbsC*bsdTsdTsdTsdAsdTsdC*sdC*sdTsdAsTbsGbsAb |
| 355 | 14 | 143f | C*bsTbsC*bsdGsdTsdC*sdAsdTsdAsdGsdAsC*bsC*bsGb |
| 1393 | 16 | 199h | GbsAbsTbsGbsdAsdC*sdAsdTsdGsdC*sdC*sdGsC*bsGbsTbsC*b |
| 1393 | 16 | 199i | GbsAbsTbsGbsdAsdC*sdAsdTsdGsdC*sdC*sdGsdC*sGbsTbsC*b |
| 4217 | 16 | 218k | C*bsAbsTbsdGsdAsdAsdTsdGsdGsdGsdAsdC*sdC*sdAsGbsTbsAb |
| 2285 | 14 | 212g | AbsGbsdC*sdTsdTsdAsdTsdC*sdC*sdTsdAsTbsGbsAb |
| 434 | 13 | 162d | TbsGbsGbsdC*sdGsdAsdTsdAsdC*sdGsdC*sGbsTb |
| 383 | 14 | 148e | AbsGbsC*bsdC*sdC*sdC*sdC*sdGsdAsdC*sdC*sdC*sAbsTb |
| 431 | 13 | 153e | C*bsGbsdAsdTsdAsdC*sdGsdC*sdGsdTsC*bsC*bsAb |
| 2284 | 15 | 211e | AbsGbsC*bsdTsdAsdTsdC*sdC*sdTsdAsdTsGbsAbsC*b |
| 355 | 14 | 143g | C*bsTbsC*bsdGsdTsdC*sdAsdTsdAsdGsdAsdC*sC*bsGb |
| 2284 | 15 | 211f | AbsGbsC*bsdTsdTsdAsdTsdC*sdC*sdTsdAsTbsGbsAbsC*b |
| 383 | 14 | 148f | AbsGbsC*bsdC*sdC*sdC*sdC*sdGsdAsdC*sdC*sC*bsAbsTb |
| 383 | 14 | 148g | AbsGbsdC*sdC*sdC*sdC*sdGsdAsdC*sdC*sC*bsAbsTb |
| 382 | 16 | 147g | C*bsAbsGbsdC*sdC*sdC*sdC*sdC*sdGsdAsdC*sdC*sdC*sAbsTbsGb |
| 2072 | 16 | 210m | GbsC*bsTbsdAsdTsdTsdTsdGsdGsdTsdAsdGsTbsGbsTbsTb |
| 2072 | 16 | 210n | GbsC*bsTbsAbsdTsdTsdTsdGsdGsdTsdAsdGsTbsGbsTbsTb |
| 434 | 13 | 162e | TbsGbsdGsdC*sdGsdAsdTsdAsdC*sdGsC*bsGbsTb |
| 2284 | 15 | 211g | AbsGbsC*bsTbsdTsdAsdTsdC*sdC*sdTsdAsdTsGbsAbsC*b |
| 382 | 16 | 147h | C*bsAbsGbsdC*sdC*sdC*sdC*sdC*sdGsdAsdC*sdC*sdC*sC*bsAbsTbsGb |
| 382 | 16 | 147i | C*bsAbsGbsC*bsdC*sdC*sdC*sdC*sdGsdAsdC*sdC*sdC*sAbsTbsGb |
| 382 | 16 | 147j | C*bsAbsGbsdC*sdC*sdC*sdC*sdC*sdGsdAsdC*sdC*sdC*sAbsTbsGb |
| 2355 | 17 | 213i | C*bsAbsGbsGbsdC*sdAsdTsdTsdAsdAsdTsdAsdAsGbsTbsGb |
| 382 | 16 | 147k | C*bsAbsGbsC*bsdC*sdC*sdC*sdC*sdGsdAsdC*sdC*sC*bsAbsTbsGb |

Preferred Antisense-Oligonucleotides

In the following preferred antisense-oligonucleotides of the present invention are disclosed.

Thus, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the anti sense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^1$-GTCATAGA-N$^2$-3' (Seq. ID No. 12) or 5'-N$^3$-ACGCGTCC-N$^4$-3' (Seq. ID No. 98) or 5'-N$^{11}$-TGTT-TAGG-N$^{12}$-3' (Seq. ID No. 10) or 5'-N$^5$-TTTGGTAG-N$^6$-3' (Seq. ID No. 11) or 5'-N$^7$-AATGGACC-N$^8$-3' (Seq. ID No. 100) or 5'-N$^9$-ATTAATAA-N$^{10}$-3' (Seq. ID No. 101), wherein N$^1$ represents: CATGGCAGACCCCGCTGCTC-, ATGGCAGACCCCGCTGCTC-, TGGCAGACCCCGCTGCTC-, GGCAGACCCCGCTGCTC-, GCAGACCCCGCTGCTC-, CAGACCCCGCTGCTC-, AGACCCCGCTGCTC-, GACCCCGCTGCTC-, ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-;

N$^2$ represents: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCCCAG, -CCGAGCCCCAGC, -CCGAGCCCCAGCG, -CCGAGCCCCAGCGC, -CCGAGCCCCAGCGCA, -CCGAGCCCCAGCGCAG, -CCGAGCCCCAGCGCAGC, -CCGAGCCCCAGCGCAGCG, or -CCGAGCCCCAGCGCAGCGG;

N$^3$ represents: GGTGGGATCGTGCTGGCGAT-, GTGGGATCGTGCTGGCGAT-, TGGGATCGTGCTGGCGAT-, GGGATCGTGCTGGCGAT-, GGATCGTGCTGGCGAT-, GATCGTGCTGGCGAT-, ATCGTGCTGGCGAT-, TCGTGCTGGCGAT-, CGTGCTGGCGAT-, GTGCTGGCGAT-, TGCTGGCGAT-, GCTGGCGAT-, CTGGCGAT-, TGGCGAT-, GGCGAT-, GCGAT-, CGAT-, GAT-, AT-, or T-;

N$^4$ represents: -ACAGGACGATGTGCAGCGGC, -ACAGGACGATGTGCAGCGG, -ACAGGACGATGTGCAGCG, -ACAGGACGATGTGCAGC, -ACAGGACGATGTGCAG, -ACAGGACGATGTGCA, -ACAGGACGATGTGC, -ACAGGACGATGTG, -ACAGGACGATGT, -ACAGGACGATG, -ACAGGACGAT, -ACAGGACGA, -ACAGGACG, -ACAGGAC, -ACAGGA, -ACAGG, -ACAG, -ACA, -AC, or -A;

N$^5$ represents: GCCCAGCCTGCCCCAGAAGAGCTA-, CCCAGCCTGCCCCAGAAGAGCTA-, CCAGCCTGCCCCAGAAGAGCTA-, CAGCCTGCCCCAGAAGAGCTA-, AGCCTGCCCCAGAAGAGCTA-, GCCTGCCCCAGAAGAGCTA-, CCTGCCCCAGAAGAGCTA-, CTGCCCCAGAAGAGCTA-, TGCCCCAGAAGAGCTA-, GCCCCAGAAGAGCTA-, CCCCAGAAGAGCTA-, CCCAGAAGAGCTA-, CCAGAAGAGCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-;

N$^6$ represents: -TGTTTAGGGAGCCGTCTTCAGGAA, -TGTTTAGGGAGCCGTCTTCAGGA, -TGTTTAGGGAGCCGTCTTCAGG, -TGTTTAGGGAGCCGTCTTCAG, -TGTTTAGGGAGCCGTCTTCA, -TGTTTAGGGAGCCGTCTTC, -TGTTTAGGGAGCCGTCTT, -TGTTTAGGGAGCCGTCT, -TGTTTAGGGAGCCGTC, -TGTTTAGGGAGCCGT, -TGTTTAGGGAGCCG, -TGTTTAGGGAGCC, -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T;

N$^7$ represents: TGAATCTTGAATATCTCATG-, GAATCTTGAATATCTCATG-, AATCTTGAATATCTCATG-, ATCTTGAATATCTCATG-, TCTTGAATATCTCATG-, CTTGAATATCTCATG-, TTGAATATCTCATG-, TGAATATCTCATG-, GAATATCTCATG-, AATATCTCATG-, ATATCTCATG-, TATCTCATG-, ATCTCATG-, TCTCATG-, CTCATG-, TCATG-, CATG-, ATG-, TG-, or G-;

N$^8$ represents: -AGTATTCTAGAAACTCACCA, -AGTATTCTAGAAACTCACC, -AGTATTCTAGAAACTCAC, -AGTATTCTAGAAACTCA, -AGTATTCTAGAAACTC, -AGTATTCTAGAAACT, -AGTATTCTAGAAAC, -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A;

N$^9$ represents: ATTCATATTTATATACAGGC-, TTCATATTTATATACAGGC-, TCATATTTATATACAGGC-, CATATTTATATACAGGC-, ATATTTATATACAGGC-, TATTTATATACAGGC-, ATTTATATACAGGC-, TTTATATACAGGC-, TTATATACAGGC-, TATATACAGGC-, ATATACAGGC-, TATACAGGC-, ATACAGGC-, TACAGGC-, ACAGGC-, CAGGC-, AGGC-, GGC-, GC-, or C-;

N$^{10}$ represents: -AGTGCAAATGTTATTGGCTA, -AGTGCAAATGTTATTGGCT, -AGTGCAAATGTTATTGGC, -AGTGCAAATGTTATTGG, -AGTGCAAATGTTATTG, -AGTGCAAATGTTATT, -AGTGCAAATGTTAT, -AGTGCAAATGTTA, -AGTGCAAATGTT, -AGTGCAAATGT, -AGTGCAAATG, -AGTGCAAAT, -AGTGCAAA, -AGTGCAA, -AGTGCA, -AGTGC, -AGTG, -AGT, -AG, or -A;

N$^{11}$ represents: TGCCCCAGAAGAGCTATTTGGTAG-, GCCCCAGAAGAGCTATTTGGTAG-, CCCCAGAAGAGCTATTTGGTAG-, CCCAGAAGAGCTATTTGGTAG-, CCAGAAGAGCTATTTGGTAG-, CAGAAGAGCTATTTGGTAG-, AGAAGAGCTATTTGGTAG-, GAAGAGCTATTTGGTAG-, AAGAGCTATTTGGTAG-, AGAGCTATTTGGTAG-, GAGCTATTTGGTAG-, AGCTATTTGGTAG-, GCTATTTGGTAG-, CTATTTGGTAG-, TATTTGGTAG-, ATTTGGTAG-, TTTGGTAG-, TTGGTAG-, TGGTAG-, GGTAG-, GTAG-, TAG-, AG- or G-, N$^{12}$ represents: -GAGCCGTCTTCAGGAATCTTCTCC, -GAGCCGTCTTCAGGAATCTTCTC, -GAGCCGTCTTCAGGAATCTTCT, -GAGCCGTCTTCAGGAATCTTC, -GAGCCGTCTTCAGGAATCTT, -GAGCCGTCTTCAGGAATCT, -GAGCCGTCTTCAGGAATC, -GAGCCGTCTTCAGGAAT, -GAGCCGTCTTCAGGAA, -GAGCCGTCTTCAGGA, -GAGCCGTCTTCAGG, -GAGCCGTCTTCAG, -GAGCCGTCTTCA, -GAGCCGTCTTC, -GAGCCGTCTT, -GAGCCGTCT, -GAGCCGTC, -GAGCCGT, -GAGCCG, -GAGCC, -GAGC, -GAG, -GA, or -G;

or wherein N$^1$ to N$^{12}$ represent any of the limited lists of residues as disclosed herein, and salts and optical isomers of the antisense-oligonucleotide.

Moreover, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^1$-GTCATAGA-N$^2$-3' (Seq. ID No. 12), wherein N$^1$ represents: GGCAGACCCCGCTGCTC-, GCAGACCCCGCTGCTC-, CAGACCCCGCTGCTC-, AGACCCCGCTGCTC-, GACCCCGCTGCTC-, ACCCC-GCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-;

$N^2$ represents: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCC-CAG, -CCGAGCCCCAGC, -CCGAGCCCCAGCG, -CCGAGCCCCAGCGC, -CCGAGCCCCAGCGCA, or —CCGAGCCCCAGCGCAG;

and salts and optical isomers of the antisense-oligonucleotide.

$N^1$ and/or $N^2$ may also represent any of the further limited lists of 3' and 5' residues as disclosed herein.

Especially preferred gapmer antisense-oligonucleotides falling under general formula S1:

5'-$N^1$-GTCATAGA-$N^2$-3' S1 (Seq. ID No. 12)

are the following:

CCGCTGCTCGTCATAGAC (Seq. ID No. 19)

CGCTGCTCGTCATAGACC (Seq. ID No. 20)

GCTGCTCGTCATAGACCG (Seq. ID No. 21)

CTGCTCGTCATAGACCGA (Seq. ID No. 22)

TGCTCGTCATAGACCGAG (Seq. ID No. 23)

GCTCGTCATAGACCGAGC (Seq. ID No. 24)

CTCGTCATAGACCGAGCC (Seq. ID No. 25)

TCGTCATAGACCGAGCCC (Seq. ID No. 26)

CGTCATAGACCGAGCCCC (Seq. ID No. 27)

CGCTGCTCGTCATAGAC (Seq. ID No. 28)

GCTGCTCGTCATAGACC (Seq. ID No. 29)

CTGCTCGTCATAGACCG (Seq. ID No. 30)

TGCTCGTCATAGACCGA (Seq. ID No. 31)

GCTCGTCATAGACCGAG (Seq. ID No. 32)

CTCGTCATAGACCGAGC (Seq. ID No. 33)

TCGTCATAGACCGAGCC (Seq. ID No. 34)

CGTCATAGACCGAGCCC (Seq. ID No. 35)

GCTGCTCGTCATAGAC (Seq. ID No. 36)

CTGCTCGTCATAGACC (Seq. ID No. 37)

TGCTCGTCATAGACCG (Seq. ID No. 38)

GCTCGTCATAGACCGA (Seq. ID No. 39)

CTCGTCATAGACCGAG (Seq. ID No. 40)

TCGTCATAGACCGAGC (Seq. ID No. 41)

CGTCATAGACCGAGCC (Seq. ID No. 42)

CTGCTCGTCATAGAC (Seq. ID No. 43)

TGCTCGTCATAGACC (Seq. ID No. 44)

GCTCGTCATAGACCG (Seq. ID No. 45)

CTCGTCATAGACCGA (Seq. ID No. 46)

TCGTCATAGACCGAG (Seq. ID No. 47)

CGTCATAGACCGAGC (Seq. ID No. 48)

TGCTCGTCATAGAC (Seq. ID No. 49)

GCTCGTCATAGACC (Seq. ID No. 50)

CTCGTCATAGACCG (Seq. ID No. 51)

TCGTCATAGACCGA (Seq. ID No. 52)

CGTCATAGACCGAG (Seq. ID No. 53)

The antisense-oligonucleotides of formula S1 in form of gapmers (LNA segment 1-DNA segment—LNA segment 2) contain an LNA segment at the 5' terminal end consisting of 2 to 5, preferably 2 to 4 LNA units and contain an LNA segment at the 3' terminal end consisting of 2 to 5, preferably 2 to 4 LNA units and between the two LNA segments one DNA segment consisting of 6 to 14, preferably 7 to 12 and more preferably 8 to 11 DNA units.

The antisense-oligonucleotides of formula S1 contain the LNA nucleotides (LNA units) as disclosed herein, especially these disclosed in the chapter "Locked Nucleic Acids (LNA®)" and preferably these disclosed in the chapter "Preferred LNAs". The LNA units and the DNA units may comprise standard nucleobases such as adenine (A), cytosine (C), guanine (G), thymine (T) and uracil (U), but may also contain modified nucleobases as disclosed in the chapter "Nucleobases". The antisense-oligonucleotides of formula S1 or the LNA segments and the DNA segment of the antisense-oligonucleotide may contain any internucleotide linkage as disclosed herein and especially these disclosed in the chapter "Internucleotide Linkages (IL)". The antisense-oligonucleotides of formula S1 may optionally also contain endgroups at the 3' terminal end and/or the 5' terminal end and especially these disclosed in the chapter "Terminal groups".

Experiments have shown that modified nucleobases do not considerably increase or change the activity of the inventive antisense-oligonucleotides in regard to tested neurological and oncological indications. The modified nucleobases 5-methylcytosine or 2-aminoadenine have been demonstrated to further increase the activity of the antisense-oligonucleotides of formula S1 especially if 5-methylcytosine is used in the LNA nucleotides only or in the LNA nucleotides and in the DNA nucleotides and/or if 2-aminoadenine is used in the DNA nucleotides and not in the LNA nucleotides.

The preferred gapmer structure of the antisense-oligonucleotides of formula S1 is as follows: 3-8-3, 4-8-2, 2-8-4, 3-8-4, 4-8-3, 4-8-4, 3-9-3, 4-9-2, 2-9-4, 4-9-3, 3-9-4, 4-9-4, 3-10-3, 2-10-4, 4-10-2, 3-10-4, 4-10-3, 4-10-4, 2-11-4, 4-11-2, 3-11-4, 4-11-3 and still more preferred: 3-8-3, 3-8-4, 4-8-3, 4-8-4, 3-9-3, 4-9-3, 3-9-4, 4-9-4, 3-10-3, 3-10-4, 4-10-3, 4-10-4, 3-11-4, and 4-11-3.

As LNA units for the antisense-oligonucleotides of formula S1 especially β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-($NCH_3$)-LNA ($b^7$), β-D-(ONH)-LNA ($b^8$) and β-D-($ONCH_3$)-LNA ($b^9$) are preferred. Experiments have been shown that all of these LNA units $b^1$, $b^2$, $b^4$, $b^5$, $b^6$, $b^7$, $b^8$, and $b^9$ can be synthesized with the required effort and lead to antisense-oligonucleotides of comparable stability and activity. However based on the experiments the LNA units $b^1$, $b^2$, $b^4$, $b^5$, $b^6$, and $b^7$ are further preferred. Still further preferred are the LNA units $b^1$, $b^2$, $b^4$, $b^6$, and $b^7$, and even more preferred are the LNA units $b^1$ and $b^4$ and most preferred also in regard to the complexity of the chemical synthesis is the β-D-oxy-LNA ($b^1$).

So far no special 3' terminal group or 5' terminal group could be found which remarkably had changed or increased the stability or activity for oncological or neurological indications, so that 3' and 5' end groups are possible but not explicitly preferred.

Various internucleotide bridges or internucleotide linkages are possible. In the formulae disclosed herein the internucleotide linkage IL is represented by -IL'-Y-. Thus, IL=-IL'-Y—=—X"—P(=$X^-$)($X^-$)—Y—, wherein IL is preferably selected form the group consisting of:
—O—P(O)($O^-$)—O—, —O—P(O)($S^-$)—O—, —O—P(S)($S^-$)—O—, —S—P(O)($O^-$)—O—, —S—P(O)($S^-$)—O—, —O—P(O)($O^-$)—S—, —O—P(O)($S^-$)—S—, —S—P(O)($O^-$)—S—, —O—P(O)($CH_3$)—O—, —O—P(O)($OCH_3$)—O—, —O—P(O)($NH(CH_3)$)—O—, —O—P(O)[$N(CH_3)_2$]—O—, —O—P(O)($BH_3^-$)—O—, —O—P(O)($OCH_2CH_2OCH_3$)—O—, —O—P(O)($OCH_2CH_2SCH_3$)—O—, —O—P(O)($O^-$)—N($CH_3$)—, —N($CH_3$)—P(O)($O^-$)—O—.

Preferred are the internucleotide linkages IL selected from —O—P(O)($O^-$)—O—, —O—P(O)($S^-$)—O—, —O—P(S)($S^-$)—O—, —S—P(O)($O^-$)—O—, —S—P(O)($S^-$)—O—, —O—P(O)($O^-$)—S—, —O—P(O)($S^-$)—S—, —S—P(O)($O^-$)—S—, —O—P(O)($CH_3$)—O—, —O—P(O)(NH($CH_3$))—O—, —O—P(O)[$N(CH_3)_2$]—O—, —O—P(O)($OCH_2CH_2OCH_3$)—O—, and more preferred selected from —O—P(O)($O^-$)—O—, —O—P(O)($S^-$)—O—, —O—P(S)($S^-$)—O—, —S—P(O)($O^-$)—O—, —S—P(O)($S^-$)—O—, —O—P(O)($O^-$)—S—, —O—P(O)($S^-$)—S—, —S—P(O)($O^-$)—S—, and still more preferred selected from —O—P(O)($O^-$)—O—, —O—P(O)($S^-$)—O—, —O—P(S)($S^-$)—O—, and most preferably selected from —O—P(O)($O^-$)—O— and —O—P(O)($S^-$)—O—.

Thus, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^1$-GTCATAGA-$N^2$-3' (Seq. ID No. 12), wherein $N^1$ represents: GGCAGACCCCGCTGCTC-, GCAGACCCCGCTGCTC-, CAGACCCCGCTGCTC-, AGACCCCGCTGCTC-, GACCCCGCTGCTC-, ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-;

$N^2$ represents: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCCCAG, -CCGAGCCCCAGC, -CCGAGCCCCAGCG, -CCGAGCCCCAGCGC, -CCGAGCCCCAGCGCA, or —CCGAGCCCCAGCGCAG; and the LNA nucleotides are selected from β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-($NCH_3$)-LNA ($b^7$), β-D-(ONH)-LNA ($b^8$) and β-D-($ONCH_3$)-LNA ($b^9$); and preferably from β-D-oxy-LNA ($b^1$), β-D-thio-LNA ($b^2$), α-L-oxy-LNA ($b^4$), β-D-(NH)-LNA ($b^6$), and β-D-($NCH_3$)-LNA ($b^7$); and the internucleotide linkages are selected from
—O—P(O)($O^-$)—O—, —O—P(O)($S^-$)—O—, —O—P(S)($S^-$)—O—, —S—P(O)($O^-$)—O—, —S—P(O)($S^-$)—O—, —O—P(O)($O^-$)—S—, —O—P(O)($S^-$)—S—, —S—P(O)($O^-$)—S—, —O—P(O)($CH_3$)—O—, —O—P(O)($OCH_3$)—O—, —O—P(O)(NH($CH_3$))—O—, —O—P(O)[$N(CH_3)_2$]—O—, —O—P(O)($BH_3^-$)—O—, —O—P(O)($OCH_2CH_2OCH_3$)—O—, —O—P(O)($OCH_2CH_2SCH_3$)—O—, —O—P(O)($O^-$)—N($CH_3$)—, —N($CH_3$)—P(O)($O^-$)—O-; and preferably from —O—P(O)($O^-$)—O—, —O—P(O)($S^-$)—O—, —O—P(S)($S^-$)—O—, —S—P(O)($O^-$)—O—, —S—P(O)($S^-$)—O—, —O—P(O)($O^-$)—S—, —O—P(O)($S^-$)—S—, —S—P(O)($O^-$)—S—;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

More preferably $N^1$ represents: CAGACCCCGCTGCTC-, AGACCCCGCTGCTC-, GACCCCGCTGCTC-, ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-; and $N^2$ represents: -C, -CC, -CCG, -CCGA, -CCGAG, -CCGAGC, -CCGAGCC, -CCGAGCCC, -CCGAGCCCC, -CCGAGCCCCC, -CCGAGCCCCCA, -CCGAGCCCCAG, -CCGAGCCCCCAGC, -CCGAGC-CCCCAGCG, or -CCGAGCCCCCAGCGC.

Still further preferred, the present invention is directed to an antisense-oligonucleotide in form of a gapmer consisting of 11 to 24 nucleotides, more preferably 12 to 20, and still more preferably 13 to 19 or 14 to 18 nucleotides and 2 to 5 of these nucleotides at the 5' terminal end and 2 to 5 nucleotides at the 3' terminal end of the antisense-oligonucleotide are LNA nucleotides and between the LNA nucleotides at the 5' terminal end and the 3' terminal end a sequence of at least 7, preferably at least 8 DNA nucleotides is present, and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^1$-GTCATAGA-$N^2$-3' (Seq. ID No. 12), wherein $N^1$ represents: ACCCCGCTGCTC-, CCCCGCTGCTC-, CCCGCTGCTC-, CCGCTGCTC-, CGCTGCTC-, GCTGCTC-, CTGCTC-, TGCTC-, GCTC-, CTC-, TC-, or C-; preferably $N^1$ represents: CCCGCTGCTC-, CCGCTGCTC-, CGCTGCTC-, GCTGCTC-, CTGCTC-, TGCTC-, GCTC-, CTC-, TC-, or C-; and $N^2$ represents: -C, -CC, -CCG, -CCGA, -CCGAG, -CCGAGC, -CCGAGCC, -CCGAGCCC, -CCGAGCCCC, or —CCGAGCCCCC, -CCGAGCCCCCA, or -CCGAGCCCCCAG; preferably $N^2$ represents: -C, -CC, -CCG, -CCGA, -CCGAG, -CCGAGC, -CCGAGCC, -CCGAGCCC, -CCGAGCCCC, or —CCGAGCCCCC;

and the LNA nucleotides are selected from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$); and the internucleotide linkages are selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—; and preferably selected from phosphate, phosphorothioate and phosphorodithioate;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

Especially preferred are the gapmer antisense-oligonucleotides of Seq. ID No. 19 to Seq. ID No. 53 containing a segment of 2 to 5, preferably 2 to 4 and more preferably 3 to 4 LNA units at the 3' terminus and a segment of 2 to 5, preferably 2 to 4 and more preferably 3 to 4 LNA units at the 5' terminus and a segment of at least 6, preferably 7 and more preferably 8 DNA units between the two segments of LNA units, wherein the LNA units are selected from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$) and the internucleotide linkages are selected from phosphate, phosphorothioate and phosphorodithioate. Such preferred antisense-oligonucleotides may not contain any modified 3' and 5' terminal end or may not contain any 3' and 5' terminal group and may as modified nucleobase contain 5-methylcytosine in the LNA units, preferably all the LNA units and/or 2-aminoadenine in some or all DNA units and/or 5-methylcytosine in some or all DNA units.

Also especially preferred are the gapmer antisense-oligonucleotides of Table 4 (Seq. ID No. 232a to 244b).

Moreover, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^3$-ACGCGTCC-$N^4$-3' (Seq. ID No. 98), wherein $N^3$ represents: GGGATCGTGCTGGCGAT-, GGATCGTGCTGGCGAT-, GATCGTGCTGGCGAT-, ATCGTGCTGGCGAT-, TCGTGCTGGCGAT-, CGTGCTGGCGAT-, GTGCTGGCGAT-, TGCTGGCGAT-, GCTGGCGAT-, CTGGCGAT-, TGGCGAT-, GGCGAT-, GCGAT-, CGAT-, GAT-, AT-, or T-;

$N_4$ represents: -ACAGGACGATGTGCAGC, -ACAGGACGATGTGCAG, -ACAGGACGATGTGCA, -ACAGGACGATGTGC, -ACAGGACGATGTG, -ACAGGACGATGT, -ACAGGACGATG, -ACAGGAC-GAT, -ACAGGACGA, -ACAGGACG, -ACAGGAC, -ACAGGA, -ACAGG, -ACAG, -ACA, -AC, or -A;

and salts and optical isomers of the antisense-oligonucleotide.

$N^3$ and/or $N_4$ may also represent any of the further limited lists of 3' and 5' residues as disclosed herein.

Especially preferred gapmer antisense-oligonucleotides falling under general formula S2:

(Seq. ID No. 98)
5'-$N^3$-ACGCGTCC-$N^4$-3' S2 are the following:

(Seq. ID No. 54)
GCTGGCGATACGCGTCCA

(Seq. ID No. 55)
CTGGCGATACGCGTCCAC (Seq. ID No. 56)
TGGCGATACGCGTCCACA (Seq. ID No. 57)
GGCGATACGCGTCCACAG (Seq. ID No. 58)
GCGATACGCGTCCACAGG (Seq. ID No. 59)
CGATACGCGTCCACAGGA (Seq. ID No. 60)
GATACGCGTCCACAGGAC (Seq. ID No. 61)
ATACGCGTCCACAGGACG (Seq. ID No. 62)
TACGCGTCCACAGGACGA (Seq. ID No. 63)
CTGGCGATACGCGTCCA

(Seq. ID No. 64)
TGGCGATACGCGTCCAC (Seq. ID No. 65)
GGCGATACGCGTCCACA

-continued

GCGATACGCGTCCACAG (Seq. ID No. 66)

CGATACGCGTCCACAGG (Seq. ID No. 67)

GATACGCGTCCACAGGA (Seq. ID No. 68)

ATACGCGTCCACAGGAC (Seq. ID No. 349)

TACGCGTCCACAGGACG (Seq. ID No. 350)

TGGCGATACGCGTCCA (Seq. ID No. 351)

GGCGATACGCGTCCAC (Seq. ID No. 352)

GCGATACGCGTCCACA (Seq. ID No. 353)

CGATACGCGTCCACAG (Seq. ID No. 354)

GATACGCGTCCACAGG (Seq. ID No. 355)

ATACGCGTCCACAGGA (Seq. ID No. 356)

TACGCGTCCACAGGAC (Seq. ID No. 357)

GGCGATACGCGTCCA (Seq. ID No. 358)

GCGATACGCGTCCAC (Seq. ID No. 359)

CGATACGCGTCCACA (Seq. ID No. 360)

GATACGCGTCCACAG (Seq. ID No. 361)

ATACGCGTCCACAGG (Seq. ID No. 362)

TACGCGTCCACAGGA (Seq. ID No. 363)

GCGATACGCGTCCA (Seq. ID No. 364)

CGATACGCGTCCAC (Seq. ID No. 365)

GATACGCGTCCACA (Seq. ID No. 366)

ATACGCGTCCACAG (Seq. ID No. 367)

TACGCGTCCACAGG (Seq. ID No. 368)

The antisense-oligonucleotides of formula S2 in form of gapmers (LNA segment 1-DNA segment—LNA segment 2) contain an LNA segment at the 5' terminal end consisting of 2 to 5, preferably 2 to 4 LNA units and contain an LNA segment at the 3' terminal end consisting of 2 to 5, preferably 2 to 4 LNA units and between the two LNA segments one DNA segment consisting of 6 to 14, preferably 7 to 12 and more preferably 8 to 11 DNA units.

The antisense-oligonucleotides of formula S2 contain the LNA nucleotides (LNA units) as disclosed herein, especially these disclosed in the chapter "Locked Nucleic Acids (LNA®)" and preferably these disclosed in the chapter "Preferred LNAs". The LNA units and the DNA units may comprise standard nucleobases such as adenine (A), cytosine (C), guanine (G), thymine (T) and uracil (U), but may also contain modified nucleobases as disclosed in the chapter "Nucleobases". The antisense-oligonucleotides of formula S2 or the LNA segments and the DNA segment of the antisense-oligonucleotide may contain any internucleotide linkage as disclosed herein and especially these disclosed in the chapter "Internucleotide Linkages (IL)". The antisense-oligonucleotides of formula S2 may optionally also contain endgroups at the 3' terminal end and/or the 5' terminal end and especially these disclosed in the chapter "Terminal groups".

Experiments have shown that modified nucleobases do not considerably increase or change the activity of the inventive antisense-oligonucleotides in regard to tested neurological and oncological indications. The modified nucleobases 5-methylcytosine or 2-aminoadenine have been demonstrated to further increase the activity of the antisense-oligonucleotides of formula S2 especially if 5-methylcytosine is used in the LNA nucleotides only or in the LNA nucleotides and in the DNA nucleotides and/or if 2-aminoadenine is used in the DNA nucleotides and not in the LNA nucleotides.

The preferred gapmer structure of the antisense-oligonucleotides of formula S2 is as follows: 3-8-3, 4-8-2, 2-8-4, 3-8-4, 4-8-3, 4-8-4, 3-9-3, 4-9-2, 2-9-4, 4-9-3, 3-9-4, 4-9-4, 3-10-3, 2-10-4, 4-10-2, 3-10-4, 4-10-3, 4-10-4, 2-11-4, 4-11-2, 3-11-4, 4-11-3 and still more preferred: 3-8-3, 3-8-4, 4-8-3, 4-8-4, 3-9-3, 4-9-3, 3-9-4, 4-9-4, 3-10-3, 3-10-4, 4-10-3, 4-10-4, 3-11-4, and 4-11-3.

As LNA units for the antisense-oligonucleotides of formula S2 especially β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-(NCH$_3$)-LNA ($b^7$), β-D-(ONH)-LNA ($b^8$) and β-D-(ONCH$_3$)-LNA ($b^9$) are preferred. Experiments have been shown that all of these LNA units $b^1$, $b^2$, $b^4$, $b^5$, $b^6$, $b^7$, ba, and $b^9$ can be synthesized with the required effort and lead to antisense-oligonucleotides of comparable stability and activity. However based on the experiments the LNA units $b^1$, $b^2$, $b^4$, $b^5$, $b^6$, and $b^7$ are further preferred. Still further preferred are the LNA units $b^1$, $b^2$, $b^4$, $b^6$, and $b^7$, and even more preferred are the LNA units $b^1$ and $b^4$ and most preferred also in regard to the complexity of the chemical synthesis is the β-D-oxy-LNA ($b^1$).

So far no special 3' terminal group or 5' terminal group could be found which remarkably had changed or increased the stability or activity for oncological or neurological indications, so that 3' and 5' end groups are possible but not explicitly preferred.

Various internucleotide bridges or internucleotide linkages are possible. In the formulae disclosed herein the internucleotide linkage IL is represented by -IL'-Y-. Thus, IL=-IL'-Y—=—X"—P(=X$^-$)(X$^-$)—Y—, wherein IL is preferably selected form the group consisting of:
—O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O—. Preferred are the internucleotide linkages IL selected from —O—P(O)(O$^-$)—O—, —O—P(O)(S$^-$)—O—, —O—P(S)(S$^-$)—O—, —S—P(O)(O$^-$)—O—, —S—P(O)(S⁻)—O—, —O—P(O)(O⁻)—S—, —O—P(O)(S⁻)—S—, —S—P(O)(O⁻)—S—, —O—P(O)(OCH₃)—O—, —O—P(O)(NH(CH₃))—O—, —O—P(O)[N(CH₃)₂]—O—, —O—P(O)(OCH₂CH₂OCH₃)—O—, and more preferred selected from —O—P(O)(O⁻)—O—, —O—P(O)(S⁻)—O—, —O—P(S)(S⁻)—O—, —S—P(O)(O⁻)—O—, —S—P(O)(S⁻)—O—, —O—P(O)(O⁻)—S—, —O—P(O)(S⁻)—S—, —S—P(O)(O⁻)—S—, and still more preferred selected from —O—P(O)(O⁻)—O—, —O—P(O)(S⁻)—O—, —O—P(S)(S⁻)—O—, and most preferably selected from -O—P(O)(O⁻)—O— and -O—P(O)(S⁻)—O—.

Thus, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N³-ACGCGTCC-N⁴-3' (Seq. ID No. 98), wherein N³ represents: GGGATCGTGCTGGCGAT-, GGATCGTGCTGGCGAT-, GATCGTGCTGGCGAT-, ATCGTGCTGGCGAT-, TCGTGCTGGCGAT-, CGTGCTGGCGAT-, GTGCTGGCGAT-, TGCTGGCGAT-, GCTGGCGAT-, CTGGCGAT-, TGGCGAT-, GGCGAT-, GCGAT-, CGAT-, GAT-, AT-, or T-; and N⁴ represents: -ACAGGACGATGTGCAGC, -ACAGGACGATGTGCAG, -ACAGGACGATGTGCA, -ACAGGACGATGTGC, -ACAGGACGATGTG, -ACAGGACGATGT, -ACAGGACGATG, -ACAGGACGAT, -ACAGGACGA, -ACAGGACG, -ACAGGAC, -ACAGGA, -ACAGG, -ACAG, -ACA, -AC, or -A, and the LNA nucleotides are selected from -D-oxy-LNA (b¹), β-D-thio-LNA (b²), α-L-oxy-LNA (b⁴), β-D-ENA (b⁵), β-D-(NH)-LNA (b⁶), β-D-(NCH₃)-LNA (b⁷), β-D-(ONH)-LNA (b⁶) and β-D-(ONCH₃)-LNA (b⁹); and preferably from β-D-oxy-LNA (b¹), β-D-thio-LNA (b²), α-L-oxy-LNA (b⁴), β-D-(NH)-LNA (b⁶), and β-D-(NCH₃)-LNA (b⁷); and the internucleotide linkages are selected from
—O—P(O)(O⁻)—O—, —O—P(O)(S⁻)—O—, —O—P(S)(S⁻)—O—, —S—P(O)(O⁻)—O—, —S—P(O)(S⁻)—O—, —O—P(O)(O⁻)—S—, —O—P(O)(S⁻)—S—, —S—P(O)(O⁻)—S—, —O—P(O)(CH₃)—O—, —O—P(O)(OCH₃)—O—, —O—P(O)(NH(CH₃))—O—, —O—P(O)[N(CH₃)₂]—O—, —O—P(O)(BH₃⁻)—O—, —O—P(O)(OCH₂CH₂OCH₃)—O—, —O—P(O)(OCH₂CH₂SCH₃)—O—, —O—P(O)(O⁻)—N(CH₃)—, —N(CH₃)—P(O)(O⁻)—O-; and preferably from —O—P(O)(O⁻)—O—, —O—P(O)(S⁻)—O—, —O—P(S)(S⁻)—O—, —S—P(O)(O⁻)—O—, —S—P(O)(S⁻)—O—, —O—P(O)(O⁻)—S—, —O—P(O)(S⁻)—S—, —S—P(O)(O⁻)—S—;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

More preferably N³ represents: GATCGTGCTGGCGAT-, ATCGTGCTGGCGAT-, TCGTGCTGGCGAT-, CGTGCTGGCGAT-, GTGCTGGCGAT-, TGCTGGCGAT-, GCTGGCGAT-, CTGGCGAT-, TGGCGAT-, GGCGAT-, GCGAT-, CGAT-, GAT-, AT-, or T-; and N₄ represents: -ACAGGACGATGTGCA, -ACAGGACGATGTGC, -ACAGGACGATGTG, -ACAGGACGATGT, -ACAGGACGATG, -ACAGGACGAT, -ACAGGACGA, -ACAGGACG, -ACAGGAC, -ACAGGA, -ACAGG, -ACAG, -ACA, -AC, or -A.

Still further preferred, the present invention is directed to an antisense-oligonucleotide in form of a gapmer consisting of 11 to 24 nucleotides, more preferably 12 to 20, and still more preferably 13 to 19 or 14 to 18 nucleotides and 2 to 5 of these nucleotides at the 5' terminal end and 2 to 5 nucleotides at the 3' terminal end of the antisense-oligonucleotide are LNA nucleotides and between the LNA nucleotides at the 5' terminal end and the 3' terminal end a sequence of at least 7, preferably at least 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N³-ACGCGTCC-N₄-3' (Seq. ID No. 98), wherein N³ represents: CGTGCTGGCGAT-, GTGCTGGCGAT-, TGCTGGCGAT-, GCTGGCGAT-, CTGGCGAT-, TGGCGAT-, GGCGAT-, GCGAT-, CGAT-, GAT-, AT-, or T-; preferably N³ represents: TGCTGGCGAT-, GCTGGCGAT-, CTGGCGAT-, TGGCGAT-, GGCGAT-, GCGAT-, CGAT-, GAT-, AT-, or T-; and N₄ represents: -ACAGGACGATGT, -ACAGGACGATG, -ACAGGACGAT, -ACAGGACGA, -ACAGGACG, -ACAGGAC, -ACAGGA, -ACAGG, -ACAG, -ACA, -AC, or -A; preferably N₄ represents: -ACAGGACGAT, -ACAGGACGA, -ACAGGACG, -ACAGGAC, -ACAGGA, -ACAGG, -ACAG, -ACA, -AC, or -A; and the LNA nucleotides are selected from β-D-oxy-LNA (b¹), β-D-thio-LNA (b²), α-L-oxy-LNA (b⁴), β-D-(NH)-LNA (b⁶), and β-D-(NCH₃)-LNA (b⁷); and the internucleotide linkages are selected from
—O—P(O)(O⁻)—O—, —O—P(O)(S⁻)—O—, —O—P(S)(S⁻)—O—, —S—P(O)(O⁻)—O—, —S—P(O)(S⁻)—O—, —O—P(O)(O⁻)—S—, —O—P(O)(S⁻)—S—, —S—P(O)(O⁻)—S—; and preferably selected from phosphate, phosphorothioate and phosphorodithioate;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

Especially preferred are the gapmer antisense-oligonucleotides of Seq. ID No. 54 to Seq. ID No. 68 and Seq. ID No. 349 to Seq. ID No. 368 containing a segment of 2 to 5, preferably 2 to 4 and more preferably 3 to 4 LNA units at the 3' terminus and a segment of 2 to 5, preferably 2 to 4 and more preferably 3 to 4 LNA units at the 5' terminus and a segment of at least 6, preferably 7 and more preferably 8 DNA units between the two segments of LNA units, wherein the LNA units are selected from β-D-oxy-LNA (b¹), β-D-thio-LNA (b²), α-L-oxy-LNA (b4), β-D-(NH)-LNA (b⁶), and β-D-(NCH₃)-LNA (b⁷) and the internucleotide linkages are selected from phosphate, phosphorothioate and phosphorodithioate. Such preferred antisense-oligonucleotides may not contain any modified 3' and 5' terminal end or may not contain any 3' and 5' terminal group and may as modified nucleobase contain 5-methylcytosine in the LNA units, preferably all the LNA units and/or 2-aminoadenine in some or all DNA units and/or 5-methylcytosine in some or all DNA units.

Also especially preferred are the gapmer antisense-oligonucleotides of Table 5 (Seq. ID No. 245a to 257b).

Moreover, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-$R_{II}$ or with a region of the mRNA encoding the TGF-$R_{II}$, wherein the antisense-oligonucleotide is represented by the following sequence 5'-$N^{11}$-TGTTTAGG-$N^{12}$-3' (Seq. ID No. 10), wherein $N^{11}$ represents: GAAGAGCTATTTGGTAG-, AAGAGCTATTTGGTAG-, AGAGCTATTTGGTAG-, GAGCTATTTGGTAG-, AGCTATTTGGTAG-, GCTATTTGGTAG-, CTATTTGGTAG-, TATTTGGTAG-, ATTTGGTAG-, TTTGGTAG-, TTGGTAG-, TGGTAG-, GGTAG-, GTAG-, TAG-, AG- or G-, $N^{12}$ represents: -GAGCCGTCTTCAGGAAT, -GAGCCGTCTTCAGGAA, -GAGCCGTCTTCAGGA, -GAGCCGTCTTCAGG, -GAGCCGTCTTCAG, -GAGCCGTCTTCA, -GAGCCGTCTTC, -GAGCCGTCTT, -GAGCCGTCT, -GAGCCGTC, -GAGCCGT, -GAGCCG, -GAGCC, -GAGC, -GAG, -GA, or -G;

and salts and optical isomers of the antisense-oligonucleotide.

$N^{11}$ and/or $N^{12}$ may also represent any of the further limited lists of 3' and 5' residues as disclosed herein.

Especially preferred gapmer antisense-oligonucleotides falling under general formula S3:

5'-$N^{11}$-TGTTTAGG-$N^{12}$-3'   S3   (Seq. ID No. 10)

are the following:

ATTTGGTAGTGTTTAGGG (Seq. ID No. 369)

TTTGGTAGTGTTTAGGGA (Seq. ID No. 370)

TTGGTAGTGTTTAGGGAG (Seq. ID No. 371)

TGGTAGTGTTTAGGGAGC (Seq. ID No. 372)

GGTAGTGTTTAGGGAGCC (Seq. ID No. 373)

GTAGTGTTTAGGGAGCCG (Seq. ID No. 374)

TAGTGTTTAGGGAGCCGT (Seq. ID No. 375)

AGTGTTTAGGGAGCCGTC (Seq. ID No. 376)

GTGTTTAGGGAGCCGTCT (Seq. ID No. 377)

TTTGGTAGTGTTTAGGG (Seq. ID No. 378)

TTGGTAGTGTTTAGGGA (Seq. ID No. 379)

TGGTAGTGTTTAGGGAG (Seq. ID No. 380)

GGTAGTGTTTAGGGAGC (Seq. ID No. 381)

GTAGTGTTTAGGGAGCC (Seq. ID No. 382)

TAGTGTTTAGGGAGCCG (Seq. ID No. 383)

AGTGTTTAGGGAGCCGT (Seq. ID No. 384)

GTGTTTAGGGAGCCGTC (Seq. ID No. 385)

TTGGTAGTGTTTAGGG (Seq. ID No. 386)

TGGTAGTGTTTAGGGA (Seq. ID No. 387)

GGTAGTGTTTAGGGAG (Seq. ID No. 388)

GTAGTGTTTAGGGAGC (Seq. ID No. 389)

TAGTGTTTAGGGAGCC (Seq. ID No. 390)

AGTGTTTAGGGAGCCG (Seq. ID No. 391)

GTGTTTAGGGAGCCGT (Seq. ID No. 392)

TGGTAGTGTTTAGGG (Seq. ID No. 393)

GGTAGTGTTTAGGGA (Seq. ID No. 394)

GTAGTGTTTAGGGAG (Seq. ID No. 395)

TAGTGTTTAGGGAGC (Seq. ID No. 396)

AGTGTTTAGGGAGCC (Seq. ID No. 397)

GTGTTTAGGGAGCCG (Seq. ID No. 398)

GGTAGTGTTTAGGG (Seq. ID No. 399)

GTAGTGTTTAGGGA (Seq. ID No. 400)

TAGTGTTTAGGGAG (Seq. ID No. 401)

AGTGTTTAGGGAGC (Seq. ID No. 402)

GTGTTTAGGGAGCC (Seq. ID No. 403)

The antisense-oligonucleotides of formula S3 in form of gapmers (LNA segment 1—DNA segment—LNA segment 2) contain an LNA segment at the 5' terminal end consisting of 2 to 5, preferably 2 to 4 LNA units and contain an LNA segment at the 3' terminal end consisting of 2 to 5, preferably 2 to 4 LNA units and between the two LNA segments one DNA segment consisting of 6 to 14, preferably 7 to 12 and more preferably 8 to 11 DNA units.

The antisense-oligonucleotides of formula S3 contain the LNA nucleotides (LNA units) as disclosed herein, especially these disclosed in the chapter "Locked Nucleic Acids (LNA®)" and preferably these disclosed in the chapter "Preferred LNAs". The LNA units and the DNA units may comprise standard nucleobases such as adenine (A), cytosine (C), guanine (G), thymine (T) and uracil (U), but may also contain modified nucleobases as disclosed in the chapter "Nucleobases". The antisense-oligonucleotides of formula S3 or the LNA segments and the DNA segment of the antisense-oligonucleotide may contain any internucleotide linkage as disclosed herein and especially these disclosed in the chapter "Internucleotide Linkages (IL)". The antisense-oligonucleotides of formula S3 may optionally also contain endgroups at the 3' terminal end and/or the 5' terminal end and especially these disclosed in the chapter "Terminal groups".

Experiments have shown that modified nucleobases do not considerably increase or change the activity of the inventive antisense-oligonucleotides in regard to tested neurological and oncological indications. The modified nucleobases 5-methylcytosine or 2-aminoadenine have been demonstrated to further increase the activity of the antisense-oligonucleotides of formula S3 especially if 5-methylcytosine is used in the LNA nucleotides only or in the LNA nucleotides and in the DNA nucleotides and/or if 2-aminoadenine is used in the DNA nucleotides and not in the LNA nucleotides.

The preferred gapmer structure of the antisense-oligonucleotides of formula S3 is as follows: 3-8-3, 4-8-2, 2-8-4, 3-8-4, 4-8-3, 4-8-4, 3-9-3, 4-9-2, 2-9-4, 4-9-3, 3-9-4, 4-9-4, 3-10-3, 2-10-4, 4-10-2, 3-10-4, 4-10-3, 4-10-4, 2-11-4, 4-11-2, 3-11-4, 4-11-3 and still more preferred: 3-8-3, 3-8-4, 4-8-3, 4-8-4, 3-9-3, 4-9-3, 3-9-4, 4-9-4, 3-10-3, 3-10-4, 4-10-3, 4-10-4, 3-11-4, and 4-11-3.

As LNA units for the antisense-oligonucleotides of formula S3 especially β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-(NCH$_3$)-LNA ($b^7$), β-D-(ONH)-LNA ($b^8$) and β-D-(ONCH$_3$)-LNA ($b^9$) are preferred. Experiments have been shown that all of these LNA units $b^1$, $b^2$, $b^4$, $b^5$, $b^6$, $b^7$, $b^8$, and $b^9$ can be synthesized with the required effort and lead to antisense-oligonucleotides of comparable stability and activity. However based on the experiments the LNA units $b^1$, $b^2$, $b^4$, $b^5$, $b^6$, and $b^7$ are further preferred. Still further preferred are the LNA units $b^1$, $b^2$, $b^4$, $b^6$, and $b^7$, and even more preferred are the LNA units $b^1$ and $b^4$ and most preferred also in regard to the complexity of the chemical synthesis is the β-D-oxy-LNA ($b^1$).

So far no special 3' terminal group or 5' terminal group could be found which remarkably had changed or increased the stability or activity for oncological or neurological indications, so that 3' and 5' end groups are possible but not explicitly preferred.

Various internucleotide bridges or internucleotide linkages are possible. In the formulae disclosed herein the internucleotide linkage IL is represented by -IL'-Y-. Thus, IL=-IL'-Y—=—X"—P(=X$^-$)(X$^-$)—Y—, wherein IL is preferably selected form the group consisting of:

—O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3$$^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O—. Preferred are the internucleotide linkages IL selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(OCH$_3$)—O—, —O—P(O)(NH(CH$_3$))—O—, —O—P(O)[N(CH$_3$)$_2$]—O—, —O—P(O)(OCH$_2$CH$_2$OCH$_3$)—O—, and more preferred selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, and still more preferred selected from —O—P(O)(O$^-$)—O—, —O—P(O)(S$^-$)—O—, —O—P(S)(S$^-$)—O—, and most preferably selected from —O—P(O)(O$^-$)—O— and —O—P(O)(S$^-$)—O—.

Thus, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^{11}$-TGTTTAGG-N$^{12}$-3' (Seq. ID No. 10), wherein N$^{11}$ represents: GAAGAGCTATTTGGTAG-, AAGAGCTATTTGGTAG-, AGAGCTATTTGGTAG-, GAGCTATTTGGTAG-, AGCTATTTGGTAG-, GCTATTTGGTAG-, CTATTTGGTAG-, TATITGGTAG-, ATTTGGTAG-, TTTGGTAG-, TTGGTAG-, TGGTAG-, GGTAG-, GTAG-, TAG-, AG- or G-;

N$^{12}$ represents: -GAGCCGTCTTCAGGAAT, -GAGCCGTCTTCAGGAA, -GAGCCGTCTTCAGGA, -GAGCCGTCTTCAGG, -GAGCCGTCTTCAG, -GAGCCGTCTTCA, -GAGCCGTCTTC, -GAGCCGTCTT, -GAGCCGTCT, -GAGCCGTC, -GAGCCGT, -GAGCCG, -GAGCC, -GAGC, -GAG, -GA, or -G;

the LNA nucleotides are selected from β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-(NCH$_3$)-LNA ($b^7$), β-D-(ONH)-LNA ($b^8$) and β-D-(ONCH$_3$)-LNA ($b^9$); and preferably from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$); and the internucleotide linkages are selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3$$^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O-; and preferably from —O—P(O)(O$^-$)—O—, —O—P(O)(S$^-$)—O—, —O—P(S)(S$^-$)—O—, —S—P(O)

(O⁻)—O—, —S—P(O)(S⁻)—O—, —O—P(O)(O⁻)—S—, —O—P(O)(S⁻)—S—, —S—P(O)(O⁻)—S—;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

More preferably N¹¹ represents: AGAGCTATTTGGTAG-, GAGCTATTTGGTAG-, AGCTATTTGGTAG-, GCTATTTGGTAG-, CTATTTGGTAG-, TATTTGGTAG-, ATTTGGTAG-, TTTGGTAG-, TTGGTAG-, TGGTAG-, GGTAG-, GTAG-, TAG-, AG- or G-; and N¹² represents: -GAGCCGTCTTCAGGA, -GAGCCGTCTTCAGG, -GAGCCGTCTTCAG, -GAGCCGTCTTCA, -GAGCCGTCTT, -GAGCCGTCTT, -GAGCCGTCT, -GAGCCGTC, -GAGCCGT, -GAGCCG, -GAGCC, -GAGC, -GAG, -GA, or -G.

Still further preferred, the present invention is directed to an antisense-oligonucleotide in form of a gapmer consisting of 11 to 24 nucleotides, more preferably 12 to 20, and still more preferably 13 to 19 or 14 to 18 nucleotides and 2 to 5 of these nucleotides at the 5' terminal end and 2 to 5 nucleotides at the 3' terminal end of the antisense-oligonucleotide are LNA nucleotides and between the LNA nucleotides at the 5' terminal end and the 3' terminal end a sequence of at least 7, preferably at least 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N¹¹-TGTTTAGG-N¹²-3' (Seq. ID No. 10), wherein N¹¹ represents: GCTATTTGGTAG-, CTATTTGGTAG-, TATTTGGTAG-, ATTTGGTAG-, TTTGGTAG-, TTGGTAG-, TGGTAG-, GGTAG-, GTAG-, TAG-, AG- or G-; preferably N¹¹ represents: TATTTGGTAG-, ATTTGGTAG-, TTTGGTAG-, TTGGTAG-, TGGTAG-, GGTAG-, GTAG-, TAG-, AG- or G-; and N¹² represents: -GAGCCGTCTTCA, -GAGCCGTCTTC, -GAGCCGTCTT, -GAGCCGTCT, -GAGCCGTC, -GAGCCGT, -GAGCCG, -GAGCC, -GAGC, -GAG, -GA, or -G; preferably N¹² represents: -GAGCCGTCTT, -GAGCCGTCT, -GAGCCGTC, -GAGCCGT, -GAGCCG, -GAGCC, -GAGC, -GAG, -GA, or -G; and the LNA nucleotides are selected from β-D-oxy-LNA (b¹), β-D-thio-LNA (b²), α-L-oxy-LNA (b⁴), β-D-(NH)-LNA (b⁶), and β-D-(NCH₃)-LNA (b⁷); and the internucleotide linkages are selected from —O—P(O)(O⁻)—O—, —O—P(O)(S⁻)—O—, —O—P(S)(S⁻)—O—, —S—P(O)(O⁻)—O—, —S—P(O)(S⁻)—O—, —O—P(O)(O⁻)—S—, —O—P(O)(S⁻)—S—, —S—P(O)(O⁻)—S—; and preferably selected from phosphate, phosphorothioate and phosphorodithioate;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

Especially preferred are the gapmer antisense-oligonucleotides of Seq. ID No. 369 to Seq. ID No. 403 containing a segment of 2 to 5, preferably 2 to 4 and more preferably 3 to 4 LNA units at the 3' terminus and a segment of 2 to 5, preferably 2 to 4 and more preferably 3 to 4 LNA units at the 5' terminus and a segment of at least 6, preferably 7 and more preferably 8 DNA units between the two segments of LNA units, wherein the LNA units are selected from β-D-oxy-LNA (b¹), β-D-thio-LNA (b²), α-L-oxy-LNA (b⁴), β-D-(NH)-LNA (b⁶), and β-D-(NCH₃)-LNA (b⁷) and the internucleotide linkages are selected from phosphate, phosphorothioate and phosphorodithioate. Such preferred antisense-oligonucleotides may not contain any modified 3' and 5' terminal end or may not contain any 3' and 5' terminal group and may as modified nucleobase contain 5-methylcytosine in the LNA units, preferably all the LNA units and/or 2-aminoadenine in some or all DNA units and/or 5-methylcytosine in some or all DNA units.

Also especially preferred are the gapmer antisense-oligonucleotides of Table 6 (Seq. ID No. 258a to 270b).

Moreover, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N⁵-TTTGGTAG-N⁶-3' (Seq. ID No. 11), wherein N⁵ represents: CTGCCCCAGAAGAGCTA-, TGCCCCAGAAGAGCTA-, GCCCCAGAAGAGCTA-, CCCCAGAAGAGCTA-, CCCAGAAGAGCTA-, CCAGAAGAGCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-;

N⁶ represents: -TGTTTAGGGAGCCGTCT, -TGTTTAGGGAGCCGTC, -TGTTTAGGGAGCCGT, -TGTTTAGGGAGCCG, -TGTTTAGGGAGCC, -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T;

and salts and optical isomers of the antisense-oligonucleotide.

N⁵ and/or N⁶ may also represent any of the further limited lists of 3' and 5' residues as disclosed herein.

Especially preferred gapmer antisense-oligonucleotides falling under general formula S4:

```
                                    (Seq. ID No. 11)
        5'-N⁵-TTTGGTAG-N⁶-3'  S4
``` are the following:

```
                                   (Seq. ID No. 404)
            GAAGAGCTATTTGGTAGT (Seq. ID No. 405)
            AAGAGCTATTTGGTAGTG (Seq. ID No. 406)
            AGAGCTATTTGGTAGTGT (Seq. ID No. 407)
            GAGCTATTTGGTAGTGTT (Seq. ID No. 408)
            AGCTATTTGGTAGTGTTT
```

GCTATTTGGTAGTGTTTA (Seq. ID No. 409)

CTATTTGGTAGTGTTTAG (Seq. ID No. 410)

TATTTGGTAGTGTTTAGG (Seq. ID No. 411)

ATTTGGTAGTGTTTAGGG (Seq. ID No. 412)

AAGAGCTATTTGGTAGT (Seq. ID No. 413)

AGAGCTATTTGGTAGTG (Seq. ID No. 414)

GAGCTATTTGGTAGTGT (Seq. ID No. 415)

AGCTATTTGGTAGTGTT (Seq. ID No. 416)

GCTATTTGGTAGTGTTT (Seq. ID No. 417)

CTATTTGGTAGTGTTTA (Seq. ID No. 418)

TATTTGGTAGTGTTTAG (Seq. ID No. 419)

ATTTGGTAGTGTTTAGG (Seq. ID No. 420)

AGAGCTATTTGGTAGT (Seq. ID No. 421)

GAGCTATTTGGTAGTG (Seq. ID No. 422)

AGCTATTTGGTAGTGT (Seq. ID No. 423)

GCTATTTGGTAGTGTT (Seq. ID No. 424)

CTATTTGGTAGTGTTT (Seq. ID No. 425)

TATTTGGTAGTGTTTA (Seq. ID No. 426)

ATTTGGTAGTGTTTAG (Seq. ID No. 427)

GAGCTATTTGGTAGT (Seq. ID No. 428)

AGCTATTTGGTAGTG (Seq. ID No. 429)

GCTATTTGGTAGTGT (Seq. ID No. 430)

CTATTTGGTAGTGTT (Seq. ID No. 431)

TATTTGGTAGTGTTT (Seq. ID No. 432)

ATTTGGTAGTGTTTA (Seq. ID No. 433)

AGCTATTTGGTAGT (Seq. ID No. 434)

GCTATTTGGTAGTG (Seq. ID No. 435)

CTATTTGGTAGTGT (Seq. ID No. 436)

TATTTGGTAGTGTT (Seq. ID No. 437)

ATTTGGTAGTGTTT (Seq. ID No. 438)

The antisense-oligonucleotides of formula S4 in form of gapmers (LNA segment 1—DNA segment—LNA segment 2) contain an LNA segment at the 5' terminal end consisting of 2 to 5, preferably 2 to 4 LNA units and contain an LNA segment at the 3' terminal end consisting of 2 to 5, preferably 2 to 4 LNA units and between the two LNA segments one DNA segment consisting of 6 to 14, preferably 7 to 12 and more preferably 8 to 11 DNA units.

The antisense-oligonucleotides of formula S4 contain the LNA nucleotides (LNA units) as disclosed herein, especially these disclosed in the chapter "Locked Nucleic Acids (LNA®)" and preferably these disclosed in the chapter "Preferred LNAs". The LNA units and the DNA units may comprise standard nucleobases such as adenine (A), cytosine (C), guanine (G), thymine (T) and uracil (U), but may also contain modified nucleobases as disclosed in the chapter "Nucleobases". The antisense-oligonucleotides of formula S4 or the LNA segments and the DNA segment of the antisense-oligonucleotide may contain any internucleotide linkage as disclosed herein and especially these disclosed in the chapter "Internucleotide Linkages (IL)". The antisense-oligonucleotides of formula S4 may optionally also contain endgroups at the 3' terminal end and/or the 5' terminal end and especially these disclosed in the chapter "Terminal groups".

Experiments have shown that modified nucleobases do not considerably increase or change the activity of the inventive antisense-oligonucleotides in regard to tested neurological and oncological indications. The modified nucleobases 5-methylcytosine or 2-aminoadenine have been demonstrated to further increase the activity of the antisense-oligonucleotides of formula S4 especially if 5-methylcytosine is used in the LNA nucleotides only or in the LNA nucleotides and in the DNA nucleotides and/or if 2-aminoadenine is used in the DNA nucleotides and not in the LNA nucleotides.

The preferred gapmer structure of the antisense-oligonucleotides of formula S4 is as follows: 3-8-3, 4-8-2, 2-8-4, 3-8-4, 4-8-3, 4-8-4, 3-9-3, 4-9-2, 2-9-4, 4-9-3, 3-9-4, 4-9-4, 3-10-3, 2-10-4, 4-10-2, 3-10-4, 4-10-3, 4-10-4, 2-11-4, 4-11-2, 3-11-4, 4-11-3 and still more preferred: 3-8-3, 3-8-4, 4-8-3, 4-8-4, 3-9-3, 4-9-3, 3-9-4, 4-9-4, 3-10-3, 3-10-4, 4-10-3, 4-10-4, 3-11-4, and 4-11-3.

As LNA units for the antisense-oligonucleotides of formula S4 especially β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-(NCH$_3$)-LNA ($b^7$), β-D-(ONH)-LNA (ba) and β-D-(ONCH$_3$)-LNA ($b^9$) are preferred. Experiments have been shown that all of these LNA units $b^1$, $b^2$, $b^4$, $b^5$, $b^6$, $b^7$, $b^8$, and $b^9$ can be synthesized with the required effort and lead to antisense-oligonucleotides of comparable stability and activity. However based on the experiments the LNA units $b^1$, $b^2$, $b^4$, $b^5$, $b^6$, and $b^7$ are further preferred. Still further preferred are the LNA units $b^1$, $b^2$, $b^4$, $b^6$, and $b^7$, and even more preferred are the LNA units $b^1$ and $b^4$ and most preferred also in regard to the complexity of the chemical synthesis is the β-D-oxy-LNA ($b^1$).

So far no special 3' terminal group or 5' terminal group could be found which remarkably had changed or increased the stability or activity for oncological or neurological indications, so that 3' and 5' end groups are possible but not explicitly preferred.

Various internucleotide bridges or internucleotide linkages are possible. In the formulae disclosed herein the internucleotide linkage IL is represented by -IL'-Y-. Thus, IL=-IL'-Y——X''—P(=X$^-$)(X'')—Y—, wherein IL is preferably selected form the group consisting of:
—O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3$$^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O—. Preferred are the internucleotide linkages IL selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(NH(CH$_3$))—O—, —O—P(O)[N(CH$_3$)$_2$]—O—, —O—P(O)(OCH$_2$CH$_2$OCH$_3$)—O—, and more preferred selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, and still more preferred selected from —O—P(O)(O$^-$)—O—, —O—P(O)(S$^-$)—O—, —O—P(S)(S$^-$)—O—, and most preferably selected from —O—P(O)(O$^-$)—O— and —O—P(O)(S$^-$)—O—.

Thus, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^5$-TTTGGTAG-N$^6$-3' (Seq. ID No. 11), wherein N$^5$ represents: CTGCCCCAGAAGAGCTA-, TGCCCCAGAAGAGCTA-, GCCCCAGAAGAGCTA-, CCCCAGAAGAGCTA-, CCCAGAAGAGCTA-, CCAGAAGAGCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-; and N$^6$ represents: -TGTTTAGGGAGCCGTCT, -TGTTTAGGGAGCCGTC, -TGTTTAGGGAGCCGT, -TGTTTAGGGAGCCG, -TGTTTAGGGAGCC, -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T; and the LNA nucleotides are selected from β-D-oxy-LNA (b$^1$), β-D-thio-LNA (b$^2$), α-L-oxy-LNA (b$^4$), β-D-ENA (b$^5$), β-D-(NH)-LNA (b$^6$), β-D-(NCH$_3$)-LNA (b$^7$), β-D-(ONH)-LNA (b$^8$) and β-D-(ONCH$_3$)-LNA (b9); and preferably from β-D-oxy-LNA (b$^1$), β-D-thio-LNA (b$^2$), α-L-oxy-LNA (b$^4$), β-D-(NH)-LNA (b$^6$), and β-D-(NCH$_3$)-LNA (b$^7$); and the internucleotide linkages are selected from
—O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3$$^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O-; and preferably from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

More preferably N$^5$ represents: GCCCCAGAAGAGCTA-, CCCCAGAAGAGCTA-, CCCAGAAGAGCTA-, CCAGAAGAGCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-; and N$^6$ represents: -TGTTTAGGGAGCCGT, -TGTTTAGGGAGCCG, -TGTTTAGGGAGCC, -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T.

Still further preferred, the present invention is directed to an antisense-oligonucleotide in form of a gapmer consisting of 11 to 24 nucleotides, more preferably 12 to 20, and still more preferably 13 to 19 or 14 to 18 nucleotides and 2 to 5 of these nucleotides at the 5' terminal end and 2 to 5 nucleotides at the 3' terminal end of the antisense-oligonucleotide are LNA nucleotides and between the LNA nucleotides at the 5' terminal end and the 3' terminal end a sequence of at least 7, preferably at least 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^5$-TTTGGTAG-N$^6$-3' (Seq. ID No. 11)), wherein N$^5$ represents: CCAGAAGAGCTA-, CAGAAGAGCTA-, AGAAGAGCTA-, GAAGAGCTA-, AAGAGCTA-, AGAGCTA-, GAGCTA-, AGCTA-, GCTA-, CTA-, TA-, or A-; preferably N$^5$ represents: AGAAGAGCTA-, GAAGAGCTA-, AAGAGCTA-, AGAGCTA-, GAGCTA-, AGCTA-, GCTA-, CTA-, TA-, or A-; and N$^6$ represents: -TGTTTAGGGAGC, -TGTTTAGGGAG, -TGTTTAGGGA, -TGTTTAGGG, -TGTTTAGG, -TGTTTAG, -TGTTTA, -TGTTT, -TGTT, -TGT, -TG, or -T; preferably N$^6$ represents: -TGTTTAGGGA, -TGTTTAGGG, -TGTTTAGG, -TGTTTAG, -TGTTTA, -TGTTT, -TGTT, -TGT, -TG, or -T; and the LNA nucleotides are selected from β-D-oxy-LNA (b$^1$), β-D-thio-LNA (b$^2$), α-L-oxy-LNA (b$^4$), β-D-(NH)-LNA (b$^6$), and β-D-(NCH$_3$)-LNA (b$^7$); and the internucleotide linkages are selected from
—O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O⁻)—S—; and preferably selected from phosphate, phosphorothioate and phosphorodithioate;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

Especially preferred are the gapmer antisense-oligonucleotides of Seq. ID No. 404 to Seq. ID No. 438 containing a segment of 2 to 5, preferably 2 to 4 and more preferably 3 to 4 LNA units at the 3' terminus and a segment of 2 to 5, preferably 2 to 4 and more preferably 3 to 4 LNA units at the 5' terminus and a segment of at least 6, preferably 7 and more preferably 8 DNA units between the two segments of LNA units, wherein the LNA units are selected from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$) and the internucleotide linkages are selected from phosphate, phosphorothioate and phosphorodithioate. Such preferred antisense-oligonucleotides may not contain any modified 3' and 5' terminal end or may not contain any 3' and 5' terminal group and may as modified nucleobase contain 5-methylcytosine in the LNA units, preferably all the LNA units and/or 2-aminoadenine in some or all DNA units and/or 5-methylcytosine in some or all DNA units.

Also especially preferred are the gapmer antisense-oligonucleotides of Table 7 (Seq. ID No. 271a to 283b).

Moreover, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^7$-AATGGACC-N$^8$-3' (Seq. ID No. 100), wherein N$^7$ represents: ATCTTGAATATCTCATG-, TCTTGAATATCTCATG-, CTTGAATATCTCATG-, TTGAATATCTCATG-, TGAATATCTCATG-, GAATATCTCATG-, AATATCTCATG-, ATATCTCATG-, TATCTCATG-, ATCTCATG-, TCTCATG-, CTCATG-, TCATG-, CATG-, ATG-, TG-, or G-;

N$^8$ represents: -AGTATTCTAGAAACTCA, -AGTATTCTAGAAACTC, -AGTATTCTAGAAACT, -AGTATTCTAGAAAC, -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A;

and salts and optical isomers of the antisense-oligonucleotide.

N$^7$ and/or N$^8$ may also represent any of the further limited lists of 3' and 5' residues as disclosed herein.

Especially preferred gapmer antisense-oligonucleotides falling under general formula S6:

```
5'-N⁷-AATGGACC-N⁸-3'  S6    (Seq. ID No. 100)
``` are the following:

```
TATCTCATGAATGGACCA            (Seq. ID No. 439)

ATCTCATGAATGGACCAG            (Seq. ID No. 440)

TCTCATGAATGGACCAGT            (Seq. ID No. 441)

CTCATGAATGGACCAGTA            (Seq. ID No. 442)

TCATGAATGGACCAGTAT            (Seq. ID No. 443)

CATGAATGGACCAGTATT            (Seq. ID No. 444)

ATGAATGGACCAGTATTC            (Seq. ID No. 445)

TGAATGGACCAGTATTCT            (Seq. ID No. 446)

GAATGGACCAGTATTCTA            (Seq. ID No. 447)

ATCTCATGAATGGACCA             (Seq. ID No. 448)

TCTCATGAATGGACCAG             (Seq. ID No. 449)

CTCATGAATGGACCAGT             (Seq. ID No. 450)

TCATGAATGGACCAGTA             (Seq. ID No. 451)

CATGAATGGACCAGTAT             (Seq. ID No. 452)

ATGAATGGACCAGTATT             (Seq. ID No. 453)

TGAATGGACCAGTATTC             (Seq. ID No. 454)

GAATGGACCAGTATTCT             (Seq. ID No. 455)

TCTCATGAATGGACCA              (Seq. ID No. 456)

CTCATGAATGGACCAG              (Seq. ID No. 457)

TCATGAATGGACCAGT              (Seq. ID No. 458)

CATGAATGGACCAGTA              (Seq. ID No. 459)

ATGAATGGACCAGTAT              (Seq. ID No. 460)

TGAATGGACCAGTATT              (Seq. ID No. 461)

GAATGGACCAGTATTC              (Seq. ID No. 462)

CTCATGAATGGACCA               (Seq. ID No. 463)

TCATGAATGGACCAG               (Seq. ID No. 464)
```

CATGAATGGACCAGT (Seq. ID No. 465)

ATGAATGGACCAGTA (Seq. ID No. 466)

TGAATGGACCAGTAT (Seq. ID No. 467)

GAATGGACCAGTATT (Seq. ID No. 468)

TCATGAATGGACCA (Seq. ID No. 469)

CATGAATGGACCAG (Seq. ID No. 470)

ATGAATGGACCAGT (Seq. ID No. 471)

TGAATGGACCAGTA (Seq. ID No. 472)

GAATGGACCAGTAT (Seq. ID No. 473)

The antisense-oligonucleotides of formula S6 in form of gapmers (LNA segment 1—DNA segment—LNA segment 2) contain an LNA segment at the 5' terminal end consisting of 2 to 5, preferably 2 to 4 LNA units and contain an LNA segment at the 3' terminal end consisting of 2 to 5, preferably 2 to 4 LNA units and between the two LNA segments one DNA segment consisting of 6 to 14, preferably 7 to 12 and more preferably 8 to 11 DNA units.

The antisense-oligonucleotides of formula S6 contain the LNA nucleotides (LNA units) as disclosed herein, especially these disclosed in the chapter "Locked Nucleic Acids (LNA®)" and preferably these disclosed in the chapter "Preferred LNAs". The LNA units and the DNA units may comprise standard nucleobases such as adenine (A), cytosine (C), guanine (G), thymine (T) and uracil (U), but may also contain modified nucleobases as disclosed in the chapter "Nucleobases". The antisense-oligonucleotides of formula S6 or the LNA segments and the DNA segment of the antisense-oligonucleotide may contain any internucleotide linkage as disclosed herein and especially these disclosed in the chapter "Internucleotide Linkages (IL)". The antisense-oligonucleotides of formula S6 may optionally also contain endgroups at the 3' terminal end and/or the 5' terminal end and especially these disclosed in the chapter "Terminal groups".

Experiments have shown that modified nucleobases do not considerably increase or change the activity of the inventive antisense-oligonucleotides in regard to tested neurological and oncological indications. The modified nucleobases 5-methylcytosine or 2-aminoadenine have been demonstrated to further increase the activity of the antisense-oligonucleotides of formula S6 especially if 5-methylcytosine is used in the LNA nucleotides only or in the LNA nucleotides and in the DNA nucleotides and/or if 2-aminoadenine is used in the DNA nucleotides and not in the LNA nucleotides.

The preferred gapmer structure of the antisense-oligonucleotides of formula S6 is as follows: 3-8-3, 4-8-2, 2-8-4, 3-8-4, 4-8-3, 4-8-4, 3-9-3, 4-9-2, 2-9-4, 4-9-3, 3-9-4, 4-9-4, 3-10-3, 2-10-4, 4-10-2, 3-10-4, 4-10-3, 4-10-4, 2-11-4, 4-11-2, 3-11-4, 4-11-3 and still more preferred: 3-8-3, 3-8-4, 4-8-3, 4-8-4, 3-9-3, 4-9-3, 3-9-4, 4-9-4, 3-10-3, 3-10-4, 4-10-3, 4-10-4, 3-11-4, and 4-11-3.

As LNA units for the antisense-oligonucleotides of formula S6 especially β-D-oxy-LNA ($b^1$), β-D-thio-LNA ($b^2$), α-L-oxy-LNA ($b^4$), β-D-ENA ($b^5$), β-D-(NH)-LNA (be), β-D-(NCH$_3$)-LNA ($b^7$), β-D-(ONH)-LNA ($b^8$) and β-D-(ONCH$_3$)-LNA ($b^9$) are preferred. Experiments have been shown that all of these LNA units $b^1$, $b^2$, $b^4$, $b^5$, $b^6$, $b^1$, $b^8$, and $b^9$ can be synthesized with the required effort and lead to antisense-oligonucleotides of comparable stability and activity. However based on the experiments the LNA units $b^1$, $b^2$, $b^4$, $b^5$, $b^6$, and $b^7$ are further preferred. Still further preferred are the LNA units $b^1$, $b^2$, $b^4$, $b^6$, and $b^7$, and even more preferred are the LNA units $b^1$ and $b^4$ and most preferred also in regard to the complexity of the chemical synthesis is the β-D-oxy-LNA ($b^1$).

So far no special 3' terminal group or 5' terminal group could be found which remarkably had changed or increased the stability or activity for oncological or neurological indications, so that 3' and 5' end groups are possible but not explicitly preferred.

Various internucleotide bridges or internucleotide linkages are possible. In the formulae disclosed herein the internucleotide linkage IL is represented by -IL'-Y-. Thus, IL=-IL'-Y—=—X"—P(=X$^-$)(X")—Y—, wherein IL is preferably selected form the group consisting of: —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O—. Preferred are the internucleotide linkages IL selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(OCH$_3$)—O—, —O—P(O)(NH(CH$_3$))—O—, —O—P(O)[N(CH$_3$)$_2$]—O—, —O—P(O)(OCH$_2$CH$_2$OCH$_3$)—O—, and more preferred selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, and still more preferred selected from —O—P(O)(O$^-$)—O—, —O—P(O)(S$^-$)—O—, —O—P(S)(S$^-$)—O—, and most preferably selected from —O—P(O)(O$^-$)—O— and —O—P(O)(S$^-$)—O—.

Thus, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^7$-AATGGACC-N$^8$-3' (Seq. ID No. 100), wherein N$^7$ represents: ATCTTGAATATCTCATG-, TCTT-GAATATCTCATG-, CTTGAATATCTCATG-, TTGAATATCTCATG-, TGAATATCTCATG-, GAATATCTCATG-, AATATCTCATG-, ATATCTCATG-, TATCTCATG-, ATCTCATG-, TCTCATG-, CTCATG-, TCATG-, CATG-, ATG-, TG-, or G-; and $N^8$ represents: -AGTATTCTAGAAACTCA, -AGTATTCTAGAAACTC, -AGTATTCTAGAAACT, -AGTATTCTAGAAAC, -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A; and the LNA nucleotides are selected from β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-(NCH$_3$)-LNA ($b^7$), β-D-(ONH)-LNA ($b^8$) and β-D-(ONCH$_3$)-LNA ($b^9$); and preferably from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$); and the internucleotide linkages are selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, -O—P(O)[N(CH$_3$)$_2$]—O—, —O—P(O)(BH$_3^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O-; and preferably from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

More preferably $N^7$ represents: CTTGAATATCTCATG-, TTGAATATCTCATG-, TGAATATCTCATG-, GAATATCTCATG-, AATATCTCATG-, ATATCTCATG-, TATCTCATG-, ATCTCATG-, TCTCATG-, CTCATG-, TCATG-, CATG-, ATG-, TG-, or G-; and $N^8$ represents: -AGTATTCTAGAAACT, -AGTATTCTAGAAAC, -AGTATTCTAGAAA, -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A.

Still further preferred, the present invention is directed to an antisense-oligonucleotide in form of a gapmer consisting of 11 to 24 nucleotides, more preferably 12 to 20, and still more preferably 13 to 19 or 14 to 18 nucleotides and 2 to 5 of these nucleotides at the 5' terminal end and 2 to 5 nucleotides at the 3' terminal end of the antisense-oligonucleotide are LNA nucleotides and between the LNA nucleotides at the 5' terminal end and the 3' terminal end a sequence of at least 7, preferably at least 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-$N^7$-AATGGACC-$N^8$-3' (Seq. ID No. 100), wherein $N^7$ represents: GAATATCTCATG-, AATATCTCATG-, ATATCTCATG-, TATCTCATG-, ATCTCATG-, TCTCATG-, CTCATG-, TCATG-, CATG-, ATG-, TG-, or G-; preferably $N^7$ represents: ATATCTCATG-, TATCTCATG-, ATCTCATG-, TCTCATG-, CTCATG-, TCATG-, CATG-, ATG-, TG-, or G-; and $N^8$ represents: -AGTATTCTAGAA, -AGTATTCTAGA, -AGTATTCTAG, -AGTATTCTA, -AGTATTCT, -AGTATTC, -AGTATT, -AGTAT, -AGTA, -AGT, -AG, or -A; preferably $N^8$ represents: -AGTATTCTAG, -AGTATTCTA, -AGTATTCT, -AGTATTC, -AGTATT, -AGTAT, -AGTA, -AGT, -AG, or -A; and the LNA nucleotides are selected from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$); and the internucleotide linkages are selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—; and preferably selected from phosphate, phosphorothioate and phosphorodithioate;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

Especially preferred are the gapmer antisense-oligonucleotides of Seq. ID No. 439 to Seq. ID No. 473 containing a segment of 2 to 5, preferably 2 to 4 and more preferably 3 to 4 LNA units at the 3' terminus and a segment of 2 to 5, preferably 2 to 4 and more preferably 3 to 4 LNA units at the 5' terminus and a segment of at least 6, preferably 7 and more preferably 8 DNA units between the two segments of LNA units, wherein the LNA units are selected from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$) and the internucleotide linkages are selected from phosphate, phosphorothioate and phosphorodithioate. Such preferred antisense-oligonucleotides may not contain any modified 3' and 5' terminal end or may not contain any 3' and 5' terminal group and may as modified nucleobase contain 5-methylcytosine in the LNA units, preferably all the LNA units and/or 2-aminoadenine in some or all DNA units and/or 5-methylcytosine in some or all DNA units.

Also especially preferred are the gapmer antisense-oligonucleotides of Table 8 (Seq. ID No. 219a to 231b).

Moreover, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-$N^9$-ATTAATAA-$N^{10}$-3' (Seq. ID No. 101), wherein $N^9$ represents: CATATTTATATACAGGC-, ATATTTATATACAGGC-, TATTTATATACAGGC-, ATTTATATACAGGC-, TTTATATACAGGC-, TTATATACAGGC-, TATATACAGGC-, ATATACAGGC-, TATACAGGC-, ATACAGGC-, TACAGGC-, ACAGGC-, CAGGC-, AGGC-, GGC-, GC-, or C-;

$N^{10}$ represents: -AGTGCAAATGTTATTGG, -AGTGCAAATGTTATTG, -AGTGCAAATGTTATT, -AGTGCAAATGTTAT, -AGTGCAAATGTTA, -AGTGCAAATGTT, -AGTGCAAATGT, -AGTGCAAATG, -AGTGCAAAT, -AGTGCAAA, -AGTGCAA, -AGTGCA, -AGTGC, -AGTG, -AGT, -AG, or -A;

and salts and optical isomers of the antisense-oligonucleotide.

$N^9$ and/or $N^{10}$ may also represent any of the further limited lists of 3' and 5' residues as disclosed herein.

Especially preferred gapmer antisense-oligonucleotides falling under general formula S7:

$$5'-N^9\text{-ATTAATAA-}N^{10}\text{-}3' \quad S7 \qquad (Seq.\ ID\ No.\ 101)$$

are the following:

| | |
|---|---|
| TATACAGGCATTAATAAA | (Seq. ID No. 474) |
| ATACAGGCATTAATAAAG | (Seq. ID No. 475) |
| TACAGGCATTAATAAAGT | (Seq. ID No. 476) |
| ACAGGCATTAATAAAGTG | (Seq. ID No. 477) |
| CAGGCATTAATAAAGTGC | (Seq. ID No. 478) |
| AGGCATTAATAAAGTGCA | (Seq. ID No. 479) |
| GGCATTAATAAAGTGCAA | (Seq. ID No. 480) |
| GCATTAATAAAGTGCAAA | (Seq. ID No. 481) |
| CATTAATAAAGTGCAAAT | (Seq. ID No. 482) |
| ATACAGGCATTAATAAA | (Seq. ID No. 483) |
| TACAGGCATTAATAAAG | (Seq. ID No. 484) |
| ACAGGCATTAATAAAGT | (Seq. ID No. 485) |
| CAGGCATTAATAAAGTG | (Seq. ID No. 486) |
| AGGCATTAATAAAGTGC | (Seq. ID No. 487) |
| GGCATTAATAAAGTGCA | (Seq. ID No. 488) |
| GCATTAATAAAGTGCAA | (Seq. ID No. 489) |
| CATTAATAAAGTGCAAA | (Seq. ID No. 490) |
| TACAGGCATTAATAAA | (Seq. ID No. 491) |
| ACAGGCATTAATAAAG | (Seq. ID No. 492) |
| CAGGCATTAATAAAGT | (Seq. ID No. 493) |
| AGGCATTAATAAAGTG | (Seq. ID No. 494) |
| GGCATTAATAAAGTGC | (Seq. ID No. 495) |
| GCATTAATAAAGTGCA | (Seq. ID No. 496) |
| CATTAATAAAGTGCAA | (Seq. ID No. 497) |
| ACAGGCATTAATAAA | (Seq. ID No. 498) |
| CAGGCATTAATAAAG | (Seq. ID No. 499) |
| AGGCATTAATAAAGT | (Seq. ID No. 500) |
| GGCATTAATAAAGTG | (Seq. ID No. 501) |
| GCATTAATAAAGTGC | (Seq. ID No. 502) |
| CATTAATAAAGTGCA | (Seq. ID No. 503) |
| CAGGCATTAATAAA | (Seq. ID No. 504) |
| AGGCATTAATAAAG | (Seq. ID No. 505) |
| GGCATTAATAAAGT | (Seq. ID No. 506) |
| GCATTAATAAAGTG | (Seq. ID No. 507) |
| CATTAATAAAGTGC | (Seq. ID No. 508) |

The antisense-oligonucleotides of formula S7 in form of gapmers (LNA segment 1—DNA segment—LNA segment 2) contain an LNA segment at the 5' terminal end consisting of 2 to 5, preferably 2 to 4 LNA units and contain an LNA segment at the 3' terminal end consisting of 2 to 5, preferably 2 to 4 LNA units and between the two LNA segments one DNA segment consisting of 6 to 14, preferably 7 to 12 and more preferably 8 to 11 DNA units.

The antisense-oligonucleotides of formula S7 contain the LNA nucleotides (LNA units) as disclosed herein, especially these disclosed in the chapter "Locked Nucleic Acids (LNA®)" and preferably these disclosed in the chapter "Preferred LNAs". The LNA units and the DNA units may comprise standard nucleobases such as adenine (A), cytosine (C), guanine (G), thymine (T) and uracil (U), but may also contain modified nucleobases as disclosed in the chapter "Nucleobases". The antisense-oligonucleotides of formula S7 or the LNA segments and the DNA segment of the antisense-oligonucleotide may contain any internucleotide linkage as disclosed herein and especially these disclosed in the chapter "Internucleotide Linkages (IL)". The antisense-oligonucleotides of formula S7 may optionally also contain endgroups at the 3' terminal end and/or the 5' terminal end and especially these disclosed in the chapter "Terminal groups".

Experiments have shown that modified nucleobases do not considerably increase or change the activity of the inventive antisense-oligonucleotides in regard to tested neurological and oncological indications. The modified nucleobases 5-methylcytosine or 2-aminoadenine have been demonstrated to further increase the activity of the antisense-oligonucleotides of formula S7 especially if 5-methylcytosine is used in the LNA nucleotides only or in the LNA nucleotides and in the DNA nucleotides and/or if 2-aminoadenine is used in the DNA nucleotides and not in the LNA nucleotides.

The preferred gapmer structure of the antisense-oligonucleotides of formula S7 is as follows: 3-8-3, 4-8-2, 2-8-4, 3-8-4, 4-8-3, 4-8-4, 3-9-3, 4-9-2, 2-9-4, 4-9-3, 3-9-4, 4-9-4, 3-10-3, 2-10-4, 4-10-2, 3-10-4, 4-10-3, 4-10-4, 2-11-4, 4-11-2, 3-11-4, 4-11-3 and still more preferred: 3-8-3, 3-8-4, 4-8-3, 4-8-4, 3-9-3, 4-9-3, 3-9-4, 4-9-4, 3-10-3, 3-10-4, 4-10-3, 4-10-4, 3-11-4, and 4-11-3.

As LNA units for the antisense-oligonucleotides of formula S7 especially β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-(NCH$_3$)-LNA ($b^7$), β-D-(ONH)-LNA ($b^8$) and β-D-(ONCH$_3$)-LNA ($b^9$) are preferred. Experiments have been shown that all of these LNA units $b^1$, $b^2$, $b^4$, $b^5$, $b^6$, $b^7$, $b^8$, and $b^9$ can be synthesized with the required effort and lead to antisense-oligonucleotides of comparable stability and activity. However based on the experiments the LNA units $b^1$, $b^2$, $b^4$, $b^5$, $b^6$, and $b^7$ are further preferred. Still further preferred are the LNA units $b^1$, $b^2$, $b^4$, $b^6$, and $b^7$, and even more preferred are the LNA units $b^1$ and $b^4$ and most preferred also in regard to the complexity of the chemical synthesis is the β-D-oxy-LNA ($b^1$).

So far no special 3' terminal group or 5' terminal group could be found which remarkably had changed or increased the stability or activity for oncological or neurological indications, so that 3' and 5' end groups are possible but not explicitly preferred.

Various internucleotide bridges or internucleotide linkages are possible. In the formulae disclosed herein the internucleotide linkage IL is represented by -IL'-Y-. Thus, IL=-IL'-Y—=—X"—P(=X$^-$)(X$^-$)—Y—, wherein IL is preferably selected form the group consisting of:

—O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O—. Preferred are the internucleotide linkages IL selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(OCH$_3$)—O—, —O—P(O)(NH(CH$_3$))—O—, —O—P(O)[N(CH$_3$)$_2$]—O—, —O—P(O)(OCH$_2$CH$_2$OCH$_3$)—O—, and more preferred selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, and still more preferred selected from —O—P(O)(O$^-$)—O—, —O—P(O)(S$^-$)—O—, —O—P(S)(S$^-$)—O—, and most preferably selected from —O—P(O)(O$^-$)—O— and —O—P(O)(S$^-$)—O—.

Thus, the present invention is preferably directed to an antisense-oligonucleotide in form of a gapmer consisting of 10 to 28 nucleotides, preferably 11 to 24 nucleotides, more preferably 12 to 20, and still more preferably 13 to 19 or 14 to 18 nucleotides and 1 to 5 of these nucleotides at the 5' terminal end and 1 to 5 nucleotides at the 3' terminal end of the antisense-oligonucleotide are LNA nucleotides and between the LNA nucleotides at the 5' terminal end and the 3' terminal end a sequence of at least 6, preferably 7 and more preferably 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^9$-ATTAATAA-N$^{10}$-3' (Seq. ID No. 101), wherein N$^9$ represents: CATATTTATATACAGGC-, ATATTTATATACAGGC-, TATTTATATACAGGC-, ATTTATATACAGGC-, TTTATATACAGGC-, TTATATACAGGC-, TATATACAGGC-, ATATACAGGC-, TATACAGGC-, ATACAGGC-, TACAGGC-, ACAGGC-, CAGGC-, AGGC-, GGC-, GC-, or C-;

N$^{10}$ represents: -AGTGCAAATGTTATTGG, -AGTGCAAATGTTATTG, -AGTGCAAATGTTATT, -AGTGCAAATGTTAT, -AGTGCAAATGTTA, -AGTGCAAATGTT, -AGTGCAAATGT, -AGTGCAAATG, -AGTGCAAAT, -AGTGCAAA, -AGTGCAA, -AGTGCA, -AGTGC, -AGTG, -AGT, -AG, or -A; and the LNA nucleotides are selected from β-D-oxy-LNA ($b^1$), β-D-thio-LNA ($b^2$), α-L-oxy-LNA ($b^4$), β-D-ENA ($b^5$), β-D-(NH)-LNA ($b^6$), β-D-(NCH$_3$)-LNA ($b^7$), β-D-(ONH)-LNA ($b^8$) and β-D-(ONCH$_3$)-LNA ($b^9$); and preferably from β-D-oxy-LNA ($b^1$), β-D-thio-LNA ($b^2$), α-L-oxy-LNA ($b^4$), β-D-(NH)-LNA ($b^6$), and β-D-(NCH$_3$)-LNA ($b^7$); and the internucleotide linkages are selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—, —O—P(O)(CH$_3$)—O—, —O—P(O)(OCH$_3$)—O—, —O—P(O)(NH(CH$_3$))—O—, —O—P(O)[N(CH$_3$)$_2$]—O—, —O—P(O)(BH$_3^-$)—O—, —O—P(O)(OCH$_2$CH$_2$OCH$_3$)—O—, —O—P(O)(OCH$_2$CH$_2$SCH$_3$)—O—, —O—P(O)(O$^-$)—N(CH$_3$)—, —N(CH$_3$)—P(O)(O$^-$)—O-; and preferably from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

More preferably N$^9$ represents: TATTTATATACAGGC-, ATTTATATACAGGC-, TTTATATACAGGC-, TTATATACAGGC-, TATATACAGGC-, ATATACAGGC-, TATACAGGC-, ATACAGGC-, TACAGGC-, ACAGGC-, CAGGC-, AGGC-, GGC-, GC-, or C-; and N$^{10}$ represents: -AGTGCAAATGTTATT, -AGTGCAAATGTTAT, -AGTGCAAATGTTA, -AGTGCAAATGTT, -AGTGCAAATGT, -AGTGCAAATG, -AGTGCAAAT, -AGTGCAAA, -AGTGCAA, -AGTGCA, -AGTGC, -AGTG, -AGT, -AG, or -A.

Still further preferred, the present invention is directed to an antisense-oligonucleotide in form of a gapmer consisting of 11 to 24 nucleotides, more preferably 12 to 20, and still more preferably 13 to 19 or 14 to 18 nucleotides and 2 to 5 of these nucleotides at the 5' terminal end and 2 to 5 nucleotides at the 3' terminal end of the antisense-oligonucleotide are LNA nucleotides and between the LNA nucleotides at the 5' terminal end and the 3' terminal end a sequence of at least 7, preferably at least 8 DNA nucleotides is present, and the antisense-oligonucleotide is capable of hybridizing with a region of the gene encoding the TGF-R$_{II}$ or with a region of the mRNA encoding the TGF-R$_{II}$, wherein the antisense-oligonucleotide is represented by the following sequence 5'-N$^9$-ATTAATAA-N$^{10}$-3' (Seq. ID No. 101), wherein N$^9$ represents: TTATATACAGGC-, TATATACAGGC-, ATATACAGGC-, TATACAGGC-, ATACAGGC-, TACAGGC-, ACAGGC-, CAGGC-, AGGC-, GGC-, GC-, or C-; preferably N$^9$ represents: ATATACAGGC-, TATACAGGC-, ATACAGGC-, TACAGGC-, ACAGGC-, CAGGC-, AGGC-, GGC-, GC-, or C-; and N$^{10}$ represents: -AGTGCAAATGTT, -AGTGCAAATGT, -AGTGCAAATG, -AGTGCAAAT, -AGTGCAAA, -AGTGCAA, -AGTGCA, -AGTGC, -AGTG, -AGT, -AG, or -A; preferably N$^{10}$ represents: -AGTGCAAATG, -AGTGCAAAT, -AGTGCAAA, -AGTGCAA, -AGTGCA, -AGTGC, -AGTG, -AGT, -AG, or -A; and the LNA nucleotides are selected from β-D-oxy-LNA (b$^1$), β-D-thio-LNA (b$^2$), α-L-oxy-LNA (b$^4$), β-D-(NH)-LNA (b$^6$), and β-D-(NCH$_3$)-LNA (b$^7$); and the internucleotide linkages are selected from —O—P(O)(O$^-$)—O—, —O—P(O)(S$^-$)—O—, —O—P(S)(S$^-$)—O—, —S—P(O)(O$^-$)—O—, —S—P(O)(S$^-$)—O—, —O—P(O)(O$^-$)—S—, —O—P(O)(S$^-$)—S—, —S—P(O)(O$^-$)—S—; and preferably selected from phosphate, phosphorothioate and phosphorodithioate;

and salts and optical isomers of the antisense-oligonucleotide. Such preferred antisense-oligonucleotides may not contain any modified 3' and 5' terminal end or may not contain any 3' and 5' terminal group and may as modified nucleobase contain 5-methylcytosine and/or 2-aminoadenine.

Especially preferred are the gapmer antisense-oligonucleotides of Seq. ID No. 474 to Seq. ID No. 508 containing a segment of 2 to 5, preferably 2 to 4 and more preferably 3 to 4 LNA units at the 3' terminus and a segment of 2 to 5, preferably 2 to 4 and more preferably 3 to 4 LNA units at the 5' terminus and a segment of at least 6, preferably 7 and more preferably 8 DNA units between the two segments of LNA units, wherein the LNA units are selected from β-D-oxy-LNA (b$^1$), β-D-thio-LNA (b$^2$), α-L-oxy-LNA (b$^4$), β-D-(NH)-LNA (b$^6$), and β-D-(NCH$_3$)-LNA (b$^7$) and the internucleotide linkages are selected from phosphate, phosphorothioate and phosphorodithioate. Such preferred antisense-oligonucleotides may not contain any modified 3' and 5' terminal end or may not contain any 3' and 5' terminal group and may as modified nucleobase contain 5-methylcytosine in the LNA units, preferably all the LNA units and/or 2-aminoadenine in some or all DNA units and/or 5-methylcytosine in some or all DNA units.

Also especially preferred are the gapmer antisense-oligonucleotides of Table 9 (Seq. ID No. 284a to 236b).

TABLE 4

| SP | L | Seq ID No. | Sequence, 5'-3' |
|---|---|---|---|
| 357 | 10 | 232a | C*b$^1$sGb$^1$sdTsdC*sdAsdTsdAsdGsAb$^1$sC*b$^1$ |
| 357 | 10 | 232b | C*b$^1$Gb$^1$dTdC*dAdTdAdGAb$^1$C*b$^1$ |
| 356 | 12 | 233a | Tb$^1$sC*b$^1$sGb$^1$sdTsdC*sdAsdTsdAsdGsAb$^1$sC*b$^1$sC*b$^1$ |
| 356 | 12 | 233b | Tb$^1$C*b$^1$Gb$^1$dTdC*dAdTdAdGAb$^1$C*b$^1$C*b$^1$ |
| 356 | 12 | 233c | Tb$^1$sC*b$^1$sGb$^1$sdTsdC*sdAsdTsdAsdGsdAsC*b$^1$sC*b$^1$ |
| 356 | 12 | 233d | Tb$^1$sdC*sdGsdTsdC*sdAsdTsdAsdGsdAsC*b$^1$sC*b$^1$ |
| 356 | 12 | 233e | Tb$^1$sC*b$^1$sdGsdTsdCsdAsdTsdAsdGsdAsdC*sC*b$^1$ |
| 355 | 13 | 234a | Tb$^1$sC*b$^1$sGb$^1$sTb$^1$sdCsdAsdTsdAsdGsdAsC*b$^1$sC*b$^1$sGb$^1$ |
| 355 | 13 | 234b | Tb$^1$C*b$^1$Gb$^1$Tb$^1$dCdAdUdAdGdAC*b$^1$C*b$^1$Gb$^1$ |
| 355 | 13 | 234c | Tb$^1$sC*b$^1$sGb$^1$sTb$^1$sdC*sdAsdTsdAsdGsdAsC*b$^1$sC*b$^1$sGb$^1$ |
| 355 | 13 | 234d | Tb$^1$sC*b$^1$sGb$^1$sdTsdC*sdA*sdTsdA*sdGsdA*sdC*sC*b$^1$sGb$^1$ |
| 355 | 13 | 234e | Tb$^1$sC*b$^1$sdGsdTsdC*sdAsdTsdA*sdGsdA*sdC*sdCsGb$^1$ |
| 355 | 13 | 234f | Tb$^1$sdCsdGsdTsdC*sdA*sdTsdAsdGsAb$^1$sC*b$^1$sC*b$^1$sGb$^1$ |
| 354 | 13 | 142c | C*b$^1$sGb$^1$sTb$^1$sdCsdAsdTsdAsdGsdAsdCsdCsGb$^1$sAb$^1$ |
| 355 | 14 | 143i | C*b$^1$sTb$^1$sC*b$^1$sGb$^1$sdTsdCsdAsdTsdAsdGsAb$^1$sC*b$^1$sC*b$^1$sGb$^1$ |
| 355 | 14 | 143j | C*b$^4$ssTb$^4$ssC*b$^4$ssdGssdTssdCssdAssdTssdAssdGssdA*ssC*b$^4$ssC*b$^4$ssGb$^4$ |
| 355 | 14 | 143h | C*b$^1$sTb$^1$sdCsdGsdTsdCsdAsdTsdAsdGsdAsC*b$^1$sC*b$^1$sGb$^1$ |
| 355 | 14 | 143k | C*b$^2$ssTb$^2$ssC*b$^2$ssdGssdTssdCssdAssdTssdAssdGssdAssC*b$^2$ssC*b$^2$ssGb$^2$ |
| 355 | 14 | 143m | C*b$^1$Tb$^1$C*b$^1$Gb$^1$dUsdCsdAsdTsdAsdGsAb$^1$C*b$^1$C*b$^1$Gb$^1$ |
| 355 | 14 | 143n | C*b$^1$sTb$^1$sC*b$^1$sGb$^1$sTb$^1$sdCsdA*sdTsdA*sdGsdA*sC*b$^1$sC*b$^1$sGb$^1$ |
| 355 | 14 | 143o | C*b$^1$sTb$^1$sdCsdGsdUsdCsdAsdUsdAsGb$^1$sAb$^1$sC*b$^1$sC*b$^1$sGb$^1$ |

TABLE 4-continued

| SP | L | Seq ID No. | Sequence, 5'-3' |
|---|---|---|---|
| 355 | 14 | 143p | C*b$^6$sTb$^6$sC*b$^6$sGb$^6$sdTsdCsdAsdTsdAsdGsdAsC*b$^6$sC*b$^6$sGb$^6$ |
| 355 | 14 | 143q | C*b$^7$sTb$^7$sC*b$^7$sdGsdUsdCsdA*sdUsdA*sdGsdA*sC*b$^7$sC*b$^7$sGb$^7$ |
| 355 | 14 | 143r | C*b$^4$sTb$^4$sC*b$^4$sGb$^4$sdTsdC*sdA*sdTsdAsdGsdAsdC*sC*b$^4$sGb$^4$ |
| 355 | 14 | 143s | C*b$^4$Tb$^4$C*b$^4$Gb$^4$dTdCdAdTdAdGdAdCC*b$^4$Gb$^4$ |
| 355 | 14 | 143t | C*b$^1$ssTb$^1$ssC*b$^1$ssdGssdTssdC*ssdAssdTssdAssdGssdAssC*b$^1$ssC*b$^1$ssGb$^1$ |
| 355 | 14 | 143u | C*b$^1$Tb$^1$sdCsdGsdUsdC*sdAsdUsdAsdGsdAsC*b$^1$C*b$^1$Gb$^1$ |
| 355 | 14 | 143v | C*b$^1$Tb$^1$sdC*sdGsdTsdC*sdA*sdTsdAsdGsdAsC*b$^1$C*b$^1$Gb$^1$ |
| 355 | 14 | 143w | C*b$^6$sTb$^6$sdC*dGdTdC*dAdTdAdGdAsC*b$^6$sC*b$^6$sGb$^6$ |
| 355 | 14 | 143x | C*b$^7$sTb$^7$sC*b$^7$sGb$^7$sdTsdC*sdAsdTsdAsdGsdAsC*b$^7$sC*b$^7$sGb$^7$ |
| 355 | 14 | 143y | C*b$^7$sTb$^7$sdC*sdGsdTsdCsdAsdUsdAsdGsAb$^7$sC*b$^7$sC*b$^7$sGb$^7$ |
| 355 | 14 | 143z | C*b$^1$sTb$^1$sdC*sdGsdTsdC*sdAsdTsdAsdGsdAsC*b$^1$sC*b$^1$sGb$^1$ |
| 355 | 14 | 143aa | C*b$^1$Tb$^1$sdC*sdGsdTsdC*sdAsdTsdAsdGsdAsC*b$^1$C*b$^1$Gb$^1$ |
| 355 | 14 | 143ab | C*b$^1$sTb$^1$sdC*sdGsdTsdC*sdA*sdTsdAsdGsdA*sC*b$^1$sC*b$^1$sGb$^1$ |
| 355 | 14 | 143ac | C*b$^1$sTb$^1$sdC*sdGsdTsdCsdAsdTsdAsdGsdAsC*b$^1$sC*b$^1$sGb$^1$ |
| 355 | 14 | 143ad | C*b$^1$Tb$^1$dC*dGdTdCdAdTdAdGdAC*b$^1$C*b$^1$Gb$^1$ |
| 355 | 14 | 143ae | C*b$^1$sTb$^1$sdC*dGdTdC*dAdTdAdGdAsC*b$^1$sC*b$^1$sGb$^1$ |
| 355 | 14 | 143af | /5SpC3s/C*b$^1$sTb$^1$sdC*dGdTdC*dA*dTdAdGdA*sC*b$^1$sC*b$^1$sGb$^1$ |
| 355 | 14 | 143ag | C*b$^1$sTb$^1$sdC*dGdTdC*dA*dTdAdGdA*sC*b$^1$sC*b$^1$sGb$^1$/3SpC3s/ |
| 355 | 14 | 143ah | /5SpC3s/C*b$^1$sTb$^1$sdC*dGdTdC*dA*dTdAdGdA*sC*b$^1$sC*b$^1$sGb$^1$/3SpC3s/ |
| 355 | 14 | 143ai | C*b$^1$sTb$^1$sdC*sdGsdUsdC*sdA*sdUsdA*sdGsdA*sC*b$^1$sC*b$^1$sGb$^1$ |
| 355 | 14 | 143aj | C*b$^1$sTb$^1$sC*b$^1$sdGsdTsdCsdAsdTsdAsdGsdAsC*b$^1$sC*b$^1$sGb$^1$ |
| 356 | 14 | 145c | Gb$^1$sC*b$^1$sTb$^1$sdCsdGsdTsdCsdAsdTsdAsdGsAb$^1$sC*b$^1$sC*b$^1$ |
| 354 | 15 | 235i | C*b$^1$sTb$^1$sC*b$^1$sGb$^1$sdTdC*dAdTdAdGdAsC*b$^1$sC*b$^1$sGb$^1$sAb$^1$ |
| 354 | 15 | 235a | C*b$^1$ssTb$^1$ssdCssdGssdTssdCssdAssdTssdAssdGssdAssdCssdCssdGssAb$^1$ |
| 354 | 15 | 235b | C*b$^1$Tb$^1$dCdGdTdCdAdTdAdGdAdCdCdGAb$^1$ |
| 354 | 15 | 235c | C*b$^1$sTb$^1$sdCsdGsdTsdCsdA*sdUsdAsdGsdAsdCsC*b$^1$sGb$^1$sAb$^1$ |
| 354 | 15 | 235d | C*b$^1$Tb$^1$sdCsdGsdTsdCsdAsdTsdAsdGsdAsC*b$^1$C*b$^1$Gb$^1$Ab$^1$ |
| 354 | 15 | 235e | C*b$^4$sTb$^4$sC*b$^4$sdGsdTsdCsdAsdTsdAsdGsdAsdCsdCsGb$^4$sAb$^4$ |
| 354 | 15 | 235f | C*b$^6$sTb$^6$sC*b$^6$sdGsdTsdCsdA*dTsdAdGdAdCsC*b$^6$sGb$^6$sAb$^6$ |
| 354 | 15 | 235g | C*b$^1$sTb$^1$sC*b$^1$sGb$^1$sdTsdC*sdAsdTsdAsdGsdAsdC*sdC*sdGsAb$^1$ |
| 354 | 15 | 235h | C*b$^1$ssTb$^1$ssdCssdGssdUssdCssdAssdUssdAssdGssdAssdCssdCssGb$^1$ssAb$^1$ |
| 355 | 15 | 144c | Gb$^1$sC*b$^1$sTb$^1$sdCsdGsdTsdCsdAsdTsdAsdGsdAsC*b$^1$sC*b$^1$sGb$^1$ |
| 354 | 16 | 141c | Gb$^1$sC*b$^1$sTb$^1$sC*b$^1$sdGsdTsdC*sdAsdTsdAsdGsdAsC*b$^1$sC*b$^1$sGb$^1$sAb$^1$ |
| 354 | 16 | 141d | Gb$^1$C*b$^1$Tb$^1$C*b$^1$sdGsdTsdC*sdAsdTsdAsdGsdAsdCsC*b$^1$Gb$^1$Ab$^1$ |
| 354 | 16 | 141e | Gb$^4$sC*b$^4$sTb$^4$sC*b$^4$sdGsdTsdC*sdAsdTsdAsdGsdA*sdC*sdC*sGb$^4$sAb$^4$ |
| 354 | 16 | 141f | Gb$^1$sdC*sdTsdCsdGsdTsdC*sdA*sdTsdAsdGsdA*sdC*sdC*sdGsAb$^1$ |
| 354 | 16 | 141g | Gb$^2$sC*b$^2$sTb$^2$sdCsdGsdUsdCsdAsdTsdA*sdGsdAsdCsC*b$^2$sGb$^2$sAb$^2$ |

TABLE 4-continued

| SP | L | Seq ID No. | Sequence, 5'-3' |
|---|---|---|---|
| 354 | 16 | 141h | **Gb$^4$ssC*b$^4$ssTb$^4$ssdCssdGssdTssdCssdAssdTssdAssdGssdAssC*b$^4$ssC*b$^4$ssGb$^4$ssAb$^4$** |
| 354 | 16 | 141i | **Gb$^1$C*b$^1$**dTdCdGdTdCdA*dTdA*dGdA*dC**C*b$^1$Gb$^1$Ab$^1$** |
| 354 | 16 | 141j | **Gb$^1$sC*b$^1$sTb$^1$sdCsdGsdTsdCsdAsdTsdAsdGsdAsdCsC*b$^1$sGb$^1$sAb$^1$** |
| 351 | 16 | 139c | **C*b$^1$sGb$^1$sTb$^1$sdCsdAsdTsdAsdGsdAsdCsdCsdGsdAsGb$^1$sC*b$^1$sC*b$^1$** |
| 354 | 17 | 237a | **Tb$^1$sGb$^1$sC*b$^1$sTb$^1$sC*b$^1$**sdGsdTsdC*sdAsdTsdAsdGs**Ab$^1$sC*b$^1$sC*b$^1$sGb$^1$sAb$^1$** |
| 354 | 17 | 237b | **Tb$^2$sGb$^2$sC*b$^2$**sdTsdGsdTsdC*sdAsdTsdAsdGs**Ab$^2$sC*b$^2$sC*b$^2$sGb$^2$sAb$^2$** |
| 354 | 17 | 237c | **Tb$^1$sGb$^1$sC*b$^1$sTb$^1$**sdC*sdGsdTsdCsdAsdTsdAsdGsdAsdC*s**C*b$^1$sGb$^1$sAb$^1$** |
| 354 | 17 | 237d | Tb$^1$sdGsdCsdUsdC*sdGsdTsdC*sdAsdUsdAsdGs**Ab$^1$sC*b$^1$sC*b$^1$sGb$^1$sAb$^1$** |
| 354 | 17 | 237e | **Tb$^1$sGb$^1$sC*b$^1$**sdTsdGsdTsdC*sdA*sdTsdA*sdGs**Ab$^1$sC*b$^1$sC*b$^1$sGb$^1$sAb$^1$** |
| 354 | 17 | 237f | Tb$^1$Gb$^1$dC*dTdGdTdC*dAdTdAdGdA**C*b$^1$C*b$^1$Gb$^1$Ab$^1$** |
| 354 | 17 | 237g | Tb$^1$sdGsdC*sdTsdGsdTsdC*sdAsdTsdAsdGsdAsdC*s**C*b$^1$sGb$^1$sAb$^1$** |
| 354 | 17 | 237h | **Tb$^1$Gb$^1$C*b$^1$Tb$^1$C*b$^1$**dGdTdC*dA*dTdA*dGdA*dC*dCGb$^1$Ab$^1$ |
| 354 | 17 | 237i | **Tb$^1$ssGb$^1$ssC*b$^1$ssTb$^1$ssC*b$^1$ssdGssdTssdCssdAssdTssdAssdGssdAssdCssC*b$^1$ssGb$^1$ssAb$^1$** |
| 354 | 17 | 237j | **Tb$^4$sGb$^4$sC*b$^4$**sdTdGdTdCdA*dTdA*dGdA*s**C*b$^4$sC*b$^4$sGb$^4$sAb$^4$** |
| 354 | 17 | 237k | **Tb$^6$sGb$^6$sC*b$^6$**sdUsdGsdUsdC*sdA*sdUsdA*sdGsdA*sdC*s**C*b$^6$sGb$^6$sAb$^6$** |
| 354 | 17 | 237m | **Tb$^7$sGb$^7$sC*b$^7$sTb$^7$**sdC*dGdTdC*dAdTdAdGdAs**C*b$^7$sC*b$^7$sGb$^7$sAb$^7$** |
| 353 | 18 | 238a | **Tb$^1$sGb$^1$sC*b$^1$sTb$^1$sC*b$^1$**sdGsdTsdC*sdAsdTsdAsdGsdAs**C*b$^1$sC*b$^1$sGb$^1$sAb$^1$sGb$^1$** |
| 353 | 18 | 238b | **Tb$^7$sGb$^7$sC*b$^7$sTb$^7$sC*b$^7$**sdGsdTsdC*sdAsdTsdAsdGsdAsdC*sdC*sdGsdAsGb$^7$ |
| 353 | 18 | 238c | **Tb$^1$sGb$^1$sC*b$^1$sTb$^1$**sdC*sdGsdTsdCsdAsdTsdAsdGsdAsdC***C*b$^1$sGb$^1$sAb$^1$sGb$^1$** |
| 353 | 18 | 238d | Tb$^1$sGb$^1$sdC*sdTsdC*sdGsdTsdCsdAsdTsdAsdGsdAsdC*sdC*sGb$^1$sAb$^1$sGb$^1$ |
| 353 | 18 | 238e | **Tb$^1$sGb$^1$sC*b$^1$sTb$^1$**sdC*sdGsdTsdCsdAsdTsdAsdGsdAsdC*sdC*sGb$^1$sAb$^1$sGb$^1$ |
| 353 | 18 | 238f | Tb$^1$Gb$^1$dC*dUdC*dGdTdC*dAdTdAdGdA***C*b$^1$C*b$^1$Gb$^1$Ab$^1$Gb$^1$** |
| 353 | 18 | 238g | **Tb$^4$Gb$^4$C*b$^4$Tb$^4$sdCsdGsdTsdCsdAsdTsdAsdGsdAsdCb$^4$C*b$^4$Gb$^4$Ab$^4$Gb$^4$** |
| 353 | 18 | 238h | **Tb$^1$ssGb$^1$ssC*b$^1$**ssdTssdC*ssdGssdTssdC*ssdAssdTssdA*ssdGssdAssdC*ssdC*ssGb$^1$ssAb$^1$ssGb$^1$ |
| 353 | 18 | 238i | **Tb$^2$Gb$^2$C*b$^2$**dTdCdGdTdC*dAdTdAdGdA**C*b$^2$C*b$^2$Gb$^2$Ab$^2$Gb$^2$** |
| 352 | 19 | 239a | **Tb$^1$sGb$^1$sC*b$^1$sTb$^1$sC*b$^1$**sdGsdTsdCsdAsdTsdAsdGsdAsdC*s**C*b$^1$sGb$^1$sAb$^1$sGb$^1$sC*b$^1$** |
| 352 | 19 | 239b | **Tb$^6$Gb$^6$C*b$^6$Tb$^6$C*b$^6$**dGdTdC*dAdTdAdGdAdC***C*b$^6$Gb$^6$Ab$^6$Gb$^6$C*b$^6$** |
| 352 | 19 | 239c | **Tb$^1$sGb$^1$sC*b$^1$sTb$^1$**sdC*sdGsdTsdCsdAsdTsdAsdGsdAsdCsdGs**Ab$^1$sGb$^1$sC*b$^1$** |
| 352 | 19 | 239d | Tb$^1$sdGsdCsdTsdCsdGsdTsdCsdAsdTsdAsdGsdA*sdC*s**C*b$^1$sGb$^1$sAb$^1$sGb$^1$sC*b$^1$** |
| 352 | 19 | 239e | Tb$^4$sGb$^4$sdCsdUsdCsdGsdUsdCsdTsdAsdAsdGsdA*sdC*sdC*s**Gb$^4$sAb$^4$sGb$^4$sC*b$^4$** |
| 352 | 19 | 239f | **Tb$^2$ssGb$^2$ssC*b$^2$ssTb$^2$ssC*b$^2$ssdGssdTssdCssdAssdTssdAssdGssdAssdCssdCssdGssdAssGb$^2$ssC*b$^2$** |

TABLE 4-continued

| SP | L | Seq ID No. | Sequence, 5'-3' |
|---|---|---|---|
| 352 | 20 | 240a | C*b¹sTb¹sGb¹sC*b¹sTb¹sdC*sdGsdTsdCsdAsdTsdAsdGsdAsdC*sC*b¹sGb¹sAb¹sGb¹sC*b¹ |
| 352 | 20 | 240b | C*b²sTb²sGb²sdC*sdTsdC*sdGsdTsdCsdAsdTsdAsdGsdAsdC*sC*b²sGb²sAb²sGb²sC*b² |
| 352 | 20 | 240c | C*b¹Tb¹Gb¹dC*dTdC*dGdTdCdAdTdAdGdAdC*dC*Gb¹Ab¹Gb¹C*b¹ |
| 352 | 20 | 240d | C*b¹sdUsdGsdCsdUsdC*sdGsdTsdCsdAsdTsdAsdGsdAsdC*sC*b¹sGb¹sAb¹sGb¹sC*b¹ |
| 352 | 20 | 240e | C*b⁴sTb⁴sGb⁴sC*b⁴sdTsdCsdGsdTsdCsdAsdTsdAsdGsdAsdCsdCsGb⁴sAb⁴sGb⁴sC*b⁴ |
| 351 | 22 | 241a | Gb¹sC*b¹sTb¹sGb¹sC*b¹sdTsdC*sdGsdTsdCsdAsdTsdAsdGsdAsdCsdC*sGb¹sAb¹sGb¹sC*b¹sC*b¹ |
| 351 | 22 | 241b | Gb¹C*b¹Tb¹Gb¹C*b¹dTdC*dGdTdC*dAdTdAdGdAdC*dC*Gb¹Ab¹Gb¹C*b¹C*b¹ |
| 351 | 22 | 241c | Gb¹sC*b¹sTb¹sGb¹sC*b¹sdTsdCsdGsdTsdCsdAsdTsdAsdGsdAsdCsdCsGb¹sAb¹sGb¹sC*b¹sC*b¹ |
| 350 | 24 | 242a | C*b¹sGb¹sC*b¹sTb¹sGb¹sC*b¹sdCsdTsdCsdGsdTsdCsdAsdTsdAsdGsdAsdCsdC*sdGsAb¹sGb¹sC*b¹sC*b¹sC*b¹ |
| 350 | 24 | 242b | C*b¹Gb¹C*b¹Tb¹Gb¹dC*dTdCdGdTdCdAdTdAdGdAdCdC*dGAb¹Gb¹C*b¹C*b¹C*b¹ |
| 349 | 26 | 243a | C*b¹sC*b¹sGb¹sC*b¹sTb¹sdGsdC*sdTsdCsdGsdTsdC*sdAsdTsdAsdGsdAsdCsdC*sdGsdAsGb¹sC*b¹sC*b¹sC*b¹sC*b¹ |
| 349 | 26 | 243b | C*b¹C*b¹Gb¹C*b¹Tb¹dGdC*dTdCdGdTdC*dAdTdAdGdAdCdC*dGdAGb¹C*b¹C*b¹C*b¹C*b¹ |
| 348 | 28 | 244a | C*b¹sC*b¹sC*b¹sGb¹sC*b¹sdTsdGsdCsdTsdCsdGsdTsdC*sdAsdTsdAsdGsdAsdC*sdCsdGsdAsGsC*b¹sC*b¹sC*b¹sC*b¹sC*b¹sC*b¹ |
| 348 | 28 | 244b | C*b¹C*b¹C*b¹Gb¹C*b¹dTdGdC*dTdCdGdTdC*dAdTdAdGdAdC*dCdGdAdGC*b¹C*b¹C*b¹C*b¹C*b¹C*b¹ |

TABLE 5

| SP | L | Seq ID No. | Sequence, 5'-3' |
|---|---|---|---|
| 431 | 10 | 245a | Tb¹sAb¹sdC*sdGsdCsdGsdTsdC*sC*b¹sAb¹ |
| 431 | 10 | 245b | Tb¹Ab¹dCdGdC*dGdTdCC*b¹Ab¹ |
| 430 | 12 | 246a | Ab¹sTb¹sAb¹sdC*sdGsdCsdGsdTsdCsC*b¹sAb¹sC*b¹ |
| 430 | 12 | 246b | Ab¹Tb¹Ab¹dCdGdCdGdTdC*C*b¹Ab¹C*b¹ |
| 430 | 12 | 246c | Ab¹sTb¹sAb¹sdCsdGsdCsdGsdTsdC*sdC*sAb¹sC*b¹ |
| 430 | 12 | 246d | Ab¹sTb¹sdA*sdC*sdGsdCsdGsdTsdC*sdC*sdA*sC*b¹ |
| 430 | 12 | 246e | Ab¹sdTsdA*sdC*sdGsdC*sdGsdTsdC*sdC*sAb¹sC*b¹ |
| 430 | 13 | 247a | Gb¹sAb¹sTb¹sAb¹sdCsdGsdCsdGsdTsdCsC*b¹sAb¹sC*b¹ |
| 430 | 13 | 247b | Gb¹Ab¹Tb¹Ab¹dCdGdCdGdUdCC*b¹Ab¹C*b¹ |
| 430 | 13 | 247c | Gb¹sAb¹sTb¹sAb¹sdC*sdGsdCsdGsdTsdC*sC*b¹sAb¹sC*b¹ |
| 430 | 13 | 247d | Gb¹sAb¹sTb¹sdA*sdCsdGsdCsdGsdTsdCsdC*sAb¹sC*b¹ |
| 430 | 13 | 247e | Gb¹sAb¹sdTsdA*sdCsdGsdC*sdGsdTsdCsdC*sdA*sC*b¹ |
| 430 | 13 | 247f | Gb¹sdA*sdTsdA*sdC*sdGsdCsdGsdTsC*b¹sC*b¹sAb¹sC*b¹ |
| 431 | 13 | 153f | C*b¹sGb¹sAb¹sdTsdAsdCsdGsdCsdGsdTsdCsC*b¹sAb¹ |

TABLE 5-continued

| SP | L | Seq ID No. | Sequence, 5'-3' |
|---|---|---|---|
| 429 | 14 | 248a | Gb¹sAb¹sTb¹sAb¹sdC*sdGsdC*sdGsdTsdC*sC*b¹sAb¹sC*b¹sAb¹ |
| 429 | 14 | 248b | Gb¹Ab¹Tb¹Ab¹sdC*sdGsdCsdGsdTsdC*sdC*sAb¹C*b¹Ab¹ |
| 429 | 14 | 248c | Gb⁴sAb⁴sTb⁴sAb⁴sdC*sdGsdCsdGsdTsdC*sdC*sdA*sC*b⁴sAb⁴ |
| 429 | 14 | 248d | Gb¹sdA*sdTsdAsdCsdGsdCsdGsdTsdCsdC*sdA*sdCsAb¹ |
| 429 | 14 | 248e | Gb²sAb²sTb²sdA*sdCsdGsdCsdGsdUsdCsdCsAb²sC*b²sAb² |
| 429 | 14 | 248f | Gb⁴ssAb⁴ssdTssdAssdCssdGssdCssdGssdTssdCssdCssAb⁴ssC*b⁴ssAb⁴ |
| 429 | 14 | 248g | Gb¹Ab¹dTdA*dCdGdCdGdTdCC*b¹Ab¹C*b¹Ab¹ |
| 429 | 15 | 152h | C*b¹sGb¹sAb¹sTb¹sdAsdCsdGsdCsdGsdTsdCsdCsAb¹sC*b¹sAb¹ |
| 429 | 15 | 152i | C*b¹Gb¹Ab¹Tb¹sdAsdCsdGsdCsdGsdUsdCsdC*sAb¹C*b¹Ab¹ |
| 429 | 15 | 152j | C*b¹Gb¹Ab¹Tb¹sdA*sdCsdGsdCsdGsdUsdCsdCsAb¹C*b¹Ab¹ |
| 429 | 15 | 152k | C*b⁶sGb⁶sAb⁶sTb⁶sdAdC*dGdCdGdTdCdC*sAb⁶sC*b⁶sAb⁶ |
| 429 | 15 | 152m | C*b¹sGb¹sAb¹sTb¹sdAsdCsdGsdCsdGsdTsdC*sdC*sAb¹sC*b¹sAb¹ |
| 429 | 15 | 152n | C*b¹Gb¹Ab¹Tb¹sdAsdC*sdGsdC*sdGsdTsdC*sdC*sAb¹C*b¹Ab¹ |
| 429 | 15 | 152o | C*b¹sGb¹sAb¹sTb¹sdA*sdCsdGsdCsdGsdTsdCsdC*sAb¹sC*b¹sAb¹ |
| 429 | 15 | 152p | C*b¹sGb¹sAb¹sTb¹sdAsdCsdGsdCsdGsdTsdC*sAb¹sC*b¹sAb¹ |
| 429 | 15 | 152q | C*b¹Gb¹Ab¹Tb¹dAdCdGdC*dGdTdCdC*Ab¹C*b¹Ab¹ |
| 429 | 15 | 152r | C*b¹sGb¹sAb¹sTb¹sdAdC*dGdC*dGdTdC*dC*sAb¹sC*b¹sAb¹ |
| 429 | 15 | 152s | /5SpC3s/C*b¹sGb¹sAb¹sTb¹sdAsdC*sdGsdC*sdGsdTsdCsdCsAb¹sC*b¹sAb¹ |
| 429 | 15 | 152t | C*b¹sGb¹sAb¹sTb¹sdAsdC*sdGsdC*sdGsdTsdCsdCsAb¹sC*b¹sAb¹/3SpC3s/ |
| 429 | 15 | 152u | /5SpC3s/C*b¹sGb¹sAb¹sTb¹sdAsdC*sdGsdC*sdGsdTsdCsdCsAb¹sC*b¹sAb¹/3SpC3s/ |
| 429 | 15 | 152v | C*b¹sGb¹sAb¹sTb¹sdA*sdC*sdGsdC*sdGsdUsdC*sdC*sAb¹sC*b¹sAb¹ |
| 429 | 15 | 152w | C*b⁷sGb⁷sAb⁷sdTsdAsdCsdGsdC*sdGsdTsdCsCsC*b⁷sAb⁷sC*b⁷sAb⁷ |
| 429 | 15 | 152z | C*b⁷sGb⁷sdAsdUsdAsdCsdGsdC*sdGsdUsdCsC*b⁷sAb⁷sC*b⁷sAb⁷ |
| 429 | 15 | 152aa | C*b¹ssGb¹ssAb¹ssdTssdAssdC*ssdGssdCssdGssdTssdCssdC*ssAb¹ssC*b¹ssAb¹ |
| 429 | 15 | 152ab | C*b⁴ssGb⁴ssAb⁴ssdTssdA*ssdCssdGssdCssdGssdTssdCssdCssdA*ssC*b⁴ssAb⁴ |
| 429 | 15 | 152ac | C*b²ssGb²ssAb²ssTb²ssdAssdCssdGssdCssdGssdTssdCssdCssdAssdCssAb² |
| 429 | 15 | 152ad | C*b¹Gb¹Ab¹Tb¹dAdCdGdCdGdUdCC*b¹Ab¹C*b¹Ab¹ |
| 429 | 15 | 152ae | C*b¹sGb¹sAb¹sTb¹sAb¹sdCsdGsdCsdGsdUsdCsdCsAb¹sC*b¹sAb¹ |
| 429 | 15 | 152af | C*b¹sGb¹sdA*sdTsdA*sdCsdGsdCsdGsdCsdTsC*b¹sC*b¹sAb¹sC*b¹sAb¹ |
| 429 | 15 | 152ag | C*b⁶sGb⁶sAb⁶sdTsdAsdCsGsdCsdGsdCsdGsdTsdCsC*b⁶sAb⁶sC*b⁶sAb⁶ |
| 429 | 15 | 152ah | C*b⁷sGb⁷sAb⁷sdUsdA*sdCsdGsdCsdGsdUsdCsdCsAb⁷sC*b⁷sAb⁷ |
| 429 | 15 | 152ai | C*b⁴sGb⁴sAb⁴sTb⁴sdA*sdCsdGsdCsdGsdTsdC*sdC*sdA*sC*b⁴sAb⁴ |
| 429 | 15 | 152aj | C*b⁴Gb⁴Ab⁴Tb⁴dAdCdGdCdGdTdCdCdAC*b⁴Ab⁴ |
| 429 | 15 | 152ak | C*b¹sGb¹sAb¹sdTsdAsdCsdGsdCsdGsdCsdGsdTsdCsdCsAb¹sC*b¹sAb¹ |
| 428 | 16 | 249a | C*b¹sGb¹sAb¹sTb¹sdAdCdGdCdGdTdCdC*sAb¹sC*b¹sAb¹sGb¹ |

TABLE 5-continued

| SP | L | Seq ID No. | Sequence, 5'-3' |
|---|---|---|---|
| 428 | 16 | 249b | C*b¹ssGb¹ssdAssdTssdAssdCssdGssdCssdGssdTssdCssdCssdAssdCssdAssGb¹ |
| 428 | 16 | 249c | C*b¹Gb¹dAdTdAdCdGdCdGdTdCdCdAdCdAGb¹ |
| 428 | 16 | 249d | C*b¹sGb¹sdAsdUsdAsdC*sdGsdCsdGsdUsdCsdC*sdAsC*b¹sAb¹sGb¹ |
| 428 | 16 | 249e | C*b¹Gb¹sdAsdTsdAsdC*sdGsdC*sdGsdTsdCsdC*sAb¹C*b¹Ab¹Gb¹ |
| 428 | 16 | 249f | C*b⁴sGb⁴sAb⁴sdTsdAsdCsdGsdCsdGsdTsdCsdCsdAsdCsAb⁴sGb⁴ |
| 428 | 16 | 249g | C*b⁶Gb⁶Ab⁶dTdA*dCdGdCdGdTdC*dCdA*C*b⁶Ab⁶Gb⁶ |
| 428 | 16 | 249h | C*b¹sGb¹sAb¹sTb¹sdAsdC*sdGsdCsdGsdTsdCsdC*sdAsdC*sdAsGb¹ |
| 428 | 16 | 249i | C*b¹ssGb¹ssdAssdUssdAssdCssdGssdCssdGssdUssdCssdCssdAssdCssAb¹ssGb¹ |
| 428 | 17 | 250a | Gb¹sC*b¹sGb¹sAb¹sTb¹sdAsdCsdGsdC*sdGsdTsdCsC*b¹sAb¹sC*b¹sAb¹sGb¹ |
| 428 | 17 | 250b | Gb¹sC*b¹sGb¹sAb¹sdTsdAsdC*sdGsdC*sdGsdTsdC*sdC*sdAsC*b¹sAb¹sGb¹ |
| 428 | 17 | 250c | Gb¹sdC*sdGsdAsdUsdAsdCsdGsdC*sdGsdUsdCsC*b¹sAb¹sC*b¹sAb¹sGb¹ |
| 428 | 17 | 250d | Gb¹sC*b¹sGb¹sdA*sdTsdA*sdC*sdGsdC*sdGsdTsdC*sC*b¹sAb¹sC*b¹sAb¹sGb¹ |
| 428 | 17 | 250e | Gb¹C*b¹dGdAdTdAdCdGdC*dGdTdCdC*Ab¹C*b¹Ab¹Gb¹ |
| 428 | 17 | 250f | Gb¹sdC*sdGsdAsdTsdAsdCsdGsdC*sdGsdTsdCsdCsdAsC*b¹sAb¹sGb¹ |
| 428 | 17 | 250g | Gb²sC*b²sGb²sdAsdTsdAsdCsdGsdC*sdGsdTsdC*sC*b²sAb²sC*b²sAb²sGb² |
| 428 | 17 | 250h | Gb¹C*b¹Gb¹Ab¹Tb¹dA*dCdGdC*dGdTdC*dCdA*dC*Ab¹Gb¹ |
| 428 | 17 | 250i | Gb¹ssC*b¹ssGb¹ssAb¹ssTb¹ssdAssdCssdGssdCssdGssdTssdCssdCssdAssC*b¹ssAb¹ssGb¹ |
| 428 | 17 | 250j | Gb⁴sC*b⁴sGb⁴sdA*sdTsdA*sdCsdGsdCsdGsdTsdCsdCsAb⁴sC*b⁴sAb⁴sGb⁴ |
| 428 | 17 | 250k | Gb⁶sC*b⁶sGb⁶sdA*sdUsdAsdCsdGsdCsdGsdUsdC*sdAs*C*b⁶sAb⁶sGb⁶ |
| 428 | 17 | 250m | Gb⁷sC*b⁷sGb⁷sAb⁷sdTdAdCdGdCdGdTdC*dCsAb⁷sC*b⁷sAb⁷sGb⁷ |
| 427 | 18 | 251a | Gb¹sC*b¹sGb¹sAb¹sTb¹sdAsdCsdGsdCsdGsdTsdCsdC*sAb¹sC*b¹sAb¹sGb¹sGb¹ |
| 427 | 18 | 251b | Gb⁷sC*b⁷sGb⁷sAb⁷sTb⁷sdAsdC*sdGsdCsdGsdTsdCsdCsdAsdCsdAsdGsGb⁷ |
| 427 | 18 | 251c | Gb¹sC*b¹sGb¹sAb¹sdTsdAsdC*sdGsdCsdGsdTsdCsdC*sdAsC*b¹sAb¹sGb¹sGb¹ |
| 427 | 18 | 251d | Gb¹sC*b¹sGb¹sdAsdTsdAsdC*sdGsdC*sdGsdTsdCsdC*sdAsC*b¹sAb¹sGb¹sGb¹ |
| 427 | 18 | 251e | Gb¹sC*b¹sGb¹sAb¹sdTsdAsdC*sdGsdCsdGsdTsdCsdC*sdAsdC*sAb¹sGb¹sGb¹ |
| 427 | 18 | 251f | Gb¹C*b¹dGdAdUdA*dCdGdCdGdTdC*dC*Ab¹C*b¹Ab¹Gb¹Gb¹ |
| 427 | 18 | 251g | Gb⁴C*b⁴Gb⁴Ab⁴sdTsdAsdCsdGsdCsdGsdTsdCsdCsdAsAb⁴C*b⁴Ab⁴Gb⁴Gb⁴ |
| 427 | 18 | 251h | Gb¹ssC*b¹ssGb¹ssdA*ssdTssdA*ssdCssdGssdCssdGssdTssdCssdCssdA*ssdC*ssAb¹ssGb¹ssGb¹ |
| 427 | 18 | 251i | Gb²C*b²Gb²dAdTdAdCdGdC*dGdTdCdC*Ab²C*b²Ab²Gb²Gb² |
| 426 | 19 | 252a | Gb¹sC*b¹sGb¹sAb¹sTb¹sdAsdC*sdGsdCsdGsdTsdCsdCsdAsC*b¹sAb¹sGb¹sGb¹sAb¹ |
| 426 | 19 | 252b | Gb⁶C*b⁶Gb⁶Ab⁶Tb⁶dAdC*dGdCdGdTdCdC*dAC*b⁶Ab⁶Gb⁶Gb⁶Ab⁶ |

TABLE 5-continued

| SP | L | Seq ID No. | Sequence, 5'-3' |
|---|---|---|---|
| 426 | 19 | 252c | Gb$^1$**sC*b$^1$sGb$^1$sdAsdTsdAsdCsdGsdCsdGsdTsdCsdCsdAsdC*sAb$^1$sGb$^1$sGb$^1$sAb**$^1$ |
| 426 | 19 | 252d | Gb$^1$sdC*sdGsdA*sdTsdA*sdC*sdGsdCsdGsdTsdCsdCsdA*s**C*b$^1$sAb$^1$sGb$^1$sGb$^1$sAb**$^1$ |
| 426 | 19 | 252e | Gb$^4$**sC*b$^4$sdGsdAsdUsdAsdCsdGsdCsdGsdUsdCsdCsdAsdC*sAb$^4$sGb$^4$sGb$^4$sAb**$^4$ |
| 426 | 19 | 252f | Gb$^2$**ssC*b$^2$ssGb$^2$ssAb$^2$ssTb$^2$ssdAssdCssdGssdCssdGssdTssdCssdCssdAssdCssdAssdGssGb$^2$ssAb**$^2$ |
| 426 | 20 | 253a | Gb$^1$sGb$^1$**sC*b$^1$sGb$^1$sAb**$^1$sdTsdAsdCsdGsdCsdGsdTsdC*sdC*sdAs**C*b$^1$sAb$^1$sGb$^1$sGb$^1$sAb**$^1$ |
| 426 | 20 | 253b | Gb$^2$sGb$^2$**sC*b**$^2$sdGsdAsdTsdAsdC*sdGsdCsdGsdTsdC*sdC*sdAs**C*b$^2$sAb$^2$sGb$^2$sGb$^2$sAb**$^2$ |
| 426 | 20 | 253c | Gb$^1$Gb$^1$**C*b$^1$dGdAdTdAdCdGdCdGdTdCdCdAdC*Ab$^1$Gb$^1$Gb$^1$Ab**$^1$ |
| 426 | 20 | 253d | Gb$^1$sdGsdCsdGsdAsdTsdAsdCsdGsdC*sdGsdUsdCsdCsdAs**C*b$^1$sAb$^1$sGb$^1$sGb$^1$sAb**$^1$ |
| 426 | 20 | 253e | Gb$^4$sGb$^4$**sC*b$^4$sGb$^4$sdAsdTsdAsdCsdGsdCsdGsdTsdCsdCsdAsdCsAb$^4$sGb$^4$sGb$^4$sAb**$^4$ |
| 425 | 22 | 254a | Tb$^1$sGb$^1$sGb$^1$**sC*Gb$^1$sdAsdTsdAsdCsdGsdCsdGsdTsdCsdCsdAsdC*sAb$^1$sGb$^1$sGb$^1$sAb$^1$sC*b**$^1$ |
| 425 | 22 | 254b | Tb$^1$Gb$^1$Gb$^1$**C*b$^1$Gb**$^1$dAdTdAdC*dGdCdGdTdCdC*dAdCAb$^1$Gb$^1$Gb$^1$Ab$^1$**C*b**$^1$ |
| 425 | 22 | 254c | Tb$^6$sGb$^6$sGb$^6$**sC*b**$^6$sdAsdTsdAsdCsdGsdCsdGsdTsdCsdCsdAsdCsdAsdGsGb$^6$sAb$^6$**sC*b**$^6$ |
| 424 | 24 | 255a | **C*b$^1$sTb$^1$sGb$^1$sGb$^1$sC*b**$^1$sdAsdTsdAsdCsdGsdC*sdGsdTsdCsdC*sdAsdCsdAsGb$^1$sGb$^1$sAb$^1$**sC*b$^1$sGb**$^1$ |
| 424 | 24 | 255b | **C*b$^1$Gb$^1$Gb$^1$Gb$^1$C*b**$^1$dGdAdTdAdCdGdC*dGdTdCdC*dAdC*dAGb$^1$Gb$^1$Ab$^1$**C*b$^1$Gb**$^1$ |
| 423 | 26 | 256a | Gb$^1$**sC*b$^1$sTb$^1$sGb$^1$sGb**$^1$sdC*sdGsdAsdTsdAsdCsdGsdCsdGsdTsdCsdAsdCsdAsdGsGb$^1$sAb$^1$**sC*b$^1$sGb$^1$sAb**$^1$ |
| 423 | 26 | 256b | Gb$^1$**C*b$^1$Tb$^1$Gb$^1$Gb**$^1$dC*dGdAdTdAdCdGdCdGdTdCdCdAdC*dAdGGb$^1$Ab$^1$**C*b$^1$Gb$^1$Ab**$^1$ |
| 422 | 28 | 257a | Tb$^1$sGb$^1$**sC*b$^1$sTb$^1$sGb**$^1$sdGsdCsdGsdAsdTsdAsdC*sdGsdC*sdGsdTsdCsdCsdAsdCsdAsdGsGb$^1$sAb$^1$**sC*b$^1$sGb$^1$sAb**$^1$ |
| 422 | 28 | 257b | Tb$^1$Gb$^1$**C*b$^1$Tb$^1$Gb**$^1$dGdCdGdAdTdAdCdGdCdGdTdCdC*dAdC*dAdGGb$^1$Ab$^1$**C*b$^1$Gb$^1$Ab**$^1$ |

TABLE 6

| SP | L | Seq ID No. | Sequence, 5'-3' |
|---|---|---|---|
| 2067 | 10 | 258a | Gb$^1$sTb$^1$sdGsdTsdTsdTsdA*sdGsGb$^1$sGb$^1$ |
| 2067 | 10 | 258b | Gb$^1$sTb$^1$sdGsdUsdTsdTsdA*sdGsGb$^1$sGb$^1$ |
| 2066 | 12 | 259a | Ab$^1$sGb$^1$sTb$^1$sdGsdTsdTsdTsdA*sdGsGb$^1$sGb$^1$sAb$^1$ |
| 2066 | 12 | 259b | Ab$^1$Gb$^1$Tb$^1$dGdUdUdUdA*dGGb$^1$Gb$^1$Ab$^1$ |
| 2066 | 12 | 259c | Ab$^1$sGb$^1$sTb$^1$sdGsdTsdTsdTsdA*sdGsdGsGb$^1$sAb$^1$ |
| 2066 | 12 | 259d | Ab$^1$sGb$^1$sdTsdGsdTsdTsdTsdA*sdGsdGsdGsAb$^1$ |
| 2066 | 12 | 259e | Ab$^1$sdGsdTsdGsdTsdTsdTsdA*sdGsdGsGb$^1$sAb$^1$ |
| 2066 | 13 | 260a | Tb$^1$sAb$^1$sGb$^1$sTb$^1$sdGsdTsdTsdTsdAsdGsGb$^1$sGb$^1$sAb$^1$ |

TABLE 6-continued

| SP | L | Seq ID No. | Sequence, 5'-3' |
|---|---|---|---|
| 2066 | 13 | 260b | Tb$^1$Ab$^1$Gb$^1$Tb$^1$dGdUdUdUdAdGGb$^1$Gb$^1$Ab$^1$ |
| 2066 | 13 | 260c | Tb$^1$sAb$^1$sGb$^1$sTb$^1$sdGsdTsdTsdTsdA*sdGsGb$^1$sGb$^1$sAb$^1$ |
| 2066 | 13 | 260d | Tb$^1$sAb$^1$sGb$^1$**sdUsdGsdTsdTsdA*sdGsdGsGb$^1$sAb$^1$ |
| 2066 | 13 | 260e | Tb$^1$sAb$^1$sdGsdUsdGsdUsdUsdUsdA*sdGsdGsdGsAb$^1$ |
| 2066 | 13 | 260f | Tb$^1$sdA*sdGsdTsdGsdTsdTsdUsdA*sGb$^1$sGb$^1$sGb$^1$sAb$^1$ |
| 2065 | 14 | 261a | Tb$^1$sAb$^1$sGb$^1$sTb$^1$sdGsdTsdTsdTsdA*sdGsGb$^1$sGb$^1$sAb$^1$sGb$^1$ |
| 2065 | 14 | 261b | Tb$^1$Ab$^1$Gb$^1$Tb$^1$sdGsdTsdTsdTsdA*sdGsdGGb$^1$Ab$^1$Gb$^1$ |
| 2065 | 14 | 261c | Tb$^4$sAb$^4$sGb$^4$sTb$^4$sdGsdUsdTsdUsdA*sdGsdGsdGsAb$^4$sGb$^4$ |
| 2065 | 14 | 261d | Tb$^1$sdA*sdGsdUsdGsdTsdTsdUsdA*sdGsdGsdGsdA*sGb$^1$ |
| 2065 | 14 | 261e | Tb$^2$sAb$^2$sGb$^2$sdUsdGsdUsdUsdTsdAsdGsdGsGb$^2$sAb$^2$sGb$^2$ |
| 2065 | 14 | 261f | Tb$^4$sAb$^4$sdGsdTsdGsdTsdTsdTsdAsdGsdGsGb$^4$sAb$^4$sGb$^4$ |
| 2065 | 14 | 261g | Tb$^1$dGdTdGdTdTdA*dGGb$^1$Gb$^1$Ab$^1$Gb$^1$ |
| 2064 | 15 | 262a | Tb$^1$sAb$^1$sGb$^1$sTb$^1$sdGdTdTdA*dGdGsGb$^1$sAb$^1$sGb$^1$**sC*b**$^1$ |
| 2064 | 15 | 262b | Tb$^1$ssAb$^1$ssdGssdTssdGssdTssdTssdAssdGssdGssdGssdAssdGss**C*b**$^1$ |
| 2064 | 15 | 262c | Tb$^1$sAb$^1$sdGsdUsdGsdUsdUsdA*sdGsdGsdGsAb$^1$sGb$^1$**sC*b**$^1$ |
| 2064 | 15 | 262d | Tb$^1$dAdGdTdGdTdTdTdAdGdGdGdAd**GC*b**$^1$ |
| 2064 | 15 | 262e | Tb$^1$Ab$^1$sdGsdUsdGsdUsdTsdUsdAsdGsdGsGb$^1$Ab$^1$Gb$^1$**C*b**$^1$ |
| 2064 | 15 | 262f | Tb$^4$sAb$^4$sGb$^4$sdTsdGsdTsdTsdAsdGsdGsdGsdsdAsGb$^4$**sC*b**$^4$ |
| 2064 | 15 | 262g | Tb$^6$Ab$^6$Gb$^6$dUdGdTdTdUdAdGdGdGAb$^6$Gb$^6$**C*b**$^6$ |
| 2064 | 15 | 262h | Tb$^1$sAb$^1$sGb$^1$sTb$^1$sdGsdTsdTsdTsdAsdGsdGsdGsdAsdGs**C*b**$^1$ |
| 2064 | 15 | 262i | Tb$^1$ssAb$^1$ssdGssdTssdGssdUssdUssdUssdAssdGssdGssdGssdAssGb$^1$ssC*b$^1$ |
| 2064 | 16 | 209s | Gb$^1$Tb$^1$dAsdGsdTsdGsdTsdTsdTsdAsdGsdGsdGsAb$^1$Gb$^1$**C*b**$^1$ |
| 2064 | 16 | 209t | Gb$^1$sTb$^1$sdA*sdGsdTsdGsdTsdTsdTsdA*sdGsdGsdGsAb$^1$sGb$^1$**sC*b**$^1$ |
| 2064 | 16 | 209u | Gb$^1$Tb$^1$dAdGdTdGdTdTdTdAdGdGdGAb$^1$Gb$^1$**C*b**$^1$ |
| 2064 | 16 | 209v | /5SpC3s/Gb$^1$sTb$^1$sdAsdGsdTsdGsdTsdTsdTsdAsdGsdGsdGsAb$^1$sGb$^1$**sC*b**$^1$ |
| 2064 | 16 | 209w | Gb$^1$sTb$^1$sdAsdGsdTsdGsdTsdTsdTsdAsdGsdGsdGsAb$^1$sGb$^1$**sC*b**$^1$/s3SpC3/ |
| 2064 | 16 | 209x | /5SpC3s/Gb$^1$sTb$^1$sdAsdGsdTsdGsdTsdTsdTsdAsdGsdGsdGsAb$^1$sGb$^1$**sC*b**$^1$/3SpC3s/ |
| 2064 | 16 | 209y | Gb$^1$sTb$^1$sdAsdGsdTsdGsdTsdTsdTsdAsdGsdGsdGsAb$^1$sGb$^1$**sC*b**$^1$ |
| 2064 | 16 | 209aa | Gb$^1$Tb$^1$dA*sdGsdUsdGsdUsdUsdUsdAsdGsdGsdGsAb$^1$Gb$^1$**C*b**$^1$ |
| 2064 | 16 | 209ab | Gb$^1$Tb$^1$dA*sdGsdTsdGsdTsdTsdTsdAsdGsdGsdGsAb$^1$Gb$^1$**C*b**$^1$ |
| 2064 | 16 | 209ac | Gb$^6$sTb$^6$sdA*dGdTdGdTdTdA*dGdGdGAb$^6$sGb$^6$**sC*b**$^6$ |
| 2064 | 16 | 209ad | Gb$^1$sTb$^1$sdA*sdGsdUsdGsdUsdUsdUsdA*sdGsdGsdGsAb$^1$sGb$^1$**sC*b**$^1$ |
| 2064 | 16 | 209ae | Gb$^1$sTb$^1$sdA*sdGsdTsdGsdTsdTsdTsdAsdGsdGsdGsAb$^1$sGb$^1$**sC*b**$^1$ |
| 2064 | 16 | 209af | Gb$^1$sTb$^1$sdAsdGsdTsdGsdTsdTsdTsdA*sdGsdGsdGsAb$^1$sGb$^1$**sC*b**$^1$ |
| 2064 | 16 | 209ag | Gb$^1$Tb$^1$dA*dGdTdGdTdTdTdA*dGdGdGAb$^1$Gb$^1$**C*b**$^1$ |
| 2064 | 16 | 209ah | Gb$^1$Tb$^1$dAdGdTdGdTdTdTdA*dGdGdGAb$^1$Gb$^1$**C*b**$^1$ |
| 2064 | 16 | 209ai | Gb$^6$sTb$^6$sdA*dGdTdGdTdTdTdAdGdGdGAb$^6$sGb$^6$**sC*b**$^6$ |
| 2064 | 16 | 209aj | Gb$^1$sTb$^1$sdA*sdGsdUsdGsdTsdTsdTsdUsdA*sdGsdGsdGsAb$^1$sGb$^1$**sC*b**$^1$ |

TABLE 6-continued

| SP | L | Seq ID No. | Sequence, 5'-3' |
|---|---|---|---|
| 2064 | 16 | 209ak | Gb⁷sTb⁷sAb⁷sGb⁷sdTsdGsdTsdTsdTsdA*sdGsdGsdGsdGs**Ab⁷sGb⁷sC*b⁷** |
| 2064 | 16 | 209am | Gb⁷sTb⁷sdAsdGsdTsdGsdTsdTsdUsdA*sdGsdGsdGs**b⁷sAb⁷sGb⁷sC*b⁷** |
| 2064 | 16 | 209an | Gb¹ssTb¹ssAb¹ssdGssdTssdGssdTssdTssdTssdA*ssdGssdGssdGss**Ab¹ssGb¹ssC*b¹** |
| 2064 | 16 | 209ao | Gb⁴ssTb⁴ssAb⁴ssdGssdTssdGssdTssdTssdTssdAssdGssdGssdGssdA*ss**Gb⁴ssC*b⁴** |
| 2064 | 16 | 209ap | Gb²ssTb²ssAb²ssGb²ssdTssdGssdTssdTssdTssdAssdGssdGssdGssdAssd**GssC*b²** |
| 2064 | 16 | 209aq | Gb¹Tb¹Ab¹Gb¹dUdGdUdUdUdAdGdG**Gb¹Ab¹Gb¹C*b¹** |
| 2064 | 16 | 209ar | Gb¹sTb¹sAb¹sGb¹sTb¹sdGsdTsdTsdTsdA*sdGsdGsdGs**Ab¹sGb¹sC*b¹** |
| 2064 | 16 | 209as | Gb¹sTb¹sdAsdGsdTsdGsdTsdTsdUsdAsdGs**Gb¹sGb¹sAb¹sGb¹sC*b¹** |
| 2064 | 16 | 209at | Gb⁶sTb⁶sAb⁶sGb⁶sdTsdGsdTsdTsdTsdAsdGsdGsdGsdGs**Ab⁶sGb⁶sC*b⁶** |
| 2064 | 16 | 209au | Gb⁷sTb⁷sAb⁷sdGsdUsdGsdTsdTsdTsdA*sdGsdGsdGs**Ab⁷sGb⁷sC*b⁷** |
| 2064 | 16 | 209av | Gb⁴sTb⁴sAb⁴sGb⁴sdUsdGsdTsdUsdTsdA*sdGsdGsdGsdA*s**Gb⁴sC*b⁴** |
| 2064 | 16 | 209aw | Gb⁴Tb⁴Ab⁴Gb⁴dTdGdTdTdTdAdGdGdGdA**Gb⁴C*b⁴** |
| 2064 | 16 | 209ax | Gb¹sTb¹sAb¹sdGsdTsdGsdTsdTsdTsdAsdGsdGsdGs**Ab¹sGb¹sC*b¹** |
| 2064 | 16 | 209az | Gb¹sTb¹sAb¹sdGsdTsdGsdTsdTsdTsdAsdGsdGsdGs**sAb¹sGb¹sC*b¹** |
| 2064 | 16 | 209ba | Gb¹sTb¹sAb¹sGb¹sdTsdGsdTsdTsdTsdAsdGsdGsdGs**sAb¹sGb¹sC*b¹** |
| 2064 | 16 | 209bb | Gb¹sTb¹sAb¹sdGsdTsdGsdTsdTsdTsdAsdGsdGsdGsdGsdAs**Gb¹sC*b¹** |
| 2063 | 17 | 263a | Gb¹sTb¹sAb¹sGb¹sTb¹sdGsdTsdTsdTsdA*sdGsdGsdGs**Gb¹sAb¹sGb¹sC*b¹sC*b¹** |
| 2063 | 17 | 263b | Gb²sTb²sAb²sdGsdTsdGsdTsdTsdTsdA*sdGsdGsdGs**b²sAb²sGb²sC*b²sC*b²** |
| 2063 | 17 | 263c | Gb¹sTb¹sAb¹sGb¹sdTsdGsdTsdTsdTsdA*sdGsdGsdGs**Ab¹sGb¹sC*b¹sC*b¹** |
| 2063 | 17 | 263d | Gb¹sdUsdA*sdGsdUsdGsdUsdTsdTsdA*sdGsdGsdGs**Gb¹sAb¹sGb¹sC*b¹sC*b¹** |
| 2063 | 17 | 263e | Gb¹sTb¹sAb¹sdGsdTsdGsdUsdTsdTsdA*sdGsdGsdGs**Gb¹sAb¹sGb¹sC*b¹sC*b¹** |
| 2063 | 17 | 263f | Gb¹Tb¹dA*dGdTdGdTdTdTdA*dGdGdG**Ab¹Gb¹C*b¹C*b¹** |
| 2063 | 17 | 263g | Gb¹sdTsdA*sdGsdTsdGsdTsdTsdTsdA*sdGsdGsdGsdA*s**Gb¹sC*b¹sC*b¹** |
| 2063 | 17 | 263h | Gb¹Tb¹Ab¹Gb¹Tb¹dGdTdUdTdAdGdGdGdA*dG**C*b¹C*b¹** |
| 2063 | 17 | 263i | Gb¹ssTb¹ssAb¹ssGb¹ssTb¹ssdGssdTssdTssdTssdAssdGssdGssdGssdAss**Gb¹ssC*b¹ssC*b¹** |
| 2063 | 17 | 263j | Gb⁴Tb⁴dA*dGdTdGdTdTdTdAdGdGdGdA***Gb⁴C*b⁴C*b⁴** |
| 2063 | 17 | 263k | Gb⁶sTb⁶sAb⁶sdGsdTsdGsdUsdUsdTsdAsdGsdGsdGsdGsdA*s**Gb⁶sC*b⁶sC*b⁶** |
| 2063 | 17 | 263m | Gb⁷sTb⁷sAb⁷sGb⁷sdTdGdTdTdTdA*dGdGdGs**Ab⁷sGb⁷sC*b⁷sC*b⁷** |
| 2063 | 18 | 264a | Gb¹sGb¹sTb¹sAb¹sGb¹sdTsdGsdTsdTsdTsdA*sdGsdGsdGs**Gb¹sAb¹sGb¹sC*b¹sC*b¹** |
| 2063 | 18 | 264b | Gb⁷sGb⁷sTb⁷sAb⁷sGb⁷sdTsdGsdTsdTsdTsdAsdGsdGsdGsdGsdAsdGsdC*sC*b⁷** |
| 2063 | 18 | 264c | Gb¹sGb¹sTb¹sAb¹sGb¹sdTsdGsdTsdTsdTsdAsdGsdGsdGsdGsdA*sdGsdC*s**C*b¹** |
| 2063 | 18 | 264d | Gb¹sGb¹sTb¹sAb¹sGb¹sdUsdGsdTsdTsdTsdAsdGsdGsdGsdGsdA*sdGsdC*s**C*b¹** |
| 2063 | 18 | 264e | Gb¹sGb¹sTb¹sAb¹sdGsdTsdTsdGsdTsdTsdTsdA*sdGsdGsdGs**Ab¹sGb¹sC*b¹sC*b¹** |

TABLE 6-continued

| SP | L | Seq ID No. | Sequence, 5'-3' |
|---|---|---|---|
| 2063 | 18 | 264f | Gb¹sGb¹sTb¹sdA*sdGsdTsdGsdTsdTsdTsdA*sdGsdGsdGsGsAb¹sGb¹sC*b¹sC*b¹ |
| 2063 | 18 | 264g | Gb¹sGb¹sTb¹sAb¹sdGsdTsdGsdTsdTsdA*sdGsdGsdGsdA*sGb¹sC*b¹sC*b¹ |
| 2063 | 18 | 264h | Gb¹Gb¹dUdA*dGdTdGdTdTdTdAdGdGGb¹Ab¹Gb¹C*b¹C*b¹ |
| 2063 | 18 | 264i | Gb⁴Gb⁴Tb⁴Ab⁴dGsdTsdGsdTsdTsdTsdAsdGsdGsGb⁴Ab⁴Gb⁴C*b⁴C*b⁴ |
| 2063 | 18 | 264j | Gb¹ssGb¹ssTb¹ssdA*ssdGssdTssdGssdUssdTssdTssdA*ssdGssdGssdGssdA*ssGb¹ssC*b¹ssC*b¹ |
| 2063 | 18 | 264k | Gb²Gb²Tb²dA*dGdTdGdTdTdTdAdGdGGb²Ab²Gb²C*b²C*b² |
| 2062 | 19 | 265a | Gb¹sGb¹sTb¹sAb¹sGb¹sdTsdGsdTsdTsdTsdA*sdGsdGsdGsAb¹sGb¹sC*b¹sC*b¹sGb¹ |
| 2062 | 19 | 265b | Gb⁶Gb⁶Tb⁶Ab⁶Gb⁶dTdGdTdTdTdA*dGdGdGAb⁶Gb⁶C*b⁶C*b⁶Gb⁶ |
| 2062 | 19 | 265c | Gb¹sGb¹sTb¹sAb¹sdGsdTsdGsdTsdTsdTsdA*sdGsdGsdGsdA*sdGsC*b¹sC*b¹sGb¹ |
| 2062 | 19 | 265d | Gb¹sdGsdTsdA*sdGsdUsdGsdTsdUsdTsdA*sdGsdGsdGsAb¹sGb¹sC*b¹sC*b¹sGb¹ |
| 2062 | 19 | 265e | Gb⁴sGb⁴sdUsdAsdGsdTsdGsdTsdTsdTsdAsdGsdGsdGsdA*sGb⁴sC*b⁴sC*b⁴sGb⁴ |
| 2062 | 19 | 265f | Gb²ssGb²ssTb²ssAb²ssGb²ssdTssdGssdTssdTssdTssdAssdGssdGssdGssdAssdGssdCssC*b²ssGb² |
| 2062 | 20 | 266a | Tb¹sGb¹sGb¹sTb¹sAb¹sdGsdTsdGsdTsdTsdTsdA*sdGsdGsdGsAb¹sGb¹sC*b¹sC*b¹sGb¹ |
| 2062 | 20 | 266b | Tb²sGb²sGb²sdTsdA*sdGsdTsdGsdTsdTsdTsdA*sdGsdGsdGsAb²sGb²sC*b²sC*b²sGb² |
| 2062 | 20 | 266c | Gb¹Gb¹Tb¹dA*dGdTdGdTdTdTdA*dGdGdGdA*Gb¹C*b¹C*b¹Gb¹ |
| 2062 | 20 | 266d | Tb¹sdGsdGsdGsdUsdA*sdGsdTsdGsdTsdTsdUsdA*sdGsdGsdGsAb¹sGb¹sC*b¹sC*b¹sGb¹ |
| 2062 | 20 | 266e | Tb⁴sGb⁴sGb⁴sTb⁴sdAsdGsdTsdGsdTsdTsdTsdAsdGsdGsdGsdAsGb⁴sC*b⁴sC*b⁴sGb⁴ |
| 2061 | 22 | 267a | Tb¹sTb¹sGb¹sGb¹sTb¹sdAsdGsdTsdGsdTsdTsdTsdAsdGsdGsdGsdA*sGb¹sC*b¹sC*b¹sGb¹sTb¹ |
| 2061 | 22 | 267b | Tb¹Tb¹Gb¹Gb¹Tb¹dA*dGdTdGdTdTdTdAdGdGdGdA*Gb¹C*b¹C*b¹Gb¹Tb¹ |
| 2061 | 22 | 267c | Tb⁶sTb⁶sGb⁶sdTsdAsdGsdTsdGsdTsdTsdTsdAsdGsdGsdGsdGsdAsGb⁶sC*b⁶sC*b⁶sGb⁶sTb⁶ |
| 2060 | 24 | 268a | Tb¹sTb¹sTb¹sGb¹sGb¹sdTsdA*sdGsdTsdGsdTsdTsdTsdTsdAsdGsdGsdGsdAsdGC*b¹sC*b¹sGb¹sTb¹sC*b¹ |
| 2060 | 24 | 268b | Tb¹Tb¹Tb¹Gb¹Gb¹dTdA*dGdTdGdTdTdTdAdGdGdGdA*dGC*b¹C*b¹Gb¹Tb¹C*b¹ |
| 2059 | 26 | 269a | Ab¹sTb¹sTb¹sTb¹sGb¹sdGsdTsdAsdGsdTsdGsdTsdTsdTsdAsdGsdGsdGsdAsdGsdC*sC*b¹sGb¹sTb¹sC*b¹sTb¹ |
| 2059 | 26 | 269b | Ab¹Tb¹Tb¹Tb¹Gb¹dGdTdAdGdTdGdTdTdTdAdGdGdGdGdAdGdC*C*b¹Gb¹Tb¹C*b¹Tb¹ |
| 2058 | 28 | 270a | Tb¹sAb¹sTb¹sTb¹sTb¹sdGdGsdTsdAsdGsdTsdGsdTsdTsdTsdAsdGsdGsdGsdAsdGsdC*sdCsGb¹sTb¹sC*b¹sTb¹sTb¹ |
| 2058 | 28 | 270b | Tb¹Ab¹Tb¹Tb¹Tb¹dGdGdTdAdGdTdGdTdTdTdAdGdGdGdGdAdGdC*dC*Gb¹Tb¹C*b¹Tb¹Tb¹ |

TABLE 7

| SP | Seq L | ID No. | Sequence, 5'-3' |
|---|---|---|---|
| 2075 | 10 | 271a | Ab$^1$sTb$^1$sdTsdTsdGsdGsdTsdA*sGb$^1$sTb$^1$ |
| 2075 | 10 | 271b | Ab$^1$Tb$^1$dTdTdGdGdTdA*Gb$^1$Tb$^1$ |
| 2074 | 12 | 272a | Tb$^1$sAb$^1$sTb$^1$sdTsdTsdGsdGsdTsdA*sGb$^1$sTb$^1$sGb$^1$ |
| 2074 | 12 | 272b | Tb$^1$Ab$^1$Tb$^1$dTdTdGdGdTdA*Gb$^1$Tb$^1$Gb$^1$ |
| 2074 | 12 | 272c | Tb$^1$sAb$^1$sTb$^1$sdTsdTsdGsdGsdTsdA*sdGsTb$^1$sGb$^1$ |
| 2074 | 12 | 272d | Tb$^1$sAb$^1$sdTsdTsdTsdGsdGsdTsdA*sdGsdUsGb$^1$ |
| 2074 | 12 | 272e | Tb$^1$sdAsdTsdUsdTsdGsdGsdUsdA*sdGsTb$^1$sGb$^1$ |
| 2073 | 13 | 273a | Tb$^1$sAb$^1$sTb$^1$sdTsdTsdGsdGsdGsdTsdAsGb$^1$sTb$^1$sGb$^1$sTb$^1$ |
| 2073 | 13 | 273b | Tb$^1$Ab$^1$Tb$^1$dUdUdGdGdUdAGb$^1$Tb$^1$Gb$^1$Tb$^1$ |
| 2073 | 13 | 273c | Tb$^1$sAb$^1$sTb$^1$sdTsdTsdGsdGsdGsdTsdA*sGb$^1$sTb$^1$sGb$^1$sTb$^1$ |
| 2073 | 13 | 273d | Tb$^1$sAb$^1$sTb$^1$sdTsdTsdGsdGsdGsdTsdA*sdGsdUsGb$^1$sTb$^1$ |
| 2073 | 13 | 273e | Tb$^1$sAb$^1$sdUsdUsdUsdGsdGsdGsdUsdA*sdGsdUsdGsTb$^1$ |
| 2073 | 13 | 273f | Tb$^1$sdA*sdTsdTsdUsdGsdGsdGsdTsdA*sGb$^1$sTb$^1$sGb$^1$sTb$^1$ |
| 2073 | 14 | 274a | **C*b$^1$Tb$^1$Ab**$^1$sdUsdTsdTsdGsdGsdGsdTsdA*sGb$^1$Tb$^1$Gb$^1$Tb$^1$ |
| 2073 | 14 | 274b | **C*b$^4$sTb$^4$sAb$^4$sTb**$^4$sdTsdTsdGsdGsdGsdTsdA*sdGsdUsGb$^4$sTb$^4$ |
| 2073 | 14 | 274c | **C*b**$^1$sdUsdA*sdTsdTsdGsdGsdGsdTsdAsdGsdTsdGsTb$^1$ |
| 2073 | 14 | 274d | **C*b$^2$sTb$^2$sAb**$^2$sdTsdTsdUsdGsdGsdGsdTsdA*sdGsTb$^2$sGb$^2$sTb$^2$ |
| 2073 | 14 | 274e | **C*b**$^4$ssTb$^4$ssdAssdTssdTssdTssdGssdGssdGssdTssdAssdGssTb**$^4$ssGb$^4$ssTb$^4$ |
| 2073 | 14 | 274f | **C*b$^1$Tb$^1$Ab$^1$dTdTdTdGdGdTdA*Gb$^1$Tb$^1$Gb$^1$Tb**$^1$ |
| 2073 | 14 | 274g | **C*b$^1$sTb$^1$sAb$^1$sTb**$^1$sdTsdTsdGsdGsdGsdTsdA*sGb$^1$sTb$^1$sGb$^1$sTb$^1$ |
| 2072 | 15 | 275a | **C*b$^1$sTb$^1$sAb$^1$sTb**$^1$sdTsdTsdGsdGsdGsdTsdA*sdGsdTsdGsdTsTb$^1$ |
| 2072 | 15 | 275b | **C*b$^1$sTb**$^1$sdA*sdUsdTsdUsdGsdGsdGsdTsdAsdGsdUsGb$^1$sTb$^1$sTb$^1$ |
| 2072 | 15 | 275c | **C*b$^4$sTb$^4$sAb$^4$sdTsdTsdTsdGsdGsdTsdAsdGsdTsdGsTb$^4$sTb**$^4$ |
| 2072 | 15 | 275d | **C*b**$^1$ssTb$^1$ssdAssdTssdTssdTssdGssdGssdTssdAssdGssdTssdGssdTssTb**$^1$ |
| 2072 | 15 | 275e | **C*b**$^1$ssTb$^1$ssdAssdUssdTssdTssdGssdGssdTssdAssdGssdUssdGssTb**$^1$ssTb$^1$ |
| 2072 | 15 | 275f | **C*b$^1$sTb$^1$sAb$^1$sTb**$^1$sdTdTdGdGdTdA*dGsTb$^1$sGb$^1$sTb$^1$sTb$^1$ |
| 2072 | 15 | 275g | **C*b$^1$Tb**$^1$sdAsdTsdTsdTsdGsdGsdGsdTsdA*sdGsTb$^1$Gb$^1$Tb$^1$Tb$^1$ |
| 2072 | 15 | 275h | **C*b$^6$Tb$^6$Ab**$^6$dUdTdTdGdGdTdA*dGdUGb$^6$Tb$^6$Tb$^6$ |
| 2072 | 15 | 275i | **C*b$^1$dTdAdTdTdTdGdGdTdAdGdTdGdTTb**$^1$ |
| 2072 | 16 | 210o | Gb$^1$**C*b$^1$Tb$^1$Ab$^1$dTsdTsdTsdGsdGsdGsdTsdAsdGsdTsGb$^1$Tb$^1$Tb**$^1$ |
| 2072 | 16 | 210p | Gb$^1$**sC*b$^1$sTb$^1$sAb**$^1$sdTsdTsdTsdGsdGsdGsdTsdA*sdGsdTsGb$^1$sTb$^1$sTb$^1$ |
| 2072 | 16 | 210q | Gb$^1$**sC*b$^1$sTb$^1$sAb$^1$sdTsdTsdTsdGsdGsdGsdTsdAsdGsdTsGb$^1$sTb$^1$sTb**$^1$ |
| 2072 | 16 | 210r | Gb$^1$**C*b$^1$Tb$^1$Ab**$^1$dTdTdTdGdGdTdA*dGdTGb$^1$Tb$^1$Tb$^1$ |
| 2072 | 16 | 210s | Gb$^1$**sC*b$^1$sTb$^1$sAb**$^1$sdUsdUsdTdGsdGsdGsdTsdA*sdGsdTsGb$^1$sTb$^1$sTb$^1$ |
| 2072 | 16 | 210t | Gb$^1$**sC*b$^1$sTb$^1$sAb$^1$sdUsdTsdTsdGsdGsdGsdTsdAsdGsdUsGb$^1$sTb$^1$sTb**$^1$ |
| 2072 | 16 | 210u | Gb$^1$**sC*b$^1$sTb$^1$sAb**$^1$sdUsdUsdUsdGsdGsdGsdUsdA*sdGsdUsGb$^1$sTb$^1$sTb$^1$ |
| 2072 | 16 | 210v | /5SpC3s/Gb$^1$**sC*b$^1$sTb$^1$sAb$^1$sdTsdTsdTsdGsdGsdGsdTsdAsdGsdTsGb$^1$sTb$^1$sTb**$^1$ |

TABLE 7-continued

| SP | L | Seq ID No. | Sequence, 5'-3' |
|---|---|---|---|
| 2072 | 16 | 210w | Gb$^1$sC*b$^1$sTb$^1$sAb$^1$sdTsdTsdTsdGsdGsdTsdAsdGsdTsGb$^1$sTb$^1$sTb$^1$/3SpC3s/ |
| 2072 | 16 | 210x | /5SpC3s/Gb$^1$sC*b$^1$sTb$^1$sAb$^1$sdTsdTsdTsdGsdGsdTsdAsdGsdTsGb$^1$sTb$^1$sTb$^1$/3SpC3s/ |
| 2072 | 16 | 210y | Gb$^1$C*b$^1$Tb$^1$Ab$^1$sdTsdTsdTsdGsdGsdTsdA*sdGsdTsGb$^1$Tb$^1$Tb$^1$ |
| 2072 | 16 | 210z | Gb$^1$C*b$^1$Tb$^1$Ab$^1$sdUsdTsdTsdGsdGsdGsdUsdA*sdGsdTsGb$^1$Tb$^1$Tb$^1$ |
| 2072 | 16 | 210aa | Gb$^1$sC*b$^1$sTb$^1$sAb$^1$sdTdTdTdGdGdTdA*dGdTsGb$^1$sTb$^1$sTb$^1$ |
| 2072 | 16 | 210ab | Gb$^6$sC*b$^6$sTb$^6$sAb$^6$sdTdTdTdGdGdTdA*dGdTsGb$^6$sTb$^6$sTb$^6$ |
| 2072 | 16 | 210ac | Gb$^6$sC*b$^6$sTb$^6$sdAsdTsdTsdTsdGsdGsdTsdAsdGsTb$^6$sGb$^6$sTb$^6$sTb$^6$ |
| 2072 | 16 | 210ad | Gb$^7$sC*b$^7$sTb$^7$sdA*sdTsdTsdTsdGsdGsdTsdA*sdGsTb$^7$sGb$^7$sTb$^7$sTb$^7$ |
| 2072 | 16 | 210ae | Gb$^7$sC*b$^7$sdUsdAsdTsdTsdUsdGsdGsdUsdA*sdGsTb$^7$sGb$^7$sTb$^7$sTb$^7$ |
| 2072 | 16 | 210af | Gb$^1$ssC*b$^1$ssTb$^1$ssdAssdTssdTssdTssdGssdGssdTssdA*ssdGssdTssGb$^1$ssTb$^1$ssTb$^1$ |
| 2072 | 16 | 210ag | Gb$^4$ssC*b$^4$ssTb$^4$ssdA*ssdTssdTssdTssdGssdGssdTssdAssdGssdTssdGssTb$^4$ssTb$^4$ |
| 2072 | 16 | 210ah | Gb$^2$ssC*b$^2$ssTb$^2$ssAb$^2$ssdTssdTssdTssdGssdGssdTssdAssdGssdTssdGssdTssTb$^2$ |
| 2072 | 16 | 210ai | Gb$^1$C*b$^1$Tb$^1$Ab$^1$dUsdTsdTsdGsdGsdTsdAsdGsTb$^1$Gb$^1$Tb$^1$Tb$^1$ |
| 2072 | 16 | 210aj | Gb$^4$C*b$^4$Tb$^4$Ab$^4$dTsdTsdTsdGsdGsdTsdAsdGsdTdGTb$^4$Tb$^4$ |
| 2072 | 16 | 210ak | Gb$^1$sC*b$^1$sTb$^1$sAb$^1$sTb$^1$sdTsdTsdGsdGsdTsdA*sdGsdTsGb$^1$sTb$^1$sTb$^1$ |
| 2072 | 16 | 210am | Gb$^4$sC*b$^4$sTb$^4$sAb$^4$sdTsdUsdGsdGsdTsdA*sdGsdTsdGsTb$^4$sTb$^4$ |
| 2072 | 16 | 210an | Gb$^7$sC*b$^7$sTb$^7$sdA*sdTsdTsdUsdGsdGsdTsdA*sdGsTb$^7$sTb$^7$sTb$^7$ |
| 2072 | 16 | 210ao | Gb$^1$sC*b$^1$sdUsdAsdUsdUsdTsdGsdGsdUsdAsGb$^1$sTb$^1$sGb$^1$sTb$^1$sTb$^1$ |
| 2072 | 16 | 210ap | Gb$^1$sC*b$^1$sTb$^1$sdAsdTsdTsdTsdGsdGsdTsdAsdGsdTsGb$^1$sTb$^1$sTb$^1$ |
| 2072 | 16 | 210aq | Gb$^1$sC*b$^1$sTb$^1$sdAsdTsdTsdTsdGsdGsdGsdTsdAsdGsdTsdGsTb$^1$sTb$^1$ |
| 2071 | 17 | 276a | Gb$^1$sC*b$^1$sTb$^1$sAb$^1$sTb$^1$sdTsdTsdGsdGsdTsdA*sdGsTb$^1$sGb$^1$sTb$^1$sTb$^1$sTb$^1$ |
| 2071 | 17 | 276b | Gb$^2$sC*b$^2$sTb$^2$sdAsdTsdTsdTsdGsdGsdGsdTsdA*sdGsTb$^2$sGb$^2$sTb$^2$sTb$^2$sTb$^2$ |
| 2071 | 17 | 276c | Gb$^1$sC*b$^1$sTb$^1$sdAsdTsdTsdTsdGsdGsdTsdA*sdGsTb$^1$sGb$^1$sTb$^1$sTb$^1$sTb$^1$ |
| 2071 | 17 | 276d | Gb$^2$sdC*sdTsdAsdTsdTsdTsdGsdGsdTsdAsdGsTb$^2$sGb$^2$sTb$^2$sTb$^2$sTb$^2$ |
| 2071 | 17 | 276e | Gb$^6$sC*b$^6$sTb$^6$sdA*sdUsdUsdUsdGsdGsdUsdA*sdGsdUsdGsTb$^6$sTb$^6$sTb$^6$ |
| 2071 | 17 | 276f | Gb$^1$sdC*sdTsdA*sdUsdUsdUsdGsdGsdUsdAsdGsdUsdGsTb$^1$sTb$^1$sTb$^1$ |
| 2071 | 17 | 276g | Gb$^1$C*b$^1$dTdA*dTdTdTdGdGdTdA*dGdTGb$^1$Tb$^1$Tb$^1$Tb$^1$ |
| 2071 | 17 | 276h | Gb$^4$C*b$^4$Tb$^4$Ab$^4$dTdTdTdGdGdTdA*dGdTdGTb$^4$Tb$^4$Tb$^4$ |
| 2071 | 17 | 276i | Gb$^1$C*b$^1$Tb$^1$Ab$^1$Tb$^1$dUdTdGdGdTdA*dGdTdGdUTb$^1$Tb$^1$ |
| 2071 | 17 | 276j | Gb$^1$ssC*b$^1$ssTb$^1$ssAb$^1$ssTb$^1$ssdTssdTssdGssdGssdTssdAssdGssdTssdGssTb$^1$ssTb$^1$ssTb$^1$ |
| 2071 | 17 | 276k | Gb$^7$sC*b$^7$sTb$^7$sAb$^7$sdTdTdTdGdGdTdA*dGdTsGb$^7$sTb$^7$sTb$^7$sTb$^7$ |
| 2071 | 18 | 277a | Ab$^1$sGb$^1$sC*b$^1$sTb$^1$sAb$^1$sdTsdTsdTsdGsdGsdTsdA*sdGsTb$^1$sGb$^1$sTb$^1$sTb$^1$sTb$^1$ |
| 2071 | 18 | 277b | Ab$^7$sGb$^7$sC*b$^7$sTb$^7$sAb$^7$sdTsdTsdTsdGsdGsdTsdA*sdGsdTsdGsdTsTb$^7$ |
| 2071 | 18 | 277c | Ab$^1$sGb$^1$sdC*sdTsdAsdTsdTsdTsdGsdGsdTsdAsdGsTb$^1$sGb$^1$sTb$^1$sTb$^1$sTb$^1$ |
| 2071 | 18 | 277d | Ab$^1$sGb$^1$sdC*sdTsdAsdTsdTsdTsdGsdGsdTsdA*sdGsTb$^1$sGb$^1$sTb$^1$sTb$^1$sTb$^1$ |

TABLE 7-continued

| SP | L | Seq ID No. | Sequence, 5'-3' |
|---|---|---|---|
| 2071 | 18 | 277e | Ab¹Gb¹dC*dTdAdUdTdTdGdGdTdA*dGTb¹Gb¹Tb¹Tb¹Tb¹ |
| 2071 | 18 | 277f | **Ab²Gb²C*b²**dTdAdTdTdTdGdGdTdA*dGTb²Gb²Tb²Tb²Tb² |
| 2071 | 18 | 277g | **Ab¹sGb¹sC*b¹sTb¹**sdA*sdTsdTsdTsGsGsdTsdA*sdGsdTsGb¹sTb¹sTb¹sTb¹ |
| 2071 | 18 | 277h | **Ab¹sGb¹sC*b¹sTb¹**sdA*sdTsdTsdTsdTsGsGsdTsdAsdGsdTsGsTb¹sTb¹sTb¹ |
| 2071 | 18 | 277i | **Ab¹sGb¹sC*b¹**sdTsdA*sdTsdTsdTsdTsGsGsdTsdA*sdGsdTsGb¹sTb¹sTb¹sTb¹ |
| 2071 | 18 | 277j | **Ab⁴Gb⁴C*b⁴Tb⁴sdAsdTsdTsdTsdGsdGsdTsdAsdGsTb⁴Gb⁴Tb⁴Tb⁴Tb⁴** |
| 2071 | 18 | 277k | **Ab¹ssGb¹ssC*b¹**ssdTssdA*ssdTssdTssdTssdGssdGssdTssdA*ssdGssdUssdGssTb¹ssTb¹ssTb¹ |
| 2070 | 19 | 278a | **Ab¹sGb¹sC*b¹sTb¹sAb¹**sdTsdTsdTsdGsdGsdTsdA*sdGsdTsGb¹sTb¹sTb¹sTb¹sAb¹ |
| 2070 | 19 | 278b | **Ab²ssGb²ssC*b²ssTb²ssAb²ssdTssdTssdTssdGssdGssdTssdAssdGssdTssdGssdTssdTssTb²ssAb²** |
| 2070 | 19 | 278c | Ab¹sdGsdC*sdTsdAsdTsdTsdTsdGsdGsdTsdA*sdGsdTsGb¹sTb¹sTb¹sTb¹sAb¹ |
| 2070 | 19 | 278d | Ab¹sdGsdC*sdTsdAsdTsdTsdTsdTsdGsdGsdUsdA*sdGsdUsGb¹sTb¹sTb¹sTb¹sAb¹ |
| 2070 | 19 | 278e | **Ab¹sGb¹sC*b¹**sdTsdAsdTsdTsdTsdGsdGsdTsdA*sdGsdTsGsTb¹sTb¹sTb¹sAb¹ |
| 2070 | 19 | 278f | Ab⁴sGb⁴sdC*sdTsdAsdTsdTsdTsdGsdGsdTsdAsdGsdTsGsTb⁴sTb⁴sTb⁴sAb⁴ |
| 2070 | 19 | 278g | **Ab⁶Gb⁶C*b⁶Tb⁶Ab⁶**dTdTdTdGdGdTdA*dGdTGb⁶Tb⁶Tb⁶Tb⁶Ab⁶ |
| 2070 | 20 | 279a | **Gb¹sAb¹sGb¹sC*b¹sTb¹**sdAsdTsdTsdTsdGsdGsdTsdA*sdGsdTsGb¹sTb¹sTb¹sTb¹sAb¹ |
| 2070 | 20 | 279b | Gb²sAb²sGb²sdC*sdTsdAsdTsdTsdTsdGsdGsdTsdAsdGsdTsGb²sTb²sTb²sTb²sAb² |
| 2070 | 20 | 279c | Gb¹sdAsdGsdC*sdUsdAsdTsdTsdTsdGsdGsdTsdA*sdGsdTsGb¹sTb¹sTb¹sTb¹sAb¹ |
| 2070 | 20 | 279d | **Gb⁴sAb⁴sGb⁴sC*b⁴sdTsdAsdTsdTsdTsdGsdGsdTsdAsdGsdTsGsTb⁴sTb⁴sTb⁴sAb⁴** |
| 2070 | 20 | 279e | Gb¹Ab¹Gb¹dC*dTdAdTdTdTdGdGdTdAdGdTGb¹Tb¹Tb¹Tb¹Ab¹ |
| 2069 | 22 | 280a | **Ab¹sGb¹sAb¹sGb¹sC*b¹sdTsdAsdTsdTsdTsdGsdGsdTsdAsdGsdTsGsTb¹sTb¹sTb¹sAb¹sGb¹** |
| 2069 | 22 | 280b | **Ab¹Gb¹Ab¹Gb¹C*b¹dTdAdTdTdTdGdGdTdAdGdTGb¹Tb¹Tb¹Ab¹Gb¹** |
| 2069 | 22 | 280c | Ab¹sGb¹sAb¹sGb¹sdC*sdTsdAsdTsdTsdTsdGsdGsdTsdAsdGsdTsGsTb¹sTb¹sTb¹sAb¹sGb¹ |
| 2069 | 22 | 280d | Ab⁶sGb⁶sAb⁶sGb⁶sdC*sdTsdAsdTsdTsdTsdGsdGsdTsdA*sdGsdTsdGsdTsTb⁶sAb⁶sGb⁶ |
| 2068 | 24 | 281a | Ab¹sAb¹sGb¹sAb¹sGb¹sdC*sdTsdAsdTsdTsdTsdGsdGsdTsdAsdGsdTsdGsdTsTb¹sTb¹sAb¹sGb¹sGb¹ |
| 2068 | 24 | 281b | Ab¹Ab¹Gb¹Ab¹Gb¹dC*dTdAdTdTdTdGdGdTdAdGdTdGdTTb¹Tb¹Ab¹Gb¹Gb¹ |
| 2067 | 26 | 282a | Gb¹sAb¹sAb¹sGb¹sAb¹sdGsdC*sdTsdAsdTsdTsdTsdTsdGsdGsdTsdAsdGsdTsdGsdTsdTsTb¹sAb¹sGb¹sGb¹sGb¹ |
| 2067 | 26 | 282b | Gb¹Ab¹Ab¹Gb¹Ab¹dGdC*dTdAdTdTdTdGdGdTdAdGdTdGdTTb¹Ab¹Gb¹Gb¹Gb¹ |
| 2066 | 28 | 283a | Ab¹sGb¹sAb¹sAb¹sGb¹sdAsdGsdC*sdTsdAsdTsdTsdTsdTsdGsdGsdTsdAsdGsdTsdGsdTsdTsAb¹sGb¹sGb¹sGb¹sAb¹ |

TABLE 7-continued

| SP | L | Seq ID No. | Sequence, 5'-3' |
|---|---|---|---|
| 2066 | 28 | 283b | Ab$^1$Gb$^1$Ab$^1$Ab$^1$Gb$^1$dAdGdC*dTdAdTdTdTdGdGdTdAdGdTdGdTdTdTAb$^1$Gb$^1$Gb$^1$Gb$^1$Ab$^1$ |

TABLE 8

| SP | L | Seq ID No. | Sequence, 5'-3' |
|---|---|---|---|
| 4220 | 10 | 219a | Gb$^1$sAb$^1$sdAsdTsdGsdGsdAsdCs**C*b$^1$sAb**$^1$ |
| 4220 | 10 | 219b | Gb$^1$Ab$^1$dAdTdGdGdAdCCb$^1$Ab$^1$ |
| 4219 | 12 | 220a | Tb$^1$sGb$^1$sAb$^1$sdAsdTsdGsdGsdAsdCs**C*b$^1$sAb$^1$sGb**$^1$ |
| 4219 | 12 | 220b | Tb$^1$Gb$^1$Ab$^1$dAdTdGdGdAdCCb$^1$Ab$^1$Gb$^1$ |
| 4219 | 12 | 220c | Tb$^1$sGb$^1$sAb$^1$sdAsdTsdGsdGsdAsdCsdC*sAb$^1$sGb$^1$ |
| 4219 | 12 | 220d | Tb$^1$sdGsdA*sdAsdTsdGsdGsdAsdC*sdCsAb$^1$sGb$^1$ |
| 4219 | 12 | 220e | Tb$^1$sGb$^1$sdA*sdA*sdTsdGsdGsdA*sdC*sdC*sdAsGb$^1$ |
| 4218 | 13 | 221a | Tb$^1$sGb$^1$sAb$^1$sAb$^1$sdTsdGsdGsdAsdCsdCAb$^1$sGb$^1$sTb$^1$ |
| 4218 | 13 | 221b | Tb$^1$Gb$^1$Ab$^1$Ab$^1$dUdGdGdAdCdCAb$^1$Gb$^1$Tb$^1$ |
| 4218 | 13 | 221c | Tb$^1$sGb$^1$sAb$^1$sAb$^1$sdTsdGsdGsdAsdCsdC*sAb$^1$sGb$^1$sTb$^1$ |
| 4218 | 13 | 221d | Tb$^1$sGb$^1$sAb$^1$sdAsdTsdGsdGsdA*sdCsdC*sdAsGb$^1$sTb$^1$ |
| 4218 | 13 | 221e | Tb$^1$sGb$^1$sdA*sdAsdTsdGsdGsdAsdC*sdCsdAsdGsTb$^1$ |
| 4218 | 13 | 221f | Tb$^1$sdGsdAsdA*sdTsdGsdGsdAsdCsC*b$^1$sAb$^1$sGb$^1$sTb$^1$ |
| 4218 | 14 | 222a | Ab$^1$sTb$^1$sGb$^1$sAb$^1$sdAsdTsdGsdGsdAsdCsC*b$^1$sAb$^1$sGb$^1$sTb$^1$ |
| 4218 | 14 | 222b | Ab$^1$Tb$^1$Gb$^1$Ab$^1$dAsdTsdGsdGsdAsdCsdC*sAb$^1$Gb$^1$Tb$^1$ |
| 4218 | 14 | 222c | Ab$^1$Tb$^1$dGdA*dAdTdGdGdA*dCC*b$^1$Ab$^1$Gb$^1$Tb$^1$ |
| 4218 | 14 | 222d | Ab$^4$sTb$^4$sGb$^4$sdA*sdAsdTsdGsdGsdAsdCsdC*sAbsGb$^4$sTb$^4$ |
| 4218 | 14 | 222e | Ab$^1$sdTsdGsdA*sdA*sdTsdGsdGsdA*sdC*sdC*sdA*sdGsTb$^1$ |
| 4218 | 14 | 222f | Ab$^2$sTb$^2$sGb$^2$sdA*sdAsdUsdGsdGsdAsdCsdCsAb$^2$sGb$^2$sTb$^2$ |
| 4218 | 14 | 222g | Ab$^4$ssTb$^4$ssdGssdAssdAssdTssdGssdGssdAssdCssdCssAb$^4$ssGb$^4$ssTb**$^4$ |
| 4217 | 15 | 223a | Ab$^1$sTb$^1$sGb$^1$sAb$^1$sdAdTdGdGdAdCdC*sAb$^1$sGb$^1$sTb$^1$sAb$^1$ |
| 4217 | 15 | 223b | Ab$^1$ssTb$^1$ssdGssdAssdAssdTssdGssdGssdAssdCssdCssdAssdGssdTssAb**$^1$ |
| 4217 | 15 | 223c | Ab$^1$dTdGdAdAdTdGdGdAdCdCdAdGdTAb$^1$ |
| 4217 | 15 | 223d | Ab$^1$sTb$^1$sdGsdAsdAsdUsdGsdGsdA*sdCsdCsdAsGb$^1$sTb$^1$sAb$^1$ |
| 4217 | 15 | 223e | Ab$^6$Tb$^6$Gb$^6$dA*dAdTdGdGdAdCdC*dAGb$^6$Tb$^6$Ab$^6$ |
| 4217 | 15 | 223f | Ab$^1$Tb$^1$dGsdAsdAsdTsdGsdGsdAsdC*sdC*sAb$^1$Gb$^1$Tb$^1$Ab$^1$ |
| 4217 | 15 | 223g | Ab$^4$sTb$^4$sGb$^4$sdAsdAsdTsdGsdGsdAsdCsdCsdAsdGsTb$^4$sAb$^4$ |
| 4217 | 15 | 223h | Ab$^1$sTb$^1$sGb$^1$sAb$^1$sdAsdTsdGsdGsdAsdC*sdC*sdAsdGsdTsAb$^1$ |
| 4217 | 15 | 223i | Ab$^1$ssTb$^1$**ssdGssdAssdAssdUssdGssdGssdA*ssdCssdCssdAssdGssTb$^1$ssAb$^1$ |
| 4217 | 16 | 218y | **C*b$^1$sAb$^2$sTb$^2$sdGsdAsdAsdTsdGsdGsdAsdCsdCsAb$^2$sGb$^2$sTb$^2$sAb**$^2$ |
| 4217 | 16 | 218z | **C*b$^1$sAb$^1$sTb**$^1$sdGsdAsdAsdTsdGsdGsdAsdC*sdC*sAb$^1$sGb$^1$sTb$^1$sAb$^1$ |
| 4217 | 16 | 218aa | **C*b**$^1$ssAb$^1$ssTb$^1$ssdGssdAssdAssdTssdGssdGssdAssdCssdCssAb**$^1$ssGb$^1$ssTb$^1$ssAb$^1$ |

TABLE 8-continued

| SP | L | Seq ID No. | Sequence, 5'-3' |
|---|---|---|---|
| 4217 | 16 | 218ab | C*b¹Ab¹Tb¹dGsdAsdAsdUsdGsdGsdAsdC*sdC*sAb¹Gb¹Tb¹Ab¹ |
| 4217 | 16 | 218ac | C*b¹Ab¹Tb¹dGsdA*sdA*sdTsdGsdGsdA*sdCsdCsAb¹Gb¹Tb¹Ab¹ |
| 4217 | 16 | 218ad | C*b⁶sAb⁶sTb⁶sdGdAdAdTdGdGdAdCdCAb⁶sGb⁶sTb⁶sAb⁶ |
| 4217 | 16 | 218ae | C*b⁷sAb⁷sTb⁷sGb⁷sdAsdAsdTsdGsdGsdAsdCsdCsdAsGb⁷sTb⁷sAb⁷ |
| 4217 | 16 | 218af | C*bsAb¹sdUsdGsdAsdAsdUsdGsdGsdUsdCsdCsAb¹sGb¹sTb¹sAb¹ |
| 4217 | 16 | 218b | C*b¹sAb¹sTb¹sdGsdAsdAsdTsdGsdGsdAsdCsdCsAb¹sGb¹sTb¹sAb¹ |
| 4217 | 16 | 218m | C*b¹sAb¹sTb¹sdGsdAsdAsdTsdGsdGsdAsdC*sdC*sAb¹sGb¹sTb¹sAb¹ |
| 4217 | 16 | 218n | C*b¹Ab¹Tb¹dGsdAsdAsdTsdGsdGsdAsdC*sdC*sAb¹Gb¹Tb¹Ab¹ |
| 4217 | 16 | 218o | C*b¹sAb¹sTb¹sdGsdA*sdA*sdTsdGsdGsdA*sdCsdCsAb¹sGb¹sTb¹sAb¹ |
| 4217 | 16 | 218p | C*b¹sAb¹sTb¹sdGsdA*sdA*sdTsdGsdGsdA*sdC*sdC*sAb¹sGb¹sTb¹sAb¹ |
| 4217 | 16 | 218q | C*b¹sAb¹sTb¹sdGsdAsdAsdTsdGsdGsdAsdC*sdCsAb¹sGb¹sTb¹sAb¹ |
| 4217 | 16 | 218c | C*b¹sAb¹sTb¹sdGsdAsdAsdTsdGsdGsdAsdCsdC*sAb¹sGb¹sTb¹sAb¹ |
| 4217 | 16 | 218r | C*b¹Ab¹Tb¹dGdAdAdTdGdGdAdCdCAb¹Gb¹Tb¹Ab¹ |
| 4217 | 16 | 218s | C*b¹sAb¹sTb¹sdGdAdAdTdGdGdAdC*sdC*sAb¹sGb¹sTb¹sAb¹ |
| 4217 | 16 | 218t | /5SpC3s/C*b¹sAb¹sTb¹sdGsdAsdAsdTsdGsdGsdAsdCsdCsAb¹sGb¹sTb¹sAb¹ |
| 4217 | 16 | 218u | C*b¹sAb¹sTb¹sdGsdAsdAsdTsdGsdGsdAsdCsdCsAb¹sGb¹sTb¹sAb¹/3SpC3s/ |
| 4217 | 16 | 218v | /5SpC3s/C*b¹sAb¹sTb¹sdGsdAsdAsdTsdGsdGsdAsdCsdCsAb¹sGb¹sTb¹sAb¹/3SpC3s/ |
| 4217 | 16 | 218ag | C*b¹sAb¹sTb¹sdGsdA*sdA*sdUsdGsdGsdA*sdCsdCsAb¹sGb¹sTb¹sAb¹ |
| 4217 | 16 | 218ah | C*b⁴ssAb⁴ssTb⁴ssdGssdA*ssdA*ssdTssdGssdGssdA*ssdCssdCssdAssdGssTb⁴ssAb⁴ |
| 4217 | 16 | 218ai | C*b²ssAb²ssTb²ssGb²ssdAssdAssdTssdGssdGssdAssdCssdCssdAssdGssdTssAb² |
| 4217 | 16 | 218aj | C*b¹Ab¹Tb¹Gb¹dAdAdUdGdGdAdCdCAb¹Gb¹Tb¹Ab¹ |
| 4217 | 16 | 218ak | C*b¹sAb¹sTb¹sGb¹sAb¹sdA*sdUsdGsdGsdAsdCsdCsdA*sGb¹sTb¹sAb¹ |
| 4217 | 16 | 218am | C*b¹sAb¹sdUsdGsdAsdAsdUsdGsdGsdAsdCsC*b¹sAb¹sGb¹sTb¹sAb¹ |
| 4217 | 16 | 218an | C*b⁶sAb⁶sTb⁶sGb⁶sdAsdAsdTsdGsdGsdAsdCsdCsdAsGb⁶sTb⁶sAb⁶ |
| 4217 | 16 | 218ao | C*b⁷sAb⁷sTb⁷sdGsdA*sdA*sdUsdGsdGsdAsdCsdCsdA*sGb⁷sTb⁷sAb⁷ |
| 4217 | 16 | 218ap | C*b⁴sAb⁴sTb⁴sGb⁴sdA*sdAsdTsdGsdGsdAsdCsdC*sdAsdGsTb⁴sAb⁴ |
| 4217 | 16 | 218aq | C*b⁴Ab⁴Tb⁴Gb⁴dAdAdTdGdGdAdCdCdAdGTb⁴Ab⁴ |
| 4217 | 16 | 218ar | C*b¹sAb¹sTb¹sdGsdAsdAsdTsdGsdGsdAsdCsdCsdAsGb¹sTb¹sAb¹ |
| 4216 | 17 | 224a | C*b¹sAb¹sTb¹sGb¹sAb¹sdAsdTsdGsdGsdAsdCsdCsAb¹sGb¹sTb¹sAb¹sTb¹ |
| 4216 | 17 | 224b | C*b²sAb²sTb²sdGsdAsdAsdTsdGsdGsdAsdCsdCsAb²sGb²sTb²sAb²sTb² |
| 4216 | 17 | 224c | C*b¹sAb¹sTb¹sGb¹sdAsdAsdTsdGsdGsdAsdCsdCsdAsdGsTb¹sAb¹sTb¹ |
| 4216 | 17 | 224d | C*b¹sdAsdUsdGsdAsdAsdUsdGsdGsdAsdC*sdC*sAb¹sGb¹sTb¹sAb¹sTb¹ |
| 4216 | 17 | 224e | C*b¹sAb¹sTb¹sdGsdA*sdA*sdTsdGsdGsdA*sdC*sdC*sAb¹sGb¹sTb¹sAb¹sTb¹ |
| 4216 | 17 | 224f | C*b¹Ab¹dTdGdAdAdTdGdGdAdCdCdAGb¹Tb¹Ab¹Tb¹ |
| 4216 | 17 | 224g | C*b¹sdAsdTsdGsdAsdAsdTsdGsdGsdAsdCsdCsdAsdGsTb¹sAb¹sTb¹ |
| 4216 | 17 | 224h | C*b¹Ab¹Tb¹Gb¹Ab¹dA*dTdGdGdA*dC*dC*dAdGdTAb¹Tb¹ |

TABLE 8-continued

| SP | L | Seq ID No. | Sequence, 5'-3' |
|---|---|---|---|
| 4216 | 17 | 224i | C*b$^1$ssAb$^1$ssTb$^1$ssGb$^1$ssAb$^1$ssdAssdTssdGssdGssdAssdCssdCssdAssdGssTb$^1$ssAb$^1$ssTb$^1$ |
| 4216 | 17 | 224j | C*b$^4$Ab$^4$Tb$^4$dGdA*dA*dTdGdGdA*dCdCdAGb$^4$Tb$^4$Ab$^4$Tb$^4$ |
| 4216 | 17 | 224k | C*b$^6$sAb$^6$sTb$^6$sdGsdA*sdA*sdUsdGsdGsdA*sdC*sdC*sdAsdGsTb$^6$sAb$^6$sTb$^6$ |
| 4216 | 17 | 224m | C*b$^7$sAb$^7$sTb$^7$sGb$^7$sdAsdAsdTdGdGdAdC*dC*dAsGb$^7$sTb$^7$sAb$^7$sTb$^7$ |
| 4216 | 18 | 225a | Tb$^1$sC*b$^1$sAb$^1$sTb$^1$sGb$^1$sdAsdAsdTsdGsdGsdAsdCsdCsAb$^1$sGb$^1$sTb$^1$sAb$^1$sTb$^1$ |
| 4216 | 18 | 225b | Tb$^7$sC*b$^7$sAb$^7$sTb$^7$sGb$^7$sdAsdAsdTsdGsdGsdAsdCsdCsdAsdGsdTsdAsTb$^7$ |
| 4216 | 18 | 225c | Tb$^1$sC*b$^1$sAb$^1$sTb$^1$sdGsdAsdAsdTsdGsdGsdGsdAsdC*sdC*sdAsGb$^1$sTb$^1$sAb$^1$sTb$^1$ |
| 4216 | 18 | 225d | Tb$^1$sC*b$^1$sAb$^1$sdTsdGsdAsdAsdTsdGsdGsdAsdCsdCsdAsGb$^1$sTb$^1$sAb$^1$sTb$^1$ |
| 4216 | 18 | 225e | Tb$^1$sC*b$^1$sAb$^1$sTb$^1$sdGsdAsdAsdTsdGsdGsdGsdAsdCsdCsdAsdGsTb$^1$sAb$^1$sTb$^1$ |
| 4216 | 18 | 225f | Tb$^1$C*b$^1$dA*dTdGdAdAdUdGdGdAdCdC*Ab$^1$Gb$^1$Tb$^1$Ab$^1$Tb$^1$ |
| 4216 | 18 | 225g | Tb$^4$C*b$^4$Ab$^4$Tb$^4$sdGsdAsdAsdTsdGsdGsdAsdCsdCsAb$^4$Gb$^4$Tb$^4$Ab$^4$Tb$^4$ |
| 4216 | 18 | 225h | Tb$^1$ssC*b$^1$ssAb$^1$ssdTssdGssdA*ssdA*ssdTssdGssdGssdAssdCssdC*ssdA*ssdGssTb$^1$ssAb$^1$ssTb$^1$ |
| 4216 | 18 | 225i | Tb$^2$C*b$^2$Ab$^2$dTdGdAdAdTdGdGdAdC*dC*Ab$^2$Gb$^2$Tb$^2$Ab$^2$Tb$^2$ |
| 4215 | 19 | 226a | Tb$^1$sC*b$^1$sAb$^1$sTb$^1$sGb$^1$sdAsdAsdTsdGsdGsdAsdCsdCsAsGb$^1$sTb$^1$sAb$^1$sTb$^1$sTb$^1$ |
| 4215 | 19 | 226b | Tb$^6$C*b$^6$Ab$^6$Tb$^6$Gb$^6$dAdAdTdGdGdAdCdCdAGb$^6$Tb$^6$Ab$^6$Tb$^6$Tb$^6$ |
| 4215 | 19 | 226c | Tb$^1$sC*b$^1$sAb$^1$sTb$^1$sdGsdAsdAsdTsdGsdGsdGsdAsdCsdCsdAsdGsdTsAb$^1$sTb$^1$sTb$^1$ |
| 4215 | 19 | 226d | Tb$^1$sdCsdAsdTsdGsdAsdA*sdUsdGsdGsdAsdCsdCsdAsGb$^1$sTb$^1$sAb$^1$sTb$^1$sTb$^1$ |
| 4215 | 19 | 226e | Tb$^4$sC*b$^4$sdAsdUsdGsdAsdAsdUsdGsdGsdAsdCsdC*sdAsdGsTb$^4$sAb$^4$sTb$^4$sTb$^4$ |
| 4215 | 19 | 226f | Tb$^2$ssC*b$^2$ssAb$^2$ssTb$^2$ssGb$^2$ssdAssdAssdTssdGssdGssdAssdCssdCssdAssdGssdTssdAssTb$^2$ssTb$^2$ |
| 4215 | 20 | 227a | C*b$^1$sTb$^1$sC*b$^1$sAb$^1$sTb$^1$sdGsdAsdAsdTsdGsdGsdGsdAsdCsdCsdAsGb$^1$sTb$^1$sAb$^1$sTb$^1$sTb$^1$ |
| 4215 | 20 | 227b | C*b$^2$sTb$^2$sC*b$^2$sdAsdTsdGsdAsdAsdTsdGsdGsdGsdAsdCsdCsdAsGb$^2$sTb$^2$sAb$^2$sTb$^2$sTb$^2$ |
| 4215 | 20 | 227c | C*b$^1$Tb$^1$C*b$^1$dAdTdGdAdAdTdGdGdAdCdC*dAdGTb$^1$Ab$^1$Tb$^1$Tb$^1$ |
| 4215 | 20 | 227d | C*b$^1$sdUsdCsdAsdTsdGsdAsdAsdTsdGsdGsdGsdAsdCsdCsdAsGb$^1$sTb$^1$sAb$^1$sTb$^1$sTb$^1$ |
| 4215 | 20 | 227e | C*b$^4$sTb$^4$sC*b$^4$sAb$^4$sdTsdGsdAsdAsdTsdGsdGsdAsdCsdCsdAsdGsTb$^4$sAb$^4$sTb$^4$sTb$^4$ |
| 4214 | 22 | 228a | Tb$^1$sC*b$^1$sTb$^1$sC*b$^1$sAb$^1$sdTsdGsdAsdAsdTsdGsdGsdGsdAsdCsdCsdAsdGsTb$^1$sAb$^1$sTb$^1$sTb$^1$sC*b$^1$ |
| 4214 | 22 | 228b | Tb$^1$C*b$^1$Tb$^1$C*b$^1$Ab$^1$dTdGdAdAdTdGdGdAdC*dC*dAdGTb$^1$Ab$^1$Tb$^1$Tb$^1$C*b$^1$ |
| 4214 | 22 | 228c | Tb$^6$sC*b$^6$sTb$^6$sdCsdAsdTsdGsdAsdAsdTsdGsdGsdAsdCsdCsdAsdGsdTsAb$^6$sTb$^6$sTb$^6$sC*b$^6$ |
| 4213 | 24 | 229a | Ab$^1$sTb$^1$sC*b$^1$sTb$^1$sC*b$^1$sdAsdTsdGsdAsdAsdTsdGsdGsdAsdC*sdCsdAsdGsdTsAb$^1$sTb$^1$sTb$^1$sC*b$^1$sTb$^1$ |
| 4213 | 24 | 229b | Ab$^1$Tb$^1$C*b$^1$Tb$^1$C*b$^1$AdTdGdAdAdTdGdGdAdCdCdAdGdTAb$^1$Tb$^1$Tb$^1$C*b$^1$Tb$^1$ |
| 4212 | 26 | 230a | Tb$^1$sAb$^1$sTb$^1$sC*b$^1$sTb$^1$sdCsdAsdTsdGsdAsdAsdTsdGsdGsdAsdCsdCsdAsdGsdTsdAsTb$^1$sTb$^1$sC*b$^1$sTb$^1$sAb$^1$ |

TABLE 8-continued

| SP | L | Seq ID No. | Sequence, 5'-3' |
|---|---|---|---|
| 4212 | 26 | 230a | Tb$^1$sAb$^1$sTb$^1$sC*b$^1$sTb$^1$sdCsdAsdTsdGsdAsdAsdTsdGsdGsdAsdCsdCsdAsdGsdTsdAsTb$^1$sTb$^1$sC*b$^1$sTb$^1$sAb$^1$ |
| 4212 | 26 | 230b | Tb$^1$Ab$^1$Tb$^1$C*b$^1$Tb$^1$dCdAdTdGdAdAdTdGdGdAdCdCdAdGdTdATb$^1$Tb$^1$C*b$^1$Tb$^1$Ab$^1$ |
| 4211 | 28 | 231a | Ab$^1$sTb$^1$sAb$^1$sTb$^1$sC*b$^1$sdTsdCsdAsdTsdGsdAsdAsdTsdGsdGsdAsdCsdCsdAsdGsdTsdAsdTsTb$^1$sC*b$^1$sTb$^1$sAb$^1$sGb$^1$ |
| 4211 | 28 | 231b | Ab$^1$Tb$^1$Ab$^1$Tb$^1$C*b$^1$dTdCdAdTdGdAdAdTdGdGdAdCdCdAdGdTdAdTTb$^1$C*b$^1$Tb$^1$Ab$^1$Gb$^1$ |

TABLE 9

| SP | L | Seq ID No. | Sequence, 5'-3' |
|---|---|---|---|
| 2358 | 10 | 284a | C*b$^1$sAb$^1$sdTsdTsdAsdAsdTsdA*sAb$^1$sAb$^1$ |
| 2358 | 10 | 284b | C*b$^1$Ab$^1$dTdTdA*dAdTdA*Ab$^1$Ab$^1$ |
| 2357 | 12 | 285a | Gb$^1$sC*b$^1$sAb$^1$sdTsdTsdA*sdA*sdTsdAsAb$^1$sAb$^1$sGb$^1$ |
| 2357 | 12 | 285b | Gb$^1$sC*b$^1$sAb$^1$sdTsdTsdA*sdA*sdTsdAsdA*sAb$^1$sGb$^1$ |
| 2357 | 12 | 285c | Gb$^1$sC*b$^1$sdAsdTsdTsdA*sdA*sdUsdAsdA*sdA*sGb$^1$ |
| 2357 | 12 | 285d | Gb$^1$sdC*sdAsdTsdTsdAsdAsdTsdAsdAsAb$^1$sGb$^1$ |
| 2357 | 12 | 285e | Gb$^1$sdC*sdAsdTsdTsdAsdAsdTsdAsdA*sAb$^1$sGb$^1$ |
| 2357 | 12 | 285f | Gb$^1$C*b$^1$Ab$^1$dTdTdA*dA*dTdAAb$^1$Ab$^1$Gb$^1$ |
| 2356 | 13 | 286a | Gb$^1$sC*b$^1$sAb$^1$sTb$^1$sdTsdAsdAsdTsdAsdAsAb$^1$sGb$^1$sTb$^1$ |
| 2356 | 13 | 286b | Gb$^1$sC*b$^1$sAb$^1$sTb$^1$sdTsdA*sdA*sdTsdAsdAsAb$^1$sGb$^1$sTb$^1$ |
| 2356 | 13 | 286c | Gb$^1$sC*b$^1$sAb$^1$sdUsdTsdAsdAsdTsdAsdAsdA*sGb$^1$sTb$^1$ |
| 2356 | 13 | 286d | Gb$^1$sC*b$^1$sdAsdTsdTsdAsdA*sdUsdAsdAsdAsdGsTb$^1$ |
| 2356 | 13 | 286e | Gb$^1$sdC*sdAsdTsdTsdAsdAsdTsdAsAb$^1$sAb$^1$sGb$^1$sTb$^1$ |
| 2356 | 13 | 286f | Gb$^1$sdC*sdAsdTsdTsdAsdAsdTsdA*sAb$^1$sAb$^1$sGb$^1$sTb$^1$ |
| 2356 | 13 | 286g | Gb$^1$C*b$^1$Ab$^1$Tb$^1$dUdAdAdUdAdAAb$^1$Gb$^1$Tb$^1$ |
| 2356 | 14 | 287a | Gb$^1$sGb$^1$sC*b$^1$sAb$^1$sdTsdTsdA*sdAsdTsdAsAb$^1$sAb$^1$sGb$^1$sTb$^1$ |
| 2356 | 14 | 287b | Gb$^4$sGb$^4$sC*b$^1$sAb$^4$sdTsdTsdA*sdAsdUsdAsdAsdA*sGb$^4$sTb$^4$ |
| 2356 | 14 | 287c | Gb$^1$sdGsdCsdAsdUsdUsdAsdAsdTsdA*sdA*sdA*sdGsTb$^1$ |
| 2356 | 14 | 287d | Gb$^2$sGb$^2$sC*b$^1$sdA*sdUsdTsdA*sdAsdTsdAsdA*sAb$^2$sGb$^2$sTb$^2$ |
| 2356 | 14 | 287e | Gb$^1$Gb$^1$C*b$^1$Ab$^1$sdTsdTsdAsdAsdTsdA*sdA*sAb$^1$Gb$^1$Tb$^1$ |
| 2356 | 14 | 287f | Gb$^1$sGb$^1$sdC*sdAsdTsdTsdAsdAsdTsdAsAb$^1$sAb$^1$sGb$^1$sTb$^1$ |
| 2356 | 14 | 287g | Gb$^1$sGb$^1$sdC*sdA*sdTsdA*sdA*sdTsdA*sAb$^1$sAb$^1$sGb$^1$sTb$^1$ |
| 2356 | 14 | 287h | Gb$^1$Gb$^1$dC*dAdTdTdAdAdTdAAb$^1$Ab$^1$Gb$^1$Tb$^1$ |
| 2356 | 14 | 287i | Gb$^4$ssGb$^4$ssdCssdAssdTssdTssdAssdAssdTssdAssAb$^4$ssAb$^4$ssGb$^4$ssTb$^4$ |
| 2356 | 14 | 287j | Gb$^4$ssGb$^4$ssdC*ssdAssdTssdTssdAssdAssdTssdAssAb$^4$ssAb$^4$ssGb$^4$ssTb$^4$ |
| 2355 | 15 | 288a | Gb$^1$sGb$^1$sdC*sdAsdTsdTsdAsdAsdTsdAsdAsdGb$^1$sTb$^1$sGb$^1$ |
| 2355 | 15 | 288b | Gb$^1$sGb$^1$sC*b$^1$sAb$^1$sdTsdTsdA*sdA*sdTsdAsdAsdAsdGsdTsGb$^1$ |
| 2355 | 15 | 288c | Gb$^4$sGb$^4$sC*b$^1$sdAsdTsdTsdAsdAsdTsdAsdAsdAsdGsTb$^4$sGb$^4$ |

TABLE 9-continued

| SP | L | Seq ID No. | Sequence, 5'-3' |
|---|---|---|---|
| 2355 | 15 | 288d | Gb¹sGb¹sC*b¹sAb¹sdTdTdAdAdTdAdAsAb¹sGb¹sTb¹sGb¹ |
| 2355 | 15 | 288e | Gb¹Gb¹sdC*sdAsdTsdTsdAsdAsdTsdAsdAsAb¹Gb¹Tb¹Gb¹ |
| 2355 | 15 | 288f | Gb¹ssGb¹ssdCssdAssdUssdUssdAssdAssdUssdAssdAssdGssTb¹ssGb¹ |
| 2355 | 15 | 288g | Gb¹ssGb¹ssdCssdAssdTssdTssdAssdAssdTssdAssdAssdGssdTssGb¹ |
| 2355 | 15 | 288h | Gb⁶Gb⁶C*b⁶dA*dTdTdAdAdUdA*dA*dAGb⁶Tb⁶Gb⁶ |
| 2355 | 15 | 288i | Gb¹Gb¹C*b¹dAdTdTdAdAdUdAdAdAGb¹Tb¹Gb¹ |
| 2355 | 16 | 289a | Ab¹sGb¹sGb¹sC*b¹sAb¹sdTsdTsdA*sdA*sdTsdA*sAb¹sAb¹sGb¹sTb¹sGb¹ |
| 2355 | 16 | 289b | Ab¹sGb¹sGb¹sdC*sdAsdTsdTsdAsdAsdTsdAsAb¹sAb¹sGb¹sTb¹sGb¹ |
| 2355 | 16 | 289c | Ab¹sGb¹sGb¹sdC*sdA*sdTsdTsdA*sdA*sdTsdA*sAb¹sAb¹sGb¹sTb¹sGb¹ |
| 2355 | 16 | 289d | Ab²sGb²sGb²sdC*sdAsdTsdTsdAsdAsdTsdAsAb²sAb²sGb²sTb²sGb² |
| 2355 | 16 | 289e | Ab¹sdGsdGsdC*sdAsdTsdTsdAsdAsdTsdAsAb¹sAb¹sGb¹sTb¹sGb¹ |
| 2355 | 16 | 289f | Ab¹sdGsdGsdC*sdAsdTsdUsdAsdAsdUsdAsAb¹sAb¹sGb¹sTb¹sGb¹ |
| 2355 | 16 | 289g | Ab¹sGb¹sGb¹sdC*sdAsdTsdTsdAsdAsdTsdAsdAsAb¹sGb¹sTb¹sGb¹ |
| 2355 | 16 | 289h | Ab¹sGb¹sGb¹sC*b¹sdA*sdTsdTsdA*sdA*sdTsdA*sdAsdAsGb¹sTb¹sGb¹ |
| 2355 | 16 | 289i | Ab⁶sGb⁶sGb⁶sdC*sdA*sdUsdTsdAsdAsdTsdAsdAsdAsGb⁶sTb⁶sGb⁶ |
| 2355 | 16 | 289j | Ab¹sGb¹sGb¹sdC*sdAsdTsdTsdAsdAsdTsdAsdAsdAsGb¹sTb¹sGb¹ |
| 2355 | 16 | 289k | Ab¹sdGsdGsdC*sdAsdTsdTsdAsdAsdTsdAsdAsdAsGb¹sTb¹sGb¹ |
| 2355 | 16 | 289m | Ab¹Gb¹Gb¹C*b¹Ab¹dUdTdA*dA*dTdAdAdAdGTb¹Gb¹ |
| 2355 | 16 | 289n | Ab¹Gb¹dGdC*dAdTdTdAdAdTdAdAdAAb¹Gb¹Tb¹Gb¹ |
| 2355 | 16 | 289o | Ab⁴Gb⁴Gb⁴dCdA*dTdTdAdAdTdAdA*Ab⁴Gb⁴Tb⁴Gb⁴ |
| 2355 | 16 | 289p | Ab¹ssGb¹ssGb¹ssC*b¹ssAb¹ssdTssdTssdAssdAssdTssdAssdAssdAssGb¹ssTb¹ssGb¹ |
| 2355 | 16 | 289q | Ab⁷sGb⁷sGb⁷sC*b¹sdA*dTdTdAdAdTdAdA*sAb⁷sGb⁷sTb⁷sGb⁷ |
| 2355 | 17 | 213j | C*b¹sAb¹sGb¹sdGsdC*sdAsdTsdTsdAsdAsdTsdAsdAsdAsGb¹sTb¹sGb¹ |
| 2355 | 17 | 213k | C*b¹sAb¹sGb¹sdGsdCsdAsdTsdTsdAsdAsdTsdAsdAsdAsGb¹sTb¹sGb¹ |
| 2355 | 17 | 213m | C*b¹sAb¹sGb¹sdGsdC*sdAsdTsdTsdAsdAsdTsdAsdA*sdA*sGb¹sTb¹sGb¹ |
| 2355 | 17 | 213n | C*b¹Ab¹Gb¹dGdC*dAdTdTdAdAdTdAdAdAGb¹Tb¹Gb¹ |
| 2355 | 17 | 213o | /5SpC3s/C*b¹sAb¹sGb¹sdGsdC*sdAsdTsdTsdAsdAsdTsdAsdAsdAsGb¹sTb¹sGb¹ |
| 2355 | 17 | 213p | C*b¹sAb¹sGb¹sdGsdC*sdAsdTsdTsdAsdAsdTsdAsdAsdAsGb¹sTb¹sGb¹/3SpC3s/ |
| 2355 | 17 | 213q | /5SpC3s/C*b¹sAb¹sGb¹sdGsdC*sdAsdTsdTsdAsdAsdTsdAsdAsdAsGb¹sTb¹sGb¹/3SpC3s/ |
| 2355 | 17 | 213r | C*b¹sAb¹sGb¹sdGsdC*sdAsdTsdTsdAsdAsdUsdAsdAsdA*sGb¹sTb¹sGb¹ |
| 2355 | 17 | 213s | C*b⁶sAb⁶sGb⁶sdGdC*dAdTdTdAdAdTdAdAdAsGb⁶sTb⁶sGb⁶ |
| 2355 | 17 | 213t | C*b¹sAb¹sGb¹sdGdC*dAdTdTdAdAdTdAdAdAsGb¹sTb¹sGb¹ |
| 2355 | 17 | 213u | C*b¹Ab¹Gb¹sdGsdC*sdAsdUsdUsdAsdAsdUsdAsdAsdAsGb¹Tb¹Gb¹ |
| 2355 | 17 | 213v | C*b¹Ab¹Gb¹sdGsdC*sdAsdTsdTsdAsdA*sdTsdAsdAsdA*sGb¹Tb¹Gb¹ |
| 2355 | 17 | 213w | C*b¹Ab¹Gb¹sdGsdC*sdAsdTsdTsdAsdAsdTsdAsdAsdAsGb¹Tb¹Gb¹ |
| 2355 | 17 | 213x | C*b⁷sAb⁷sGb⁷sGb⁷sdC*sdAsdTsdTsdAsdAsdTsdAsdAsdAsGb⁷sTb⁷sGb⁷ |

TABLE 9-continued

| SP | Seq L | ID No. | Sequence, 5'-3' |
|---|---|---|---|
| 2355 | 17 | 213y | C*b⁶sAb⁶sGb⁶sGb⁶sdCsdAsdTsdTsdAsdAsdTsdAsdAsdAsGb⁶sTb⁶sGb⁶ |
| 2355 | 17 | 213z | C*b⁷sAb⁷sGb⁷sdGsdCsdA*sdUsdTsdAsdAsdTsdAsdAAb⁷sGb⁷sTb⁷sGb⁷ |
| 2355 | 17 | 213aa | C*b⁴sAb⁴sGb⁴sGb⁴sdC*sdA*sdTsdTsdAsdAsdTsdAsdA*sdAsdGsTb⁴sGb⁴ |
| 2355 | 17 | 213ab | C*b¹sAb¹sGb¹sGb¹sC*b¹sdA*sdTsdTsdA*sdA*sdTsdAsdA*sdA*sGb¹sTb¹sGb¹ |
| 2355 | 17 | 213ac | C*b¹sAb¹sGb¹sdGsdCsdAsdTsdTsdA*sdA*sdTsdAsAb¹sAb¹sGb¹sTb¹sGb¹ |
| 2355 | 17 | 213ad | C*b¹sAb¹sdGsdGsdC*sdAsdTsdTsdAsdAsdUsdAsdAsAb¹sGb¹sTb¹sGb¹ |
| 2355 | 17 | 213ae | C*b¹ssAb¹ssGb¹ssdGssdC*ssdAssdTssdTssdAssdAssdTssdAssdAssAb¹ssGb¹ssTb¹ssGb¹ |
| 2355 | 17 | 213af | C*b⁴ssAb⁴ssGb⁴ssdGssdCssdAssdTssdTssdA*ssdAssdTssdAssdAssdAssdGssTb⁴ssGb⁴ |
| 2355 | 17 | 213ag | C*b²ssAb²ssGb²ssGb²ssdCssdAssdTssdTssdAssdAssdTssdAssdAssdAssdGssdTssGb² |
| 2355 | 17 | 213ah | C*b¹Ab¹Gb¹Gb¹dCdAdTdTdAdAdUdAdAAb¹Gb¹Tb¹Gb¹ |
| 2355 | 17 | 213ai | C*b⁴Ab⁴Gb⁴Gb⁴dCdAdTdTdAdAdTdAdAdAdGTb⁴Gb⁴ |
| 2355 | 17 | 213aj | C*b¹Ab¹Gb¹dGdCdAdTdTdAdAdUdAdAdAGb¹Tb¹Gb¹ |
| 2355 | 17 | 213ak | C*b¹sAb¹sGb¹sGb¹sdCsdAsdTsdTsdAsdAsdTsdAsdAsAb¹sGb¹sTb¹sGb¹ |
| 2354 | 18 | 290a | C*b¹sAb¹sGb¹sGb¹sC*b¹sdAsdTsdTsdAsdAsdTsdA*sdAsAb¹sGb¹sTb¹sGb¹sC*b¹ |
| 2354 | 18 | 290b | C*b¹sAb¹sGb¹sGb¹sdC*sdAsdTsdTsdAsdAsdTsdAsdAsAsGb¹sTb¹sGb¹sC*b¹ |
| 2354 | 18 | 290c | C*b¹sAb¹sGb¹sGb¹sdC*sdAsdTsdTsdAsdAsdTsdAsdAsdAsdGsTb¹sGb¹sC*b¹ |
| 2354 | 18 | 290d | C*b¹sAb¹sGb¹sdGsdC*sdAsdTsdTsdAsdAsdTsdAsdAsdAsAsGb¹sTb¹sGb¹sC*b¹ |
| 2354 | 18 | 290e | C*b⁷sAb⁷sGb⁷sGb⁷sC*b⁷sdA*sdTsdTsdAsdAsdTsdAsdAsdAsdGsdTsdGsC*b⁷ |
| 2354 | 18 | 290f | C*b⁴Ab⁴Gb⁴Gb⁴sdCsdAsdTsdTsdAsdAsdTsdA*sdAsAb⁴Gb⁴Tb⁴Gb⁴C*b⁴ |
| 2354 | 18 | 290g | C*b¹ssAb¹ssGb¹ssdGssdC*ssdAssdTssdTssdA*ssdAssdTssdA*ssdAssdA*ssdGssTb¹ssGb¹ssC*b¹ |
| 2354 | 18 | 290h | C*b²Ab²Gb²dGdC*dAdTdTdAdAdTdAdAAb²Gb²Tb²Gb²C*b² |
| 2354 | 18 | 290i | C*b¹Ab¹dGdGdC*dA*dUdUdAdAdUdA*dA*Ab¹Gb¹Tb¹Gb¹C*b¹ |
| 2354 | 19 | 291a | Ab¹sC*b¹sAb¹sGb¹sGb¹sdC*sdAsdTsdTsdAsdAsdTsdAsdAsAb¹sGb¹sTb¹sGb¹sC*b¹ |
| 2354 | 19 | 291b | Ab¹sC*b¹sAb¹sGb¹sdGsdC*sdAsdTsdTsdAsdAsdTsdAsdAsdAsdGsTb¹sGb¹sC*b¹ |
| 2354 | 19 | 291c | Ab⁴sC*b⁴sdAsdGsdGsdC*sdAsdTsdTsdAsdAsdUsdAsdAsdAsGb⁴sTb⁴sGb⁴sC*b⁴ |
| 2354 | 19 | 291d | Ab¹sdC*sdAsdGsdGsdC*sdA*sdTsdAsdAsdTsdAsdAsAb¹sGb¹sTb¹sGb¹sC*b¹ |
| 2354 | 19 | 291e | Ab²ssC*b²ssAb²ssGb²ssGb²ssdCssdAssdTssdTssdAssdAssdTssdAssdAssdAssdGssdTssGb²ssC*b² |
| 2354 | 19 | 291f | Ab⁶C*b⁶Ab⁶Gb⁶Gb⁶dC*dAdTdTdAdAdTdAdAAb⁶Gb⁶Tb⁶Gb⁶C*b⁶ |
| 2353 | 20 | 292a | Ab¹sC*b¹sAb¹sGb¹sGb¹sdC*sdAsdTsdTsdAsdAsdTsdAsdAsdAsGb¹sTb¹sGb¹sC*b¹sAb¹ |
| 2353 | 20 | 292b | Ab²sC*b²sAb²sdGsdGsdC*sdAsdTsdTsdAsdAsdTsdAsdAsdAsGb²sTb²sGb²sC*b²sAb² |

TABLE 9-continued

| SP | L | Seq ID No. | Sequence, 5'-3' |
|---|---|---|---|
| 2353 | 20 | 292c | Ab¹sdC*sdAsdGsdGsdC*sdAsdUsdUsdAsdAsdUsdAsdAsdAsGb¹sTb¹sGb¹sC*b¹sAb¹ |
| 2353 | 20 | 292d | Ab⁴sC*b⁴sAb⁴sGb⁴sdGsdCsdAsdTsdTsdAsdAsdTsdAsdAsdAsdGsTb⁴sGb⁴sC*b⁴sAb⁴ |
| 2353 | 20 | 292e | Ab¹C*b¹Ab¹dGdGdC*dAdTdTdAdAdTdAdAdAdGTb¹Gb¹C*b¹Ab¹ |
| 2352 | 22 | 293a | Tb¹sAb¹sC*b¹sAb¹sGb¹sdGsdC*sdAsdTsdTsdAsdAsdTsdAsdAsdAsdGsTb¹sGb¹sC*b¹sAb¹sAb¹ |
| 2352 | 22 | 293b | Tb¹Ab¹C*b¹Ab¹Gb¹dGdC*dAdTdTdAdAdTdAdAdAdGTb¹Gb¹C*b¹Ab¹Ab¹ |
| 2352 | 22 | 293c | Tb⁶sAb⁶sC*b⁶sdAsdGsdGsdCsdAsdTsdTsdAsdAsdTsdAsdAsdAsdGsTb⁶sGb⁶sC*b⁶sAb⁶sAb⁶ |
| 2351 | 24 | 294a | Ab¹sTb¹sAb¹sC*b¹sAb¹sdGsdGsdC*sdAsdTsdTsdAsdAsdTsdAsdAsdAsdGsdTsGb¹sC*b¹sAb¹sAb¹sAb¹ |
| 2351 | 24 | 294b | Ab¹Tb¹Ab¹C*b¹Ab¹dGdGdC*dAdTdTdAdAdTdAdAdAdGdTGb¹C*b¹Ab¹Ab¹Ab¹ |
| 2350 | 26 | 295a | Tb¹sAb¹sTb¹sAb¹sC*b¹sdAsdGsdGsdC*sdAsdTsdTsdAsdAsdTsdAsdAsdAsdGsdTsdGsC*b¹sAb¹sAb¹sAb¹sTb¹ |
| 2350 | 26 | 295b | Tb¹Ab¹Tb¹Ab¹C*b¹dAdGdGdC*dAdTdTdAdAdTdAdAdAdGdTdGC*b¹Ab¹Ab¹Ab¹Tb¹ |
| 2349 | 28 | 236a | Ab¹sTb¹sAb¹sTb¹sAb¹sdC*sdAsdGsdGsdC*sdAsdTsdTsdAsdAsdTsdAsdAsdAsdGsdTsdGsdC*sAb¹sAb¹sAb¹sTb¹sGb¹ |
| 2349 | 28 | 236b | Ab¹Tb¹Ab¹Tb¹Ab¹dC*dAdGdGdCdAdTdTdAdAdTdAdAdAdGdTdGdC*Ab¹Ab¹Ab¹Tb¹Gb¹ |

Pharmaceutical Compositions

The antisense-oligonucleotides of the present invention are preferably administered in form of their pharmaceutically active salts optionally using substantially nontoxic pharmaceutically acceptable carriers, excipients, adjuvants, solvents or diluents. The medications of the present invention are prepared in a conventional solid or liquid carrier or diluents and a conventional pharmaceutically-made adjuvant at suitable dosage level in a known way. The preferred preparations and formulations are in administrable form which is suitable for infusion or injection (intrathecal, intracerebroventricular, intracranial, intravenous, intraparenchymal, intratumoral, intra- or extraocular, intraperitoneal, intramuscular, subcutaneous), local administration into the brain, inhalation, local administration into a solid tumor or oral application. However also other application forms are possible such as absorption through epithelial or mucocutaneous linings (oral mucosa, rectal and vaginal epithelial linings, nasopharyngial mucosa, intestinal mucosa), rectally, transdermally, topically, intradermally, intragastrically, intracutaneously, intravaginally, intravasally, intranasally, intrabuccally, percutaneously, sublingually application, or any other means available within the pharmaceutical arts. The administrable formulations, for example, include injectable liquid formulations, retard formulations, powders especially for inhalation, pills, tablets, film tablets, coated tablets, dispersible granules, dragees, gels, syrups, slurries, suspensions, emulsions, capsules and deposits. Other administratable galenical formulations are also possible like a continuous injection through an implantable pump or a catheter into the brain.

As used herein the term "pharmaceutically acceptable" refers to any carrier which does not interfere with the effectiveness of the biological activity of the antisense-oligonucleotides as active ingredient in the formulation and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose.

An "effective dose" refers to an amount of the antisense-oligonucleotide as active ingredient that is sufficient to affect the course and the severity of the disease, leading to the reduction or remission of such pathology. An "effective dose" useful for treating and/or preventing these diseases or disorders may be determined using methods known to one skilled in the art. Furthermore, the antisense-oligonucleotides of the present invention may be mixed and administered together with liposomes, complex forming agents, receptor targeted molecules, solvents, preservatives and/or diluents.

Preferred are pharmaceutical preparations in form of infusion solutions or solid matrices for continuous release of the active ingredient, especially for continuous infusion for intrathecal administration, intracerebroventricular administration or intracranial administration of at least one antisense-oligonucleotide of the present invention. Also preferred are pharmaceutical preparations in form of solutions or solid matrices suitable for local administration into the brain. For fibrotic diseases of the lung, inhalation formulations are especially preferred.

A ready-to-use sterile solution comprises for example at least one antisense-oligonucleotide at a concentration ranging from 1 to 10 mg/ml, preferably from to 10 mg/ml and an isotonic agent selected, for example, amongst sugars such as sucrose, lactose, mannitol or sorbitol. A suitable buffering agent, to control the solution pH to 6 to 8 (preferably 7-8), may be also included. Another optional ingredient of the formulation can be a non-ionic surfactant, such as Tween 20 or Tween 80.

A sterile lyophilized powder to be reconstituted for use comprises at least one antisense-oligonucleotide, and optionally a bulking agent (e.g. mannitol, trehalose, sorbitol, glycine) and/or a cryoprotectent (e.g. trehalose, mannitol). The solvent for reconstitution can be water for injectable compounds, with or without a buffering salt to control the pH to 6 to 8.

Aerosol preparations suitable for inhalation may include solutions and solids in powder form, which may be in combination with a pharmaceutically acceptable carrier such as inert compressed gas, e.g. nitrogen.

A particularly preferred pharmaceutical composition is a lyophilized (freeze-dried) preparation (lyophilisate) suitable for administration by inhalation or for intravenous administration. To prepare the preferred lyophilized preparation at least one antisense-oligonucleotide of the invention is solubilized in a 4 to 5% (w/v) mannitol solution and the solution is then lyophilized. The mannitol solution can also be prepared in a suitable buffer solution as described above.

Further examples of suitable cryo-/lyoprotectants (otherwise referred to as bulking agents or stabilizers) include thiol-free albumin, immunoglobulins, polyalkyleneoxides (e.g. PEG, polypropylene glycols), trehalose, glucose, sucrose, sorbitol, dextran, maltose, raffinose, stachyose and other saccharides (cf. for instance WO 97/29782), while mannitol is used preferably. These can be used in conventional amounts in conventional lyophilization techniques. Methods of lyophilization are well known in the art of preparing pharmaceutical formulations.

For administration by inhalation the particle diameter of the lyophilized preparation is preferably between 2 to 5 μm, more preferably between 3 to 4 μm. The lyophilized preparation is particularly suitable for administration using an inhalator, for example the OPTINEB® or VENTA-NEB® inhalator (NEBU-TEC, Elsenfeld, Germany). The lyophilized product can be rehydrated in sterile distilled water or any other suitable liquid for inhalation administration. Alternatively, for intravenous administration the lyophilized product can be rehydrated in sterile distilled water or any other suitable liquid for intravenous administration.

After rehydration for administration in sterile distilled water or another suitable liquid the lyophilized preparation should have the approximate physiological osmolality of the target tissue for the rehydrated peptide preparation i.e. blood for intravenous administration or lung tissue for inhalation administration. Thus it is preferred that the rehydrated formulation is substantially isotonic.

The preferred dosage concentration for either intravenous, oral, or inhalation administration is between 10 to 2000 μmol/ml, and more preferably is between 200 to 800 μmol/ml.

For oral administration in the form of tablets or capsules, the at least one antisense-oligonucleotide may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like.

Additionally, the compositions of the present invention may be formulated in sustained release form to provide the rate controlled release of the at least one antisense-oligonucleotide to optimize the therapeutic effects. Suitable dosage forms for sustained release include implantable biodegradable matrices for sustained release containing the at least one antisense-oligonucleotide, layered tablets containing layers of varying disintegration rates or controlled release polymeric matrices impregnated with the at least one antisense-oligonucleotide.

Liquid form preparations include solutions, suspensions and emulsions. As an example may be mentioned water or water-propylene glycol solutions for parenteral injections or addition of sweeteners and opacifiers for oral solutions, suspensions and emulsions.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluents in the composition can range from about 5% to about 95% by weight of the total composition, preferably from about 25% to about 75% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates, such as magnesium stearate, calcium stearate or potassium stearate, stearic acid; high melting point waxes; and water soluble lubricants, such as sodium chloride, sodium benzoate, sodium acetate, sodium oleate, polyethylene glycols and D,L-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

In the pharmaceutical compositions disclosed herein the antisense-oligonucleotides are incorporated preferably in the form of their salts and optionally together with other components which increase stability of the antisense-oligonucleotides, increase recruitment of RNase H, increase target finding properties, enhance cellular uptake and the like. In order to achieve these goals, the antisense-oligonucleotides may be chemically modified instead of or in addition to the use of the further components useful for achieving these purposes. Thus the antisense-oligonucleotides of the invention may be chemically linked to moieties or components which enhance the activity, cellular distribution or cellular uptake etc. of the antisense-oligonucleotides. Such moieties include lipid moieties such as a cholesterol moiety, cholic acid, a thioether, hexyl-S-tritylthiol, a thiocholesterol, an aliphatic chain, e.g., dodecandiol or undecyl residues, a phospholipid such as dihexadecyl-rac-glycerol or triethylammonium-1,2-di-O-hexadecyl-rac-glycero-3H-phosphonate, a polyamine or a polyethylene glycol chain, or adamantine acetic acid, a palmityl moiety, or an octadecylamine or hexylamino-carbonyl-oxycholesterol moiety. The present invention also includes antisense-oligonucleotides which are chimeric compounds. "Chimeric" antisense-oligonucleotides in the context of this invention, are antisense-oligonucleotides, which contain two or more chemically distinct regions, one is the oligonucleotide sequence as disclosed herein which is connected to a moiety or component for increasing cellular uptake, increasing resistance to nuclease degradation, increasing binding affinity for the target nucleic acid, increasing recruitment of RNase H and so on. For instance, the additional region or moiety or component of the antisense-oligonucleotide may serve as a substrate for enzymes capable of cleaving RNA:DNA hybrids or RNA:RNA molecules. By way of example, RNase H is a cellular endoribonuclease which cleaves the RNA strand of an RNA:DNA duplex. Activation of RNase H, therefore, results in cleavage of the RNA target which is the mRNA coding for the TGF-$R_{II}$, thereby greatly enhancing the efficiency of antisense-oligonucleotide inhibition of gene expression. Consequently, comparable results can often be obtained with shorter oligonucleotides when chimeric oligonucleotides are used.

Indications

The present invention relates to the use of the antisense-oligonucleotides disclosed herein for prophylaxis and treatment of neurodegenerative diseases, neurotrauma, neurovascular and neuroinflammatory diseases, including postinfectious and inflammatory disorders of the central nervous system (CNS).

The antisense-oligonucleotides of the present invention are especially useful for promoting regeneration and functional reconnection of damaged nerve pathways and/or for the treatment and compensation of age induced decreases in neuronal stem cell renewal.

Thus, another aspect of the present invention relates to the use of an antisense-oligonucleotide as disclosed herein for promoting regeneration neuronal tissue by reactivating neurogenesis, allowing neuronal differentiation and migration, and inducing integration of new neurons into anatomic and functional neuronal circuits.

A further aspect of the present invention relates to the use of an antisense-oligonucleotide as disclosed herein for promoting regeneration and clinical (structural) repair in patients with damage to the nervous system or damage to other organ systems induced by fibrosis or loss of stem cell turnover.

Moreover, the antisense-oligonucleotides are useful for compensation and treatment of decreases in neuronal stem cell renewal induced by age, inflammation or a gene defect.

The antisense-oligonucleotides of the present invention inhibit the TGF-$R_{II}$ expression and are consequently used for the treatment of diseases associated with up-regulated or enhanced TGF-$R_{II}$ and/or TGF-$R_{II}$ levels.

Thus, another aspect of the present invention relates to the use of the antisense-oligonucleotides in the prophylaxis and treatment of neurodegenerative diseases, neuroinflammatory disorders, traumatic or posttraumatic disorders, vascular or more precisely neurovascular disorders, hypoxic disorders, postinfectious central nervous system disorders, fibrotic diseases, hyperproliferative diseases, cancer, tumors, presbyakusis and presbyopie.

The term "neurodegenerative disease" or "neurological disease" or "neuroinflammatory disorder" refers to any disease, disorder, or condition affecting the central or peripheral nervous system, including ADHD, AIDS-neurological complications, absence of the Septum Pellucidum, acquired epileptiform aphasia, acute disseminated encephalomyelitis, adrenoleukodystrophy, agenesis of the Corpus Callosum, agnosia, Aicardi Syndrome, Alexander Disease, Alpers' Disease, alternating hemiplegia, Alzheimer's Disease, amyotrophic lateral sclerosis (ALS), anencephaly, aneurysm, Angelman Syndrome, angiomatosis, anoxia, aphasia, apraxia, arachnoid cysts, arachnoiditis, Arnold-Chiari Malformation, arteriovenous malformation, aspartame, Asperger Syndrome, ataxia telangiectasia, ataxia, attention deficit-hyperactivity disorder, autism, autonomic dysfunction, back pain, Barth Syndrome, Batten Disease, Behcet's Disease, Bell's Palsy, benign essential blepharospasm, benign focal amyotrophy, benign intracranial hypertension, Bernhardt-Roth Syndrome, Binswanger's Disease, blepharospasm, Bloch-Sulzberger Syndrome, brachial plexus birth injuries, brachial plexus injuries, Bradbury-Eggleston Syndrome, brain aneurysm, brain injury, brain and spinal tumors, Brown-Sequard Syndrome, bulbospinal muscular atrophy, Canavan Disease, Carpal Tunnel Syndrome, causalgia, cavernomas, cavernous angioma, cavernous malformation, central cervical cord syndrome, central cord syndrome, central pain syndrome, cephalic disorders, cerebellar degeneration, cerebellar hypoplasia, cerebral aneurysm, cerebral arteriosclerosis, cerebral atrophy, cerebral beriberi, cerebral gigantism, cerebral hypoxia, cerebral palsy, cerebro-oculo-facio-skeletal syndrome, Charcot-Marie-Tooth Disorder, Chiari Malformation, chorea, choreoacanthocytosis, chronic inflammatory demyelinating polyneuropathy (CIDP), chronic orthostatic intolerance, chronic pain, Cockayne Syndrome Type II, Coffin Lowry Syndrome, coma, including persistent vegetative state, complex regional pain syndrome, congenital facial diplegia, congenital myasthenia, congenital myopathy, congenital vascular cavernous malformations, corticobasal degeneration, cranial arteritis, craniosynostosis, Creutzfeldt-Jakob Disease, cumulative trauma disorders, Cushing's Syndrome, cytomegalic inclusion body disease (CIBD), cytomegalovirus infection, dancing eyes-dancing feet syndrome, Dandy-Walker Syndrome, Dawson Disease, De Morsier's Syndrome, Dejerine-Klumpke Palsy, dementia-multi-infarct, dementia-subcortical, dementia with Lewy Bodies, dermatomyositis, developmental dyspraxia, Devic's Syndrome, diabetic neuropathy, diffuse sclerosis, Dravet's Syndrome, dysautonomia, dysgraphia, dyslexia, dysphagia, dyspraxia, dystonias, early infantile epileptic encephalopathy, Empty Sella Syndrome, encephalitis lethargica, encephalitis and meningitis, encephaloceles, encephalopathy, encephalotrigeminal angiomatosis, epilepsy, Erb's Palsy, Erb-Duchenne and Dejerine-Klumpke Palsies, Fabry's Disease, Fahr's Syndrome, fainting, familial dysautonomia, familial hemangioma, familial idiopathic basal ganglia calcification, familial spastic paralysis, febrile seizures (e.g., GEFS and GEFS plus), Fisher Syndrome, Floppy Infant Syndrome, Friedreich's Ataxia, Gaucher's Disease, Gerstmann's Syndrome, Gerstmann-Straussler-Scheinker Disease, giant cell arteritis, giant cell inclusion disease, globoid cell leukodystrophy, glossopharyngeal neuralgia, Guillain-Barre Syndrome, HTLV-1 associated myelopathy, Hallervorden-Spatz Disease, head injury, headache, hemicrania continua, hemifacial spasm, hemiplegia alterans, hereditary neuropathies, hereditary spastic paraplegia, heredopathia atactica polyneuritiformis, Herpes Zoster Oticus, Herpes Zoster, Hirayama Syndrome, holoprosencephaly, Huntington's Disease, hydranencephaly, hydrocephalus-normal pressure, hydrocephalus (in particular TGFβ-induced hydrocephalus), hydromyelia, hypercortisolism, hypersomnia, hypertonia, hypotonia, hypoxia, immune-mediated encephalomyelitis, inclusion body myositis, incontinentia pigmenti, infantile hypotonia, infantile phytanic acid storage disease, infantile refsum disease, infantile spasms, inflammatory myopathy, intestinal lipodystrophy, intracranial cysts, intracranial hypertension, Isaac's Syndrome, Joubert Syndrome, Kearns-Sayre Syndrome, Kennedy's Disease, Kinsbourne syndrome, Kleine-Levin syndrome, Klippel Feil Syndrome, Klippel-Trenaunay Syndrome (KTS), KlOver-Bucy Syndrome, Korsakoff's Amnesic Syndrome, Krabbe Disease, Kugelberg-Welander Disease, kuru, Lambert-Eaton Myasthenic Syndrome, Landau-Kleffner Syndrome, lateral femoral cutaneous nerve entrapment, lateral medullary syndrome, learning disabilities, Leigh's Disease, Lennox-Gastaut Syndrome, Lesch-Nyhan Syndrome, leukodystrophy, Levine-Critchley Syndrome, Lewy Body Dementia, lissencephaly, locked-in syndrome, Lou Gehrig's Disease, lupus-neurological sequelae, Lyme Disease-Neurological Complications, Machado-Joseph Disease, macrencephaly, megalencephaly, Melkersson-Rosenthal Syndrome, meningitis, Menkes Disease, meralgia paresthetica, metachromatic leukodystrophy, microcephaly, migraine, Miller Fisher Syndrome, mini-strokes, mitochondrial myopathies, Mobius Syndrome, monomelic amyotrophy, motor neuron diseases, Moyamoya Disease, mucolipidoses, mucopolysaccharidoses, multi-infarct dementia, multifocal motor neuropathy, multiple sclerosis (MS), multiple systems atrophy (MSA-C and MSA-P), multiple system atrophy with orthostatic hypotension, muscular dystrophy, myasthenia-congenital, myasthenia gravis, myelinoclastic diffuse sclerosis, myoclonic encephalopathy of infants, myoclonus, myopathy-congenital, myopathy-thyrotoxic, myopathy, myotonia congenita, myotonia, narcolepsy, neuroacanthocytosis, neurodegeneration with brain iron accumulation, neurofibromatosis, neuroleptic malignant syndrome, neurological complications of AIDS, neurological manifestations of Pompe Disease, neuromyelitis optica, neuromyotonia, neuronal ceroid lipofuscinosis, neuronal migration disorders, neuropathy-hereditary, neurosarcoidosis, neurotoxicity, nevus cavernosus, Niemann-Pick Disease, O'Sullivan-McLeod Syndrome, occipital neuralgia, occult spinal dysraphism sequence, Ohtahara Syndrome, olivopontocerebellar atrophy, opsoclonus myoclonus, orthostatic hypotension, Overuse Syndrome, pain-chronic, paraneoplastic syndromes, paresthesia, Parkinson's Disease, parmyotonia congenita, paroxysmal choreoathetosis, paroxysmal hemicrania, Parry-Romberg, Pelizaeus-Merzbacher Disease, Pena Shokeir II Syndrome, perineural cysts, periodic paralyses, peripheral neuropathy, periventricular leukomalacia, persistent vegetative state, pervasive developmental disorders, phytanic acid storage disease, Pick's Disease, Piriformis Syndrome, pituitary tumors, polymyositis, Pompe Disease, porencephaly, Post-Polio Syndrome, postherpetic neuralgia, postinfectious encephalomyelitis, postural hypotension, postural orthostatic tachycardia syndrome, postural tachycardia syndrome, primary lateral sclerosis, prion diseases, progressive hemifacial atrophy, progressive locomotor ataxia, progressive multifocal leukoencephalopathy, progressive sclerosing poliodystrophy, progressive supranuclear palsy, pseudotumor cerebri, pyridoxine dependent and pyridoxine responsive siezure disorders, Ramsay Hunt Syndrome Type I, Ramsay Hunt Syndrome Type II, Rasmussen's Encephalitis and other autoimmune epilepsies, reflex sympathetic dystrophy syndrome, refsum disease-infantile, refsum disease, repetitive motion disorders, repetitive stress injuries, restless legs syndrome, retrovirus-associated myelopathy, Rett Syndrome, Reye's Syndrome, Riley-Day Syndrome, SUNCT headache, sacral nerve root cysts, Saint Vitus Dance, Salivary Gland Disease, Sandhoff Disease, Schilder's Disease, schizencephaly, seizure disorders, septo-optic dysplasia, severe myoclonic epilepsy of infancy (SMEI), shaken baby syndrome, shingles, Shy-Drager Syndrome, Sjogren's Syndrome, sleep apnea, sleeping sickness, Soto's Syndrome, spasticity, spina bifida, spinal cord infarction, spinal cord injury, spinal cord tumors, spinal muscular atrophy, spinocerebellar atrophy, Steele-Richardson-Olszewski Syndrome, Stiff-Person Syndrome, striatonigral degeneration, stroke, Sturge-Weber Syndrome, subacute sclerosing panencephalitis, subcortical arteriosclerotic encephalopathy, Swallowing Disorders, Sydenham Chorea, syncope, syphilitic spinal sclerosis, syringohydromyelia, syringomyelia, systemic lupus erythematosus, Tabes Dorsalis, Tardive Dyskinesia, Tarlov Cysts, Tay-Sachs Disease, temporal arteritis, tethered spinal cord syndrome, Thomsen Disease, thoracic outlet syndrome, thyrotoxic myopathy, Tic Douloureux, Todd's Paralysis, Tourette Syndrome, transient ischemic attack, transmissible spongiform encephalopathies, transverse myelitis, traumatic brain injury, tremor, trigeminal neuralgia, tropical spastic paraparesis, tuberous sclerosis, vascular erectile tumor, vasculitis including temporal arteritis, Von Economo's Disease, Von Hippel-Lindau disease (VHL), Von Recklinghausen's Disease, Wallenberg's Syndrome, Werdnig-Hoffinan Disease, Wernicke-Korsakoff Syndrome, West Syndrome, Whipple's Disease, Williams Syndrome, Wilson's Disease, X-Linked Spinal and Bulbar Muscular Atrophy, and Zellweger Syndrome.

Preferred examples of neurodegenerative diseases and neuroinflammatory disorders are selected from the group comprising or consisting of:

Alzheimer's disease, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontotemporal dementia, motor neuron disorders of multiple spontaneous or genetic background, amyotrophic lateral sclerosis (ALS), spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, multiple sclerosis (MS), acute ischemic/hypoxic lesions, stroke, CNS and spinal cord trauma, head and spinal trauma, brain traumatic injuries, arteriosclerosis, atherosclerosis, microangiopathic dementia, Binswanger' disease (Leukoaraiosis), retinal degeneration, cochlear degeneration, macular degeneration, cochlear deafness, AIDS-related dementia, retinitis pigmentosa, fragile X-associated tremor/ataxia syndrome (FXTAS), progressive supranuclear palsy (PSP), striatonigral degeneration (SND), olivopontocerebellar degeneration (OPCD), Shy Drager syndrome (SDS), age dependent memory deficits, neurodevelopmental disorders associated with dementia, Down's Syndrome, synucleinopathies, superoxide dismutase mutations, trinucleotide repeat disorders as Huntington's Disease, trauma, hypoxia, vascular diseases, vascular inflammations, CNS-ageing. Also age dependent decrease of stem cell renewal may be addressed.

Particularly referred examples of neurodegenerative diseases and neuroinflammatory disorders are selected from the group comprising or consisting of:

Alzheimer's disease, Parkinson's disease, Huntington's disease, amyotrophic lateral sclerosis (ALS), hydrocephalus (in particular TGFβ-induced hydrocephalus), CNS and spinal cord trauma such as spinal cord injury, head and spinal trauma, brain traumatic injuries, retinal degeneration, macular degeneration, cochlear deafness, AIDS-related dementia, trinucleotide repeat disorders as Huntington's Disease, and CNS-ageing.

The antisense-oligonucleotides are also useful for prophylaxis and treatment of fibrotic diseases. Fibrosis or fibrotic disease is the formation of excess fibrous connective tissue in an organ or tissue in a reparative or reactive process. This can be a reactive, benign, or pathological state. In response to injury this is called scarring and if fibrosis arises from a single cell line this is called a fibroma. Physiologically this acts to deposit extracellular matrix, which can obliterate the architecture and function of the underlying organ or tissue. Fibrosis can be used to describe the pathological state of excess deposition of fibrous tissue, as well as the process of connective tissue deposition in healing. Fibrosis is a process involving stimulated cells to form connective tissue, including collagen and glycosaminoglycans. Subsequently macrophages and damaged tissue between the interstitium release TGF-β. TGF-β stimulates the proliferation and activation of fibroblasts which deposit connective tissue. Reducing the TGF-β levels prevents and decreases the formation of connective tissue and thus prevents and treats fibrosis.

Examples for fibrotic diseases are
Lungs: • pulmonary fibrosis
  idiopathic pulmonary fibrosis (idiopathic means cause is unknown)
  cystic fibrosis
Liver: • hepatic cirrhosis of multiple origin
Heart: • endomyocardial fibrosis
  old myocardial infarction
  atrial fibrosis
Other: • mediastinal fibrosis (soft tissue of the mediastinum)
  glaucoma (eye, ocular)
  myelofibrosis (bone marrow)
  retroperitoneal fibrosis (soft tissue of the retroperitoneum)
  progressive massive fibrosis (lungs); a complication of coal workers' pneumoconiosis
  nephrogenic systemic fibrosis (skin)
  Crohn's Disease (intestine)
  keloid (skin)
  scleroderma/systemic sclerosis (skin, lungs)
  arthrofibrosis (knee, shoulder, other joints)
  Peyronie's disease (penis)
  Dupuytren's contracture (hands, fingers)
  some forms of adhesive capsulitis (shoulder)
  residuums after Lupus erythematodes Thus another aspect of the present invention relates to the use of an antisense-oligonucleotide for prophylaxis and/or treatment of or to the use of an antisense-oligonucleotide for the preparation of a pharmaceutical composition for prophylaxis and/or treatment of pulmonary fibrosis, cystic fibrosis, hepatic cirrhosis, endomyocardial fibrosis, old myocardial infarction, atrial fibrosis, mediastinal fibrosis, myelofibrosis, retroperitoneal fibrosis, progressive massive fibrosis, nephrogenic systemic fibrosis, glaucoma, such as primary open angle glaucoma, Crohn's Disease, keloid, systemic sclerosis, arthrofibrosis, Peyronie's disease, Dupuytren's contracture, and residuums after Lupus erythematodes.

Still another aspect of the present invention relates to the use of an antisense-oligonucleotide for prophylaxis and/or treatment of hyperproliferative diseases, cancer, tumors and their metastases or to the use of an antisense-oligonucleotide for the preparation of a pharmaceutical composition for prophylaxis and/or treatment of hyperproliferative diseases, cancer, tumors and their metastases.

Examples for hyperproliferative diseases, cancer, tumors are selected from the group comprising or consisting of: adenocarcinoma, melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas, e.g. astrocytomas, oligodendrogliomas, medulloblastomas, PNET's, mixed gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye/ocular tumors, urethral cancer, urologic tumors, urothelial carcinoma, vulva cancer, wart appearance, soft tissue tumors, soft tissue sarcoma, Wilm's tumor, cervical carcinoma and tongue cancer.

The term "cancer" refers preferably to a cancer selected from the group consisting of or comprising Lung cancer, such as Lung carcinoma, liver cancer such as hepatocellular carcinoma, melanoma or malignant melanoma, pancreatic cancer, such as pancreatic epithelioid carcinoma or pancreatic adenocarcinoma, colon cancer, such as colorectal adenocarcinoma, gastric cancer or gastric carcinoma, mamma carcinoma, malignant astrocytoma, prostatic cancer, such as gastric carcinoma, leukemia, such as acute myelogenous leukemia, chronic myelogenous leukemia, monocytic leukemia, promyelocytic leukemia, lymphocytic leukemia, acute lymphoblastic leukemia, lymphocytic leukemia, and acute lymphoblastic leukemia, and lymphoma, such as histiocytic lymphoma.

For the treatment of hyperproliferative diseases, cancer, tumors and their metastases the antisense-oligonucleotides may be administered at regular intervals (dose intervals, DI) of between 3 days and two weeks, such as 4, 5, 6, 7, 8, 9, 10, 11, 12, or 13 days, such as about 1 week, such as 6, 7 or 8 days. Suitably at least two doses are provide with a DI period between the two dosages, such as 3, 4, 5, 6, 7, 8, 9 or 10 dosages, each with a dose interval (DI) between each dose of the antisense-oligonucleotide. The DI period between each dosage may the same, such as between 3 days and two weeks, such as 4, 5, 6, 7, 8, 9, 10, 11, 12, 13 days, such as about 1 week, such as 6, 7 or 8 days.

Preferably, each dose of the antisense-oligonucleotide may be between about 0.25 mg/kg-about 10 mg/kg, such as about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg. In some embodiments, each does of the antisense-oligonucleotide may be between about 2 mg/kg-about 8 mg/kg, or about 4 to about 6 mg/kg or about 4 mg/kg to about 5 mg/kg. In some embodiments, each does of the antisense-oligonucleotide is at least 2 mg/kg, such as 2, 3, 4, 5, 6, 7 or 8 mg/kg, such as 6 mg/kg. In some embodiments the dosage regime for the antisense-oligonucleotide may be repeated after an initial dosage regime, for example after a rest period where no antisense-oligonucleotide is administered. Such as rest period may be more than 2 weeks in duration, such as about 3 weeks or about 4 weeks, or about 5 weeks or about 6 weeks. In some embodiments the dosage regimen for the antisense-oligonucleotide is one weekly dosage, repeated three, four or five times. This dosage regimen may then be repeated after a rest period of, for example, about 3-5 weeks, such as about 4 weeks. In some embodiments, the antisense-oligonucleotide is administered during a first dosage regimen at regular dosage intervals (DI) of between 4 and 13 days for between 2-10 administrations.

Administration of the antisense-oligonucleotide is typically performed by parenteral administration, such as subcutaneous, intramuscular, intravenous or intraperitoneal administration.

DESCRIPTION OF FIGURES

The patent or application file contains at least one drawing executed in color. Copies of this patent or patent application publication with color drawing(s) will be provided by the Office upon request and payment of the necessary fee.

| SP | L | Seq ID No | Sequence, 5'-3' |
|---|---|---|---|
| 4217 | 16 | 218b | C*b$^1$sAb$^1$sTb$^1$sdGsdAsdAsdAsdTsdGsdGsdAsd CsdCsAb$^1$sGb$^1$sTb$^1$sAb$^1$ |

Figure 1:
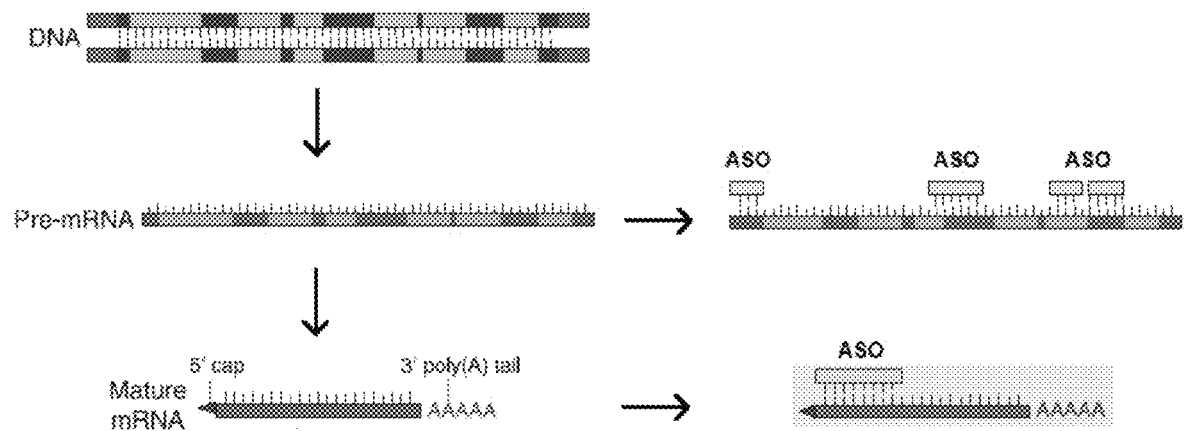
FIG. 1 shows the inhibitory effect of the antisense-oligonucleotides (ASO). The DNA is transcribed to the Pre-mRNA to which in the nucleus of the cell, the antisense-oligonucleotides (ASO) can bind or hybridize to the complementary sequence within an exon (as represented by the first ASO from the right side and the first ASO from the left side) or within an intron (as represented by the second ASO from the right side) or at allocation consisting of an area of an exon and an area of an adjacent intron (as represented by the second ASO from the left side). By post-transcriptional modification, i.e. the splicing, the mRNA is formed to which the ASO can bind or hybridize in the cytoplasma of the cell in order to inhibit translation of the mRNA into the protein sequence. Thus, the ASO knock down the target gene and the protein expression selectively.
Figure 2:
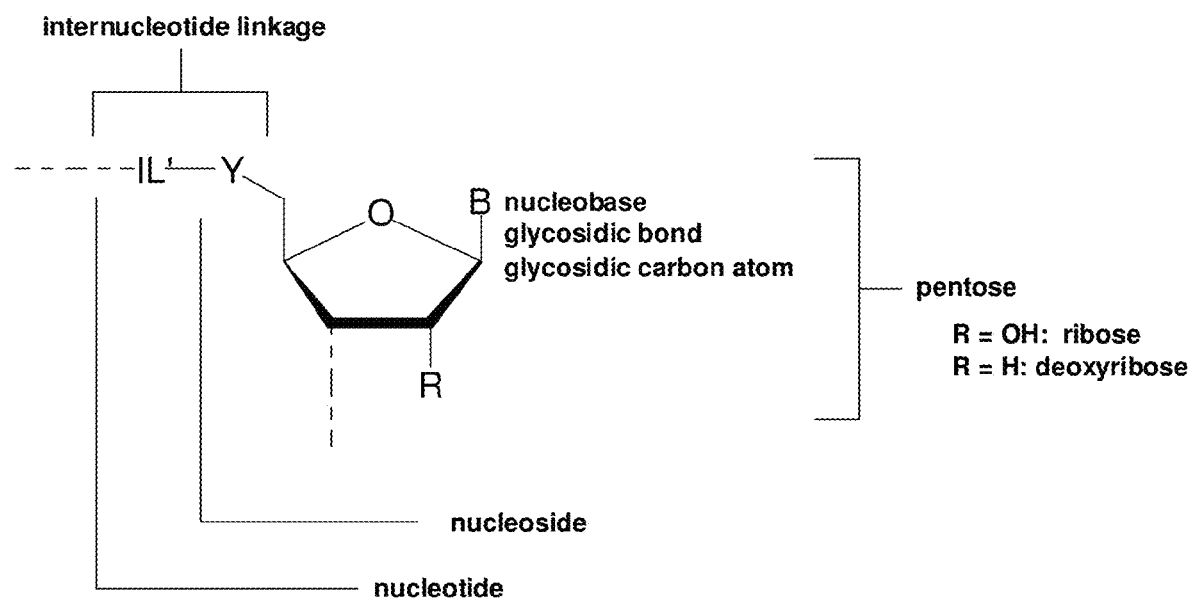
FIG. 2 shows a nucleoside unit (without internucleotide linkage) or nucleotide unit (with internucleotide linkage) which are non-LNA units and which may be contained in the antisense-oligonucleotides of the present invention especially in the region B in case the antisense-oligonucleotide of the present invention is a gapmer.
Figure 3:
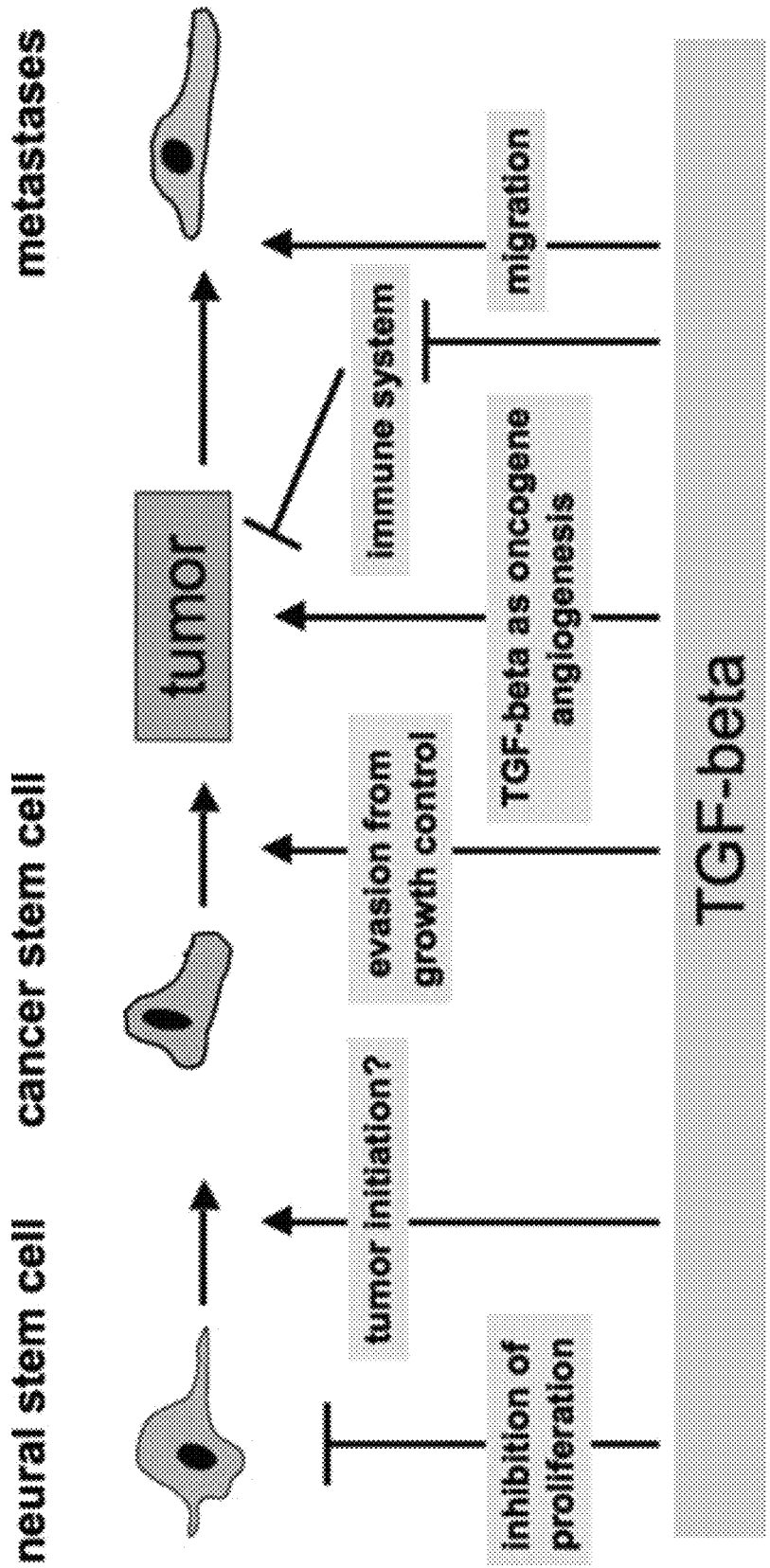
FIG. 3 shows TGF-beta and its effects on neural stem cells, cancer stem cells, and tumors. TGFbeta inhibits neural stem cell proliferation. It may affect the transition to a cancer stem cell, which might escape from TGF-beta growth control. Later in tumor progression, TGF-beta acts as an oncogene; it further promotes tumor growth by promoting angiogenesis and suppressing the immune system. In addition, it promotes cellular migration, thereby driving cells into metastasis.
Figure 4:
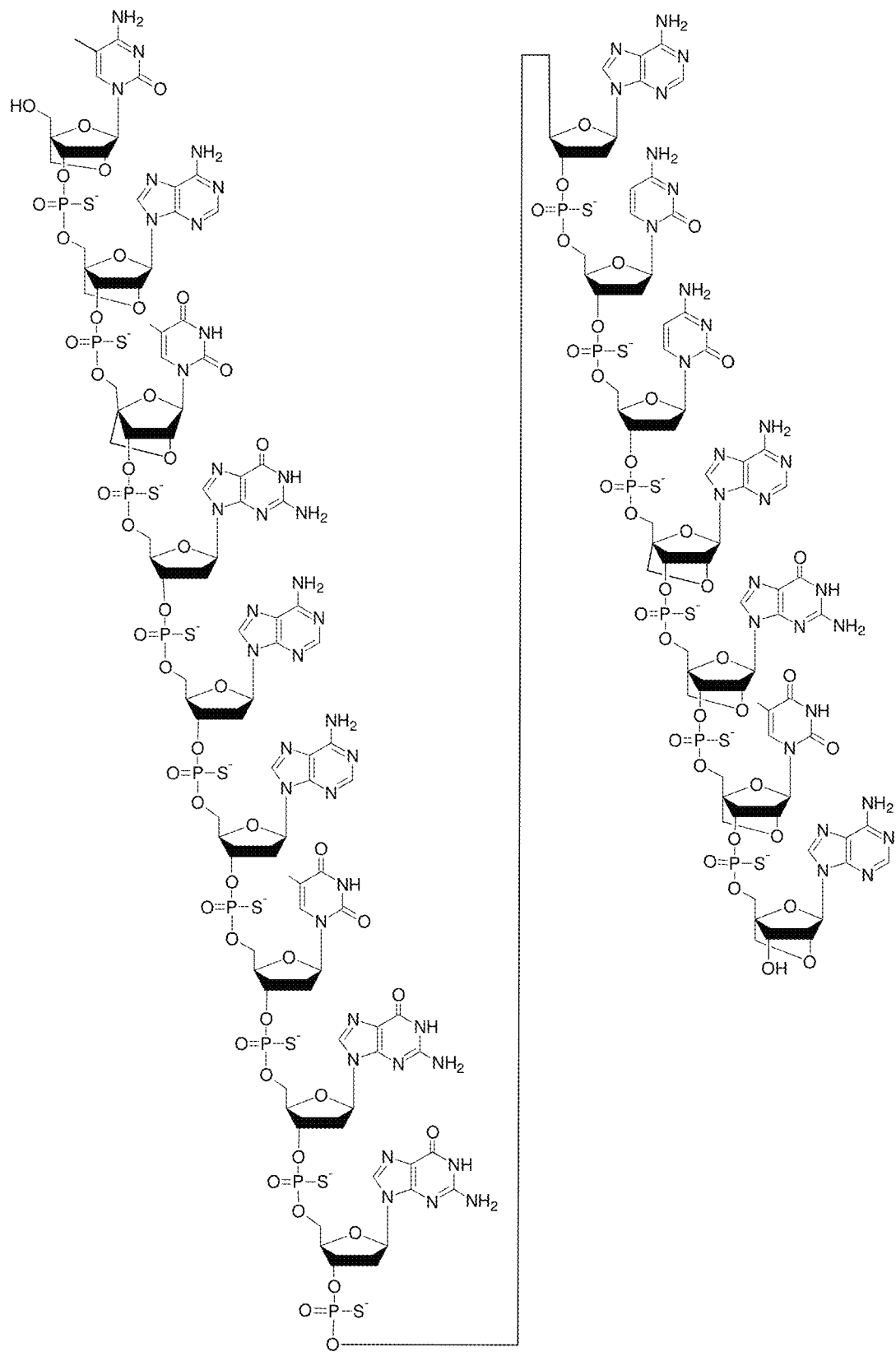
FIG. 4 shows the antisense-oligonucleotide of Seq ID No 218b in form of a gapmer consisting of 16 nucleotides with 3 LNA units (C*b$^1$ and Ab$^1$ and Tb$^1$) at the 5' terminal end and 4 LNA units (Ab$^1$ and Gb$^1$ and Tb$^1$ and Ab$^1$) at the 3' terminal end and 9 DNA nucleotides (dG, dA, dA, dT, dG, dG, dA, dC, and dC) in between the LNA segments, with phosphorothioate internucleotides linkages (s) and the nucleobase 5-methylcytosine (C*) in the first LNA unit from the 5' terminal end.
Figure 5:
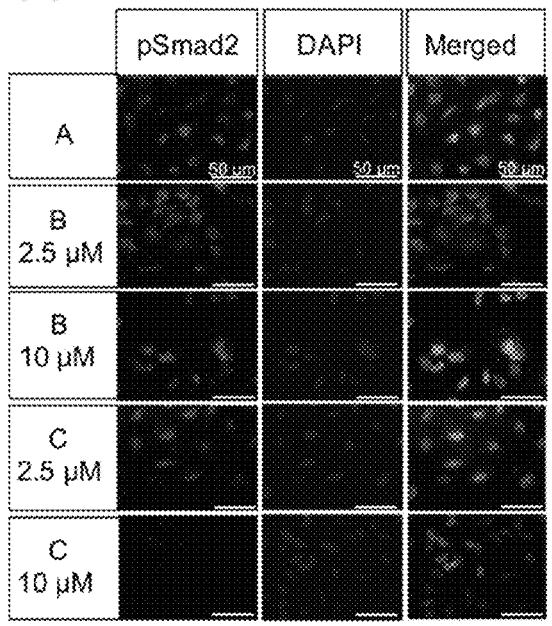
Figure 5:
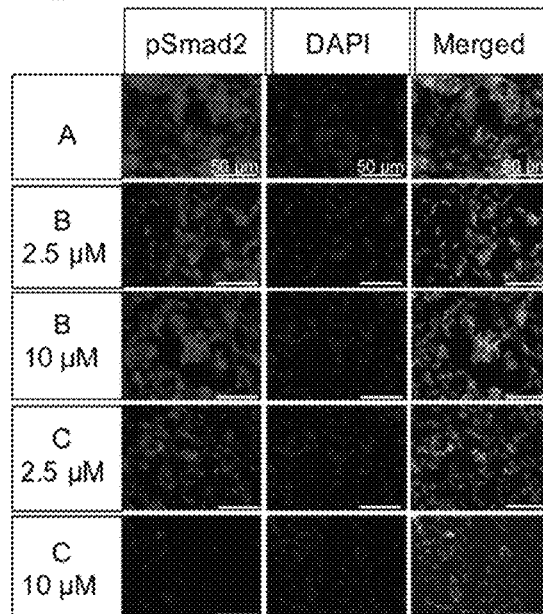

FIG. 5: ASO (Seq. ID No. 218b) treatment leads to intracellular pSmad2 protein reduction. Labeling with an antibody against pSmad2 (left column, red) in A549 (FIG. 5A) and ReNcell CX® (FIG. 5B) cells after gymnotic transfer with ASO Seq. ID No. 218b for 72 h or 96 h respectively. Nuclear DNA was stained with DAPI (central column, blue). Examination of cells was performed by fluorescence microscopy (Zeiss Axio® Observer.Z1). Images were analyzed with Image J Software and Corel-DRAW® X7 Software. A=untreated control, B=Ref.1, C=Seq. ID No. 218b.

Figure 6:
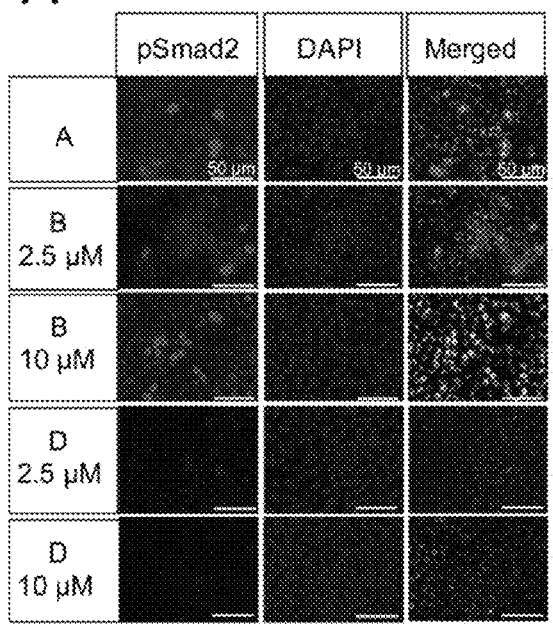
Figure 6:
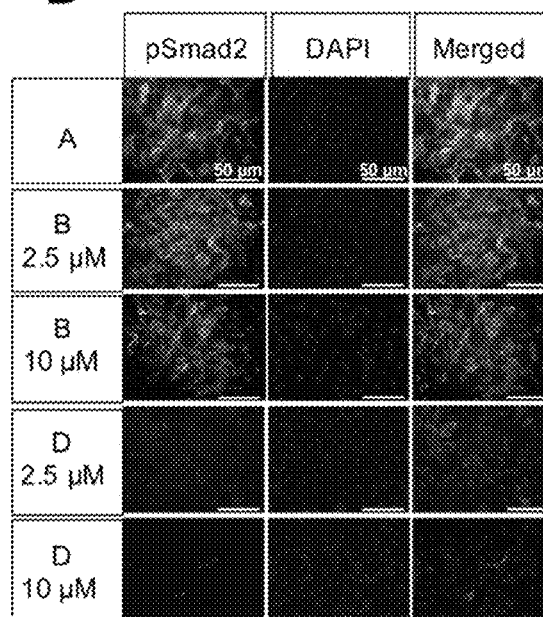

FIG. 6: ASO (Seq. ID No. 218c) treatment leads to intracellular pSmad2 protein reduction. Labeling with an antibody against pSmad2 (left column, red) in A549 (FIG. 6A) and ReNcell CX® (FIG. 6B) cells after gymnotic transfer with ASO Seq. ID No. 218c for 72 h or 96 h respectively. Nuclear DNA was stained with DAPI (central column, blue). Examination of cells was performed by fluorescence microscopy (Zeiss Axio® Observer.Z1). Images were analyzed with Image J Software and Corel DRAW® X7 Software. A=untreated control, B=Ref.1, D=Seq. ID No. 218c.

Figure 7:
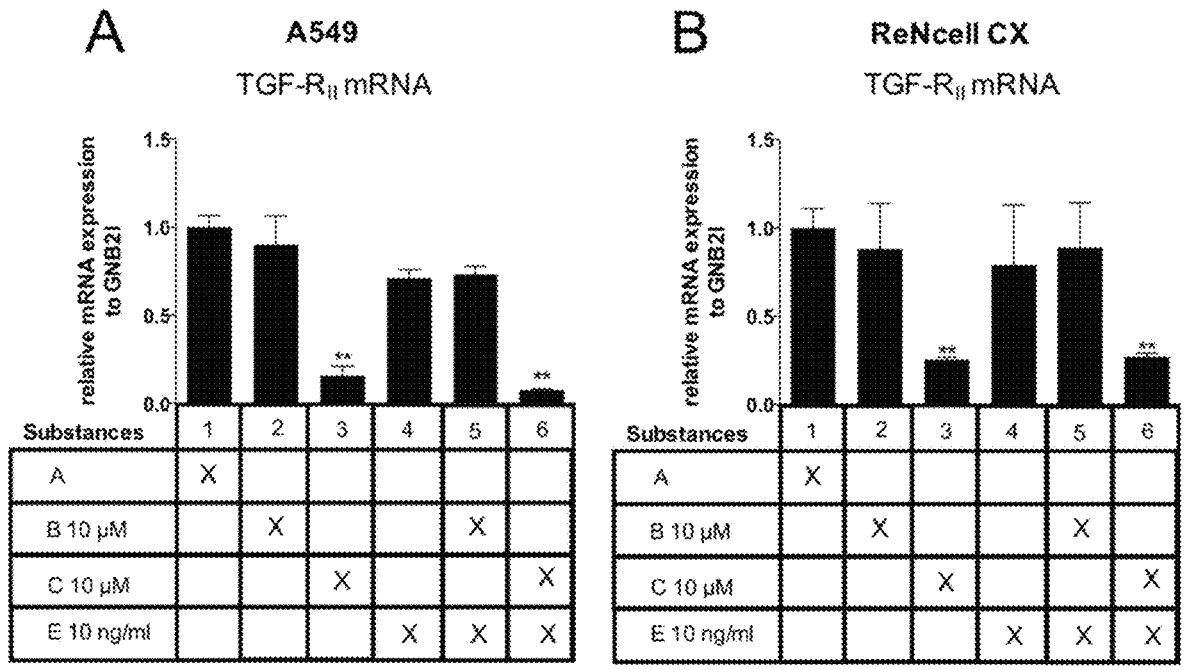

FIG. 7: In presence of TGF-β1, ASO (Seq. ID No. 218b) treatment leads to downregulation of TGF-R$_{II}$ mRNA. Potent downregulation of TGF-R$_{II}$ mRNA after gymnotic transfer of TGF-R$_{II}$ specific ASO in TGF-β1 pre-incubated (48 h) A549 (FIG. 7A) and ReNcell CX® (FIG. 7B) cells. ASOs were incubated for 72 h or 96 h in presence of TGF-β1, respectively. mRNA expression levels were quantified relative to housekeeping gene GNB2L1 using quantitative real-time RT-PCR and normalized to untreated controls. A=untreated control, B=Ref.1, C=Seq. ID No. 218b, E=TGF-β1, ±=SEM, *p<0.05, **p<0.01 in reference to A, ++p<0.01 in reference to E+B. Statistics was calculated using the Ordinary-one-way-ANOVA followed by "Tukey's" post hoc comparisons.

Figure 8:
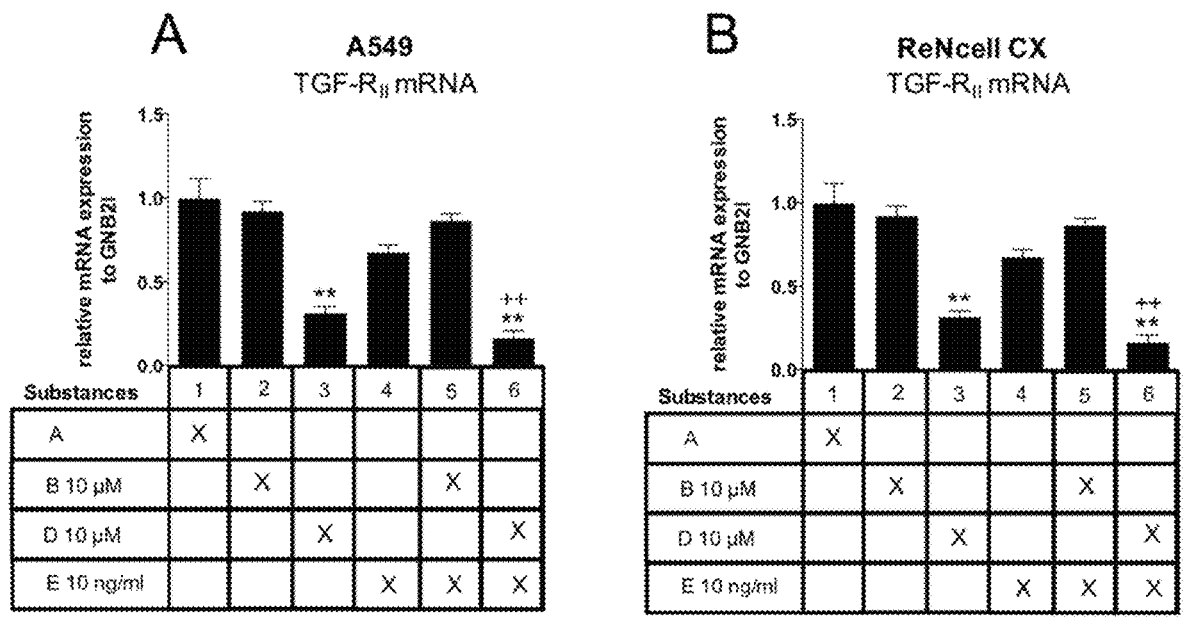

FIG. 8: In presence of TGF-β1, ASO (Seq. ID No. 218c) treatment leads to downregulation of TGF-R$_{II}$ mRNA. Potent downregulation of TGF-R$_{II}$ mRNA after gymnotic transfer of TGF-R$_{II}$ specific ASO in TGF-β1 pre-incubated (48 h) A549 (FIG. 8A) and ReNcell CX® (FIG. 8B) cells. ASOs were incubated for 72 h or 96 h in presence of TGF-β1, respectively. mRNA expression levels were quantified relative to housekeeping gene GNB2L1 using quantitative real-time RT-PCR and normalized to untreated controls. A=untreated control, B=Ref.1, D=Seq. ID No. 218c, E=TGF-β1, ±=SEM, *p<0.05, **p<0.01 in reference to A, ++p<0.01 in reference to E+B. Statistics was calculated using the Ordinary-one-way-ANOVA followed by "Tukey's" post hoc comparisons.

Figure 9:
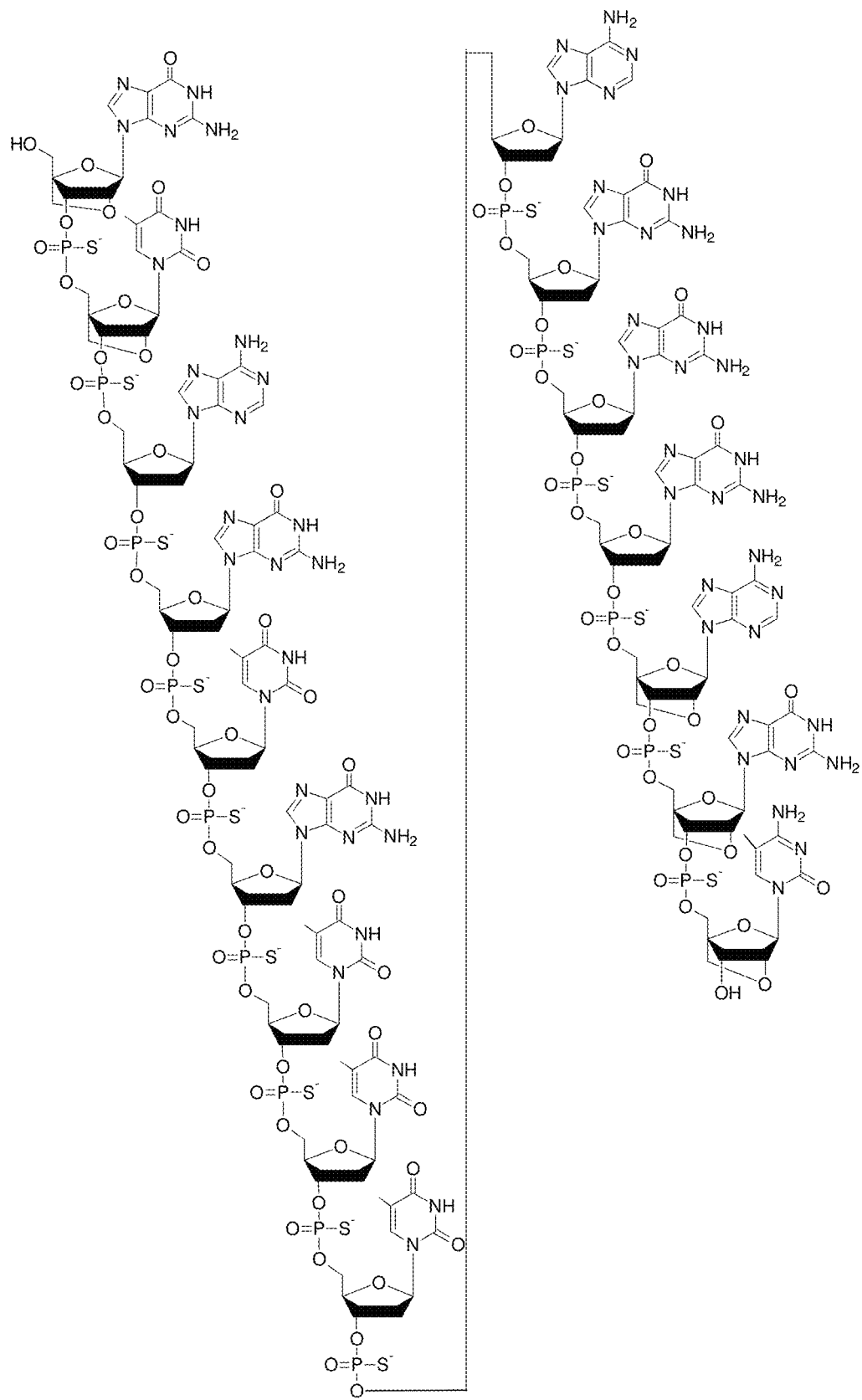

FIG. 9 shows the antisense-oligonucleotide of Seq ID No 209y in form of a gapmer consisting of 16 nucleotides with 2 LNA units (Gb$^1$ and Tb$^1$) at the 5' terminal end and 3 LNA units (Ab$^1$ and Gb$^1$ and C*b$^1$) at the 3' terminal end and 11 DNA nucleotides (dA, dG, dT, dG, dT, dT, dT, dA, dG, dG, and dG) in between the LNA segments, with phosphorothioate internucleotides linkages (s) and the nucleobase 5-methylcytosine (C*) in the last LNA unit from the 5' terminal end.

| SP | L | Seq ID No | Sequence, 5'-3' |
|---|---|---|---|
| 2064 | 16 | 209y | Gb$^1$sTb$^1$sdAsdGsdTsdGsdTsdTsdTsdAsdGsd GsdGsAb$^1$sGb$^1$sC*b$^1$ |

Figure 10:
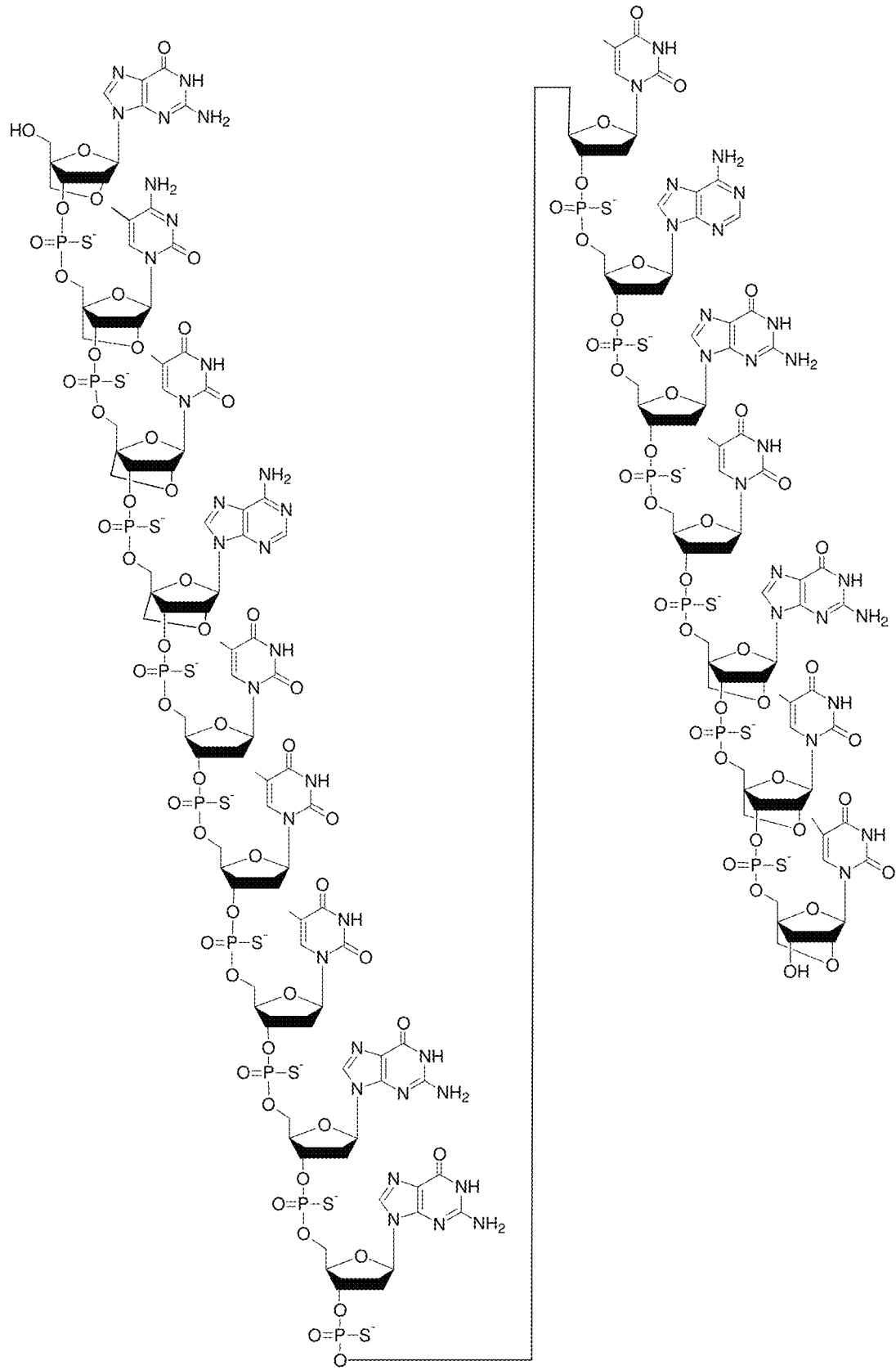

FIG. 10 shows the antisense-oligonucleotide of Seq ID No 210q in form of a gapmer consisting of 16 nucleotides with 4 LNA units (Gb$^1$ and C*b$^1$ and Tb$^1$ and Ab$^1$) at the 5' terminal end and 3 LNA units (Gb$^1$ and Tb$^1$ and Tb$^1$) at the 3' terminal end and 9 DNA nucleotides (dT, dT, dT, dG, dG, dT, dA, dG, and dTs) in between the LNA segments, with phosphorothioate internucleotides linkages (s) and the nucleobase 5-methylcytosine (C*) in the second LNA unit from the 5' terminal end.

| SP | L | Seq ID No | Sequence, 5'-3' |
|---|---|---|---|
| 2072 | 16 | 210q | Gb$^1$sC*b$^1$sTb$^1$sAb$^1$sdTsdTsdTsdGsdGsdTsd AsdGsdTsGb$^1$sTb$^1$sTb$^1$ |

Figure 11:
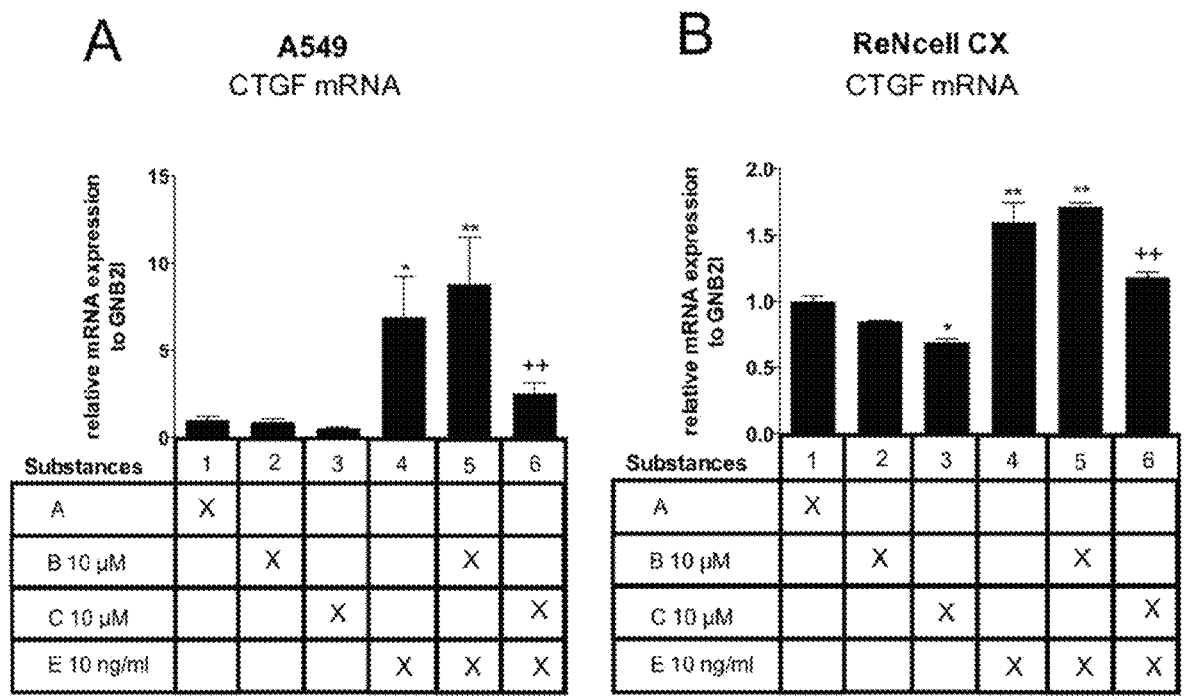

FIG. 11: In presence of TGF-β1, ASO (Seq. ID No. 218b) treatment leads to downregulation of CTGF mRNA. Potent downregulation of CTGF mRNA after gymnotic transfer of TGF-R$_{II}$ specific ASO in TGF-β1 pre-incubated (48 h) A549 (FIG. 11A) and ReNcell CX® (FIG. 11B) cells. ASOs were incubated for 72 h or 96 h in presence of TGF-β1, respectively. mRNA expression levels were quantified relative to housekeeping gene GNB2L1 using quantitative real-time RT-PCR and normalized to untreated controls. A=untreated control, B=Ref.1, C=Seq. ID No. 218b, E=TGF-β1, ±=SEM, *p<0.05, **p<0.01 in reference to A, ++p<0.01 in reference to E+B. Statistics was calculated using the Ordinary-one-way-ANOVA followed by "Tukey's" post hoc comparisons.

Figure 12:
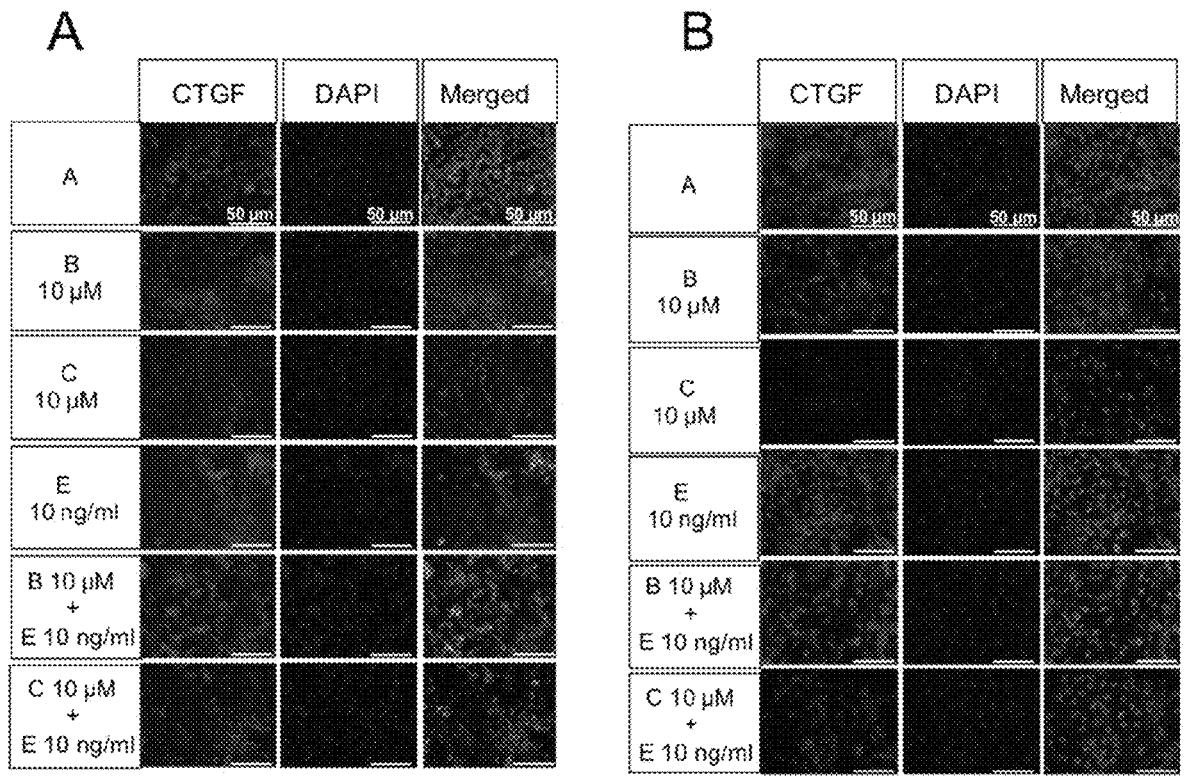

FIG. 12: In presence of TGF-β1, ASO (Seq. ID No. 218b) treatment leads to reduction of CTGF cellular protein. CTGF protein expression was reduced after gymnotic transfer of TGF-R$_{II}$ specific ASO in TGF-β1 pre-incubated (48 h) A549 (FIG. 12A) and ReNcell CX® (FIG. 12B) cells. ASOs were incubated for 72 h or 96 h in presence of TGF-β1, respectively. Cells were labeled with an antibody against CTGF (left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID. 218b, E=TGF-β1.

Figure 13:
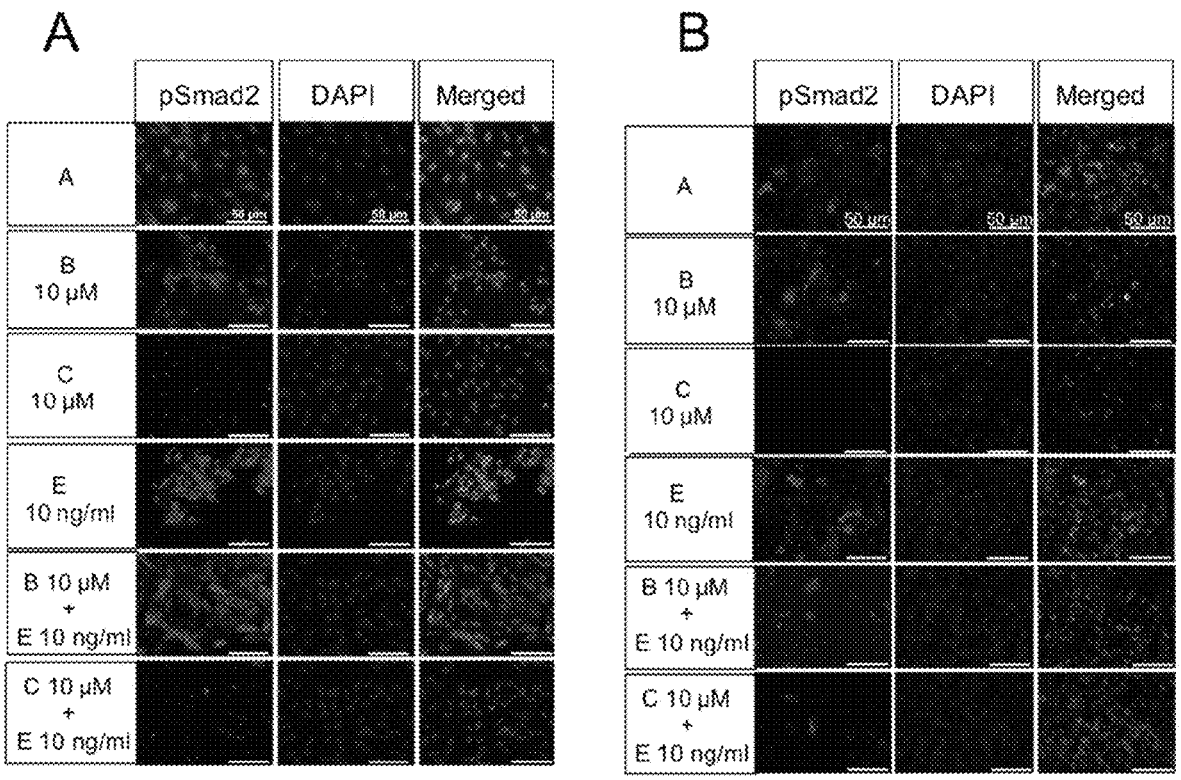

FIG. 13: In presence of TGF-β1, ASO (Seq. ID No. 218b) treatment leads to intracellular pSmad2 protein reduction. pSmad2 protein expression was reduced after gymnotic transfer of TGF-R$_{II}$ specific ASO in TGF-β1 pre-incubated (48 h) A549 (FIG. 13A) and ReNcell CX® (FIG. 13B) cells. ASOs were incubated for 72 h or 96 h in presence of TGF-β1, respectively. Cells were labeled with an antibody against pSmad2 (left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID. 218b, E=TGF-β1.

Figure 14:
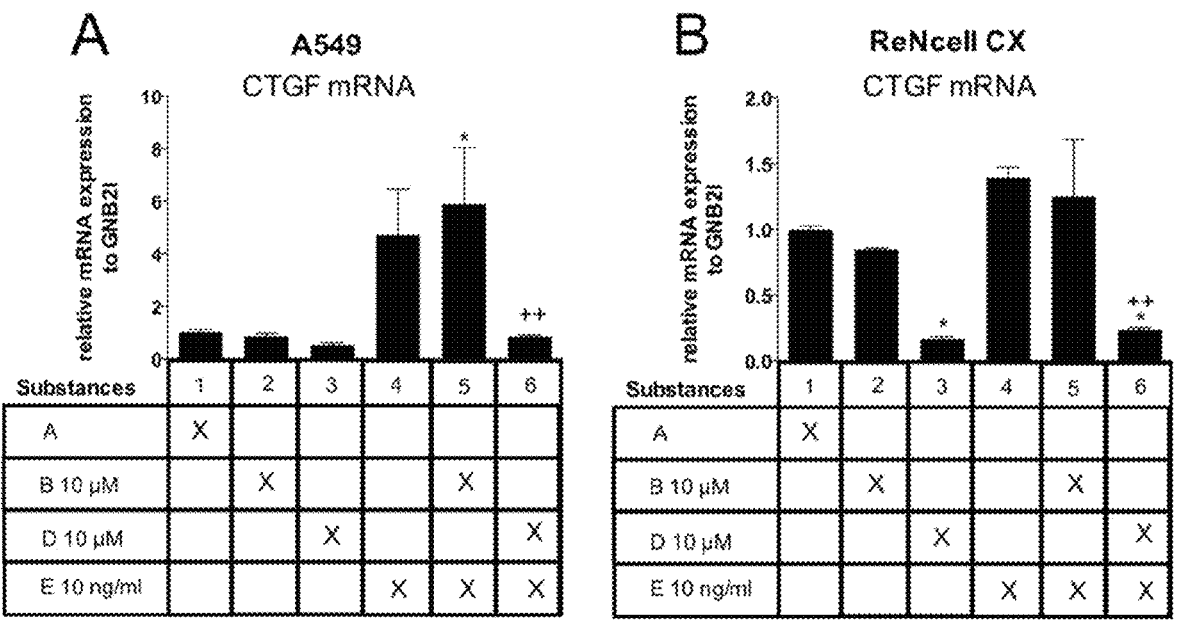

FIG. 14: In presence of TGF-β1, ASO (Seq. ID No. 218c) treatment leads to downregulation of CTGF mRNA. Potent downregulation of CTGF mRNA after gymnotic transfer of TGF-R$_{II}$ specific ASO in TGF-β1 pre-incubated (48 h) A549 (FIG. 14A) and ReNcell CX® (FIG. 14B) cells. ASOs were incubated for 72 h or 96 h in presence of TGF-β1, respectively. mRNA expression levels were quantified relative to housekeeping gene GNB2L1 using quantitative real-time RT-PCR and normalized to untreated controls. A=untreated control, B=Ref.1, D=Seq. ID No. 218c, E=TGF-β1, ±=SEM, *p<0.05, **p<0.01 in reference to A, Statistics were calculated using the Ordinary-one-way-ANOVA followed by "Dunnett's" post hoc comparisons. Note different scales.

Figure 15:
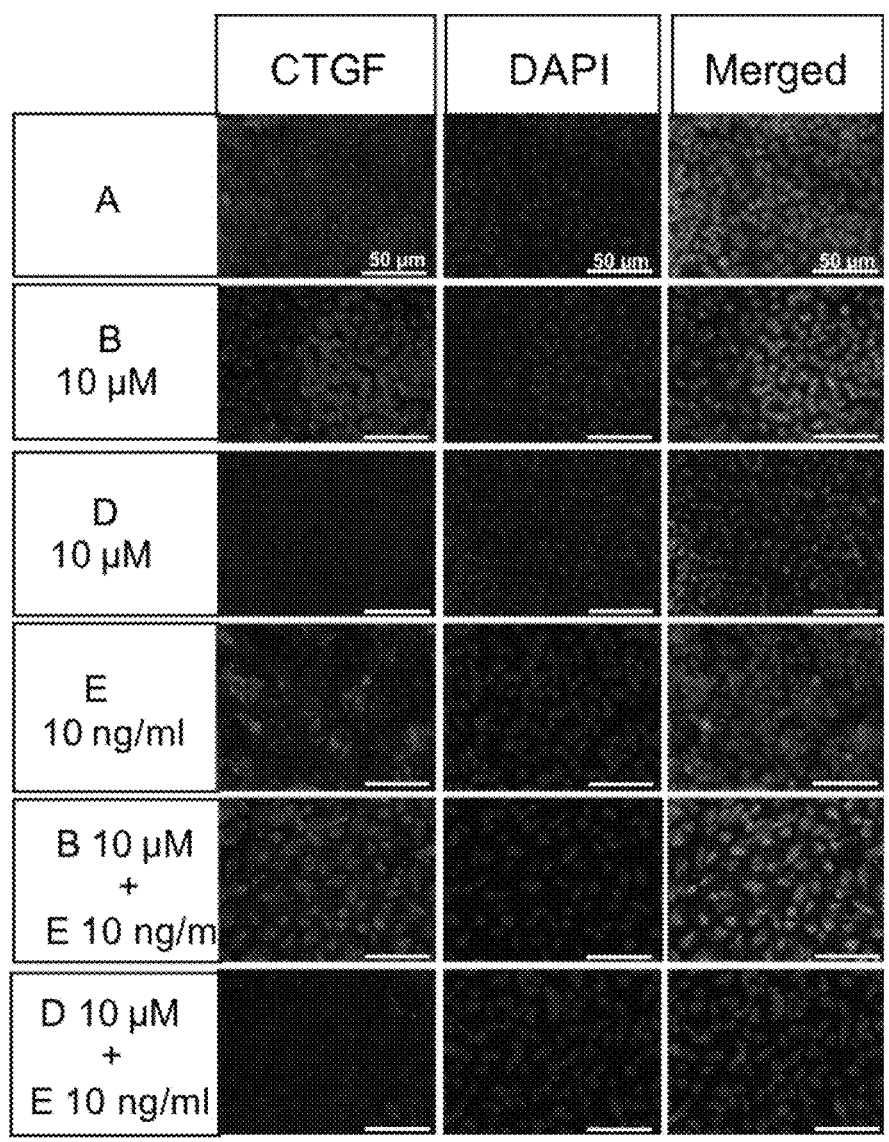

FIG. 15: In presence of TGF-β1, ASO (Seq. ID No. 218c) treatment leads to reduction of CTGF cellular protein.

CTGF protein expression was reduced after gymnotic transfer of TGF-R$_{II}$ specific ASO in TGF-β1 pre-incubated (48 h) A549 cells. ASOs were incubated for 72 h in presence of TGF-β1. Cells were labeled with an antibody against CTGF (left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, D=Seq. ID. 218c, E=TGF-β1.

Figure 16:

FIG. 16: In presence of TGF-β1, ASO (Seq. ID No. 218c) treatment leads to intracellular pSmad2 protein reduction. pSmad2 protein expression was reduced after gymnotic transfer of TGF-R$_{II}$ specific ASO in TGF-β1 pre-incubated (48 h) A549 (FIG. 16A) and ReNcell CX® (FIG. 16B) cells. ASOs were incubated for 72 h or 96 h in presence of TGF-β1, respectively. Cells were labeled with an antibody against pSmad2 (left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, D=Seq. ID. 218c, E=TGF-β1.

Figure 17:
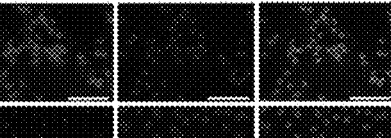

FIG. 17: ASO (Seq. ID No. 218b) pretreatment and subsequent TGF-β1 co-exposure leads to reduction of TGF-R$_{II}$ membrane protein. TGF-R$_{II}$ protein was reduced after gymnotic transfer of TGF-R$_{II}$ specific ASO followed by co-exposure of TGF-β1 (48 h) A549 (FIG. 17A) and ReNcell CX® (FIG. 17B) cells. ASOs were incubated for 72 h or 96 h, respectively, in advance to 48 h TGF-β1 co-exposure. Cells were labeled with an antibody against TGF-R$_{II}$ (left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID. 218b, E=TGF-β1.

Figure 18:
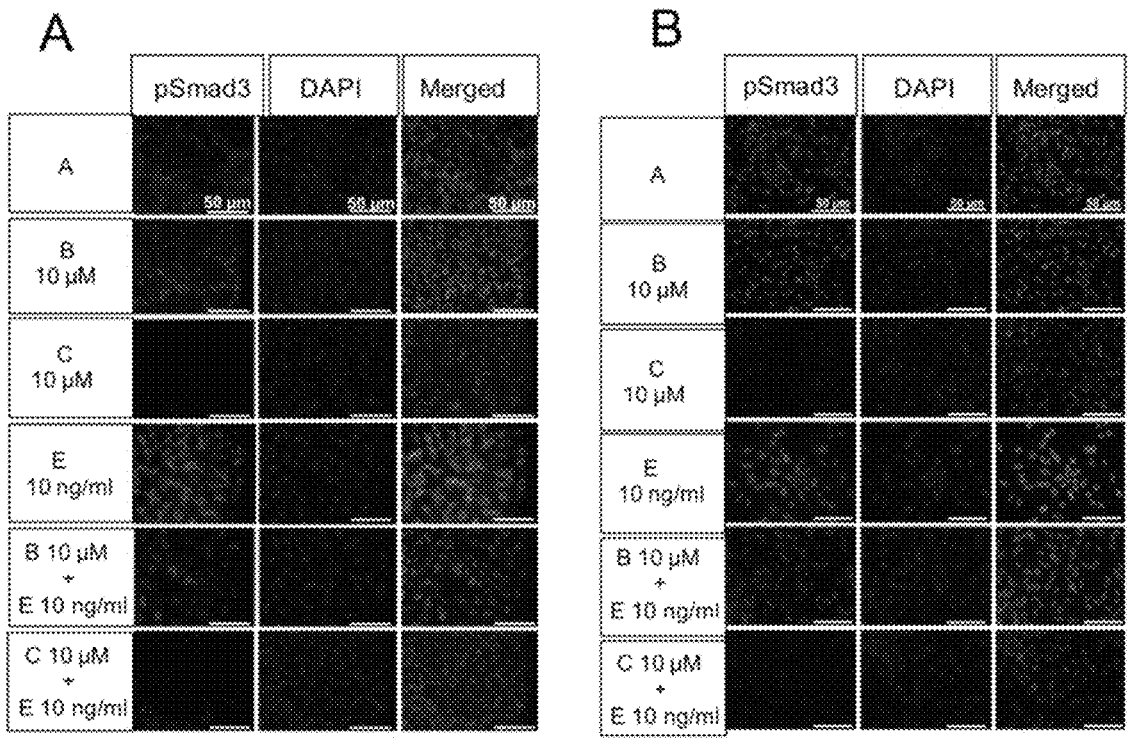

FIG. 18: ASO (Seq. ID No. 218b) pretreatment and subsequent TGF-β1 co-exposure leads to intracellular pSmad3 protein reduction. pSmad3 protein expression was reduced after gymnotic transfer of TGF-R$_{II}$ specific ASO followed by co-exposure of TGF-β1 (48 h) A549 (FIG. 18A) and ReNcell CX® (FIG. 18B) cells. ASOs were incubated for 72 h or 96 h, respectively, in advance to 48 h TGF-β1 co-exposure. Cells were labeled with an antibody against pSmad3 (left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID. 218b, E=TGF β1.

Figure 19:
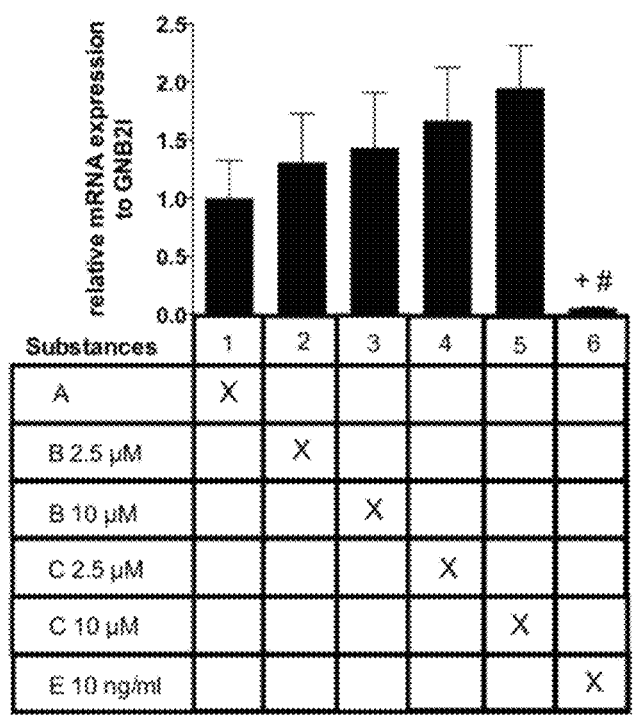

FIG. 19: ASO (Seq. ID No. 218b) enhances and TGF-β1 reduces neurogenesis in human neural precursor ReNcell CX® cells. Neurogenesis marker DCX mRNA is upregulated in ReNcell CX® cells after repeated gymnotic transfer (2×96 h) of inventive ASOs. A strong reduction of DCX mRNA expression was recognized after an 8-day TGF-β1 exposure. mRNA levels were quantified relative to housekeeping gene GNB2L1 using quantitative real-time RT-PCR and normalized to untreated controls. Statistics was calculated using the Ordinary-one-way-ANOVA followed by "Tukey's" multiple post-hoc comparison. A=untreated control, B=Ref.1, C=Seq. ID No. 218b, E=TGF-β1, =SEM, +p<0.05 in reference to C 2.5 μM, #p<0.05 in reference to C 10 μM.

Figure 20:
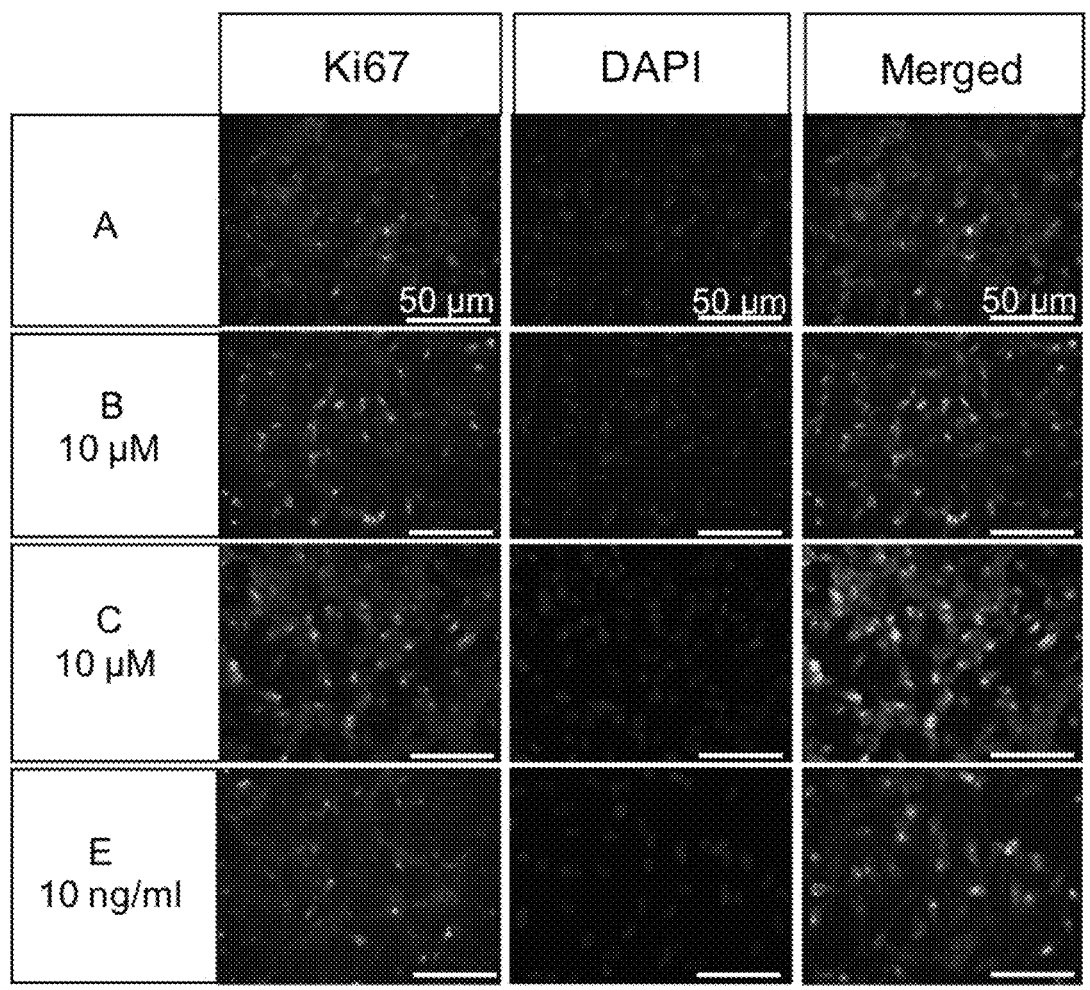

FIG. 20: ASO (Seq. ID No. 218b) enhances and TGF-β1 reduces proliferation in human neural precursor ReNcell CX® cells. Proliferation marker Ki67 protein expression is increased in ReNcell CX® cells after repeated gymnotic transfer (2×96 h) of inventive ASOs. Reduced Ki67 protein expression was recognized after an 8-day TGF-β1 exposure. Cells were labeled with an antibody against Ki67 (left column, green). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID No. 218b, E=TGF-β1.

Figure 21:
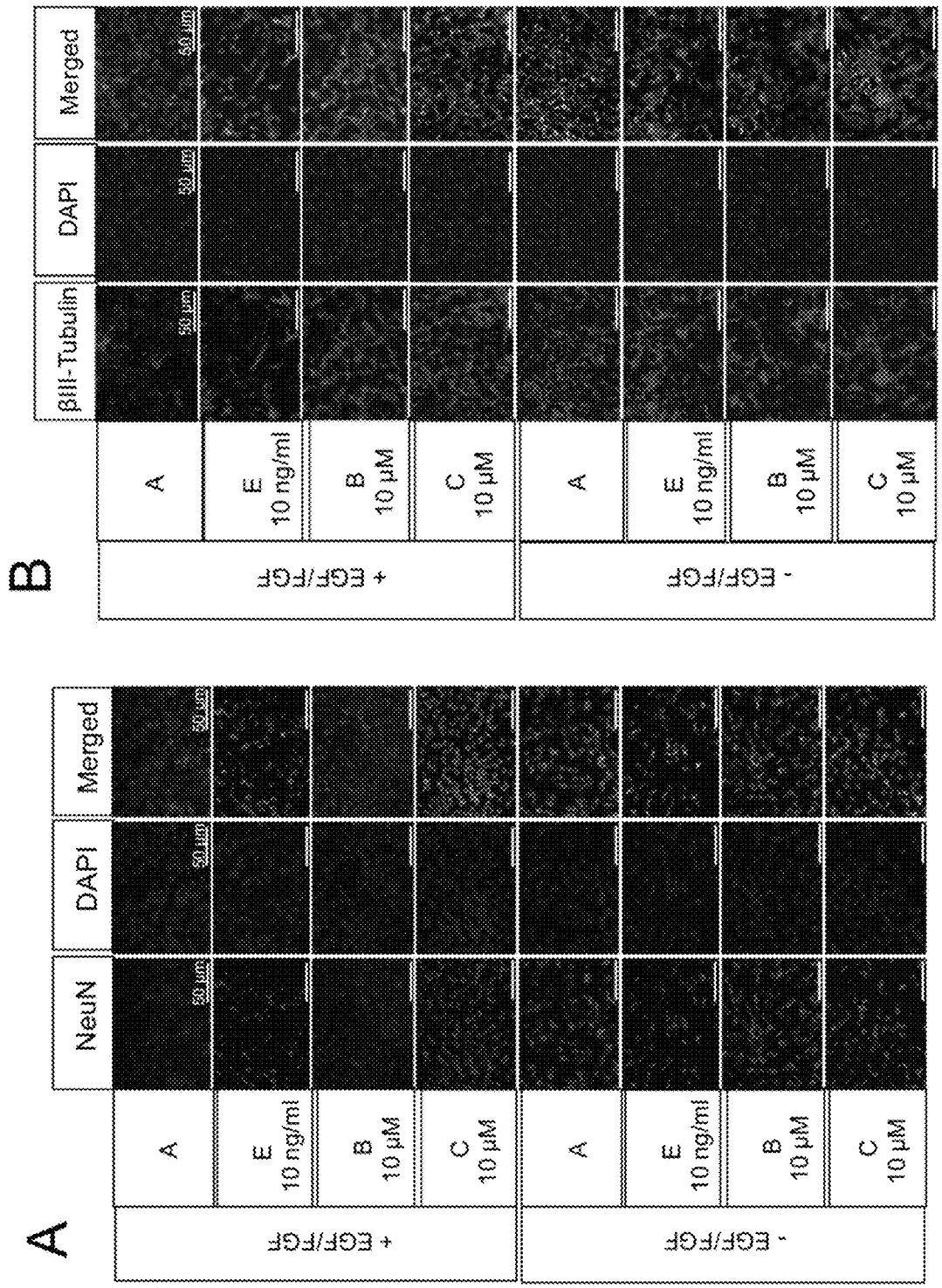

FIGS. 21A-B: Despite proliferative conditions ASO (Seq. ID No. 218b) enhances differentiation in human neural precursor ReNcell CX® cells. Neural markers NeuN (FIG. 21 A, left column, red) and βIII-Tubulin (FIG. 21 B, left column, red) in ReNcell CX® were observed. ASO treatment was applied for initial 4 days under proliferative conditions followed by further 4 days under either proliferative (+EGF/FGF) or differentiating conditions (−EGF/FGF). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID No. 218b, E=TGF-β1, +EGF/FGF=proliferation, −EGF/FGF=differentiation.

Figure 22:
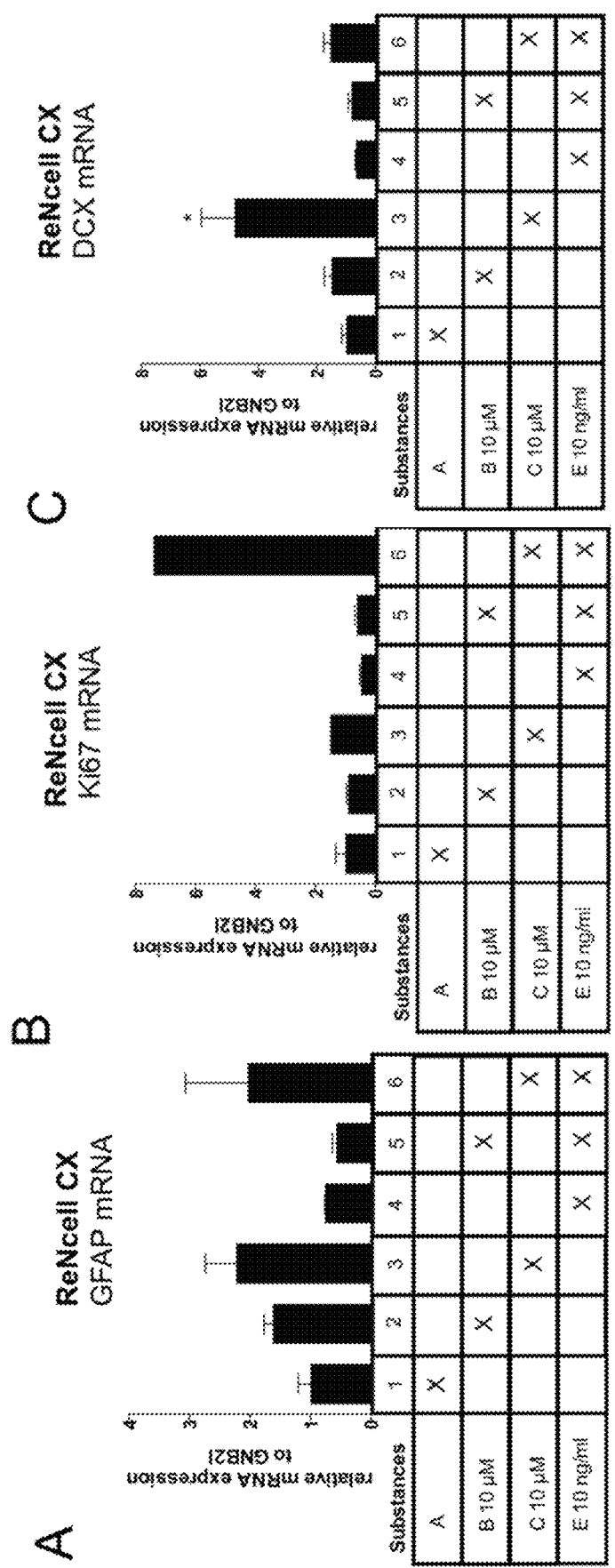

FIGS. 22A-C: ASO-mediated (Seq. ID No. 218b) rescue from TGF-β-induced neural stem cell proliferation arrest. Human neural precursor ReNcell CX® cells proliferation was observed with or without TGF-β1 exposure for 7 days followed by ASO treatment for 8 days. Upregulation of GFAP (FIG. 22A), Ki67 (FIG. 22B) and DCX (FIG. 22C) mRNA 7 days after TGF-β1 pre-incubation indicates recovery of stem cell proliferation. mRNA expression levels were quantified relative to housekeeping gene GNB2L1 using quantitative real-time RT-PCR and normalized to untreated control. A=untreated control, B=Ref.1, C=Seq. ID No. 218b, E=TGF-β1, ±=SEM, *p<0.05 in reference to A, Statistics were calculated using the Ordinary-one-way-ANOVA followed by "Tukey's" post hoc multiple comparisons.

Figure 23:
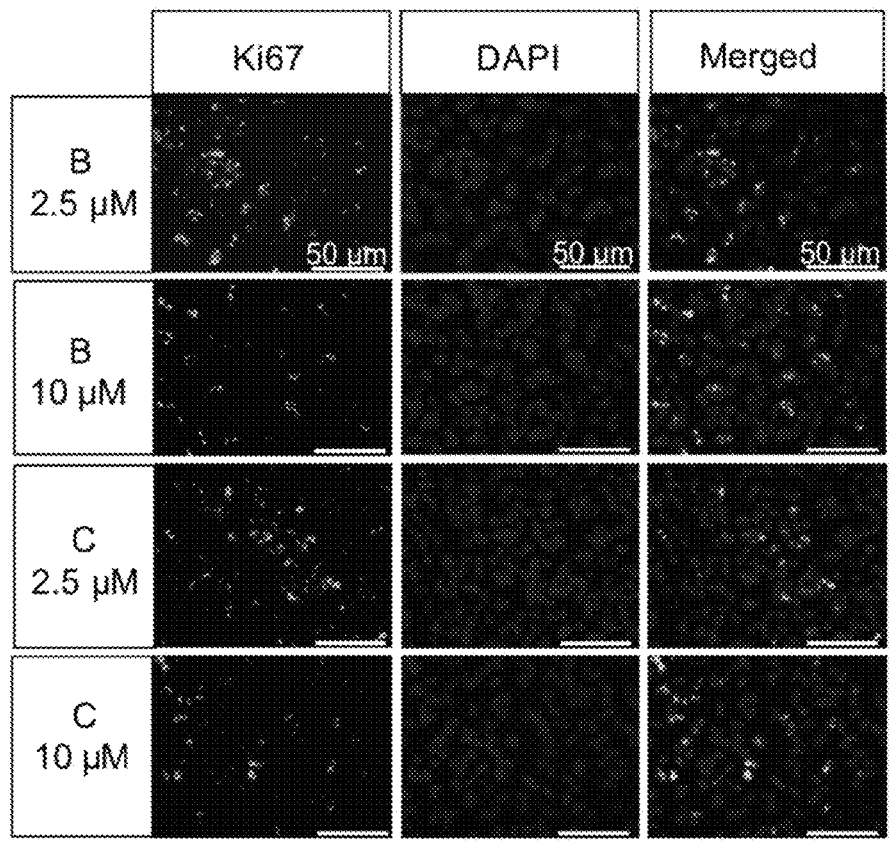

FIG. 23: ASO reduces proliferation of human lung-cancer cells (A549). Proliferation marker Ki67 protein expression is decreased in A549 cells after gymnotic transfer (72 h) of inventive ASOs. Reduced Ki67 protein expression was recognized (left column, green). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID No. 218b, E=TGF-β1.

Figure 24:
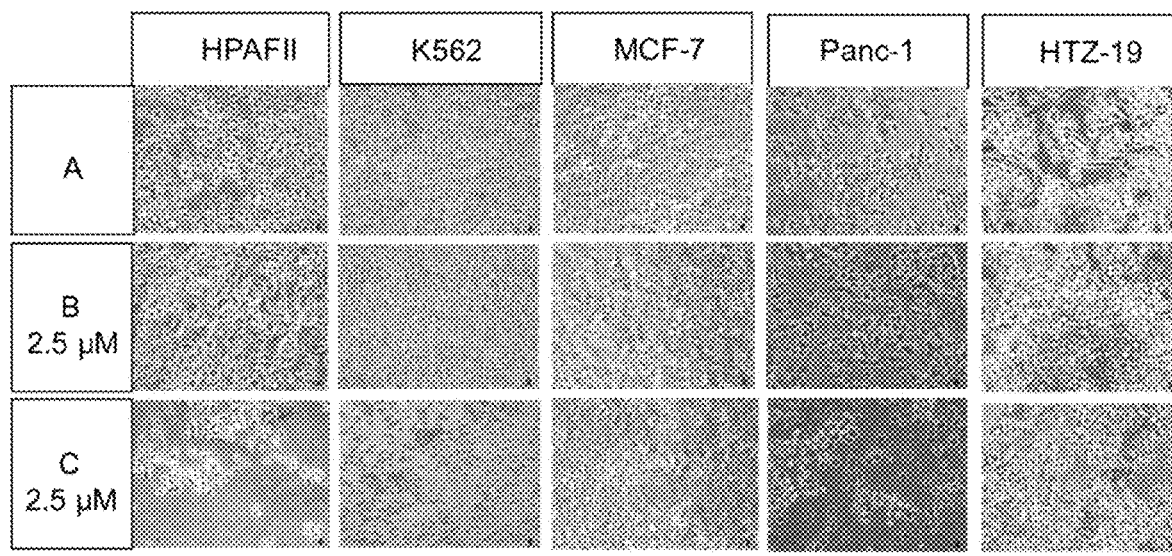

FIG. 24: ASO reduces proliferation of several human tumor cell-lines. HPAFII, K562, MCF-7, Panc-1, and HTZ-19 cells were exposed 4×72 h to inventive ASOs and proliferation was analyzed by light microscopy (Nikon, TS-100® F LED). A=untreated control, B=Ref.1, C=Seq. ID No. 218b.

Figure 25:
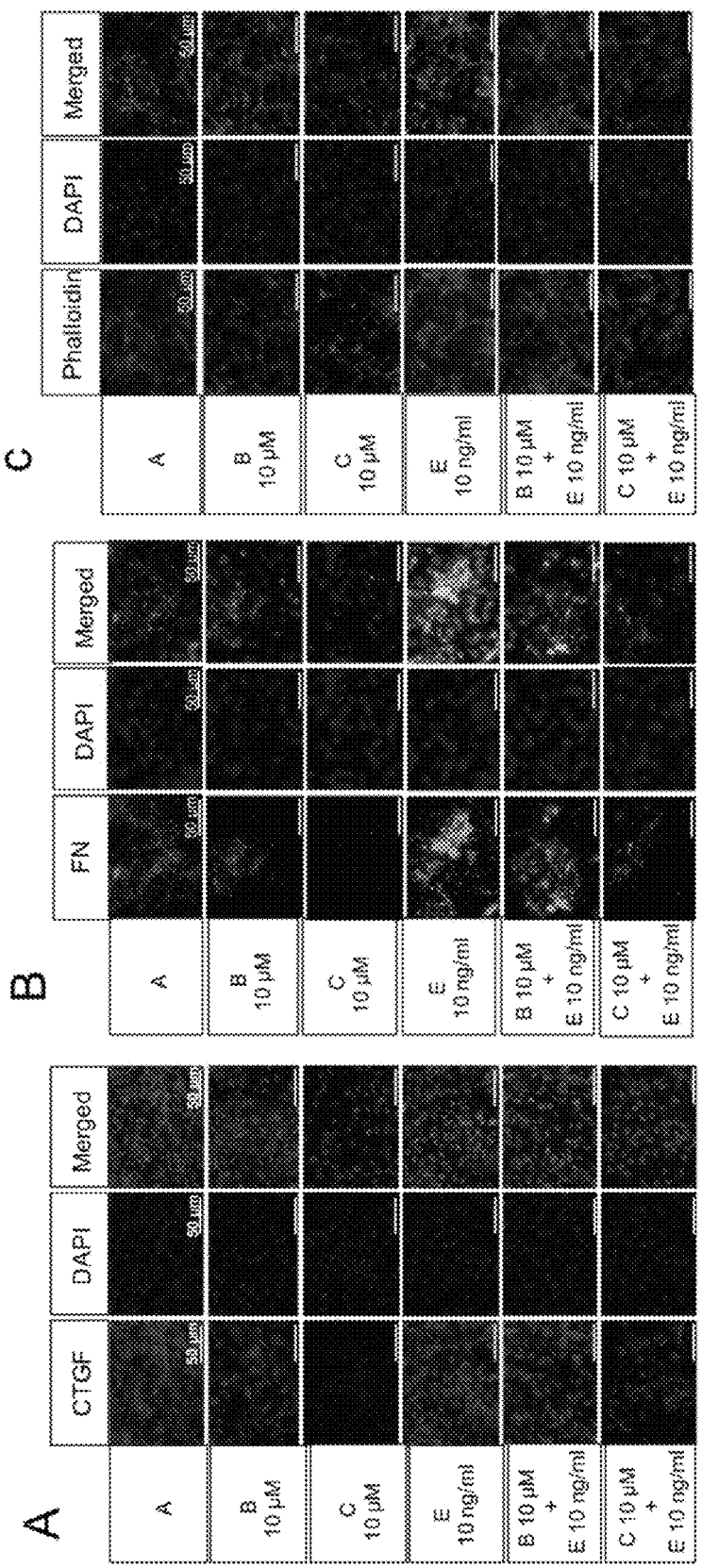

FIGS. 25A-C: ASO treatment mediates neural anti-fibrotic effects and ameliorates cellular stress. ReNcell CX® cells were observed after TGF-β1-preincubation (48 h) followed by gymnotic transfer of inventive ASO and co-exposure with TGF-β1 treatment for 96 h. Cells were labeled with an antibody against CTGF (FIG. 25A, left column, red), FN (FIG. 25B, left column, green) and of Phalloidin (actin-cytoskeleton, FIG. 25C, left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID No. 218b, E=TGF-β1.

Figure 26:
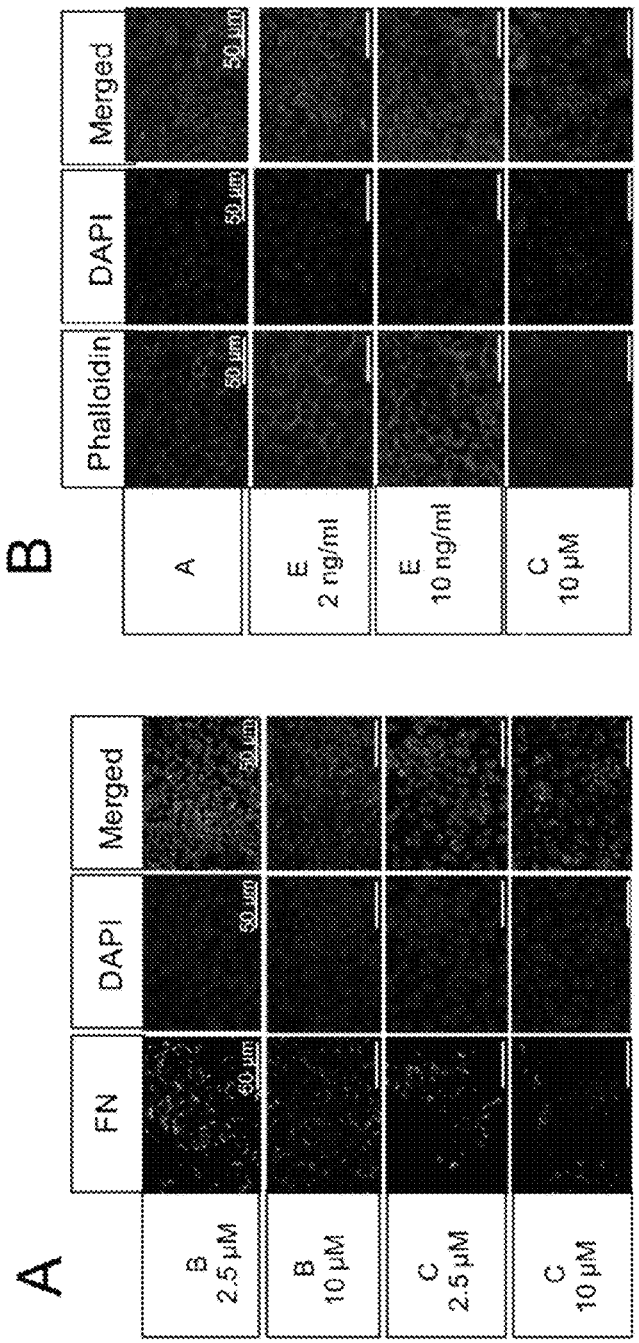

FIGS. 26A-B: ASO treatment mediates tumor anti-fibrotic effects and ameliorates cellular stress. A549 cells were observed after treatment with either TGF-β1 or gymnotic transfer of inventive ASO (72 h). Cells were labeled with an antibody against FN (FIG. 26A, left column, green), Phalloidin (actin-cytoskeleton, FIG. 26B, left column, red). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID No. 218b, E=TGF-β1.

Figure 27:
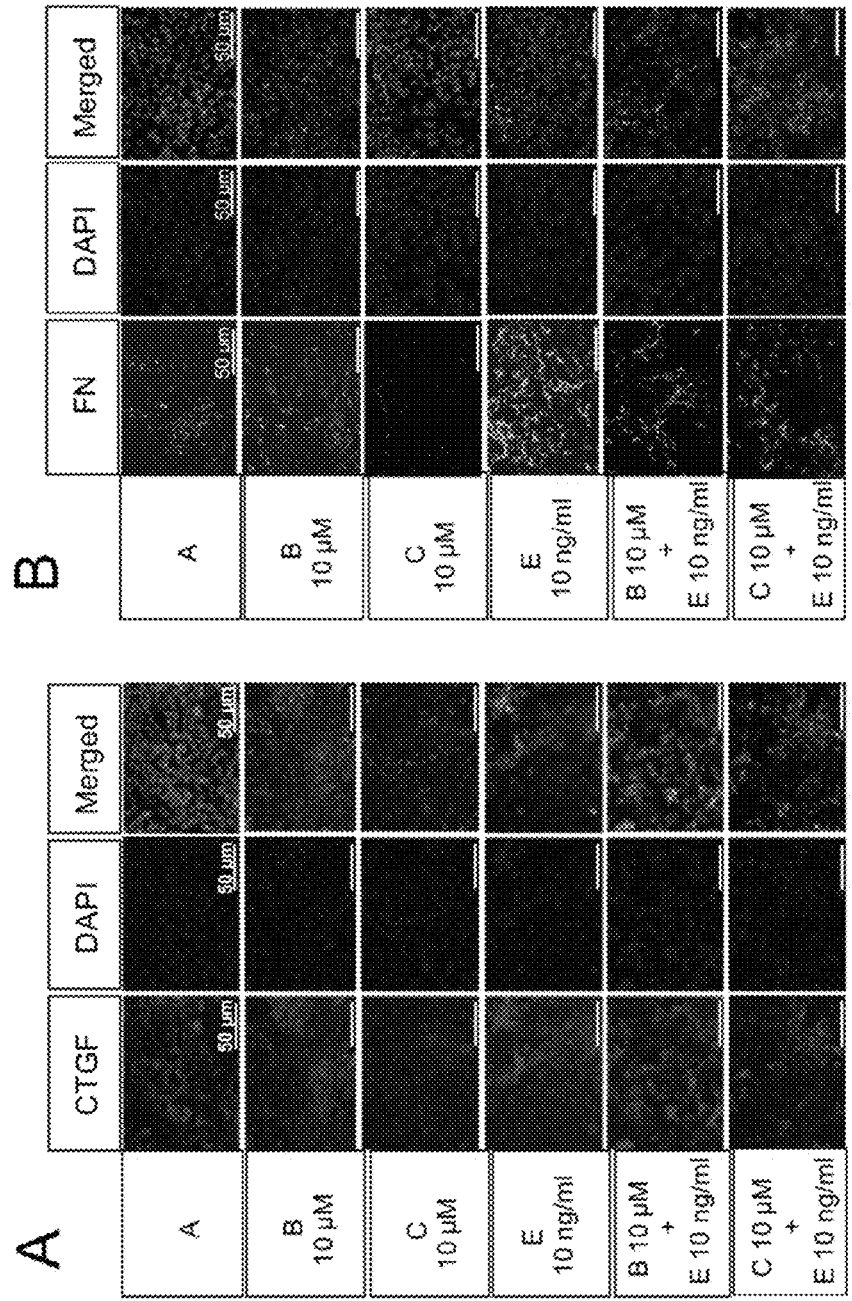

FIGS. 27A-B: ASO treatment mediates tumor anti-fibrotic effects. A549 human lung cancer cells were observed after TGF-β1-preincubation (48 h) followed by gymnotic transfer of inventive ASO and co-exposure with TGF-β1 treatment for 72 h. Cells were labeled with an antibody against CTGF (FIG. 27A, left column, red) and FN (FIG. 27B, left column, green). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, C=Seq. ID No. 218b, E=TGF-β1.

Figure 28:
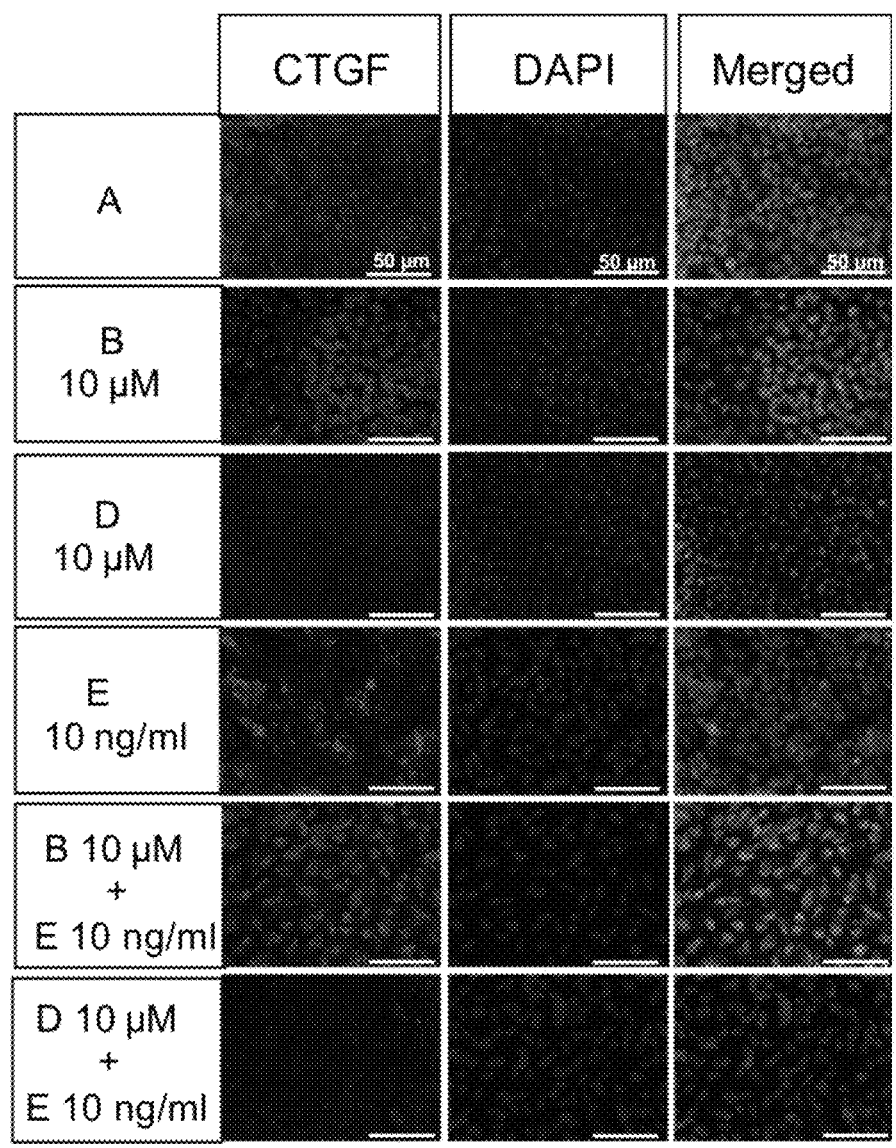

FIG. 28: ASO treatment mediates tumor anti-fibrotic effects. A549 human lung cancer cells were observed after TGF-β1-preincubation (48 h) followed by gymnotic transfer of inventive ASO and co-exposure with TGF-β1 treatment for 72 h. Cells were labeled with an antibody against CTGF (FIG. 32A, left column, red) and FN (FIG. 32B, left column, green). Nuclear DNA was stained with DAPI (central column, blue). Examination of cells was performed by fluorescence microscopy (Zeiss Axio® Observer.Z1). Images were analyzed with Image J Software and CorelDRAW® X7 Software. A=untreated control, B=Ref.1, D=Seq. ID No. 218c, E=TGF-β1.

Figure 29:
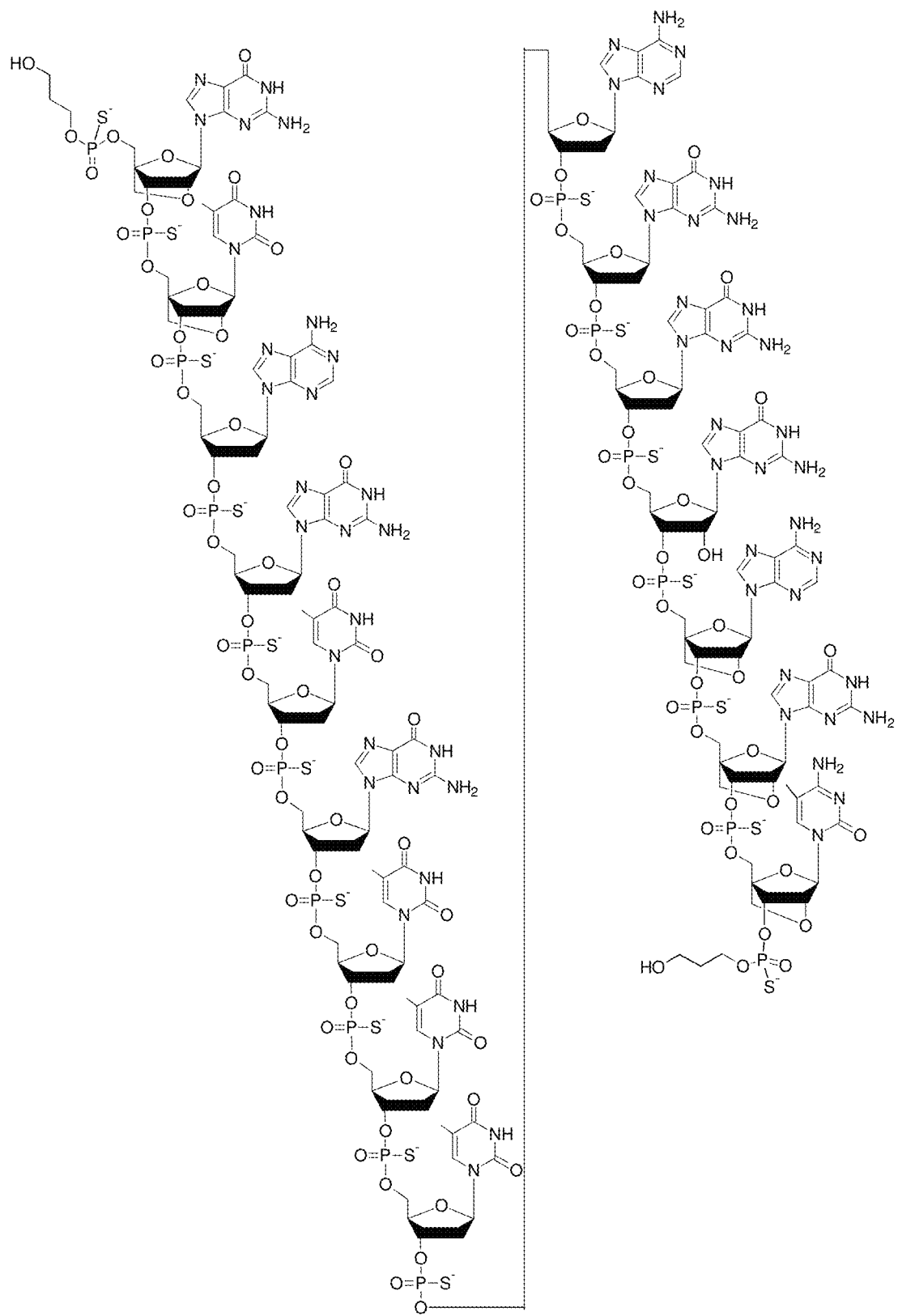

FIG. 29 shows the antisense-oligonucleotide of Seq ID No 209x in form of a gapmer consisting of 16 nucleotides with 2 LNA units ($Gb^1$ and $Tb^1$) at the 5' terminal end and 3 LNA units ($Ab^1$ and $Gb^1$ and $C*b^1$) at the 3' terminal end and 11 DNA nucleotides (dA, dG, dT, dG, dT, dT, dT, dA, dG, dG, and dG) in between the LNA segments, with phosphorothioate internucleotides linkages (s), the nucleobase 5-methylcytosine (C*) in the last LNA unit from the 5' terminal end, and with -O—P(O)(S⁻)OC$_3$H$_6$OH as terminal end groups at the 5' terminal end and at the 3' terminal end.

| SP | L | Seq ID No | Sequence, 5'-3' |
|---|---|---|---|
| 2064 | 16 | 209x | /5SpC3s/$Gb^1sTb^1$sdAsdGsdTsdGsdTsdTsd TsdAsdGsdGsdGs$Ab^1sGb^1sC*b^1$/3SpC3s/ |

Figure 30:

FIG. 30 shows the antisense-oligonucleotide of Seq ID No 152h in form of a gapmer consisting of 15 nucleotides with 4 LNA units ($C*b^1$ and $Gb^1$ and $Ab^1$ and $Tb^1$) at the 5' terminal end and 3 LNA units ($Ab^1$ and $C*b^1$ and $Ab^1$) at the 3' terminal end and 8 DNA nucleotides (dA, dC, dG, dC, dG, dT, dC, and dC) in between the LNA segments, with phosphorothioate internucleotides linkages (s) and the nucleobase 5-methylcytosine (C*) in the first and second last LNA unit from the 5' terminal end.

| SP | L | Seq ID No | Sequence, 5'-3' |
|---|---|---|---|
| 429 | 15 | 152h | $C*b^1sGb^1sAb^1sTb^1$sdAsdCsdGsdCsdGsdTsd CsdCs$Ab^1sC*b^1sAb^1$ |

Figure 31:
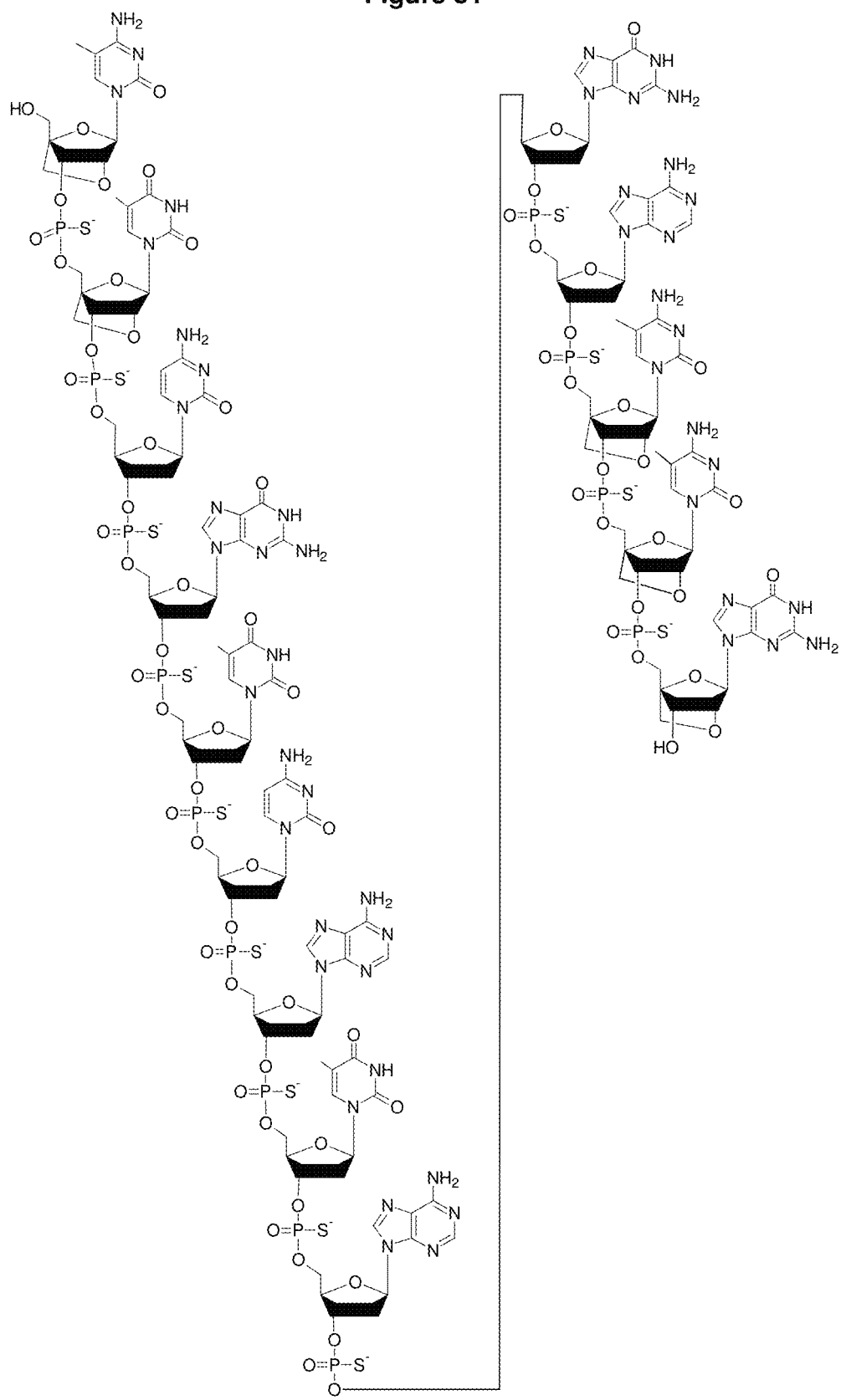

FIG. 31 shows the antisense-oligonucleotide of Seq ID No 143h in form of a gapmer consisting of 14 nucleotides with 2 LNA units ($C*b^1$ and Tb's) at the 5' terminal end and 3 LNA units ($C*b^1$ and $C*b^1$ and $Gb^1$) at the 3' terminal end and 9 DNA nucleotides (dC, dG, dT, dC, dA, dT, dA, dG, and dA) in between the LNA segments, with phosphorothioate internucleotides linkages (s) and the nucleobase 5-methylcytosine (C*) in the first, third from last and second LNA unit from the 5' terminal end.

| SP | L | Seq ID No | Sequence, 5'-3' |
|---|---|---|---|
| 355 | 14 | 143h | $C*b^1sTb^1$sdCsdGsdTsdCsdAsdTsdAsdGsdAs$C*b^1sC*b^1sGb^1$ |

Figure 32:
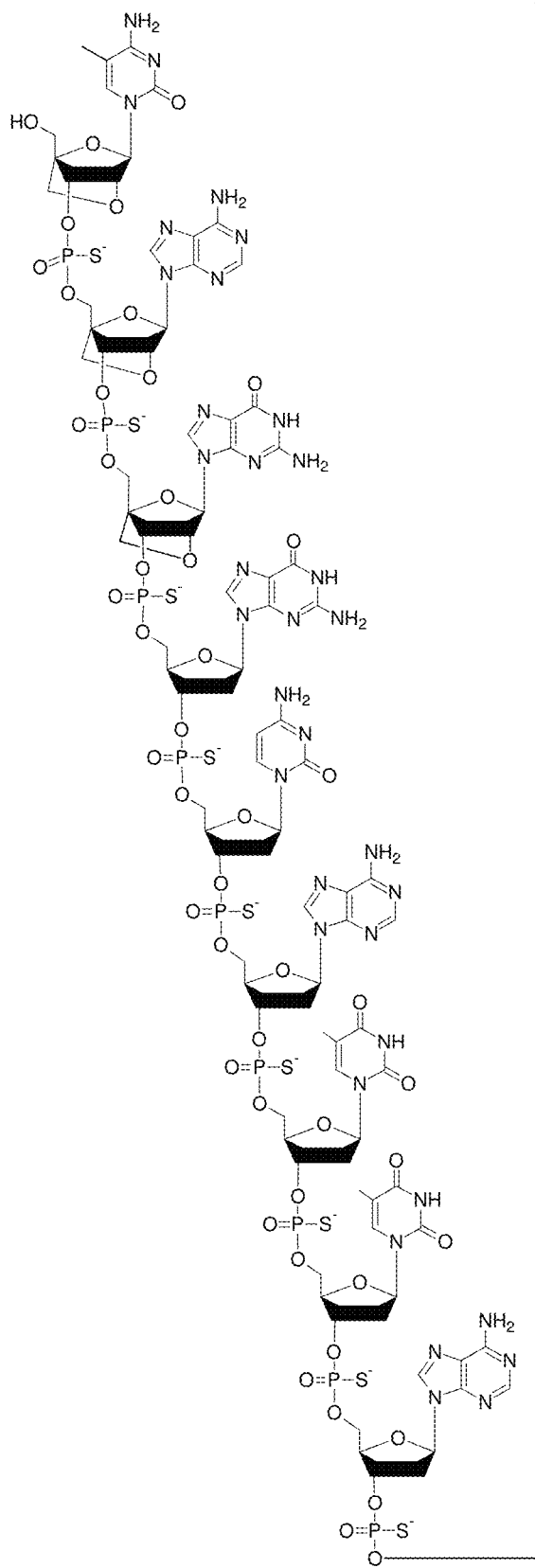
Figure 32:
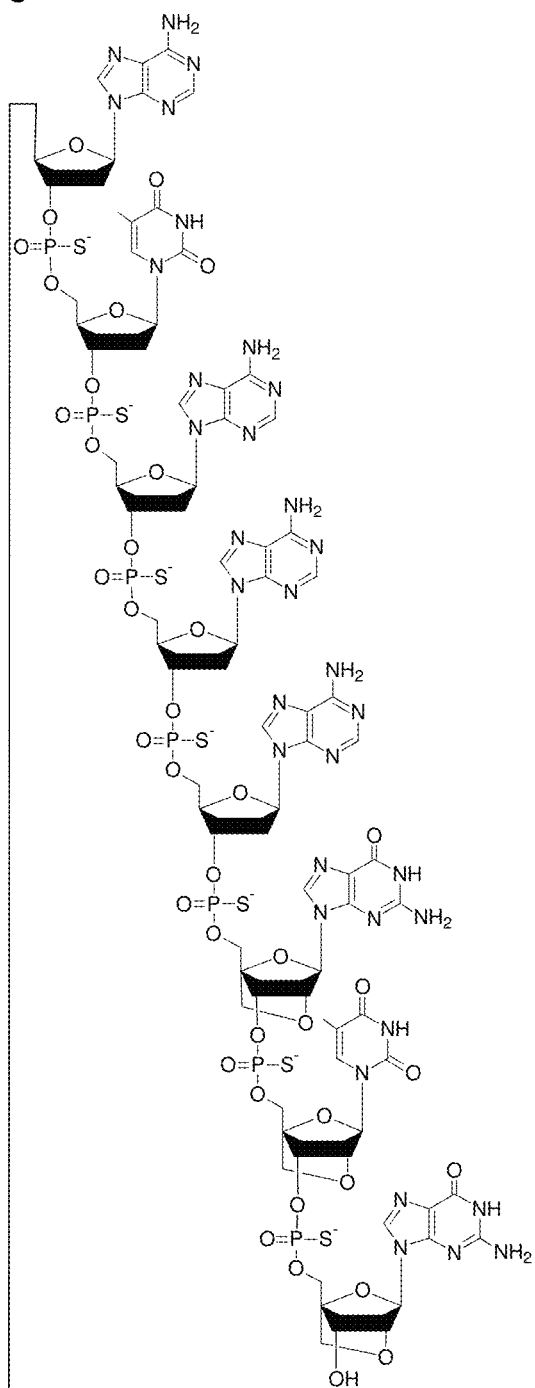

FIG. 32 shows the antisense-oligonucleotide of Seq ID No 213k in form of a gapmer consisting of 17 nucleotides with 3 LNA units ($C*b^1$ and $Ab^1$ and $Gb^1$) at the 5' terminal end and 3 LNA units ($Gb^1$ and $Tb^1$ and $Gb^1$) at the 3' terminal end and 11 DNA nucleotides (dG, dC, dA, dT, dT, dA, dA, dT, dA, dA, and dA) in between the LNA segments, with phosphorothioate internucleotides linkages (s) and the nucleobase 5-methylcytosine (C*) in the first LNA unit from the 5' terminal end.

| SP | L | Seq ID No | Sequence, 5'-3' |
|---|---|---|---|
| 2355 | 17 | 213k | $C*b^1sAb^1sGb^1$sdGsdCsdAsdTsdTsdAsdAsd TsdAsdAsdAs$Gb^1sTb^1sGb^1$ |

EXAMPLES

Material and Methods

Most Antisense-Oligonucleotides as well as control or reference oligonucleotides used herein were synthesized by EXIQON as custom oligonucleotides according to the needs of the inventors/applicant. Oligonucleotides having the following sequences were used as references:

(Seq. ID No. 147c)
Ref.0 = dCsdAsdGsdCsdCsdCsdCsdCsdGsdAsdCsdCsdCsd AsdTsdG;

(Seq. ID No. 76)
Ref. 1 = Ab1sAb1sC*b1sdAsdCsdGsdTsdCsdTsdAsdTsdAs C*b1sGb1sC*b1;

(Seq. ID No. 147m)
Ref. 2 = C*b1sAb1sGb1sdCsdCsdCsdCsdCsdGsdAsdCsdCsd CsAb1sTb1sGb1;

(Seq. ID No. 80)
Ref. 3 = TTGAATATCTCATGAATGGA;
having 2'-MOE-wings (5 units 5' and 3') and phosphorothioate linkages;

Ref. 4 = ; CAGAAGAGCTATTTGGTAGT, (Seq. ID No. 82)
having 2'-MOE-wings (5 units 5' and 3') and
phosphorothioate linkages;

Ref. 5 = TGGTAGTGTTTAGGGAGCCG, (Seq. ID No. 85)

Ref. 6 = GTGCAGGGGAAAGATGAAAA, (Seq. ID No. 344)

Ref. 7 = GAGCTCTTGAGGTCCCTGTG, (Seq. ID No. 345)

Ref. 8 = AGCCTCTTTCCTCATGCAAA, (Seq. ID No. 346)

Ref. 9 = CCTTCTCTGCTTGGTTCTGG, and (Seq. ID No. 347)

Ref. 10 = GCCATGGAGTAGACATCGGT. (Seq. ID No. 348)

Standard Procedures Protocols
Cell Culture:

TABLE 10

The following human cell lines were used for antisense-oligonucleotide experiments:

| Description | Cell line | $CO_2$—Content | Medium |
|---|---|---|---|
| Melanoma | HTZ-19 | 5% | DMEM F12 (Gibco 31331-018) + 1% dM-Mix (Transferrin (30 mg/ml in water 835 µl, non-essential AS (100x) 10 ml, Sodium-selenite (0.2 mg/ml in water) 70 µl, 10 ml PBS), 1% P/S |
| Lung carcinoma | A549 | 5% | Kaighn's F12 K + 10% FCS + 1% P/S |
| hepatocellular carcinoma | HepG2 | 5% | DMEM (Sigma D6429) + 10% FCS + 1% P/S |
| hepatocellular carcinoma | Hep3B | 5% | DMEM (Sigma D6429) + 10% FCS + 1% P/S |
| pancreatic epithelioid carcinoma | Panc-1 | 5% | DMEM (Sigma D6429) + 10% FCS + 1% P/S |
| pancreatic adenocarcinoma | HPAFII | 5% | DMEM (Sigma D5796) + 15 FCS, 1% P/S, 1% Antibiotic/Antimycotic, 1% MEM Vitamin Solution, 1% non-essential AS (100x) |
| pancreatic adenocarcinoma | BxPC-3 | 5% | RPMI (Gibco A10491-01) + 10% FCS + 1% P/S + 1% Antibiotic/Antimycotic, 1% MEM Vitamin Solution |
| pancreatic cancer liver metastasis | L3.6pl | 5% | DMEM (Sigma D5796) + 15% FCS, 1% P/S, 1% Antibiotic/Antimycotic, 1% Vitamin, 1% non-essential AS (100x) |
| colorectal adenocarcinoma | HT-29 | 5% | DMEM (Sigma D5796) + 15% FCS, 1% P/S, 1% Antibiotic/Antimycotic, 1% MEM Vitamin Solution, 1% non-essential AS (100x) |
| epithelial colorectal adenocarcinoma | CaCo2 | 5% | DMEM (Sigma D5796) + 20% FCS + 1% P/S |
| gastric carcinoma | TMK-1 | 5% | DMEM (Sigma D5796) + 10% FCS + 1% P/S, 1% Antibiotic/Antimycotic, 1% MEM Vitamin Solution |
| malignant astrocytoma | HTZ-243 | 5% | DMEM (Sigma D6046) + 10% FCS + 1% P/S + 1% non-essential AS + 1% MEM Vitamin Solution |
| Mamma-Carcinoma | MCF-7 | 5% | DMEM (Sigma D6046) + 10% FCS + 1% P/S |
| prostatic adenocarcinoma | PC-3M | 5% | RPMI (Gibco #61870-010), 10% FCS, 1% Sodium pyruvate, 1% Sodium bicarbonate, 1% P/S |
| acute myelogenous leukemia | KG-1 | 5% | RPMI (Gibco #61870-010) + 10% FCS + 1% P/S |
| chronic myelogenous leukemia | K562 | 5% | RPMI (Gibco #61870-010) + 10% FCS + 1% P/S |
| monocytic leukemia | THP-1 | 5% | RPMI (Gibco #61870-010) + 10% FCS + 0.5% P/S |
| promyelocytic leukemia | HL60 | 5% | RPMI (Gibco #61870-010) + 10% FCS + 0.5% P/S |
| lymphocytic leukemia | CEM-C7H2 | 5% | RPMI (Gibco #61870-010) + 10% FCS + 0.5% P/S |
| acute lymphoblastic leukemia | Pre-B697 | 5% | RPMI (Gibco #61870-010) + 10% FCS + 0.5% P/S |
| histiocytic lymphoma | U937 | 5% | RPMI (Gibco #61870-010) + 10% FCS + 0.5% P/S |
| Neuronal precursor cells of cortical brain region | ReNcell CX | 5% | ReNcell Neural Stem Cell Maintenance Medium (Millipore #SCM005) + human FGF Basic human + human EGF + N2-Supplement |

Material:
FCS (ATCC #30-2020)
Sodium pyruvate (Sigma #S8636)
Sodium bicarbonate (Sigma #S8761-100ML)
Transferrin (Sigma #T8158-100MG)
Natrium Selenite (Sigma #S5261-10G)
Penicillin/Streptomycin (P/S) (Sigma-Aldrich #P4458)
Non-essential Amino Acids (AS) 100× (Sigma #M7145)
Antibiotic/Antimycotic (Sigma #A5955)
MEM Vitamin Solution (Sigma #M6895)
PBS (Sigma #D8537)
FGF Basic human (Millipore #GF003)
EGF human (Millipore #GF144)
N-2 Supplement (Life Technologies #17502048)
ReNcell Neural Stem Cell Maintenance Medium (Millipore #SCM005)

Culturing and Disseminating Cells:

After removing the medium, cells were washed with PBS and incubated with accutase (Sigma-Aldrich #P4458) (5 min, RT). Following incubation, cells were peened and full medium (3 ml, company: see Tab.10 for respective cell lines) was added. Afterwards, cells were transferred into a 5 ml Eppendorf Cup and centrifuged (5 min, 1000 rpm, RT). Pellet from 1 T75-bottle (Sarstedt #833.910.302) was resuspended in 2.5 ml fresh medium. Cell number of cell suspension was determined with Luna-FL™ automated cell counter (Biozym #872040) by staining with acridine orange/propidium iodide assay viability kit (Biozym #872045). Laminin-coating (Millipore #CC095) of dishes was necessary for adhesion of ReNcell CX® cells before seeding the cells for experiments in a concentration of 2 µg/cm². Laminin-PBS solution was given in the respective amount directly to wells and flasks and was incubated for 1.5 h at 37° C. For experiments cells were seeded and harvested as mentioned in method part of respective experimental chapter. After overnight incubation of cells at 37° C. and 5% $CO_2$, cells were treated as explained in respective experimental description. 500 µl of remaining cell suspension was given into a new T75-bottle filled with 10 ml fresh full medium for culturing cells.

RNA-Analysis

Total RNA for cDNA synthesis was isolated using innuPREP® RNA Mini Kit (Analytik Jena #845-KS-2040250) according to manufacturer's instructions. In order to synthesize cDNA, total RNA content was determined using a photometer (Eppendorf, BioPhotometer D30 #6133000907), diluted with nuclease-free water. Afterwards first-strand cDNA was prepared with iScript™ cDNA Synthesis Kit (BioRad #170-8891) according to manufacturer's recommendations. For mRNA analysis real-time RT-PCR was performed using a CFX96 Touch™ Real Time PCR Detection System (BioRad #185-5196).

All primer pairs were ready-to-use standardized and were mixed with the respective ready-to-use Mastermix solution (SsoAdvanced™ Universal SYBR® Green Supermix (BioRad #172-5271) according to manufacturer's instructions (BioRad Prime PCR Quick Guide). Primer-pairs for in vivo experiments were adapted according to individual species.

TABLE 11

Primer pairs used for mRNA Analysis

| Primer pair | Company | Unique Assay ID |
|---|---|---|
| Human CDKN1A | BioRad | qHsaCID0014498 |
| Human CDNK1B | BioRad | qHsaCID0012509 |
| Human CFLAR | BioRad | qHsaCID0038905 |
| Human Col4A1 | BioRad | qHsaCID0010223 |
| Human CTGF | BioRad | qHsaCED0002044 |
| Human DCX | BioRad | qHsaCID0010869 |
| Human FN1 | BioRad | qHsaCID0012349 |
| Human GFAP | BioRad | qHsaCID0022307 |
| Human GNB2L1 | BioRad | qHsaCEP0057912 |
| Human ID-2 | BioRad | qHsaCED0043637 |
| Human MKi67 | BioRad | qHsaCID0011882 |
| Human Nestin | BioRad | qHsaCED0044457 |
| Human SERPINE1 | BioRad | qHsaCED0043144 |
| Human SOX2 | BioRad | qHsaCED0036871 |
| Human TGFβ-RII | BioRad | qHsaCID0016240 |
| Human TP53 | BioRad | qHsaCID0013658 |

As template, 1 µl of respective cDNA was used. RNA that was not reverse transcribed served as negative control for real-time RT-PCR. For relative quantification housekeeping gene Guanine nucleotide-binding protein subunit beta-2-like 1 (GNB2L1) was used. Real-time RT-PCR was performed with the following protocol:

TABLE 12

Protocol for real-time RT-PCR.

| | | | |
|---|---|---|---|
| Initiation period | 2 min | 95° C. | 1x |
| Denaturation | 5 s | 95° C. | 40x |
| Annealing, Extension | 30 s | 60° C. | 40x |
| Melting curve | | 65° C.-95° C. (0.5° C. gradient) | 1x |

Afterwards, BioRad CFX Manager 3.1 was used for quantification of respective mRNA-level relative to GNB2L1 mRNA and then normalized to untreated control.

Western Blot:

For protein analysis, cells/tissues were lysed using M-PER® Mammalian Protein Extraction Reagent/T-PER® Tissue Protein Extraction Reagent (Thermo Scientific, #78501/#78510) according to manufacturer instructions, respectively. SDS-acrylamide-gels (10%) were produced using TGX Stain Free™ Fast Cast™ Acrylamide Kit (BioRad #161-0183) according to manufacturer instructions. Protein samples (20 µl) were diluted 1:5 with Lämmli-buffer (6.5 µl, Roti®-Load1, Roth #K929.1), incubated at 60° C. for 30 min and loaded on the gel with the entire volume of the protein solution. Separation of proteins was performed by electrophoresis using PowerPac™ Basic Power Supply (Biorad #164-5050SP) and Mini-PROTEAN® Tetra cell electrophoresis chamber (BioRad #165-8001-SP) (200 V, 45 min). Following electrophoresis, the proteins were blotted using Trans-Blot® Turbo Transfer System (BioRad #170-4155SP). All materials for western blotting were included in Trans-Blot® Turbo RTA PVDF-Midi Kit (BioRad #170-4273).

The PVDF-membrane for blotting procedure was activated in methanol (Merck #1.06009.2511) and equilibrated in 1× transfer buffer. Following blotting (25 V, 1 A, 30 min), membranes were washed (3×, 10 min, RT) with 1× TBS (Roth #10.60.1) containing 0.5 ml Tween-20 (Roth #9127.1). Afterwards, the membranes were blocked with 5% BSA (Albumin-IgG-free, Roth #3737.3) diluted with TBS-T for 1 h at RT, the primary antibodies (diluted in 0.5% BSA in TBS-T, Table 13) were added and incubated at 4° C. for 2 days. Antibodies for in vivo experiments were chosen for species specificity accordingly.

TABLE 13

Antibodies used for Western Blot analysis.

| | Dilution | Company | Order Number |
|---|---|---|---|
| Primary Antibody | | | |
| Alpha-Tubulin HRP-linked (rabbit) | 1:2000 | Cell Signaling | cs12351s |
| ColIV (rabbit) | 1:1000 | Abcam | ab6586 |
| CTGF (rabbit) | 1:1000 | Genetex | GTX-26992 |
| FN (rabbit) | 1:250 | Proteintech | 15613-1-AP |
| GAPDH XP HRP-linked (rabbit) | 1:1000 | Cell Signaling | cs8884s |
| Ki67 (rabbit) | 1:500 | Abcam | ab15580 |
| pAkt (rabbit) | 1:1000 | Cell signaling | cs4060s |
| pErk1/2 (rabbit) | 1:1000 | Cell signaling | cs4370s |
| pSmad2 (rabbit) | 1:500 | Cell Signaling | cs3104 |
| TGF-βRII (rabbit) | 1:400 | Aviva | ARP44743-T100 |
| Secondary Antibody | | | |
| Anti-rabbit IgG, HRP-linked | 1:10000 | Cell signaling | cs#12351S |

In the next step, membranes were washed in TBS-T (3×10 min, RT) and incubated with the secondary antibody (1 h, RT, Table 13). Following incubation, blots were washed with TBS-T, emerged using Luminata™ Forte Western HRP Substrate (Millipore #WBLUF0500) and bands were detected with a luminescent image analyzer (ImageQuant™ LAS 4000, GE Healthcare). Afterwards, the blots were washed in TBS-T (3×10 min, RT) and blocked with 5% BSA diluted in TBS-T (1 h, RT). For housekeeper comparison, the membranes were incubated with HRP-conjugated anti alpha-tubulin (1:2000 in 0.5% BSA, 4° C., overnight). The next day blots were emerged using Luminata™ Forte Western HRP Substrate (Millipore #WBLUF0500) and bands were detected with the luminescent image analyzer. Finally, the blots were washed with TBS-T (3×, 5 min) and stained using 1× Roti®-Blue solution (Roth #A152.2) and dried at RT.

Immunocytochemistry

Cells were treated and harvested as described before. Following fixation of cells with Roti®-Histofix 4% (Roth #P087.4) on 8-well, cell culture slide dishes (6 min, RT) were washed three times with PBS. After blocking cells for 1 h at RT with Blocking Solution (Zytomed #ZUC007-100) cells were incubated with respective primary antibodies listed in Table 14 and incubated at 4° C. overnight.

Afterwards, cell culture slides were washed three times with PBS following incubation with secondary antibody (1 h, RT). All antibody-dilutions were prepared with Antibody-Diluent (Zytomed #ZUC025-100).

TABLE 14

Antibodies used for immunocytochemistry.

| | Dilution | Company | Order Number |
|---|---|---|---|
| Primary Antibody | | | |
| ColIV (rabbit) | 1:50 | Abcam | ab6586 |
| CTGF (rabbit) | 1:50 | Genetex | GTX26992 |
| βIII-Tubulin (rabbit) | 1:100 | cell signaling | cs5568 |
| FN (rabbit) | 1:50 | Proteintech | 15613-1-AP |
| Ki67 (rabbit) | 1:100 | Abcam | ab15580 |
| NeuN (rabbit) | 1:250 | Abcam | Ab104225 |
| Phalloidin Alexa Fluor 555 | 1:20 | Cell signaling | cs8953 |
| pSmad2 (rabbit) | 1:50 | Cell signaling | cs3104s |
| pSmad3 (rabbit) | 1:50 | Cell signaling | cs9520s |
| TGF-R$_{II}$ (rabbit) | 1:50 | Millipore | 06-227 |
| Secondary Antibody | | | |
| Alexa Fluor 488 | 1:750 | Life Technologies | A21441 |
| Cy3 goat-anti-rabbit | 1:1000 | Life Technologies | A10520 |

Following incubation with secondary antibody, cells were washed three times with PBS, coverslips were separated from cell culture dish and mounted with VECTASHIELD® HardSet™ with DAPI (Biozol #VEC-H-1500). Slides were dried overnight at 4° C. before fluorescence microscopy (Zeiss, Axio® Observer.Z1). Images were analyzed with Image J Software and CorelDRAW® X7 Software.

In Vivo Experiments

Peripheral Blood Mononuclear Cell (PBMC) Assay

PBMCs were isolated from buffy coats corresponding to 500 ml full blood transfusion units. Each unit was obtained from healthy volunteers and glucose-citrate was used as an anti-agglutinant. The buffy coat blood was prepared and delivered by the Blood Bank Suhl of the Institute for Transfusion Medicine, Germany. Each blood donation was monitored for HIV antibody, HCV antibody, HBs antigen, TPHA, HIV RNA, and SPGT (ALAT). Only blood samples tested negative for infectious agents and with a normal SPGT value were used for leukocyte and erythrocyte separation by low-speed centrifugation. The isolation of PBMCs was performed about 40 h following blood donation by gradient centrifugation using Ficoll-Histopague® 1077 (Heraeus™ Multifuge™ 3 SR). For IFNα assay, PBMCs were seeded at 100,000 cells/96-well in 100 µl complete medium plus additives (RPMI1640, +L-Glu, +10% FCS, +PHA-P (5 µg/ml), +IL-3 (10 µg/ml)) and test compounds (5 µl) were added for direct incubation (24 h, 37° C., 5% CO$_2$). For TNFα assay, PBMCs were seeded at 100,000 cells/96-well in 100 µl complete medium w/o additives (RPMI1640, +L-Glu, +10% FCS) and test compounds (5 µl) were added for direct incubation (24 h, 37° C., 5% CO$_2$). ELISA (duplicate measurement out of pooled supernatants, 20 µl) for huIFNα (eBioscience, #BMS2161NSTCE) was performed according to the manufacturer's protocol. ELISA (duplicate measurement out of pooled supernatants, 20 µl) for huTNFα (eBioscience, #BMS2231NSTCE) was performed according to the manufacturer's protocol.

bDNA Assay

TGF-R$_{II}$ mRNA levels were determined in liver, kidney, and lung lysate by bDNA assay according to manufacturer's instructions (QuantiGene® kit, Panomics/Affimetrix).

Immunofluorescence

Paraffin-embedded spinal cord and brain tissue was cut into 5 µm sections (3-4 slides per object plate). Paraffin sections were deparaffinized and demasked by heating in citrate buffer (10 mM, 40 min) in a microwave oven. Afterwards, deparaffinized sections were incubated with 0.3% H$_2$O$_2$ (30 min, RT), washed with PBS (10 min, RT) and blocked with Blocking Solution (Zytomed #ZUC007-100) for 30 min. After blocking for 1 h at RT with Blocking Solution (Zytomed) slides were incubated with 150 µl of the respective primary antibodies and incubated at 4° C. overnight. After washing with PBS (three times, 5 min RT) the slices were incubated with the secondary antibody for 1 h at RT. All antibody dilutions were prepared with Antibody Diluent (Zytomed #ZU0025-100). Afterwards the slices were washed again with PBS (three times, 5 min, RT) and mounted using VECTASHIELD® Mounting Medium with DAPI (Vector). Antibodies for immunofluorescence were comparable to cell culture experiments and adapted for each species.

Electrochemiluminescence

For immunological and hematological alterations, electrochemiluminescence technique (MesoScale Discovery®, Maryland, United States) was used. For each assay, 25 µl of the protein, blood, and liquor samples were used and the procedure was performed according to manufacturer's instructions.

BrdU Assay

Labeling of dividing cells was performed by intraperitoneal injection of the thymidine analogue BrdU (Sigma, Steinheim, Germany) at 50 mg/kg of body weight using a sterile solution of 10 mg/ml of BrdU dissolved in a 0.9% (w/v) NaCl solution. The BrdU injections were performed daily within the last experimental week.

Surgery

For chronic central infusion, animals underwent surgery for an icv cannula attached to an Alzet® osmotic minipump (mice, rats, infusion rate: 0.25 µl/h, Alzet®, Model 2004, Cupertino, USA) or a gas pressure pump (Cynomolgus monkeys, infusion rate 0.25 ml/24 h, Tricumed®, Model IP 2000V, Germany). The cannula and the pump were stereotaxically implanted under ketamine/xylacin anesthesia (Baxter, GmbH, Germany) and semi-sterile conditions. Each osmotic minipump/gas pressure pump was implanted subcutaneously in the abdominal region via a skin incision at the neck of the animals and connected with the icv cannula by silicone tubing. Animals were placed into a stereotaxic frame, and the icv cannula was lowered into the right lateral ventricle. The cannula was fixed with two stainless steel screws using dental cement (Kallocryl, Speiko®-Dr. Speier GmbH, Münster, Germany). The skin of the neck was closed with sutures. During surgery, the body temperature was maintained by a heating pad. To avoid post-surgical infections, animals were locally treated with Betaisodona® (Mundipharma GmbH, Limburg, Germany) and received antibiotics (sc, Baytril® 2.5% Bayer Vital GmbH, Leverkusen, Germany). The tubing was filled with the respective solution. Blood, liquor, and tissues were collected for analysis. Histological verification of the icv implantation sites was performed at 40 µm coronal, cresyl violet-stained brain sections.

Outcome Parameters and Functional Analysis

Onset of symptomatic disease, onset of first paresis and survival were used as in vivo endpoints. Onset of symptomatic disease was defined as a lack of leg stretching in reaction to tail suspending. Time point at which gait impairments were first detected (e.g., hobbling or waddling) was classified as onset of first paresis. These parameters were determined daily starting at age 40 days.

To monitor disease progression, running wheel testing (LMTB, Berlin, Germany) was performed. Animals were caged separately with access to a running wheel starting at 33 days of age. Motor activity was directly correlated with the rotations per minute, generated by each animal in the running wheel. Each full turn of the wheel triggered two electromagnetic signals, directly fed into a computer attached to a maximum of 120 wheels. Running wheel data were recorded and analyzed with "Maus Vital" software (Laser- und Medizin-Technologie, Berlin, Germany). Assessment time lasted for 12 hours from 6:00 µm to 6:00 am.

Spatial Learning Test (Morris-Water-Maze)

Behavioral testing was performed between 8:00 and 13:00.

Rats were trained in a black circular pool (1.4 m in diameter, 50 cm high, filled with 20° C. warm water to a height of 30 cm) to find a visible white target (10 cm in diameter, raised above the water's surface of approximately 1 cm) that was located throughout the study in the center of the same imaginary quadrant (proximally cued). Each animal was trained to navigate to the platform in 3 consecutive sessions with 12 trials/sessions, one session per day and an inter-trial interval of 10-20 s.

Microbiological Analysis

Antisense-oligonucleotide samples were microbiologically analyzed according to Ph. Eur. 2.6.12, USP 30<61> regarding the Total Aerobic Microbial Count (TAMC) and the Total Combined Yeast and Mould Count (TYMC).

Anion-Exchange High-Performance Liquid Chromatography (AEX-HPLC)

Integrity and stability of antisense-oligonucleotide (ASO) samples was determined by AEX-HPLC using ÄKTAexplorer™ System (GE healthcare, Freiburg, Germany). The purified ASO samples were desalinated by ethanol precipitation. The identity of the ASO was confirmed by electrospray-ionization-mass-spectrometry (ESI-MS) and the purity was determined by AEX-HPLC with a Dionex DNAPac™ 200 (4×250 mm) column.

Example 1: Determination of Inhibitory Activity of Inventive Antisense-Oligonucleotides on mRNA Level 1.1 Transfection of Antisense-Oligonucleotides The inhibitory activity of several antisense-oligonucleotides directed to TGF-$R_{II}$ was tested in human epithelial lung cancer cells (A549). TGF-$R_{II}$ mRNA was quantified by branched DNA assay in total mRNA isolated from cells incubated with TGF-$R_{II}$ specific oligonucleotides.

Description of Method:

Cells were obtained and cultured as described above. Transfection of antisense-oligonucleotides was performed directly after seeding 10,000 A549 cells/well on a 96-well plate, and was carried out with Lipofectamine® 2000 (Invitrogen GmbH, Karlsruhe, Germany, cat. No. 11668-019) as described by the manufacturer. In two independent single dose experiments performed in quadruplicates, oligonucleotides were transfected at a concentration of 20 nM. After transfection, cells were incubated for 24 h at 37° C. and 5% $CO_2$ in a humidified incubator (Heraeus GmbH, Hanau, Germany). For measurement of TGF-$R_{II}$ mRNA, cells were harvested and lysed at 53° C. following procedures recommended by the manufacturer of the QuantiGene® Explore Kit (Panomics, Fremont, Calif., USA, cat. No. QG0004) for isolation of branched DNA (bDNA). For quantitation of housekeeping gene Glyceraldehyde-3-phosphate dehydrogenase (GAPDH) mRNA the QuantiGene® Explore Kit was used, whereas quantitation of TGF-$R_{II}$ mRNA was conducted with QuantiGene® 2.0 (custom manufacturing for Axolabs GmbH, Kulmbach, Germany). After incubation and lysis, 10 µl of the lysates were incubated with probe sets specific to human TGF-$R_{II}$ and human GAPDH. Both reaction types were processed according to the manufacturer's protocol for the respective QuantiGene® kit. Chemoluminescence was measured in a Victor$^2$™ multilabel counter (Perkin Elmer, Wiesbaden, Germany) as RLUs (relative light units) and values obtained with the TGF-R$_{II}$ probe sets were normalized to the respective GAPDH values for each well and then normalized to the corresponding mRNA readout from mock-treated cells.

Results

Results show the efficient downregulation of TGF-R$_{II}$ by several ASOs after transfection of A549 cells. Downregulation after transfection of reference oligonucleotides Ref. 6-Ref. 10 was not as efficient and resulted in downregulation of >60%.

TABLE 15

Downregulation of TGF-R$_{II}$ mRNA. Transfection with TGF-R$_{II}$ specific antisense-oligonucleotides (ASOs) in human epithelial lung carcinoma cells (A549). Quantitation of mRNA expression levels was performed relative to housekeeping gene GAPDH using QuantiGene ® Kit. Probes were then normalized to the corresponding mRNA readout from mock-treated cells.

| | A549 (c = 20 nM) | | | |
|---|---|---|---|---|
| | GAPDH | | TGF-R$_{II}$ | |
| ASO | mean | SD | mean | SD |
| Seq. ID No. 141j | 1.41 | 0.05 | 0.02 | 0.01 |
| Seq. ID No. 143aj | 0.76 | 0.03 | 0.02 | 0.01 |
| Seq. ID No. 139c | 0.9 | 0.03 | 0.02 | 0.01 |
| Seq. ID No. 145c | 0.91 | 0.05 | 0.03 | 0.01 |
| Seq. ID No. 209ax | 1.52 | 0.58 | 0.03 | 0.01 |
| Seq. ID No. 152ak | 0.88 | 0.03 | 0.04 | 0 |
| Seq. ID No. 218ar | 1.08 | 0.03 | 0.04 | 0 |
| Seq. ID No. 144c | 0.5 | 0.07 | 0.05 | 0.03 |
| Seq. ID No. 210ap | 0.92 | 0.05 | 0.05 | 0.01 |
| Seq. ID No. 142c | 1.33 | 0.05 | 0.06 | 0.03 |
| Seq. ID No. 213ak | 1.2 | 0.03 | 0.07 | 0.01 |
| Seq. ID No. 153f | 1.09 | 0.07 | 0.08 | 0.03 |

Conclusion

TGF-R$_{II}$ mRNA was efficiently targeted by the inventive ASOs. The named ASOs achieved an effective target mRNA downregulation after transfection of A549 cells.

1.2 Gymnotic Uptake of Antisense-Oligonucleotides 1.2.1a Comparison of Target-Knockdown Between Inventive ASOs and Prior-Art Sequences by Gymnotic Transfer in A549 and Panc-1 Cells The downregulatory activity of several antisense-oligonucleotides directed to TGF-R$_{II}$ was tested in human epithelial lung tumor cells (A549) by direct uptake without transfection reagents ("gymnotic uptake"). TGF-R$_{II}$ mRNA was quantified by branched DNA assay in total mRNA isolated from cells incubated with TGF-R$_{II}$ specific oligonucleotides.

Description of Method:

Cells were obtained and cultured as described in general methods. Gymnotic transfer of antisense-oligonucleotides was performed by preparing a 96-well plate with the respective antisense-oligonucleotides and subsequently seeding of 10,000 cells (Panc-1) or 8,000 cells (A549)/well. Experiments were performed in quadruplicates, oligonucleotides were used at final concentrations of 5 µM (Panc-1) and 7.5 µM (A549). Cells were incubated for 72 h at 37° C. and 5% $CO_2$ in a humidified incubator (Heraeus GmbH, Hanau, Germany). For measurement of TGF-R$_{II}$ mRNA, cells were harvested and lysed at 53° C. following procedures recommended by the manufacturer of the QuantiGene® Explore Kit (Panomics, Fremont, Calif., USA, cat. No. QG0004) for branched DNA (bDNA). For quantitation of housekeeping gene GAPDH mRNA the QuantiGene® Explore Kit was used, whereas quantitation of TGF-R$_{II}$ mRNA was conducted with QuantiGene® 2.0 (custom manufacturing for Axolabs GmbH, Kulmbach, Germany). After incubation and lysis, 10 µl of the lysates were incubated with probe sets specific to human TGF-R$_{II}$ and human GAPDH. Both reaction types were processed according to the manufacturer's protocol for the respective QuantiGene® kit. Chemoluminescence was measured in a Victor$^{2\text{TM}}$ multilabel counter (Perkin Elmer, Wiesbaden, Germany) as RLUs (relative light units) and values obtained with the TGF-Ru probe sets were normalized to the respective GAPDH values for each well and then normalized to the corresponding mRNA readout from PBS treated cells.

Selected results are shown in Table 16a. Further modifications of Seq. ID No. 209ay, Seq. ID No. 209ax and Seq. ID No. 209y, namely ASOs listed in Table 6 of the description, showed comparable values to these three antisense-oligonucleotides. In addition, modifications of Seq. ID No. 152h, namely ASOs listed in Table 5 of the description, showed comparable values to this antisense-oligonucleotide. Modifications of Seq. ID No. 218b, namely ASOs listed in Table 8 of the description, showed comparable values to the antisense-oligonucleotide Seq. ID No. 218b. Modifications of Seq. ID No. 213k, namely ASOs listed in Table 9 of the description, showed comparable values to the antisense-oligonucleotide Seq. ID No. 213k. Also modifications of Seq. ID No. 210q, namely ASOs listed in Table 7 of the description, showed comparable values to the antisense-oligonucleotide Seq. ID No. 210q. Finally, modifications of Seq. ID No. 143h, namely ASOs listed in Table 4 of the description, showed comparable values to the antisense-oligonucleotide Seq. ID No. 143h. Transfer of antisense-oligonucleotides listed in Tables 4-9 resulted in a more potent downregulation of the target TGF-RII mRNA compared to the transfer of tested reference sequences (A549: downregulation <0.5; Panc1 cells: downregulation <0.4).

TABLE 16a

Efficacy of target mRNA downregulation by gymnotic transfer. Remaining TGF-R$_{II}$ mRNA after gymnotic uptake of selected TGF-R$_{II}$ specific ASOs in A549 and Panc-1 cells. mRNA expression levels were determined relative to housekeeping gene Glyceraldehyde-3-phosphate dehydrogenase (GAPDH) and compared to PBS treated cells as reference control (=1) using QuantiGene ® Kit.

| | Remaining mRNA of TGF-R$_{II}$ (PBS treated cells = 1) | | | |
|---|---|---|---|---|
| | A549 cells | | Panel cells | |
| ASO | mean | SD | mean | SD |
| Seq. ID No. 209ay | 0.11 | 0.01 | 0.07 | 0.02 |
| Seq. ID No. 209ax | 0.14 | 0.02 | 0.08 | 0.01 |
| Seq. ID No. 209bb | 0.19 | 0.01 | 0.11 | 0.01 |
| Seq. ID No. 209az | 0.19 | 0.03 | 0.13 | 0.02 |
| Seq. ID No. 209ba | 0.23 | 0.02 | 0.18 | 0.03 |
| Seq. ID No. 209y | 0.27 | 0.04 | 0.17 | 0.01 |
| Seq. ID No. 152h | 0.29 | 0.04 | 0.12 | 0.02 |
| Seq. ID No. 218b | 0.30 | 0.02 | 0.07 | 0.01 |
| Seq. ID No. 213k | 0.34 | 0.04 | 0.17 | 0.04 |
| Seq. ID No. 210q | 0.37 | 0.05 | 0.18 | 0.02 |
| Seq. ID No. 210aq | 0.39 | 0.03 | 0.18 | 0.02 |
| Seq. ID No. 143h | 0.43 | 0.04 | 0.35 | 0.05 |
| Ref. 2 | 0.59 | 0.05 | 0.40 | 0.04 |
| Ref. 0 | 0.89 | 0.06 | 1.10 | 0.07 |
| Ref. 3 | 0.68 | 0.03 | 0.62 | 0.03 |
| Ref. 4 | 0.74 | 0.04 | 0.71 | 0.01 |

Conclusion

Gymnotic transfer of inventive ASOs results in a continuously stronger downregulation of the target TGF-R$_{II}$ mRNA than the transfer of tested reference sequences. The claimed antisense-oligonucleotides outperformed all tested sequences known from prior-art, independently of the chosen human cell line. Nevertheless, in general antisense-oligonucleotides having a length of 12-20 nucleotides result in a more effective downregulation of the target TGF-R$_{II}$ mRNA than shorter or longer antisense-oligonucleotides. This effect was even more noticeable for antisense-oligonucleotides having a length of 14-18 nucleotides, which in general show the most potent effects.

1.2.1b Analysis of Gymnotic Transfer in A549 Cells by Branched DNA Assay

Most effective antisense-oligonucleotides against TGF-R$_{II}$ from the transfection screens were further characterized by gymnotic uptake in A549 cells. TGF-R$_{II}$ mRNA was quantified by branched DNA in total mRNA isolated from cells incubated with TGF-R$_{II}$ specific antisense-oligonucleotides.

Description of Method:

A549 cells were cultured as described before under standard conditions. For single-dose and dose-response experiments 80,000 A549 cells/well were seeded in a 6-well culture dish and incubated directly with oligonucleotides at a concentration of 7.5 µM. For measurement of TGF-R$_{II}$ mRNA, cells were harvested, lysed at 53° C. and analyzed by branched DNA Assay following procedures recommended by the manufacturer of the QuantiGene® Explore Kit (Panomics, Fremont, Calif., USA, cat. No. QG0004) as described above (see 1.1).

Results

Listed ASOs in Table 16b showed reduced target mRNA level of TGF-R$_{II}$ relative to the housekeeping gene GAPDH in A549 cells. The ten most efficient ASOs were also tested for inhibitory concentration 50 (IC$_{50}$). All together Seq. ID No. 209t, Seq. ID No. 218b, Seq. ID No. 218c and Seq. ID No. 209y lead to most proper knockdown of TGF-R$_{II}$ at low concentration levels.

TABLE 16b

Downregulation of TGF-R$_{II}$ mRNA after gymnotic uptake of TGF-R$_{II}$ specific ASOs in A549 cells. mRNA levels were determined relative to housekeeping gene GAPDH using QuantiGene ® Kit.

| ASO | TGF-R$_{II}$ | | GAPDH | | IC$_{50}$ |
|---|---|---|---|---|---|
| | n = 4 | SD | n = 4 | SD | n = 4 |
| Seq. ID No. 209t | 0.19 | 0.05 | 1.13 | 0.11 | 1.63 |
| Seq. ID No. 218c | 0.25 | 0.04 | 0.94 | 0.18 | 1.17 |
| Seq. ID No. 218b | 0.26 | 0.08 | 1.08 | 0.28 | 2.54 |
| Seq. ID No. 218q | 0.27 | 0.07 | 1.11 | 0.08 | 2.39 |
| Seq. ID No. 209y | 0.34 | 0.06 | 0.96 | 0.06 | 1.57 |
| Seq. ID No. 218t | 0.36 | 0.12 | 0.76 | 0.04 | 2.57 |
| Seq. ID No. 218m | 0.41 | 0.06 | 1.16 | 0.29 | 1.66 |
| Seq. ID No. 209w | 0.44 | 0.07 | 1.00 | 0.11 | 5.76 |
| Seq. ID No. 218p | 0.46 | 0.12 | 0.88 | 0.07 | |
| Seq. ID No. 209v | 0.48 | 0.25 | 0.96 | 0.07 | 3.10 |
| Seq. ID No. 209x | 0.52 | 0.02 | 0.87 | 0.06 | 5.60 |
| Seq. ID No. 218u | 0.53 | 0.20 | 0.79 | 0.05 | |
| Seq. ID No. 218v | 0.54 | 0.13 | 0.77 | 0.04 | |
| Seq. ID No. 210q | 0.60 | 0.23 | 1.11 | 0.11 | |
| Seq. ID No. 218o | 0.61 | 0.15 | 0.96 | 0.06 | |
| Seq. ID No. 210p | 0.65 | 0.24 | 1.01 | 0.23 | |
| Seq. ID No. 218n | 0.89 | 0.36 | 1.07 | 0.22 | |
| Seq. ID No. 210o | 0.95 | 0.08 | 0.97 | 0.14 | |

TABLE 16b-continued

Downregulation of TGF-R$_{II}$ mRNA after gymnotic uptake of TGF-R$_{II}$ specific ASOs in A549 cells. mRNA levels were determined relative to housekeeping gene GAPDH using QuantiGene ® Kit.

| ASO | TGF-R$_{II}$ | | GAPDH | | IC$_{50}$ |
|---|---|---|---|---|---|
| | n = 4 | SD | n = 4 | SD | n = 4 |
| Seq. ID No. 209s | 0.96 | 0.31 | 1.14 | 0.24 | |
| pos. Ctrl aha-1 | 0.22 | 0.04 | 0.77 | 0.02 | |
| Ref. 1 | 1.43 | 0.40 | 1.27 | 0.18 | |

IC$_{50}$ = inhibitory concentration for 50% of downregulation,
Pos. Ctrl: aha-1 = activator of heat shock 90 kDa protein ATPase homolog 1 (Aha1) directed LNA as positive control,
Ref. 1 = Scrambled control.

Conclusion

The target downregulation by the most efficient inventive ASOs was again excellent without transfection reagents. Thus, gymnotic transfer is feasible and the preferred method for further drug development.

1.2.2 Analysis of Gymnotic Uptake in A549 and ReNcell CX® Cells

Inhibitory activity on the target mRNA by antisense-oligonucleotides (ASOs) was determined in human neuronal progenitor cells from cortical brain region (ReNcell CX® cells, Millipore #SCM007). Questions regarding adult neurogenesis as therapeutic target were assessed by gymnotic transfer studies with most effective ASOs. A549 cells were used as reference cell line.

Description of Method:

A549 and ReNcell CX® cells were cultured as described above. For treatment studies cells were seeded in a 24-well culture dish (Sarstedt #83.1836.300) (50,000 cells/well) and were incubated overnight at 37° C. and 5% CO$_2$. For treatment of A549 and ReNcell CX® cells, medium was removed and replaced by fresh full medium (0.5 ml for 24-well). Ref.1, ASO with Seq. ID No. 218b, and ASO with Seq. ID No. 218c were then added in medium at concentrations of 2.5 and 10 µM for analysis of target downregulation at different time points (A549 cells: 18 h, 72 h, 6 d, ReNcell CX® cells: 18 h, 96 h, 8 d) at 37° C. and 5% CO$_2$. For harvesting, cells were washed twice with PBS and frozen at −20° C. For analysis of mRNA by real-time RT-PCR, cells were processed as described above. Ready-to-use and standardized primer pairs for real-time RT-PCR (see Table 11) were used and mixed with the respective ready-to-use Mastermix solution (SsoAdvanced™ Universial SYBR® Green Supermix (BioRad #172-5271) according to manufacturer's instructions (BioRad Prime PCR Quick Guide). Probes were analyzed as triplicates and data was quantified relative to GNB2L1 mRNA using BioRad CFX Manager™ 3.1 and then normalized to untreated control. Statistics were calculated using the Ordinary-one-way-ANOVA followed by "Dunnett's" post hoc comparisons.

Results:

Results showed that gymnotic transfer with Seq. ID No. 218b and 218c result in a proper downregulation of TGF-R$_{II}$ mRNA in A549 and ReNcell CX® cells in a dose- and time dependent manner (Table 17). Target mRNA in A549 cells was significantly reduced after 18 h, and was even more efficient reduced after 72 h and 6 d. After 18 h in ReNcell CX® only a depression of TGF-R$_{II}$ mRNA after gymnotic uptake of 10µM could be observed, but target downregulation was significant after 72 h for both tested concentrations and was stable until day 8.

TABLE 17

Dose- and time-dependent downregulation of TGF-$R_{II}$ mRNA after gymnotic transfer with TGF-$R_{II}$ specific ASO in A549 and ReNcell CX ® cells. mRNA expression levels were determined relative to housekeeping gene GNB2L1 using quantitative real-time RT-PCR and then normalized to untreated control.

| | Cell line A549 | | |
|---|---|---|---|
| Target | TGF-$R_{II}$ | TGF-$R_{II}$ | TGF-$R_{II}$ |
| Time point | 18 h, n = 3 | 72 h, n = 3 | 6 d, n = 3 |
| A | 1.00 ± 0.03 | 1.00 ± 0.20 | 1.00 ± 0.38 |
| B 2.5 µM | 1.17 ± 0.06 | 0.87 ± 0.21 | 0.88 ± 0.14 |
| B 10 µM | 0.98 ± 0.10 | 0.77 ± 0.06 | 1.03 ± 0.10 |
| C 2.5 µM | 0.60*++ ± 0.09 | 0.41* ± 0.07 | 0.13 ± 0.03 |
| C 10 µM | 0.49**++ ± 0.02 | 0.15** ± 0.02 | 0.02*+ ± 0.00 |
| D 2.5 µM | | 0.46** ± 0.09 | |
| D 10 µM | | 0.21* ± 0.04 | |

| | Cell line ReNcell CX | | |
|---|---|---|---|
| Target | TGF-$R_{II}$ | TGF-$R_{II}$ | TGF-$R_{II}$ |
| Time point | 18 h, n = 3 | 96 h, n = 3 | 8 d, n = 3 |
| A | 1.00 ± 0.41 | 1.00 ± 0.04 | 1.00 ± 0.18 |
| B 2.5 µM | 1.38 ± 0.58 | 0.89 ± 0.09 | 0.80 ± 0.33 |
| B 10 µM | 1.70 ± 0.68 | 0.81 ± 0.10 | 1.16 ± 0.43 |
| C 2.5 µM | 1.04 ± 0.36 | 0.32** ± 0.06 | 0.42 ± 0.16 |
| C 10 µM | 0.64 ± 0.24 | 0.16** ± 0.02 | 0.21 ± 0.09 |
| D 2.5 µM | | 0.53 ± 0.07 | |
| D 10 µM | | 0.23** ± 0.03 | |

A = untreated control,
B = Ref. 1,
C = Seq. ID No. 218b,
D = Seq. ID No. 218c,
± = SEM,
*p < 0.05,
**p < 0.01 in reference to A,
+p < 0.05,
++p < 0.01 in reference to B.
Statistics were calculated using the Ordinary-one-way-ANOVA followed by "Dunnett's" post hoc comparisons.

Conclusion:

Efficient and stable downregulation of target mRNA by gymnotic uptake of ASOs is achieved even in long-term applications. ReNcell CX® cells could therefore be used e.g. for experiments addressing recovery of adult neurogenesis as a therapeutic option in patients. The same applies for other indications as shown by A549 experiments.

Taken together, efficient downregulation of TGF-$R_{II}$ is suitable independently from method of transfer and cell type. Gymnotic uptake of ASOs is the preferred transfer method as in clinical applications the absence of additional transfection agents suggests high safety for patients.

Example 2: Determination of Inhibitory Activity of the Antisense-Oligonucleotides Directed to TGF-$R_{II}$ on Protein Level Western Blot Analysis and Immunocytochemistry was performed to determine whether reduced TGF-$R_{II}$ mRNA level, mediated by inventive antisense-oligonucleotides (ASOs) in human lung cancer cells (A549) and human neuronal precursor cells (ReNcell CX®) results in a reduction of target protein.

Description of Method:

Cells were cultured as described above. For treatment, cells were seeded in a 6-well culture dish (Sarstedt #83.3920.300, 80,000 cells/well) and 8-well cell culture slide dishes (Sarstedt #94.6140.802, 10,000 cells/well) and were incubated overnight at 37° C. and 5% $CO_2$. For gymnotic transfer of A549 and ReNcell CX® cell medium was removed and replaced by fresh full medium (1 ml for 6-well and 0.5 ml for 8-well). Ref. 1 (scrambled control), the respective inventive ASO was then added in medium at concentrations of 2.5 and 10 µM for protein analysis of target downregulation after 72 h in A549 cells and 96 h in ReNcell CX® cells. The cells were lysed and examined by Western Blot as described in general method part. The primary antibody anti-TGF-$R_{II}$ was diluted in 0.5% BSA in TBS-T and incubated at 4° C. for 2 days. Afterward membranes were incubated with the second antibody anti-rabbit IgG HRP-linked diluted in 0.5% BSA in TBS-T (1 h, RT). Following incubation, blots were washed with TBS-T, emerged using Luminata™ Forte Western HRP Substrate (Millipore #WBLUF0500) and bands were detected with a luminescent image analyzer (ImageQuant™ LAS 4000, GE Healthcare). For housekeeper comparison, the membranes were incubated with HRP-conjugated anti-GAPDH (1:1000 in 0.5% Blotto, 4° C., overnight). Densitometric quantification was calculated relative to GAPDH and then normalized to untreated control with Image Studio™ Lite Software.

Procedure for immunocytochemistry was performed as described in standard protocol. For verification of target-downregulation anti-TGF-$R_{II}$ was diluted and incubated overnight at 4° C. Cy3 goat-anti-rabbit was used as secondary antibody. All antibody-dilutions were prepared with Antibody-Diluent (Zytomed® #ZUC025-100). Examination of cells was performed by fluorescence microscopy (Zeiss Axio® Observer.Z1). Images were analyzed with Image J Software and CorelDRAW® X7 Software.

Results after Gymnotic Transfer:

Western Blot Analysis and immunocytochemistry were used to verify the reduction of TGF-$R_{II}$ protein level. 72 h after gymnotic transfer, TGF-$R_{II}$ protein was significantly reduced using high concentration of different ASOs according to the invention in comparison to untreated control in A549 cells (Table 18). Reduced TGF-$R_{II}$ levels were also observed in ReNcell CX® cells (Table 18). For both cell lines, reduction of TGF-$R_{II}$ protein level was shown by Western Blot Analysis. Immunocytochemistry revealed a strong dose-dependent reduction of TGF-$R_{II}$ protein in both cell lines in comparison to untreated cells and scrambled control treated cells.

TABLE 18

Densitometric analysis after TGF-$R_{II}$ Western Blot. Reduction of TGF-$R_{II}$ protein after gymnotic transfer with TGF-$R_{II}$ specific ASOs in A549 and ReNcell CX ® cells could be observed after 72 h or 96 h, respectively. Protein levels were determined relative to housekeeping gene GAPDH using Image Studio ™ Lite Software and were normalized to untreated control.

| | Cell line | |
|---|---|---|
| Target<br>Time point | A549<br>TGF-$R_{II}$<br>72 h, n = 3 | ReNcell CX<br>TGF-$R_{II}$<br>96 h, n = 2 |
| A | 1.00 ± 0.00 | 1.00 ± 0.00 |
| B 2.5 µM | 0.85 ± 0.13 | 0.91 ± 0.12 |
| B 10 µM | 1.06 ± 0.47 | 1.23 ± 0.16 |
| C 2.5 µM | 0.34 ± 0.11 | 0.59 ± 0.05 |
| C 10 µM | 0.39* ± 0.11 | 0.63 ± 0.17 |
| D 2.5 µM | 0.68 ± 0.14 | 1.21 ± 0.28 |
| D 10 µM | 0.39* ± 0.07 | 0.77 ± 0.10 |
| F 2.5 µM | 0.51 ± 0.08 | 0.71 ± 0.16 |
| F 10 µM | 0.45 ± 0.09 | 0.57 ± 0.12 |
| G 2.5 µM | 0.41 ± 0.13 | 0.61 ± 0.10 |
| G 10 µM | 0.40* ± 0.06 | 0.58 ± 0.08 |
| H 2.5 µM | 0.75 ± 0.12 | 0.83 ± 0.13 |
| H 10 µM | 0.51 ± 0.07 | 0.77 ± 0.06 |
| I 2.5 µM | 0.58 ± 0.14 | 0.91 ± 0.21 |
| I 10 µM | 0.38* ± 0.14 | 0.67 ± 0.09 |
| J 2.5 µM | 0.42 ± 0.15 | 0.75 ± 0.23 |
| J 10 µM | 0.34* ± 0.05 | 0.59 ± 0.08 |
| K 2.5 µM | 0.45 ± 0.17 | 0.69 ± 0.16 |
| K 10 µM | 0.36* ± 0.09 | 0.49 ± 0.09 |

A = untreated control,
B = Ref. 1,
C = Seq. ID No. 218b,
D = Seq. ID No. 218c,
F = Seq. ID No. 210q,
G = Seq. ID No. 213k,
H = Seq. ID No. 143h,
I = Seq. ID No. 152h,
J = Seq. ID No. 209az,
K = Seq. ID No. 209y,
± = SEM,
*p < 0.05 in reference to A.
Statistics were calculated using the Ordinary-one-way-ANOVA followed by "Dunnett's" post hoc comparisons.

Conclusion:

In addition to target mRNA downregulation, gymnotic transfer of Seq. ID No. 218b, Seq. ID No. 218c, Seq. ID No. 210q, Seq. ID No. 213k, Seq. ID No. 143h, Seq. ID No. 152h, Seq. ID No. 209az, and Seq. ID No. 209y resulted in excellent reduction of protein level in A549 and ReNcell CX® cells. Staining of TGF-$R_{II}$ revealed a dose-dependent reduction of TGF-$R_{II}$ protein after treatment with these ASOs in both cell lines.

Results after Gymnotic Transfer with Further ASOs:

Protein analysis showed a reduced amount of TGF-$R_{II}$ in A549 cells and ReNcell CX® cells gymnotic transfer of tested ASOs (10 µM, Table 19). This was also verified by immunocytochemistry. For both cell lines, reduction of TGF-$R_{II}$ protein level by gymnotic transfer of the tested ASOs could be detected in comparison to untreated cells and scrambled control treated cells.

TABLE 19

Densitometric analysis after TGF-$R_{II}$ Western Blot. Reduction of TGF-$R_{II}$ protein after gymnotic transfer with further TGF-$R_{II}$-specific antisense-oligonucleotides (ASO) in A549 and ReNcell CX ® cells could be observed after 72 h or 96 h, respectively. Protein levels were determined relative to housekeeping-gene GAPDH using Studio ™ Lite Software and were then normalized to untreated control.

| ASO No. in Test | Seq ID No. | Result |
|---|---|---|
| 1 | 233d | B |
| 2 | 234d | A |
| 3 | 143j | C |
| 4 | 143p | A |
| 5 | 143q | A |
| 6 | 143r | A |
| 7 | 143w | A |
| 8 | 143af | C |
| 9 | 143ag | C |
| 10 | 143ah | C |
| 11 | 235b | B |
| 12 | 235d | A |
| 13 | 141d | A |
| 14 | 141g | A |
| 15 | 141i | A |
| 16 | 237b | A |
| 17 | 237c | A |
| 18 | 237i | C |
| 19 | 237m | A |
| 20 | 238c | A |
| 21 | 238f | A |
| 22 | 239e | B |
| 23 | 240c | B |
| 24 | 241b | C |
| 25 | 242a | C |
| 26 | 246e | C |
| 27 | 247d | A |
| 28 | 248b | A |
| 29 | 248e | B |
| 30 | 248g | A |
| 31 | 152k | B |
| 32 | 152s | B |
| 33 | 152t | B |
| 34 | 152u | B |
| 35 | 152ab | C |
| 36 | 152ag | B |
| 37 | 152ah | C |
| 38 | 152ai | C |
| 39 | 249c | A |
| 40 | 249e | A |
| 41 | 250b | A |
| 42 | 250g | B |
| 43 | 251c | A |
| 44 | 251f | A |
| 45 | 252e | B |
| 46 | 253c | A |
| 47 | 254b | C |
| 48 | 255a | C |
| 49 | 259e | C |
| 50 | 260d | B |
| 51 | 261b | A |
| 52 | 261e | B |
| 53 | 261g | A |
| 54 | 262d | B |
| 55 | 262e | A |
| 56 | 209s | A |
| 57 | 209v | B |
| 58 | 209w | B |

TABLE 19-continued

Densitometric analysis after TGF-R$_{II}$ Western Blot. Reduction of TGF-R$_{II}$ protein after gymnotic transfer with further TGF-R$_{II}$-specific antisense-oligonucleotides (ASO) in A549 and ReNcell CX ® cells could be observed after 72 h or 96 h, respectively. Protein levels were determined relative to housekeeping-gene GAPDH using Studio ™ Lite Software and were then normalized to untreated control.

| ASO No. in Test | Seq ID No. | Result |
|---|---|---|
| 59 | 209x | C |
| 60 | 209ai | B |
| 61 | 209an | C |
| 62 | 209at | A |
| 63 | 209au | B |
| 64 | 209av | B |
| 65 | 263b | B |
| 66 | 263c | A |
| 67 | 263i | B |
| 68 | 263m | A |
| 69 | 264e | A |
| 70 | 264h | A |
| 71 | 265e | B |
| 72 | 266c | A |
| 73 | 267b | B |
| 74 | 268a | B |
| 75 | 272e | B |
| 76 | 273d | A |
| 77 | 274a | A |
| 78 | 274d | B |
| 79 | 274f | A |
| 80 | 275g | A |
| 81 | 275i | B |
| 82 | 210o | A |
| 83 | 210v | B |
| 84 | 210w | B |
| 85 | 210x | C |
| 86 | 210ab | B |
| 87 | 210ac | A |
| 88 | 210ad | B |
| 89 | 210af | A |
| 90 | 210am | B |
| 91 | 276b | B |
| 92 | 276c | A |
| 93 | 276j | B |
| 94 | 276k | B |
| 95 | 277d | A |
| 96 | 277e | A |
| 97 | 278f | B |
| 98 | 279c | B |
| 99 | 280b | C |
| 100 | 281a | C |
| 101 | 220d | C |
| 102 | 221d | B |
| 103 | 222b | A |
| 104 | 222c | A |
| 105 | 222f | B |
| 106 | 223c | B |
| 107 | 223f | A |
| 108 | 218ad | B |
| 109 | 218n | A |
| 110 | 218t | B |
| 111 | 218u | B |
| 112 | 218v | C |
| 113 | 218ah | C |
| 114 | 218an | A |
| 115 | 218ao | B |
| 116 | 218ap | B |
| 117 | 224i | B |
| 118 | 224m | B |
| 119 | 225c | A |
| 120 | 225f | A |
| 121 | 226e | B |
| 122 | 227c | A |
| 123 | 228b | C |
| 124 | 229a | C |
| 125 | 285d | C |
| 126 | 286d | A |
| 127 | 287d | B |
| 128 | 287e | A |
| 129 | 287f | A |
| 130 | 288e | A |
| 131 | 288i | A |
| 132 | 289d | B |
| 134 | 289h | A |
| 135 | 289o | B |
| 136 | 289p | B |
| 137 | 289q | B |
| 138 | 213o | B |
| 139 | 213p | B |
| 140 | 213q | B |
| 141 | 213s | B |
| 142 | 213y | B |
| 143 | 213z | B |
| 144 | 213aa | B |
| 145 | 213af | B |
| 146 | 290c | A |
| 147 | 290f | B |
| 148 | 290i | A |
| 149 | 291c | B |
| 150 | 292c | C |
| 151 | 293b | C |
| 152 | 294a | C |

Statistics was calculated using the Ordinary-one-way-ANOVA followed by "Dunnett's" post hoc comparisons.
Reduction of protein level for ASO 1-25 is indicated with the following key:
A = less than 10% inferior to SEQ ID No. 143h;
B = more than 10% but less than 20% inferior to SEQ ID No. 143h;
C = more than 20% but less than 30% inferior to SEQ ID No. 143h.
Reduction of protein level for ASO 26-48 is indicated with the following key:
A = less than 10% inferior to SEQ ID No. 152h;
B = more than 10% but less than 20% inferior to SEQ ID No. 152h;
C = more than 20% but less than 30% inferior to SEQ ID No. 152h.
Reduction of protein level for ASO 49-74 is indicated with the following key:
A = less than 10% inferior to the mean value derived from Seq. ID No. 209az and Seq. ID No. 209y;
B = more than 10% but less than 20% inferior to the mean value derived from Seq. ID No. 209az and Seq. ID No. 209y;
C = more than 20% but less than 30% inferior to the mean value derived from Seq. ID No. 209az and Seq. ID No. 209y.
Reduction of protein level for ASO 75-100 is indicated with the following key:
A = less than 10% inferior to SEQ ID No. 210q;
B = more than 10% but less than 20% inferior to SEQ ID No. 210q;
C = more than 20% but less than 30% inferior to SEQ ID No. 210q.
Reduction of protein level for ASO 101-124 is indicated with the following key:
A = less than 10% inferior to the mean value derived from Seq. ID No. 218b and Seq. ID No. 218c;
B = more than 10% but less than 20% inferior to the mean value derived from Seq. ID No. 218b and Seq. ID No. 218c;
C = more than 20% but less than 30% inferior to the mean value derived from Seq. ID No. 218b and Seq. ID No. 218c.
Reduction of protein level for ASO 125-152 is indicated with the following key:
A = less than 10% inferior to SEQ ID No. 213k;
B = more than 10% but less than 20% inferior to SEQ ID No. 213k;
C = more than 20% but less than 30% inferior to SEQ ID No. 213k.

Conclusion:

Taken together, dose-dependent downregulation of TGF-R$_{II}$ mRNA by gymnotic transfer in A549 and ReNcell CX® cells resulted in a dose-dependent reduction of protein levels. Inventive ASOs are potent in protein target down-regulation as demonstrated in A549 and ReNcell CX® cells.

Example 3: Analysis of the Effects of the Antisense-Oligonucleotides to the Downstream Signaling Pathway of TGF-R$_{II}$ Functional analyses were performed in human lung cancer cells (A549) and human neuronal precursor cells (ReNcell CX®). TGF-β downstream signaling pathway was analyzed, following to an effective downregulation of TGF-$R_{II}$ mRNA and reduction of protein levels by gymnotic transfer of the inventive ASOs. Therefore, mRNA and protein levels of Connective Tissue Growth Factor (CTGF), known as downstream-mediator of TGF-β, were evaluated. In addition, phosphorylation of Smad2 (mothers against decapentaphlegic homolog 2) was examined. The phosphorylation of Smad2 is a marker for an active TGF-β pathway followed by the upregulation of the downstream target gene CTGF.

Description of Method:

Cells were cultured as described before. For treatment, cells were seeded in a 6-well culture dish (Sarstedt #83.3920.300) (80,000 cells/well) and 8-well cell culture slide dishes (Sarstedt #94.6140.802) (10,000 cells/well) and were incubated overnight at 37° C. and 5% $CO_2$. For gymnotic transfer, A549 and ReNcell CX® cell medium was removed and replaced by fresh full medium (1 ml for 6-well and 0.5 ml for 8-well). Ref. 1 (Scrambled control), ASO with sequence identification number 218b (Seq. ID No. 218b), No. 218c (Seq.ID No. 218c) was then added in medium at concentrations of 2.5 and 10 μM and respective analysis was performed after 72 h in A549 cells and 96 h in ReNcell CX® cells. To evaluate effects on CTGF mRNA level, real-time RT-PCR was performed as described before. The primer pair for analysis of CTGF was ready-to-use and standardized. To check for CTGF and pSmad2 protein levels, Western Blot and immunocytochemistry were used as described before. Type and used dilutions of antibodies for respective method are listed in Table 13 and 14.

3.1. Results for Seq.ID No.218b 3.1.1 Effects on CTGF mRNA and Protein Level

CTGF mRNA was significantly and dose-dependently reduced after gymnotic transfer with ASO Seq. ID No. 218b in A549 (72 h) and ReNcell CX® (96 h) cells. Downstream-mediator of TGF-β was reduced to 52%±0.02 in ReNcell CX® cells and to 39%±0.03 in A549 cells after gymnotic transfer with 10 μM Seq.ID No.218b (Table 20). According to these downregulated CTGF mRNA levels, a strong reduction of CTGF protein expression was observed in A549 cells (Table 21).

TABLE 20

Dose-dependent and significant downregulation of CTGF mRNA after gymnotic transfer with Seq. ID No. 218b in A549 and ReNcell CX ® cells. mRNA expression levels were quantified relative to housekeeping gene GNB2L1 using quantitative real-time RT-PCR and normalized to untreated control.

| | Cell line | |
| --- | --- | --- |
| Target<br>Time point | A549<br>CTGF<br>72 h, n = 3 | ReNcell CX<br>CTGF<br>96 h, n = 3 |
| A | 1.00 ± 0.08 | 1.00 ± 0.04 |
| B 2.5 μM | 0.87 ± 0.06 | 0.97 ± 0.06 |
| B 10 μM | 0.80 ± 0.03 | 0.86 ± 0.17 |
| C 2.5 μM | 0.60** ± 0.04 | 0.66** ± 0.02 |
| C 10 μM | 0.39** ± 0.03 | 0.52** ± 0.02 |

A = untreated control,
B = Ref. 1,
C = Seq. ID No. 218b.
± = SEM,
*p < 0.05,
**p < 0.01 in reference to A.
Statistics was calculated using the Ordinary-one-way-ANOVA followed by "Dunnett's" post hoc comparisons.

TABLE 21

Densitometric analysis of CTGF Western Blot. Downregulation of CTGF protein 72 h after gymnotic transfer with ASO Seq. ID No. 218b in A549 was recognized. Protein levels were determined relative to housekeeping gene alpha-Tubulin using Studio ™ Lite Software and were normalized to untreated control.

| | Cell line<br>A549 |
| --- | --- |
| Target<br>Time point | CTGF<br>72 h, n = 1 |
| A | 1.00 |
| B 2.5 μM | 0.91 |
| B 10 μM | 1.31 |
| C 2.5 μM | 0.05 |
| C 10 μM | 0.086 |

A = untreated control,
B = Ref. 1,
C = Seq. ID No. 218b.

Conclusion:

Functional inhibition of TGF-β signaling was achieved with gymnotic transfer of Seq. ID No. 218b as shown by downregulation of target CTGF mRNA and reduced CTGF protein levels in A549 and ReNcell CX® cells.

3.1.2 Effects on pSmad2 Protein Level pSmad2 protein levels were analyzed to proof the CTGF downregulation as a specific result of the ASO-mediated TGF-β signaling inhibition.

Staining against pSmad2 after gymnotic transfer of ASO Seq. ID No. 218b after 72 h in A549 and 96 h in ReNcell CX® cells showed a dose-dependent inhibition of Smad2 phosphorylation (FIG. 5). In addition, reduction of pSmad2 expression levels by ASO Seq. ID No. 218b was verified by Western Blot Analysis in A549 cells (Table 22).

TABLE 22

Densitometric analysis of pSmad2 Western Blot. Downregulation of pSmad2 protein 72 h after gymnotic transfer with ASO Seq. ID No. 218b in A549 was recognized. Protein levels were determined relative to housekeeping gene GAPDH using Studio ™ Lite Software and normalized to untreated control.

| | Cell line<br>A549 |
| --- | --- |
| Target<br>Time point | pSmad2<br>72 h, n = 1 |
| A | 1.00 |
| B 2.5 μM | 1.81 |
| B 10 μM | 1.79 |
| C 2.5 μM | 0.66 |
| C 10 μM | 0.72 |

A = untreated control,
B = Ref. 1,
C = Seq. ID No. 218b.

Conclusion:

Gymnotic transfer of Seq. ID No. 218b in A549 and ReNcell CX® cells resulted in a dose-dependent inhibition of downstream mediators of TGF-D signaling. CTGF and phosphorylation of Smad2 was reduced by ASO Seq. ID No. 218b, both indicating an inhibited TGF-β pathway.

3.2 Results for Seq.ID No. 218c 3.2.1 Effects on CTGF mRNA and pSmad2 Protein Level Gymnotic transfer of ASO Seq. ID No. 218c downregulates CTGF mRNA in A549 and ReNcell CX® cells (Table 23). Immunocytochemistry against pSmad2 confirmed an inhibition of TGF-β signaling (FIG. 6). Therefore, downregulation of CTGF mRNA is an direct effect of reduced TGF-β signaling.

TABLE 23

Significant downregulation of CTGF mRNA was observed in A549 and ReNcell CX ® cells. mRNA expression levels were quantified relative to housekeeping gene GNB2L1 using quantitative real-time RT-PCR and normalized to untreated controls.

| | Cell line | |
| --- | --- | --- |
| | A549 | ReNcell CX |
| Target | CTGF | CTGF |
| Time point | 72 h, n = 4 | 96 h, n = 3 |
| A | 1.00 ± 0.08 | 1.00 ± 0.10 |
| B 2.5 µM | 0.97 ± 0.07 | 0.88 ± 0.08 |
| B 10 µM | 0.85 ± 0.06 | 0.89 ± 0.07 |
| D 2.5 µM | 0.49** ± 0.05 | 1.10 ± 0.08 |
| D 10 µM | 0.31** ± 0.03 | 0.82 ± 0.02 |

A = untreated control,
B = Ref. 1,
D = Seq. ID No. 218c.
± = SEM,
**p < 0.01 in reference to A.
Statistics was calculated using the Ordinary-one-way-ANOVA followed by "Dunnett's" post hoc comparisons.

Conclusion:

ASO Seq. ID No. 218c was efficient in inhibiting TGF-β signaling after downregulation of target TGF-R$_{II}$ mRNA. This was examined by determination of downregulated CTGF mRNA and reduced pSmad2 protein levels as a marker for TGF-β signaling.

Taken together, inventive ASOs are efficient in mediating a functional inhibition of TGF-β signaling by downregulation of TGF-R$_{II}$. Thus, inventive ASOs will be beneficial for medical indications in which elevated TGF-β levels are involved, e.g. neurological disorders, fibrosis and tumor progression.

Example 4: Inhibitory Activity of the Inventive ASOs on Target mRNA Levels in TGF-β1 Treated Cells 4.1 Gymnotic Uptake of ASOs in A549 and ReNcell CX® Cells after TGF-β1 Pre-Treatment To analyze inhibitory activity of antisense oligonucleotides (ASOs) in human neuronal progenitor cells from cortical brain region (ReNcell CX®) under pathological conditions, cells were pre-treated with Transforming Growth Factor-β1 (TGF-β1). From previous studies it is known that TGF-β1 is found in high concentrations in Cerebrospinal Fluid (CSF) of all neural disorders e.g. ALS. Therefore, inhibitory efficacy of ASOs on TGFβ-signaling was examined after pre-treatment and in presence with TGF-β1. A549 cells were used as reference cell line.

Description of Method:

A549 and ReNcell CX® were cultured as described above. For treatment studies cells were seeded in a 24-well culture dish (Sarstedt #83.1836.300) (50,000 cells/well) and were incubated overnight at 37° C. and 5% CO$_2$. For treatment of A549 and ReNcell CX® cells, medium was removed and replaced by fresh full medium (0.5 ml for 24-well). Following TGF-β1 (10 ng/ml, PromoCell #C-63499) exposition for 48 h, medium was changed, TGF-β1 re-treatment was performed in combination with Ref.1 (Scrambled control, 10 µM), ASO Seq. ID No. 218b (10 µM), or ASO Seq. ID No. 218c (10 µM) in medium. A549 cells were incubated for further 72 h, whereas ReNcell CX® cells were harvested after 96 h. Therefore, cells were washed twice with PBS and subsequently used for RNA isolation (24-well dishes) as described before. Used primer pairs for real-time RT-PCR are listed in Table 11.

4.1.1 Results for Seq. ID No. 218b

Efficacy in mRNA downregulation of TGF-R$_{II}$ by ASO Seq. ID No. 218b was not influenced by TGF-β1 pre-incubation in A549 and ReNcell CX® cells (Table 24, FIG. 7). Target mRNA in A549 cells was significantly downregulated after single treatment (remaining mRNA: 15%±0.05) with ASO, but also after treatment in presence of TGF-P1, following pre-treatment (remaining mRNA: 7%±0.01). In ReNcell CX® cells ASO Seq. ID No. 218b showed similar potency in inhibiting TGF-R$_{II}$ mRNA in absence of TGF-β1 (25%±0.01) or in presence of TGF-β1, following pre-treatment of TGF-β1 (17%±0.02).

TABLE 24

In presence of TGF-β1, ASO Seq. ID No. 218b leads to a potent downregulation of TGF-R$_{II}$ mRNA after gymnotic transfer in A549 and ReNcell CX ® cells. mRNA expression levels were quantified relative to housekeeping gene GNB2L1 using quantitative real-time RT-PCR and normalized to untreated controls.

| | Target | |
| --- | --- | --- |
| | Time point | |
| | TGF-R$_{II}$ | |
| | 48 h TGF-β1 –> 72 h/96 h TGF-β1 + ASOs/single treatment | |
| | A549 | ReNcell CX |
| Cell line | n = 4 | n = 3 |
| A | 1.00 ± 0.07 | 1.00 ± 0.11 |
| B 10 µM | 0.90 ± 0.17 | 0.89 ± 0.26 |
| C 10 µM | 0.15** ± 0.05 | 0.25 ± 0.01 |
| E 10 ng/ml | 0.71 ± 0.05 | 0.79 ± 0.34 |
| E 10 ng/ml + B 10 µM | 0.74 ± 0.05 | 0.89 ± 0.25 |
| E 10 ng/ml + C 10 µM | 0.07** ± 0.01 | 0.27 ± 0.02 |

A = untreated control,
B = Ref. 1,
C = Seq. ID No. 218b,
E = TGF-β1,
± = SEM,
*p < 0.05,
**p < 0.01 in reference to A.
Statistics was calculated using the Ordinary-one-way-ANOVA followed by "Dunnett's" post hoc comparisons.

Conclusion:

Target mRNA was efficiently downregulated to approx. 20% by gymnotic uptake of inventive ASOs in presence of TGF-β1, following pre-incubation in both tested cell lines.

4.1.2 Results for Seq. ID No. 218c

Downregulation of TGF-R$_{II}$ mRNA by ASO Seq. ID No. 218c was effective in presence of TGF-β1 in A549 and ReNcell CX® cells (Table 25, FIG. 8). Target mRNA in both tested cell lines was significantly downregulated, regardless of a single treatment with ASO Seq. ID No. 218c or in presence with TGF-β1.

TABLE 25

In presence of TGF-β1, ASO Seq. ID No. 218c leads to a potent downregulation of TGF-R$_{II}$ mRNA after gymnotic transfer in A549 and ReNcell CX ® cells. mRNA expression levels were quantified relative to housekeeping gene GNB2L1 using quantitative real-time RT-PCR and normalized to untreated control.

| | Target Time point TGF-R$_{II}$ 48 h TGF-β1 -> 72 h/96 h TGF-β1 + ASOs/single treatment | |
|---|---|---|
| Cell line | A549 n = 2 | ReNcell CX n = 2 |
| A | 1.00 ± 0.12 | 1.00 ± 0.18 |
| B 10 μM | 0.92 ± 0.06 | 0.51 ± 0.14 |
| D 10 μM | 0.31** ± 0.04 | 0.05** ± 0.01 |
| E 10 ng/ml | 0.68 ± 0.05 | 0.88 ± 0.73 |
| E 10 ng/ml + B 10 μM | 0.86 ± 0.04 | 0.45 ± 0.09 |
| E 10 ng/ml + D 10 μM | 0.16** ± 0.05 | 0.03** ± 0.01 |

A = untreated control,
B = Ref. 1,
D = Seq. ID No. 218c,
E = TGF-β1,
± = SEM,
*p < 0.05,
**p < 0.01 in reference to A.
Statistics was calculated using the Ordinary-one-way-ANOVA followed by "Dunnett's" post hoc comparisons.

Conclusion:

Taken together, the inventive ASOs were effective in downregulating TGF-R$_{II}$ mRNA in presence of TGF-β1, indicating that ASOs are functional under pathological conditions.

Example 5: Inhibitory Activity of the Inventive ASOs on Target Protein Levels in TGF-β1 Treated Cells To analyze inhibitory activity of antisense oligonucleotides (ASOs) in human neuronal progenitor cells from cortical brain region (ReNcell CX®) under pathological conditions, cells were pre-treated with Transforming Growth Factor-β 1 (TGF-β1). From previous studies it is known that TGF-β1 is found in high concentrations in Cerebrospinal Fluid (CSF) of all neural disorders e.g. ALS. Therefore, inhibitory efficacy of ASOs on TGFβ-signaling was examined after pre-treatment and in presence with TGF-β1. A549 cells were used as reference cell line.

Description of Method:

Cells were cultured as described before in standard protocol. For treatment, cells were seeded in a 6-well culture dish (Sarstedt #83.3920.300) (80,000 cells/well) and 8-well cell culture slide dishes (Sarstedt #94.6140.802) (10,000 cells/well) and were incubated overnight at 37° C. and 5% CO$_2$. For investigation of gymnotic transfer effects (A549 and ReNcell CX), after pre-incubation with TGF-β1 (Promocell #C-63499), medium was removed and replaced by fresh full medium (1 ml for 6-well dishes and 8-well cell culture slide dishes). Following exposition of TGF-β1 (10 ng/ml, 48 h) medium was changed, TGF-β1 (10 ng/ml), Ref.1 (Scrambled control, 10 μM), and inventive ASOs (10 μM) was added, in combination and in single treatment, to the cells. A549 cells were incubated for further 72 h, whereas ReNcell CX® cells were harvested after 96 h. Therefore, cells were washed twice with PBS and subsequently used for protein isolation (6-well dishes) following Western Blot analysis or immunocytochemical examination of cells (in 8-well cell culture slide dishes). Procedures for used techniques were performed as described before. Used antibodies and dilutions for respective methods are listed in Table 13 and 14.

Results after Gymnotic Transfer

Western Blot and immunocytochemical analysis for A549 cells showed that the ASOs having Seq. ID No. 218b, Seq. ID No. 218c, Seq. ID No. 210q, Seq. ID No. 213k, Seq. ID No. 143h, Seq. ID No. 152h, Seq. ID No. 209az, Seq. ID No. 209y generate a potent target downregulation in presence of TGF-β1 (Table 26). Staining of TGF-R$_{II}$ on fixed ReNcell CX® cells confirmed the results observed in A549 cells. Tested ASOs revealed a strong target downregulation after single treatment but also in presence with TGF-β1.

TABLE 26

Densitometric analysis of TGF-R$_{II}$ Western Blot. Reduction of TGF-R$_{II}$ protein after TGF-β1 pre-incubation followed by gymnotic transfer with different ASOs in A549 was observed. Protein levels were determined relative to housekeeping gene GAPDH using Studio ™ Lite Software and were then normalized to untreated control.

| Cell line | Target Time point TGF-R$_{II}$ 48 h TGF-β1 -> 72 h TGF-β1 + ASOs/single treatment A549 n = 1 |
|---|---|
| A | 1.00 |
| B 10 μM | 1.20 |
| C 10 μM | 0.31 |
| D 10 μM | 0.42 |
| F 10 μM | 0.45 |
| G 10 μM | 0.35 |
| H 10 μM | 0.47 |
| I 10 μM | 0.33 |
| J 10 μM | 0.27 |
| K 10 μM | 0.30 |
| E 10 ng/ml | 2.03 |
| E 10 ng/ml + B 10 μM | 1.50 |
| E 10 ng/ml + C 10 μM | 0.78 |
| E 10 ng/ml + D 10 μM | 1.16 |
| E 10 ng/ml + F 10 μM | 1.21 |
| E 10 ng/ml + G 10 μM | 0.83 |
| E 10 ng/ml + H 10 μM | 1.02 |
| E 10 ng/ml + I 10 μM | 0.76 |
| E 10 ng/ml + J 10 μM | 0.69 |
| E 10 ng/ml + K 10 μM | 0.77 |

A = untreated control,
B = Ref. 1,
C = Seq. ID No. 218b,
C = Seq. ID No. 218b,
D = Seq. ID No. 218c,
F = Seq. ID No. 210q,
G = Seq. ID No. 213k,
H = Seq. ID No. 143h,
I = Seq. ID No. 152h,
J = Seq. ID No. 209az,
K = Seq. ID No. 209y,
E = TGF-β1.

Conclusion:

TGF-β1 pre-incubation followed by gymnotic transfer of Seq. ID No. 218b, Seq. ID No. 218c, Seq. ID No. 210q, Seq. ID No. 213k, Seq. ID No. 143h, Seq. ID No. 152h, Seq. ID No. 209az, and Seq. ID No. 209y resulted, in addition to target mRNA downregulation, in a reduction of protein level in A549 and ReNcell CX® cells.

Results after Gymnotic Transfer with Further ASOs:

Western Blot analysis showed a reduced amount of TGF-R$_{II}$ protein in A549 cells (Table 27) after gymnotic transfer for 72 h in comparison to untreated cells and cells treated with scrambled control. Pre-incubation of TGF-β1 followed by gymnotic transfer of tested ASOs evoked a reduction in comparison to cells which were pre-treated with TGF-β1 followed by gymnotic transfer with scrambled control. Immunocytochemical examination of A549 and ReNcell CX® after staining against TGF-R$_{II}$ showed that tested ASOs mediated a strong reduction of target protein after gymnotic transfer with or without pre-treatment of TGF-β1.

TABLE 27

Densitometric analysis of TGF-R$_{II}$ Western Blot. Reduction of TGF-R$_{II}$ protein after TGF-β1 pre-incubation followed by gymnotic transfer with further TGF-RII- specific antisense oligonucleotides (ASOs) in A549 could be detected. Protein levels were determined relative to housekeeping gene GAPDH using Studio ™ Lite Software and were then normalized to untreated control.

| ASO No. in Test | Seq ID No. | Result |
|---|---|---|
| 1 | 233d | B |
| 2 | 234d | A |
| 3 | 143j | C |
| 4 | 143p | A |
| 5 | 143q | A |
| 6 | 143r | A |
| 7 | 143w | A |
| 8 | 143af | B |
| 9 | 143ag | C |
| 10 | 143ah | C |
| 11 | 235b | B |
| 12 | 235d | A |
| 13 | 141d | A |
| 14 | 141g | A |
| 15 | 141i | B |
| 16 | 237b | A |
| 17 | 237c | A |
| 18 | 237i | C |
| 19 | 237m | A |
| 20 | 238c | A |
| 21 | 238f | A |
| 22 | 239e | B |
| 23 | 240c | B |
| 24 | 241b | C |
| 25 | 242a | C |
| 26 | 246e | C |
| 27 | 247d | A |
| 28 | 248b | A |
| 29 | 248e | B |
| 30 | 248g | A |
| 31 | 152k | B |
| 32 | 152s | B |
| 33 | 152t | B |
| 34 | 152u | B |
| 35 | 152ab | C |
| 36 | 152ag | B |
| 37 | 152ah | A |
| 38 | 152ai | A |
| 39 | 249c | A |
| 40 | 249e | A |
| 41 | 250b | A |
| 42 | 250g | B |
| 43 | 251c | A |
| 44 | 251f | A |
| 45 | 252e | B |
| 46 | 253c | A |
| 47 | 254b | C |
| 48 | 255a | C |
| 49 | 259e | C |
| 50 | 260d | B |
| 51 | 261b | A |
| 52 | 261e | B |
| 53 | 261g | A |
| 54 | 262d | B |
| 55 | 262e | A |
| 56 | 209s | A |
| 57 | 209v | B |
| 58 | 209w | A |
| 59 | 209x | C |
| 60 | 209ai | B |
| 61 | 209an | C |
| 62 | 209at | B |
| 63 | 209au | B |
| 64 | 209av | B |
| 65 | 263b | B |
| 66 | 263c | A |
| 67 | 263i | B |
| 68 | 263m | A |
| 69 | 264e | A |
| 70 | 264h | A |
| 71 | 265e | B |
| 72 | 266c | A |
| 73 | 267b | B |
| 74 | 268a | B |
| 75 | 272e | B |
| 76 | 273d | B |
| 77 | 274a | A |
| 78 | 274d | B |
| 79 | 274f | A |
| 80 | 275g | A |
| 81 | 275i | B |
| 82 | 210o | A |
| 83 | 210v | B |
| 84 | 210w | B |
| 85 | 210x | C |
| 86 | 210ab | B |
| 87 | 210ac | A |
| 88 | 210ad | B |
| 89 | 210af | A |
| 90 | 210am | B |
| 91 | 276b | B |
| 92 | 276c | A |
| 93 | 276j | B |
| 94 | 276k | B |
| 95 | 277d | A |
| 96 | 277e | A |
| 97 | 278f | B |
| 98 | 279c | B |
| 99 | 280b | C |
| 100 | 281a | C |
| 101 | 220d | C |
| 102 | 221d | B |
| 103 | 222b | A |
| 104 | 222c | A |
| 105 | 222f | B |
| 106 | 223c | B |
| 107 | 223f | A |
| 108 | 218ad | B |
| 109 | 218n | A |
| 110 | 218t | B |
| 111 | 218u | B |
| 112 | 218v | C |
| 113 | 218ah | C |
| 114 | 218an | A |
| 115 | 218ao | B |
| 116 | 218ap | B |
| 117 | 224i | B |
| 118 | 224m | B |
| 119 | 225c | A |
| 120 | 225f | A |
| 121 | 226e | B |
| 122 | 227c | B |
| 123 | 228b | C |
| 124 | 229a | C |
| 125 | 285d | C |
| 126 | 286d | A |
| 127 | 287d | B |
| 128 | 287e | A |
| 129 | 287f | A |
| 130 | 288e | A |

TABLE 27-continued

Densitometric analysis of TGF-R$_{II}$ Western Blot. Reduction of TGF-R$_{II}$ protein after TGF-β1 pre-incubation followed by gymnotic transfer with further TGF-RII- specific antisense oligonucleotides (ASOs) in A549 could be detected. Protein levels were determined relative to housekeeping gene GAPDH using Studio™ Lite Software and were then normalized to untreated control.

| ASO No. in Test | Seq ID No. | Result |
|---|---|---|
| 131 | 288i | A |
| 132 | 289d | B |
| 134 | 289h | A |
| 135 | 289o | B |
| 136 | 289p | A |
| 137 | 289q | B |
| 138 | 213o | B |
| 139 | 213p | B |
| 140 | 213q | B |
| 141 | 213s | B |
| 142 | 213y | B |
| 143 | 213z | B |
| 144 | 213aa | B |
| 145 | 213af | C |
| 146 | 290c | A |
| 147 | 290f | B |
| 148 | 290i | A |
| 149 | 291c | B |
| 150 | 292c | C |
| 151 | 293b | C |
| 152 | 294a | C |
| 125 | 285d | C |

Reduction of protein level for ASO 1-25 is indicated with the following key:
A = less than 10% inferior to SEQ ID No. 143h;
B = more than 10% but less than 20% inferior to SEQ ID No. 143h;
C = more than 20% but less than 30% inferior to SEQ ID No. 143h.
Reduction of protein level for ASO 26-48 is indicated with the following key:
A = less than 10% inferior to SEQ ID No. 152h;
B = more than 10% but less than 20% inferior to SEQ ID No. 152h;
C = more than 20% but less than 30% inferior to SEQ ID No. 152h.
Reduction of protein level for ASO 49-74 is indicated with the following key:
A = less than 10% inferior to the mean value derived from Seq. ID No. 209az and Seq. ID No. 209y;
B = more than 10% but less than 20% inferior to the mean value derived from Seq. ID No. 209az and Seq. ID No. 209y;
C = more than 20% but less than 30% inferior to the mean value derived from Seq. ID No. 209az and Seq. ID No. 209y.
Reduction of protein level for ASO 75-100 is indicated with the following key:
A = less than 10% inferior to SEQ ID No. 210q;
B = more than 10% but less than 20% inferior to SEQ ID No. 210q;
C = more than 20% but less than 30% inferior to SEQ ID No. 210q.
Reduction of protein level for ASO 101-124 is indicated with the following key:
A = less than 10% inferior to the mean value derived from Seq. ID No. 218b and Seq. ID No. 218c;
B = more than 10% but less than 20% inferior to the mean value derived from Seq. ID No. 218b and Seq. ID No. 218c;
C = more than 20% but less than 30% inferior to the mean value derived from Seq. ID No. 218b and Seq. ID No. 218c.
Reduction of protein level for ASO 125-152 is indicated with the following key:
A = less than 10% inferior to SEQ ID No. 213k;
B = more than 10 % but less than 20% inferior to SEQ ID No. 213k;
C = more than 20% but less than 30% inferior to SEQ ID No. 213k.

Conclusion:

Even after TGF-β1 pre-incubation, gymnotic transfer of inventive ASOs results in reduction of TGF-R$_{II}$ protein in A549 and ReNcell CX® cells.

Example 6: Analysis of the Effects of the Inventive ASOs to the Downstream Signaling Pathway of TGF-R$_{II}$ after TGF-β1-Preincubation Functional analyses were performed in human lung cancer cells (A549) and human neuronal precursor cells (ReNcell CX®). TGF-β1 downstream signaling pathway was analyzed, following to an effective downregulation of TGF-R$_{II}$ mRNA and reduction of protein levels by gymnotic transfer of the inventive ASOs in presence of TGF-β1. Therefore, mRNA and protein levels of Connective Tissue Growth Factor (CTGF), known as downstream-mediator of TGF-β, were evaluated. In addition, phosphorylation of Smad2 (mothers against decapentaphlegic homolog 2) was examined. The phosphorylation of Smad2 is a marker for an active TGF-β pathway followed by the upregulation of the downstream target gene CTGF.

Description of Method:

Cells were cultured as described before in standard protocol. For treatment, cells were seeded in 24-well culture dishes (Sarstedt #83.1836.300) (50,000 cells/well), 6-well culture dishes (Sarstedt #83.3920.300) (80,000 cells/well) and 8-well cell culture slide dishes (Sarstedt #94.6140.802) (10,000 cells/well) and were incubated overnight at 37° C. and 5% $CO_2$. For investigation of gymnotic transfer effects (A549 and ReNcell CX® cells), after pre-incubation with TGF-β1, medium was removed and replaced by fresh full medium (1 ml for 6-well dishes and 8-well cell culture slide dishes). Following exposition of TGF-β1 (10 ng/ml, 48 h) medium was changed, TGF-β1 (10 ng/ml), Ref.1 (Scrambled control, 10 µM), ASO with Seq. ID No. 218b (10 µM), and ASO with Seq. ID No. 218c (10 µM) was added in combination and in single treatment to cells. A549 cells were incubated for further 72 h, whereas ReNcell CX® cells were harvested after 96 h. Therefore, cells were washed twice with PBS and subsequently used for RNA (24-well dishes) and protein isolation (6-well dishes) or immunocytochemical examination of cells (in 8-well cell culture slide dishes). To evaluate effects on CTGF mRNA level, real-time RT-PCR was performed as described before. The primer pair for analysis of CTGF was ready-to-use and standardized. To check for CTGF and pSmad2 protein levels, Western Blot and immunocytochemistry were used as described before. Type and used dilutions of antibodies for respective method are listed in Table 13 and 14.

6.1. Results for Seq. ID No. 218b 6.1.1 Effects on CTGF mRNA and Protein Levels

CTGF mRNA was downregulated after gymnotic transfer with ASO Seq. ID No. 218b in A549 (72 h, 0.52±0.05) and ReNcell CX® (96 h, 0.70±0.25) cells, whereas TGF-β1 incubation for 5 days (A549: 48 h+72 h, 6.92±2.32) or 6 days (ReNcell CX: 48 h+96 h, 1.60±015) respectively, caused significant upregulation of CTGF mRNA. ASO Seq. ID No. 218b was potent enough to evoke a CTGF mRNA downregulation by blocking TGF-β1 effects in presence of TGF-β1 (Table 28, FIG. 11). According to observations for mRNA levels, immunochemical staining against CTGF also confirmed these observations for protein levels (FIG. 12).

TABLE 28

Downregulation of CTGF mRNA in presence of TGF-β1 followed by gymnotic transfer with Seq. ID No. 218b in A549 and ReNcell CX ® cells. MRNA expression levels were quantified relative to housekeeping GNB2L1 using quantitative real-time RT-PCR normalized to untreated control.

| | Target Time point CTGF 48 h TGF-β1 -> 72 h/96 h TGF-β1 + ASOs/single treatment | |
|---|---|---|
| Cell line | A549 n = 5 | ReNcell CX n = 3 |
| A | 1.00 ± 0.22 | 1.00 ± 0.04 |
| B 10 µM | 0.89 ± 0.19 | 0.85 ± 0.01 |
| C 10 µM | 0.52 ± 0.05 | 0.70* ± 0.25 |

TABLE 28-continued

Downregulation of CTGF mRNA in presence of TGF-β1 followed by gymnotic transfer with Seq. ID No. 218b in A549 and ReNcell CX ® cells. MRNA expression levels were quantified relative to housekeeping GNB2L1 using quantitative real-time RT-PCR normalized to untreated control.

| | Target<br>Time point<br>CTGF<br>48 h TGF-β1 -> 72 h/96 h TGF-β1 +<br>ASOs/single treatment | |
|---|---|---|
| Cell line | A549<br>n = 5 | ReNcell CX<br>n = 3 |
| E 10 ng/ml | 6.92* ± 2.32 | 1.60** ± 0.15 |
| E 10 ng/ml + B 10 μM | 8.79** ± 2.72 | 1.71** ± 0.03 |
| E 10 ng/ml + C 10 μM | 2.53++ ± 0.59 | 1.19++ ± 0.04 |

A = untreated control,
B = Ref. 1,
C = Seq. ID No. 218b,
E = TGF-β1,
± = SEM,
*p < 0.05,
**p < 0.01 in reference to A,
++p < 0.01 in reference to E + B.
Statistics was calculated using the Ordinary-one-way-ANOVA followed by "Tukey's" post hoc comparisons.

Conclusion:

In presence of TGF-β1 and following treatment of ASO Seq. ID No. 218b resulted firstly in downregulation of TGF-$R_{II}$ mRNA and secondary in reduced CTGF mRNA and protein levels in A549 and ReNcell CX® cells. That indicates that ASO Seq. ID No. 218b is potent enough to be active under high TGF-β1 pathological conditions and is able to rescue from TGF-β1 mediated effects.

6.1.2 Effects on pSmad2 Protein Level

To verify if CTGF downregulation is a consequence of specific TGF-β signaling inhibition, mediated by ASO Seq. ID No. 218b in presence of TGF-β1, pSmad2 protein levels were analyzed.

Staining pSmad2 after TGF-β1 pre-incubation followed by gymnotic transfer of ASO Seq. ID No. 218b with parallel TGF-β1 exposition leads to an inhibition of Smad2 phosphorylation in both tested cell lines (FIG. 13). In addition, reduced pSmad2 protein levels were verified by Western Blot Analysis in A549 and ReNcell CX® cells (Table 29).

TABLE 29

Densitometric analysis of pSmad2 Western Blot. Downregulation of pSmad2 protein after gymnotic transfer with ASO Seq. ID No. 218b was recognized. Also reversion of TGF-β1 mediated effects by inventive ASOs was found, when combination treatments were compared. Protein levels were determined relative to housekeeping gene GAPDH using Studio ™ Lite Software and were then normalized to untreated control.

| | Target<br>Time point<br>pSmad2<br>48 h TGF-β1 -> 72 h/96 h TGF-β1 +<br>ASOs/single treatment | |
|---|---|---|
| Cell line | A549<br>n = 2 | ReNcell CX<br>n = 2 |
| A | 1.00 ± 0.00 | 1.00 ± 0.00 |
| B 10 μM | 1.23 ± 0.47 | 0.89 ± 0.22 |
| C 10 μM | 0.58 ± 0.08 | 0.66 ± 0.14 |
| E 10 ng/ml | 1.40 ± 0.31 | 1.19 ± 0.61 |
| E 10 ng/ml + B 10 μM | 1.27 ± 0.46 | 2.19 ± 0.76 |
| E 10 ng/ml + C 10 μM | 0.81 ± 0.31 | 1.55 ± 0.42 |

A = untreated control,
B = Ref. 1,
C = Seq. ID No. 218b,
E = TGF-β1.
Statistics was calculated using the Ordinary-one-way-ANOVA followed by "Dunnett's" post hoc comparisons.

Conclusion:

ASO Seq. ID No. 218b results in a functional inhibition of TGF-β signaling in A549 and ReNcell CX® cells in presence of TGF-β1, confirmed by reduced phosphorylation of Smad2.

6.2 Results for Seq. ID No. 218c 6.2.1 Effects on CTGF mRNA and Protein Level

Data show CTGF mRNA downregulation after combination treatment with ASO Seq. ID No. 218c and TGF-β1 (A549: 0.86, ReNcell CX®: 0.23) compared to combination treatment with scrambled control and TGF-β1 (A549: 5.89, ReNcell CX®: 1.25) (Table and FIG. 14). In addition to these observations, immunochemical staining of CTGF confirmed prevention of TGF-β1 mediated effects on protein level by ASO Seq. ID No. 218c (FIG. 15).

TABLE 30

CTGF mRNA levels after TGF-β1 pre-incubation followed by gymnotic transfer of Seq. ID No. 218c and parallel TGF-β1 treatment in A549 and ReNcell CX ® cells. Data confirmed effective prevention of TGF-β1 effects on CTGF mRNA levels by ASO Seq. ID No. 218c. mRNA expression levels were quantified relative to housekeeping gene GNB2L1 using quantitative real-time RT-PCR normalized to untreated controls.

| | Target<br>Time point<br>CTGF<br>48 h TGF-β1 -> 72 h/96 h TGF-β1 +<br>ASOs/single treatment | |
|---|---|---|
| Cell line | A549<br>n = 3 | ReNcell CX<br>n = 2 |
| A | 1.00 ± 0.05 | 1.00 ± 0.03 |
| B 10 μM | 0.86 ± 0.11 | 0.85 ± 0.01 |
| D 10 μM | 0.53 ± 0.10 | 0.17* ± 0.02 |
| E 10 ng/ml | 4.71 ± 1.76 | 1.39 ± 0.08 |
| E 10 ng/ml + B 10 μM | 5.89* ± 2.16 | 1.25 ± 0.44 |
| E 10 ng/ml + D 10 μM | 0.86++ ± 0.06 | 0.23*** ± 0.02 |

A = untreated control,
B = Ref. 1,
D = Seq. ID No. 218c,
E = TGF-β1,
± = SEM,
**p < 0.01 in reference to A,
++p < 0.01 in reference to E + B.
Statistics was calculated using the Ordinary-one-way-ANOVA followed by "Tukey's" post hoc comparisons.

Conclusion:

Data confirmed an effective prevention of TGF-β1 induced effects on CTGF mRNA and protein levels by ASO Seq. ID No. 218c.

6.2.2 Effects on pSmad2 Protein Level

To verify if CTGF downregulation (6.2.1) is a consequence of TGF-β1 signaling-inhibition mediated by ASO Seq. ID No. 218c, even in presence of TGF-β1-preincubation, pSmad2 protein levels were analyzed.

Phosphorylation of Smad2 was induced by TGF-β1 incubation (1.52±0.19), whereas ASO gymnotic transfer mediated a reduction of pSmad2 in A549 cells (0.89±0.05). TGF-β1 pre-incubation with following combination treatment results in suppression of TGF-β1 effects on phosphorylation of Smad2 (Western Blot Analysis, Table 31). Immunocytochemistry supported the data observed by Western Blot Analysis (FIG. 16).

TABLE 31

Densitometric analysis of pSmad2 Western Blot. Downregulation of pSmad2 protein after gymnotic transfer with ASO Seq. ID No. 218c was measured. Suppression of TGF-β1 mediated effects by inventive ASOs was shown, when combination treatments were compared. Protein levels were determined relative to housekeeping gene GAPDH using Studio ™ Lite Software and normalized to untreated controls.

| Cell line | Target Time point pSmad2 48 h TGF-β1 -> 72 h TGF-β1 + ASOs/single treatment A549 n = 2 |
|---|---|
| A | 1.00 ± 0.00 |
| B 10 μM | 1.23 ± 0.27 |
| D 10 μM | 0.89 ± 0.05 |
| E 10 ng/ml | 1.52 ± 0.19 |
| E 10 ng/ml + B 10 μM | 1.27 ± 0.29 |
| E 10 ng/ml + D 10 μM | 0.93 ± 0.35 |

A = untreated control,
B = Ref. 1,
D = Seq. ID No. 218c,
E = TGF-β1.
Statistics was calculated using the Ordinary-one-way-ANOVA followed by "Dunnett's" post hoc comparisons.

Conclusion:

ASO Seq. ID No. 218c is efficiently inhibiting TGF-β signaling after TGF-β1 pre-incubation followed by ASO gymnotic transfer. This was shown by examination of downstream pSmad2 protein levels.

Taken together, inventive ASOs are extraordinary capable in mediating a functional inhibition of TGF-β signaling in presence of pathological, high TGF-β1 levels by efficiently downregulating TGF-$R_{II}$ mRNA. Thus, inventive ASOs will be beneficial in medical indications in which elevated TGF-β levels are involved, e.g. neurological disorders, fibrosis, tumor progression and others.

Example 7: Determination of Prophylactic Activity of the Antisense-Oligonucleotides on mRNA Level (TGF-β1 Post-Treatment)

To analyze prophylactic activity of antisense-oligonucleotides (ASOs) in human neuronal progenitor cells from cortical brain region (ReNcell CX®), ASOs were transferred to cells by gymnotic uptake following Transforming Growth Factor-β1 (TGF-β1) treatment.

Description of Method:

A549 and ReNcell CX® cells were cultured as described above. For prophylactic treatment studies, cells were seeded in a 24-well culture dish (Sarstedt #83.1836.300) (50,000 cells/well) and were incubated overnight at 37° C. and 5% $CO_2$. Afterwards, Ref.1 (Scrambled control, 10 μM) or ASO with Seq. ID No. 218b (10 μM) were added to media for 72 h (A549) or 96 h (ReNcell CX®). Following incubation time after gymnotic transfer, TGF-β1 (10 ng/ml, Promocell #C-63499) was added, without medium replacement, to the cells for further 48 h. For harvesting, cells were washed twice with PBS and subsequently used for RNA isolation (24-well dishes) following mRNA analysis by real-time RT-PCR. Ready-to-use and standardized primer pairs for real-time RT-PCR were used and mixed with the respective ready-to-use Mastermix solution (SsoAdvanced™ Universal SYBR® Green Supermix (BioRad #172-5271) according to manufacturer's instructions (BioRad Prime PCR Quick Guide). Methods were performed as described above.

7.1 Results for Seq. ID No. 218b

Efficacy in TGF-$R_{II}$ mRNA downregulation by ASO Seq. ID No. 218b was not influenced by TGF-β1 post-incubation in A549 and ReNcell CX® cells (Table 32). Significant decrease of target mRNA in ReNcell CX® cells was shown after single treatment (0.33*±0.11) with ASO Seq. ID No. 218b. ASO gymnotic transfer with post-treatment of TGF-β1, strongly reduced the target TGF-$R_{II}$ mRNA. In A549 cells, Seq. ID No. 218b showed similar potency in inhibiting TGF-$R_{II}$ mRNA in single (0.25±0.07) or combination treatment with post-incubation of TGF-β1 (0.24±0.06).

TABLE 32

Downregulation of TGF-$R_{II}$ mRNA after gymnotic transfer following TGF-β1 treatment of inventive ASO in A549 and ReNcell CX ® cells. mRNA expression levels were quantified relative to housekeeping gene GNB2L1 using quantitative real-time RT-PCR normalized to untreated control.

| | Target Time point TGF-$R_{II}$ 72 h/96 h ASOs -> 48 h TGF-β1 | |
|---|---|---|
| Cell line | A549 n = 3 | ReNcell CX n = 3 |
| A | 1.00 ± 0.44 | 1.00 ± 0.19 |
| B 10 μM | 0.95 ± 0.22 | 1.42 ± 0.14 |
| C 10 μM | 0.25 ± 0.07 | 0.33* ± 0.11 |
| E 10 ng/ml | 1.96 ± 0.16 | 1.42 ± 0.08 |
| E 10 ng/ml + B 10 μM | 1.14 ± 0.39 | 1.25 ± 0.14 |
| E 10 ng/ml + C 10 μM | 0.24++ ± 0.06 | 0.56++ ± 0.10 |

A = untreated control,
B = Ref. 1,
C = Seq. ID No. 218b,
E = TGF-β1.
± = SEM,
*p < 0.05 in reference to A,
++p < 0.01 in reference to E + B.
Statistics was calculated using the Ordinary-one-way-ANOVA followed by "Tukey's" post hoc comparisons.

Conclusion:

Gymnotic uptake of ASO Seq. ID No. 218b followed by TGF-β1 post-incubation was effective in target TGF-$R_{II}$ mRNA downregulation, indicating that ASO Seq. ID No. 218b is feasible for prophylactic treatment in medical indications.

Example 8: Determination of Inhibitory Activity of the Inventive ASOs on Protein Level Following TGF-β1 Treatment To analyze prophylactic activity of inventive ASOs in human neuronal progenitor cells from cortical brain region (ReNcell CX®), ASOs were transferred to cells by gymnotic uptake following TGF-β1 treatment.

Description of Method:

Cells were cultured as described before in standard protocol. For treatment cells were seeded in 8-well cell culture slide dishes (Sarstedt #94.6140.802) (10,000 cells/well) and were incubated overnight at 37° C. and 5% $CO_2$. Afterwards, Ref.1 (Scrambled control, 10 µM) or ASO sequence identification number 218b (Seq. ID No. 218b, 10 µM) were added to media for 72 h (A549) or 96 h (ReNcell CX®). Following gymnotic transfer TGF-β1 (10 ng/ml, Promocell #C-63499) was added, without medium replacement, to the cells for further 48 h. For harvesting, cells were washed twice with PBS and subsequently used for immunocytochemical analysis. Procedure was performed as described before. Used antibodies and dilutions for respective methods are listed in Table 13 and 14.

8.1 Results of TGF-$R_{II}$ Protein Reduction after Gymnotic Transfer with Seq. ID No. 218b Following TGF-β1 Treatment Immunocytochemical analysis against TGF-$R_{II}$ for A549 and ReNcell CX® cells showed that ASO Seq. ID No. 218b generates potent TGF-$R_{II}$ mRNA target downregulation after following TGF-β1 treatment (FIG. 17).

Conclusion:

Gymnotic transfer of ASO Seq. ID No. 218b following TGF-β1 treatment resulted in target mRNA downregulation, as well as a strong reduction of TGF-$R_{II}$ protein level in A549 and ReNcell CX® cells.

Taken together, efficacy of downregulating TGF-$R_{II}$ protein mediated by ASO Seq. ID No. 218b in combination with post-treatment of TGF-β1 was still given, concluding that the inventive ASOs are effective for prophylactic applications.

Example 9: ASO Treatment Effects on Downstream Signaling Pathway of TGF-$R_{II}$ Following TGF-β1 Treatment Efficacy of inventive ASOs in mediating an inhibition of TGF-β signaling was evaluated for TGF-β1 treatment followed gymnotic transfer in human lung cancer cells (A549) and human neuronal precursor cells (ReNcell CX®). Therefore, downstream molecules of TGF-β signaling, Smad3 (mothers against decapentaplegic homolog 3) and Connective Tissue Growth factor (CTGF), were analyzed.

Description of Method:

Cells were cultured as described before in standard protocol. For treatment, cells were seeded in 24-well culture dishes (Sarstedt #83.1836.300) (50,000 cells/well) and 8-well cell culture slide dishes (Sarstedt #94.6140.802) (10,000 cells/well) and were incubated overnight at 37° C. and 5% $CO_2$. Afterwards, Ref.1 (Scrambled control, 10 µM) or ASO Seq. ID No. 218b (10 µM) were added to media for 72 h (A549) or 96 h (ReNcell CX®). Following gymnotic transfer, TGF-β1 (10 ng/ml, Promocell #C-63499) was added without medium replacement for further 48 h. For harvesting, cells were washed twice with PBS and subsequently used for RNA isolation (24-well dishes) or immunocytochemical examination of cells (in 8-well cell culture slide dishes). To evaluate effects on CTGF mRNA level, real-time RT-PCR was performed as described before. The primer pair for analysis of CTGF was ready-to-use and standardized. To determine pSmad3 protein levels, immunocytochemistry was used as described before. Type and used dilutions of antibodies for respective method are listed in Table 13 and 14.

9.1. Results for Seq. ID No. 218b 9.1.1 Effects on CTGF mRNA and pSmad3 Protein Level CTGF mRNA was reduced after gymnotic transfer with ASO Seq. ID No. 218b in A549 (5 days: 0.67±0.02) and ReNcell CX® (6 days: 0.70±0.02) cells. Adding TGF-β1 after 72 h or 96 h respectively, cells react with an increase of CTGF mRNA, but in comparison to gymnotic transfer of scrambled control following TGF-β1 treatment, induction of CTGF mRNA was strongly reduced (Table 33). To verify if CTGF mRNA downregulation was a consequence of TGF-β signaling inhibition, mediated by ASO Seq. ID No. 218b, also after followed TGF-β1 treatment, pSmad3 protein levels were examined. FIG. 18 demonstrates that TGF-β signaling was in fact blocked by gymnotic transfer of ASO Seq. ID No. 218b in A549 (FIG. 18 A) and ReNcell CX® cells (FIG. 18 B). This effect was also present after gymnotic transfer of tested ASO following TGF-β1 treatment.

TABLE 33

Downregulation of CTGF mRNA after gymnotic transfer of ASO Seq. ID No. 218b followed by TGF-β1 treatment in A549 and ReNcell CX ® cells. Quantification of mRNA expression levels were performed relative to housekeeping gene GNB2L1 using quantitative real-time RT-PCR and then normalized to untreated control.

| | Target Time point CTGF | |
|---|---|---|
| | 72 h/96 h ASOs -> +/− 48 h TGF-β1 | |
| Cell line | A549 n = 3 | ReNcell CX n = 3 |
| A | 1.00 ± 0.13 | 1.00 ± 0.09 |
| B 10 µM | 0.80 ± 0.03 | 1.07 ± 0.07 |
| C 10 µM | 0.67 ± 0.02 | 0.70 ± 0.02 |
| E 10 ng/ml | 4.54** ± 0.68 | 1.56* ± 0.08 |
| E 10 ng/ml + B 10 µM | 4.07** ± 0.38 | 1.62* ± 0.09 |
| E 10 ng/ml + C 10 µM | 1.90⁺ ± 0.03 | 0.97⁺⁺ ± 0.10 |

A = untreated control,
B = Ref. 1,
C = Seq. ID No. 218b,
E = TGF-β1.
± = SEM,
*p < 0.05,
**p < 0.01 in reference to A,
⁺p < 0.05,
⁺⁺p < 0.01 in reference to E + B.
Statistics was calculated using the Ordinary-one-way-ANOVA followed by "Tukey's" post hoc comparisons.

Conclusion:

Gymnotic transfer of ASO Seq. ID No. 218b resulted in downregulation of TGF-$R_{II}$ mRNA and protein, as well as in reduced CTGF mRNA and pSmad3 protein levels in A549 and ReNcell CX® cells, independently of TGF-β1 treatment.

That indicates that ASO Seq. ID No. 218b is potent enough to be also active under prophylactic conditions to resume or reduce ongoing TGF-β1 mediated effects.

Example 10: Analysis of Potential Proinflammatory and Toxicological Effects of Antisense-Oligonucleotides 10.1 Peripheral Blood Mononuclear Cell (PBMC) Assay To analyze antisense-oligonucleotide (ASO) for immunostimulatory properties, peripheral blood mononuclear cells (PBMCs) were incubated with control ASOs and test compounds followed by ELISAs for IFNα and TGFα.

Description of Method:

PBMCs were isolated from buffy coats corresponding to 500 ml full blood transfusion units. Each unit was obtained from healthy volunteers and glucose-citrate was used as an anti-agglutinant. The buffy coat was prepared and delivered by the Blood Bank Suhl on the Institute for Transfusion Medicine, Germany. Each blood donation was monitored for HIV antibody, HCV antibody, HBs antigen, TPHA, HIV RNA, and SPGT (ALAT). Only blood samples tested negative for infectious agents and with a normal SPGT value were used for leukocyte and erythrocyte separation by low-speed centrifugation. The isolation of PBMCs was performed about 40 h following blood donation by gradient centrifugation using Ficoll-Histopague® 1077 (Heraeus™ Multifuge™ 3 SR). For IFNα assay, PBMCs were seeded at 100,000 cells/96-well in 100 μl complete medium plus additives (RPMI1640, +L-Glu, +10% FCS, +PHA-P (5 μg/ml), +IL-3 (10 μg/ml)) and test compounds (5 μl) were added for direct incubation (24 h, 37° C., 5% $CO_2$). For TNFα assay, PBMCs were seeded at 100,000 cells/96-well in 100 μl complete medium w/o additives (RPMI1640, +L-Glu, +10% FCS) and test compounds (5 μl) were added for direct incubation (24 h, 37° C., 5% $CO_2$). ELISA (duplicate measurement out of pooled supernatants, 20 μl) for huIFNα (eBioscience, #BMS216INSTCE) was performed according to the manufacturer's protocol. ELISA (duplicate measurement out of pooled supernatants, 20 μl) for huTNFα (eBioscience, #BMS2231NSTCE) was performed according to the manufacturer's protocol.

Results:

There was no immunostimulatory effect of ASO treatment on PBMCs indicated by no detectable IFNα (Table 34) and TNFα (Table 35) secretion upon ASO incubation. Assay functionality is proven by the immunostimulatory effect of immunostimulatory, cholesterol-conjugated siRNA (XD-01024; IFNα) and polyinosinic:polycytidylic acid (poly I:C; TNFα; InvivoGen #tirl-pic) which is a synthetic analog of double-stranded RNA, binds to TLR3 and stimulates the immune system.

TABLE 34

IFNα response to inventive ASO exposure: shows the IFNα response of PBMCs upon ASO incubation. Quantification of expression levels were determined to positive controls (ODN2216 [class A CpG oligonucleotide; recognized by TLR9 and leading to strong immunostimulatory effects; InvivoGen tlrl-2216], poly I:C, XD-01024) using ELISA assay.

| | Mean of duplicates [pg/ml] | |
|---|---|---|
| Test candidate | Donor 1 | Donor 2 |
| mock | −0.084 | 0.720 |
| Seq. ID No. 209y | −0.061 | −0.039 |
| Seq. ID No. 209t | −0.308 | −0.520 |
| Seq. ID No. 209v | −0.191 | −1.252 |
| Seq. ID No. 218b | −0.001 | −0.093 |
| Seq. ID No. 218m | −0.140 | −0.163 |
| Seq. ID No. 218q | −0.755 | 0.005 |
| Seq. ID No. 218c | −0.852 | −0.805 |

TABLE 34-continued

IFNα response to inventive ASO exposure: shows the IFNα response of PBMCs upon ASO incubation. Quantification of expression levels were determined to positive controls (ODN2216 [class A CpG oligonucleotide; recognized by TLR9 and leading to strong immunostimulatory effects; InvivoGen tlrl-2216], poly I:C, XD-01024) using ELISA assay.

| | Mean of duplicates [pg/ml] | |
|---|---|---|
| Test candidate | Donor 1 | Donor 2 |
| Seq. ID No. 218t | −0.469 | 0.450 |
| ODN2216 | 0.300 | 1.311 |
| poly I:C | −1.378 | 2.053 |
| XD-01024 | 13.961 | 26.821 |

All values except positive control (XD-01024) below limit of quantification

TABLE 35

TNFα response to inventive ASO exposure: Quantification of expression levels were determined to control candidates (ODN2216, poly I:C, XD-01024) using ELISA assay.

| | Mean of duplicates [pg/ml] | |
|---|---|---|
| Test candidate | Donor 1 | Donor 2 |
| mock | 0.647 | −0.137 |
| Seq. ID No. 209y | 2.397 | −0.117 |
| Seq. ID No. 209t | 0.734 | 0.193 |
| Seq. ID No. 209v | 0.360 | 0.063 |
| Seq. ID No. 218b | 0.670 | 0.183 |
| Seq. ID No. 218m | 0.594 | 0.519 |
| Seq. ID No. 218q | 0.049 | 0.194 |
| Seq. ID No. 218c | −0.212 | 0.029 |
| Seq. ID No. 218t | 0.593 | 0.758 |
| ODN2216 | 0.085 | 0.894 |
| poly I:C | 115.026 | 102.042 |
| XD-01024 | 1.188 | 1.418 |

All values except positive control (poly I:C) below limit of quantification 10.2 In Vivo Toxicology of Inventive Antisense-Oligonucleotides To analyze antisense-oligonucleotides (ASOs) for toxicological properties, C57/Bl6N mice received three intravenous ASO injections, and following scarification, transaminase levels within serum, liver and kidney were examined.

Description of Method:

Female C57/Bl6N mice at the age of 6 weeks were treated with test compounds (Seq. ID No. 218b, Seq. ID No. 218c) for seven days. ASOs (200 μl, 15 mg/kg/BW) were injected intravenously on day one, two, and three of the treatment period. Body weight development (Seq. ID No. 218c) was monitored on every consecutive day and on day four serum was collected from the vena fascicularis. On day eight the animals were sacrificed ($CO_2$) and serum from the vena cava, the liver (pieces of ≈50 mg), the kidneys, and the lung were collected for mRNA and transaminase quantification. TGF-$R_{II}$ mRNA levels were determined in liver, kidney, and lung lysate by bDNA assay (QuantiGene® kit, Panomics/Affimetrix). Aspartate transaminase (ASP) and alanine transaminase (ALT) were measured on Cobas Integra® 400 from 1:10 diluted serum.

TABLE 36

Serum expression levels of alanine transaminase and aspartate transaminase of C57/Bl6N mice following repeated ASO iv injection. Quantification of expression levels was achieved by comparing to the expression levels of saline-treated animals.

| | Serum transaminases [U/L] | | | |
|---|---|---|---|---|
| | 3 days post injection | | 7 days post injection | |
| Test compound | ALT | AST | ALT | AST |
| Seq. ID No. 209ax | 13.87 ± 1.44 | 47.33 ± 15.88 | 64.91 ± 21.01 | 108.99 ± 13.56 |
| Seq. ID No. 143h | 13.68 ± 3.33 | 53.50 ± 6.99 | 12.47 ± 1.64 | 33.35 ± 8.17 |
| Seq. ID No. 152h | 16.66 ± 6.29 | 67.23 ± 29.91 | 17.49 ± 2.81 | 45.75 ± 17.14 |
| Seq. ID No. 209ay | 18.29 ± 6.37 | 69.96 ± 35.44 | 287.29 ± 65.39 | 273.45 ± 101.33 |
| Seq. ID No. 210q | 11.70 ± 3.80 | 36.44 ± 5.36 | 11.11 ± 6.31 | 40.81 ± 13.32 |
| Seq. ID No. 218b | 19.60 ± 8.62 | 67.61 ± 42.75 | 18.38 ± 4.60 | 48.91 ± 17.86 |
| Seq. ID No. 213k | 13.59 ± 3.28 | 54.47 ± 36.15 | 96.00 ± 46.74 | 89.12 ± 21.82 |
| Saline | 9.52 ± 9.21 | 67.18 ± 28.60 | 9.99 ± 2.29 | 28.29 ± 2.23 |

± = SEM.

TABLE 37

Expression levels of TGF-R$_{II}$ within liver, kidney, and lung tissue of C57/Bl6N mice following repeated ASO iv injection. Quantification of expression levels was achieved by comparing to the expression levels of saline-treated animals.

| | TGF-RII mRNA/GAPDH mRNA expression | | |
|---|---|---|---|
| Test compound | Liver | Kidney | Lung |
| Seq. ID No. 209ax | 0.64 ± 0.03 | 1.31 ± 0.11 | 13.25 ± 0.67 |
| Seq. ID No. 143h | 0.26 ± 0.02 | 0.65 ± 0.22 | 11.10 ± 0.11 |
| Seq. ID No. 152h | 0.58 ± 0.10 | 0.87 ± 0.17 | 13.42 ± 0.69 |
| Seq. ID No. 209ay | 0.62 ± 0.06 | 1.30 ± 0.10 | 13.93 ± 0.57 |
| Seq. ID No. 210q | 0.39 ± 0.06 | 0.83 ± 0.15 | 13.53 ± 1.23 |
| Seq. ID No. 218b | 0.72 ± 0.08 | 0.97 ± 0.06 | 15.63 ± 1.45 |
| Seq. ID No. 213k | 0.42 ± 0.01 | 1.20 ± 0.04 | 14.44 ± 1.03 |
| Saline | 0.66 ± 0.04 | 1.10 ± 0.08 | 15.14 ± 0.65 |

± = SEM.

TABLE 38

Serum expression levels of alanine transaminase and aspartate transaminase of C57/Bl6N mice following repeated ASO iv injection. Quantification of expression levels was achieved by comparing to the expression levels of saline-treated animals.

| | Serum transaminases [U/L] | | | |
|---|---|---|---|---|
| | 3 days post injection | | 7 days post injection | |
| Test compound | ALT | AST | ALT | AST |
| Seq. ID No. 218c | 24.63 ± 2.10 | 51.87 ± 5.99 | 18.10 ± 4.01 | 39.99 ± 2.09 |
| Saline | 28.68 ± 3.23 | 79.95 ± 30.24 | 14.52 ± 4.89 | 36.08 ± 3.32 |

± = SEM.

TABLE 39

Expression levels of TGF-R$_{II}$ within liver and kidney tissue of C57/Bl6N mice following repeated ASO iv injection. Quantification of expression levels was achieved by comparing to the expression levels of saline-treated animals.

| | TGF-RII mRNA/GAPDH mRNA expression | |
|---|---|---|
| Test compound | Liver | Kidney |
| Seq. ID No. 218c | 0.21 ± 0.03 | 0.16 ± 0.02 |
| Saline | 0.35 ± 0.05 | 0.24 ± 0.03 |

± = SEM.

TABLE 40

Body weight development during the 7-day ASO treatment paradigm.

| | Body weight development [%] | | | | | |
|---|---|---|---|---|---|---|
| Test compound | Day 0 | Day 1 | Day 2 | Day 3 | Day 4 | Day 7 |
| Seq. ID No. 218c | 100% | 99% | 99% | 99% | 102% | 104% |
| Saline | 100% | 99% | 100% | 100% | 101% | 103% |

Body weight gain was quantified compared to body weight on day 0, which was set to 100%.

Conclusion: There were no proinflammatory or toxic effects of relevant inventive ASOs on PBMCs or C57/B16N mice. Therefore, ASO treatment targeting TGF-R$_{II}$ reflects a safe method to treat a variety of TGF-B associated disorders.

Example 11: Determination of Intracerebroventricular Infusion of Inventive ASOs on TGF-β Induced Neural Stem Inhibition and Neural Progenitor Cell Proliferation In Vivo The goal of the present study was to evaluate the potential of inventive ASOs against TGF-R$_{II}$ i) to prevent and ii) to treat the TGF-β1 induced effects on neural stem and progenitor cell proliferation in vivo.

Description of Method:

11.1 Prevention of TGF-β1 Associated Downregulation of Neurogenesis

Two-month-old female Fischer-344 rats (n=32) received intracerebroventricular infusions via osmotic minipumps (Model 2002, Alzet) connected to stainless steel cannulas. The surgical implantation of the minipumps was performed under deep anesthesia using intramuscular injections. Animals were infused with inventive ASOs according to the invention (1.64 mM concentration present in the pump), scrambled ASO (1.64 mM concentration present in the pump) or aCSF (artificial cerebrospinal fluid) for 7 days. At day 8, pumps were changed and the animals were infused with either i) aCSF, ii) TGF-β1 (500 ng/ml present in the pump), iii) TGF-§ 1 (500 ng/ml present in the pump) plus scrambled ASO (1.64 mM concentration present in the pump), or iv) TGF-β1 (500 ng/ml present in the pump) plus inventive ASO (1.64 mM concentration present in the pump) for 14 days. At the end of the infusion-period all animals were transcardially perfused with 4% paraformaldehyde. The brains were analyzed for cannula tract localization and animals with incorrect cannula placement were excluded from the analysis. During the last 24 hours of the pump period, the animals received an intraperitoneal injection of 200 mg/kg bromo-deoxyuridine (BrdU).

The tissue was processed for chromogenic immunodetection of BrdU-positive cells in 40 µm sagital sections. BrdU positive cells were counted within three 50 µm×50 µm counting frames per section located at the lowest, middle and upper part of the subventricular zone. Positive profiles that intersected the uppermost focal plane (exclusion plane) or the lateral exclusion boundaries of the counting frame were not counted. For hippocampal analysis, the volume of the hippocampus was determined and all positive cells within and adjacent to the boundaries were counted. The total counts of positive profiles were multiplied by the ratio of reference volume to sampling volume in order to obtain the estimated number of BrdU-positive cells for each structure. All extrapolations were calculated for one cerebral hemisphere and should be doubled to represent the total brain values. Data are presented as mean values±standard deviations (SD). Statistical analysis was performed using the unpaired, two-sided t-test comparison -Student's t-test between the TGF-β1 treated and control groups (GraphPad Prism 4 software, USA). The significance level was assumed at $p<0.05$.

11.2 Treatment of TGF-β1 Associated Down-Regulation of Neurogenesis

Animals received either aCSF or recombinant human TGF-β1 (500 ng/ml present in pump) at a flow rate of 0.5 µl per hour for 14 days. After 14 days, pumps were changed and the animals were infused with either i) aCSF, ii) recombinant human TGF-β1 (500 ng/ml present in pump) or co-infused with iii) inventive ASO (1.64 mM concentration present in the pump) plus recombinant human TGF-β1 (500 ng/ml present in pump) or iv) scrambled ASO (1.64 mM concentration present in the pump) plus recombinant human TGF-B31 (500 ng/ml present in pump). At the end of the infusion-period all animals were transcardially perfused with 4% paraformaldehyde. The brains were analyzed for cannula tract localization and animals with incorrect cannula placement were excluded from the analysis. During the last 24 hours of the pump period, the animals received an intraperitoneal injection of 200 mg/kg bromo-deoxyuridine (BrdU). Histological analysis was done as described above (11.1).

Results:

The treatment with ASO of Seq. ID No. 143aj, Seq. ID No. 143h and Seq. ID No. 210q specifically and partially reduced the effect of TGF-β1 on cell proliferation in the hippocampus and in the ventricle wall. Treatment with an inventive ASO specifically and partially rescues from the inhibitory effect of TGF-β1 on neurogenesis.

Conclusion: The ASOs of the present invention demonstrating cross-reactivity with rodents induce neurogenesis in this in vivo experiment. The ASOs of the present invention demonstrating no cross-reactivity, exert mostly even more potential effects in in vitro experiments. As a result, it is assumed that these inventive ASOs are also more effective in in vivo set ups for non-human primates and humans and therefore act as a highly potent medication for preventing or treating TGF-β1 induced inhibition of neural stem and progenitor proliferation.

Example 12: Analysis of the Effect of the Inventive Antisense-Oligonucleotides on Proliferation and Specific Markers of Human Neural Progenitor Cells Amyotrophic lateral sclerosis (ALS) is a neurodegenerative lethal disorder with no effective treatment so far. The current molecular genetic campaign is increasingly elucidating the molecular pathogenesis of this fatal disease, from previous studies it is known that TGF-β is found in high concentrations in Cerebrospinal Fluid (CSF) of ALS patients. These high levels of circulating TGF-β are known to promote stem cell quiescence and therefore cause inhibition of adult neurogenesis within the subventricular zone (SVZ) of the brain. Thus, regeneration of degenerating neurons seems to be prevented by an enhanced TGF-β signaling.

To figure out if selective inhibition of TGF-β signaling mediated by the inventive antisense-oligonucleotides might allow reactivation of adult neurogenesis, evidence of TGF-β mediated cell cycle arrest has to be proofed.

Description of Methods:

Cell cycle arrest studies: Cells were cultured as described before in standard protocol. For experiments, cells were seeded in 24-well culture dishes (Sarstedt #83.1836.300) (30,000 cells/well) and were incubated overnight at 37° C. and 5% $CO_2$. For determination of TGF-β1 mediated effects on cell cycle under proliferative (+EGF/FGF) (Millipore: EGF #GF144, bFGF #GF003) or differentiating (−EGF/FGF) conditions, cells were treated for 4 d with TGF-β1 (PromoCell #C-63499, 10 or 50 ng/ml) after removing and replacement of respective medium. At day 4 medium was refreshed and TGF-β1 treatment was repeated until day 7. On day 7, cells were harvested by washing twice with PBS and subsequently used for RNA (24-well dishes) isolation as described above. For evaluating TGF-β1-mediated effects on cell cycle by real-time RT-PCR, mRNA of proliferation marker Ki67, tumor suppressor gene p53, cyclin-dependent kinase inhibitor 1 (p21) and of neurogenesis marker Doublecortin (DCX) were analyzed. Respective primer pairs are listed in Table 11.

mRNA Analysis for Effects of ASO Seq. ID No. 218b on Human Neural Progenitor Cells:

Cells were cultured as described before in standard protocol. For experiments, cells were seeded in 24-well culture dishes (Sarstedt #83.1836.300) (30,000 cells/well) and were incubated overnight at 37° C. and 5% $CO_2$. For present experiments, cell medium was changed and Ref.1 (Scrambled control, 2.5 and 10 µM), ASO with Seq. ID No. 218b (2.5 and 10 µM) or TGF-β1 (10 ng/ml, Promocell #C-63499) were added to cells for 96 h. After incubation time, medium was changed once more and further treatment was performed for further 96 h. After 8 days of treatment cells were harvested. Cells were washed twice with PBS and subsequently used for RNA (24-well dishes) isolation. To evaluate effects on progenitor cells, Nestin (early neuronal marker), Sox2 (early neuronal marker), DCX (indicator of neurogenesis) and Ki67 (proliferation marker) mRNA levels were determined by real-time RT-PCR as described before. Respective primer pairs are listed in Table 11.

Proliferative and differentiating effects of TGFR$_{II}$ specific ASOs by gymnotic transfer on ReNcell CX® cells: The next goal was to investigate, whether TGF-R$_{II}$ specific ASO influence the proliferation of ReNcell CX® cells. Therefore, cells were cultured as described before and seeded in 24-well culture dishes (Sarstedt #83.1836.300) (30,000 cells/well) or 8-well cell culture slide dishes (Sarstedt #94.6140.802) (10,000 cells/well) and were incubated overnight at 37° C. and 5% $CO_2$. For obtaining a proliferation curve, cells were treated after medium change for 72 h with Ref.1 (Scrambled control, 2.5 and 10 µM,) and with ASO Seq. ID No. 218b (2.5 and 10 µM). After incubation time, medium change and treatment was repeated two times. After collecting supernatant, remaining cells were harvested from 24-well dishes for determination of cell number. For this purpose, remaining cells were washed with PBS (2×), treated with accutase (500 µl/well) and incubated for 5 min at 37° C. Afterwards 500 µl medium were added and cell number was determined using Luna FL™ Automated Cell Counter Fluorescence and Bright Field (Biozym, #872040) according to manufacturer's instructions. Briefly, 18 µl of the cell suspension were added to 2 µl of acridine orange/propidium iodide assay viability kit (Biozym #872045). After 1 min of settling, 10 µl were added onto Cell Counting Slide (Biozym #872011), cells were counted and calculated in total cells/ml and percentage of alive cells compared to dead cells. After gymnotic transfer of Ref.1 (10 µM), Seq. ID No. 218b (10 µM) and corresponding treatment of TGF-β1 (10 ng/ml) for 8 days, cells of 8-well cell culture slide dishes were fixed and stained with an antibody against Ki67. For investigating differentiation ability of ReNcell CX® cells after gymnotic transfer, other 8-well cell culture slide dishes were treated with Ref.1 (10 µM), Seq. ID No. 218b (10 µM) and corresponding treatment of TGF-β1 (10 ng/ml) for 96 h under proliferative conditions (+EGF/FGF). Afterwards, one part of the cells was treated for further 96 h under proliferative conditions whereas the other part of cells was treated and hold under differentiating conditions (-EGF/FGF). Following staining of cells, Neurofilament N (NeuN) and βIII-Tubulin expression levels were determined by fluorescence microscopy. Protocol for harvesting, fixing and staining cells was described above and respective antibody dilutions are listed in Table 14.

mRNA Analysis of markers for proliferation and neurogenesis after gymnotic transfer following TGF-β1 pre-incubation: Cells were cultured as described before in standard protocol. For experiments cells were seeded in 24-well culture dishes (Sarstedt #83.1836.300) (30,000 cells/well) and incubated overnight at 37° C. and 5% $CO_2$. For inducing cell cycle arrest, ReNcell CX® cells were treated with TGF-β1 for 4 days. Afterwards medium was changed and TGF-β1 (10 ng/ml) was added freshly. One day 8 medium was changed on more time, and gymnotic transfer was performed for 96 h by adding Ref.1 (10 µM), Seq. ID No. 218b (10 µM) in combination with TGF-β1 (10 ng/ml). Cells were harvested after incubation by washing twice with PBS. Following RNA isolation and mRNA analysis by real-time RT-PCR were performed as described.

12.1.1 Mediation of Cell Cycle Arrest by TGF-β1 in Human Neural Progenitor Cells Detection of stem cell quiescence markers showed that TGF-β1 mediates cell cycle arrest 7 days after exposure of cells. Proliferation marker Ki67 mRNA expression was dose-dependently reduced. Also mRNA expression of tumor suppressor gene p53 was downregulated correlating to TGF-β1 concentration. In contrast, cyclin-dependent kinase inhibitor 1 (p21) was significantly upregulated by TGF-β1. In summary these results indicate stem cell quiescence induced by TGF-β1. Interestingly, DCX, a marker for neurogenesis, was strongly reduced by TGF-β1 (Table 41).

TABLE 41 mRNA expression of Ki67, p27, p21, and DCX 7 days after TGF-β1 treatment in ReNcell CX ® cells.
mRNA expression levels were determined relative to housekeeping gene GNB2L1 using quantitative real-time RT-PCR and then normalized to untreated control.

| | Cell line ReNcell CX mRNA levels 7 days after TGF-β1 exposure | | | |
|---|---|---|---|---|
| Target | Ki67 n = 3 | p53 n = 3 | p21 n = 3 | DCX n = 3 |
| A + EGF/FGF | 1.00 ± 0.38 | 1.00 ± 0.38 | 1.00 ± 0.25 | 1.00 ± 0.49 |
| E 10 ng/ml + EGF/FGF | 0.67 ± 0.20 | 0.66 ± 0.18 | 1.90* ± 0.22 | 0.37 ± 0.06 |
| E 50 ng/ml + EGF/FGF | 0.43 ± 0.09 | 0.42 ± 0.06 | 1.45 ± 0.16 | 0.16 ± 0.01 |
| A - EGF/FGF | 1.00 ± 0.15 | 1.00 ± 0.13 | 1.00 ± 0.14 | 1.00 ± 0.31 |
| E 10 ng/ml - EGF/FGF | 0.87 ± 0.08 | 0.97 ± 0.10 | 1.00 ± 0.04 | 0.72 ± 0.14 |
| E 50 ng/ml - EGF/FGF | 0.93 ± 0.11 | 0.93 ± 0.09 | 0.90 ± 0.09 | 0.71 ± 0.24 |

A = untreated control,
E = TGF-β1.
± = SEM,
*$p < 0.05$ in reference to A.
Statistics was calculated using the Ordinary-one-way-ANOVA followed by "Tukey's" multiple post hoc comparison.

Conclusion

Proliferation of ReNcell CX® cells was blocked by TGF-β1.

12.1.2 Results of Antisense-Oligonucleotide Effects on Markers of Human Neuronal Stem Cells To figure out the effect of ASO Seq. ID No. 218b on stem cell markers, 8 days after repeated gymnotic transfer (2×96 h) in ReNcell CX® cells, different markers of early neural progenitor cells were tested (Table 42). Gene expression levels of Nestin and Sox2 were not influenced by ASO Seq. ID No. 218b. GFAP mRNA was slightly upregulated after gymnotic transfer with 10 µM ASO Seq. ID No. 218b and in contrast, DCX was clearly induced after gymnotic uptake of ASO Seq. ID No. 218b. Expression of all tested markers was strongly reduced after TGF-β1 treatment (8 d) (Table 42, FIG. 19).

TABLE 42 mRNA expression of Nestin, Sox2, GFAP and DCX 8 days after gymnotic transfer of Seq. ID No. 218b in ReNcell CX ® cells. mRNA expression levels were determined relative to housekeeping gene GNB2L1 using quantitative real-time RT-PCR and then normalized to untreated control.

| Target | Cell line ReNcell CX mRNA levels 8 days after gymnotic transfer or TGF-β1 exposure | | | |
|---|---|---|---|---|
| | Nestin n = 4 | Sox2 n = 4 | GFAP n = 4 | DCX n = 4 |
| A | 1.00 ± 0.18 | 1.00 ± 0.25 | 1.00 ± 0.22 | 1.00 ± 0.32 |
| B 2.5 µM | 0.97 ± 0.32 | 0.88 ± 0.33 | 0.78 ± 0.13 | 1.31 ± 0.42 |
| B 10 µM | 0.89 ± 0.16 | 0.79 ± 0.13 | 1.02 ± 0.20 | 1.44 ± 0.48 |
| C 2.5 µM | 1.09 ± 0.21 | 0.93 ± 0.09 | 0.99 ± 0.14 | 1.67 ± 0.46 |
| C 10 µM | 0.90 ± 0.09 | 0.89 ± 0.11 | 1.21 ± 0.11 | 1.95 ± 0.37 |
| E 10 ng/ml | 0.48 ± 0.12 | 0.32 ± 0.06 | 0.41# ± 0.13 | 0.05+# ± 0.01 |

A = untreated control,
B = Ref. 1,
C = Seq. ID No. 218b,
E = TGF-β1,
± = SEM,
+$p < 0.05$ in reference to C 2.5 µM,
$p < 0.05$ in reference to C 10 µM.
Statistics was calculated using the Ordinary-one-way-ANOVA followed by "Tukey's" multiple post hoc comparison.

Conclusion:

Results for mRNA analysis indicate that ASO Seq. ID No. 218b guides ReNcell CX® cells into the direction of an even more stem cell like state (GFAP upregulation). In addition, induction of DCX indicates an elevated neurogenesis. TGF-β1 treatment results in an opposite direction.

12.1.3 Results of Antisense-Oligonucleotide Effects on Proliferation of Human Neuronal Stem Cells Further analysis was performed to investigate whether gymnotic transfer of ASO Seq. ID No. 218b has really effects on proliferation rate by counting cells 9 days after repeated gymnotic transfer (3×72 h) and determination of Ki67 protein levels 8 days after gymnotic uptake (2×96 h).

Results

Cell number was increased after gymnotic uptake of ASO Seq. ID No. 218b in accordance to an increased protein expression of proliferation marker Ki67 observed in immunochemical staining of cells (Table 43, FIG. 20). Fluorescence analysis of immunocytochemical staining also revealed a proliferation stop mediated by TGF-β1.

TABLE 43

Increased cell number 9 days after repeated gymnotic transfer (3 × 72 h) of ReNcell CX ® cells. Cell number was determined using Luna FL ™ Automated Cell Counter Fluorescence and Bright Field (Biozym, #872040) according to manufacturer's instructions.

| Cell number | Cell line ReNcell CX | |
|---|---|---|
| | alive cells × $10^5$, n = 2 | dead cells × $10^5$, n = 2 |
| A | 3.34 ± 0.09 | 0.51 ± 0.05 |
| B 2.5 µM | 4.34 ± 0.56 | 0.60 ± 0.09 |
| B 10 µM | 4.36 ± 0.96 | 0.58 ± 0.09 |
| C 2.5 µM | 4.63 ± 1.28 | 0.47 ± 0.02 |
| C 10 µM | 5.24 ± 0.42 | 0.37 ± 0.02 |

A = untreated control,
B = Ref. 1,
C = Seq. ID No. 218b,
± = SEM.

Conclusion

Gymnotic transfer of ASO Seq. ID No. 218b in ReNcell CX® cells results in an increased cell number, paralleled by an enhanced Ki67 protein expression, altogether indicating increased neuronal precursor proliferation.

12.1.3 Results of Antisense-Oligonucleotide Effects on Differentiation Ability of Human Neuronal Stem Cells To exclude an influence of ASO Seq. ID No. 218b on cell ability to differentiate, ASO Seq. ID No. 218b was transferred to cells by gymnotic uptake for 96 h under proliferative conditions (+EGF/FGF). After incubation time, medium was changed and to one part of cells proliferative medium was added whereas to the other part of cells differentiating medium (−EGF/FGF) was added. Afterwards, another gymnotic transfer for 96 h was performed. Cells were analyzed by expression levels of neuronal markers Neurofilament N (NeuN) and βIII-Tubulin.

Results

Immunochemical staining against NeuN (FIG. 23A) and βIII-Tubulin (FIG. 23B) demonstrates no effects on the ability to differentiate after gymnotic ASO transfer under proliferative conditions followed by gymnotic transfer under differentiating conditions. Signal for βIII-Tubulin, a human neuron specific protein, was not influenced by ASO Seq. ID No. 218b under differentiating conditions and was comparable to untreated control. Also NeuN expression was not influenced after gymnotic transfer under differentiating conditions. Thus, cells are still capable to differentiate into neural cells. Strikingly, ReNcell CX® cells expressed neuronal marker NeuN and βIII-Tubulin after gymnotic transfer of ASO under proliferative conditions (2×96 h) for both periods, indicating that gymnotic transfer of ASO could promote a specific shift into differentiation of neurons even under proliferative conditions. In addition, elevated proliferation rates of neural precursor cells were observed (Table 43, FIG. 20). Further, staining against NeuN revealed that cells treated with ASO Seq. ID 218b look more viable compared to all other treatments (FIG. 21A). Obviously, cells which were treated with TGF-β1 were significantly less proliferative.

Conclusion

The ability to differentiate was not influenced by inventive ASO Seq. ID No. 218b. Interestingly, ReNcell CX® cells showed differentiation to neurons after gymnotic transfer under proliferative and differentiating conditions. This indicates in context to the observation of an increased proliferation rate, that inventive ASO Seq. ID No. 218b promotes neurogenesis with a tendency towards elevated neuronal differentiation.

12.1.4 Results of Inventive Antisense-Oligonucleotides on Proliferation of Human Neuronal Stem Cells after TGF-β1 Pre-Incubation To analyze whether gymnotic transfer of ASO Seq. ID No. 218b is efficient in reversing TGF-β1 mediated effects on ReNcell CX® cells, further studies were performed with TGF-β1 pre-incubation for 7 days followed by gymnotic transfer for 8 days (2×96 h).

Results

Gene expression of GFAP (Table 44, FIG. 22A) as an early neuronal marker, Ki67 (Table 44, FIG. 22B), as a marker for proliferation, and DCX (Table 44, FIG. 22C) as marker for neurogenesis were elevated after single ASO treatment, whereas TGF-β1 resulted in the opposite. In addition, 7 days after TGF-β1 pre-incubation, inventive ASO treatment reversed TGF-β1-induced effects. Thus the analysis demonstrates that ASO Seq. ID No. 218b is potent in recovering TGF-β1 mediated effects upon stem cell and proliferation markers

TABLE 44 mRNA expression of GFAP, Ki67 and DCX 7 days after TGF-β1 pre-incubation followed by 2 × 96 h gymnotic transfer of Seq. ID No. 218b in ReNcell CX ® cells. mRNA expression levels were determined relative to housekeeping gene GNB2L1 using quantitative real-time RT-PCR and then normalized to untreated control.

| | Cell line ReNcell CX mRNA levels 7 d after TGF-β1 pre-incubation followed by 2 × 96 h gymnotic transfer | | |
|---|---|---|---|
| Target | GFAP $n = 2$ | Ki67 $n = 1$ | DCX $n = 2$ |
| A | 1.00 ± 0.20 | 1.00 | 1.00 ± 0.16 |
| B 10 µM | 1.62 ± 0.15 | 0.91 | 1.52 ± 0.24 |
| C 10 µM | 2.23 ± 0.52 | 1.52 | 4.82 ± 1.15 |
| E 10 ng/ml | 0.76 ± 0.01 | 0.48 | 0.68 ± 0.03 |
| E 10 ng/ml + B 10 µM | 0.58 ± 0.07 | 0.61 | 0.83 ± 0.10 |
| E 10 ng/ml + C 10 µM | 2.04 ± 1.04 | 7.40 | 1.55 ± 0.24 |

A = untreated control,
B = Ref. 1,
C = Seq. ID No. 218b,
E = TGF-β1,
± = SEM,
Statistics was calculated using the Ordinary-one-way-ANOVA followed by "Tukey's" multiple post hoc comparisons.

Conclusion

Results indicate that adult neurogenesis could be reactivated by inventive TGF-$R_{II}$ specific ASO-mediated blocking of TGF-β signaling.

Taken together, TGF-$R_{II}$ specific ASO Seq. ID No. 218b rescued cells from TGF-β mediated stem cell quiescence and promotes adult neurogenesis without having an impact on differentiation. This makes it an ideal treatment drug for brain repair.

Example 13: Determination of Therapeutic Activity of Inventive Antisense-Oligonucleotides Disease Progression of ALS in SOD1 Mice To analyze the therapeutic potential of ASOs as a medication for amyotrophic lateral sclerosis (ALS) male and female transgenic, SOD1 G93A mice were treated with different doses of inventive ASOs by icv administration into the lateral ventricle via osmotic ALZET® minipumps. In addition, riluzole was used as a reference. Riluzole is a drug used to treat amyotrophic lateral sclerosis and is marketed by Sanofi Pharmaceuticals. It delays the onset of ventilator-dependence or tracheostomy in selected patients and may increase survival by approximately two to three months Description of Method:

For long-lasting central infusion an icv cannula attached to an Alzet® osmotic minipump (infusion rate: 0.25 µl/h, Alzet®, Model 2004, Cupertino, USA), was stereotaxically implanted under isoflurane anesthesia (Baxter, GmbH, Germany) and semi-sterile conditions. Each osmotic minipump was implanted subcutaneously in the abdominal region via a 1 cm long skin incision at the neck of the mouse and connected with the icv cannula by silicone tubing. Animals were placed into a stereotaxic frame, and the icv cannula (23 G, 3 mm length) was lowered into the right lateral ventricle (posterior 0.3 mm, lateral 1 mm, depth 3 mm relative to bregma). The cannula was fixed with two stainless steel screws using dental cement (Kallocryl, Speiko® Dr. Speier GmbH, Münster, Germany). The skin of the neck was closed with sutures. During surgery, the body temperature was maintained by a heating pad. To avoid post-surgical infections, mice were locally treated with Betaisodona® (Mundipharma GmbH, Limburg, Germany) and received 0.1 ml antibiotics (sc, Baytril® 2.5% Bayer Vital GmbH, Leverkusen, Germany). The tubing was filled with the respective solution. To determine the effects of ASOs on the development and the progression of ALS, the onset of symptoms, paresis, and survival were used as in vivo endpoints. At the age of nine weeks, mice were sacrificed and brains were removed for neuropathology analysis. Histological verification of the icv implantation sites was performed at 40-µm coronal, cresyl violet-stained brain sections.

The inventive ASOs exert potential effects in in vitro experiments. Quite in line, the rodent cross-reactive inventive ASOs with Seq. ID No. 143aj, Seq. ID No. 143h and Seq. ID No. 210q were also effective in the above experiments proving an effect in the treatment of ALS model animals. The ASOs of the present invention demonstrating no cross-reactivity exert more potential effects in in vitro experiments. As a result, it is assumed that these inventive ASOs are also more effective in in vivo set ups for non-human primates and humans and therefore act as a highly potent medication for preventing or treating TGF-β1 induced inhibition of neural stem and progenitor proliferation, and thereby treating ALS and other neurodegenerative disorders.

Examples 14: Determination of the Therapeutic Activity of Antisense-Inventive ASOs Directed to TGF-$R_{II}$ on Disease Development and Progression of Huntington's Disease in R6/2 Mice To analyze the therapeutic potential of ASOs as a medication for Huntington's disease (HD), male and female transgenic R6/2 mice were treated with different doses of inventive TGF-$R_{II}$ specific ASO by icv administration into the lateral ventricle via osmotic minipumps.

Description of Method: For chronic central infusion, mice underwent surgery for an icv cannula attached to an Alzet® osmotic minipump (infusion rate: 0.25 µl/h, Alzet®, Model 2004, Cupertino, USA) at the age of five weeks. The cannula and the pump were stereotaxically implanted under ketamine/xylacin anesthesia (Baxter, GmbH, Germany) and semi-sterile conditions. Each osmotic minipump was implanted subcutaneously in the abdominal region via a 1 cm long skin incision at the neck of the mouse and connected with the icv cannula by a silicone tubing. Animals were placed into a stereotaxic frame, and the icv cannula (23 G, 3 mm length) was lowered into the right lateral ventricle (posterior 0.3 mm, lateral 1 mm, depth 3 mm relative to bregma). The cannula was fixed with two stainless steel screws using dental cement (Kallocryl, Speiko®-Dr. Speier GmbH, Münster, Germany). The skin of the neck was closed with sutures. During surgery, the body temperature was maintained by a heating pad. To avoid post-surgical infections, mice were locally treated with Betaisodona® (Mundipharma GmbH, Limburg, Germany) and received 0.1 ml antibiotics (sc, Baytril® 2.5% Bayer Vital GmbH, Leverkusen, Germany). The tubing was filled with the respective solution. To determine the effects of ASOs on the development and the progression of HD the onset of symptoms, grip strength, general motoric, and survival were used as in vivo endpoints. At the age of nine weeks, mice were sacrificed and brains were removed for histological analyzation. Histological verification of the icv implantation sites was performed at 40-μm coronal, cresyl violet-stained brain sections.

The inventive ASOs exert potential effects in in vitro experiments. Quite in line, the rodent cross-reactive inventive ASOs with Seq. ID No. 143aj, Seq. ID No. 143h and Seq. ID No. 210q were also effective in the above experiments proving an effect in the treatment of Huntington model animals. The ASOs of the present invention demonstrating no cross-reactivity exert more potential effects in in vitro experiments. As a result, it is assumed that these inventive ASOs are also more effective in in vivo set ups for non-human primates and humans and therefore act as a highly potent medication for preventing or treating TGF-β1 induced inhibition of neural stem and progenitor proliferation, and thereby treating HD and other neurodegenerative disorders.

Example 15: Determination of Therapeutic Activity of the Inventive ASOs on Disease Progression of TGFβ-Induced Hydrocephalus and Associated Cognitive Deficits in Fischer-344 Rats The goal of the present study is to treat animals suffering from the TGFβ induced effects on i) neural stem cell proliferation and neurogenesis, ii) formation of hydrocephalus, and iii) spatial learning deficits by intraventricular infusion of inventive ASO in a dose-dependent manner.

Description of Method: Osmotic minipumps for intracerebroventricular infusion were implanted into female Fischer-344 rats of 180 to 200 g body weight ($n_{total}$=70, $n_{group}$=10). Infused were a) artificial cerebrospinal fluid (aCSF: 148.0 mM NaCl, 3.0 mM KCl, 1.4 mM $CaCl_2$), 0.8 mM $MgCl_2$, 1.5 mM $Na_2HPO_4$, 0.2 mM $NaH_2PO_4$, 100 μg/ml rat serum albumin, 50 μg/ml Gentamycin, pH 7.4) as control, or b) TGF-β1 1 μg/mL in aCSF using an Alzet® osmotic pump 2004 with flow rate of 0.25 μl/h for 14 days. After 14 days the pumps are changed and Alzet® osmotic pumps 2004 (flow rate 0.25 μl/h) were used for the following infusions: aCSF or TGF-β1 (1 μg/ml) in combination with varying concentrations of TGF-$R_{II}$ ASO (1.1 mmol/L, 3.28 mmol/l, 9.84 mmol/l) or scrambled ASO (3.28 mmol/l) were infused (2×4 weeks). During the last four days of the infusion period, animals received a daily intraperitoneal injection of BrdU (50 mg/kg of body weight) to label proliferating cells. Pumps are removed, and two weeks later animals are functionally analyzed in a spatial learning test (Morris-Water-Maze) for 14 days. One day later, animals are perfused with 0.9% NaCl, brains are removed, the ipsilateral hemisphere is postfixed in 4% paraformaldehyde for quantitative histological analysis of PCNA, BrdU, DCX, BrdU/NeuN, and BrdU/GFAP, and for stereological analysis of the volume of the lateral ventricles as a measure for the hydrocephalus. The contralateral hemisphere is further dissected and different areas (ventricle wall, hippocampus, cortex) are processed for quantitative RT-PCR to analyze TGF-$R_{II}$ expression levels. MR images were taken of 4 animals of group 1, group 3, and group 6 at day four before pump implantation, one week after pump implantation, at the day of the first pump change and from then on every 2 weeks until the end of the infusion period. Histological verification of the icv implantation sites was performed at 40-μm coronal, cresyl violet-stained brain sections.

TABLE 46

Treatment scheme and the group classification of the Hydrocephalus experiment.

| Group | 1. aCSF | 2. aCSF + ASO | 3. TGF-β1 | 4. TGF-β1 + scramb-ASO | 5.-7. TGF-β1 + ASO |
|---|---|---|---|---|---|
| treatment | aCSF-infusion | aCSF plus ASO infusion | TGF-β1-infusion | TGF-β1 plus ASO infusion | TGF-β1 plus ASO infusion |
| treatment scheme | week 1 to 10 | week 1 and 2: aCSF week 3 to 10: ASO: 3.28 mmol/l | week 1 and 2: 1 μg/ml week 3 to 10: 1 μg/ml | week 1 and 2: TGF-β1: 1 μg/ml week 3 to 10: TGF-β1: 1 μg/ml scramb.-ASO: 3.28 mmol/l | week 1 and 2: TGF-β1: 1 μg/ml week 3 to 10: TGF-β1: 1 μg/ml ASO: 1.1 mmol/l 3.28 mmol/l 9.84 mmol/l |
| n | 10 | 10 | 10 | 10 | 10 per dose |
| n-total | 10 | 10 | 10 | 10 | 30 |

The inventive ASOs exert potential effects in in vitro experiments. Quite in line, the rodent cross-reactive inventive ASOs with Seq. ID No. 143aj, Seq. ID No. 143h and Seq. ID No. 210q were also effective in the above experiments proving an effect in the treatment of Hydrocephalus model animals. The ASOs of the present invention demonstrating no cross-reactivity exert more potential effects in in vitro experiments. As a result, it is assumed that these inventive ASOs are also more effective in in vivo set ups for non-human primates and humans and therefore act as a highly potent medication for preventing or treating TGF-β1 induced inhibition of neural stem and progenitor proliferation, and thereby treating Hydrocephalus and other neurodegenerative disorders.

Example 16: Determination of Therapeutic Activity of the Antisense-Oligonucleotides Directed to TGF-R$_{II}$ on Rehabilitation of Spinal Cord Injury in Fischer 344 Rats To analyze the therapeutic potential of ASOs as a medication for spinal cord injury (SCI), male and female Fischer-344 rats were treated with different doses of inventive ASOs by icv administration into the lateral ventricle via osmotic minipumps.

Description of Method: SCI was simulated by cervical tungsten wire knife dorsal column transection at the C3 level. In the next step, for chronic central infusion rats, (180-200 g body weight) underwent surgery for an icv cannula attached to an Alzet® osmotic minipump (infusion rate: 0.25 µl/h, Alzet®, Model 2004, Cupertino, USA). The cannula and the pump were stereotaxically implanted under ketamine/xylacin anesthesia (Baxter, GmbH, Germany) and semi-sterile conditions. Each osmotic minipump was implanted subcutaneously in the abdominal region via a 1 cm long skin incision at the neck of the rat and connected with the icv cannula by a silicone tubing. Animals were placed into a stereotaxic frame, and the icv cannula (23 G, 3 mm length) was lowered into the right lateral ventricle (posterior 1.0 mm, lateral 1.0 mm, depth 1.8 mm relative to bregma). The cannula was fixed with two stainless steel screws using dental cement (Kallocryl, Speiko®-Dr. Speier GmbH, Münster, Germany). The skin of the neck was closed with sutures. During surgery, the body temperature was maintained by a heating pad. To avoid post-surgical infections, rats were locally treated with Betaisodona® (Mundipharma GmbH, Limburg, Germany) and received 0.5 ml antibiotics (sc, Baytril® 2.5% Bayer Vital GmbH, Leverkusen, Germany). The tubing was filled with the respective solution. To determine the effects of ASOs on the rehabilitation process following SCI, 4 weeks post-surgery an in vivo MRI structural analysis was performed (3T MRI, Allegra Siemens, phased array—small animal coil). 6 weeks after surgery, animals were sacrificed and the spinal cord was removed for histological and immunohistochemical analysis. Histological verification of the icv implantation sites was performed at 40-µm coronal, cresyl violet-stained brain sections.

The inventive ASOs exert potential effects in in vitro experiments. Quite in line, the rodent cross-reactive inventive ASOs with Seq. ID No. 143aj, Seq. ID No. 143h and Seq. ID No. 210q were also effective in the above experiments proving an effect in the treatment of a Fischer-344—rat spinal cord paraplegia model. In MRI images and neuropathological analysis, the inventive ASOs showed high treatment efficacy. The ASOs of the present invention demonstrating no cross-reactivity exert more potential effects in in vitro experiments. As a result, it is assumed that these inventive ASOs are also more effective in in vivo set ups for non-human primates and humans and therefore act as a highly potent medication for preventing or treating TGF-β1 induced inhibition of neural stem and progenitor proliferation, and thereby treating spinal cord injury and other neurodegenerative disorders.

Example 17: ASO-Mediated Effects on Proliferation of Human Lung Cancer Cell Line A549 mRNA of Ki67, p53, Caspase 8 (Casp8) and of DNA-binding protein inhibitor 2 (ID2) were analyzed as representative markers on proliferation in several tumor cells. It is known from previous studies, that expression of tumor suppressor gene p53 and ID2 is often dramatically elevated in tumor tissues. Ki67 is a proliferation marker and Casp8 is an indicator for apoptosis. In addition, cell numbers were determined after gymnotic transfer.

Description of Method:

A549 were cultured as described above. For treating cells, medium was removed and replaced by fresh full medium in 24-well culture dishes (Sarstedt #83.1836.300) (30,000 cells/well), 6-well culture dishes (Sarstedt #83.3920.300) (50,000 cells/well) or 8-x-well cell culture slide dishes (Sarstedt #94.6140.802) (20,000 cells/well) (0.5 ml for 24-well and 8-well cell culture slide dishes and 1 ml for 6-well dishes) and were incubated overnight at 37° C. and 5% $CO_2$. To analyze mRNA expression and influence on proliferation, cells were treated with Ref.1 (Scrambled control) and ASO Seq. ID No. 218b at concentrations of 2.5 µM and 10 µM and were incubated for 72 h at 37° C. and 5% $CO_2$. Treatment including medium replacement was repeated for 3 times every 72 h (12 days in total). For immunocytochemical analysis of proliferation (Ki67), gymnotic transfer of ASO Seq. ID No. 218b was limited to 72 h. Afterwards, cells were washed twice with PBS and subsequently used for protein isolation (6-well dishes), immunocytochemistry (in 8-well cell culture slide dishes), proliferation curve and RNA isolation (24-well dishes). Protocols for RNA, protein and immunocytochemistry were performed as described above. For proliferation curve, remaining cells were harvested from 24-well dishes for determination of cell number. For this purpose, remaining cells were washed with PBS (2×), treated with accutase (500 µl/well) and incubated for 7 min at 37° C. Afterwards 500 µl medium was added and cell number was determined using Luna FL™ Automated Cell Counter Fluorescence and Bright Field (Biozym, #872040) according to manufacturer's instructions. Briefly, 18 µl of the cell suspension was added to 2 µl of acridine orange/propidium iodide assay viability kit (Biozym #872045). After 1 min of settling, 10 µl were added onto Cell Counting Slide (Biozym #872011). Cells were counted and calculated in distinction of alive and dead cells.

17.1 Results for ASO Seq. ID No. 218b mRNA analysis showed reduced Ki67, p53 and ID2 expression levels 12 days after gymnotic transfer of ASO Seq. ID No. 218b. In contrast, Casp8 was elevated at low levels of ASO Seq. ID No. 218b (Table 46). These observations indicate that a reduced tumor growth is associated with a slight increase in apoptotic cells. Furthermore, Western Blot analysis showed reduction in protein level of Ki67 and pAkt 12 days after gymnotic transfer of inventive ASOs (Table 47). Immunochemical examination of A549 cells after gymnotic transfer of ASO Seq. ID No. 218b showed a reduced level of Ki67 signals in comparison to scrambled control for both concentrations applied (FIG. 23). Finally, cell number of A549 cells was reduced about nearly 50% 12 days after gymnotic transfer of ASO Seq. ID No. 218b (Table 48).

TABLE 46 mRNA expression of Ki67, p53, Casp8 and ID2, 12 days after gymnotic transfer of ASO Seq. ID No. 218b in A549 cells.

| Cell line Target | A549 mRNA levels 12 days after repeated gymnotic transfer (4 × 72 h) | | | |
|---|---|---|---|---|
| | Ki67 n = 2 | p53 n = 2 | Casp8 n = 2 | ID2 n = 2 |
| A | 1.00 ± 0.37 | 1.00 ± 0.31 | 1.00 ± 0.05 | 1.00 ± 0.03 |
| B 2.5 µM | 0.92 ± 0.05 | 1.06 ± 0.02 | 1.36 ± 0.37 | 0.73 ± 0.01 |
| B 10 µM | 0.96 ± 0.03 | 1.11 ± 0.92 | 1.52 ± 0.15 | 0.82 ± 0.15 |
| C 2.5 µM | 0.55 ± 0.33 | 0.27 ± 0.04 | 1.59 ± 0.48 | 0.59 ± 0.01 |
| C 10 µM | 0.57 ± 0.20 | 0.53 ± 0.07 | 0.98 ± 0.17 | 0.35 ± 0.02 |

Regulation of examined genes demonstrates diminished proliferation rates after gymnotic transfer of inventive ASOs.
Reduced ID2 mRNA levels are beneficial in dampening expansion of tumor cells.
mRNA expression levels were determined relative to housekeeping gene GNB2L1 using quantitative real-time RT-PCR normalized to untreated control.
A = untreated control, B = Ref.1, C = Seq. ID No. 218b, ± = SEM, Statistics was calculated using the Ordinary-one-way-ANOVA followed by "Tukey's" multiple post hoc comparisons.

TABLE 47

Densitometric analysis of Ki67 and pAkt Western Blot.

| Cell line Target | A549 protein levels 12 days after repeated gymnotic transfer (4 × 72 h) | |
|---|---|---|
| | Ki67 n = 1 | pAKT n = 1 |
| A | 1.00 | 1.00 |
| B 10 µM | 1.18 | 0.80 |
| C 10 µM | 0.57 | 0.39 |

Downregulation of Ki67 and pAkt protein 12 days after gymnotic transfer with TGF-R$_{II}$ specific ASO Seq. ID No. 218b was observed in A549 cells.
Protein levels were determined relative to housekeeping gene GAPDH using Image Studio™ Lite Software and were then normalized to untreated control.
A = untreated control, B = Ref.1, C = Seq. ID No. 218b, ± = SEM.

TABLE 48

Cell numbers 12 days after repeated gymnotic transfer.

| Cell line Cell number | A549 cell number 12 days after repeated gymnotic transfer (4 × 72 h) | |
|---|---|---|
| | alive cells × $10^5$ n = 3 | dead cells × $10^5$ n = 3 |
| A | 4.25 ± 0.50 | 0.47 ± 0.09 |
| B 10 µM | 3.88 ± 0.95 | 0.31 ± 0.11 |
| C 10 µM | 2.35 ± 0.07 | 0.35 ± 0.16 |

Cell numbers were determined 12 days after repeated gymnotic transfers (4 × 72 h) of A549 cells using Luna FL™ Automated Cell Counter Fluorescence and Bright Field (Biozym, #872040) according to manufacturer's instructions.
A = untreated control, C = Seq. ID No. 218b, ± = SEM.

Conclusion

These observations indicate that reduced tumorous growth is associated with an increase in apoptotic cells. Notably, ID2, which is a possible therapeutic target gene in tumors, is reduced after gymnotic transfer of TGF-R$_{II}$ specific ASO Seq. ID No. 218b. Taken together, ASO Seq. ID No. 218b is efficient in minimizing proliferation rates and reduces tumor promoting gene expression.

Example 18: Effect of ASO Gymnotic Transfer on Proliferation of Several Tumor Cell Lines TGF-β signaling is a critical pathway in cancer development. On the one hand TGF-β promotes factors, which act tumor suppressive but on the other hand, this growth factor leads to stimulation of cell migration, cell invasion, cell proliferation, immune regulation, and promotes an environmental reorganization in advantage to progression and metastasis of tumor cells. Thus, TGF-β is a key target in cancer treatment. mRNA and protein levels of proliferation marker (Ki67) and cell numbers were determined after gymnotic uptake of inventive ASOs as markers of proliferation rate in tumor cells. Furthermore, mRNA levels of tumor suppressor gene p53 and of DNA-binding protein inhibitor 2 (ID2) were examined.

Description of Methods

Several tumor cell lines were cultured as described above (Table 10). For treating cells, medium was removed and replaced by fresh full medium in 24-well culture dishes (Sarstedt #83.1836.300) (30,000 cells/well), 6-well culture dishes (Sarstedt #83.3920.300) (50,000 cells/well) (0.5 ml for 24-well and 1 ml for 6-well dishes) and were incubated overnight at 37° C. and 5% $CO_2$. To analyze mRNA expression and influence on proliferation, cells were treated with Ref.1 (Scrambled control) and ASO Seq. ID No. 218b at concentrations of 2.5 µM and 10 µM and were incubated for 72 h at 37° C. and 5% $CO_2$. Treatment including medium replacement was repeated 3 times every 72 h (12 days in total). For harvesting, cells were washed twice with PBS and subsequently used for RNA isolation (24-well dishes), protein isolation (6-well dishes), or proliferation curve. Protocols for RNA and protein isolation were performed as described above. Before counting cells for proliferation curve, cells were analyzed by using light microscopy (Nikon, TS-100 F LED #MFA33500). Remaining cells were then harvested from 24-well dishes for determination of cell number. For this purpose, remaining cells were washed with PBS (2×), treated with accutase (500 µl/well) and incubated for 5-7 min at 37° C. Afterwards 500 µl medium was added and cell number was determined using Luna FL™ Automated Cell Counter Fluorescence and Bright Field (Biozym, #872040) according to manufacturer's instructions. Briefly, 18 µl of the cell suspension were added to 2 µl of acridine orange/propidium iodide assay viability kit (Biozym #872045). After 1 min of settling, 10 µl were added onto Cell Counting Slide (Biozym #872011). Cells were counted and calculated in distinction of alive and dead cells.

18.1 Results for Seq. ID No. 218b

Ki67 mRNA levels were efficiently decreased independently (A549, L3.6 µl, Panc-1) or dependently (HT-29, Panc-1, CaCo2) of used ASO concentrations, 12 days after gymnotic transfer (Table 40). Gene expression level of p53 was also affected in A549, HT-29, K562, KG-1, CaCo2 and TMK-1 by tested ASO (Table 50). Verification of reduced Ki67 protein expression was shown for A549, L3.6 µl, TMK-1, HT-29 and K562 (Table 51). Notably, ID2 mRNA expression showed a consistent efficiently and dose-dependently downregulation in A549, HT-29, K562 and TMK-1 cells mediated by ASO Seq. ID No. 218b (Table 51). In addition, ASO Seq. ID No. 218b resulted in a reduced proliferation rate of several tumor cell lines (Table 53). A dose-dependent decrease of cell number was recognized for HPAFII, MCF-7, KG1, K562, U937 and HTZ-19 cells. Lung cancer cells (A549) showed approx. 50% reduction of cell numbers elicited by ASO Seq. ID No. 218b. Reduced cell numbers were additionally confirmed by light microscopy for HPAFII, K562, MCF-7, Panc-1 and HTZ-1, 12 days after gymnotic transfer of ASO Seq. ID No. 218b (FIG. 24).

Comparable results are obtainable for the antisense-oligonucleotides of the Seq. ID No.s 141d, 141g, 141i, 143r, 143w, 143af, 143ag, 143ah, 143j, 143p, 143q, 233d, 234d, 235b, 235d, 237b, 237c, 237i, 237m, 238c, 238f, 239e, 240c, 241b, 242a, 246e, 247d, 248b, 248e, 248g, 152k, 152s, 152t, 152u, 152ab, 152ag, 152ah, 152ai, 249c, 249e, 250b, 250g, 251c, 251f, 252e, 253c, 254b, 255a, 259e, 260d, 261b, 261e, 261g, 262d, 262e, 209s, 209v, 209w, 209x, 209ai, 209an, 209at, 209au, 209av, 210o, 210v, 210w, 210x, 210ab, 210ac, 210ad, 210af, 210am, 263b, 263c, 263i, 263m, 264e, 264h, 265e, 266c, 267b, 268a, 272e, 273d, 274a, 274d, 274f, 275g, 275i, 276b, 276c, 276j, 276k, 277d, 277e, 278f, 279c, 280b, 281a, 218ad, 218n, 218t, 218u, 218v, 218ah, 218an, 218ao, 218ap, 220d, 221d, 222b, 222c, 222f, 223c, 223f, 224i, 224m, 225c, 225f, 226e, 227c, 213o, 213p, 213q, 213s, 213y, 213z, 213aa, 213af, 228b, 229a, 285d, 286d, 287d, 287e, 287f, 288e, 288i, 289d, 289h, 289o, 289p, 289q, 290c, 290f, 290i, 291c, 292c, 293b, and 294a. Most of the aforementioned antisense-oligonucleotides could not beat Seq. ID Nos. 218b and 218c, but are still far more advantageous than the state of the art antisense-oligonucleotides. Thus the antisense-oligonucleotides of the present invention are highly useful for the treatment of hyperproliferative diseases such as cancer and tumors.

TABLE 49 mRNA expression of proliferation marker Ki67.

Ki67
mRNA levels 12 days after repeated gymnotic transfer (4 × 72 h)

| Target Cell line | A549 n = 2 | HT-29 n = 2 | L3.6pl n = 2 | KG1 n = 1 | Panc-1 n = 1 | CaCo2 n = 1 |
|---|---|---|---|---|---|---|
| A | 1.00 ± 0.37 | 1.00 ± 0.00 | 1.00 ± 0.25 | 1.00 | 1.00 | 1.00 |
| B 2.5 μM | 0.92 ± 0.05 | 0.89 ± 0.46 | 0.93 ± 0.03 | 0.72 | 0.76 | 1.21 |
| B 10 μM | 0.96 ± 0.03 | 0.60 ± 0.11 | 0.96 ± 0.16 | 0.76 | 0.79 | 1.07 |
| C 2.5 μM | 0.55 ± 0.33 | 0.34 ± 0.11 | 0.42 ± 0.03 | 0.16 | 0.68 | 0.99 |
| C 10 μM | 0.57 ± 0.20 | 0.17 ± 0.02 | 0.64 ± 0.05 | 0.33 | 0.37 | 0.37 |

12 days after gymnotic transfer of ASO Seq. ID No. 218b in A549, HT-29, L3.6pl, KG1, Panc-1 and CaCo2 cells, Ki67 mRNA was decreased in all cell lines, respectively.
mRNA levels were determined relative to housekeeping gene GNB2L1 using quantitative real-time RT-PCR normalized to untreated control.
A = untreated control,
B = Ref. 1,
C = Seq. ID No. 218b,
± = SEM,
Statistics was calculated using the Ordinary-one-way-ANOVA followed by "Tukey's" multiple post hoc comparisons.

TABLE 50 mRNA expression of tumor suppressor p53.

p53
mRNA levels 12 days after repeated gymnotic transfer (4 × 72 h)

| Target Cell line | A549 n = 2 | HT-29 n = 1 | K562 n = 1 | KG1 n = 1 | TMK-1 n = 1 | CaCo2 n = 1 |
|---|---|---|---|---|---|---|
| A | 1.00 ± 0.31 | 1.00 | 1.00 | 1.00 | 1.00 ± 0.04 | 1.00 |
| B 2.5 μM | 1.06 ± 0.02 | 0.72 | 0.90 | 1.37 | 0.74 ± 0.11 | 0.82 |
| B 10 μM | 1.11 ± 0.92 | 0.68 | 1.35 | 0.87 | 0.71 ± 0.15 | 1.25 |
| C 2.5 μM | 0.27 ± 0.04 | 0.51 | 0.27 | 0.65 | 0.14* ± 0.14 | 0.99 |
| C 10 μM | 0.53 ± 0.07 | 0.32 | 0.46 | 0.67 | 0.21* ± 0.05 | 0.30 |

12 days after gymnotic transfer of ASO Seq. ID No. 218b in A549, HT-29, K562, KG1, CaCo2 and TMK-1 cells, p53 mRNA was decreased in all cell lines, respectively.
mRNA expression levels were determined relative to housekeeping gene GNB2L1 using quantitative real-time RT-PCR and then normalized to untreated control.
A = untreated control,
B = Ref. 1,
C = Seq. ID No. 218b,
± = SEM,
*p < 0.05 in reference to A,
Statistics was calculated using the Ordinary-one-way-ANOVA followed by "Tukey's" multiple post hoc comparisons.

TABLE 51 mRNA expression of ID2.

ID2
mRNA levels 12 days after repeated gymnotic transfer (4 × 72 h)

| Target Cell line | A549 n = 2 | HT-29 n = 1 | K562 n = 1 | TMK-1 n = 1 |
|---|---|---|---|---|
| A | 1.00 ± 0.03 | 1.00 | 1.00 ± 0.23 | 1.00 ± 0.23 |
| B 2.5 μM | 0.73 ± 0.01 | 0.93 | 0.97 ± 0.15 | 0.88 ± 0.15 |
| B 10 μM | 0.82 ± 0.15 | 1.00 | 0.82 ± 0.05 | 0.82 ± 0.05 |
| C 2.5 μM | 0.59 ± 0.01 | 0.31 | 0.70 ± 0.10 | 0.70 ± 0.10 |
| C 10 μM | 0.35 ± 0.02 | 0.25 | 0.29* ± 0.09 | 0.30* ± 0.09 |

12 days after gymnotic transfer of ASO Seq. ID No. 218b in A549, HT-29, K562 and TMK-1 cells, ID2 mRNA was dose-dependently downregulated in all cell lines, respectively.
mRNA expression levels were determined relative to housekeeping gene GNB2L1 using quantitative real-time RT-PCR and then normalized to untreated control.
A = untreated control, B = Ref.1, C = Seq. ID No. 218b, ± = SEM, *p < 0.05 in reference to A, Statistics was calculated using the Ordinary-one-way-ANOVA followed by "Tukey's" post hoc multiple comparisons.

TABLE 52

Densitometric analysis of Ki67 Western Blot.

Ki67
protein level 12 days after repeated gymnotic transfer (4 × 72 h)

| Target Cell line | A549 n = 1 | L3.6pl n = 2 | TMK-1 n = 2 | HT29 n = 2 | K562 n = 1 |
|---|---|---|---|---|---|
| A | 1.00 | 1.00 ± 0.00 | 1.00 ± 0.00 | 1.00 ± 0.00 | 1.00 |
| B 10 μM | 1.18 | 0.59 ± 0.00 | 0.75 ± 0.00 | 1.19 ± 0.68 | 1.05 |
| C 10 μM | 0.57 | 0.19 ± 0.17 | 0.53 ± 0.26 | 0.69 ± 0.05 | 0.35 |

Downregulation of Ki67 protein after gymnotic transfer with ASO Seq. ID No. 218b was recognized.
Protein level was quantified relative to housekeeping gene alpha-tubulin using Image Studio ™ Lite Software and normalized to untreated controls.

A = untreated control, B = Ref.1, C = Seq. ID No. 218b.

Statistics was calculated using the Ordinary-one-way-ANOVA followed by "Tukey's" post hoc comparisons.

TABLE 53

Cell numbers in several cancer cell lines 12 days after repeated gymnotic transfer (4 × 72 h).

| Cell Line | Treatment A (cell number × 10⁵) | | B 2.5 µM | | B 10 µM | |
|---|---|---|---|---|---|---|
| | a | d | a | d | a | d |
| A549 | 4.25 ± 0.50 | 0.47 ± 0.09 | | | 3.88 ± 0.95 | 0.31 ± 0.11 |
| HPAFII | 2.80 ± 0.33 | 0.35 ± 0.11 | 2.88 ± 2.04 | 0.36 ± 0.06 | 2.56 ± 0.45 | 0.39 ± 0.06 |
| KG1 | 17.40 ± 3.00 | 0.43 ± 0.16 | 16.5 ± 0.85 | 0.58 ± 0.24 | 13.80 ± 0.80 | 0.26 ± 0.17 |
| K562 | 10.93 ± 1.58 | 1.37 ± 0.40 | 7.44 ± 1.05 | 2.40 ± 0.62 | 6.40 ± 0.38 | 2.36 ± 0.30 |
| MCF-7 | 6.73 | 2.37 | 6.51 | 1.57 | 6.51 | 3.35 |
| U937 | 26.43 ± 2.05 | 7.04 ± 0.28 | 14.5 ± 2.73 | 2.88 ± 0.37 | 17.67 ± 0.50 | 2.36 ± 0.30 |
| Panc-1 | 2.16 ± 0.08 | 0.11 ± 0.02 | 1.82 ± 0.36 | 0.15 ± 0.04 | 2.98 ± 0.27 | 0.16 ± 0.02 |
| HTZ-19 | 2.06 ± 0.02 | 3.05 ± 0.36 | 2.57 ± 0.16 | 1.78 ± 0.15 | 2.55 ± 0.22 | 1.22 ± 0.15 |

| Cell Line | Treatment C 2.5 µM (cell number × 10⁵) | | C 10 µM | | n | p = |
|---|---|---|---|---|---|---|
| | a | d | a | d | | |
| A549 | | | 2.35 ± 0.07 | 0.35 ± 0.16 | 3 | |
| HPAFII | 0.66 ± 0.47 | 0.25 ± 0.07 | 0.20 ± 0.09 | 0.06 ± 0.02 | 2 | |
| KG1 | 10.90 ± 0.20 | 0.59 ± 0.18 | 7.63 ± 3.08 | 0.48*+ ± 0.14 | 3 | A vs. C 10 µM *p < 0.01 B 2.5 µM vs. C 10 µM +p < 0.01 C 10 µM vs. D 10 #p < 0.01 |
| K562 | 5.60 ± 0.08 | 2.66 ± 0.41 | 3.33 ± 0.54 | 0.62* ± 0.07 | 3 | A vs. C 10 µM *p < 0.01 |
| MCF-7 | 5.21 | 1.64 | 2.47 | 0.73 | 1 | |
| U937 | 11.34* ± 2.85 | 3.07 ± 0.97 | 7.56* ± 1.49 | 2.25 ± 0.44 | 3 | A vs. C 2.5 µM *p < 0.01 A vs. C 10 µM *p < 0.01 |
| Panc-1 | 1.15* ± 0.51 | 0.07 ± 0.02 | 1.20*+ ± 0.23 | 0.36 ± 0.02 | 3 | A vs. C 2.5 µM *p < 0.05 A vs. C 10 µM *p < 0.05 B 10 µM vs. C 10 µM +p < 0.01 |
| HTZ-19 | 1.78 ± 0.25 | 0.88 ± 0.09 | 1.17+ ± 0.14 | 0.49 ± 0.05 | 3 | B 10 µM vs. C 10 µM +p < 0.05 |

ASO Seq. ID No. 218b was transferred to several cancer cell lines.
Cell numbers were determined using Luna FL ™ Automated Cell Counter Fluorescence and Bright Field (Biozym, #872040) according to manufacturer's instructions.
A = untreated control,
B = Ref. 1,
C = Seq. ID No. 218b,
a = alive cells,
d = dead cells.
± = SEM.
Statistics was calculated using the Ordinary-one-way-ANOVA followed by "Tukey's" post hoc comparisons test.

Conclusion

Modulation of Ki67, p53 and ID2 mRNA by ASO Seq. ID No. 218b indicates a beneficial effect in dampening tumor expansion in several organs and with different origin. Ki67, ID2 and p53 are known to be upregulated and promote cell proliferation in different cancer types. Proliferation marker Ki67, p53 and ID2 were efficiently downregulated. Cell counting and light microscopy of several tumor cells 12 days after gymnotic transfer revealed ASO Seq. ID No. 218b as a potent agent to reduce cell proliferation.

Taken together, TGF-R$_{II}$ specific ASO Seq. ID No. 218b was efficiently reducing proliferation rates parallel to recognized mRNA modulations of Ki67, p53 and ID2. These data suggest that the inventive ASOs are promising drug candidates for dampening tumor cell progression and metastasis of tumor cells.

Example 19: Analysis of the Effect of the Antisense-Oligonucleotides to Angiogenesis in Several Tumor Cell Lines Modulation of angiogenesis is essential for organ growth and repair. An imbalance in blood vessel growth contributes to different diseases like e.g. tumor growth, ischemia, inflammatory and immune disorders. TGF-β is known to be a pro-angiogenic factor. This may be most relevant in inflammatory and neoplastic processes, when overshooting angiogenesis is responsible for disease progression. These effects may go hand in hand with TGF-β1 induced fibrosis. Therefore Inhibition of TGF-β signaling by TGFR$_{II}$ specific ASO may represent an adequate therapeutic approach.

To test this assumption, these ASOs were transferred to several tumor cell lines by gymnotic uptake. 12 days after repeated gymnotic transfers, cell supernatant was analyzed for protein levels of pro-angiogenic factors by multiplex analysis. This technology allowed investigation of multiple pro-angiogenic proteins (VEGF, Tie-2, FLt-1, PlGF and bFGF) by electro-chemiluminescence. Vascular endothelial growth factor (VEGF) is a potent tumor secreted cytokine that promotes angiogenesis and therewith contributes to e.g. tumor proliferation. Tie-2 is a protein which is expressed from actively growing blood vessels. Fms-like tyrosine kinase 1 (Flt-1), also known as vascular endothelial growth factor receptor 1 (VEGFR1), is a transmembrane tyrosine receptor kinase that is highly expressed in vascular endothelial cells and Placental Growth Factor (PlGF) acts together with VEGF and is upregulated under pathological conditions e.g. in tumor formation. Besides, basic Fibroblast Growth Factor (bFGF) is a growth factor that also induces angiogenesis. PAI-1 is a target gene of TGF-β and mediates scar formation and angiogenic effects of TGF-β. Therefore, PAI-1 demonstrates also a key factor for tumor invasion and metastasis. Patients showing a high PAI-1 concentration level are considered to a poor prognostic factor e.g. in breast cancer, lung, colorectal and gastric cancer. High PAI-1 concentrations also are a risk factor for diseases where thrombosis plays a role (e.g. myocardial infarction, stroke). Thus, PAI-1 mRNA regulation by TGF-β specific antisense oligonucleotides was also tested.

Description of Methods:

Tumor cell lines were cultured as described above (Table 10). For treating cells, medium was removed and replaced by fresh full medium in 24-well culture dishes (Sarstedt #83.1836.300) (30,000 cells/well) incubated overnight at 37° C. and 5% CO$_2$. The next day, Ref.1 (Scrambled control,) and ASO Seq. ID No. 218b (were added to refreshed medium at concentrations of 2.5 and 10 µM and were incubated for 72 h at 37° C. and 5% CO$_2$. Treatment including medium replacement was repeated 3 times every 72 h (12 days in total). Afterwards cell supernatant was collected and analyzed by a MesoScale Discovery® Assay (MSD Discovery). This technology allowed investigation of multiple pro-angiogenic proteins (VEGF, Tie-2, FLt-1, PlGF and bFGF) by electro-chemiluminescence. Experiment performance and information about the individual growth factors were extracted by manufacturer instructions (MSD MesoScale Discovery®, #K15198G). The results were evaluated by GraphPad Prism® 6.0 Software.

Afterwards, cells were washed twice with PBS and subsequently used for RNA isolation (24-well dishes) to analyze, whether gymnotic transfer of ASO may regulate mRNA levels of Plasminogen Activator inhibitor-1 (PAI-1) by real-time RT-PCR. Protocols and primers were used and listed as described before.

19.1 Results for Seq. ID 218b

Table 54 demonstrates that PAI-1 mRNA was downregulated in a dose-dependent manner in several tested cancer cells (A549: lung cancer, HPAFII: pancreatic adenocarcinoma, HT-29: colorectal adenocarcinoma, HTZ-19: melanoma, TMK-1: gastric carcinoma, THP-1: monocytic leukemia) after repeated gymnotic transfer of ASO Seq. ID No. 218b. In addition, VEGF protein levels in stimulated cell supernatants showed also a dose-dependent decrease in A549, HTZ-19, HPAFII and PC3M (prostatic adenocarcinoma). For HPAFII and PC3M cells downregulation was significant (Table 55). Influence of ASO Seq. ID No. 218b to bFGF confirmed observations for VEGF, meaning that ASO Seq. ID No. 218b is potent to suppress angiogenesis (Table 56) In A549 and PC3M results showed also a significant reduction of bFGF. Protein amount of PlGF in cell supernatants was only slightly but dose-dependently depressed in A549 and HTZ-19 cells. In PC3M cells basic endogenous PlGF level was higher than in all other tested cells and ASO effect was also stronger (Table 57). Finally, downregulation of Flt-1 protein in HT-29 cells (Table 58) and Tie-2 depression in HTZ-19 (ASO Seq. ID No. 218b 2.5 µM) and MCF-7 (mamma-carcinoma, 10 µM) could be detected (Table 59).

Comparable results are obtainable for the antisense-oligonucleotides of the Seq. ID No.s 141d, 141g, 141i, 143r, 143w, 143af, 143ag, 143ah, 143j, 143p, 143q, 152k, 152s, 152t, 152u, 152ab, 152ag, 152ah, 152ai, 209s, 209v, 209w, 209x, 209ai, 209an, 209at, 209au, 209av, 210o, 210v, 210w, 210x, 210ab, 210ac, 210ad, 210af, 210am, 213o, 213p, 213q, 213s, 213y, 213z, 213aa, 213af, 218ad, 218n, 218t, 218u, 218v, 218ah, 218an, 218ao, 218ap, 220d, 221d, 222b, 222c, 222f, 223c, 223f, 224i, 224m, 225c, 225f, 226e, 227c, 228b, 229a, 233d, 234d, 235b, 235d, 237b, 237c, 237i, 237m, 238c, 238f, 239e, 240c, 241b, 242a, 246e, 247d, 248b, 248e, 248g, 249c, 249e, 250b, 250g, 251c, 251f, 252e, 253c, 254b, 255a, 259e, 260d, 261b, 261e, 261g, 262d, 262e, 263b, 263c, 263i, 263m, 264e, 264h, 265e, 266c, 267b, 268a, 272e, 273d, 274a, 274d, 274f, 275g, 275i, 276b, 276c, 276j, 276k, 277d, 277e, 278f, 279c, 280b, 281a, 285d, 286d, 287d, 287e, 287f, 288e, 288i, 289d, 289h, 289o, 289p, 289q, 290c, 290f, 290i, 291c, 292c, 293b, and 294a. Most of the afore-mentioned antisense-oligonucleotides could not beat Seq. ID Nos. 218b and 218c, but are still far more advantageous than the state of the art antisense-oligonucleotides. Thus the antisense-oligonucleotides of the present invention are highly useful for the treatment of hyperproliferative diseases such as cancer and tumors.

TABLE 54 mRNA expression of PAI-1 12 days after gymnotic transfer of Seq. ID No. 218b in A549, HPAFII, HT-29, HTZ-19, TMK-1 and THP-1 cells.

| Target Cell line | PAI-1 mRNA levels 12 days after repeated gymnotic transfer (4 × 72 h) | | | | | |
|---|---|---|---|---|---|---|
| | A549 n = 3 | HPAFII n = 1 | HT-29 n = 2 | HTZ-19 n = 2 | TMK-1 n = 2 | THP-1 n = 2 |
| A | 1.00 ± 0.10 | 1.00 | 1.00 ± 0.11 | 1.00 ± 0.21 | 1.00 ± 0.06 | 1.00 ± 0.11 |
| B 2.5 µM | 1.28 ± 0.03 | 1.48 | 0.88 ± 0.27 | 0.99 ± 0.34 | 0.89 ± 0.04 | 1.14 ± 0.79 |

TABLE 54-continued mRNA expression of PAI-1 12 days after gymnotic transfer of Seq. ID No. 218b in A549, HPAFII, HT-29, HTZ-19, TMK-1 and THP-1 cells.

| | PAI-1 mRNA levels 12 days after repeated gymnotic transfer (4 × 72 h) | | | | | |
|---|---|---|---|---|---|---|
| Target Cell line | A549 n = 3 | HPAFII n = 1 | HT-29 n = 2 | HTZ-19 n = 2 | TMK-1 n = 2 | THP-1 n = 2 |
| B 10 µM | 1.03 ± 0.27 | 1.05 | 0.81 ± 0.08 | 1.30 ± 0.00 | 1.16 ± 0.00 | 1.21 ± 0.37 |
| C 2.5 µM | 0.91 ± 0.28 | 0.62 | 0.60 ± 0.13 | 1.13 ± 0.10 | 0.56 ± 0.04 | 0.83 ± 0.20 |
| C 10 µM | 0.56 ± 0.13 | 0.32 | 0.50 ± 0.18 | 0.77 ± 0.10 | 0.45 ± 0.23 | 0.09 ± 0.02 |

Regulation of PAI-1 gene expression is dose-dependently affected by ASO Seq. ID No. 218b in a manner for an improved disease prognosis.
mRNA levels were determined relative to housekeeping gene GNB2L1 using quantitative real-time RT-PCR and then normalized to untreated control.
A = untreated control,
B = Ref. 1,
C = Seq. ID No. 218b,
± = SEM,
Statistics was calculated using the Ordinary-one-way-ANOVA followed by "Tukey's" multiple post hoc comparisons.

TABLE 55

VEGF protein levels in cell supernatant 12 days after gymnotic transfer of Seq. ID No. 218b in A549, HPAFII, HTZ-19, PC3M cells by MesoScale Discovery ® Assay (MSD Mesoscale Discovery, #K15198G).

| | VEGF protein (pg/ml) 12 days after repeated gymnotic transfer (4 × 72 h) | | | |
|---|---|---|---|---|
| Target Cell line | A549 n = 1 | HPAFII n = 2 | HTZ-19 n = 2 | PC3M n = 2 |
| A | 8186 | 23266 ± 876 | 4411 ± 66 | 2657 ± 103 |
| B 2.5 µM | 8387 | 22278 ± 5711 | 3385 ± 57 | 1993 ± 5.4 |
| B 10 µM | 8623 | 20776 ± 497 | 4044 ± 21 | 813 ± 0.8 |
| C 2.5 µM | 8846 | 15479**++ ± 512 | 3444 ± 197 | 1266*+ ± 20.5 |
| C 10 µM | 6842 | 11214** ± 898 | 2882 ± 90 | 442** ± 14.3 |

Protein levels were determined by measuring electro-chemiluminescence.
A = untreated control, B = Ref.1, C = Seq. ID No. 218b, ± = SEM, *p < 0.05 and **p < 0.01 in reference to A, +p < 0.05 and ++p < 0.01 in reference to B 2.5 µM.
Statistics were calculated using the Ordinary-one-way-ANOVA followed by "Tukey's" multiple post hoc comparisons.

TABLE 56 bFGF protein levels in cell supernatant 12 days after gymnotic transfer of Seq. ID No. 218b in A549 and PC3M cells by MesoScale Discovery ® Assay (MSD Mesoscale Discovery, #K15198G).

| | bFGF protein (pg/ml) 12 days after repeated gymnotic transfer (4 × 72 h) | |
|---|---|---|
| Target Cell line | A549 n = 2 | PC3M n = 2 |
| A | 50.7 ± 2.9 | 21.2 ± 0.2 |
| B 2.5 µM | 54.4 ± 3.1 | 16.8 ± 0.1 |
| B 10 µM | 51.8 ± 2.7 | 14.7 ± 0.2 |
| C 2.5 µM | 26.7**++ ± 2.1 | 11.3**+ ± 0.0 |
| C 10 µM | 24.2 ± 3.4 | 7.6**++ ± 0.0 |

Protein levels were determined by measuring electro-chemiluminescence.
A = untreated control, B = Ref.1, C = Seq. ID No. 218b, ± = SEM, *p < 0.05 and **p < 0.01 in reference to A, +p < 0.05 and ++p < 0.01 in reference to B 2.5 µM, #p < 0.05 and ##p < 0.01 in reference to B 10 µM.
Statistics was calculated using the Ordinary-one-way-ANOVA followed by "Tukey's" multiple post hoc comparisons.

TABLE 57

PlGF protein levels in cell supernatant 12 days after gymnotic transfer of Seq. ID No. 218b in A549, HTZ-19 and PC3M cells by MesoScale Discovery ® Assay (MSD MesoScale Discovery ®, #K15198G).

| | PlGF protein (pg/ml) 12 days after repeated gymnotic transfer (4 × 72 h) | | |
|---|---|---|---|
| Target Cell line | A549 n = 2 | HTZ-19 n = 1 | PC3M n = 2 |
| A | 9.9 ± 0.4 | 11.6 | 61.7 ± 2.1 |
| B 2.5 µM | 9.6 ± 0.2 | 8.1 | 54.1 ± 1.9 |
| B 10 µM | 8.6 ± 0.1 | 8.4 | 59.5 ± 3.2 |
| C 2.5 µM | 8.2 ± 0.8 | 8.2 | 69.4 ± 2.4 |
| C 10 µM | 6.3** ± 0.9 | 6.5 | 45.0 ± 3.5 |

Protein levels were determined by measuring electro-chemiluminescence.
A = untreated control, B = Ref.1, C = Seq. ID No. 218b, ± = SEM, **p < 0.01 in reference to A, Statistics was calculated using the Ordinary-one-way-ANOVA followed by "Tukey's" multiple post hoc comparisons

TABLE 58

Flt-1 protein levels in cell supernatant 12 days after gymnotic transfer of Seq. ID No. 218b in HTZ-19 cells by MesoScale Discovery ® assay (MSD Mesoscale Discovery, #K15198G).

| Target Cell line | Flt-1 protein (pg/ml) 12 days after repeated gymnotic transfer (4 × 72 h) HT-29 n = 1 |
|---|---|
| A | 33.9 |
| B 2.5 μM | 27.7 |
| B 10 μM | 27.7 |
| C 2.5 μM | 18.2 |
| C 10 μM | 18.7 |

Protein levels were determined by measuring electro-chemiluminescence.
A = untreated control, B = Ref.1, C = Seq. ID No. 218b, ± = SEM, **p < 0.01 in reference to A, Statistics was calculated using the Ordinary-one-way-ANOVA followed by "Tukey's" multiple post hoc comparisons.

TABLE 59 shows Tie-2 protein levels in cell supernatant 12 days after gymnotic transfer of Seq. ID No. 218b in HTZ-19 and MCF-7 cells by MesoScale Discovery ® Assay (MSD Mesoscale Discovery, #K15198G).

| Target Cell line | Tie-2 protein (pg/ml) 12 days after repeated gymnotic transfer (4 × 72 h) | |
|---|---|---|
| | HTZ-19 n = 1 | MCF-7 n = 1 |
| A | 13.5 | 98.1 |
| B 2.5 μM | 6.2 | |
| B 10 μM | | 149.2 |
| C 2.5 μM | 3.2 | |
| C 10 μM | | 76.9 |

Protein levels were determined by measuring electro-chemiluminescence.
A = untreated control, B = Ref.1, C = Seq. ID No. 218b, ± = SEM, **p < 0.01 in reference to A, Statistics was calculated using the Ordinary-one-way-ANOVA followed by "Tukey's" multiple post hoc comparisons.

Conclusion

All analyzed pro-angiogenic factors (VEGF, bFGF, PlGF, Flt-1 and Tie-2) could be regulated by ASO Seq. ID No. 218b in a manner that would have a favorable impact on suppressing tumor progression and other pathological mechanisms dependent on enhanced angiogenesis. Furthermore, PAI-1 mRNA was dose-dependently reduced by ASO Seq. ID No. 218b. This factor, a TGF-β target gene and e.g. an approved prognostic marker in breast cancer, was also dose-dependently downregulated.

Taken together, all tested inventive ASOs were efficient in reducing angiogenic processes that favors tumor progression, metastasis, inflammation, and thrombosis. Thus, the inventive ASOs directed against TGF-$R_{II}$ are potent therapeutic candidate in different types of cancer and thrombosis related diseases.

Example 20: Analysis of the Effect of Inventive ASOs Upon Fibrosis

TGF-s is involved in a lot of processes such as cell proliferation, migration, wound healing, angiogenesis and cell-cell interactions. It's known from several studies, that this factor is often elevated during pathogenesis in several diseases including primary open angle glaucoma, Alzheimer disease, pulmonal fibrosis and diabetic nephropathy. These diseases are related to pathologic modifications in extracellular matrix (ECM) and the aktin-cytoskeleton. Often, these observed alterations correlate with severity disease progression and resistance to treatment (Epithelial Mesenchymal transition—EMT—in tumors). Connective tissue growth factor (CTGF) is a downstream-mediator of TGF-β and mediates fibrotic effects of TGF-β. Thus, it is shown that CTGF mediates deposition of ECM and modulates reorganization of aktin-cytoskeleton. To investigate whether the inventive ASOs contribute to a resolution of fibrotic processes by inhibiting TGF-β signaling, CTGF levels were evaluated in addition to fibronectin (FN) and Collagen IV (ColIV), which represent two main components of ECM in several different cancer cells. Furthermore, effects of ASOs on CTGF, FN and on aktin-cytoskeleton were examined in neural precursor (ReNcell CX) and human lung cancer (A549) cells.

20.1 Fibrosis in Neurodegeneration
Description of Methods

Cells were cultured as described before in standard protocol. For treatment, cells were seeded in 24-well culture dishes (Sarstedt #83.1836.300) (50,000 cells/well), 6-well culture dishes (Sarstedt #83.3920.300) (80,000 cells/well) and 8-well cell culture slide dishes (Sarstedt #94.6140.802) (10,000 cells/well) and were incubated overnight at 37° C. and 5% $CO_2$. To investigate a response of ReNcell CX® cells to TGF-β1 cells were treated after refreshing of medium with TGF-β1 (2 and 10 ng/ml, PromoCell #C63499) for 48 h, followed by mRNA analysis for CTGF. To figure out the ASO effect on CTGF and FN, ReNcell CX® cells, medium was removed and replaced by fresh full medium (1 ml for 6-well and 0.5 ml for 8-well). Ref. 1 (Scrambled control), ASO Seq. ID No. 218b and Seq.ID No. 218b were then added in medium at concentrations of 2.5 and 10 μM and respective analysis (real-time RT-PCR, Western Blot analysis and Immunocytochemistry) was performed after 96 h. To examine the ASO impact after investigation of pre-incubation with TGF-β1, medium was removed and replaced by fresh full medium (1 ml for 6-well dishes and 8-well cell culture slide dishes). Following exposition of TGF-β1 (10 ng/ml, 48 h) medium was changed, TGF-β1 (10 ng/ml), Ref.1 (10 μM), ASO with Seq. ID No. 218b (10 μM) and ASO with Seq. ID No. 218c (10 μM) were added in combination and in single treatment to cells. ReNcell CX® cells were then harvested 96 h after gymnotic transfer. Therefore, cells were washed twice with PBS and subsequently used for RNA (24-well dishes) and protein isolation (6-well dishes) or immunocytochemical examination of cells (in 8-well cell culture slide dishes). Protocols, antibodies, dilutions and primers were used as described before.

20.1.1 Results of TGF-β1 Effects on Neural Precursor Cells (ReNcell CX)

Nothing was known about reaction of ReNcell CX® to TGF-β1 exposure. Thus ReNcell CX® cells were treated for 48 h with TGF-β1 in two different concentrations (Table 60). Evaluation of real-time RT-PCR revealed a dose-dependent induction of CTGF- and TGF-β1 gene expression.

TABLE 60

CTGF and TGF-β1 mRNA expression 48 h after stimulation with TGF-β1.

| Cell line Target Time point | ReNcell CX mRNA levels after 48 h TGF-β1 treatment | |
|---|---|---|
| | CTGF 48 h n = 3 | TGF-β1 48 h n = 3 |
| A | 1.00 ± 0.43 | 1.00 ± 0.10 |
| E 2 ng/ml | 1.73 ± 0.92 | 1.34 ± 0.45 |
| E 10 ng/ml | 2.15 ± 1.14 | 1.85 ± 0.65 | mRNA levels were determined relative to housekeeping gene GNB2L1 using quantitative real-time RT-PCR and then normalized to untreated control.
A = untreated control, E = TGF-β1.
± = SEM, Statistics was calculated using the Ordinary-one-way-ANOVA followed by "Tukey's" multiple post hoc comparison.

Conclusion

ReNcell CX® cells showed a response to TGF-β1 exposure presenting self-induction of TGF-β1 and elevation of TGF-β1 target gene CTGF. Taken together, ReNcell CX® cells are ideal to examine questions addressing TGF-β effects.

20.1.2 Results for Seq. ID No. 218b 20.1.2.1 Effects of Gymnotic Transfer

Gymnotic transfer of ASO Seq. ID No. 218b results in a dose-dependent and significant reduction of CTGF and FN (Table 61). This impact of ASO Seq. ID No. 218b was verified for FN protein level. FN protein level was depressed by about 70% 96 h after gymnotic transfer of tested ASO, whereas TGF-β1 treatment of ReNcell CX® cells resulted in a 3.4-fold induction of FN (Table 62).

TABLE 61

Dose-dependent and significant downregulation of CTGF mRNA after gymnotic transfer with Seq. ID No. 218b in ReNcell CX ® cells.

| Cell line | ReNcell CX mRNA levels after gymnotic transfer | |
|---|---|---|
| Target Time point | CTGF 96 h, n = 3 | FN 96 h, n = 3 |
| A | 1.00 ± 0.04 | 1.00 ± 0.00 |
| B 2.5 μM | 0.97 ± 0.06 | 0.81 ± 0.14 |
| B 10 μM | 0.86 ± 0.17 | 0.67 ± 0.07 |
| C 2.5 μM | 0.66** ± 0.02 | 0.59 ± 0.02 |
| C 10 μM | 0.52** ± 0.02 | 0.39* ± 0.03 | mRNA levels were determined relative to housekeeping gene GNB2L1 using quantitative real-time RT-PCR and then normalized to untreated control.
A = untreated control, B = Ref.1, C = Seq. ID No. 218b.
± = SEM, *p < 0.05, **p < 0.01 in reference to A.
Statistics was calculated using the Ordinary-one-way-ANOVA followed by "Dunnett's" post hoc comparisons.

TABLE 62

Densitometric analysis after Western Blotting for Fibronectin.

| Cell line Target Time point | ReNcell CX protein levels after gymnotic transfer FN 96 h, n = 1 |
|---|---|
| A | 1.00 |
| B 2.5 μM | 1.06 |
| B 10 μM | 0.60 |
| C 2.5 μM | 0.46 |

TABLE 62-continued

Densitometric analysis after Western Blotting for Fibronectin.

| Cell line Target Time point | ReNcell CX protein levels after gymnotic transfer FN 96 h, n = 1 |
|---|---|
| C 10 μM | 0.30 |
| E 10 ng/ml | 3.43 |

Downregulation of FN protein 96 h after gymnotic transfer of ASO Seq. ID No. 218b in ReNcell CX ® cells could be recognized.
Protein level was determined relative to housekeeping gene alpha-Tubulin using Image Studio ™ Lite Software and was then normalized to untreated control.
A = untreated control, B = Ref.1, C = Seq. ID No. 218b.

Conclusion

ASO Seq. ID No. 218b was potent in downregulating mRNA levels of CTGF and FN in human neuronal precursor cells. ASO Seq. ID No. 218b treatment reduced FN protein, 96 h after gymnotic transfer. Thus, TGF-$R_{II}$ specific ASO mediates blocking of TGF-β induced fibrotic effects ReNcell CX® cells.

20.1.2.2 Effects of Gymnotic Transfer after TGF-β Pre-Incubation

To analyze whether ASO Seq. ID No. 218b is also potent in inhibiting fibrotic effects mediated by TGF-β under pathological conditions, ReNcell CX® cells were pre-incubated with TGF-β pre-incubation followed by gymnotic transfer for 96 h. Afterwards, determined mRNA levels of CTGF and FN indicate a strong anti-fibrotic effect of ASO Seq. ID No. 218b also after TGF-β induction of CTGF and FN gene expression (Table 63). Immunocytochemical staining for CTGF (FIG. 25A) and FN (FIG. 25B) confirmed data from mRNA analysis. In addition, staining with phalloidin for analysis of actin-cytoskeleton showed an induction of stress-fibers after TGF-β treatment, whereas ASO Seq. ID No. 218b was efficient in blocking TGF-β-mediated stress fiber induction (FIG. 25C).

TABLE 63

Downregulation of CTGF and FN mRNA after TGF-β1-pre-incubation followed by gymnotic transfer with Seq. ID No. 218b in ReNcell CX ® cells (compared to scrambled control).

| Cell line | ReNcell CX mRNA levels after 48 h TGF-β1 -> 96 h TGF-β1 + ASOs/single treatment | |
|---|---|---|
| Target Time point | CTGF 96 h, n = 3 | FN 96 h, n = 3 |
| A | 1.00 ± 0.04 | 1.00 ± 0.10 |
| B 10 μM | 0.85 ± 0.01 | 0.78 ± 0.20 |
| C 10 μM | 0.70* ± 0.25 | 0.44 ± 0.04 |
| E 10 ng/ml | 1.60** ± 0.15 | 2.25 ± 0.31 |
| E 10 ng/ml + B 10 μM | 1.71** ± 0.03 | 4.08*++ ± 0.90 |
| E 10 ng/ml + C 10 μM | 1.19++ ± 0.04 | 1.74++ ± 0.61 | mRNA levels were determined relative to housekeeping gene GNB2L1 using quantitative real-time RT-PCR and was then normalized to untreated control.
A = untreated control, B = Ref.1, C = Seq. ID No. 218b, E = TGF-β, ± = SEM, *p < 0.05, **p < 0.01 in reference to A.
Statistics was calculated using the Ordinary-one-way-ANOVA followed by "Dunnett's" post hoc comparisons.

Conclusion

ASO Seq. ID No. 218b showed strong anti-fibrotic effects under simulated pathological conditions (TGF-β1 pre-incubation). Aside from downregulation of FN as one main component of ECM, actin-cytoskeleton was also affected by inventive ASO in a manner that may be beneficial for a better outcome in fibrotic diseases.

20.1.3 Results for Seq. ID No. 218c 20.1.3.1 Effects of Gymnotic Transfer

Gymnotic transfer of ASO Seq. ID No. 218c results in a strong and significant reduction of CTGF mRNA after gymnotic transfer of 10 μM ASO Seq. ID No. 218c (Table 64).

TABLE 64

Downregulation of CTGF mRNA after gymnotic transfer of Seq. ID No. 218c in ReNcell CX ® cells.

| Cell line<br>Target<br>Time point | ReNcell CX<br>mRNA levels after gymnotic transfer<br>CTGF<br>96 h, n = 3 |
|---|---|
| A | 1.00 ± 0.10 |
| B 2.5 μM | 0.88 ± 0.08 |
| B 10 μM | 0.89 ± 0.07 |
| D 2.5 μM | 0.48 ± 0.08 |
| D 10 μM | 0.17* ± 0.02 | mRNA levels were determined relative to housekeeping gene GNB2L1 using quantitative real-time RT-PCR and then normalized to untreated control.
A = untreated control, B = Ref.1, D = Seq. ID No. 218c.
± = SEM, *p < 0.05 in reference to A.
Statistics was calculated using the Ordinary-one-way-ANOVA followed by "Dunnett's" post hoc comparisons.

Conclusion

ASO Seq. ID No. 218c was efficient in dose-dependent reduction of CTGF mRNA.

20.1.3.2 Effects of Gymnotic Transfer after TGF-β Pre-Incubation

Results for gymnotic transfer for ASO Seq. ID 218c followed by TGF-β1 pre-incubation verified an effective blockage of TGF-β1 induced effects on CTGF mRNA levels (Table 65). ASO was such potent in blocking TGF-β1 effect on CTGF that combination treatment is comparable to ASO Seq. ID No. 218c single treatment.

TABLE 65

CTGF mRNA level after TGF-β1 pre-incubation following gymnotic transfer of Seq. ID No. 218c and parallel TGF-β1 treatment in ReNcell CX ® cells. Data confirmed an effective blocking of TGF-β1 induced effects on CTGF mRNA level by ASO Seq. ID No. 218c in comparison to combination treatments. mRNA levels were determined relative to housekeeping gene GNB2L1 using quantitative real-time RT-PCR and then normalized to untreated control.

| Cell line | Target<br>Time point<br>ReNcell CX<br>mRNA levels 48 h TGF-β1 –> 96 h TGF-β1 +<br>ASOs/single treatment<br>CTGF<br>n = 3 |
|---|---|
| A | 1.00 ± 0.03 |
| B 10 μM | 0.85 ± 0.01 |
| D 10 μM | 0.17* ± 0.02 |
| E 10 ng/ml | 1.39 ± 0.08 |
| E 10 ng/ml + B 10 μM | 1.25 ± 0.44 |
| E 10 ng/ml + D 10 μM | 0.23* ± 0.02 |

A = untreated control,
B = Ref. 1,
D = Seq. ID No. 218c,
E = TGF-β1.
± = SEM,
*p < 0.05 in reference to A.
Statistics was calculated using the Ordinary-one-way-ANOVA followed by "Dunnett's" post hoc comparisons.

Conclusion

ASO Seq. ID No. 218c showed a strong downregulation of CTGF mRNA and protein even under artificial pathological conditions (TGF-β1 pre-incubation).

Taken together, aside from strong anti-fibrotic effects, TGF-$R_{II}$ specific ASOs showed a modulation of actin-cytoskeleton. Induction of stress fibers may cause an elevation of cell rigidity and stiffness that may play a role e.g. in Alzheimer disease and other Neurodegenerative Disorders. ECM deposition may also mediate fast pathogenic modifications e.g. in primary open angle glaucoma. Thus, reduction of ECM deposition and suppression of stress fiber formation may be profitable for a better prognosis in fibrotic related neurological disorders. Thereby, TGF-$R_{II}$ specific ASOs are potent therapeutic agents for the treatment e.g. Alzheimer disease and primary open angle glaucoma.

20.2. Pulmonary Fibrosis

Description of Methods

For investigation of ASO effects to ECM and actin-cytoskeleton in lung, human lung cancer (A549) cells were examined and cultured as described before. For treatment, cells were seeded in 24-well culture dishes (Sarstedt #83.1836.300) (50,000 cells/well), 6-well culture dishes (Sarstedt #83.3920.300) (80,000 cells/well) and 8-well cell culture slide dishes (Sarstedt #94.6140.802) (10,000 cells/well) and were incubated overnight at 37° C. and 5% $CO_2$. To investigate a response of A549 cells to TGF-β1 cells were treated after refreshing of medium with TGF-β1 (2 and 10 ng/ml, PromoCell #$C_{63499}$) for 48 h following mRNA analysis for CTGF. To investigate the ASO effect on CTGF and FN A549 cells, medium was removed and replaced by fresh full medium (1 ml for 6-well and 0.5 ml for 8-x-well). Ref. 1 (scrambled control), ASO Seq. ID No. 218b and Seq.ID No. 218b were then added in medium at concentrations of 2.5 and 10 μM and respective analysis (real-time RT-PCR, Western Blot analysis and Immunocytochemistry) was performed after 72 h in ReNcell CX® cells. To show possible ASO impact after pre-incubation with TGF-β1, medium was removed and replaced by fresh full medium (1 ml for 6-well dishes and 8-well cell culture slide dishes). Following exposition of TGF-β1 (10 ng/ml, 48 h) medium was changed, TGF-β1 (10 ng/ml), Ref.1 (10 μM), ASO with Seq. ID No. 218b (10 μM) and ASO with Seq. ID No. 218c (10 μM) was added in combination and in single treatment to cells. A549 cells were then harvested 72 h after gymnotic transfer. Therefore, cells were washed twice with PBS and subsequently used for RNA (24-well dishes) and protein isolation (6-well dishes) or immunocytochemical examination of cells (in 8-well cell culture slide dishes). Protocols, used antibodies, dilutions and primers were as described before.

20.2.1 Results of TGF-β1 Effects on Lung Cancer Cells (A549)

To investigate the ability of A549 cells to react to TGF-β1 exposure, cells were treated for 48 h with TGF-β1 in two different concentrations (Table 66). Evaluation of real-time RT-PCR revealed for CTGF and TGF-β1 itself a dose-dependent induction of gene expression.

TABLE 66

Induced CTGF and TGF-β1 mRNA expression 48 h after stimulation with TGF-β1 in A549 cells. mRNA expression levels were determined relative to housekeeping gene GNB2L1 using quantitative real-time RT-PCR and then normalized to untreated control.

| | Cell line A549 mRNA levels after 48 h TGF-β1 treatment | |
|---|---|---|
| Target<br>Time point | CTGF<br>48 h,<br>n = 3 | TGF-β1<br>48 h,<br>n = 3 |
| A | 1.00 ± 0.23 | 1.00 ± 0.31 |
| E 2 ng/ml | 2.44* ± 0.18 | 1.60 ± 0.34 |
| E 10 ng/ml | 11.35**++ ± 0.52 | 2.37 ± 0.36 |

A = untreated control,
E = TGF-β1.
± = SEM,
*p < 0.05 and
**p < 0.01 in reference to A,
++p < 0.05 in reference to E 2 ng/ml.
Statistics was calculated using the Ordinary-one-way-ANOVA followed by "Tukey's" multiple post hoc comparison.

Conclusion

A549 cells showed a dose-dependent and significant mRNA upregulation of CTGF upon TGF-β1 exposure. In addition, self-induction of TGF-β1 was observed. Taken together, A549 cells are a good model to examine questions addressing TGF-f effects in lung and lung cancer.

20.2.2 Results for Seq. ID No. 218b 20.2.2.1 Results for Effects of Gymnotic Transfer Gymnotic transfer of ASO Seq. ID No. 218b causes a dose-dependent and highly significant reduction of CTGF gene expression (Table 67). FN mRNA level was also affected by tested ASO but not dose-dependently. In contrast, staining against FN revealed a dose-dependent reduction of FN in comparison to scrambled control (FIG. 260A). Furthermore, ASO and TGF-β impact on actin-cytoskeleton was examined. FIG. 26B showed an induction of actin-fibers including stress-fiber formation after TGF-β1 treatment in A549 cells in doss-dependent manner, whereas signal after gymnotic transfer of ASO Seq. ID No. 218b in A549 cells was significantly downregulated parallel to recognized reversion of TGF-β1-mediated effects. For protein analysis a proper downregulation of CTGF parallel to an inhibition of pErk1/2 by which CTGF mediates its fibrotic effects could have been shown (Table 68). Furthermore, 72 h after gymnotic transfer of ASO Seq. ID No. 218b a decrease of both ECM main components FN and ColIV was remarkable (Table 68).

TABLE 67

Dose-dependent and significant downregulation of CTGF mRNA after gymnotic transfer with Seq. ID No. 218b in A549 cells. mRNA levels were determined relative to housekeeping gene GNB2L1 using quantitative real-time RT-PCR and then normalized to untreated control.

| | Cell line A549 mRNA levels after gymnotic transfer | |
|---|---|---|
| Target<br>Time point | CTGF<br>72 h,<br>n = 3 | FN<br>72 h,<br>n = 3 |
| A | 1.00 ± 0.08 | 1.00 ± 0.07 |
| B 2.5 μM | 0.87 ± 0.06 | 1.08 ± 0.02 |
| B 10 μM | 0.80 ± 0.03 | 0.87 ± 0.08 |
| C 2.5 μM | 0.60** ± 0.04 | 0.77 ± 0.17 |
| C 10 μM | 0.39** ± 0.03 | 0.74 ± 0.16 |

A = untreated control,
B = Ref. 1,
C = Seq. ID No. 218b.
± = SEM,
**p < 0.01 in reference to A.

Statistics was calculated using the Ordinary-one-way-ANOVA followed by "Dunnett's" post hoc comparisons.

TABLE 68

Densitometric analysis after CTGF, FN, ColIV and pErk11/2 Western Blot: 72 h after gymnotic transfer with ASO Seq. ID No 218b in A549. Protein level was determined relative to housekeeping gene alpha-Tubulin using Image Studio ™ Lite Software and was then normalized to untreated control.

| | Cell line A549 protein levels after gymnotic transfer | | | |
|---|---|---|---|---|
| Target<br>Time point | CTGF<br>72 h<br>n = 1 | FN<br>72 h<br>n = 1 | ColIV<br>72 h<br>n = 1 | pErk1/2<br>72 h<br>n = 2 |
| A | 1.00 | 1.00 | 1.00 | 1.00 ± 0.00 |
| B 2.5 μM | 0.91 | 0.89 | 1.19 | 1.00 ± 0.14 |
| B 10 μM | 1.31 | 0.76 | 0.87 | 0.98 ± 0.02 |
| C 2.5 μM | 0.05 | 0.81 | 1.16 | 0.67 ± 0.26 |
| C 10 μM | 0.09 | 0.46 | 0.65 | 0.61 ± 0.13 |

A = untreated control,
B = Ref. 1,
C = Seq. ID No. 218b.

Conclusion

Gymnotic transfer of Seq. ID No. 218b was efficient in modulating factors which are involved in ECM deposition and actin-cytoskeleton reorganization in human lung cells.

20.2.2.2 Results for Effects of Gymnotic Transfer after TGF-β1 Pre-Incubation

Results for gymnotic transfer of ASO Seq. ID 218b following TGF-β1 pre-incubation verified an effective blockage of strong TGF-β1 induced effects on CTGF and FN mRNA levels (Table 69). Immunocytochemical staining against CTGF (FIG. 27A) and FN (FIG. 27B) confirmed mRNA detection on protein level.

TABLE 69

CTGF and FN mRNA level after TGF-β1-pre-incubation following gymnotic transfer of Seq. ID No. 218b and parallel TGF-β1 treatment in A549 cells. Data confirmed an effective blocking of TGF-β1 induced effects on CTGF and FN mRNA levels by ASO Seq. ID No. 218b in comparison to combination treatments. mRNA levels were determined relative to housekeeping gene GNB2L1 using quantitative real-time RT-PCR and then normalized to untreated control.

| Cell line | Target<br>Time point<br>A549<br>mRNA levels 48 h TGF-β1 -> 72 h TGF-β1 + ASOs/single treatment | |
|---|---|---|
| | CTGF<br>n = 5 | FN<br>n = 3 |
| A | 1.00 ± 0.22 | 1.00 ± 0.45 |
| B 10 μM | 0.89 ± 0.19 | 1.02 ± 0.37 |
| C 10 μM | 0.52 ± 0.05 | 0.35 ± 0.06 |
| E 10 ng/ml | 6.92* ± 2.32 | 2.92 ± 1.02 |
| E 10 ng/ml + B 10 μM | 8.79** ± 2.72 | 2.90 ± 0.56 |
| E 10 ng/ml + C 10 μM | 2.53 ± 0.59 | 1.18 ± 0.28 |

A = untreated control,
B = Ref. 1,
C = Seq. ID No. 218b,
E = TGF-β1.
± = SEM,
*p < 0.05,
**p < 0.01 in reference to A.
Statistics was calculated using the Ordinary-one-way-ANOVA followed by "Dunnett's" post hoc comparisons.

Conclusion

ASO Seq. ID No. 218b was efficient in mediating anti-fibrotic effects in A549 cells under artificial pathological conditions mimicked excessive concentrations of TGF-β1.

20.2.3 Results for Seq. ID No. 218c 20.2.3.1 Results for Effects of Gymnotic Transfer Gymnotic transfer of ASO Seq. ID No. 218c mediates a strong dose-dependent and significant reduction of CTGF mRNA 72 h after gymnotic transfer in A549 cells (Table 70).

TABLE 70

Downregulation of CTGF mRNA 72 h after gymnotic transfer of Seq. ID No. 218c in A549 cells. mRNA levels were determined relative to housekeeping gene GNB2L1 using quantitative real-time RT-PCR and then normalized to untreated control.

| Target<br>Time point | Cell line<br>A549<br>mRNA level after gymnotic transfer<br>CTGF<br>72 h<br>n = 4 |
|---|---|
| A | 1.00 ± 0.08 |
| B 2.5 μM | 0.97 ± 0.07 |
| B 10 μM | 0.85 ± 0.06 |
| D 2.5 μM | 0.49** ± 0.05 |
| D 10 μM | 0.31** ± 0.03 |

A = untreated control,
B = Ref. 1,
D = Seq. ID No. 218c.
± = SEM,
**p < 0.01 in reference to A.
Statistics were calculated using the Ordinary-one-way-ANOVA followed by "Dunnett's" post hoc comparisons.

Conclusion

Gymnotic transfer of ASO Seq. ID No. 218c was efficient in reducing mRNA of TGF-β downstream-mediator CTGF.

20.2.2.2 Results for Effects of Gymnotic Transfer after TGF-β Pre-Incubation

Results for gymnotic transfer for ASO Seq. ID No. 218c following TGF-β1 pre-incubation verified an effective blockage of strong TGF-β1 induced effects on CTGF mRNA levels (Table 71). Immunocytochemical staining against CTGF confirmed these findings on protein level (FIG. 28).

TABLE 71

CTGF mRNA levels after TGF-β1 pre-incubation followed by gymnotic transfer of Seq. ID No. 218c and parallel TGF-β1 treatment in A549. Data verified an effective blockage of TGF-β1 induced effects on CTGF mRNA levels by ASO Seq. ID No. 218c in comparison to combination treatments. mRNA levels were determined relative to housekeeping gene GNB2L1 using quantitative real-time RT-PCR and then normalized to untreated control.

| Cell line | Target<br>Time point<br>A549<br>48 h TGF-β1 -> 72 h TGF-β1 + ASOs/single treatment<br>CTGF<br>n = 3 |
|---|---|
| A | 1.00 ± 0.05 |
| B 10 μM | 0.86 ± 0.11 |
| D 10 μM | 0.53 ±0.10 |
| E 10 ng/ml | 4.71 ±1.76 |
| E 10 ng/ml + B 10 μM | 5.89* ±2.16 |
| E 10 ng/ml + D 10 μM | 0.86++ ± 0.06 |

A = untreated control,
B = Ref. 1,
D = Seq. ID No. 218c,
E = TGF-β1.
± = SEM,
**p < 0.01 in reference to A,
++p < 0.01 in reference to E + B.
Statistics was calculated using the Ordinary-one-way-ANOVA followed by "Tukey's" post hoc comparisons.

Conclusion

ASO Seq. ID 218c was potent in mediating anti-fibrotic effects in A549 cells under artificial pathological conditions mimicked by excessive TGF-β1 concentrations.

Taken together, ASO Seq. ID 218c is an effective therapeutic agent, because pathology of lung fibrosis could be slowed down by reducing CTGF, FN and CollV. In addition, stress fiber formation can be reduced effectively by TGF-R$_{II}$ specific ASO, making inventive ASOs ideal therapeutic agents.

20.3 Effects on Several Cancer Cells

Description of Methods

For investigation of ASO effects addressing ECM (CTGF, FN, CollV) cells were used and cultured as described before in standard protocol (Table 10). For treatment, cells were seeded in 24-well culture dishes (Sarstedt #83.1836.300) (30,000 cells/well), 6-well culture dishes (Sarstedt #83.3920.300) (50,000 cells/well) and were incubated overnight at 37° C. and 5% $CO_2$. To analyze mRNA expression and influence on CTGF, FN and CollV mRNA and protein levels cells were treated with Ref.1 (Scrambled control) or ASO Seq. ID No. 218b at concentrations of 2.5 and 10 μM and were incubated for 72 h at 37° C. and 5% $CO_2$. Treatment including medium replacement was repeated 3 times every 72 h (12 days in total). For harvesting, cells were washed twice with PBS and subsequently used for RNA isolation (24-well dishes) or protein isolation (6-well dishes). Protocols for RNA and protein isolation as well as used antibodies and dilutions were performed as described above.

20.3.1 Results for Seq. ID No. 218b

Anti-fibrotic effects were detected by analysis of CTGF, FN, ColIV mRNA and protein levels. CTGF mRNA (Table 72) was dose-dependently reduced by Seq. ID No. 218b in HT-29, HTZ-19, MCF-7 and THP-1 cells. For KG-1 cells downregulation of TGF-β downstream-mediator was recognized for 2.5 μM ASO Seq. ID No. 218b. For A549, Panc-1 and CaCo2 cells a decrease of FN was demonstrated (Table 73) in accordance to a dose-dependently decline of ColIV mRNA (Table 74) in THP-1, HTZ-19 and L3.6 μl cells (Table 65). Western Blot analysis revealed a strong reduction of CTGF protein in HT-29, MCF-7, TMK-1 and L3.6 μl cells. Result for MCF-7 was significant (Table 75). In addition, phosphorylation of Erk1/2 in A549 and TMK-1 cells was inhibited by ASO Seq. ID No. 218b. pErk1/2 is normally activated by CTGF to induce TGF-β mediated fibrotic effects (Table 76). For FN (A549, MCF-7, HT-29, HTZ-19, HPAFII) and Col IV (A549, HTZ-19, HPAFII, PC3M) (Table 77 and 78), the two main components of ECM, protein levels were minimized by about 50%.

TABLE 72 mRNA expression of CTGF 12 days after gymnotic transfer of Seq. ID No. 218b in HT-29, HTZ-19, KG1, MCF-7 and THP-1 cells. CTGF mRNA was decreased after gymnotic transfer of Seq. ID No. 218b for all tested cell lines. mRNA levels were determined relative to housekeeping gene GNB2L1 using quantitative real-time RT-PCR and then normalized to untreated control.

| | Target CTGF mRNA levels 12 days after repeated gymnotic transfer (4 × 72 h) | | | | |
|---|---|---|---|---|---|
| Cell line | HT-29 n = 2 | HTZ-19 n = 1 | KG-1 n = 1 | MCF-7 n = 1 | THP-1 n = 2 |
| A | 1.00 ± 0.28 | 1.00 | 1.00 | 1.00 | 1.00 ± 0.28 |
| B 2.5 μM | 0.68 ± 0.11 | 1.30 | | 0.93 | 0.99 ± 0.68 |
| B 10 μM | 0.65 ± 0.03 | 1.20 | 0.88 | 0.91 | 1.15 ± 0.34 |
| C 2.5 μM | 0.40 ± 0.20 | 0.64 | | 0.24 | 0.98 ± 0.11 |
| C 10 μM | 0.33 ± 0.19 | 0.55 | 0.26 | 0.22 | 0.09 ± 0.03 |

A = untreated control,
B = Ref. 1,
C = Seq. ID No. 218b,
± = SEM,
Statistics was calculated using the Ordinary-one-way-ANOVA followed by "Tukey's" multiple post hoc comparisons.

TABLE 73 mRNA expression of FN 12 days after gymnotic transfer of Seq. ID No. 218b in A549, Panc-1 and CaCo2 cells. FN mRNA was decreased after gymnotic transfer of Seq. ID No. 218b for all tested cell lines. mRNA levels were determined relative to housekeeping gene GNB2L1 using quantitative real-time RT-PCR and then normalized to untreated control.

| | Target FN mRNA levels 12 days after repeated gymnotic transfer (4 × 72 h) | | |
|---|---|---|---|
| Cell line | A549 n = 2 | Panc-1 n = 1 | CaCo2 n = 2 |
| A | 1.00 ± 0.39 | 1.00 | 1.00 ± 0.30 |
| B 2.5 μM | 0.83 ± 0.08 | 1.29 | 0.55 ± 0.13 |
| B 10 μM | | | 1.00 ± 0.76 |
| C 2.5 μM | 0.35 ± 0.20 | 0.15 | 0.73 ± 0.54 |
| C 10 μM | | | 0.18 ± 0.17 |

A = untreated control,
B = Ref. 1,
C = Seq. ID No. 218b,
± = SEM,
**p < 0.01 in reference to A.
Statistics was calculated using the Ordinary-one-way-ANOVA followed by "Tukey's" multiple post hoc comparisons.

TABLE 74 mRNA expression of ColIV 12 days after gymnotic transfer of Seq. ID No. 218b in A549, HTZ-19, THP-1, L3.6pl, Panc-1 and CaCo2 cells.

| | Col IV mRNA levels 12 days after repeated gymnotic transfer (4 × 72 h) | | | | | |
|---|---|---|---|---|---|---|
| Target Cell line | A549 n = 2 | THP-1 n = 2 | HTZ-19 n = 1 | L3.6pl n = 2 | Panc-1 n = 1 | CaCo2 n = 2 |
| A | 1.00 ± 0.00 | 1.00 ± 0.22 | 1.00 | 1.00 ± 0.20 | 1.00 | 1.00 ± 0.71 |
| B 2.5 μM | 1.18 ± 0.31 | 0.71 ± 0.25 | 0.94 | 0.83 ± 0.09 | 0.98 | 1.37 ± 0.19 |
| B 10 μM | 1.11 ± 0.60 | 0.61 ± 0.03 | | 0.91 ± 0.29 | 0.57 | 2.61 ± 0.01 |

TABLE 74-continued mRNA expression of ColIV 12 days after gymnotic transfer of Seq. ID No.
218b in A549, HTZ-19, THP-1, L3.6pl, Panc-1 and CaCo2 cells.

Col IV
mRNA levels 12 days after repeated gymnotic transfer (4 × 72 h)

| Target Cell line | A549 n = 2 | THP-1 n = 2 | HTZ-19 n = 1 | L3.6pl n = 2 | Panc-1 n = 1 | CaCo2 n = 2 |
|---|---|---|---|---|---|---|
| C 2.5 µM | 0.84 ± 0.02 | 0.65 ± 0.19 | 0.51 | 1.14 ± 0.13 | 0.59 | 1.30 ± 0.03 |
| C 10 µM | 0.75 ± 0.02 | 0.30 ± 0.13 |  | 0.69 ± 0.05 | 0.30 | 0.57 ± 0.14 |

ColIV mRNA was decreased after gymnotic transfer of Seq. ID No. 218b for all tested cell lines.
mRNA levels were determined relative to housekeeping gene GNB2L1 using quantitative real-time RT-PCR and then normalized to untreated control.
A = untreated control,
B = Ref. 1,
C = Seq. ID No. 218b,
± = SEM,
Statistics was calculated using the Ordinary-one-way-ANOVA followed by "Tukey's" multiple post hoc comparisons.

TABLE 75

Densitometric analysis after Western Blotting in HT-29, MCF-7, L3.6pl and TMK-1 cells 12 days after gymnotic transfer of Seq. ID No. 218b. Downregulation of CTGF protein by ASO Seq. ID No. 218b could be recognized. Protein levels were determined relative to housekeeping gene alpha-Tubulin using Image Studio ™ Lite Software and was then normalized to untreated control.

Target
CTGF
protein levels 12 days after repeated gymnotic transfer (4 × 72 h)

| Cell line | HT-29 n = 1 | MCF-7 n = 2 | TMK-1 n =1 | L3.6pl n = 1 |
|---|---|---|---|---|
| A | 1.00 | 1.00 ± 0.0 | 1.00 | 1.00 |
| B 10 µM | 1.19 | 1.12 ± 0.11 | 0.85 | 0.93 |
| C 10 µM | 0.50 | 0.22**++ ± 0.03 | 0.38 | 0.22 |

A = untreated control,
B = Ref. 1,
C = Seq. ID No. 218b.
Statistics was calculated using the Ordinary-one-way-ANOVA followed by "Tukey's" multiple post hoc comparisons.

TABLE 76

Densitometric analysis after Western Blotting in A549 and TMK-1 cells 12 days after gymnotic transfer of Seq. ID No. 218b. Downregulation of pErk1/2 protein by ASO Seq. ID No. 218b was determined. Quantification of protein level was done relative to housekeeping gene alpha-Tubulin using Image Studio ™ Lite Software and was then normalized to untreated control.

Target
pErk1/2
protein levels 12 days after repeated gymnotic transfer (4 × 72 h)

| Cell line | A549 n = 1 | TMK-1 n =1 |
|---|---|---|
| A | 1.00 | 1.00 |
| B 10 µM | 1.21 | 1.14 |
| C 10 µM | 0.58 | 0.76 |

A = untreated control,
B = Ref. 1,
C = Seq. ID No. 218b.
Statistics was calculated using the Ordinary-one-way-ANOVA followed by "Tukey's" multiple post hoc comparisons.

TABLE 77

Densitometric analysis after Western Blotting in A549, MCF-7, HT-29, HTZ-19 and HPAFII cells 12 days after gymnotic transfer of Seq. ID No. 218b. Downregulation of FN protein by ASO Seq. ID No. 218b was determined. Quantification of protein level was done relative to housekeeping gene alpha-Tubulin using Image Studio ™ Lite Software and was then normalized to untreated control.

Target
FN
protein levels 12 days after repeated gymnotic transfer (4 × 72 h)

| Cell line | A549 n = 1 | MCF-7 n = 2 | HT-29 n = 1 | HTZ-19 n = 1 | HPAFII n = 1 |
|---|---|---|---|---|---|
| A | 1.00 | 1.00 ± 0.22 | 1.00 | 1.00 | 1.00 |
| B 10 µM | 1.10 | 1.08 ± 0.25 | 0.81 | 1.20 | 1.12 |
| C 10 µM | 0.56 | 0.69 ± 0.18 | 0.40 | 0.83 | 0.56 |

A = untreated control,
B = Ref. 1,
C = Seq. ID No. 218b.
Statistics was calculated using the Ordinary-one-way-ANOVA followed by "Tukey's" multiple post hoc comparisons.

TABLE 78

Densitometric analysis after Western Blotting in A549, MCF-7, HT-29, HTZ-19 and HPAFII cells 12 days after gymnotic transfer of Seq. ID No. 218b. Downregulation of FN protein by ASO Seq. ID No. 218b was determined. Protein levels were analyzed relative to housekeeping gene alpha-Tubulin using Image Studio ™ Lite Software and was then normalized to untreated control.

Target
Col IV
protein levels 12 days after repeated gymnotic transfer (4 × 72 h)

| Cell line | A549 n = 1 | HTZ-19 n = 1 | HPAFII n = 1 | PC3M n = 1 |
|---|---|---|---|---|
| A | 1.00 | 1.00 | 1.00 | 1.00 |
| B 10 µM | 1.31 | 1.01 | 1.05 | 1.07 |
| C 10 µM | 0.61 | 0.36 | 0.76 | 0.43 |

A = untreated control,
B = Ref. 1,
C = Seq. ID No. 218b.
Statistics was calculated using the Ordinary-one-way-ANOVA followed by "Tukey's" multiple post hoc comparisons.

Conclusion

Increased deposition of ECM mediated by TGF-β1, through its downstream-mediator CTGF, could be efficiently reversed by TGF-R$_{II}$ specific inventive ASOs in different tumor cell lines. A reduced level of ECM components could contribute to a less aggressive in tumor progression. Taken together, tested ASOs may demonstrate a new therapeutic strategy in different fibrosis-associated diseases.

Example 21: Threshold for Toxicity of Inventive ASOs by Chronic Intracerebroventricular Administration Using a Dose-Escalation Paradigm in Cynomolgus To evaluate the ideal dose range for the GLP-toxicity study, a pre-experiment using chronic intracerebroventricular (icv) antisense-oligonucleotide (ASO) administration with escalating doses was performed in Cynomolgus monkeys. During the administration paradigm animals were monitored for immunological, hematological and physiological alterations.

Description of Method:

For chronic central ASO infusion in male and female Cynomolgus monkeys, a gas-pressure pump (0.25 ml/24 h, Tricumed-IP 2000V®) connected to a silicone catheter, targeting the right lateral ventricle was implanted subcutaneously under ketamine/xylacin anesthesia and semi-sterile conditions. A single male and a single female monkey were used for each treatment condition (Seq. ID No. 218b, Seq. ID No. 218c, concentrations given in Table 79). Each pump was implanted subcutaneously in the abdominal region via a 10 cm long skin incision at the neck of the monkey and was connected with the icv cannula by a silicone catheter. Animals were placed into a stereotaxic frame, and the icv cannula was lowered into the right lateral ventricle. The cannula was fixed with two stainless steel screws using dental cement (Kallocryl, Speiko®-Dr. Speier GmbH, Münster, Germany). The skin of the neck was closed with sutures. During surgery, the body temperature was maintained by a heating pad. To avoid post-surgical infections, monkeys were locally treated with Betaisodona® (Mundipharma GmbH, Limburg, Germany) and received 1 ml antibiotics (sc, Baytril® 2.5% Bayer Vital GmbH, Leverkusen, Germany). The tubing and the resp. pump was filled with the respective treatment solution. ASO infusion periods (1 week for each dose) were interrupted by a one-week wash out period with 0.9% NaCl being administered exclusively. During the entire administration paradigm body weight development and food consumption were monitored. Further, blood and CSF samples were taken once a week to determine hematological as well as immunological alterations but also systemic ASO concentrations. On the last day, animals were sacrificed, and organs (liver, kidneys, brain) were removed, and analyzed for proliferation, apoptosis, mRNA knock down, and tumor formation.

oligonucleotides Seq. ID No. 214, Seq. ID No. 138b, Seq. ID No. 172b as well as Ref. 0 and Ref. 5. resulted in toxic effects early in the above scheme. Therefore, these antisense-oligonucleotides are not suitable as therapeutic agent and were not used for further studies.

Example 22: Determination of Behavioral and Physiological Abnormalities Following Central Antisense-Oligonucleotide Administration The goal of this study was to investigate the effects of a single intracerebroventricular (icv) antisense-oligonucleotide administration on neurological and resulting behavioral parameters in rats.

Description of Method:

Stereotaxic procedures were performed under ketamine/xylacin anesthesia and semi-sterile conditions. Following surgery, rats had two days for recovery.

Implantation of Icy Guide Cannula

Animals were placed into a stereotaxic frame, and the guide cannula (12 mm) was implanted 2 mm above the left lateral ventricle (coordinates relative to bregma: 1.0 mm posterior, -1.6 mm lateral to midline, 1.8 mm beneath the surface of the skull.

The guide cannula was anchored to two stainless steel screws using dental acrylic cement (Kallocryl, Speiko®-Dr. Speier GmbH, Münster, Germany) and was closed with a dummy cannula. During surgery, the body temperature was maintained by a heating pad. To avoid post-surgical infections, mice were locally treated with Betaisodona® (Mundipharma GmbH, Limburg, Germany) and received 0.1 ml antibiotics (sc, Baytril® 2.5% Bayer Vital GmbH, Leverkusen, Germany).

ICV Infusion

Slightly restrained rats received an icv infusion of either ASO (2 µM/5 µl, 10 µM/5 µl, 50 µM/5 µl, 250 µM/5 µl) or vehicle (5 µl, 0.9% NaCl, pH 7.4, Braun) using a 27-gauge cannula, which extended 2 mm beyond the guide cannula and remained in place for 30 s to allow diffusion. Rats were monitored 15, 30, 60 and 120 minutes following icv administration for behavioral reactions, motor activity, CNS excitation, posture, motor coordination, muscle tone, reflexes, and body temperature.

Verification of Cannula and Microdialysis Probe Placement

After scarification, brains were removed, snap frozen and stored at −80° C. until analyzation. Histological verification of the icv implantation sites was performed at 40-µm coronal, cresyl violet-stained brain sections.

TABLE 79

Experimental design and the doses of ASOs given during the 7-week administration paradigm.

| Treatment condition | Week 1 | Week 2 | Week 3 | Week 4 | Week 5 | Week 6 | Week 7 |
|---|---|---|---|---|---|---|---|
| Seq. ID No. 218b | 0.048 mM | 0.9% NaCl | 0.24 mM | 0.9% NaCl | 1.2 mM | 0.9% NaCl | 6 mM |
| Seq. ID No 218c | 0.048 mM | 0.9% NaCl | 0.24 mM | 0.9% NaCl | 1.2 mM | 0.9% NaCl | 6 mM |

Conclusion:

All tested, inventive ASOs were at least non-toxic in weeks 1-6 and were therefore used for further research and toxicological examination. However, infusion of antisense- The present results demonstrate a single ASO (for both sequences Seq. ID No. 218b, Seq. ID No. 218c) icv administration, for different doses, to be a safe and secure technique in rats due to no effects on neurological parameters.

Example 23: Determination of the Ideal Dose Range for the Cynomolgus GLP-Toxicity Study (Pre-Toxicity Experiment in Rats)

To investigate any general toxicological effects of a daily intravenous (iv) antisense-oligonucleotide (ASO) administration, and to localize the perfect dose-range for the GLP-pre-toxicity study in rats, a pre-toxicity experiment in rats was performed.

Description of Method:

For repeated intravenous ASO injection 20 male and 20 female rats were divided into four treatment groups, a vehicle group, an $ASO_{low}$, an $ASO_{intermediate}$, and an $ASO_{high}$ group. This paradigm was performed for Seq. ID No. 218b and Seq. ID No. 218c. Rats received a daily iv bolus ASO injection for 15 consecutive days. Rats were monitored for mortality (twice daily), clinical symptoms (once daily, bod weight development (weekly), food consumption (weekly). On day 15 of the experimental paradigm, animals were sacrificed, organs (liver, kidney, brain) were removed and trunk blood was collected. Afterwards tissues and blood was analyzed for immunological and hematological alterations.

The results of the present study demonstrate the two ASOs Seq. ID No. 218b and Seq. ID No. 218c to be a safe medication for a variety of different disorders with no toxic effects when administered at low and intermediate doses.

Example 24: Determination of any General Toxicological Effects by Repeated Intravenous Antisense-Oligonucleotide Injection The goal of this study was to investigate at which dose a daily intravenous (iv) antisense-oligonucleotide (ASO) administration exerts any general toxicological effects in rats.

Description of Method:

For repeated intravenous ASO injection 80 male and 80 female rats were divided into four treatment groups, a vehicle group, an $ASO_{low}$, an $ASO_{intermediate}$, and an $ASO_{high}$ group. Rats received a daily iv bolus ASO injection for 29 consecutive days. Rats were monitored for mortality (twice daily), clinical symptoms (once daily, bod weight development (weekly), food consumption (weekly). On day 29 of the experimental paradigm, animals were sacrificed, organs (liver, kidney, brain) were removed and trunk blood was collected. In addition, bone marrow smears were collected. Afterwards tissues and blood was analyzed for immunological and hematological, and histopathological alterations.

The results of the present study demonstrate the two ASOs Seq. ID No. 218b and Seq. ID No. 218c to be a safe medication for a variety of different disorders with no toxic effects when administered at low and intermediate doses.

Example 25: Determination of the Toxicological Properties of a Chronic Central Antisense-Oligonucleotide Administration in Cynomolgus Monkeys To determine the effective, and to identify the toxic dose, male and female Cynomolgus monkeys received different doses of an inventive antisense-oligonucleotide (ASO) by chronic intracerebroventricular administration. During the administration paradigm, animals were monitored for immunological, hematological and physiological alterations.

Description of Method:

For chronic central ASO infusion in male and female Cynomolgus monkeys, a gas-pressure pump (0.25 ml/24 h, Tricumed IP-2000V®) connected to a silicone catheter, targeting the right lateral ventricle, was implanted subcutaneously under ketamine/xylacin anesthesia and semi-sterile conditions. Three male and three female monkeys were used for each treatment condition (vehicle, $ASO_{low}$, $ASO_{high}$, concentrations given in Table 79). Further, for investigating the timeframe for recovery, two male and two female monkeys (vehicle, and $ASO_{high}$) were sacrificed four weeks after ASO administration was terminated. Each pump was implanted subcutaneously in the abdominal region via a 10 cm long skin incision at the neck of the monkey and connected with the icv cannula by a silicone catheter. Animals were placed into a stereotaxic frame, and the icv cannula was lowered into the right lateral ventricle. The cannula was fixed with two stainless steel screws using dental cement (Kallocryl, Speiko®-Dr. Speier GmbH, Münster, Germany). The skin of the neck was closed with sutures. During surgery, the body temperature was maintained by a heating pad. To avoid post-surgical infections, monkeys were locally treated with Betaisodona® (Mundipharma GmbH, Limburg, Germany) and received 1 ml antibiotics (sc, Baytril® 2.5% Bayer Vital GmbH, Leverkusen, Germany). The tubing was filled with the respective treatment solution. During the entire administration paradigm body weight development and food consumption was monitored. Further, blood and aCSF samples were taken once a week to determine hematological as well as immunological alterations but also systemic ASO concentrations. On the last day, animals of the main study were sacrificed, and organs (liver, kidneys, brain) were removed, and analyzed for proliferation, apoptosis, mRNA knock down, and tumor formation. After week 57, the additional animals used for investigating recovery periods were also sacrificed and the same read out parameters were determined.

TABLE 80

Treatment conditions and the animals per group for the 4-week GLP-toxicity study and for the additional 4-week recovery period.

| Treatment condition | Main study | | 4-week recovery period | |
|---|---|---|---|---|
| | Males [n] | Females [n] | Males [n] | Females [n] |
| Vehicle | 3 | 3 | 2 | 2 |
| $ASO_{low}$ | 3 | 3 | / | / |
| $ASO_{high}$ | 3 | 3 | 2 | 2 |

The results of the present study demonstrate a chronic intracerebroventricular ASO administration to be a non-toxic and safe medication for the treatment of a variety of different diseases.

Example 26: Determination of the Stability and the Biological Activity of an Antisense-Oligonucleotide in Different Vehicle Solutions To investigate, whether there are any interaction effects of the antisense-oligonucleotides (Seq. ID No. 218b, Seq. ID No. 218c) and the infusion solution, a 29-day pre-experiment was performed. Therefore, the two ASOs were reconstituted in different endotoxin-free vehicle solutions (PBS, water for injection [WFI], 0.9% NaCl) and stored at different conditions, respectively. Samples were collected every single week and were analyzed for pH-value, ASO stability, content, and integrity by AEX-HPLC. Any change in efficacy conditions were tested by proving the potency of TGF-RII mRNA knockdown in cell-culture assay with each sample, respectively.

Description of Method:

The lyophilized ASOs were diluted with the respective vehicle solution (Water for injection, 0.9% NaCl, PBS) under sterile conditions (laminar flow, BIOWIZARD Golden GL-170 Ergoscience®, S1 conditions). The 1.5 ml Eppendorf Cups were labeled and filled with 100 µl (AEX-HPLC) or 250 µl (target knock down) of the respective ASO solution (all steps under laminar flow, BIOWIZARD Golden GL-170 Ergoscience®, S1 conditions, see pipetting/labeling scheme table 81). In the next step, all samples were stored at their respective storing conditions and samples were collected every single week (see sampling scheme table 82) and stored at −80° C. until analyzation.

TABLE 81

Labeling scheme for the ASO-vehicle-stability study.

| Label | Vehicle (WFI, 0.9% NaCL or PBS) | Condition | Day 0 | 6 | 12 | 18 | 24 | 29 |
|---|---|---|---|---|---|---|---|---|
| ASO [10 µM] | X | Baseline | ASO [10 µM] X_Baseline | | | | | |
| ASO [10 µM] | X | −20° C. | | ASO [10 µM] X_−20° C._Day 6 | ASO [10 µM] X_−20° C._Day 12 | ASO [10 µM] X_−20° C._Day 18 | ASO [10 µM] X_−20° C._Day 24 | ASO [10 µM] X_−20° C._Day 29 |
| ASO [10 µM] | X | +4° C. | | ASO [10 µM] X_+4° C._Day 6 | ASO [10 µM] X_+4° C._Day 12 | ASO [10 µM] X_+4° C._Day 18 | ASO [10 µM] X_+4° C._Day 24 | ASO [10 µM] X_+4° C._Day 29 |
| ASO [10 µM] | X | +20° C. | | ASO [10 µM] X_+20° C._Day 6 | ASO [10 µM] X_+20° C._Day 12 | ASO [10 µM] X_+20° C._Day 18 | ASO [10 µM] X_+20° C._Day 24 | ASO [10 µM] X_+20° C._Day 29 |
| ASO [10 µM] | X | +37° C. | | ASO [10 µM] X_+37° C._Day 6 | ASO [10 µM] X_+37° C._Day 12 | ASO [10 µM] X_+37° C._Day 18 | ASO [10 µM] X_+37° C._Day 24 | ASO [10 µM] X_+37° C._Day 29 |
| ASO [10 µM] | X | +40° C. | | ASO [10 µM] X_40° C._Day 6 | ASO [10 µM] X_40° C._Day 12 | ASO [10 µM] X_40° C._Day 18 | ASO [10 µM] X_40° C._Day 24 | ASO [10 µM] X_40° C._Day 29 |
| ASO [10 µM] | X | pH value | ASO [10 µM] X_pH value_Day 0 | | | | | ASO [10 µM] X_pH value_Day 29 |
| ASO [0.24 µM] | X | Baseline | ASO [0.24 mM] X_Baseline | | | | | |
| ASO [0.24 µM] | X | −20° C. | | ASO [0.24 mM] X_−20° C._Day 6 | ASO [0.24 mM] X_−20° C._Day 12 | ASO [0.24 mM] X_−20° C._Day 18 | ASO [0.24 mM] X_−20° C._Day 24 | ASO [0.24 mM] X_−20° C._Day 29 |
| ASO [0.24 µM] | X | +4° C. | | ASO [0.24 mM] X_+4° C._Day 6 | ASO [0.24 mM] X_+4° C._Day 12 | ASO [0.24 mM] X_+4° C._Day 18 | ASO [0.24 mM] X_+4° C._Day 24 | ASO [0.24 mM] X_+4° C._Day 29 |
| ASO [0.24 µM] | X | +20° C. | | ASO [0.24 mM] X_+20° C._Day 6 | ASO [0.24 mM] X_+20° C._Day 12 | ASO [0.24 mM] X_−20° C._Day 18 | ASO [0.24 mM] X_−20° C._Day 24 | ASO [0.24 mM] X_+20° C._Day 29 |
| ASO [0.24 µM] | X | +37° C. | | ASO [0.24 mM] X_+37° C._Day 6 | ASO [0.24 mM] X_+37° C._Day 12 | ASO [0.24 mM] X_+37° C._Day 18 | ASO [0.24 mM] X_+37° C._Day 24 | ASO [0.24 mM] X_+37° C._Day 29 |

TABLE 81-continued

Labeling scheme for the ASO-vehicle-stability study.

| Label | Vehicle (WFI, 0.9% NaCL or PBS) | Condition | 0 | 6 | 12 | 18 | 24 | 29 |
|---|---|---|---|---|---|---|---|---|
| ASO [0.24 µM] | X | +40° C. | | ASO [0.24 mM] | ASO [0.24 mM] | ASO [0.24 mM] | ASO [0.24 mM] | ASO [0.24 mM] |
| | | | | X_40° C._Day 6 | X_40° C._Day 12 | X_40° C._Day 18 | X_40° C._Day 24 | X_40° C._Day 29 |
| ASO [0.24 µM] | X | pH value | ASO [0.24 mM] | | | | | ASO [0.24 mM] |
| | | | X_pH value_Day 0 | | | | | X_pH_value_Day 29 |

The labeling scheme was performed for Seq. ID No. 218b and Seq. ID No. 218c (each 10 µM and 0.24 mM) and for all three vehicles WFI, 0.9% NaCl, and PBS (=>12 different schemes).

TABLE 82

Collection scheme for the ASO-vehicle-stability study.

| Sample Condition | Day | | | | | |
|---|---|---|---|---|---|---|
| | 0 | 6 | 12 | 18 | 24 | 29 |
| Baseline | X | | | | | |
| −20° C. | | X | X | X | X | X |
| +4° C. | | X | X | X | X | X |
| +20° C. | | X | X | X | X | X |
| +37° C. | | X | X | X | X | X |
| +40° C. | | X | X | X | X | X |
| pH value | X | | | | | X |

The collection scheme was performed for Seq. ID No. 218b and Seq. ID No. 218c (each 10 µM and 0.24 mM) and for all three vehicles WFI, 0.9% NaCl, and PBS (=>12 different schemes).

Since there were no effects of any of the vehicle solutions on stability, content, and integrity of Seq. ID No. 218b and Seq. ID No. 218c, 0.9% NaCl was used for the ASO—in use-stability experiment.

Example 27: Determination of the In-Use Stability and the Biological Activity of Inventive Antisense-Oligonucleotides (ASOs) in Vehicle Solution To investigate, whether there are any interaction effects of the antisense oligonucleotides (ASO) (Seq. ID No. 218b, Seq. ID No. 218c) and a gas pressure pump or a catheter, a 29-day pre-experiment was performed. Therefore, the two ASOs were reconstituted in 0.9% NaCl and the pump and the catheter were filled according to manufacturer's description. Samples were collected every single week and were analyzed for pH-value, microbiology, and oligo stability, content, and integrity by AEX-HPLC. Any change in efficacy conditions were also tested by proofing the potency to knockdown TGF-$R_{II}$ mRNA in cell-culture assay with every sample, respectively.

Description of Method:

The lyophilized ASOs were diluted with 0.9% NaCl under sterile conditions (laminar flow, BIOWIZARD Golden GL-170 Ergoscience®, S1 conditions). The 5 ml Eppendorf Cups were labeled according to the labeling scheme (see table 83) under sterile conditions (laminar flow, BIOWIZARD Golden GL-170 Ergoscience, S1 conditions). The two gas pressure pumps (Tricumed Model IP-2000 V®) and the catheter (spinal catheter set 4000) were filled according to manufacturer's description with the respective ASO solution (all steps under laminar flow, BIOWIZARD Golden GL-170 Ergoscience®, S1 conditions, see pipetting/labeling scheme table 83). In the next step, the pump connected to the catheter which was connected to the lid of a 5 ml Eppendorf Cup and the remaining Cups were stored in a storage box with all openings being closed with Parafilm®, to avoid any contamination. Every single week the samples were collected, stored at −80° C. until analysis and the catheter connected to the lid of a 5 ml Eppendorf Cup was transferred to the following Cup to continue the sampling procedure. In addition, one sample was taken directly from the pump via the bolus port and stored at -80° C. On the last day, an additional sample for microbiological analysis was collected.

TABLE 83

Labeling scheme for the ASO in-use-stability study.

| Sample Oligo | Cup | Condition | Day | | | |
|---|---|---|---|---|---|---|
| | | | 0 | 6 | 12 | 18 |
| Seq. ID No. 218b [0.24 mM] | 5 ml | PS | Seq. ID No. 218b [10 µM] Baseline | Seq. ID No. 218b_+37° C. PS_Day 6 | Seq. ID No. 218b_+37° C. PS_Day 12 | Seq. ID No. 218b_+37° C. PS_Day 18 |
| Seq. ID No. 218b [0.24 mM] | 5 ml | AS | | Seq. ID No. 218b_+37° C. AS_Day 6 | Seq. ID No. 218b_+37° C. AS_Day 12 | Seq. ID No. 218b_+37° C. AS_Day 18 |
| Seq. ID No. 218b [0.24 mM] | 5 ml | MB | | | | |

TABLE 83-continued

Labeling scheme for the ASO in-use-stability study.

| Sample Oligo | Cup | Condition | Day 0 | 6 | 12 | 18 |
|---|---|---|---|---|---|---|
| Seq. ID No. 218b [0.24 mM] | 5 ml | pH value | Seq. ID No. 218b pH value Day 0 | | | |
| Seq. ID No. 218c [0.24 mM] | 5 ml | PS | Seq. ID No. 218c Baseline | Seq. ID No. 218c_+37° C. PS_Day 6 | Seq. ID No. 218c_+37° C. PS_Day 12 | Seq. ID No. 218c_+37° C. PS_Day 18 |
| Seq. ID No. 218c [0.24 mM] | 5 ml | AS | | Seq. ID No. 218c_+37° C. AS_Day 6 | Seq. ID No. 218c_+37° C. AS_Day 12 | Seq. ID No. 218c_+37° C. AS_Day 18 |
| Seq. ID No. 218c [0.24 mM] | 5 ml | MB | | | | |
| Seq. ID No. 218c [0.24 mM] | 5 ml | pH value | Seq. ID No. 218c pH value Day 0 | | | |

The labeling scheme was performed for Seq. ID No. 218b and Seq. ID No. 218c (each 0.24 mM).
PS: (PumpSample: sample directly from the catheter),
AS: (AdditionalSample: sample directly from the reservoir inside the pump via bolus port,
MB: (MicroBiology: 500 µM from PS and AS)

TABLE 84

Collection scheme for the ASO in-use-stability study.

| Sample | | | Day | | | | |
|---|---|---|---|---|---|---|---|
| Cup | Condition | 0 | 6 | 12 | 18 | 24 | 29 |
| 5 ml | Baseline | X | | | | | |
| 5 ml | PS | | X | X | X | X | X |
| 5 ml | AS | | X | X | X | X | X |
| 5 ml | MB | | | | | | X |
| 5 ml | pH value | X | | | | | X |

The collection scheme was performed for Seq. ID No. 218b and Seq. ID No. 218c (0.24 mM).
PS: (PumpSample: sample directly from the catheter),
AS: (AdditionalSample: sample directly from the reservoir inside the pump via bolus port,
MB: (MicroBiology: 500 µM from PS and AS)

Since there were no effects of the pump and the catheter on the stability, content, and integrity of Seq. ID No. 218b and Seq. ID No. 218c, and there were also no noticeable microbiological problems, this application paradigm represents the optimal technique for the intrathecal and intracerebroventricular administration in Cynomolgus monkeys and humans.

Chemical Synthesis

Abbreviations

Pybop: (Benzotriazol-1-yl-oxy)tripyrrolidinophosphonium-hexafluorophosphat
DCM: Dichloromethane
DMF: Dimethylformamide
DMAP: 4-Dimethylaminopyridine
DMT: 4,4'-dimethoxytrityl
LCAA: Long Chain Alkyl Amino
TRIS: Tris(hydroxymethyl)-aminomethan
TRIS-HCl: Tris(hydroxymethyl)-aminomethan hydrochloride
DEPC: Diethyl dicarbonate Gapmer Antisense-Oligonucleotide Synthesis and Purification The antisense-oligonucleotides in form of gapmers were assembled on an ABI 3900 or on an ABI 394 synthesizer, or on an Expedite™ (Applied Biosystems) according to the phosphoramidite oligomerization chemistry. On the ABI3900, the solid support was polystyrene loaded with UnySupport (purchased from Glen Research, Sterling, Va., USA) to give a synthesis scale of 0.2 µmol. On the ABI 394 the solid support was 500 A controlled pore glass (CPG) loaded with Unylinker™ purchased from Chemgenes (Wilmington, Mass., USA) to give a 3 µmol synthesis scale.

Ancillary synthesis reagents such as "Deblock", "Oxidizer", "CapA" and "CapB" as well as DNA phosphoramidites were obtained from SAFC Proligo (Hamburg, Germany). Specifically, 5'-O-(4,4'-dimethoxytrityl)-2'-O,3'-O-(2-cyanoethyl-N,N-diisopropyl) phosphoramidite monomers of deoxy thymidine (dT), 4-N-benzoyl-2'-deoxycytidine ($dC^{Bz}$), 6-N-benzoyl-2'-deoxy-adenosine ($dA^{Bz}$) and 2-N-isobutyryl-2'-deoxy-guanosine ($dG^{iBu}$) were used as DNA building-units. 5'-O-DMT-2'-O,4'-C-methylene-$N^2$-dimethylformamidine-guanosine-3'-(2-cyanoethyl-N,N-diisopropyl)phosphoramidite (LNA-$G^{DMF}$), 5'-O-DMT-2'-O,4'-C-methylene-thymidine 3'-[(2-cyanoethyl)-(N,N-diisopropyl)]phosphoramidite (LNA-Tb), 5'-O-DMT-2'-O,4'-C-methylene-$N^6$-benzoyladenosine-3'-(2-cyanoethyl-N,N-diisopropyl)phosphoramidite (LNA-$A^{Bz}$), 5'-O-DMT-2'-O—,4'-C-methylene-5-methyl-$N^4$-benzoylcytidine-3'-(2-cyanoethyl-N,N-diisopropyl)phosphoramidite (LNA-$C^{*Bz}$) were used as LNA-building-units. The LNA phosphoramidites were purchased from Exiqon (Vebaek, Denmark).

As shown by the examples of the LNAs in table 85, the phosphoramidites were dissolved in dry acetonitrile to give 0.07 M-oligonucleotide except LNA-$C^{*Bz}$ which was dissolved in a mixture of THF/acetonitrile (25/75 (v/v)).

TABLE 85

| | Molecular weight g/mole | CAS No. | Solvent | To obtain a 0.07M solution 100 mg |
|---|---|---|---|---|
| LNA-$A^{Bz}$ | 885.9 | [206055-79-0] | Anhydrous Acetonitrile | 1.6 ml |
| LNA-$C^{*Bz}$ | 875.9 | [206055-82-5] | THF/Acetonitrile 25/75 (v/v) | 1.6 ml |
| LNA-$G^{DMF}$ | 852.9 | [709641-79-2] | Anhydrous Acetonitrile | 1.7 ml |
| LNA-T | 772.8 | [206055-75-6] | Anhydrous Acetonitrile | 1.8 ml |

The β-D-thio-LNAs 5'-O-DMT-2'-deoxy-2'-mercapto-2'-S,4'-C-methylene-N$^6$-benzoyladenosine-3'-[(2-cyanoethyl-N,N-diisopropyl)]-phosphoramidite, 5'-O-DMT-2'-deoxy-2'-mercapto-2'-S,4'-C-methylene-5-methyl-N$^4$-benzoylcytidine-3'-(2-cyanoethyl-N,N-diisopropyl) phosphoramidites, 5'-O-DMT-2'-deoxy-2'-mercapto-2'-S,4'-C-methylene-N$^2$-dimethyformamidineguanosine-3'-[(2-cyanoethyl)-(N,N-diisopropyl)]-phosphoramidite, 5'-O-DMT-2'-deoxy-2'-mercapto-2'-S,4'-C-methylene-thymidine-3'-[(2-cyanoethyl)-(N,N-diisopropyl)]-phosphoramidite, and 5'-O-DMT-2'-deoxy-2'-amino-2'-N,4'-C-methylene-N$^6$-benzoyladenosine-3'-(2-cyanoethyl-N,N-diisopropyl)phosphoramidites were synthesized as described in J. Org. Chem. 1998, 63, 6078-6079.

The synthesis of the β-D-amino-LNA 5'-O-DMT-2'-deoxy-2'-amino-2'-N,4'-C-methylene-5-methyl-N$^4$-benzoylcytidine-3'-[(2-cyanoethyl-N,N-diisopropyl)]-phosphoramidites, 5'-O-DMT-2'-deoxy-2'-amino-2'-N,4'-C-methylene-N$^2$-dimethyformamidineguanosine-3'-[(2-cyanoethyl)-(N,N-diisopropyl)]-phosphoramidite, 5'-O-DMT-2'-deoxy-2'-amino-2'-N,4'-C-methylene-thymidine-3'-[(2-cyanoethyl)-(N,N-diisopropyl)]-phosphoramidite, 5'-O-DMT-2'-deoxy-2'-methylamino-2'-N,4'-C-methylene-N$^6$-benzoyladenosine-3'-[(2-cyanoethyl-N,N-diisopropyl)]-phosphoramidite, and 5'-O-DMT-2'-deoxy-2'-methylamino-2'-N,4'-C-methylene-5-methyl-N$^4$-benzoylcytidine-3'-(2-cyanoethyl-N,N-diisopropyl)phosphoramidites, 5'-O-DMT-2'-deoxy-2'-methylamino-2'-N,4'-C-methylene-N$^2$-dimethyformamidineguanosine-3'-[(2-cyanoethyl)-(N,N-diisopropyl)]-phosphoramidite 5'-O-DMT-2'-deoxy-2'-methylamino-2'-N,4'-C-methylene-thymidine-3'-[(2-cyanoethyl)-(N,N-diisopropyl)]-phosphoramidite were carry out according to the literature procedure (J. Org Chem. 1998, 63, 6078-6079).

The α-L-oxy-LNAs α-L-5'-O-DMT-2'-O,4'-C-methylene-N$^6$-benzoyladenosine-3'-(2-cyanoethyl-N,N-diisopropyl)phosphoramidite, α-L-5'-O-DMT-2'-O—,4'-C-methylene-5-methyl-N$^4$-benzoylcytidine-3'-(2-cyanoethyl-N,N-diisopropyl)phosphoramidite, α-L-5'-O-DMT-2'-O,4'-C-methylene-N$^2$-dimethyformamidineguanosine-3'-[(2-cyanoethyl)-(N,N-diisopropyl)]-phosphoramidite, and α-L-5'-O-DMT-2'-O,4'-C-methylene-thymidine-3'-[(2-cyanoethyl)-(N,N-diisopropyl)]-phosphoramidite were performed similar to the procedures described in the literature (J. Am. Chem. Soc. 2002, 124, 2164-2176; Angew. Chem. Int. Ed. 200, 39, 1656-1659).

The (β-benzoylmercapto)ethyl)pyrrolidinolthiophosphoramidites for the synthesis of the oligonucleotide with phosphorothioate backbone were prepared in analogy to the protocol reported by Caruthers (J. Org. Chem. 1996, 61, 4272-4281).

The "phosphoramidites-C3" (3-(4,4'-Dimethoxytrityloxy) propyl-1-[(2-cyanoethyl)-(N,N-diisopropyl)]-phosphoramidite and the "3'-Spacer C3 CPG" (1-Dimethoxytrityloxy-propanediol-3-succinoyl)-long chain alkylamino-CPG were purchased from Glen Research.

General Procedure

Preparation of the LNA-Solid Support:

1) Preparation of the LNA succinyl hemiester (WO2007/112754)

5'-O-DMT-3'-hydroxy-nucleoside monomer, succinic anhydride (1.2 eq.) and DMAP (1.2 eq.) were dissolved in 35 ml dichloromethane (DCM). The reaction was stirred at room temperature overnight. After extractions with $NaH_2PO_4$ 0.1 M pH 5.5 (2×) and brine (1×), the organic layer was further dried with anhydrous $NaSO_4$ filtered and evaporated. The hemiester derivative was obtained in 95% yield and was used without any further purification.

2) Preparation of the LNA-support (WO2007/112754)

The above prepared hemiester derivative (90 μmol) was dissolved in a minimum amount of DMF, DIEA and pyBOP (90 μmol) were added and mixed together for 1 min. This pre-activated mixture was combined with LCAA-CPG (500 Å, 80-120 mesh size, 300 mg) in a manual synthesizer and stirred. After 1.5 hours at room temperature, the support was filtered off and washed with DMF, DCM and MeOH. After drying, the loading was determined to be 57 μmol/g (see Tom Brown, Dorcas J. S. Brown. Modern machine-aided methods of oligodeoxyribonucleotide synthesis. In: F. Eckstein, editor. Oligonucleotides and Analogues A Practical Approach. Oxford: IRL Press, 1991: 13-14).

Elongation of the Oligonucleotide (Coupling)

5-ethylthio-1H-tetrazole (ETT) as activator (0.5 M in acetonitrile) was employed for the coupling of the phosphoramidites. Instead of ETT other reagents such as 4,5-dicyanoimidazole (DCI) as described in WO2007/112754, 5-benzylthio-1H-tetrazole or saccharin-1-methylimidazol can be used as activator. 0.25 M DCI in acetonitrile was used for the coupling with LNA.

Capping

10% acetic anhydride ($Ac_2O$) in THF (HPLC grade) and 10% N-methylimidazol (NMI) in THF/pyridine (8:1) (HPLC grade) were added and allowed to react.

Oxidation

Phosphorous(III) to Phosphorous(V) is normally done with e.g. iodine/THF/pyridine/$H_2O$ using 0.02 M iodine in THF/Pyridine/$H_2O$ purchased from Glen Research or 0.5 M 1S)-(+)-(10-camphorsulfonyl)-oxaziridine (CSO) in anhydrous acetonitrile from Glen Research.

In the case that a phosphorthioate internucleoside linkage is prepared, a thiolation step is performed using a 0.05 M solution of 3-((dimethylamino-methylidene)amino)-3H-1,2,4-dithiazole-3-thione (DDTT, obtained from Chemgenes (Wilmington, Mass., USA)) in anhydrous acetonitrile/pyridine (1:1 v/v). In case LNAs are used, the thiolation was carried out usind 0.2 M 3,H-1,2-benzothiole-3-one 1,1-dioxide (Beaucage reagent) in anhydrous acetonitrile.

In general, the thiolation can also be carried out by using xanthane chloride (0.01 M in acetonitrile/pyridine 10%) as described in WO2007/112754.

Alternative, other reagents for the thiolation step such as xanthane hydride (5-imino-(1,2,4)dithiazolidine-3-thione), phenylacetyl disulfide (PADS) can be applied.

In the case that a phosphordithioate was synthesized, the resulting thiophosphite triester was oxidized to the phosphorothiotriester by addition of 0.05 M DDTT (3-((Dimethylamino-methylidene)amino)-3H-1,2,4-dithiazole-3-thione) in pyridine/acetonitrile (4:1 v/v).

Cleavage from the Solid Support and Deprotection

At the end of the solid phase synthesis, the antisense-oligonucleotide can either be cleaved "DMT-on" or "DMT-off". "DMT off" means that the final 5'-O-(4,4'-dimethoxytrityl) group was removed on the synthesizer using the "Deblock" reagent and DMT-on means that the group is present while the oligonucleotide is cleaved from the solid support. The DMT groups were removed with trichloroacetic acid.

"DMT-Off"

Upon completion of the solid phase synthesis antisense-oligonucleotides were treated with a 20% diethylamine solution in acetonitrile (Biosolve BV, Valkenswaard, The Netherlands) for 20 min. to remove the cyanoethyl protecting groups on the phosphate backbone. Subsequently, the antisense-oligonucleotides were cleaved from the solid support and deprotected using 1 to 5 mL concentrated aqueous ammonia (obtained from Sigma Aldrich) for 16 hours at 55° C. The solid support was separated from the antisense-oligonucleotides by filtration or centrifugation.

If the oligonucleotides contain phosphorodithioate triester, the thiol-groups were deprotected with thiophenol: triethylamine:dioxane, 1:1:2, v/v/v for 24 h, then the oligonucleotides were cleaved from the solid support using aqueous ammonia for 1-2 hours at room temperature, and further deprotected for 4 hours at 65° C.

"DMT-On"

The oligonucleotides were cleaved from the solid support using aqueous ammonia for 1-2 hours at room temperature, and further deprotected for 4 hours at 65° C. The oligonucleotides were purified by reverse phase HPLC (RP-HPLC), and then the DMT-group is removed with trichloroacetic acid.

If the oligonucleotides contain phosphorodithioate triester, the cleavage from the solid-support and the deprotection of the thiol-group were performed by the addition of 850 µl ammonia in concentrated ethanol (ammonia/ethanol 3:1 v/v) at 55° C. for 15-16 h.

Terminal Groups

Terminal groups at the 5'-end of the antisense oligonucleotide The solid supported oligonucleotide was treated with 3% trichloroacetic acid in dichloromethane (w/v) to completely remove the 5'-DMT protection group. Further, the compound was converted with an appropriate terminal group with cyanoethyl-N,N-diisopropyl)phosphoramidite-moiety. After the oxidation of the phosphorus(III) to phosphorus(V), the deprotection, detachment from the solid support and deprotection sequence were performed as described above.

Purification

Next, the crude antisense-oligonucleotides were purified by anion-exchange high-performance liquid chromatography (HPLC) on an AKTA Explorer System (GE Healthcare, Freiburg, Germany) and a column packed with Source Q15 (GE Healthcare). Buffer A was 10 mM sodium perchlorate, 20 mM Tris, 1 mM EDTA, pH 7.4 and contained 20% acetonitrile and buffer B was the same as buffer A with the exception of 500 mM sodium perchlorate. A gradient of 15% B to 55% B within 32 column volumes (CV) was employed. UV traces at 280 nm were recorded. Appropriate fractions were pooled and precipitated with 3 M NaOAc, pH=5.2 and 70% ethanol. Finally, the pellet was washed with 70% ethanol. Analytics Identity of the antisense-oligonucleotides was confirmed by electrospray ionization mass spectrometry (ESI-MS) and purity was by analytical OligoPro Capillary Electrophoresis (CE).

The purification of the dithioate was performed on an Amersham Biosciences P920 FPLC instrument fitted with a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0.

Example 28

$Gb^1sTb^1sdAsdGsdTsdGsdTsdTsdTsdAsdGsdGsdGsAb^1sGb^1sC*b^1$ (Seq. ID No. 209y) 5'-O-DMT-2'-O,4'-C-methylene-5-methyl-$N^4$-benzoxylcytidine-3'-O-succinoyl-linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene-$N^2$-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene-$N^6$-benzoyladenosine-3'-(2-cyanoethyl-N, N-diisopropyl)phosphoramidites (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^2$-isobutyryl-2'-deoxyguanosine-3'-(2-cyanoethyl-N,N-diisopropyl)phosphoramidites (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^2$-isobutyryl-2'-deoxyguanosine-3'-(2-cyanoethyl-N,N-diisopropyl)phosphoramidites (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^2$-isobutyryl-2'-deoxyguanosine-3'-(2-cyanoethyl-N,N-diisopropyl)phosphoramidites (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M).

The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^2$-isobutyryl-2'-deoxyguanosine-3'-(2-cyanoethyl-N,N-diisopropyl)phosphoramidites (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^2$-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidites (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene-$N^2$-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

Upon completion of the solid phase synthesis, the antisense-oligonucleotides were treated with a 20% diethylamine solution in acetonitrile (Biosolve BV, Valkenswaard, The Netherlands) for 20 min. to remove the cyanoethyl protecting groups on the phosphate backbone.

Subsequently, the antisense-oligonucleotides were cleaved from the solid support and further deprotected using 5 mL concentrated aqueous ammonia for 16 hours at 55° C. The solid support was separated from the antisense-oligonucleotides by filtration or centrifugation.

Next, the crude antisense-oligonucleotides were purified by anion-exchange high-performance liquid chromatography (HPLC) on an AKTA Explorer System (GE Healthcare, Freiburg, Germany) and a column packed with Source Q15 (GE Healthcare). Buffer A was 10 mM sodium perchlorate, 20 mM Tris, 1 mM EDTA, pH 7.4 and contained 20% acetonitrile and buffer B was the same as buffer A with the exception of 500 mM sodium perchlorate. A gradient of 15% B to 55% B within 32 column volumes (CV) was employed. UV traces at 280 nm were recorded. Appropriate fractions were pooled and precipitated with 3 M NaOAc, pH=5.2 and 70% ethanol. Finally, the pellet was washed with 70% ethanol. The antisense oligonucleotide was received with a purity of 93.7%. ESI-MS: experimental: 5387.3 Da; calculated: 5387.80 Da.

Example 29

(Seq. ID No. 209u)
Gb¹Tb¹dAdGdTdGdTdTdTdAdGdGdGAb¹Gb¹C*b¹

The LNA was bound to CPG according to the general procedure. The coupling reaction and capping step were also carried out as described in example 28. After the capping step, the system was flushed out with 800 µl acetonitrile, and 400 µl of 0.02 M Iodine in THF/pyridine/$H_2O$ were inserted to the column for 45 s. The system was flushed after the oxidation step with 24 µl acetonitrile. After purification, the antisense oligonucleotide was received with a purity of 95.3%. ESI-Ms: experimental: 5146.80 Da; calculated: 5146.4 Da.

Example 30

(Seq. ID No. 209v)
/5SpC3s/Gb¹sTb¹sdAsdGsdTsdGsdTsdTsdTsdAsdGsdGsdGs

Ab¹sGb¹sC*b¹

The compound was synthesized according to the general procedure with the appropriate DNA and LNA building units as exemplified in example 28. But with the exception that after the last nucleotide has been coupled to the oligonucleotide and the subsequent oxidation and capping steps were carried out, 80 µl of phosphoramidite-C3 (0.07 M) and 236 µl DCI in acetonitrile (0.25 M) were added. The coupling was allowed to take place for 250 sec., and excess reagents were flashed out with 800 µl acetonitrile. The subsequent steps were performed as described in example 28. After purification, the antisense oligonucleotide was received with a purity of 97.4%. HRMS (ESI): experimental: 5540.70 Da; calculated: 5541.4 Da.

Example 31

(Seq. ID No. 209w)
Gb¹sTb¹sdAsdGsdTsdGsdTsdTsdTsdAsdGsdGsdGsAb¹sGb¹s

C*b¹/3SpC3s/

3'-Spacer C3 CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O—,4'-C-methylene-5-methyl-$N^4$-benzoylcytidine-3'-[(2-cyanoethyl-N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group. The subsequent reactions were performed as described in example 28. After purification, the antisense oligonucleotide was received with a purity of 92.7%. ESI-sMS: experimental: 5541.70 Da; calculated: 5541.4 Da.

Example 32

(Seq. ID No. 209an)
Gb¹ssTb¹ssAb¹ssdGssdTssdGssdTssdTssdTssdA*ssdGss dGssdGssAb¹ssGb¹ssC*b¹

5'-O-DMT-2'-O,4'-C-methylene-5-methyl-$N^4$-benzoxyl-cytidine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 38 µl 5'-O-DMT-2'-O,4'-C-methylene-N²-dimethylformamidineguanosine-3'-[(p-benzoylmercapto)ethyl]pyrrolidinolthiophosphoramidite (0.15 M) in 10% dichloromethane (v/V) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 38 µl 5'-O-DMT-2'-O,4'-C-methylene-N⁶-benzoyladenosine-3'-[(p-benzoylmercapto)ethyl]pyrrolidinolthiophosphoramidite (0.15 M) in 10% dichloromethane (v/v) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The further elongation of the oligonucleotide was performed in the same way.

Upon completion of the solid phase synthesis, the antisense-oligonucleotides were treated 850 µl ammonia in concentrated ethanol (ammonia/ethanol 3:1 v/v) at 55° C. for 15-16 h in order to cleave antisense-oligonucleotide from the solid-support and to deprotect the thiol-group.

Next, the crude antisense-oligonucleotide was purified by anion-exchange chromatography using a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0.

Example 33

(Seq. ID No. 209az)
Gb¹sTb¹sAb¹sdGsdTsdGsdTsdTsdTsdAsdGsdGsGbsAb¹sGb¹ sC*b¹

The compound was synthesized according to the general procedure with the appropriate DNA and LNA building units as exemplified in example 28. After purification, the antisense oligonucleotide was received with a purity of 90.5%. ESI-MS: experimental: 5442.9 Da; calculated: 5443.3 Da.

Example 34

(Seq. ID No. 209ba)
Gb¹sTb¹sAb¹sGb¹sdTsdGsdTsdTsdTsdAsdGsdGsGb¹sAb¹ sGb¹sC*b¹

The compound was synthesized according to the general procedure with the appropriate DNA and LNA building units as exemplified in example 28. After purification, the antisense oligonucleotide was received with a purity of 89.4%. ESI-MS: experimental: 5469.9 Da; calculated: 5471.3 Da.

Example 35

(Seq. ID No. 209bb)
Gb¹sTb¹sAb¹sdGsdTsdGsdTsdGsdTsdTsdTsdAsdGsdGsdGsdAsGb¹ sC*b¹

The compound was synthesized according to the general procedure with the appropriate DNA and LNA building units as exemplified in example 28. After purification, the antisense oligonucleotide was received with a purity of 88.4%. ESI-MS: experimental: 5386.5 Da; calculated: 5387.3 Da.

Example 36

(Seq. ID No. 209s)
Gb¹Tb¹dAsdGsdTsdGsdTsdTsdTsdAsdGsdGsdGsAb¹Gb¹C*b¹

The compound was synthesized according to the pocedure as described in example 28 and example 29 with the appropriate DNA, DNA-derivatives and the LNA building units. After purification, the antisense oligonucleotide was received with a purity of 96.8%. ESI-MS: experimental: 5323.30 Da; calculated: 5323.0 Da.

Example 37

(Seq. ID No. 209t)
Gb¹sTb¹sdA*sdGsdTsdGsdTsdTsdTsdA*sdGsdGsdGsAb¹sGb¹ sC*b¹

The compound was synthesized according to the general procedure and as described in example 28 with the appropriate DNA and LNA building units. After purification, the antisense oligonucleotide was received with a purity of 91.4%. ESI-MS: experimental: 5416.30 Da; calculated: 5417.3 Da.

Example 38

(Seq. ID No. 209x)
/5SpC3s/Gb¹sTb¹sdAsdGsdTsdGsdTsdTsdTsdAsdGsdGsdGs

Ab¹sGb¹sC*b¹/3SpC3s/

The compound was synthesized according to the general procedure with the appropriate DNA and LNA building units as exemplified in example 28, example 30 and example 31. After purification, the antisense oligonucleotide was received with a purity of 95.1%. ESI-MS: experimental: 5696.30 Da; calculated: 5695.5 Da.

Examples 39-132

The other oligonucleotides of Table 6 were synthesized according to the general procedure and as shown in the examples. The preparation of the antisense-oligonucleotide including β-D-thio-LNA, α-L-oxy-LNA, β-D-(NH)-LNA, or β-D-(NCH₃)-LNA units were performed in the same way as the antisense-oligonucleotides containing β-D-oxy-LNA units.

Example 133

(Seq. ID No. 210q)
Gb'sC*b'sTb'sAb'sdTsdTsdTsdGsdGsdTsdAsdGsdTsGb'sTb'sTb'

5'-O-DMT-2'-O,4'-C-methylene thymidine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2',4'-C-methylene-N²-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N²-isobutyryl-2'-deoxyguanosine-3'-(2-cyanoethyl-N,N-diisopropyl)phosphoramidites (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N⁶-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N²-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N²-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene-$N^6$-benzoyladenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O—,4'-C-methylene-5-methyl-$N^4$-benzoylcytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene-$N^2$-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

Upon completion of the solid phase synthesis antisense-oligonucleotides were treated with a 20% diethylamine solution in acetonitrile (Biosolve BV, Valkenswaard, The Netherlands) for 20 min. to remove the cyanoethyl protecting groups on the phosphate backbone.

Subsequently, the antisense-oligonucleotides were cleaved from the solid support and further deprotected using 5 ml concentrated aqueous ammonia for 16 hours at 55° C. The solid support was separated from the antisense-oligonucleotides by filtration or centrifugation.

Next, the crude antisense-oligonucleotides were purified by anion-exchange high-performance liquid chromatography (HPLC) on an AKTA Explorer System (GE Healthcare, Freiburg, Germany) and a column packed with Source Q15 (GE Healthcare). Buffer A was 10 mM sodium perchlorate, 20 mM Tris, 1 mM EDTA, pH 7.4 and contained 20% acetonitrile and buffer B was the same as buffer A with the exception of 500 mM sodium perchlorate. A gradient of 15% B to 55% B within 32 column volumes (CV) was employed. UV traces at 280 nm were recorded. Appropriate fractions were pooled and precipitated with 3 M NaOAc, pH=5.2 and 70% ethanol. Finally, the pellet was washed with 70% ethanol.

The antisense oligonucleotide was received with a purity of 87.1%. ESI-MS: experimental: 5384.30 Da; calculated: 5384.3 Da.

Example 134

(Seq. ID No. 210r)
Gb$^1$C*b$^1$Tb$^1$Ab$^1$dTdTdTdGdGdTdA*dGdTGb$^1$Tb$^1$Tb$^1$

The LNA was bound to CPG according to the general procedure. The coupling reaction and capping step were also carried out as described in example 133. After the capping step, the system was flushed out with 800 µl acetonitrile, and 400 µl of 0.02 M Iodine in THF/pyridine/H$_2$O were inserted to the column for 45 s. The system was flushed after the oxidation step with 24 µl acetonitrile. After purification, the antisense oligonucleotide was received with a purity of 95.3%.

Example 135

(Seq. ID No. 210v)
/5SpC3s/Gb$^1$sC*b$^1$sTb$^1$sAb$^1$sdTsdTsdTsdGsdGsdTsdAsdGsdTsGb$^1$sTb$^1$sTb$^1$

The compound was synthesized according to the general procedure with the appropriate DNA and LNA building units as exemplified in example 133. But with the exception that after the last nucleotide has been coupled to the oligonucleotide and the subsequent oxidation and capping steps were carried out, 80 µl of phosphoramidite-C3 (0.07 M) and 236 µl DCI in acetonitrile (0.25 M) were added. The coupling was allowed to take place for 250 sec., and excess reagents were flashed out with 800 µl acetonitrile. The subsequent steps were performed as described in example 133. After purification, the antisense oligonucleotide was received with a purity of 93.9%.

Example 136

(Seq. ID No. 210w)
Gb$^1$sC*b$^1$sTb$^1$sAb$^1$sdTsdTsdTsdGsdGsdTsdAsdGsdTsGb$^1$sTb$^1$sTb$^1$/3SpC3s/

3'-Spacer C3 CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene-thymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group. The subsequent reactions were performed as described in example 133. After purification, the antisense oligonucleotide was received with a purity of 89.7%.

Example 137

(Seq. ID No. 210o)
Gb$^1$C*b$^1$Tb$^1$Ab$^1$dTsdTsdTsdGsdGsdTsdAsdGsdTsGb$^1$Tb$^1$Tb$^1$

The compound was synthesized according to the general procedure with the appropriate DNA and LNA building units as exemplified in example 133 and example 134. After purification, the antisense oligonucleotide was received with a purity of 83.8%. ESI-MS: experimental: 5288.10 Da; calculated: 5287.9 Da.

Example 138

(Seq. ID No. 210p)
Gb$^1$sC*b$^1$sTb$^1$sAb$^1$sdTsdTsdTdGsdGsdTsdA*sdGsdTsGb$^1$sTb$^1$sTb$^1$

The compound was synthesized according to the general procedure with the appropriate DNA and LNA building units as exemplified in example 133. After purification, the antisense oligonucleotide was received with a purity of 80.7%. ESI-MS: experimental: 5398.40 Da; calculated: 5399.3 Da.

Example 139

(Seq. ID No. 210af)
Gb$^1$ssC*b$^1$ssTb$^1$ssdAssdTssdTssdTssdGssdGssdTssdA*ssdGssdTssGb$^1$ssTb$^1$ssTb$^1$ 5'-O-DMT-2'-O,4'-C-methylene-thymidine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 38 µl 5'-O-DMT-2'-O,4'-C-methylene-thymidine-3'-[(R-benzoylmercapto)ethyl]pyrrolidinolthiophosphoramidite (0.15 M) in 10% dichloromethane (v/V) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 38 µl 5'-O-DMT-2'-O,4'-C-methylene-N$^2$-dimethyformamidineguanosine-3'-[(3-benzoylmercapto)ethyl]pyrrolidinolthiophosphoramidite (0.15 M) in 10% dichloromethane (v/v) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The further elongation of the oligonucleotide was performed in the same way.

Upon completion of the solid phase synthesis, the antisense-oligonucleotides were treated 850 µl ammonia in concentrated ethanol (ammonia/ethanol 3:1 v/v) at 55° C. for 15-16 h in order to cleave antisense-oligonucleotide from the solid-support and to deprotect the thiol-group.

Next, the crude antisense-oligonucleotide was purified by anion-exchange chromatography using a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0.

Example 140-233

The other oligonucleotides of Table 7 were synthesized according to the general procedure and as shown in the examples. The preparation of the antisense-oligonucleotide including β-D-thio-LNA, α-L-oxy-LNA, β-D-(NH)-LNA, or β-D-(NCH$_3$)-LNA units were performed in the same way as the antisense-oligonucleotides containing β-D-oxy-LNA units.

Example 234

(Seq. ID No. 218b)
C*b$^1$sAb$^1$sTb$^1$sdGsdAsdAsdTsdGsdGsdAsdCsdCsAb$^1$sGb$^1$s
Tb$^1$sAb$^1$

5'-O-DMT-2'-O,4'-C-methylene-N$^6$-benzoyladenosine-3'-O-succinate

5'-O-DMT-2'-O,4'-C-methylene-N$^6$-benzoyladenosine (500 mg, 0.73 mmol), 95 mg succinic anhydride (0.95 mmol, 1.2 eq.) and 116 mg DMAP (0.95 mmol, 1.2 eq.) were dissolved in 35 ml dichloromethane. The reaction was stirred at room temperature overnight. The reaction solution was washed 2 times with 10 ml NaH$_2$PO$_4$ (0.1 M, pH 5.5) and one time with 10 ml brine. The organic phase was dried under anhydrous NaSO$_4$, filtered and concentrated to dryness in vacuo. The hemiester derivative was obtained in 95% yield and was used without further purification for the next step.

5'-O-DMT-2'-O,4'-C-methylene-N$^6$-benzoyladenosine-3'-O-succinoyl-linked LCAA CPG 70 mg hemiester derivative (90 µmol) was dissolved in 0.3 ml DMF, 11.6 µl DIEA (90 µmol) and pyBOP (90 µmol) were added and mixed together for 1 min. This mixture was combined with LCAA-CPG (500 Å, 80-120 mesh size, 300 mg) in a manual synthesizer and stirred for 1.5 hours at room temperature. The support was filtered off and washed with DMF, DCM and MeOH. After drying, the loading was determined to be 57 µmol/g.

Elongation
5'-O-DMT-2'-O,4'-C-methylene-N$^6$-benzoyladenosine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene-thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene-N$^2$-dimethyformamidineguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene-N$^6$-benzoyladenosine-3'-(2-cyanoethyl-N, N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^4$-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^4$-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800

µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^2$-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^2$-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^2$-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene-$N^6$-benzoyladenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O—,4'-C-methylene-5-methyl-N⁴-benzoylcytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for sec. At the end of this cycle, the system was washed with 480 µl acetonitrile. The compound was treated with 1400 µl 3% trichloroacetic acid in dichloromethane for 60 s to completely remove the 5'-DMT protection group.

Upon completion of the solid phase synthesis antisense-oligonucleotides were treated with a 20% diethylamine solution in acetonitrile (Biosolve BV, Valkenswaard, The Netherlands) for 20 min. to remove the cyanoethyl protecting groups on the phosphate backbone.

Subsequently, the antisense-oligonucleotides were cleaved from the solid support and further deprotected using 5 mL concentrated aqueous ammonia for 16 hours at 55° C. The solid support was separated from the antisense-oligonucleotides by filtration or centrifugation.

Next, the crude antisense-oligonucleotides were purified by anion-exchange high-performance liquid chromatography (HPLC) on an AKTA Explorer System (GE Healthcare, Freiburg, Germany) and a column packed with Source Q15 (GE Healthcare). Buffer A was 10 mM sodium perchlorate, 20 mM Tris, 1 mM EDTA, pH 7.4 and contained 20% acetonitrile and buffer B was the same as buffer A with the exception of 500 mM sodium perchlorate. A gradient of 15% B to 55% B within 32 column volumes (CV) was employed. UV traces at 280 nm were recorded. Appropriate fractions were pooled and precipitated with 3 M NaOAc, pH=5.2 and 70% ethanol. Finally, the pellet was washed with 70% ethanol. The antisense oligonucleotide was received with a purity of 94.8%. ESI-MS: experimental: 5365.80 Da; calculated: 5365.30 Da.

Example 235

(Seq. ID No. 218r)
C*b¹Ab¹Tb¹dGdAdAdTdGdGdAdCdCAb¹Gb¹Tb¹Ab¹

The LNA was bound to CPG according the general procedure. The coupling reaction and capping step were also carried out as described in example 234. After the capping step, the system was flushed out with 800 µl acetonitrile, and 400 µl of 0.02 M Iodine in THF/pyridine/H₂O were inserted to the column for 45 s. The system was flushed after the oxidation step with 24 µl acetonitrile. After purification, the antisense oligonucleotide was received with a purity of 97.8%. ESI-MS: experimental: 5125.10 Da.; calculated: 5124.4 Da.

Example 236

(Seq. ID No. 218t)
/5SpC3s/C*b¹sAb¹sTb¹sdGsdAsdAsdTsdGsdGsdAsdCsdCs

Ab¹sGb¹sTb¹sAb¹

The compound was synthesized according to the general procedure with the appropriate DNA and LNA building units as exemplified in example 234. But with the exception that after the last nucleotide has been coupled to the oligonucleotide and the subsequent oxidation and capping steps were carried out, 80 µl of phosphoramidite-C3 (0.07 M) and 236 µl DCI in acetonitrile (0.25 M) were added. The coupling was allowed to take place for 250 sec., and excess reagents were flashed out with 800 µl acetonitrile. The subsequent steps were performed as described in example 234. After purification, the antisense oligonucleotide was received with a purity of 94.2%. ESI-MS: experimental: 5519.60 Da; calculated: 5519.4 Da.

Example 237

(Seq. ID No. 218u)
C*b¹sAb¹sTb¹sdGsdAsdAsdTsdGsdGsdAsdCsdCsAb¹sGb¹s

Tb¹sAb¹s/3SpC3/

3'-Spacer C3 CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene-N⁶-benzoyladenosine-3'-[(2-cyanoethyl-N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group. The subsequent reactions were performed as described in example 234. After purification, the antisense oligonucleotide was received with a purity of 94.3%. ESI-MS: experimental: 5519.10 Da; calculated: 5519.4 Da.

Example 238

(Seq. ID No. 218aa)
C*b¹ssAb¹ssTb¹ssdGssdAssdAssdTssdGssdGssdAssdCssd

CssAb¹ssGb¹ssTb¹ssAb¹

5'-O-DMT-2'-O,4'-C-methylene-N⁶-benzoyladenosine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 38 µl 5'-O-DMT-2'-

O,4'-C-methylene-thymidine-3'-[(p-benzoylmercapto)ethyl] pyrrolidinolthiophosphoramidite (0.15 M) in 10% dichloromethane (v/V) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 38 µl 5'-O-DMT-2'-O, 4'-C-methylene-N²-dimethyformamidineguanosine-3'-[(R-benzoylmercapto)ethyl]pyrrolidinolthiophosphoramidite (0.15 M) in 10% dichloromethane (v/v) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The further elongation of the oligonucleotide was performed in the same way.

Upon completion of the solid phase synthesis, the antisense-oligonucleotides were treated 850 µl ammonia in concentrated ethanol (ammonia/ethanol 3:1 v/v) at 55° C. for 15-16 h in order to cleave antisense-oligonucleotide from the solid-support and to deprotect the thiol-group.

Next, the crude antisense-oligonucleotide was purified by anion-exchange chromatography using a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0.

Example 239

(Seq. ID No. 218m)
C*b¹sAb¹sTb¹sdGsdAsdAsdTsdGsdGsdAsdC*sdC*sAb¹sGb¹s

Tb¹sAb¹

The compound was synthesized according to the general procedure with the appropriate DNA and LNA building units as exemplified in example 234. After purification, the antisense oligonucleotide was received with a purity of 93.8%. ESI-MS: experimental: 5394.00 Da; calculated: 5393.3 Da.

Example 240

(Seq. ID No. 218n)
C*b¹Ab¹Tb¹dGsdAsdAsdTsdGsdGsdAsdC*sdC*sAb¹Gb¹Tb¹

Ab¹

The compound was synthesized according to the general procedure with the appropriate DNA building units and LNA building units as exemplified in example 234 and example 235. After purification, the antisense oligonucleotide was received with a purity of 94.7%. ESI-MS: experimental: 5297.30 Da; calculated: 5297.0 Da.

Example 241

(Seq. ID No. 218o)
C*b¹sAb¹sTb¹sdGsdA*sdA*sdTsdGsdGsdA*sdCsdCsAb¹sGb¹ sTb¹sAb¹

The compound was synthesized according to the general procedure with the appropriate DNA and LNA building units as exemplified in example 234. After purification, the antisense oligonucleotide was received with a purity of 92.8%. ESI-MS: experimental: 5410.40 Da; calculated: 5410.3 Da.

Example 242

(Seq. ID No. 218p)
C*b¹sAb¹sTb¹sdGsdA*sdA*sdTsdGsdGsdA*sdC*sdC*sAb¹s

Gb¹sTb¹sAb¹

The compound was synthesized according to the general procedure with the appropriate DNA and LNA building units as exemplified in example 234. After purification, the antisense oligonucleotide was received with a purity of 95.3%. ESI-MS: experimental: 5437.40 Da; calculated: 5438.4 Da.

Example 243

(Seq. ID No. 218q)
C*b¹sAb¹sTb¹sdGsdAsdAsdTsdGsdGsdAsdC*sdCsAbsGb¹s

Tb¹sAb¹

The compound was synthesized according to the general procedure with the appropriate DNA and LNA building units as exemplified in example 234. After purification, the antisense oligonucleotide was received with a purity of 93.9%. ESI-MS: experimental: 5378.80 Da; calculated: 5379.3 Da.

Example 244

(Seq. ID No. 218c)
C*b¹sAb¹sTb¹sdGsdAsdAsdTsdGsdGsdAsdCsdC*sAb¹sGb¹ sTb¹sAb¹

The compound was synthesized according to the general procedure with the appropriate DNA and LNA building units as exemplified in example 234. After purification, the antisense oligonucleotide was received with a purity of 92.9%. ESI-MS: experimental: 5379.10 Da; calculated: 5379.3 Da.

Example 245

(Seq. ID No. 218s)
C*b¹sAb¹sTb¹sdGdAdAdTdGdGdAdC*sdC*sAb¹sGb¹sTb¹sAb¹

The compound was synthesized according to the general procedure with the appropriate DNA and LNA building units as exemplified in example 234. After purification, the antisense oligonucleotide was received with a purity of 94.5%. ESI-MS: experimental: 5152.70 Da; calculated: 5152.4 Da.

Example 246

(Seq. ID No. 218v)
/5SpC3/sC*b¹sAb¹sTb¹sdGsdAsdAsdTsdGsdGsdAsdCsdCs
Ab¹sGb¹sTb¹sAb¹s/3SpC3/

The compound was synthesized according to the general procedure with the appropriate DNA building units and LNA building units as exemplified in example 234, example 236 and example 237. After purification, the antisense oligonucleotide was received with a purity of 94.4%. ESI-MS: experimental: 5673.50 Da; calculated: 5673.5 Da

Example 247-335

The other oligonucleotides of Table 8 were synthesized according to the general procedure and as shown in the examples. The preparation of the antisense-oligonucleotide including β-D-thio-LNA, α-L-oxy-LNA, β-D-(NH)-LNA, or β-D-(NCH₃)-LNA units were performed in the same way as the antisense-oligonucleotides containing β-D-oxy-LNA units.

Example 336

(Seq. ID No. 152h)
C*b¹sGb¹sAb¹sTb¹sdAsdCsdGsdCsdGsdTsdCsdCsAb¹sC*b¹
sAb¹

5'-O-DMT-2'-O,4'-C-methylene-N⁶-benzoyladenosine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O—,4'-C-methylene-5-methyl-N⁴-benzoylcytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene-N⁶-benzoyladenosine-3'-(2-cyanoethyl-N, N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N⁴-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N⁴-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s. The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N²-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^4$-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^2$-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^4$-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene-N$^6$-benzoyladenosine-3'-(2-cyanoethyl-N, N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene-N$^2$-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O—,4'-C-methylene-5-methyl-N$^4$-benzoylcytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for sec. At the end of this cycle, the system was washed with 480 µl acetonitrile. The compound was treated with 1400 µl 3% trichloroacetic acid in dichloromethane for 60 s to completely remove the 5'-DMT protection group.

Upon completion of the solid phase synthesis antisense-oligonucleotides were treated with a 20% diethylamine solution in acetonitrile (Biosolve BV, Valkenswaard, The Netherlands) for 20 min. to remove the cyanoethyl protecting groups on the phosphate backbone.

Subsequently, the antisense-oligonucleotides were cleaved from the solid support and further deprotected using 5 mL concentrated aqueous ammonia for 16 hours at 55° C. The solid support was separated from the antisense-oligonucleotides by filtration or centrifugation.

Next, the crude antisense-oligonucleotides were purified by anion-exchange high-performance liquid chromatography (HPLC) on an AKTA Explorer System (GE Healthcare, Freiburg, Germany) and a column packed with Source Q15

(GE Healthcare). Buffer A was 10 mM sodium perchlorate, 20 mM Tris, 1 mM EDTA, pH 7.4 and contained 20% acetonitrile and buffer B was the same as buffer A with the exception of 500 mM sodium perchlorate. A gradient of 15% B to 55% B within 32 column volumes (CV) was employed. UV traces at 280 nm were recorded. Appropriate fractions were pooled and precipitated with 3 M NaOAc, pH=5.2 and 70% ethanol. Finally, the pellet was washed with 70% ethanol.

Example 337

(Seq. ID No. 152q)
C*b¹Gb¹Ab¹Tb¹dAdCdGdC*dGdTdCdC*Ab¹C*b¹Ab¹

The LNA was bound to CPG according to the general procedure. The coupling reaction and capping step were also carried out as described in example 336. After the coupling step, the system was flushed out with 800 µl acetonitrile, and 400 µl of 0.02 M Iodine in THF/pyridine/H₂O were inserted to the column for 45 s. After the oxidation step, the system was flushed with 24 µl acetonitrile. After purification, the antisense oligonucleotide was received with a purity of 93.1%.

Example 338

(Seq. ID. No. 152s)
/5SpC3s/C*b¹sGb¹sAb¹sTb¹sdAsdC*sdGsdC*sdGsdTsdCsd
CsAb¹sC*b¹sAb¹

The compound was synthesized according to the general procedure with the appropriate DNA and LNA building units as exemplified in example 336. But with the exception that after the last nucleotide has been coupled to the oligonucleotide and the subsequent oxidation and capping steps were carried out, 80 µl of phosphoramidite-C3 (0.07 M) and 236 µl DCI in acetonitrile (0.25 M) were added. The coupling was allowed to take place for 250 sec., and excess reagents were flashed out with 800 µl acetonitrile. The subsequent steps were performed as described in example 336. After purification, the antisense oligonucleotide was received with a purity of 96.5%.

Example 339

(Seq. ID No. 152t)
C*b¹sGb¹sAb¹sTb¹sdAsdC*sdGsdCsdGsdTsdCsdC*sAb¹
sC*b¹sAb¹/3SpC3s/

3'-Spacer C3 CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene-N⁶-benzoyladenosine-3'-[(2-cyanoethyl-N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group. The subsequent reactions were performed as described in example 336. After purification, the antisense oligonucleotide was received with a purity of 92.1%.

Example 340

(Seq. ID No. 152aa)
C*b¹ssGb¹ssAb¹ssdTssdAssdC*ssdGssdCssdGssdTssd
CssdC*ssAb¹ssC*b¹ssAb¹

5'-O-DMT-2'-O,4'-C-methylene-N⁶-benzoyladenosine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 38 µl 5'-O-DMT-2'-O—,4'-C-methylene-5-methyl-N⁴-benzoylcytidine-3'-[(p-benzoylmercapto)ethyl]pyrrolidinolthiophosphoramidite (0.15 M) in 10% dichloromethane (v/V) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 38 µl 5'-O-DMT-2'-O, 4'-C-methylene-N⁶-benzoyladenosine-3'-[(β-benzoylmercapto)ethyl]pyrrolidinolthiophosphoramidite (0.15 M) in 10% dichloromethane (v/v) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The further elongation of the oligonucleotide was performed in the same way.

Upon completion of the solid phase synthesis, the antisense-oligonucleotides were treated 850 µl ammonia in concentrated ethanol (ammonia/ethanol 3:1 v/v) at 55° C. for 15-16 h in order to cleave antisense-oligonucleotide from the solid-support and to deprotect the thiol-group.

Next, the crude antisense-oligonucleotide was purified by anion-exchange chromatography using a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0.

Example 341-433

The other oligonucleotides of Table 5 were synthesized according to the general procedure and as shown in the examples. The preparation of the antisense-oligonucleotide including β-D-thio-LNA, α-L-oxy-LNA, β-D-(NH)-LNA, or β-D-(NCH$_3$)-LNA units were performed in the same way as the antisense-oligonucleotides containing β-D-oxy-LNA units.

Example 434

(Seq. ID No. 143h)
C*b$^1$sTb$^1$sdCsdGsdTsdCsdAsdTsdAsdGsdAsC*b$^1$sC*b$^1$sGb$^1$

5'-O-DMT-2'-O,4'-C-methylene-N$^2$-dimethyformamidineguanosine -3'-O-succinoyl- linked LCAA CPG (0.2 μmol) was treated with 1400 μl 3% trichloroacetic acid in dichloromethane for 60 s to completely remove the 5'-DMT protection group. After several washes with a total amount of 800 μl acetonitrile, the coupling reaction was carried out with 80 μl 5'-O-DMT-2'-O—,4'-C-methylene-5-methyl-N$^4$-benzoylcytidine-3'-(2-cyanoethyl-N,N-diisopropyl)phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THF (1:9 v/v) and 448 μl N-methylimidazol (NMI)/THF/pyridine (1:8:1) were added and allowed to react for 45 sec. At the end of this cycle, the system was washed with 480 μl acetonitrile. The compound was treated with 1400 μl 3% trichloroacetic acid in dichloromethane for 60 s to completely remove the 5'-DMT protection group.

The coupling was carried out with 80 μl 5'-O-DMT-2'-O—,4'-C-methylene-5-methyl-N$^4$-benzoylcytidine-3'-(2-cyanoethyl-N,N-diisopropyl)phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THE (1:9 v/v) and 448 μl N-methylimidazol (NMI)/THF/pyridine (1:8:1) were added and allowed to react for sec. At the end of this cycle, the system was washed with 480 μl acetonitrile. The compound was treated with 1400 μl 3% trichloroacetic acid in dichloromethane for 60 s to completely remove the 5'-DMT protection group.

The coupling was carried out with 80 μl 5'-O-DMT-N$^6$-benzoyl-2'-deoxyadenosine-3'-(2-cyanoethyl-N,N-diisopropyl)phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THE (1:9 v/v) and 448 μl N-methylimidazol (NMI)/THF/pyridine (1:8:1) were added and allowed to react for 45 sec. At the end of this cycle, the system was washed with 480 μl acetonitrile. The compound was treated with 1400 μl 3% trichloroacetic acid in dichloromethane for 60 s to completely remove the 5'-DMT protection group.

The coupling was carried out with 80 μl 5'-O-DMT-N$^2$-isobutyryl-2'-deoxyguanosine-3'-(2-cyanoethyl-N,N-diisopropyl)phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THF (1:9 v/v) and 448 μl N-methylimidazol (NMI)/THF/pyridine (1:8:1) were added and allowed to react for 45 sec. At the end of this cycle, the system was washed with 480 μl acetonitrile. The compound was treated with 1400 μl 3% trichloroacetic acid in dichloromethane for 60 s to completely remove the 5'-DMT protection group.

The coupling was carried out with 80 μl 5'-O-DMT-N$^6$-benzoyl-2'-deoxyadenosine-3'-(2-cyanoethyl-N,N-diisopropyl)phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THF (1:9 v/v) and 448 μl N-methylimidazol (NMI)/THF/pyridine (1:8:1) were added and allowed to react for 45 sec. At the end of this cycle, the system was washed with 480 μl acetonitrile. The compound was treated with 1400 μl 3% trichloroacetic acid in dichloromethane for 60 s to completely remove the 5'-DMT protection group.

The coupling was carried out with 80 μl 5'-O-DMT-2'-deoxythymidine-3'-[(2-cyanoethyl)-(N,N-diisopropyl)]-phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THE (1:9 v/v) and 448 μl N-methylimidazol (NMI)/THF/pyridine (1:8:1) were added and allowed to react for 45 sec. At the end of this cycle, the system was washed with 480 μl acetonitrile. The compound was treated with 1400 μl 3% trichloroacetic acid in dichloromethane for 60 s to completely remove the 5'-DMT protection group.

The coupling was carried out with 80 μl 5'-O-DMT-N$^6$-benzoyl-2'-deoxyadenosine-3'-(2-cyanoethyl-N,N-diisopropyl)phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THF (1:9 v/v) and 448 μl N-methylimidazol (NMI)/THF/pyridine (1:8:1) were added and allowed to react for 45 sec. At the end of this cycle, the system was washed with 480 μl acetonitrile. The compound was treated with 1400 μl 3% trichloroacetic acid in dichloromethane for 60 s to completely remove the 5'-DMT protection group.

The coupling was carried out with 80 μl 5'-O-DMT-N$^4$-benzoyl-2'-deoxycytidine-3'-(2-cyanoethyl-N,N-diisopropyl)phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^2$-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-$N^4$-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O, 4'-C-methylene thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O—,4'-C-methylene-5-methyl-$N^4$-benzoylcytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for sec. At the end of this cycle, the system was washed with 480 µl acetonitrile. The compound was treated with 1400 µl 3% trichloroacetic acid in dichloromethane for 60 s to completely remove the 5'-DMT protection group.

Upon completion of the solid phase synthesis antisense-oligonucleotides were treated with a 20% diethylamine solution in acetonitrile (Biosolve BV, Valkenswaard, The Netherlands) for 20 min. to remove the cyanoethyl protecting groups on the phosphate backbone.

Subsequently, the antisense-oligonucleotides were cleaved from the solid support and further deprotected using 5 mL concentrated aqueous ammonia for 16 hours at 55° C. The solid support was separated from the antisense-oligonucleotides by filtration or centrifugation.

Next, the crude antisense-oligonucleotides were purified by anion-exchange high-performance liquid chromatography (HPLC) on an AKTA Explorer System (GE Healthcare, Freiburg, Germany) and a column packed with Source Q15 (GE Healthcare). Buffer A was 10 mM sodium perchlorate, 20 mM Tris, 1 mM EDTA, pH 7.4 and contained 20% acetonitrile and buffer B was the same as buffer A with the exception of 500 mM sodium perchlorate. A gradient of 15% B to 55% B within 32 column volumes (CV) was employed. UV traces at 280 nm were recorded. Appropriate fractions were pooled and precipitated with 3 M NaOAc, pH=5.2 and 70% ethanol. Finally, the pellet was washed with 70% ethanol.

Example 435

(Seq. ID No. 143ad)
C*b'Tb'dC*dGdTdCdAdTdAdGdAC*b'C*b'Gb'

The LNA was bound to CPG according to the general procedure. The coupling reaction and capping step were also carried out as described in example 434. After the capping step, the system was flushed out with 800 µl acetonitrile, and 400 µl of 0.02 M Iodine in THF/pyridine/$H_2O$ were inserted to the column for 45 s. The system was flushed after the oxidation step with 24 µl acetonitrile. After purification, the antisense oligonucleotide was received with a purity of 88.7%.

Example 436

(Seq. ID No. 143af)
/5SpC3s/C*b'sTb'sdC*dGdTdC*dA*dTdAdGdA*sC*b'sC*b' sGb'

The compound was synthesized according to the general procedure with the appropriate DNA and LNA building units as exemplified in example 434 and example 435. But with the exception that after the last nucleotide has been coupled to the oligonucleotide and the subsequent oxidation and capping steps were carried out, 80 µl of phosphoramidite-$C_3$ (0.07 M) and 236 µl DCI in acetonitrile (0.25 M) were added. The coupling was allowed to take place for 250 sec., and excess reagents were flashed out with 800 µl acetonitrile. The subsequent steps were performed as described in example 434 and example 435. After purification, the antisense oligonucleotide was received with a purity of 94.4%.

Example 437

(Seq. ID No. 143ag)
C*b¹sTb¹sdC*dGdTdC*dA*dTdAdGdA*sC*b¹sC*b¹sGb¹/

3SpC3s/

3'-Spacer C3 CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene-N²-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group. The subsequent reactions were performed as described in example 434 and example 435. After purification, the antisense oligonucleotide was received with a purity of 91.6%.

Example 438

(Seq. ID No. 143t)
C*b¹ssTb¹ssC*b¹ssdGssdTssdC*ssdAssdTssdAssdGssdAss

C*b¹ssC*b¹ssGb¹

5'-O-DMT-2'-O,4'-C-methylene-N²-dimethyformamidineguanosine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 38 µl 5'-O-DMT-2'-O—,4'-C-methylene-5-methyl-N⁴-benzoylcytidine-3'-[(p-benzoylmercapto)ethyl]pyrrolidinolthiophosphoramidite (0.15 M) in 10% dichloromethane (v/V) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 38 µl 5'-O-DMT-2'-O—,4'-C-methylene-5-methyl-N⁴-benzoylcytidine-3'-[(p-benzoylmercapto)ethyl]pyrrolidinolthiophosphoramidite (0.15 M) in 10% dichloromethane (v/v) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The further elongation of the oligonucleotide was performed in the same way.

Upon completion of the solid phase synthesis, the antisense-oligonucleotides were treated 850 µl ammonia in concentrated ethanol (ammonia/ethanol 3:1 v/v) at 55° C. for 15-16 h in order to cleave antisense-oligonucleotide from the solid-support and to deprotect the thiol-group.

Next, the crude antisense-oligonucleotide was purified by anion-exchange chromatography using a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0.

Example 439-534

The other oligonucleotides of Table 4 were synthesized according to the general procedure and as shown in the examples. The preparation of the antisense-oligonucleotide including β-D-thio-LNA, α-L-oxy-LNA, β-D-(NH)-LNA, or β-D-(NCH₃)-LNA units were performed in the same way as the antisense-oligonucleotides containing β-D-oxy-LNA units.

Example 535

(Seq. ID No. 213k)
C*b¹sAb¹sGb¹sdGsdCsdAsdTsdTsdAsdAsdTsdAsdAsdAsGb¹ sTb¹sGb¹

5'-O-DMT-2'-O,4'-C-methylene-N²-dimethyformamidineguanosine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene thymidine 3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene-N$^2$-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-deoxythymidine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^6$-benzoyl-2'-deoxyadenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^4$-benzoyl-2'-deoxycytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-N$^2$-isobutyryl-2'-deoxyguanosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene-N$^2$-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O,4'-C-methylene-N$^6$-benzoyladenosine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s. The system was flushed with 320 µl acetonitrile. For the capping step, 448 µl of acetic anhydride in THE (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 80 µl 5'-O-DMT-2'-O—,4'-C-methylene-5-methyl-N$^4$-benzoylcytidine-3'-(2-cyanoethyl-N,N-diisopropyl)phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for sec. At the end of this cycle, the system was washed with 480 µl acetonitrile. The compound was treated with 1400 µl 3% trichloroacetic acid in dichloromethane for 60 s to completely remove the 5'-DMT protection group.

Upon completion of the solid phase synthesis antisense-oligonucleotides were treated with a 20% diethylamine solution in acetonitrile (Biosolve BV, Valkenswaard, The Netherlands) for 20 min. to remove the cyanoethyl protecting groups on the phosphate backbone.

Subsequently, the antisense-oligonucleotides were cleaved from the solid support and further deprotected using 5 mL concentrated aqueous ammonia for 16 hours at 55° C. The solid support was separated from the antisense-oligonucleotides by filtration or centrifugation.

Next, the crude antisense-oligonucleotides were purified by anion-exchange high-performance liquid chromatography (HPLC) on an AKTA Explorer System (GE Healthcare, Freiburg, Germany) and a column packed with Source 015 (GE Healthcare). Buffer A was 10 mM sodium perchlorate, 20 mM Tris, 1 mM EDTA, pH 7.4 and contained 20% acetonitrile and buffer B was the same as buffer A with the exception of 500 mM sodium perchlorate. A gradient of 15% B to 55% B within 32 column volumes (CV) was employed. UV traces at 280 nm were recorded. Appropriate fractions were pooled and precipitated with 3 M NaOAc, pH=5.2 and 70% ethanol. Finally, the pellet was washed with 70% ethanol.

Example 536

(Seq. ID No. 213n)
C*b'Ab'Gb'dGdC*dAdTdTdAdAdTdAdAdAGb'Tb'Gb'

The LNA was bound to CPG according to general procedure. The coupling reaction and capping step were also carried out as described in example 535. After the ccapping step, the system was flushed out with 800 µl acetonitrile, and 400 µl of 0.02 M Iodine in THF/pyridine/H$_2$O were inserted to the column for 45 s. The system was flushed after the oxidation step with 24 µl acetonitrile. After purification, the antisense oligonucleotide was received with a purity of 91.4%.

Example 537

(Seq. ID No. 213o)
/5SpC3s/C*b'sAb'sGb'sdGsdC*sdAsdTsdTsdAsdAsdTsdAsd

AsdAsGb'sTb'sGb'

The compound was synthesized according to the general procedure with the appropriate DNA and LNA building units as exemplified in example 535. But with the exception that after the last nucleotide has been coupled to the oligonucleotide and the subsequent oxidation and capping steps were carried out, 80 µl of phosphoramidite-C3 (0.07 M) and 236 µl DCI in acetonitrile (0.25 M) were added. The coupling was allowed to take place for 250 sec., and excess reagents were flashed out with 800 µl acetonitrile. The subsequent steps were performed as described in example 535. After purification, the antisense oligonucleotide was received with a purity of 87.1%.

Example 538

(Seq. ID No. 213p)
C*b¹sAb¹sGb¹sdGsdC*sdAsdTsdTsdAsdAsdTsdAsdAsdAs

Gb¹sTb¹sGb¹/3SpC3s/

3'-Spacer C3 CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 80 µl 5'-O-DMT-2'-O,4'-C-methylene-N²-dimethyformamidineguanosine-3'-[(2-cyanoethyl)-(N,N-diisopropyl)]-phosphoramidite (0.07 M) and 236 µl DCI in acetonitrile (0.25 M). The coupling reaction was allowed to take place for 250 sec., and excess reagents were flashed out with 800 µl acetonitrile, and 640 µl of Beaucage (0.2 M) were inserted to the column for 180 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group. The subsequent reactions were performed as described in example 535. After purification, the antisense oligonucleotide was received with a purity of 95.7%.

Example 539

(Seq. ID No. 213ae)
C*b¹ssAb¹ssGb¹ssdGssdC*ssdAssdTssdTssdAssdAssdTssd

AssdAssAb¹ssGb¹ssTb¹ssGb¹

5'-O-DMT-2'-O,4'-C-methylene-N²-dimethyformamidineguanosine-3'-O-succinoyl- linked LCAA CPG (0.2 µmol) was treated with 1400 µl 3% trichloroacetic acid in dichloromethane for 60 s to completely remove the 5'-DMT protection group. After several washes with a total amount of 800 µl acetonitrile, the coupling reaction was carried out with 38 µl 5'-O-DMT-2'-O,4'-C-methylene-thymidine-3'-[(p-benzoylmercapto)ethyl]pyrrolidinolthiophosphoramidite (0.15 M) in 10% dichloromethane (v/V) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The coupling was carried out with 38 µl 5'-O-DMT-2'-O,4'-C-methylene-N²-dimethyformamidineguanosine-3'-[((β-benzoylmercapto)ethyl]pyrrolidinolthiophosphoramidite (0.15 M) in 10% dichloromethane (v/v) in acetonitrile and 236 µl DCI in acetonitrile (0.25 M). The coupling reaction was allowed to take place for 250 sec., and excess reagents were flashed out with 800 µl acetonitrile, and 900 µl of DDTT (0.05 M in pyridine/acetonitrile 4:1 v/v) were inserted to the column for 240 s The system was flushed with 320 µl acetonitrile. For the capping step, 448 µl of acetic anhydride in THF (1:9 v/v) and 448 µl N-methylimidazol (NMI)/THF/pyridine (1:8:1) were added and allowed to react for 45 sec. At the end of this cycle, the system was washed with 480 µl acetonitrile. The compound was treated with 1400 µl 3% trichloroacetic acid in dichloromethane for 60 s to completely remove the 5'-DMT protection group.

The further elongation of the oligonucleotide was performed in the same way.

Upon completion of the solid phase synthesis, the antisense-oligonucleotides were treated 850 µl ammonia in concentrated ethanol (ammonia/ethanol 3:1 v/v) at 55° C. for 15-16 h in order to cleave antisense-oligonucleotide from the solid-support and to deprotect the thiol-group.

Next, the crude antisense-oligonucleotide was purified by anion-exchange chromatography using a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0.

Examples 540-640

The other oligonucleotides of Table 9 were synthesized according to the general procedure and as shown in the examples. The preparation of the antisense-oligonucleotide including β-D-thio-LNA, α-L-oxy-LNA, β-D-(NH)-LNA, or β-D-(NCH₃)-LNA units were performed in the same way as the antisense-oligonucleotides containing β-D-oxy-LNA units.

```
                      Sequence Listing

Seq. ID No. 1: Homo sapiens transforming growth factor, beta
receptor II (TGFBR2), transcript variant 2, (antisense; DNA code)
TTTAGCTACT AGGAATGGGA ACAGGAGGCA GGATGCTCAC CTGAGTATTT TGCTTTATTC    60

AATCTAATAA ACATTTTATT TATGTAAAAG ACAAACAATG CATAGAATAA AAATAAGTGC   120

TTGAGACTTT TGATATAAAA AGAGTATATA GCATTCACAT TCCTATTTTA ATACATGAGT   180
```

```
ACAGCTGAAG TGTTCCATAA AAGAATAAAA CTTTCCCTTT ATGTATAGTA GTGAAAAAAG    240

TCAGTATTTT TAGGAACTAC AGAATGTTAT TCCTTGGTCT TTTTTCTTGA ATAAGAAAAA    300

AAAACATAAA CAAAACAAGC CACAGTATCC TCTGACACTA CATTCCAGTT TATGCTGATA    360

ACCCAGAAGT GAGAATACTC TTGAATCTTG AATATCTCAT GAATGGACCA GTATTCTAGA    420

AACTCACCAC TAGAGGTCAA TGGGCAACAG CTATTGGGAT GGTATCAGCA TGCCCTACGG    480

TGCAAGTGGA ATTTCTAGGC GCCTCTATGC TACTGCAGCC ACACTGTCTT TAACTCTCAG    540

CCCACCCACA CTGAGGAGGG TGCCTAGAGG TTCTATTTCC AAACCTTTGC ATGTATCTTA    600

AAAATCTCAA TAAAATGAGA CCTTCCACCA TCCAAACAGA GCTGATATTC TCACTACCAG    660

TCCCTCTCTA ATATTCCTAT TTGGCTGAAA ATAAGTAGCT TCAAAAGTT TTAAAAAGA      720

GATTACTTGC AGCATTAACA CTTCTTTGTT GATTAACAAG TTTCCTATGG AGTTTTAAAG    780

CTCATACTTT GTTCTTGTCC TTGTGGACAC AAATTTTCTA ACTGCAAATG GGACCTTTGT    840

GTCCCACATT CAAATCCTCT CTAGTAATTT CTGCAAAGGT TGAGAAGGCT GGCATGATGG    900

AGAGAACGGT AACCATGAGG AAAGCTTCTT GGAGTAAAGC ACTCCTCTCT CCAATGCAGA    960

GGGTAAAACT ATTAACATAT AAGCAAAGA AACTTGGGCT AACTGAGACC CTTAAAGGAG    1020

TTCCCCTTTA GTCCAATAAA AGGCCAACTT CAAATCTTAA CACCAGATAA GGTAGTCAAA   1080

ATCATATTAT ATACCCAGAG AATGACTGCT TGAATGGACA TTTCTTACAA GGGACCTTGG   1140

TTAGGTGCAG ATTTAATTCC TAGACTGGGG TCCAGGTAGG CAGTGGAAAG AGCTAATGTT   1200

TACAGTGAGA AGTGAGGCAG CTTTGTAAGT GTCTCCACAC CTTCACATTT TGTGAACGTG   1260

GACTGGAGAT AACTGAAAAC CATCTGCTAT CCTTACCTGG GGATCCAGAT TTTCCTGCAA   1320

AATCTCCAAA TATTTATAAA GTGGCTTCAC TTTTTGAAAC GCTGTGCTGA CCAAACAAAA   1380

CATATGTTTA GAGTGCCTGA GGTCATAGTC CTGACAATGA TAGTATTGTG TAGTTGAAAT   1440

CCTCTTCATC AGGCCAAACT GTGCTTGAGC AATCAGGAGC CCAGAAAGAT GGAACCCATT   1500

GGTGTTTGTA TAGAAAACTA GAAAATCAAG TCAAGTGTAA TGAAAAAGTA AACACGATAA   1560

AGCCTAGAGT GAGAATTTGC TCCTTTTTAG AAAAGGATGA AGGCTGGGAG CAGAGAATAG   1620

TAACATAAGT GCAGGGGAAA GATGAAAAAA AGAACAATTT TTCATTAGTA GATGGTGGGG   1680

CAATCGCATG GATGGGACA TCTGTTCTGA TTTTTCTGCA ACCCATGAAG GTAAAAAGTG    1740

GGGTTCAAAA CATTCAAGGT ATTAAAGATG GGGTAGAGTT TCTAAACTAG GTTGAGGGAG   1800

AGTTTCTAAA CTAGCCCCCC AGATTTGGGG CTTGGAGCTT AAATGAAAAG TCCAGGAGAA   1860

ATAAGGGCAC ACAGGAACCC CGGGAACACT GGTCCTCAAA CAGTGCCACT GTACTTAGTT   1920

CCATGGCCAG AAGAGAAGTG CTAGGCAGGG AATGATTATT TTGCAAAAGC AAGTGCAATG   1980

TGGTCATAGC TGGCTGTGAG ACATGGAGCC TCTTTCCTCA TGCAAAGTTC ACTGTTTTAC   2040

AGTCAGAGAA CCACTGCATG TGTGATTGTC AAATGCTAAT GCTGTCATGG GTCCCTTCCT   2100

TCTCTGCTTG GTTCTGGAGT TCTCCAATAA AACCAATTTC CTGGGAATAT TTGATGTTTT   2160

TCCTTGTCTC TTTTCAAGGT ATGGCTATAT ATATAGAGCT ATAGACATAT ATAGATATAT   2220

ATATATATAT ATAAAACATA GCTATTCATA TTTATATACA GGCATTAATA AAGTGCAAAT   2280

GTTATTGGCT ATTGTAAAAA TCAATCTCAT TTCCTGAGGA AGTGCTAACA CAGCTTATCC   2340

TATGACAATG TCAAAGGCAT AGAATGCTCT ATGTCACCCA CTCCCTGCTG CTGTTGTTTC   2400

TGCTTATCCC CACAGCTTAC AGGGAGGGGA GTGACCCCCT TGGTTTTCCA GGAAGCATCA   2460

GTTCAGGGGC AGCTTCCTGC TGCCTCTGTT CTTTGGTGAG AGGGGCAGCC TCTTTGGACA   2520
```

```
                       Sequence Listing

TGGCCCAGCC TGCCCCAGAA GAGCTATTTG GTAGTGTTTA GGGAGCCGTC TTCAGGAATC    2580

TTCTCCTCCG AGCAGCTCCT CCCCGAGAGC CTGTCCAGAT GCTCCAGCTC ACTGAAGCGT    2640

TCTGCCACAC ACTGGGCTGT GAGACGGGCC TCTGGGTCGT GGTCCCAGCA CTCAGTCAAC    2700

GTCTCACACA CCATCTGGAT GCCCTGGTGG TTGAGCCAGA AGCTGGGAAT TTCTGGTCGC    2760

CCTCGATCTC TCAACACGTT GTCCTTCATG CTTTCGACAC AGGGGTGCTC CCGCACCTTG    2820

GAACCAAATG GAGGCTCATA ATCTTTTACT TCTCCCACTG CATTACAGCG AGATGTCATT    2880

TCCCAGAGCA CCAGAGCCAT GGAGTAGACA TCGGTCTGCT TGAAGGACTC AACATTCTCC    2940

AAATTCATCC TGGATTCTAG GACTTCTGGA GCCATGTATC TTGCAGTTCC CACCTGCCCA    3000

CTGTTAGCCA GGTCATCCAC AGACAGAGTA GGGTCCAGAC GCAGGGAAAG CCCAAAGTCA    3060

CACAGGCAGC AGGTTAGGTC GTTCTTCACG AGGATATTGG AGCTCTTGAG GTCCCTGTGC    3120

ACGATGGGCA TCTTGGGCCT CCCACATGGA GTGTGATCAC TGTGGAGGTG AGCAATCCCC    3180

CGGGCGAGGG AGCTGCCCAG CTTGCGCAGG TCCTCCCAGC TGATGACATG CCGCGTCAGG    3240

TACTCCTGTA GGTTGCCCTT GGCGTGGAAG GCGGTGATCA GCCAGTATTG TTTCCCCAAC    3300

TCCGTCTTCC GCTCCTCAGC CGTCAGGAAC TGGAGTATGT TCTCATGCTT CAGATTGATG    3360

TCTGAGAAGA TGTCCTTCTC TGTCTTCCAA GAGGCATACT CCTCATAGGG AAAGATCTTG    3420

ACTGCCACTG TCTCAAACTG CTCTGAAGTG TTCTGCTTCA GCTTGGCCTT ATAGACCTCA    3480

GCAAAGCGAC CTTTCCCCAC CAGGGTGTCC AGCTCAATGG GCAGCAGCTC TGTGTTGTGG    3540

TTGATGTTGT TGGCACACGT GGAGCTGATG TCAGAGCGGT CATCTTCCAG GATGATGGCA    3600

CAGTGCTCGC TGAACTCCAT GAGCTTCCGC GTCTTGCCGG TTTCCCAGGT TGAACTCAGC    3660

TTCTGCTGCC GGTTAACGCG GTAGCAGTAG AAGATGATGA TGACAGATAT GGCAACTCCC    3720

AGTGGTGGCA GGAGGCTGAT GCCTGTCACT TGAAATATGA CTAGCAACAA GTCAGGATTG    3780

CTGGTGTTAT ATTCTTCTGA GAAGATGATG TTGTCATTGC ACTCATCAGA GCTACAGGAA    3840

CACATGAAGA AAGTCTCACC AGGCTTTTTT TTTTCCTTCA TAATGCACTT GGAGAAGCA    3900

GCATCTTCCA GAATAAAGTC ATGGTAGGGG AGCTTGGGGT CATGGCAAAC TGTCTCTAGT    3960

GTTATGTTCT CGTCATTCTT TCTCCATACA GCCACACAGA CTTCCTGTGG CTTCTCACAG    4020

ATGGAGGTGA TGCTGCAGTT GCTCATGCAG GATTTCTGGT TGTCACAGGT GGAAAATCTC    4080

ACATCACAAA ATTTACACAG TTGTGGAAAC TTGACTGCAC CGTTGTTGTC AGTGACTATC    4140

ATGTCGTTAT TAACCGACTT CTGAACGTGC GGTGGGATCG TGCTGGCGAT ACGCGTCCAC    4200

AGGACGATGT GCAGCGGCCA CAGGCCCCTG AGCAGCCCCC GACCCATGGC AGACCCCGCT    4260

GCTCGTCATA GACCGAGCCC CCAGCGCAGC GGACGGCGCC TTCCCGGACC CCTGGCTGCG    4320

CCTCCGCGCC GCGCCCTCTC CGGACCCCGC GCCGGGCCGG CAGCGCAGAT GTGCGGGCCA    4380

GATGTGGCGC CCGCTCGCCA GCCAGGAGGG GGCCTGGAGG CCGGCGAGGC GCGGGAGGC    4440

CCCCGGCGGC CGAGGGAAGC TGCACAGGAG TCCGGCTCCT GTCCCGAGCG GGTGCACGCG    4500

CGGGGGTGTC GTCGCTCCGT GCGCGCGAGT GACTCACTCA ACTTCAACTC AGCGCTGCGG    4560

GGGAAACAGG AAACTCCTCG CCAACAGCTG GGCAGGACCT CTCTCCGCCC GAGAGCCTTC    4620

TCCCTCTCC                                                          4629
```

-continued

Sequence Listing

Seq. ID No. 2: *Homo sapiens* transforming growth factor, beta
receptor II (TGFBR2), transcript variant 2, mRNA (sense; written
in DNA code)

| | | | | | |
|---|---|---|---|---|---|
| GGAGAGGGAG | AAGGCTCTCG | GGCGGAGAGA | GGTCCTGCCC | AGCTGTTGGC | GAGGAGTTTC | 60 |
| CTGTTTCCCC | CGCAGCGCTG | AGTTGAAGTT | GAGTGAGTCA | CTCGCGCGCA | CGGAGCGACG | 120 |
| ACACCCCGC | GCGTGCACCC | GCTCGGGACA | GGAGCCGGAC | TCCTGTGCAG | CTTCCCTCGG | 180 |
| CCGCCGGGGG | CCTCCCCGCG | CCTCGCCGGC | CTCCAGGCCC | CCTCCTGGCT | GGCGAGCGGG | 240 |
| CGCCACATCT | GGCCCGCACA | TCTGCGCTGC | CGGCCCGGCG | CGGGGTCCGG | AGAGGGCGCG | 300 |
| GCGCGGAGGC | GCAGCCAGGG | GTCCGGGAAG | GCGCCGTCCG | CTGCGCTGGG | GGCTCGGTCT | 360 |
| ATGACGAGCA | GCGGGGTCTG | CCATGGGTCG | GGGGCTGCTC | AGGGGCCTGT | GGCCGCTGCA | 420 |
| CATCGTCCTG | TGGACGCGTA | TCGCCAGCAC | GATCCCACCG | CACGTTCAGA | AGTCGGTTAA | 480 |
| TAACGACATG | ATAGTCACTG | ACAACAACGG | TGCAGTCAAG | TTTCCACAAC | TGTGTAAATT | 540 |
| TTGTGATGTG | AGATTTTCCA | CCTGTGACAA | CCAGAAATCC | TGCATGAGCA | ACTGCAGCAT | 600 |
| CACCTCCATC | TGTGAGAAGC | CACAGGAAGT | CTGTGTGGCT | GTATGGAGAA | AGAATGACGA | 660 |
| GAACATAACA | CTAGAGACAG | TTTGCCATGA | CCCCAAGCTC | CCCTACCATG | ACTTTATTCT | 720 |
| GGAAGATGCT | GCTTCTCCAA | AGTGCATTAT | GAAGGAAAAA | AAAAAGCCTG | GTGAGACTTT | 780 |
| CTTCATGTGT | TCCTGTAGCT | CTGATGAGTG | CAATGACAAC | ATCATCTTCT | CAGAAGAATA | 840 |
| TAACACCAGC | AATCCTGACT | TGTTGCTAGT | CATATTTCAA | GTGACAGGCA | TCAGCCTCCT | 900 |
| GCCACCACTG | GGAGTTGCCA | TATCTGTCAT | CATCATCTTC | TACTGCTACC | GCGTTAACCG | 960 |
| GCAGCAGAAG | CTGAGTTCAA | CCTGGGAAAC | CGGCAAGACG | CGGAAGCTCA | TGGAGTTCAG | 1020 |
| CGAGCACTGT | GCCATCATCC | TGGAAGATGA | CCGCTCTGAC | ATCAGCTCCA | CGTGTGCCAA | 1080 |
| CAACATCAAC | CACAACACAG | AGCTGCTGCC | CATTGAGCTG | GACACCCTGG | TGGGGAAAGG | 1140 |
| TCGCTTTGCT | GAGGTCTATA | AGGCCAAGCT | GAAGCAGAAC | ACTTCAGAGC | AGTTTGAGAC | 1200 |
| AGTGGCAGTC | AAGATCTTTC | CCTATGAGGA | GTATGCCTCT | TGGAAGACAG | AGAAGGACAT | 1260 |
| CTTCTCAGAC | ATCAATCTGA | AGCATGAGAA | CATACTCCAG | TTCCTGACGG | CTGAGGAGCG | 1320 |
| GAAGACGGAG | TTGGGGAAAC | AATACTGGCT | GATCACCGCC | TTCCACGCCA | AGGGCAACCT | 1380 |
| ACAGGAGTAC | CTGACGCGGC | ATGTCATCAG | CTGGGAGGAC | CTGCGCAAGC | TGGGCAGCTC | 1440 |
| CCTCGCCCGG | GGGATTGCTC | ACCTCCACAG | TGATCACACT | CCATGTGGGA | GGCCCAAGAT | 1500 |
| GCCCATCGTG | CACAGGGACC | TCAAGAGCTC | CAATATCCTC | GTGAAGAACG | ACCTAACCTG | 1560 |
| CTGCCTGTGT | GACTTTGGGC | TTTCCCTGCG | TCTGGACCCT | ACTCTGTCTG | TGGATGACCT | 1620 |
| GGCTAACAGT | GGGCAGGTGG | GAACTGCAAG | ATACATGGCT | CCAGAAGTCC | TAGAATCCAG | 1680 |
| GATGAATTTG | GAGAATGTTG | AGTCCTTCAA | GCAGACCGAT | GTCTACTCCA | TGGCTCTGGT | 1740 |
| GCTCTGGGAA | ATGACATCTC | GCTGTAATGC | AGTGGGAGAA | GTAAAAGATT | ATGAGCCTCC | 1800 |
| ATTTGGTTCC | AAGGTGCGGG | AGCACCCCTG | TGTCGAAAGC | ATGAAGGACA | ACGTGTTGAG | 1860 |
| AGATCGAGGG | CGACCAGAAA | TTCCCAGCTT | CTGGCTCAAC | CACCAGGGCA | TCCAGATGGT | 1920 |
| GTGTGAGACG | TTGACTGAGT | GCTGGGACCA | CGACCCAGAG | GCCCGTCTCA | CAGCCCAGTG | 1980 |
| TGTGGCAGAA | CGCTTCAGTG | AGCTGGAGCA | TCTGGACAGG | CTCTCGGGGA | GGAGCTGCTC | 2040 |
| GGAGGAGAAG | ATTCCTGAAG | ACGGCTCCCT | AAACACTACC | AAATAGCTCT | TCTGGGGCAG | 2100 |
| GCTGGGCCAT | GTCCAAAGAG | GCTGCCCCTC | TCACCAAAGA | ACAGAGGCAG | CAGGAAGCTG | 2160 |
| CCCCTGAACT | GATGCTTCCT | GGAAAACCAA | GGGGGTCACT | CCCCTCCCTG | TAAGCTGTGG | 2220 |

-continued

Sequence Listing

```
GGATAAGCAG AAACAACAGC AGCAGGGAGT GGGTGACATA GAGCATTCTA TGCCTTTGAC   2280

ATTGTCATAG GATAAGCTGT GTTAGCACTT CCTCAGGAAA TGAGATTGAT TTTTACAATA   2340

GCCAATAACA TTTGCACTTT ATTAATGCCT GTATATAAAT ATGAATAGCT ATGTTTTATA   2400

TATATATATA TATATCTATA TATGTCTATA GCTCTATATA TATAGCCATA CCTTGAAAAG   2460

AGACAAGGAA AAACATCAAA TATTCCCAGG AAATTGGTTT TATTGGAGAA CTCCAGAACC   2520

AAGCAGAGAA GGAAGGGACC CATGACAGCA TTAGCATTTG ACAATCACAC ATGCAGTGGT   2580

TCTCTGACTG TAAAACAGTG AACTTTGCAT GAGGAAAGAG GCTCCATGTC TCACAGCCAG   2640

CTATGACCAC ATTGCACTTG CTTTTGCAAA ATAATCATTC CCTGCCTAGC ACTTCTCTTC   2700

TGGCCATGGA ACTAAGTACA GTGGCACTGT TTGAGGACCA GTGTTCCCGG GGTTCCTGTG   2760

TGCCCTTATT TCTCCTGGAC TTTTCATTTA AGCTCCAAGC CCCAAATCTG GGGGCTAGT    2820

TTAGAAACTC TCCCTCAACC TAGTTTAGAA ACTCTACCCC ATCTTTAATA CCTTGAATGT   2880

TTTGAACCCC ACTTTTTACC TTCATGGGTT GCAGAAAAAT CAGAACAGAT GTCCCCATCC   2940

ATGCGATTGC CCCACCATCT ACTAATGAAA AATTGTTCTT TTTTTCATCT TTCCCCTGCA   3000

CTTATGTTAC TATTCTCTGC TCCCAGCCTT CATCCTTTTC TAAAAGGAG CAAATTCTCA    3060

CTCTAGGCTT TATCGTGTTT ACTTTTTCAT TACACTTGAC TTGATTTTCT AGTTTTCTAT   3120

ACAAACACCA ATGGGTTCCA TCTTTCTGGG CTCCTGATTG CTCAAGCACA GTTTGGCCTG   3180

ATGAAGAGGA TTTCAACTAC ACAATACTAT CATTGTCAGG ACTATGACCT CAGGCACTCT   3240

AAACATATGT TTTGTTTGGT CAGCACAGCG TTTCAAAAAG TGAAGCCACT TTATAAATAT   3300

TTGGAGATTT TGCAGGAAAA TCTGGATCCC CAGGTAAGGA TAGCAGATGG TTTTCAGTTA   3360

TCTCCAGTCC ACGTTCACAA AATGTGAAGG TGTGGAGACA CTTACAAAGC TGCCTCACTT   3420

CTCACTGTAA ACATTAGCTC TTTCCACTGC CTACCTGGAC CCCAGTCTAG GAATTAAATC   3480

TGCACCTAAC CAAGGTCCCT TGTAAGAAAT GTCCATTCAA GCAGTCATTC TCTGGGTATA   3540

TAATATGATT TTGACTACCT TATCTGGTGT TAAGATTTGA AGTTGGCCTT TTATTGGACT   3600

AAAGGGGAAC TCCTTTAAGG GTCTCAGTTA GCCCAAGTTT CTTTTGCTTA TATGTTAATA   3660

GTTTTACCCT CTGCATTGGA GAGAGGAGTG CTTTACTCCA AGAAGCTTTC CTCATGGTTA   3720

CCGTTCTCTC CATCATGCCA GCCTTCTCAA CCTTTGCAGA AATTACTAGA GAGGATTTGA   3780

ATGTGGGACA CAAAGGTCCC ATTTGCAGTT AGAAAATTTG TGTCCACAAG GACAAGAACA   3840

AAGTATGAGC TTTAAAACTC CATAGGAAAC TTGTTAATCA ACAAAGAAGT GTTAATGCTG   3900

CAAGTAATCT CTTTTTTAAA ACTTTTTGAA GCTACTTATT TTCAGCCAAA TAGGAATATT   3960

AGAGAGGGAC TGGTAGTGAG AATATCAGCT CTGTTTGGAT GGTGGAAGGT CTCATTTTAT   4020

TGAGATTTTT AAGATACATG CAAAGGTTTG GAAATAGAAC CTCTAGGCAC CCTCCTCAGT   4080

GTGGGTGGGC TGAGAGTTAA AGACAGTGTG GCTGCAGTAG CATAGAGGCG CCTAGAAATT   4140

CCACTTGCAC CGTAGGGCAT GCTGATACCA TCCCAATAGC TGTTGCCCAT TGACCTCTAG   4200

TGGTGAGTTT CTAGAATACT GGTCCATTCA TGAGATATTC AAGATTCAAG AGTATTCTCA   4260

CTTCTGGGTT ATCAGCATAA ACTGGAATGT AGTGTCAGAG GATACTGTGG CTTGTTTTGT   4320

TTATGTTTTT TTTTCTTATT CAAGAAAAAA GACCAAGGAA TAACATTCTG TAGTTCCTAA   4380

AAATACTGAC TTTTTTCACT ACTATACATA AAGGGAAAGT TTTATTCTTT TATGGAACAC   4440

TTCAGCTGTA CTCATGTATT AAAATAGGAA TGTGAATGCT ATATACTCTT TTTATATCAA   4500
```

| Sequence Listing | |
|---|---|
| AAGTCTCAAG CACTTATTTT TATTCTATGC ATTGTTTGTC TTTTACATAA ATAAAATGTT | 4560 |
| TATTAGATTG AATAAAGCAA AATACTCAGG TGAGCATCCT GCCTCCTGTT CCCATTCCTA | 4620 |
| GTAGCTAAA | 4629 |

Seq. ID No. 3: *Homo sapiens* transforming growth factor, beta receptor II (TGFBR2), transcript variant 2, mRNA (sense; written in RNA code)

| | |
|---|---|
| GGAGAGGGAG AAGGCUCUCG GGCGGAGAGA GGUCCUGCCC AGCUGUUGGC GAGGAGUUUC | 60 |
| CUGUUUCCCC CGCAGCGCUG AGUUGAAGUU GAGUGAGUCA CUCGCGCGCA CGGAGCGACG | 120 |
| ACACCCCCGC GCGUGCACCC GCUCGGGACA GGAGCCGGAC UCCUGUGCAG CUUCCCUCGG | 180 |
| CCGCCGGGGG CCUCCCCGCG CCUCGCCGGC CUCCAGGCCC CCUCCUGGCU GGCGAGCGGG | 240 |
| CGCCACAUCU GGCCCGCACA UCUGCGCUGC CGGCCCGGCG CGGGGUCCGG AGAGGGCGCG | 300 |
| GCGCGGAGGC GCAGCCAGGG GUCCGGGAAG GCGCCGUCCG CUGCGCUGGG GGCUCGGUCU | 360 |
| AUGACGAGCA GCGGGUCUG CCAUGGGUCG GGGGCUGCUC AGGGGCCUGU GGCCGCUGCA | 420 |
| CAUCGUCCUG UGGACGCGUA UCGCCAGCAC GAUCCCACCG CACGUUCAGA AGUCGGUUAA | 480 |
| UAACGACAUG AUAGUCACUG ACAACAACGG UGCAGUCAAG UUUCCACAAC UGUGUAAAUU | 540 |
| UUGUGAUGUG AGAUUUUCCA CCUGUGACAA CCAGAAAUCC UGCAUGAGCA ACUGCAGCAU | 600 |
| CACCUCCAUC UGUGAGAAGC CACAGGAAGU CUGUGUGGCU GUAUGGAGAA AGAAUGACGA | 660 |
| GAACAUAACA CUAGAGACAG UUUGCCAUGA CCCCAAGCUC CCCUACCAUG ACUUUAUUCU | 720 |
| GGAAGAUGCU GCUUCUCCAA AGUGCAUUAU GAAGGAAAAA AAAAAGCCUG GUGAGACUUU | 780 |
| CUUCAUGUGU UCCUGUAGCU CUGAUGAGUG CAAUGACAAC AUCAUCUUCU CAGAAGAAUA | 840 |
| UAACACCAGC AAUCCUGACU UGUUGCUAGU CAUAUUUCAA GUGACAGGCA UCAGCCUCCU | 900 |
| GCCACCACUG GGAGUUGCCA UAUCUGUCAU CAUCAUCUUC UACUGCUACC GCGUUAACCG | 960 |
| GCAGCAGAAG CUGAGUUCAA CCUGGGAAAC CGGCAAGACG CGGAAGCUCA UGGAGUUCAG | 1020 |
| CGAGCACUGU GCCAUCAUCC UGGAAGAUGA CCGCUCUGAC AUCAGCUCCA CGUGUGCCAA | 1080 |
| CAACAUCAAC CACAACACAG AGCUGCUGCC CAUUGAGCUG GACACCCUGG UGGGGAAAGG | 1140 |
| UCGCUUUGCU GAGGUCUAUA AGGCCAAGCU GAAGCAGAAC ACUUCAGAGC AGUUUGAGAC | 1200 |
| AGUGGCAGUC AAGAUCUUUC CCUAUGAGGA GUAUGCCUCU UGGAAGACAG AGAAGGACAU | 1260 |
| CUUCUCAGAC AUCAAUCUGA AGCAUGAGAA CAUACUCCAG UUCCUGACGG CUGAGGAGCG | 1320 |
| GAAGACGGAG UUGGGGAAAC AAUACUGGCU GAUCACCGCC UUCCACGCCA AGGGCAACCU | 1380 |
| ACAGGAGUAC CUGACGCGGC AUGUCAUCAG CUGGGAGGAC CUGCGCAAGC UGGGCAGCUC | 1440 |
| CCUCGCCCGG GGGAUUGCUC ACCUCCACAG UGAUCACACU CCAUGUGGGA GGCCCAAGAU | 1500 |
| GCCCAUCGUG CACAGGGACC UCAAGAGCUC CAAUAUCCUC GUGAAGAACG ACCUAACCUG | 1560 |
| CUGCCUGUGU GACUUUGGGC UUUCCCUGCG UCUGGACCCU ACUCUGUCUG UGGAUGACCU | 1620 |
| GGCUAACAGU GGGCAGGUGG GAACUGCAAG AUACAUGGCU CCAGAAGUCC UAGAAUCCAG | 1680 |
| GAUGAAUUUG GAGAAUGUUG AGUCCUUCAA GCAGACCGAU GUCUACUCCA UGGCUCUGGU | 1740 |
| GCUCUGGGAA AUGACAUCUC GCUGUAAUGC AGUGGGAGAA GUAAAAGAUU AUGAGCCUCC | 1800 |
| AUUUGGUUCC AAGGUGCGGG AGCACCCCUG UGUCGAAAGC AUGAAGGACA ACGUGUUGAG | 1860 |
| AGAUCGAGGG CGACCAGAAA UUCCCAGCUU CUGGCUCAAC CACCAGGGCA UCCAGAUGGU | 1920 |
| GUGUGAGACG UUGACUGAGU GCUGGGACCA CGACCCAGAG GCCGUCUCA CAGCCCAGUG | 1980 |
| UGUGGCAGAA CGCUUCAGUG AGCUGGAGCA UCUGGACAGG CUCUCGGGA GGAGCUGCUC | 2040 |

```
                           Sequence Listing

GGAGGAGAAG AUUCCUGAAG ACGGCUCCCU AAACACUACC AAAUAGCUCU UCUGGGGCAG    2100

GCUGGGCCAU GUCCAAAGAG GCUGCCCCUC UCACCAAAGA ACAGAGGCAG CAGGAAGCUG    2160

CCCCUGAACU GAUGCUUCCU GGAAAACCAA GGGGGUCACU CCCCUCCCUG UAAGCUGUGG    2220

GGAUAAGCAG AAACAACAGC AGCAGGGAGU GGGUGACAUA GAGCAUUCUA UGCCUUUGAC    2280

AUUGUCAUAG GAUAAGCUGU GUUAGCACUU CCUCAGGAAA UGAGAUUGAU UUUUACAAUA    2340

GCCAAUAACA UUUGCACUUU AUUAAUGCCU GUAUAUAAAU AUGAAUAGCU AUGUUUUAUA    2400

UAUAUAUAUA UAUAUCUAUA UAUGUCUAUA GCUCUAUAUA UAUAGCCAUA CCUUGAAAAG    2460

AGACAAGGAA AAACAUCAAA UAUUCCCAGG AAAUUGGUUU UAUGGAGAA CUCCAGAACC     2520

AAGCAGAGAA GGAAGGGACC CAUGACAGCA UUAGCAUUUG ACAAUCACAC AUGCAGUGGU    2580

UCUCUGACUG UAAACAGUG AACUUUGCAU GAGGAAAGAG GCUCCAUGUC UCACAGCCAG     2640

CUAUGACCAC AUUGCACUUG CUUUUGCAAA AUAAUCAUUC CCUGCCUAGC ACUUCUCUUC    2700

UGGCCAUGGA ACUAAGUACA GUGGCACUGU UUGAGGACCA GUGUUCCCGG GGUUCCUGUG    2760

UGCCCUUAUU UCUCCUGGAC UUUUCAUUUA AGCUCCAAGC CCCAAAUCUG GGGGCUAGU     2820

UUAGAAACUC UCCCUCAACC UAGUUUAGAA ACUCUACCCC AUCUUUAAUA CCUUGAAUGU    2880

UUUGAACCCC ACUUUUUACC UUCAUGGGUU GCAGAAAAAU CAGAACAGAU GUCCCCAUCC    2940

AUGCGAUUGC CCCACCAUCU ACUAAUGAAA AAUUGUUCUU UUUUUCAUCU UUCCCCUGCA    3000

CUUAUGUUAC UAUUCUCUGC UCCCAGCCUU CAUCCUUUUC UAAAAAGGAG CAAAUUCUCA    3060

CUCUAGGCUU UAUCGUGUUU ACUUUUUCAU UACACUUGAC UUGAUUUUCU AGUUUUCUAU    3120

ACAAACACCA AUGGGUUCCA UCUUUCUGGG CUCCUGAUUG CUCAAGCACA GUUUGGCCUG    3180

AUGAAGAGGA UUUCAACUAC ACAAUACAUU CAUUGUCAGG ACUAUGACCU CAGGCACUCU    3240

AAACAUAUGU UUGUUUGGU CAGCACAGCG UUUCAAAAAG UGAAGCCACU UUAUAAAUAU     3300

UUGGAGAUUU UGCAGGAAAA UCUGGAUCCC CAGGUAAGGA UAGCAGAUGG UUUUCAGUUA    3360

UCUCCAGUCC ACGUUCACAA AAUGUGAAGG UGUGGAGACA CUUACAAAGC UGCCUCACUU    3420

CUCACUGUAA ACAUUAGCUC UUUCCACUGC CUACCUGGAC CCCAGUCUAG GAAUUAAAUC    3480

UGCACCUAAC CAAGGUCCCU GUAAGAAAU GUCCAUUCAA GCAGUCAUUC UCUGGGUAUA     3540

UAAUAUGAUU UUGACUACCU UAUCUGGUGU UAAGAUUUGA AGUUGGCCUU UUAUGGACU     3600

AAAGGGGAAC UCCUUUAAGG GUCUCAGUUA GCCCAAGUUU CUUUUGCUUA UAUGUUAAUA    3660

GUUUUACCCU CUGCAUUGGA GAGAGGAGUG CUUUACUCCA AGAAGCUUUC CUCAUGGUUA    3720

CCGUUCUCUC CAUCAUGCCA GCCUUCUCAA CCUUUGCAGA AAUUACUAGA GAGGAUUUGA    3780

AUGUGGGACA CAAAGGUCCC AUUUGCAGUU AGAAAAUUUG UGCCACAAG GACAAGAACA     3840

AAGUAUGAGC UUUAAACUC CAUAGGAAAC UUGUUAAUCA ACAAGAAGU GUUAAUGCUG      3900

CAAGUAAUCU CUUUUUUAAA ACUUUUUGAA GCUACUUAUU UUCAGCCAAA UAGGAAUAUU    3960

AGAGAGGGAC UGGUAGUGAG AAUAUCAGCU CUGUUUGGAU GGUGGAAGGU CUCAUUUUAU    4020

UGAGAUUUUU AAGAUACAUG CAAAGGUUUG GAAAUAGAAC CUCUAGGCAC CCUCCUCAGU    4080

GUGGGUGGGC UGAGAGUUAA AGACAGUGUG GCUGCAGUAG CAUAGAGGCG CCUAGAAAUU    4140

CCACUUGCAC CGUAGGGCAU GCUGAUACCA UCCCAAUAGC UGUUGCCCAU UGACCUCUAG    4200

UGGUGAGUUU CUAGAAUACU GGUCCAUUCA UGAGAUAUUC AAGAUUCAAG AGUAUUCUCA    4260

CUUCUGGGUU AUCAGCAUAA ACUGGAAUGU AGUGUCAGAG GAUACUGUGG CUUGUUUUGU    4320

UUAUGUUUUU UUUUCUUAUU CAAGAAAAAA GACCAAGGAA UAACAUUCUG UAGUUCCUAA    4380
```

-continued

| Sequence Listing | |
|---|---|
| AAAUACUGAC UUUUUUCACU ACUAUACAUA AAGGGAAAGU UUUAUUCUUU UAUGGAACAC | 4440 |
| UUCAGCUGUA CUCAUGUAUU AAAAUAGGAA UGUGAAUGCU AUAUACUCUU UUUAUAUCAA | 4500 |
| AAGUCUCAAG CACUUAUUUU UAUUCUAUGC AUUGUUUGUC UUUUACAUAA AUAAAAUGUU | 4560 |
| UAUUAGAUUG AAUAAAGCAA AAUACUCAGG UGAGCAUCCU GCCUCCUGUU CCCAUUCCUA | 4620 |
| GUAGCUAAA | 4629 |

The invention claimed is:

1. Single-stranded antisense-oligonucleotide selected from the following group:

| Seq ID No. | Sequence, 5'-3' |
|---|---|
| 232a | C*b$^1$sGb$^1$sdTsdC*sdAsdTsdAsdGsAb$^1$sC*b$^1$ |
| 232b | C*b$^1$Gb$^1$dTdC*dAdTdAdGAb$^1$C*b$^1$ |
| 233a | Tb$^1$sC*b$^1$sGb$^1$sdTsdC*sdAsdTsdAsdGsAb$^1$sC*b$^1$sC*b$^1$ |
| 233b | Tb$^1$C*b$^1$Gb$^1$dTdC*dAdTdAdGAb$^1$C*b$^1$C*b$^1$ |
| 233c | Tb$^1$sC*b$^1$sGb$^1$sdTsdC*sdAsdTsdAsdGsdAsC*b$^1$sC*b$^1$ |
| 233d | Tb$^1$sdC*sdGsdTsdC*sdAsdTsdAsdGsdAsC*b$^1$sC*b$^1$ |
| 233e | Tb$^1$sC*b$^1$sdGsdTsdCsdAsdTsdAsdGsdAsdC*sC*b$^1$ |
| 234a | Tb$^1$sC*b$^1$sGb$^1$sTb$^1$sdCsdAsdTsdAsdGsdAsC*b$^1$sC*b$^1$sGb$^1$ |
| 234b | Tb$^1$C*b$^1$Gb$^1$Tb$^1$dCdAdUdAdGdAC*b$^1$C*b$^1$Gb$^1$ |
| 234c | Tb$^1$sC*b$^1$sGb$^1$sTb$^1$sdC*sdAsdTsdAsdGsdAsC*b$^1$sC*b$^1$sGb$^1$ |
| 234d | Tb$^1$sC*b$^1$sGb$^1$sdTsdC*sdAsdTsdA*sdGsdA*sdC*sC*b$^1$sGb$^1$ |
| 234e | Tb$^1$sC*b$^1$sdGsdTsdC*sdAsdTsdA*sdGsdA*sdC*sdCsGb$^1$ |
| 234f | Tb$^1$sdCsdGsdTsdC*sdA*sdTsdAsdGsAb$^1$sC*b$^1$sC*b$^1$sGb$^1$ |
| 142c | C*b$^1$sGb$^1$sTb$^1$sdCsdAsdTsdAsdGsdAsdCsdCsGb$^1$sAb$^1$ |
| 143i | C*b$^1$sTb$^1$sC*b$^1$sGb$^1$sdTsdCsdAsdTsdAsdGsAb$^1$sC*b$^1$sC*b$^1$sGb$^1$ |
| 143j | C*b$^4$ssTb$^4$ssC*b$^4$ssdGssdTssdCssdAssdTssdAssdGssdA*ssC*b$^4$ssC*b$^4$ssGb$^4$ |
| 143h | C*b$^1$sTb$^1$sdCsdGsdTsdCsdAsdTsdAsdGsdAsC*b$^1$sC*b$^1$sGb$^1$ |
| 143k | C*b$^2$ssTb$^2$ssC*b$^2$ssdGssdTssdCssdAssdTssdAssdGssdAssC*b$^2$ssC*b$^2$ssGb$^2$ |
| 143m | C*b$^1$Tb$^1$C*b$^1$Gb$^1$dUsdCsdAsdTsdAsdGsAb$^1$C*b$^1$C*b$^1$Gb$^1$ |

| Seq ID No. | Sequence, 5'-3' |
|---|---|
| 143n | C*b¹sTb¹sC*b¹sGb¹sTb¹sdCsdA*sdTsdA*sdGsdA*sC*b¹sC*b¹sGb¹ |
| 143o | C*b¹sTb¹sdCsdGsdUsdCsdAsdUsdAsGb¹sAb¹sC*b¹sC*b¹sGb¹ |
| 143p | C*b⁶sTb⁶sC*b⁶sGb⁶sdTsdCsdAsdTsdAsdGsdAsC*b⁶sC*b⁶sGb⁶ |
| 143q | C*b⁷sTb⁷sC*b⁷sdGsdUsdCsdA*sdUsdA*sdGsdA*sC*b⁷sC*b⁷sGb⁷ |
| 143r | C*b⁴sTb⁴sC*b⁴sGb⁴sdTsdC*sdA*sdTsdAsdGsdAsdC*sC*b⁴sGb⁴ |
| 143s | C*b⁴Tb⁴C*b⁴Gb⁴dTdCdAdTdAdGdAdCC*b⁴Gb⁴ |
| 143t | C*b¹ssTb¹ssC*b¹ssGssdTssdC*ssdAssdTssdAssdGssdAssC*b¹ssC*b¹ssGb¹ |
| 143u | C*b¹Tb¹sdCsdGsdUsdC*sdAsdUsdAsdGsdAsC*b¹C*b¹Gb¹ |
| 143v | C*b¹Tb¹sdC*sdGsdTsdC*sdA*sdTsdAsdGsdAsC*b¹C*b¹Gb¹ |
| 143w | C*b⁶sTb⁶sdC*dGdTdC*dAdTdAdGdAsC*b⁶sC*b⁶sGb⁶ |
| 143x | C*b⁷sTb⁷sC*b⁷sGb⁷sdTsdC*sdAsdTsdAsdGsdAsC*b⁷sC*b⁷sGb⁷ |
| 143y | C*b⁷sTb⁷sdC*sdGsdTsdCsdAsdUsdAsdGsAb⁷sC*b⁷sC*b⁷sGb⁷ |
| 143z | C*b¹sTb¹sdC*sdGsdTsdC*sdAsdTsdAsdGsdAsC*b¹sC*b¹sGb¹ |
| 143aa | C*b¹Tb¹sdC*sdGsdTsdC*sdAsdTsdAsdGsdAsC*b¹C*b¹Gb¹ |
| 143ab | C*b¹sTb¹sdC*sdGsdTsdC*sdA*sdTsdAsdGsdA*sC*b¹sC*b¹sGb¹ |
| 143ac | C*b¹sTb¹sdC*sdGsdTsdCsdAsdTsdAsdGsdAsC*b¹sC*b¹sGb¹ |
| 143ad | C*b¹Tb¹dC*dGdTdCdAdTdAdGdAC*b¹C*b¹Gb¹ |
| 143ae | C*b¹sTb¹sdC*dGdTdC*dAdTdAdGdAsC*b¹sC*b¹sGb¹ |
| 143af | /5SpC3s/C*b¹sTb¹sdC*dGdTdC*dA*dTdAdGdA*sC*b¹sC*b¹sGb¹ |
| 143ag | C*b¹sTb¹sdC*dGdTdC*dA*dTdAdGdA*sC*b¹sC*b¹sGb¹/3SpC3s/ |
| 143ah | /5SpC3s/C*b¹sTb¹sdC*dGdTdC*dA*dTdAdGdA*sC*b¹sC*b¹sGb¹/3SpC3s/ |
| 143ai | C*b¹sTb¹sdC*sdGsdUsdC*sdA*sdUsdA*sdGsdA*sC*b¹sC*b¹sGb¹ |
| 143aj | C*b¹sTb¹sC*b¹sdCsdGsdTsdCsdAsdTsdAsdGsdAsC*b¹sC*b¹sGb¹ |
| 145c | Gb¹sC*b¹sTb¹sdCsdGsdTsdCsdAsdTsdAsdGsAb¹sC*b¹sC*b¹ |
| 235i | C*b¹sTb¹sC*b¹sGb¹sdTdC*dAdTdAdGdAsC*b¹sC*b¹sGb¹sAb¹ |
| 235a | C*b¹ssTb¹ssdCssdGssdTssdCssdAssdTssdAssdGssdAssdCssdCssdGssAb¹ |
| 235b | C*b¹Tb¹dCdGdTdCdAdTdAdGdAdCdCdGAb¹ |
| 235c | C*b¹sTb¹sdCsdGsdTsdCsdA*sdUsdAsdGsdAsdCsC*b¹sGb¹sAb¹ |
| 235d | C*b¹Tb¹sdCsdGsdTsdCsdAsdTsdAsdGsdAsC*b¹C*b¹Gb¹Ab¹ |
| 235e | C*b⁴sTb⁴sC*b⁴sdGsdTsdCsdAsdTsdAsdGsdAsdCsGb⁴sAb⁴ |
| 235f | C*b⁶sTb⁶sC*b⁶sdGdTdCdA*dTdAdGdAdC*sC*b⁶sGb⁶sAb⁶ |
| 235g | C*b¹sTb¹sC*b¹sGb¹sdTsdC*sdAsdTsdAsdGsdAsdC*sdC*sdGsAb¹ |
| 235h | C*b¹ssTb¹ssdCssdGssdUssdCssdAssdUssdAssdGssdAssdCssdCssGb¹ssAb¹ |
| 144c | Gb¹sC*b¹sTb¹sdCsdGsdTsdCsdAsdTsdAsdGsdAsC*b¹sC*b¹sGb¹ |
| 141c | Gb¹sC*b¹sTb¹sC*b¹sdGsdTsdC*sdAsdTsdAsdGsdAsC*b¹sC*b¹sGb¹sAb¹ |
| 141d | Gb¹C*b¹Tb¹C*b¹sdGsdTsdC*sdAsdTsdAsdGsdAsdCsC*b¹Gb¹Ab¹ |
| 141e | Gb⁴sC*b⁴sTb⁴sC*b⁴sdGsdTsdC*sdAsdTsdAsdGsdA*sdC*sdC*sGb⁴sAb⁴ |
| 141f | Gb¹sdC*sdTsdCsdGsdTsdC*sdA*sdTsdAsdGsdA*sdC*sdC*sdGsAb¹ |
| 141g | Gb²sC*b²sTb²sdCsdGsdUsdCsdA*sdGsdAsdCsC*b²sGb²sAb² |
| 141h | Gb⁴ssC*b⁴ssTb⁴ssdCssdGssdTssdCssdAssdTssdAssGssdAssC*b⁴ssC*b⁴ssGb4ssAb⁴ |
| 141i | Gb¹C*b¹dTdCdGdTdCdA*dTdA*dGdA*dCC*b¹Gb¹Ab¹ |
| 141j | Gb¹sC*b¹sTb¹sdCsdGsdTsdCsdAsdTsdAsdGsdAsdCsC*b¹sGb¹sAb¹ |
| 139c | C*b¹sGb¹sTb¹sdCsdAsdTsdAsdGsdAsdCsdCsdGsdAsGb¹sC*b¹sC*b¹ |
| 237a | Tb¹sGb¹sC*b¹sTb¹sC*b¹sdGsdTsdC*sdAsdTsdAsdGsAb¹sC*b¹sC*b¹sGb¹sAb¹ |
| 237b | Tb²sGb²sC*b²sdTsdGsdTsdC*sdAsdTsdAsdGsAb²sC*b²sC*b²sGb²sAb² |
| 237c | Tb¹sGb¹sC*b¹sTb¹sdC*sdGsdTsdCsdAsdTsdAsdGsdAsdC*sC*b¹sGb¹sAb¹ |
| 237d | Tb¹sdGsdCsdUsdC*sdGsdTsdC*sdAsdUsdAsdGsAb¹sC*b¹sC*b¹sGb¹sAb¹ |
| 237e | Tb¹sGb¹sC*b¹sdTsdGsdTsdC*sdA*sdTsdA*sdGsAb¹sC*b¹sC*b¹sGb¹sAb¹ |
| 237f | Tb¹Gb¹dC*dTdGdTdCdAdTdAdGdAC*b¹C*b¹Gb¹Ab¹ |
| 237g | Tb¹sdGsdC*sdTsdGsdTsdC*sdAsdTsdAsdGsdAsdC*sC*b¹sGb¹sAb¹ |
| 237h | Tb¹Gb¹C*b¹Tb¹C*b¹dGdTdC*dA*dTdA*dGdA*dC*Gb¹Ab¹ |
| 237i | Tb¹ssGb¹ssC*b¹ssTb¹ssC*b¹ssdGssdTssdCssdAssdTssdAssdGssdAssdCssC*b¹ssGb¹ssAb¹ |

| Seq ID No. | Sequence, 5'-3' |
|---|---|
| 237j | Tb$^4$sGb$^4$**sC*b**$^4$sdTdGdTdCdA*dTdA*dGdA*s**C*b$^4$sC*b$^4$sGb$^4$sAb**$^4$ |
| 237k | Tb$^6$sGb$^6$**sC*b$^6$sdUsdGsdUsdC***sdA*sdUsdA*sdGsdA*sdC*s**C*b$^6$Gb$^6$sAb**$^6$ |
| 237m | Tb$^7$sGb$^7$**sC*b$^7$sTb$^7$sdC*dGdTdC*dAdTdAdGdAsC*b$^7$sC*b$^7$sGb$^7$sAb**$^7$ |
| 238a | Tb$^1$sGb$^1$**sC*b$^1$sTb$^1$sC*b$^1$sdGsdTsdC*sdAsdTsdAsdGsdAsC*b$^1$sC*b$^1$sGb$^1$sAb$^1$sGb**$^1$ |
| 238b | Tb$^7$Gb$^7$**sC*b$^7$sTb$^7$sC*b$^7$sdGsdTsdC*sdAsdTsdAsdGsdAsC*sdC*sdGsdAsGb**$^7$ |
| 238c | Tb$^1$sGb$^1$**sC*b$^1$sTb$^1$sdC*sdGsdTsdC*sdAsdTsdAsdGsdAsdC*sC*b$^1$sGb$^1$sAb$^1$sGb**$^1$ |
| 238d | Tb$^1$sGb$^1$sdC*sdTsdC*sdGsdTsdC*sdAsdTsdAsdGsdAsdC*sdC*sGb$^1$sAb$^1$ sGb$^1$ |
| 238e | Tb$^1$sGb$^1$**sC*b$^1$sTb$^1$sdC*sdGsdTsdC*sdAsdTsdAsdGsdAsdC*sdC*sGb$^1$sAb$^1$sGb**$^1$ |
| 238f | Tb$^1$Gb$^1$dC*dUdC*dGdTdC*dAdTdAdGdA***C*b$^1$C*b$^1$Gb$^1$Ab$^1$Gb**$^1$ |
| 238g | Tb$^4$Gb$^4$**C*b$^4$Tb$^4$sdCsdGsdTsdCsdAsdTsdAsdGsdAsC*b$^4$C*b$^4$Gb$^4$Ab$^4$Gb**$^4$ |
| 238h | Tb$^1$ssGb$^1$**ssC*b$^1$ssdTssdC*ssdGssdTssdC***ssdAssdTssdA*ssdGssdAssdC*ssdC*ssGb$^1$ssAb$^1$ssGb$^1$ |
| 238i | Tb$^2$Gb$^2$**C*b$^2$dTdC*dGdTdC*dAdTdAdGdAC*b$^2$C*b$^2$Gb$^2$Ab$^2$Gb**$^2$ |
| 239a | Tb$^1$sGb$^1$**sC*b$^1$sTb$^1$sC*b$^1$sdGsdTsdC*sdAsdTsdAsdGsdAsdC*sC*b$^1$sGb$^1$sAb$^1$sGb$^1$sC*b**$^1$ |
| 239b | Tb$^6$Gb$^6$**C*b$^6$Tb$^6$C*b$^6$dGdTdC*dAdTdAdGdAdC***C*b$^6$Gb$^6$Ab$^6$Gb$^6$C*b**$^6$ |
| 239c | Tb$^1$sGb$^1$**sC*b$^1$sTb$^1$sdC*sdGsdTsdC*sdAsdTsdAsdGsdAsdCsdCsdGsAb$^1$sGb$^1$sC*b**$^1$ |
| 239d | Tb$^1$sdGsdCsdTsdCsdGsdTsdCsdAsdTsdAsdGsdA*sdC*s**C*b$^1$sGb$^1$sAb$^1$sGb$^1$sC*b**$^1$ |
| 239e | Tb$^4$sGb$^4$sdCsdUsdCsdGsdGsdUsdCsdAsdTsdAsdGsdA*sdC*sdC*sGb$^4$sAb$^4$sGb$^4$**sC*b**$^4$ |
| 239f | Tb$^2$ssGb$^2$**ssC*b**$^2$ssTb$^2$**ssC*b**$^2$ssdGssdTssdCssdAssdTssdAssdGssdAssdCssdCssdGssdAssGb$^2$**ssC*b**$^2$ |
| 240a | **C*b$^1$sTb$^1$sGb$^1$sC*b$^1$sTb$^1$sdC*sdGsdTsdCsdAsdTsdAsdGsdAsdC*sC*b$^1$sGb$^1$sAb$^1$sGb$^1$sC*b**$^1$ |
| 240b | **C*b$^2$sTb$^2$sGb$^2$sC*b$^2$sdC*sdTsdCsdGsdTsdCsdAsdTsdAsdGsdAsdC*sC*b$^2$sGb$^2$sAb$^2$sGb$^2$sC*b**$^2$ |
| 240c | **C*b$^1$Tb$^1$Gb$^1$dC*dTdC*dGdTdCdAdTdAdGdAdC*dC*Gb$^1$Ab$^1$Gb$^1$**C*b**$^1$ |
| 240d | **C*b$^1$sdUsdGsdCsdUsdC*sdGsdTsdCsdAsdTsdAsdGsdAsdC*sC*b$^1$sGb$^1$sAb$^1$sGb$^1$sC*b**$^1$ |
| 240e | **C*b**$^4$sTb$^4$sGb$^4$**sC*b**$^4$sdTsdCsdGsdGsdTsdCsdAsdTsdAsdGsdAsdCsdCsdGb$^4$sAb$^4$sGb$^4$**sC*b**$^4$ |
| 241a | Gb$^1$**sC*b$^1$sTb$^1$sGb$^1$sC*b$^1$sdTsdC*sdGsdTsdCsdAsdTsdAsdGsdAsdCsdC*sGb$^1$sAb$^1$sGb$^1$sC*b$^1$sC*b**$^1$ |
| 241b | Gb$^1$**C*b$^1$Tb$^1$Gb$^1$C*b$^1$dC*dC*dGdTdCdAdTdAdGdAdC*dC*Gb$^1$Ab$^1$Gb$^1$**C*b$^1$C*b**$^1$ |
| 241c | Gb$^1$**sC*b**$^1$sTb$^1$sGb$^1$**sC*b**$^1$sdTsdCsdGsdTsdCsdAsdTsdAsdGsdAsdCsdCsdCsGb$^1$sAb$^1$sGb$^1$**sC*b**$^1$**sC*b**$^1$ |
| 242a | **C*b$^1$sGb$^1$sC*b$^1$sTb$^1$sGb$^1$sdCsdTsdCsdGsdTsdCsdAsdTsdAsdGsdAsdAsdCsdC*sdGsAb$^1$sGb$^1$sC*b$^1$sC*b$^1$sC*b**$^1$ |
| 242b | **C*b$^1$Gb$^1$C*b$^1$Tb$^1$Gb$^1$dC*dTdCdGdTdCdAdTdAdGdAdC*dC*dGAb$^1$Gb$^1$**C*b$^1$C*b$^1$C*b**$^1$ |
| 243a | **C*b$^1$sC*b$^1$sGb$^1$sC*b$^1$sTb$^1$sdGsdC*sdTsdCsdGsdTsdC*sdAsdTsdAsdGsdAsdCsdC*sdGsAb$^1$sGb$^1$sC*b$^1$sC*b$^1$sC*b**$^1$ |
| 243b | **C*b$^1$C*b$^1$Gb$^1$C*b$^1$Tb$^1$dCdTdCdGdTdCdAdTdAdGdAdC*dC*dGAGb$^1$**C*b$^1$C*b$^1$C*b$^1$C*b**$^1$ |
| 244a | **C*b**$^1$**sC*b**$^1$**sC*b**$^1$sGb$^1$**sC*b**$^1$sdTsdCsdGsdTsdCsdGsdTsdCsdAsdTsdAsdGsdAsdAsdCsdCsdGsdAsdGs**C*b**$^1$**sC*b**$^1$**sC*b**$^1$**sC*b**$^1$ |
| 244b | **C*b$^1$C*b$^1$C*b$^1$C*b$^1$Gb$^1$C*b$^1$dTdGdC*dTdCdGdTdCdAdTdAdGdAdC*dC*dGdAdGb$^1$C*b$^1$C*b$^1$C*b$^1$C*b$^1$C*b**$^1$ |
| 245a | Tb$^1$sAb$^1$sdC*sdGsdCsdGsdGsdTsdC*s**C*b$^1$sAb**$^1$ |
| 245b | Tb$^1$Ab$^1$dCdGdC*dGdTdCC*b$^1$Ab**$^1$ |
| 246a | Ab$^1$sTb$^1$sAb$^1$sdC*sdGsdCsdGsdGsdTsdC*s**C*b$^1$sAb$^1$sC*b**$^1$ |
| 246b | Ab$^1$Tb$^1$Ab$^1$dCdGdCdGdTdC*C*b$^1$Ab$^1$C*b**$^1$ |
| 246c | Ab$^1$sTb$^1$sAb$^1$sdCsdGsdCsdGsdGsdTsdC*sdC*sAb$^1$**sC*b**$^1$ |
| 246d | Ab$^1$sTb$^1$sdA*sdCsdGsdCsdGsdGsdTsdC*sdC*sdA*s**C*b**$^1$ |
| 246e | Ab$^1$sdTsdA*sdCsdGsdCsdGsdGsdTsdC*sdC*sAb$^1$**sC*b**$^1$ |
| 247a | Gb$^1$sAb$^1$sTb$^1$sAb$^1$sdCsdGsdCsdGsdGsdTsdCs**C*b**$^1$sAb$^1$**sC*b**$^1$ |
| 247b | Gb$^1$Ab$^1$Tb$^1$Ab$^1$dCdGdCdGdUdCC*b**$^1$Ab$^1$**C*b**$^1$ |
| 247c | Gb$^1$sAb$^1$sTb$^1$sAb$^1$sdC*sdGsdCsdGsdGsdTsdC*s**C*b$^1$sAb$^1$sC*b**$^1$ |
| 247d | Gb$^1$sAb$^1$sTb$^1$sdA*sdCsdGsdCsdGsdGsdTsdC*sAb$^1$**sC*b**$^1$ |
| 247e | Gb$^1$sAb$^1$sdTsdA*sdCsdGsdC*sdGsdTsdCsdC*sdA*s**C*b**$^1$ |
| 247f | Gb$^1$sdA*sdTsdA*sdCsdGsdCsdGsdGsdTs**C*b**$^1$**sC*b**$^1$sAb$^1$**sC*b**$^1$ |
| 153f | **C*b$^1$sGb$^1$sAb$^1$sdTsdAsdCsdGsdCsdGsdGsdTsdCsCsAb**$^1$ |
| 248a | Gb$^1$sAb$^1$sTb$^1$sAb$^1$sdC*sdGsdC*sdGsdTsdC*s**C*b$^1$sAb$^1$sC*b$^1$sAb**$^1$ |
| 248b | Gb$^1$Ab$^1$Tb$^1$Ab$^1$sdCsdGsdCsdGsdTsdC*sdC*sAb$^1$**C*b$^1$Ab**$^1$ |
| 248c | Gb$^4$sAb$^4$sTb$^4$sAb$^4$sdC*sdGsdCsdGsdGsdTsdC*sdC*sdA*s**C*b$^4$sAb**$^4$ |
| 248d | Gb$^1$sdA*sdTsdAsdCsdGsdCsdGsdGsdTsdCsdC*sdA*sdCsAb$^1$ |
| 248e | Gb$^2$sAb$^2$sTb$^2$sdA*sdCsdGsdCsdGsdUsdCsdCsAb$^2$**sC*b$^2$sAb**$^2$ |
| 248f | Gb$^4$ssAb$^4$ssdTssdAssdCssdGssdGssdCssdGssdTssdCssdCssAb$^4$ssC*b$^4$ssAb**$^4$ |
| 248g | Gb$^1$Ab$^1$dTdA*dCdGdCdGdTdCC*b$^1$Ab$^1$C*b$^1$Ab**$^1$ |

| Seq ID No. | Sequence, 5'-3' |
|---|---|
| 152h | C*b¹sGb¹sAb¹sTb¹sdAsdCsdGsdCsdGsdTsdCsCsAb¹sC*b¹sAb¹ |
| 152i | C*b¹Gb¹Ab¹Tb¹sdAsdCsdGsdCsdGsdUsdCsdC*sAb¹C*b¹Ab¹ |
| 152j | C*b¹Gb¹Ab¹Tb¹sdA*sdCsdGsdCsdGsdUsdCsdCsAb¹C*b¹Ab¹ |
| 152k | C*b⁶sGb⁶sAb⁶sTb⁶sdAdC*dGdCdGdTdCdC*sAb⁶sC*b⁶sAb⁶ |
| 152m | C*b¹sGb¹sAb¹sTb¹sdAsdCsdGsdCsdGsdTsdC*sdC*sAb¹sC*b¹sAb¹ |
| 152n | C*b¹Gb¹Ab¹Tb¹sdAsdC*sdGsdC*sdGsdTsdC*sdC*sAb¹C*b¹Ab¹ |
| 152o | C*b¹sGb¹sAb¹sTb¹sdA*sdCsdGsdCsdGsdTsdCsdC*sAb¹sC*b¹sAb¹ |
| 152p | C*b¹sGb¹sAb¹sTb¹sdAsdCsdGsdCsdGsdTsdCsdC*sAb¹sC*b¹sAb¹ |
| 152q | C*b¹Gb¹Ab¹Tb¹dAdCdGdC*dGdTdCdC*Ab¹C*b¹Ab¹ |
| 152r | C*b¹sGb¹sAb¹sTb¹sdAdC*dGdC*dGdTdC*dC*sAb¹sC*b¹sAb¹ |
| 152s | /5SpC3s/C*b¹sGb¹sAb¹sTb¹sdAsdC*sdGsdC*sdGsdTsdCsdCsAb¹sC*b¹ sAb¹ |
| 152t | C*b¹sGb¹sAb¹sTb¹sdAsdC*sdGsdC*sdGsdTsdCsdC*sAb¹sC*b¹sAb¹ /3SpC3s/ |
| 152u | /5SpC3s/C*b¹sGb¹sAb¹sTb¹sdAsdC*sdGsdC*sdGsdTsdCsdCsAb¹sC*b¹sAb¹/3SpC3s/ |
| 152v | C*b¹sGb¹sAb¹sTb¹sdA*sdC*sdGsdC*sdGsdUsdC*sdC*sAb¹sC*b¹sAb¹ |
| 152w | C*b⁷sGb⁷sAb⁷sTb⁷sdTsdAsdCsdGsdC*sdGsdTsdCsC*b⁷sAb⁷sC*b⁷sAb⁷ |
| 152z | C*b⁷sGb⁷sAb⁷sdAsdUsdAsdCsdGsdC*sdGsdUsdC*sC*b⁷sAb⁷sC*b⁷sAb⁷ |
| 152aa | C*b¹ssGb¹ssAb¹ssdTssdAssdC*ssdGssdCssdGssdTssdCssdC*ssAb¹ssC*b¹ssAb¹ |
| 152ab | C*b⁴ssGb⁴ssAb⁴ssdTssdA*ssdCssdGssdCssdGssdTssdCssdCssdA*ssC*b⁴ssAb⁴ |
| 152ac | C*b²ssGb²ssAb²ssTb²ssdAssdCssdGssdCssdGssdTssdCssdCssdAssdCssAb² |
| 152ad | C*b¹Gb¹Ab¹Tb¹dAdCdGdCdGdUdCC*b¹Ab¹C*b¹Ab¹ |
| 152ae | C*b¹sGb¹sAb¹sTb¹sAb¹sdCsdGsdCsdGsdUsdCsdCsAb¹sC*b¹sAb¹ |
| 152af | C*b¹sGb¹sdA*sdTsdA*sdCsdGsdCsdGsdTsC*b¹sC*b¹sAb¹sC*b¹sAb¹ |
| 152ag | C*b⁶sGb⁶sAb⁶sdTsdAsdCsdGsdCsdGsdTsdCsdCC*b⁶sAb⁶sC*b⁶sAb⁶ |
| 152ah | C*b⁷sGb⁷sAb⁷sdUsdA*sdCsdGsdCsdGsdUsdCsdCsAb⁷sC*b⁷sAb⁷ |
| 152ai | C*b⁴sGb⁴sAb⁴sTb⁴sdAsdCsdGsdCsdGsdTsdCsdC*sdA*sC*b⁴sAb⁴ |
| 152aj | C*b⁴Gb⁴Ab⁴Tb⁴dAdCdGdCdGdTdCdCdACC*b⁴Ab⁴ |
| 152ak | C*b¹sGb¹sAb¹sdTsdAsdCsdGsdCsdGsdTsdCsCsAb¹sC*b¹sAb¹ |
| 249a | C*b¹sGb¹sAb¹sTb¹sdAdCdGdCdGdTdCdC*sAb¹sC*b¹sAb¹sGb¹ |
| 249b | C*b¹ssGb¹ssdAssdTssdAssdCssdGssdCssdGssdTssdCssdCssdAssdCssdAssGb¹ |
| 249c | C*b¹Gb¹dAdTdAdCdGdCdGdTdCdCdAdCdAGb¹ |
| 249d | C*b¹sGb¹sdAsdUsdAsdC*sdGsdCsdGsdUsdCsdC*sdAsC*b¹sAb¹sGb¹ |
| 249e | C*b¹Gb¹sdAsdTsdAsdC*sdGsdC*sdGsdTsdC*sAb¹C*b¹Ab¹Gb¹ |
| 249f | C*b⁴sGb⁴sAb⁴sdTsdAsdCsdGsdCsdGsdTsdCsdCsdAsCsAb⁴sGb⁴ |
| 249g | C*b⁶Gb⁶Ab⁶dTdA*dCdGdCdGdTdC*dCdA*C*b⁶Ab⁶Gb⁶ |
| 249h | C*b¹sGb¹sAb¹sTb¹sdAsdC*sdGsdCsdGsdTsdCsdC*sdAsdC*sdAsGb¹ |
| 249i | C*b¹ssGb¹ssdAssdUssdAssdCssdGssdCssdGssdUssdCssdCssdAssdCssAb¹ssGb¹ |
| 250a | Gb¹sC*b¹sGb¹sAb¹sTb¹sdAsdCsdC*sdGsdTsdCsC*b¹sAb¹sC*b¹sAb¹sGb¹ |
| 250b | Gb¹sC*b¹sGb¹sAb¹sdTsdAsdC*sdGsdCsdGsdTsdC*sdC*sdAsC*b¹sAb¹sGb¹ |
| 250c | Gb¹sdC*sdGsdAsdUsdAsdCsdGsdC*sdGsdUsdCsC*b¹sAb¹sC*b¹sAb¹sGb¹ |
| 250d | Gb¹sC*b¹sGb¹sdA*sdTsdA*sdC*sdGsdC*sdGsdTsdC*sC*b¹sAb¹sC*b¹sAb¹sGb¹ |
| 250e | Gb¹C*b¹dGdAdTdAdCdGdC*dGdTdCdCAb¹C*b¹Ab¹Gb¹ |
| 250f | Gb¹sdC*sdGsdAsdTsdAsdCsdGsdC*sdGsdTsdCsdCsdAsC*b¹sAb¹sGb¹ |
| 250g | Gb²sC*b²sGb²sdAsdTsdAsdCsdGsdTsdC*sC*b²sAb²sC*b²sAb²sGb² |
| 250h | Gb¹C*b¹Gb¹Ab¹Tb¹dA*dCdGdC*dGdTdC*dCdA*dC*Ab¹Gb¹ |
| 250i | Gb¹ssC*b¹ssGb¹ssAb¹ssTb¹ssdAssdCssdGssdCssdGssdTssdCssdCssdAssC*b¹ssAb¹ssGb¹ |
| 250j | Gb⁴sC*b⁴sGb⁴sdA*sdTsdA*sdCsdGsdCsdGsdTsdCsdCsAb⁴sC*b⁴sAb⁴sGb⁴ |
| 250k | Gb⁶sC*b⁶sGb⁶sdA*sdUsdA*sdCsdGsdCsdGsdUsdC*sdCsdA*sC*b⁶sAb⁶sGb⁶ |
| 250m | Gb⁷sC*b⁷sGb⁷sAb⁷sdTdAdCdGdCdGdTdC*dCsAb⁷sC*b⁷sAb⁷sGb⁷ |
| 251a | Gb¹sC*b¹sGb¹sAb¹sTb¹sdAsdCsdGsdCsdGsdTsdCsdC*sAb¹sC*b¹sAb¹sGb¹sGb¹ |
| 251b | Gb⁷sC*b⁷sGb⁷sAb⁷sTb⁷sdAsdC*sdGsdCsdGsdTsdCsdCsdAsdCsdAsdGs Gb⁷ |
| 251c | Gb¹sC*b¹sGb¹sAb¹sdTsdAsdC*sdGsdCsdGsdTsdCsdCsC*sdAsC*b¹sAb¹sGb¹sGb¹ |
| 251d | Gb¹sC*b¹sGb¹sdAsdTsdAsdCsdGsdC*sdGsdTsdCsdCsC*sdAsC*b¹sAb¹sGb¹sGb¹ |

| Seq ID No. | Sequence, 5'-3' |
|---|---|
| 251e | Gb¹sC*b¹sGb¹sAb¹sdTsdAsdC*sdGsdCsdGsdTsdCsdC*sdAsdC*sAb¹sGb¹sGb¹ |
| 251f | Gb¹C*b¹dGdAdUdA*dCdGdCdGdTdC*dC*Ab¹C*b¹Ab¹Gb¹Gb¹ |
| 251g | Gb⁴C*b⁴Gb⁴Ab⁴sdTsdAsdCsdGsdCsdGsdTsdCsdCsAb⁴C*b⁴Ab⁴Gb⁴Gb⁴ |
| 251h | Gb¹ssC*b¹ssGb¹ssdA*ssdTssdA*ssdCssdGssdCssdGssdTssdCssdCssdA*ssdC*ssAb¹ssGb¹ssGb¹ |
| 251i | Gb²C*b²Gb²dAdTdAdCdGdC*dGdTdCdC*Ab²C*b²Ab²Gb²Gb² |
| 252a | Gb¹sC*b¹sGb¹sAb¹sTb¹sdAsdC*sdGsdCsdGsdTsdCsdCsdAsC*b¹sAb¹sGb¹sGb¹sAb¹ |
| 252b | Gb⁶C*b⁶Gb⁶Ab⁶Tb⁶dAdC*dGdCdGdTdCdC*dAC*b⁶Ab⁶Gb⁶Gb⁶Ab⁶ |
| 252c | Gb¹sC*b¹sGb¹sdAsdTsdAsdCsdGsdCsdGsdTsdCsdCsdAsdC*sAb¹sGb¹sGb¹sAb¹ |
| 252d | Gb¹sdC*sdGsdA*sdTsdA*sdC*sdGsdCsdGsdTsdCsdCsdA*sC*b¹sAb¹sGb¹sGb¹sAb¹ |
| 252e | Gb⁴sC*b⁴sdGsdAsdUsdAsdCsdGsdCsdGsdUsdCsdCsdAsdC*sAb⁴sGb⁴sGb⁴sAb⁴ |
| 252f | Gb²ssC*b²ssGb²ssAb²ssTb²ssAssdCssdGssdCssdGssdTssdCssdCssdAssdCssdAssdGssGb²ssAb² |
| 253a | Gb¹sGb¹sC*b¹sGb¹sAb¹sdTsdAsdCsdGsdCsdGsdTsdC*sdC*sdAsC*b¹sAb¹sGb¹sGb¹sAb¹ |
| 253b | Gb²sGb²sC*b²sGb²sdAsdTsdAsdC*sdGsdCsdGsdTsdC*sdC*sdAsC*b²sAb²sGb²sGb²sAb² |
| 253c | Gb¹sGb¹sC*b¹dGdAdTdAdCdGdCdGdTdCdCdAdC*Ab¹Gb¹Ab¹ |
| 253d | Gb¹sdGsdCsdGsdAsdTsdAsdCsdGsdC*sdGsdUsdCsdCsdAsC*b¹sAb¹sGb¹sGb¹sAb¹ |
| 253e | Gb⁴sGb⁴sC*b⁴sGb⁴sdAsdTsdAsdCsdGsdCsdGsdTsdCsdCsdAsCsAb⁴sGb⁴sGb⁴sAb⁴ |
| 254a | Tb¹sGb¹sGb¹sC*Gb¹sdAsdTsdAsdCsdGsdCsdGsdTsdCsdCsdAsdC*sAb¹sGb¹sGb¹sAb¹sC*b¹ |
| 254b | Tb¹Gb¹Gb¹C*b¹Gb¹dAdTdAdC*dGdCdGdTdCdC*dAdCAb¹Gb¹Gb¹Ab¹C*b¹ |
| 254c | Tb⁶sGb⁶sGb⁶sC*b⁶sdGsdAsdTsdAsdCsdGsdCsdGsdTsdCsdCsdAsdCsdAsdGsGb⁶sAb⁶sC*b⁶ |
| 255a | C*b¹sTb¹sGb¹sGb¹sC*b¹sdAsdTsdAsdCsdGsdC*sdGsdTsdCsdC*sdAsdCsdAsGb¹sGb¹sAb¹sC*b¹sGb¹ |
| 255b | C*b¹Tb¹Gb¹Gb¹C*b¹dGdAdTdAdCdGdC*dGdTdCdC*dAdC*dAGb¹Gb¹Ab¹C*b¹Gb¹ |
| 256a | Gb¹sC*b¹sTb¹sGb¹sGb¹sdC*sdGsdAsdTsdAsdCsdGsdCsdGsdTsdCsdCsdAsdCsdAsGb¹sAb¹sC*b¹sGb¹sAb¹ |
| 256b | Gb¹C*b¹Tb¹Gb¹Gb¹dC*dGdAdTdAdCdGdCdGdTdCdCdAdC*dAdGGb¹Ab¹C*b¹Gb¹Ab¹ |
| 257a | Tb¹sGb¹sC*b¹sTb¹sGb¹sdGsdCsdGsdAsdTsdAsdCsdGsdC*sdGsdTsdCsdCsdAsdCsdAsdGsGb¹sAb¹sC*b¹sGb¹sAb¹ |
| 257b | Tb¹Gb¹C*b¹Tb¹Gb¹dGdCdGdAdTdAdCdGdCdGdTdCdC*dAdC*dAdGGb¹Ab¹C*b¹Gb¹Ab¹ |
| 258a | Gb¹sTb¹sdGsdTsdTsdTsdA*sdGsdGb¹sGb¹ |
| 258b | Gb¹sTb¹sdGsdUsdTsdTsdA*sdGsdGb¹sGb¹ |
| 259a | Ab¹sGb¹sTb¹sdGsdTsdTsdTsdA*sdGsdGb¹sGb¹sAb¹ |
| 259b | Ab¹Gb¹Tb¹dGdUdUdUdA*dGGb¹Gb¹Ab¹ |
| 259c | Ab¹sGb¹sTb¹sdGsdTsdTsdA*sdGsdGsGb¹sAb¹ |
| 259d | Ab¹sGb¹sdTsdGsdTsdTsdA*sdGsdGsdGsAb¹ |
| 259e | Ab¹sdGsdTsdGsdTsdTsdTsdA*sdGsdGsdGsAb¹ |
| 260a | Tb¹sAb¹sGb¹sTb¹sdGsdTsdTsdTsdAsdGsGb¹sGb¹ |
| 260b | Tb¹Ab¹Gb¹Tb¹dGdUdUdUdAdGGb¹Gb¹Ab¹ |
| 260c | Tb¹sAb¹sGb¹sTb¹sdGsdTsdTsdTsdA*sdGsdGb¹sGb¹sAb¹ |
| 260d | Tb¹sAb¹sGb¹sdUsdGsdTsdTsdTsdA*sdGsdGsGb¹sAb¹ |
| 260e | Tb¹sAb¹sdGsdUsdGsdUsdUsdA*sdGsdGsdGsAb¹ |
| 260f | Tb¹sdA*sdGsdTsdGsdTsdTsdUsdA*sGb¹sGb¹sGb¹sAb¹ |
| 261a | Tb¹sAb¹sGb¹sTb¹sdGsdTsdTsdTsdA*sdGsdGb¹sGb¹sAb¹sGb¹ |
| 261b | Tb¹Ab¹Gb¹Tb¹sdGsdTsdTsdA*sdGsdGGb¹Ab¹Gb¹ |
| 261c | Tb⁴sAb⁴sGb⁴sTb⁴sdGsdUsdTsdUsdA*sdGsdGsdGsAb⁴sGb⁴ |
| 261d | Tb¹sdA*sdGsdUsdGsdUsdTsdUsdA*sdGsdGsdGsdA*sGb¹ |
| 261e | Tb²sAb²sGb²sdUsdGsdUsdUsdTsdAsdGsdGsGb²sAb²sGb² |
| 261f | Tb⁴sAb⁴sdGsdTsdGsdTsdTsdTsdAsdGsdGsGb⁴sAb⁴sGb⁴ |
| 261g | Tb¹Ab¹dGdTdGdTdTdTdA*dGGb¹Gb¹Ab¹Gb¹ |
| 262a | Tb¹sAb¹sGb¹sTb¹sdGsdTdTdTdA*dGGb¹sAb¹sGb¹sC*b¹ |
| 262b | Tb¹ssAb¹ssdGssdTssdGssdTssdTssdTssdAssdGssdGssdAssdGssC*b¹ |
| 262c | Tb¹sAb¹sdGsdUsdGsdUsdUsdUsdA*sdGsdGsdGsAb¹sGb¹sC*b¹ |
| 262d | Tb¹dAdGdTdGdTdTdTdAdGdGdGdAdGC*b¹ |
| 262e | Tb¹Ab¹sdGsdUsdGsdUsdUsdUsdAsdGsdGsGb¹Ab¹Gb¹C*b¹ |
| 262f | Tb⁴sAb⁴sGb⁴sdTsdGsdTsdTsdTsdAsdGsdGsdsdGsdAsGb⁴sC*b⁴ |
| 262g | Tb⁶Ab⁶Gb⁶dUdGdTdTdUdAdGdGdGdAAb⁶Gb⁶C*b⁶ |
| 262h | Tb¹sAb¹sGb¹sTb¹sdGsdTsdTsdTsdAsdGsdGsdGsdAsdGsC*b¹ |

-continued

| Seq ID No. | Sequence, 5'-3' |
|---|---|
| 262i | Tb$^1$ssAb$^1$ssdGssdTssdGssdUssdUssdUssdAssd GssdGssdGssdAssGb$^1$ ssC*b$^1$ |
| 209s | Gb$^1$Tb$^1$dAsdGsdTsdGsdTsdTsdTsdAsdGsdGdGs Ab$^1$Gb$^1$**C*b**$^1$ |
| 209t | Gb$^1$sTb$^1$sdA*sdGsdTsdGsdTsdTsdTsdA*sdGsd GsdGsAb$^1$sGb$^1$sC*b$^1$ |
| 209u | Gb$^1$Tb$^1$dAdGdTdGdTdTdTdAdGdGdGAb$^1$Gb$^1$**C*b**$^1$ |
| 209v | /5SpC3s/Gb$^1$sTb$^1$sdAsdGsdTsdGsdTsdTsdTsd AsdGsdGdGsAb$^1$sGb$^1$sC*b$^1$ |
| 209w | Gb$^1$sTb$^1$sdAsdGsdTsdGsdTsdTsdTsdAsdGsdGdGs Ab$^1$sGb$^1$sC*b$^1$/s3SpC3/ |
| 209x | /5SpC3s/Gb$^1$sTb$^1$sdAsdGsdTsdGsdTsdTsdTsdAsd GsdGdGsAb$^1$sGb$^1$sC*b$^1$/3SpC3s/ |
| 209y | Gb$^1$sTb$^1$sdAsdGsdTsdGsdTsdTsdTsdAsdGsdGdGs Ab$^1$sGb$^1$**sC*b**$^1$ |
| 209aa | Gb$^1$Tb$^1$dA*sdGsdUsdGsdUsdUsdUsdAsdGsdGdGs Ab$^1$Gb$^1$**C*b**$^1$ |
| 209ab | Gb$^1$Tb$^1$dA*sdGsdTsdGsdTsdTsdTsdAsdGsdGdGs Ab$^1$Gb$^1$**C*b**$^1$ |
| 209ac | Gb$^6$sTb$^6$sdA*dGdTdGdTdTdTdA*dGdGdAb$^6$sGb$^6$ sC*b$^6$ |
| 209ad | Gb$^1$sTb$^1$sdA*sdGsdUsdGsdUsdUsdUsdA*sdGsdGsd GsAb$^1$sGb$^1$sC*b$^1$ |
| 209ae | Gb$^1$sTb$^1$sdA*sdGsdTsdGsdTsdTsdTsdAsdGsdGdGs Ab$^1$sGb$^1$**sC*b**$^1$ |
| 209af | Gb$^1$sTb$^1$sdAsdGsdTsdGsdTsdTsdTsdA*sdGsdGdGs Ab$^1$sGb$^1$**sC*b**$^1$ |
| 209ag | Gb$^1$Tb$^1$dA*dGdTdGdTdTdTdA*dGdGdGAb$^1$Gb$^1$**C*b**$^1$ |
| 209ah | Gb$^1$Tb$^1$dAdGdTdGdTdTdTdA*dGdGdGAb$^1$Gb$^1$**C*b**$^1$ |
| 209ai | Gb$^6$sTb$^6$sdA*dGdTdGdTdTdTdAdGdGdGAb$^6$sGb$^6$**sC*b**$^6$ |
| 209aj | Gb$^1$sTb$^1$sdA*sdGsdUsdGsdTsdTsdUsdA*sdGsdGdGs Ab$^1$sGb$^1$**sC*b**$^1$ |
| 209ak | Gb$^7$sTb$^7$sAb$^7$sGb$^7$sdTsdGsdTsdTsdTsdA*sdGsdGdGs Ab$^7$sGb$^7$**sC*b**$^7$ |
| 209am | Gb$^7$sTb$^7$sdAsdGsdTsdGsdTsdTsdTsdUsdA*sdGsdGsGb$^7$ sAb$^7$sGb$^7$sC*b$^7$ |
| 209an | Gb$^1$ssTb$^1$ssAb$^1$ssdGssdTssdGssdTssdTssdTssdA* ssdGssdGssdGssAb$^1$ssGb$^1$ssC*b$^1$ |
| 209ao | Gb$^4$ssTb$^4$ssAb$^4$ssdGssdTssdGssdTssdTssdTssdTssdA ssdGssdGssdGssdA*ssGb$^4$ssC*b$^4$ |
| 209ap | Gb$^2$ssTb$^2$ssAb$^2$ssGb$^2$ssdTssdGssdGssdTssdTssdA ssdGssdGssdGssdAssdGssC*b$^2$ |
| 209aq | Gb$^1$Tb$^1$Ab$^1$Gb$^1$dUdGdUdUdUdAdGdGGb$^1$Ab$^1$Gb$^1$**C*b**$^1$ |
| 209ar | Gb$^1$sTb$^1$sAb$^1$sGb$^1$sTb$^1$sdGsdTsdTsdTsdA*sdGsdGsdGs |
| 209as | Gb$^1$sTb$^1$sdAsdGsdTsdGsdTsdTsdUsdAsdGsGb$^1$sGb$^1$ sAb$^1$sGb$^1$sC*b$^1$Ab$^1$sGb$^1$sC*b$^1$ |
| 209at | Gb$^6$sTb$^6$sAb$^6$sGb$^6$sdTsdGsdTsdTsdTsdTsdAsdGsdGsdGs Ab$^6$sGb$^6$**sC*b**$^6$ |
| 209au | Gb$^7$sTb$^7$sAb$^7$sdGsdUsdGsdTsdTsdTsdA*sdGsdGsdGsAb$^7$ sGb$^7$sC*b$^7$ |
| 209av | Gb$^4$sTb$^4$sAb$^4$sGb$^4$sdUsdGsdTsdUsdGsdA*sdGsdGsdGsd A*sGb$^4$sC*b$^4$ |
| 209aw | Gb$^4$Tb$^4$Ab$^4$Gb$^4$dTdGdTdTdTdAdGdGdGdAGb$^4$**C*b**$^4$ |
| 209ax | Gb$^1$sTb$^1$sAb$^1$sdGsdTsdGsdTsdTsdTsdAsdGsdGsdGsAb$^1$ sGb$^1$sC*b$^1$ |
| 209az | Gb$^1$sTb$^1$sAb$^1$sdGsdTsdGsdTsdTsdTsdAsdGsdGsGb$^1$sAb$^1$ sGb$^1$sC*b$^1$ |
| 209ba | Gb$^1$sTb$^1$sAb$^1$sGb$^1$sdTsdGsdTsdTsdTsdAsdGsdGsGb$^1$sAb$^1$ sGb$^1$sC*b$^1$ |
| 209bb | Gb$^1$sTb$^1$sAb$^1$sGb$^1$sdTsdGsdTsdTsdTsdAsdGsdGsdGsdAs Gb$^1$sC*b$^1$ |
| 263a | Gb$^1$sTb$^1$sAb$^1$sGb$^1$sTb$^1$sdGsdTsdTsdA*sdGsdGsGb$^1$ sAb$^1$sGb$^1$sC*b$^1$sC*b$^1$ |
| 263b | Gb$^2$sTb$^2$sAb$^2$sdGsdTsdGsdTsdTsdTsdA*sdGsdGsGb$^2$ sAb$^2$sGb$^2$sC*b$^2$sC*b$^2$ |
| 263c | Gb$^1$sTb$^1$sAb$^1$sGb$^1$sdTsdGsdTsdTsdA*sdGsdGsdGsAb$^1$ sGb$^1$sC*b$^1$sC*b$^1$ |
| 263d | Gb$^1$**sdUsdA*sdGsdUsdGsdUsdTsdTsdA*sdGsdGsGb$^1$ sAb$^1$sGb$^1$sC*b$^1$sC*b$^1$ |
| 263e | Gb$^1$sTb$^1$sAb$^1$sGb$^1$sdTsdGsdTsdTsdTsdA*sdGsdGsGb$^1$sAb$^1$ sGb$^1$sC*b$^1$sC*b$^1$ |
| 263f | Gb$^1$Tb$^1$dA*dGdTdGdTdTdTdA*dGdGdGAb$^1$Gb$^1$**C*b**$^1$**C*b**$^1$ |
| 263g | Gb$^1$**sdTsdA*sdGsdTsdGsdTsdTsdTsdA*sdGsdGsdGsdA* sGb$^1$sC*b$^1$sC*b$^1$ |
| 263h | Gb$^1$Tb$^1$Ab$^1$Gb$^1$Tb$^1$dGdTdUdTdAdGdGdGdA*dGC*b$^1$**C*b**$^1$ |
| 263i | Gb$^1$ssTb$^1$ssAb$^1$ssGb$^1$ssTb$^1$ssdGssdTssdTssdTssdAssd GssdGssdGssAssGb$^1$ssC*b$^1$ssC*b$^1$ |
| 263j | Gb$^4$Tb$^4$dA*dGdTdGdTdTdTdAdGdGdGdA*Gb$^4$**C*b**$^4$**C*b**$^4$ |
| 263k | Gb$^6$sTb$^6$sAb$^6$sdGsdTsdGsdUsdUsdTsdAsdGsdGsdGsdA*s Gb$^6$sC*b$^6$sC*b$^6$ |
| 263m | Gb$^7$sTb$^7$sAb$^7$sGb$^7$sdTdGdTdTdTdA*dGdGdGsAb$^7$sGb$^7$sC* b$^7$sC*b$^7$ |
| 264a | Gb$^1$sGb$^1$sTb$^1$sAb$^1$sGb$^1$sdTsdGsdTsdTsdTsdA*sdGsdGs Gb$^1$sAb$^1$sGb$^1$sC*b$^1$sC*b$^1$ |
| 264b | Gb$^1$sGb$^7$sTb$^7$sAb$^7$sGb$^7$sdTdGdTdTdTsdTsdAsdGsdGsd GsdAsdGsdC*b$^1$sC*b$^7$ |
| 264c | Gb$^1$sGb$^1$sTb$^1$sAb$^1$sGb$^1$sdTsdGsdTsdTsdTsdAsdGsdGsd GsdA*sdGsdC*s **C*b**$^1$ |
| 264d | Gb$^1$sGb$^1$sTb$^1$sAb$^1$sGb$^1$sdUsdGsdTsdTsdAsdGsdGsd GsdA*sdGsdC*s **C*b**$^1$ |
| 264e | Gb$^1$sGb$^1$sTb$^1$sAb$^1$sdGsdTsdGsdTsdTsdTsdA*sdGsdGsd GsAb$^1$sGb$^1$sC*b$^1$sC*b$^1$ |
| 264f | Gb$^1$sGb$^1$sTb$^1$sdA*sdGsdTsdGsdTsdTsdTsdA*sdGsdGsd GsAb$^1$sGb$^1$sC*b$^1$sC*b$^1$ |
| 264g | Gb$^1$sGb$^1$sTb$^1$sAb$^1$sdGsdTsdGsdTsdTsdTsdA*sdGsdGsd GsdA*sGb$^1$sC*b$^1$sC*b$^1$ |
| 264h | Gb$^1$Gb$^1$dUdA*dGdTdGdTdTdTdAdGdGGb$^1$Ab$^1$Gb$^1$**C*b**$^1$**C*b**$^1$ |

| Seq ID No. | Sequence, 5'-3' |
|---|---|
| 264i | Gb⁴Gb⁴Tb⁴Ab⁴dGsdTsdGsdTsdTsdTsdAsdGsdGsdGs**Gb⁴Ab⁴ Gb⁴C*b⁴C*b⁴** |
| 264j | Gb¹ssGb¹ssTb¹ssdA*ssdGssdTssdGssdUssdTssdTssd A*ssdGssdGssdGssdA*ssGb¹ss**C*b¹ssC*b¹** |
| 264k | Gb²Gb²Tb²dA*dGdTdGdTdTdTdAdGdG**Gb²Ab²Gb²C*b²C*b²** |
| 265a | Gb¹sGb¹sTb¹sAb¹sGb¹sdTsdGsdTsdTsdTsdA*sdGsdGsd GsAb¹sGb¹s**C*b¹sC*b¹sGb¹** |
| 265b | Gb⁶Gb⁶Tb⁶Ab⁶Gb⁶dTdGdTdTdTdA*dGdGdG**Ab⁶Gb⁶C*b⁶C*b⁶ Gb⁶** |
| 265c | Gb¹sGb¹sTb¹sAb¹sdGsdTsdGsdTsdTsdTsdA*sdGsdGsd GsdA*sdGs**C*b¹sC*b¹sGb¹** |
| 265d | Gb¹sdGsdTsdA*sdGsdUsdGsdTsdUsdTsdA*sdGsdGsdG sAb¹sGb¹s**C*b¹sC*b¹sGb¹** |
| 265e | Gb⁴Gb⁴sdUsdAsdGsdTsdGsdTsdTsdTsdAsdGsdGsdGsd A*sGb⁴s**C*b⁴C*b⁴sGb⁴** |
| 265f | Gb²ssGb²ssTb²ssAb²ssGb²ssdTssdGssdTssdGssdTssdTssd AssdGssdGssdGssdAssdGssdCss**C*b²ssGb²** |
| 266a | Tb¹sGb¹sGb¹sTb¹sAb¹sdGsdTsdGsdTsdTsdTsdA*sdGsd GsdGsAb¹sGb¹s**C*b¹sC*b¹sGb¹** |
| 266b | Tb²sGb²sdTsdA*sdGsdTsdGsdTsdTsdTsdA*sdGsd GsdGsAb²sGb²s**C*b²sC*b²sGb²** |
| 266c | Gb¹Gb¹Tb¹dA*dGdTdGdTdTdTdA*dGdGdGdA***Gb¹C*b¹C*b¹ Gb¹** |
| 266d | Tb¹sdGsdGsdUsdA*sdGsdTsdGsdTsdUsdTsdA*sdGsd GsdGsAb¹sGb¹s**C*b¹sC*b¹sGb¹** |
| 266e | Tb⁴sGb⁴Gb⁴sTb⁴sdAsdGsdTsdGsdTsdTsdTsdAsdGsd GsdGsdAsGb⁴s**C*b⁴sC*b⁴sGb⁴** |
| 267a | Tb¹sTb¹sGb¹sGb¹sTb¹sdAsdGsdTsdGsdTsdTsdTsdAsd GsdGsdGsdA*sGb¹s**C*b¹sC*b¹sGb¹sTb¹** |
| 267b | Tb¹Tb¹Gb¹Gb¹Tb¹dA*dGdTdGdTdTdTdAdGdGdGdA***Gb¹ C*b¹C*b¹Gb¹Tb¹** |
| 267c | Tb⁶sTb⁶sGb⁶sdGsdTsdAsdGsdTsdGsdTsdTsdTsdAsdGsd GsdGsdAsGb⁶s**C*b⁶sC*b⁶sGb⁶sTb⁶** |
| 268a | Tb¹sTb¹sTb¹sGb¹sGb¹sdTsdA*sdGsdTsdGsdTsdTsdTsd AsdGsdGsdGsdAsdGC*b¹sC*b¹sGb¹sTb¹sC*b¹** |
| 268b | Tb¹Tb¹Tb¹Gb¹Gb¹dTdA*dGdTdGdTdTdTdAdGdGdGdA*dG **C*b¹C*b¹Gb¹Tb¹C*b¹** |
| 269a | Ab¹sTb¹sTb¹sTb¹sGb¹sdGsdTsdGsdAsdGsdGsdTsdTsd TsdAsdGsdGsdGsdAsdGsdC*sC*b¹sGb¹sTb¹sC*b¹sTb¹** |
| 269b | Ab¹Tb¹Tb¹Tb¹Gb¹dGdTdAdGdTdGdTdTdTdAdGdGdGdAdGd **C*C*b¹Gb¹Tb¹ C*b¹Tb¹** |
| 270a | Tb¹sAb¹sTb¹sTb¹sTb¹sdGsdGsdTsdAsdGsdTsdGsdTsd TsdTsdAsdGsdGsdGsdAsdGsdC*sdCsGb¹sTb¹s**C*b¹ sTb¹sTb¹** |
| 270b | Tb¹Ab¹Tb¹Tb¹Tb¹dGdGdTdAdGdTdGdTdTdTdAdGdGdGd AdGdC*dC***Gb¹Tb¹C*b¹Tb¹Tb¹** |
| 271a | Ab¹sTb¹sdTsdTsdGsdGsdGsdTsdA*sGb¹sTb¹ |
| 271b | Ab¹Tb¹dTdTdGdGdGdTdA*Gb¹Tb¹ |
| 272a | Tb¹sAb¹sTb¹sdTsdTsdGsdGsdGsdTsdA*sGb¹sTb¹sGb¹ |
| 272b | Tb¹Ab¹Tb¹dTdTdGdGdTdA*Gb¹Tb¹Gb¹ |
| 272c | Tb¹sAb¹sTb¹sdTsdTsdGsdGsdGsdTsdA*sdGsTb¹sGb¹ |
| 272d | Tb¹sAb¹sdTsdTsdGsdGsdGsdTsdA*sdGsdUsGb¹ |
| 272e | Tb¹sdAsdTsdUsdTsdGsdGsdUsdA*sdGsTb¹sGb¹ |
| 273a | Tb¹sAb¹sTb¹sdTsdTsdGsdGsdTsdAsGb¹sTb¹sGb¹sTb¹ |
| 273b | Tb¹Ab¹Tb¹dUdUdGdGdUdAGb¹Tb¹Gb¹Tb¹ |
| 273c | Tb¹sAb¹sTb¹sdTsdTsdGsdGsdGsdTsdA*sGb¹sTb¹sGb¹sTb¹ |
| 273d | Tb¹sAb¹sTb¹sdTsdTsdGsdGsdGsdTsdA*sdGsdUsGb¹sTb¹ |
| 273e | Tb¹sAb¹sdUsdUsdUsdGsdGsdUsdA*sdGsdUsdGsTb¹ |
| 273f | Tb¹sdA*sdTsdTsdUsdGsdGsdTsdA*Gb¹sTb¹sGb¹sTb¹ |
| 274a | **C*b¹Tb¹Ab¹**sdUsdTsdGsdGsdTsdA*sGb¹Tb¹Gb¹Tb¹ |
| 274b | **C*b⁴sTb⁴sAb⁴sTb⁴**sdTsdTsdGsdGsdTsdA*sdGsdUs Gb⁴Tb⁴ |
| 274c | **C*b¹**sdUsdA*sdTsdTsdTsdGsdGsdTsdAsdGsdTsdGs Tb¹ |
| 274d | **C*b²sTb²sAb²**sdTsdUsdGsdGsdTsdA*sdGsTb²s Gb²Tb² |
| 274e | **C*b⁴ssTb⁴ssdAssdTssdTssdTssdGssdGssdTssdAssd GssTb⁴ssGb⁴ssTb⁴ |
| 274f | **C*b¹Tb¹Ab¹dTdTdTdGdGdTdA*Gb¹Tb¹Gb¹Tb¹** |
| 274g | **C*b¹sTb¹sAb¹sTb¹**sdTsdTsdGsdGsdTsdA*sGb¹sGb¹sTb¹ |
| 275a | **C*b¹sTb¹sAb¹sTb¹**sdTsdTsdGsdGsdTsdA*sdGsdTsdG sdTsTb¹ |
| 275b | **C*b¹sTb¹**sdA*sdUsdTsdUsdGsdGsdTsdAsdGsdUsGb¹ sTb¹sTb¹ |
| 275c | **C*b⁴sTb⁴sAb⁴sdTsdTsdGsdGsdTsdAsdGsdTsdGs Tb⁴sTb⁴** |
| 275d | **C*b¹ssTb¹ssdAssdTssdTssdTssdGssdGssdTssdAssd GssdTssdGssdTssTb¹** |
| 275e | **C*b¹ssTb¹ssdAssdUssdTssdTssdGssdGssdTssdAssd GssdUssdGssTb¹ssTb¹** |
| 275f | **C*b¹sTb¹sAb¹sTb¹**sdTsdTdGdGdTdA*dGsTb¹sGb¹sTb¹ sTb¹ |
| 275g | **C*b¹Tb¹**sdAsdTsdTsdTsdGsdGsdTsdA*sdGsTb¹Gb¹ Tb¹Tb¹ |
| 275h | **C*b⁶Tb⁶Ab⁶**dUdTdTdGdGdTdA*dGdUGb⁶Tb⁶Tb⁶ |
| 275i | **C*b¹dTdAdTdTdGdGdTdAdGdTdGdTTb¹ |
| 210o | **Gb¹C*b¹Tb¹Ab¹dTsdTsdTsdGsdGsdTsdAsdGsdTsGb¹ Tb¹Tb¹** |
| 210p | Gb¹s**C*b¹sTb¹sAb¹**sdTsdTsdTsdGsdGsdTsdA*sdGsdT sGb¹sTb¹sTb¹ |
| 210q | Gb¹s**C*b¹sTb¹sAb¹sdTsdTsdTsdGsdGsdTsdAsdGsdTs Gb¹sTb¹sTb¹** |
| 210r | **Gb¹C*b¹Tb¹Ab¹**dTdTdTdGdGdTdA*dGdTGb¹Tb¹Tb¹ |

| Seq ID No. | Sequence, 5'-3' |
|---|---|
| 210s | Gb¹sC*b¹sTb¹sAb¹sdUsdUsdTdGsdGsdTsdA*sdGsdTsGb¹sTb¹sTb¹ |
| 210t | Gb¹sC*b¹sTb¹sAb¹sdUsdUsdTsdTsdGsdGsdTsdAsdGsdUsGb¹sTb¹sTb¹ |
| 210u | Gb¹sC*b¹sTb¹sAb¹sdUsdUsdUsdGsdGsdUsdA*sdGsdUsGb¹sTb¹sTb¹ |
| 210v | /5SpC3s/Gb¹sC*b¹sTb¹sAb¹sdTsdTsdTsdGsdGsdTsdAsdGsdTsGb¹sTb¹sTb¹ |
| 210w | Gb¹sC*b¹sTb¹sAb¹sdTsdTsdTsdGsdGsdTsdAsdGsdTsGb¹sTb¹sTb¹/3SpC3s/ |
| 210x | /5SpC3s/Gb¹sC*b¹sTb¹sAb¹sdTsdTsdTsdGsdGsdTsdAsdGsdTsGb¹sTb¹sTb¹/3SpC3s/ |
| 210y | Gb¹C*b¹Tb¹Ab¹sdTsdTsdTsdGsdGsdTsdA*sdGsdTsGb¹Tb¹Tb¹ |
| 210z | Gb¹C*b¹Tb¹Ab¹sdUsdTsdTsdGsdGsdUsdA*sdGsdTsGb¹Tb¹Tb¹ |
| 210aa | Gb¹sC*b¹sTb¹sAb¹sdTdTdTdGdGdTdA*dGdTsGb¹sTb¹sTb¹ |
| 210ab | Gb⁶sC*b⁶sTb⁶sAb⁶sdTdTdTdGdGdTdA*dGdTsGb⁶sTb⁶sTb⁶ |
| 210ac | Gb⁶sC*b⁶sTb⁶sdAsdTsdTsdTsdGsdGsdTsdAsdGsTb⁶sGb⁶sTb⁶sTb⁶ |
| 210ad | Gb⁷sC*b⁷sTb⁷sdA*sdTsdTsdTsdGsdGsdTsdA*sdGsTb⁷sGb⁷sTb⁷sTb⁷ |
| 210ae | Gb⁷sC*b⁷sdUsdAsdTsdTsdUsdGsdGsdUsdA*sdGsTb⁷sTb⁷sTb⁷ |
| 210af | Gb¹ssC*b¹ssTb¹ssdAssdTssdTssdTssdGssdGssdTssdA*ssdGssdTssGb¹ssTb¹ssTb¹ |
| 210ag | Gb⁴ssC*b⁴ssTb⁴ssdA*ssdTssdTssdTssdGssdGssdTssdAssdGssdTssdGssTb⁴ssTb⁴ |
| 210ah | Gb²ssC*b²ssTb²ssAb²ssdTssdTssdTssdGssdGssdTssdAssdGssdTssdGssTssTb² |
| 210ai | Gb¹C*b¹Tb¹Ab¹dUsdTsdTsdGsdGsdTsdAsdGsTb¹Gb¹Tb¹Tb¹ |
| 210aj | Gb⁴C*b⁴Tb⁴Ab⁴dTsdTsdTsdGsdGsdTsdAsdGsdTdGTb⁴Tb⁴ |
| 210ak | Gb¹sC*b¹sTb¹sAb¹sTb¹sdTsdTsdGsdGsdTsdA*sdGsdTsGb¹sTb¹sTb¹ |
| 210am | Gb⁴sC*b⁴sTb⁴sAb⁴sdTsdTsdUsdGsdGsdTsdA*sdGsdTsdGsTb⁴sTb⁴ |
| 210an | Gb⁷sC*b⁷sTb⁷sdA*sdTsdTsdUsdGsdGsdTsdA*sdGsdTsGb⁷sTb⁷sTb⁷ |
| 210ao | Gb¹sC*b¹sdUsdAsdUsdUsdTsdGsdGsdUsdAsGb¹sTb¹sGb¹sTb¹sTb¹ |
| 210ap | Gb¹sC*b¹sTb¹sdAsdTsdTsdTsdGsdGsdTsdAsdGsdTsGb¹sTb¹sTb¹ |
| 210aq | Gb¹sC*b¹sTb¹sdAsdTsdTsdTsdGsdGsdTsdAsdGsdTsdGsTb¹sTb¹ |
| 276a | Gb¹sC*b¹sTb¹sAb¹sTb¹sdTsdTsdGsdGsdTsdA*sdGsTb¹sGb¹sTb¹sTb¹sTb¹ |
| 276b | Gb²sC*b²sTb²sdAsdTsdTsdGsdGsdGsdTsdA*sdGsTb²sGb²sTb²sTb²sTb² |
| 276c | Gb¹sC*b¹sTb¹sdAsdTsdTsdTsdGsdGsdGsdTsdA*sdGsdTsGb¹sTb¹sTb¹sTb¹ |
| 276d | Gb²sdC*sdTsdAsdTsdTsdTsdGsdGsdGsdTsdAsdGsTb²sGb²sTb²sTb²sTb² |
| 276e | Gb⁶sC*b⁶sTb⁶sdA*sdUsdUsdUsdGsdGsdUsdA*sdGsdUsdGsTb⁶sTb⁶sTb⁶ |
| 276f | Gb¹sdC*sdTsdA*sdUsdUsdUsdGsdGsdUsdAsdGsdUsdGsTb¹sTb¹sTb¹ |
| 276g | Gb¹C*b¹dTdA*dTdTdTdGdGdTdA*dGdTGb¹Tb¹Tb¹Tb¹ |
| 276h | Gb⁴C*b⁴Tb⁴Ab⁴dTdTdTdGdGdTdA*dGdTdGTb⁴Tb⁴Tb⁴ |
| 276i | Gb¹C*b¹Tb¹Ab¹Tb¹dUdTdGdGdTdA*dGdTdGdUTb¹Tb¹ |
| 276j | Gb¹ssC*b¹ssAb¹ssTb¹ssdTssdTssdGssdGssdTssdAssdGssdTssdGssTb¹ssTb¹ssTb¹ |
| 276k | Gb⁷sC*b⁷sTb⁷sAb⁷sdTdTdTdGdGdTdA*dGdTsGb⁷sTb⁷sTb⁷sTb⁷ |
| 277a | Ab¹sGb¹sC*b¹sTb¹sAb¹sdTsdTsdTsdGsdGsdTsdA*sdGsTb¹sGb¹sTb¹sTb¹sTb¹ |
| 277b | Ab⁷sGb⁷sC*b¹sTb¹sAb⁷sdTsdTsdTsdGsdGsdTsdA*sdGsTsdGsdTsdTsTb⁷ |
| 277c | Ab¹sGb¹sdC*sdTsdAsdTsdTsdTsdGsdGsdTsdAsdGsTb¹sGb¹sTb¹sTb¹sTb¹ |
| 277d | Ab¹sGb¹sdC*sdAsdTsdTsdTsdGsdGsdTsdAsdGsTb¹sGb¹sTb¹sTb¹sTb¹ |
| 277e | Ab¹Gb¹dC*dTdAdUdTdTdGdGdTdA*dGTb¹Gb¹Tb¹Tb¹Tb¹ |
| 277f | Ab²Gb²C*b²dTdAdTdTdTdGdGdTdA*dGTb²Gb²Tb²Tb²Tb² |
| 277g | Ab¹sGb¹sC*b¹sTb¹sdA*sdTsdTsdTsdGsdGsdTsdA*sdGsdTsGb¹sTb¹sTb¹sTb¹ |
| 277h | Ab¹sGb¹sC*b¹sTb¹sdAsdTsdTsdTsdGsdGsdTsdAsdGsdTsdGsTb¹sTb¹sTb¹ |
| 277i | Ab¹sGb¹sC*b¹sdTsdAsdTsdTsdTsdGsdGsdTsdA*sdGsdTsGb¹sTb¹sTb¹sTb¹ |
| 277j | Ab⁴Gb⁴C*b⁴Tb⁴dAsdTsdTsdTsdGsdGsdTsdAsdGsTb⁴Gb⁴Tb⁴Tb⁴Tb⁴ |
| 277k | Ab¹ssGb¹ssC*b¹ssdTssdAssdTssdTssdGssdGssdTssdA*ssdGssdUssdGssTb¹ssTb¹ssTb¹ |
| 278a | Ab¹sGb¹sC*b¹sTb¹sAb¹sdTsdTsdTsdGsdGsdTsdA*sdGsdTsGb¹sTb¹sTb¹sTb¹sAb¹ |
| 278b | Ab²ssGb²ssC*b²ssTb²ssAb²ssdTssdTssdTssdGssdGssdTssdAssdGssdTssdGssTb²ssAb² |
| 278c | Ab¹sdGsdC*sdTsdAsdTsdTsdTsdGsdGsdTsdA*sdGsdTsGb¹sTb¹sTb¹sTb¹sAb¹ |
| 278d | Ab¹sdGsdC*sdAsdTsdTsdTsdGsdGsdTsdUsdA*sdGsdUsGb¹sTb¹sTb¹sTb¹sAb¹ |
| 278e | Ab¹sGb¹sC*b¹sdTsdAsdTsdTsdTsdGsdGsdTsdA*sdGsdTsdGsTb¹sTb¹sTb¹sAb¹ |

| Seq ID No. | Sequence, 5'-3' |
|---|---|
| 278f | Ab⁴sGb⁴**sdC\*sdTsdAsdTsdTsdTsdGsdGsdTsdAsdGsdTsdGTb⁴sTb⁴sTb⁴sAb**⁴ |
| 278g | Ab⁶Gb⁶**C\*b⁶Tb⁶Ab⁶dTdTdTdGdGdTdA\*dGdTGb⁶Tb⁶Tb⁶Tb⁶Ab**⁶ |
| 279a | Gb¹sAb¹sGb¹**sC\*b¹sTb¹sdAsdTsdTsdTsdGsdGsd**TsdA\*sdGsdTsGb¹sTb¹sTb¹sTb¹sAb¹ |
| 279b | Gb²sAb²sGb²**sdC\*sdTsdAsdTsdTsdTsdGsdGsdTsdAsdGsdTsGb²sTb²sTb²sTb²sAb**² |
| 279c | Gb¹**sdAsdGsdC\*sdUsdTsdTsdTsdTsdGsdGsd**TsdA\*sdGsdTsGb¹sTb¹sTb¹sTb¹sAb¹ |
| 279d | Gb⁴sAb⁴sGb⁴**sC\*b⁴sdTsdAsdTsdTsdTsdGsdGsdTsdAsdGsdTsdGTb⁴sTb⁴sTb⁴sAb**⁴ |
| 279e | Gb¹Ab¹Gb¹**dC\*dTdAdTdTdTdGdGdTdAdGdTdGTb¹Tb¹Tb¹Ab**¹ |
| 280a | Ab¹sGb¹sAb¹sGb¹**sC\*b¹sdTsdAsdTsdTsdTsdGsdGsdTsdAsdGsdTsdGsTb¹sTb¹sTb¹sAb¹sGb**¹ |
| 280b | Ab¹Gb¹Ab¹Gb¹**C\*b¹dTdTdTdTdGdGdTdAdGdTdGTb¹Tb¹Tb¹Ab¹Gb**¹ |
| 280c | Ab¹sGb¹sAb¹sGb¹**sdC\*sdTsdAsdTsdTsdTsdGsdGsdTsdAsdGsdTsdGsTb¹sTb¹sTb¹sAb¹sGb**¹ |
| 280d | Ab⁶sGb⁶sAb⁶sGb⁶**sdC\*sdTsdAsdTsdTsdTsdGsd**GsdTsdA\*sdGsdTsdGsdTsdTb⁶sAb⁶sGb⁶ |
| 281a | Ab¹sAb¹sGb¹sAb¹sGb¹**sdC\*sdTsdAsdTsdTsdTsdGsdGsdTsdAsdGsdTsdGsdTsTb¹sTb¹sAb¹sGb¹sGb**¹ |
| 281b | Ab¹Ab¹Gb¹Ab¹Gb¹**dC\*dTdAdTdTdTdGdGdTdAdGdTdGdTTb¹Tb¹Ab¹Gb¹Gb**¹ |
| 282a | Gb¹sAb¹sAb¹sGb¹sAb¹**sdGsdC\*sdTsdAsdTsdTsdTsdGsdGsdTsdAsdGsdTsdGsdTsdTsTb¹sAb¹sGb¹sGb¹sGb**¹ |
| 282b | Gb¹Ab¹Ab¹Gb¹Ab¹**dGdC\*dTdAdTdTdTdGdGdTdAdGdTdGdTdTTb¹Ab¹Gb¹Gb¹Gb**¹ |
| 283a | Ab¹sGb¹sAb¹sAb¹sGb¹**sdAsdGsdC\*sdTsdAsdTsdTsdTsdGsdGsdTsdAsdGsdTsdGsdTsdTsAb¹sGb¹sGb¹sGb¹sAb**¹ |
| 283b | Ab¹Gb¹Ab¹Ab¹Gb¹**dAdGdC\*dTdAdTdTdTdGdGdTdAdGdTdGdTdTdTAb¹Gb¹Gb¹Gb¹Ab**¹ |
| 284a | **C\*b¹sAb¹sdTsdTsdTsdAsdAsdTsdA\*sAb¹sAb**¹ |
| 284b | **C\*b¹Ab¹dTdTdA\*dAdTdA\*Ab¹Ab**¹ |
| 285a | Gb¹**sC\*b¹sAb¹sdTsdTsdTsdA\*sdA\*sdTsdAsAb¹sAb¹sGb**¹ |
| 285b | Gb¹**sC\*b¹sAb¹sdTsdTsdA\*sdA\*sdTsdAsdAs\*sAb¹sGb**¹ |
| 285c | Gb¹**sC\*b¹sdAsdTsdTsdA\*sdA\*sdUsdAsdA\*sdA\*sGb**¹ |
| 285d | Gb¹**sdC\*sdAsdTsdTsdTsdAsdAsdTsdAsAb¹sGb**¹ |
| 285e | Gb¹**sdC\*sdTsdTsdTsdAsdAsdTsdAsdA\*sAb¹sGb**¹ |
| 285f | Gb¹**C\*b¹Ab¹dTdTdA\*dA\*dTdAAb¹Ab¹Gb**¹ |
| 286a | Gb¹**sC\*b¹sAb¹sTb¹sdTsdAsdAsdTsdAsdAsAb¹sGb¹sTb**¹ |
| 286b | Gb¹**sC\*b¹sAb¹sTb¹sdTsdA\*sdA\*sdTsdAsdAsAb¹sGb¹sTb**¹ |
| 286c | Gb¹**sC\*b¹sAb¹sdUsdTsdAsdAsdTsdAsdAsdA\*sGb¹sTb**¹ |

| Seq ID No. | Sequence, 5'-3' |
|---|---|
| 286d | Gb¹**sC\*b¹sdAsdTsdTsdTsdAsdA\*sdUsdAsdAsdAsdGsTb**¹ |
| 286e | Gb¹**sdC\*sdAsdTsdTsdAsdAsdTsdAsAb¹sAb¹sGb¹sTb**¹ |
| 286f | Gb¹**sdC\*sdAsdTsdTsdAsdAsdTsdA\*sAb¹sAb¹sGb¹sTb**¹ |
| 286g | Gb¹**C\*b¹Ab¹Tb¹dUdAdAdUdAdAAb¹Gb¹Tb**¹ |
| 287a | Gb¹sGb¹**sC\*b¹sAb¹sdTsdTsdA\*sdAsdTsdAsAb¹sAb¹sGb¹sTb**¹ |
| 287b | Gb⁴sGb⁴**sC\*b⁴sAb⁴sdTsdTsdA\*sdAsdUsdAsdAsdA\*sGb⁴sTb**⁴ |
| 287c | Gb¹**sdGsdCsdAsdUsdUsdAsdAsdTsdA\*sdA\*sdA\*sdGsTb**¹ |
| 287d | Gb²sGb²**sC\*b²sdA\*sdUsdTsdA\*sdAsdTsdAsdA\*sAb²sGb²sTb**² |
| 287e | Gb¹Gb¹**C\*b¹Ab¹sdTsdTsdAsdAsdTsdA\*sdA\*sAb¹Gb¹Tb**¹ |
| 287f | Gb¹sGb¹**sdC\*sdTsdTsdAsdAsdTsdAsAb¹sAb¹sGb¹sTb¹sTb**¹ |
| 287g | Gb¹sGb¹**sdC\*sdA\*sdTsdA\*sdAsdTsdA\*sAb¹sAb¹sGb**¹ |
| 287h | Gb¹Gb¹**dC\*dAdTdAdAdTdAAb¹Ab¹Gb¹Tb**¹ |
| 287i | Gb⁴ssGb⁴ssCssdAssdTssdAssdAssdTssdAssAb⁴ssAb⁴ssGb⁴ssTb**⁴ |
| 287j | Gb⁴ssGb⁴**ssdC\*ssdAssdTssdTssdAssdAssdTssdAssAb⁴ssAb⁴ssGb⁴ssTb⁴ |
| 288a | Gb¹sGb¹**sdC\*sdAsdTsdAsdAsdTsdAsdAsdAsGb¹sTb¹sGb**¹ |
| 288b | Gb¹sGb¹**sC\*b¹sAb¹sdTsdTsdA\*sdA\*sdTsdAsdAsdAsGsdTsGb**¹ |
| 288c | Gb⁴sGb⁴**sC\*b⁴sdAsdTsdTsdAsdAsdTsdAsdAsdAsdGsTb⁴sGb**⁴ |
| 288d | Gb¹sGb¹**sC\*b¹sAb¹sdTdTdAdAdTdAdAsAb¹sGb¹sTb¹sGb**¹ |
| 288e | Gb¹Gb¹**sdC\*sdAsdTsdTsdAsdAsdTsdAsdAsAb¹Gb¹Tb¹Gb**¹ |
| 288f | Gb¹ssGb¹ssdCssdAssdUssdUssdAssdAssdUssdAssAssdAssdGssTb¹ssGb¹ |
| 288g | Gb¹ssGb¹ssdCssdAssdTssdTssdAssdAssdTssdAssAssdAssdGssdTssGb¹ |
| 288h | Gb⁶Gb⁶**C\*b⁶dA\*dTdTdAdAdUdA\*dA\*dAGb⁶Tb⁶Gb**⁶ |
| 288i | Gb¹Gb¹**C\*b¹dAdTdTdAdAdUdAdAdAGb¹Tb¹Gb**¹ |
| 289a | Ab¹sGb¹sGb¹**sC\*b¹sAb¹sdTsdA\*sdA\*sdTsdA\*sAb¹sAb¹sGb¹sTb¹sGb**¹ |
| 289b | Ab¹sGb¹sGb¹**sdC\*sdAsdAsdTsdAsdAsdTsdAsAb¹sAb¹sGb¹sTb¹sGb**¹ |
| 289c | Ab¹sGb¹sGb¹**sdC\*sdA\*sdTsdA\*sdAsdTsdA\*sAb¹sAb¹sGb¹sTb¹sGb**¹ |
| 289d | Ab²sGb²sGb²**sdC\*sdAsdTsdTsdAsdAsdTsdAsAb²sAb²sGb²sTb²sGb**² |
| 289e | Ab¹**sdGsdGsdC\*sdAsdTsdTsdAsdAsdTsdAsAb¹sAb¹sGb¹sTb¹sGb**¹ |

| Seq ID No. | Sequence, 5'-3' |
|---|---|
| 289f | Ab¹sdGsdGsdC*sdAsdTsdUsdAsdAsdUsdAsAb¹sGb¹sTb¹sGb¹ |
| 289g | Ab¹sGb¹sGb¹sdC*sdAsdTsdTsdAsdAsdTsdAsdAsAb¹sGb¹sTb¹sGb¹ |
| 289h | **Ab¹sGb¹sGb¹sC*b¹**sdA*sdTsdTsdA*sdA*sdTsdA*sdAsdAsGb¹sTb¹sGb¹ |
| 289i | Ab⁶sGb⁶sGb⁶sdC*sdA*sdUsdTsdAsdAsdTsdAsdAsdAsGb⁶sTb⁶sGb⁶ |
| 289j | Ab¹sGb¹sGb¹sdC*sdAsdTsdTsdAsdAsdTsdAsdAsdAsGb¹sTb¹sGb¹ |
| 289k | Ab¹sdGsdGsdC*sdAsdTsdTsdAsdAsdTsdAsdAsdAsGb¹sTb¹sGb¹ |
| 289m | **Ab¹Gb¹Gb¹C*b¹Ab¹**dUdTdA*dA*dTdAdAdAdGTb¹Gb¹ |
| 289n | Ab¹Gb¹dGdC*dAdTdTdAdAdTdAdAAb¹Gb¹Tb¹Gb¹ |
| 289o | Ab⁴Gb⁴Gb⁴dCdA*dTdTdAdAdTdAdA*Ab⁴Gb⁴Tb⁴Gb⁴ |
| 289p | **Ab¹ssGb¹ssGb¹ssC*b¹ssAb¹ssdTssdTssdAssdAssdTssdAssdAssdAssGb¹ssTb¹ssGb¹** |
| 289q | **Ab⁷sGb⁷sGb⁷sC*b⁷**sdA*dTdTdAdAdTdAdA*sAb⁷sGb⁷sTb⁷sGb⁷ |
| 213j | C*b¹sAb¹sGb¹sdGsdC*sdAsdTsdTsdAsdAsdTsdAsdAsdAsGb¹sTb¹sGb¹ |
| 213k | C*b¹sAb¹sGb¹sdGsdCsdAsdTsdTsdAsdAsdTsdAsdAsdAsGb¹sTb¹sGb¹ |
| 213m | C*b¹sAb¹sGb¹sdGsdC*sdAsdTsdTsdAsdAsdTsdAsdA*sdA*sGb¹sTb¹sGb¹ |
| 213n | C*b¹Ab¹Gb¹dGdC*dAdTdTdAdAdTdAdAdAGb¹Tb¹Gb¹ |
| 213o | /5SpC3s/C*b¹sAb¹sGb¹sdGsdC*sdAsdTsdTsdAsdAsdTsdAsdAsdAsGb¹sTb¹sGb¹ |
| 213p | C*b¹sAb¹sGb¹sdGsdC*sdAsdTsdTsdAsdAsdTsdAsdAsdAsGb¹sTb¹sGb¹/3SpC3s/ |
| 213q | /5SpC3s/C*b¹sAb¹sGb¹sdGsdC*sdAsdTsdTsdAsdAsdTsdAsdAsdAsGb¹sTb¹sGb¹/3SpC3s/ |
| 213r | C*b¹sAb¹sGb¹sdGsdC*sdAsdTsdTsdAsdAsdUsdAsdAsdA*sGb¹sTb¹sGb¹ |
| 213s | C*b⁶sAb⁶sGb⁶sdGdC*dAdTdTdAdAdTdAdAdAsGb⁶sTb⁶sGb⁶ |
| 213t | C*b¹sAb¹sGb¹sdGdC*dAdTdTdAdAdTdAdAdAsGb¹sTb¹sGb¹ |
| 213u | C*b¹Ab¹Gb¹dGdGdC*sdAsdUsdUsdAsdAsdUsdAsdAsGb¹Tb¹Gb¹ |
| 213v | C*b¹Ab¹Gb¹sdGsdC*sdAsdTsdTsdAsdA*sdTsdAsdAsdA*sGb¹Tb¹Gb¹ |
| 213w | C*b¹Ab¹Gb¹sdGsdC*sdAsdTsdTsdAsdAsdTsdAsdAsdAsGb¹Tb¹Gb¹ |
| 213x | C*b⁷sAb⁷sGb⁷sGb⁷sdC*sdAsdTsdTsdAsdAsdTsdAsdAsdAsGb⁷sTb⁷sGb⁷ |
| 213y | C*b⁶sAb⁶sGb⁶sGb⁶sdCsdAsdTsdTsdAsdAsdTsdAsdAsdAsGb⁶sTb⁶sGb⁶ |
| 213z | C*b⁷sAb⁷sGb⁷sdGsdCsdA*sdUsdTsdAsdAsdTsdAsdAsAb⁷sGb⁷sTb⁷sGb⁷ |
| 213aa | C*b⁴sAb⁴sGb⁴sGb⁴sdC*sdA*sdTsdTsdAsdAsdTsdAsdA*sdAsdGsTb⁴sGb⁴ |
| 213ab | C*b¹s**Ab¹sGb¹sGb¹sC*b¹**sdA*sdTsdTsdA*sdA*sdTsdAsdA*sdA*sGb¹sTb¹sGb¹ |
| 213ac | C*b¹sAb¹sGb¹sdGsdCsdAsdTsdTsdA*sdA*sdTsdAsAb¹sAb¹sGb¹sTb¹sGb¹ |
| 213ad | C*b¹sAb¹sdGsdGsdC*sdAsdTsdTsdAsdAsdUsdAsdAsAb¹sGb¹sTb¹sGb¹ |
| 213ae | C*b¹ssAb¹ssGb¹ssdGssdC*ssdAssdTssdTssdAssdAssdTssdAssdAssAb¹ssGb¹ssTb¹ssGb¹ |
| 213af | C*b⁴ssAb⁴ssGb⁴ssdGssdCssdAssdTssdTssdA*ssdAssdTssdAssdAssdAssdGssTb⁴ssGb⁴ |
| 213ag | C*b²ssAb²ssGb²ssGb²ssdCssdAssdTssdTssdAssdAssdTssdAssdAssdAssdGssdTssGb² |
| 213ah | C*b¹Ab¹Gb¹Gb¹dCdAdTdTdAdAdUdAdAAb¹Gb¹Tb¹Gb¹ |
| 213ai | C*b⁴Ab⁴Gb⁴Gb⁴dCdAdTdTdAdAdTdAdAdAdGTb⁴Gb⁴ |
| 213aj | C*b¹Ab¹Gb¹dGdCdAdTdTdAdAdUdAdAdAdGTb¹Gb¹ |
| 213ak | C*b¹sAb¹sGb¹sGb¹sdCsdTsdTsdAsdAsdTsdAb¹sGb¹sTb¹sGb¹ |
| 290a | C*b¹s**Ab¹sGb¹sGb¹sC*b¹**sdAsdTsdTsdAsdAsdTsdA*sdAs**Ab¹sGb¹sTb¹sGb¹sC*b¹** |
| 290b | C*b¹sAb¹sGb¹sGb¹sdC*sdAsdTsdTsdAsdAsdTsdAsdAsdAs**Gb¹sTb¹sGb¹sC*b¹** |
| 290c | C*b¹sAb¹sGb¹sGb¹sdC*sdAsdTsdTsdAsdAsdTsdAsdAsdAsdGs**Tb¹sGb¹sC*b¹** |
| 290d | C*b¹sAb¹sGb¹sdGsdC*sdAsdTsdTsdAsdAsdTsdAsdAsdAs**Gb¹sTb¹sGb¹sC*b¹** |
| 290e | C*b⁷s**Ab⁷sGb⁷sGb⁷sC*b⁷**sdA*sdTsdTsdAsdAsdTsdAsdAsdAsdGsdTsdGs**C*b⁷** |
| 290f | C*b⁴Ab⁴Gb⁴Gb⁴sdCsdAsdTsdTsdAsdAsdTsdA*sdAs**Ab⁴Gb⁴Tb⁴Gb⁴C*b⁴** |
| 290 g | C*b¹ssAb¹ssGb¹ssdGssdC*ssdAssdTssdTssdA*ssdAssdTssdA*ssdAssdA*ssdGss**Tb¹ssGb¹ssC*b¹** |
| 290h | C*b²Ab²Gb²dGdC*dAdTdTdAdAdTdAdA**Ab²Gb²Tb²Gb²C*b²** |
| 290i | C*b¹Ab¹dGdGdC*dA*dUdUdAdAdUdA*dA**Ab¹Gb¹Tb¹Gb¹C*b¹** |
| 291a | **Ab¹sC*b¹sAb¹sGb¹sGb¹**sdC*sdAsdTsdTsdAsdAsdTsdAsdAs**Ab¹sGb¹sTb¹sGb¹sC*b¹** |
| 291b | **Ab¹sC*b¹sAb¹sGb¹**sdGsdC*sdAsdTsdTsdAsdAsdTsdAsdAsdAsdGs**Tb¹sGb¹sC*b¹** |
| 291c | **Ab⁴sC*b⁴**sdAsdGsdGsdC*sdAsdTsdTsdAsdAsdAsdUsdAsdAsdAs**Gb⁴sTb⁴sGb⁴sC*b⁴** |
| 291d | Ab¹sdC*sdAsdGsdGsdC*sdA*sdTsdTsdAsdAsdTsdAsdAs**Ab¹sGb¹sTb¹sGb¹sC*b¹** |

-continued

| Seq ID No. | Sequence, 5'-3' |
|---|---|
| 291e | Ab²ssC*b²ssAb²ssGb²ssGb²ssdCssdAssdTssd TssdAssdAssdTssdAssdAssdAssdGssdTssGb² ssC*b² |
| 291f | Ab⁶C*b⁶Ab⁶Gb⁶Gb⁶dC*dAdTdTdAdAdTdAdAAb⁶Gb⁶ Tb⁶Gb⁶C*b⁶ |
| 292a | Ab¹sC*b¹sAb¹sGb¹sGb¹sdC*sdAsdTsdTsdAsdAsd TsdAsdAsdAsGb¹sTb¹sGb¹sC*b¹sAb¹ |
| 292b | Ab²sC*b²sAb²sdGsdGsdC*sdAsdTsdTsdAsdAsd TsdAsdAsdAsGb²sTb²sGb²sC*b²sAb² |
| 292c | Ab¹sdC*sdAsdGsdGsdC*sdAsdUsdUsdAsdAsd UsdAsdAsdAsGb¹sTb¹sGb¹sC*b¹sAb¹ |
| 292d | Ab⁴sC*b⁴sAb⁴sGb⁴sdGsdCsdAsdTsdTsdAsdAsd TsdAsdAsdAsdGsTb⁴sGb⁴sC*b⁴sAb⁴ |
| 292e | Ab¹C*b¹Ab¹dGdGdC*dAdTdTdAdAdTdAdAdAdGTb¹ Gb¹C*b¹Ab¹ |
| 293a | Tb¹sAb¹sC*b¹sAb¹sGb¹sdGsdC*sdAsdTsdTsdAsd AsdTsdAsdAsdAsdGsTb¹sGb¹sC*b¹sAb¹sAb¹ |
| 293b | Tb¹Ab¹C*b¹Ab¹Gb¹dGdC*dAdTdTdAdAdTdAdAdAdG Tb¹Gb¹C*b¹Ab¹Ab¹ |
| 293c | Tb⁶sAb⁶sC*b⁶sdAsdGsdGsdCsdAsdTsdTsdAsdAsd TsdAsdAsdAsdGsTb⁶sGb⁶sC*b⁶sAb⁶sAb⁶ |
| 294a | Ab¹sTb¹sAb¹sC*b¹sAb¹sdGsdGsdC*sdAsdTsdTsd AsdAsdTsdAsdAsdAsdGsdTsGb¹sC*b¹sAb¹sAb¹sAb¹ |
| 294b | Ab¹Tb¹Ab¹C*b¹Ab¹dGdGdC*dAdTdTdAdAdTdAdAd AdGdTGb¹C*b¹Ab¹Ab¹ Ab¹ |
| 295a | Tb¹sAb¹sTb¹sAb¹sC*b¹sdAsdGsdGsdC*sdAsdTsd TsdAsdAsdTsdAsdAsdAsdGsdTsdGsC*b¹sAb¹sAb¹ sAb¹sTb¹ |
| 295b | Tb¹Ab¹Tb¹Ab¹C*b¹dAdGdGdC*dAdTdTdAdAdTdAdA dAdGdTdGC*b¹Ab¹Ab¹Ab¹Tb¹ |
| 236a | Ab¹sTb¹sAb¹sTb¹sAb¹sdC*sdAsdGsdGsdC*sdAsd TsdTsdAsdAsdTsdAsdAsdAsdGsdTsdGsdC*sAb¹ sAb¹sAb¹sTb¹sGb¹ |
| 236b | Ab¹Tb¹Ab¹Tb¹Ab¹dC*dAdGdGdCdAdTdTdAdAdTdAd AdAdGdTdGdC*Ab¹Ab¹Ab¹Tb¹Gb¹ | wherein the abbreviations b¹, b², b³, b⁴, b⁵, b⁶, b⁷, d, C*, A*, s, and ss have the following meaning:
b¹ is β-D-oxy-LNA,
b² is β-D-thio-LNA,
b³ is β-D-amino-LNA,
b⁴ is α-L-oxy-LNA,
b⁵ is β-D-ENA,
b⁶ is β-D-(NH)-LNA,
b⁷ is β-D-(NCH₃)-LNA,
d is 2-deoxy,
C* is 5-methylcytosine,
A* is 2-aminoadenine,
s is the internucleotide linkage is a phosphorothioate group (—O—P(O)(S⁻)—O—),
ss is the internucleotide linkage is a phosphorodithioate group (—O—P(S)(S⁻)—O—),
/5SpC3s/(—O—P(O)(S⁻)—OC₃H₆OH at 5'-terminal group of an antisense-oligonucleotide,
/3SpC3s/(—O—P(O)(S⁻)—OC₃H₆OH at 3'-terminal group of an antisense-oligonucleotide,
nucleotides in bold are LNA nucleotides,
nucleotides not in bold are non-LNA nucleotides, and
wherein the antisense-oligonucleotide inhibits expression of TGF-R$_{II}$.

2. A method for promoting regeneration and functional reconnection of damaged nerve pathways and/or for treatment and compensation of age induced decreases in neuronal stem cell renewal comprising administering to a patient an antisense-oligonucleotide according to claim 1.

3. A method for prophylaxis and treatment of a disease selected from the group consisting of neurodegenerative diseases, neuroinflammatory disorders, traumatic or post-traumatic disorders, neurovascular disorders, hypoxic disorders, postinfectious central nervous system disorders, fibrotic diseases, hyperproliferative diseases, cancer, tumors, presbyakusis and presbyopia comprising administering to a patient an antisense-oligonucleotide according to claim 1.

4. The method according to claim 3, wherein the neurodegenerative diseases and neuroinflammatory disorders are selected from the group consisting of: Alzheimer's disease, Parkinson's disease, Creutzfeldt Jakob disease, new variant of Creutzfeldt Jakobs disease, Hallervorden Spatz disease, Huntington's disease, multisystem atrophy, dementia, frontotemporal dementia, motor neuron disorders, amyotrophic lateral sclerosis, spinal muscular atrophy, spinocerebellar atrophies, schizophrenia, affective disorders, major depression, meningoencephalitis, bacterial meningoencephalitis, viral meningoencephalitis, CNS autoimmune disorders, multiple sclerosis, acute ischemic/hypoxic lesions, stroke, CNS and spinal cord trauma, head and spinal trauma, brain traumatic injuries, arteriosclerosis, atherosclerosis, microangiopathic dementia, Binswanger' disease, retinal degeneration, cochlear degeneration, macular degeneration, cochlear deafness, AIDS-related dementia, retinitis pigmentosa, fragile X-associated tremor/ataxia syndrome, progressive supranuclear palsy, striatonigral degeneration, olivopontocerebellar degeneration, Shy Drager syndrome, age dependent memory deficits, neurodevelopmental disorders associated with dementia, Down's Syndrome, synucleinopathies, superoxide dismutase mutations, trinucleotide repeat disorders, trauma, hypoxia, vascular diseases, vascular inflammations, and CNS-ageing and wherein the fibrotic diseases are selected from the group consisting of: pulmonary fibrosis, cystic fibrosis, hepatic cirrhosis, endomyocardial fibrosis, old myocardial infarction, atrial fibrosis, mediastinal fibrosis, myelofibrosis, retroperitoneal fibrosis, progressive massive fibrosis, nephrogenic systemic fibrosis, Crohn's Disease, keloid, systemic sclerosis, arthrofibrosis, Peyronie's disease, Dupuytren's contracture, and residuums after Lupus erythematodes.

5. A pharmaceutical composition comprising at least one single-stranded antisense-oligonucleotide according to claim 1 together with at least one pharmaceutically acceptable carrier, excipient, adjuvant, solvent or diluent.

* * * * *

UNITED STATES PATENT AND TRADEMARK OFFICE
CERTIFICATE OF CORRECTION

PATENT NO. : 11,213,541 B2
APPLICATION NO. : 15/525561
DATED : January 4, 2022
INVENTOR(S) : Markus Hossbach It is certified that error appears in the above-identified patent and that said Letters Patent is hereby corrected as shown below:

In the Specification

In Column 1, Line 34, delete "kDa." and insert --kDa).--.

In Column 2, Line 41, delete "III" and insert --II--.

In Column 2, Line 53, delete "caveoli," and insert --caveolae,--.

In Column 14, Line 58, delete "14 to more" and insert --14 to 20 more--.

In Column 15, Lines 10-11, delete "14 to more" and insert --14 to 20 more--.

In Column 15, Line 30, delete "14 to more" and insert --14 to 20 more--.

In Column 15, Lines 50-51, delete "14 to more" and insert --14 to 20 more--.

In Column 16, Line 3, delete "14 to more" and insert --14 to 20 more--.

In Column 16, Lines 22-23, delete "14 to more" and insert --14 to 20 more--.

In Column 16, Line 41, delete "14 to more" and insert --14 to 20 more--.

In Column 16, Lines 61-62, delete "14 to more" and insert --14 to 20 more--.

In Column 17, Line 14, delete "14 to more" and insert --14 to 20 more--.

In Column 17, Lines 34-35, delete "14 to more" and insert --14 to 20 more--.

In Column 17, Line 54, delete "14 to more" and insert --14 to 20 more--.

Signed and Sealed this
Eleventh Day of October, 2022

Katherine Kelly Vidal
*Director of the United States Patent and Trademark Office*

CERTIFICATE OF CORRECTION (continued)
U.S. Pat. No. 11,213,541 B2

In Column 19, Line 17, delete "-CCGAGCCCCCAGCGCAGCGjeq" and insert -- -CCGAGCCCCCAGCGCAGCG (Seq.--.

In Column 19, Line 35, delete "(Seq" and insert --(Seq.--.

In Column 19, Line 66, delete "574)." and insert --574),--.

In Column 20, Line 34, delete "69," and insert --609),--.

In Column 21, Line 5, delete "(Seq" and insert --(Seq.--.

In Column 21, Line 61, after "to" insert --10--.

In Column 23, Line 4, delete "3 and and" and insert --3 and 5 and--.

In Column 25, Line 43, after "to" insert --10--.

In Column 26, Line 51, delete "3 and and" and insert --3 and 5 and--.

In Column 27, Line 56, delete "68," and insert --681),--.

In Column 27, Line 66, delete "69," and insert --689),--.

In Column 29, Line 28, after "to" insert --10--.

In Column 30, Line 42 (Approx.), delete "3 and and" and insert --3 and 5 and--.

In Column 30, Lines 62-63, delete "TTCTATGGTAG-, TATGGGGTAG-," and insert --TTGGTAG-, TGGTAG-, GGTAG-, GTAG-,--.

In Column 31, Line 2, delete "-GAGUGGIC," and insert -- -GAGCCGTC,--.

In Column 31, Line 39, delete "NilA" and insert --$N^{11A}$--.

In Column 33, Line 21 (Approx.), after "to" insert --10--.

In Column 34, Line 39, delete "3 and and" and insert --3 and 5 and--.

In Column 37, Line 16 (Approx.), after "to" insert --10--.

In Column 38, Line 25, delete "3 and and" and insert --3 and 5 and--.

In Column 39, Line 22, delete "7271," and insert --727),--.

In Column 39, Line 42, delete "$N7^A$" and insert --$N^{7A}$--.

CERTIFICATE OF CORRECTION (continued)
U.S. Pat. No. 11,213,541 B2

In Column 39, Line 55, delete "N7$^A$" and insert --N$^{7A}$--.

In Column 39, Lines 62-63, delete "ATICAT-, TCTUAT-," and insert --ATCTCAT-, TCTCAT-,--.

In Column 40, Line 41, delete "GO—," and insert --GC-,--.

In Column 40, Line 53, after "to" insert --10--.

In Column 41, Line 62, delete "3 and and" and insert --3 and 5 and--.

In Column 44, Line 28, delete "86," and insert --806),--.

In Column 44, Line 46, delete "(eq." and insert --(Seq.--.

In Column 44, Line 60, after "to" insert --10--.

In Column 49, Line 67, after "interchangeably" insert --.--.

In Column 50, Line 8, delete "s-D-oxy-LNA." and insert --β-D-oxy-LNA.--.

In Column 50, Lines 21-22, delete "desoxyribose" and insert --deoxyribose--.

In Column 50, Line 23, delete "desoxyribose" and insert --deoxyribose--.

In Column 50, Lines 32-33, delete "desoxyribose" and insert --deoxyribose--.

In Column 50, Line 34, delete "desoxyribose" and insert --deoxyribose--.

In Column 52, Line 15, delete "camphersulfonic" and insert --camphorsulfonic--.

In Column 52, Line 18, delete "□-toluic acid," and insert --L-toluic acid,--.

In Column 54, Line 9, after "to" insert --20--.

In Column 54, Line 42, delete "(=X$^-$)" and insert --(=X')--.

In Column 54, Line 53, delete "—S;" and insert -- —S$^-$;--.

In Column 54, Line 59, delete "—O—," and insert -- —O$^-$,--.

In Column 54, Line 63, delete "—BH$_3$~," and insert -- —BH$_3^-$ --.

In Column 55, Line 30, delete "—O—P(O)(O$^-$)—N(CH$_3$)—and" and insert -- —O—P(O)(O$^-$)—N(CH$_3$)— and--.

In Column 60, Line 23 (Approx.), delete "(=X$^-$)" and insert --(=X')--.

CERTIFICATE OF CORRECTION (continued)  
U.S. Pat. No. 11,213,541 B2

In Column 60, Line 24 (Approx.), delete "(=X⁻)" and insert --(=X')--.

In Column 60, Line 25 (Approx.), delete "X⁻," and insert --X',--.

In Column 60, Line 27 (Approx.), delete "(=X⁻)" and insert --(=X')--.

In Column 60, Line 60, delete "—O—P(O)(O⁻)—N(CH₃)—and" and insert -- —O—P(O)(O⁻)—N(CH₃)— and--.

In Column 61, Line 60-61, delete "—O—P(O)(S⁻)—respectively." and insert -- —O—P(O)(S⁻)—respectively.--.

In Column 62, Line 3, delete "anti-sense" and insert --antisense--.

In Column 63, Line 7, delete "(LNA*)" and insert --(LNA®)--.

In Column 63, Line 30, delete "R#- R" and insert --R#-R--.

In Column 65, Line 53, delete "2'thio-thymine," and insert --2-thio-thymine,--.

In Column 66, Line 57, delete "—NJ³C(=X)NJ₁J₂" and insert -- —NJ₃C(=X)NJ₁J₂--.

In Column 66, Line 64, delete "CH₃₀CH₂-." and insert --CH₃OCH₂-.--.

In Column 67, Line 60, delete "—C(q₁)=C(q₃)—," and insert -- —C(q₁)=C(q₃)—,--.

In Column 67, Line 61, delete "—C[=C(qi)(q₂)]-C(q₃)(q₄)—or" and insert -- —C[=C(q₁)(q₂)]-C(q₃)(q₄)— or--.

In Column 67, Line 66, delete "—Na," and insert -- —N₃,--.

In Column 68, Lines 60-61, delete "—CH(CH₃)—C₄H₆—," and insert -- —CH(CH₃)—C₄H₈—,--.

In Column 70, Line 50, after ""C₁-C₆-alkyl-NH—CO—"" insert --.--.

In Column 72, Line 13, delete "O-phosphortriester," and insert --O-phosphotriester,--.

In Column 72, Line 14, delete "O-phosphordiester," and insert --O-phosphodiester,--.

In Column 73, Line 42, delete "purin" and insert --purine--.

In Column 73, Line 55, delete "3'-0-" and insert --3'-O- --.

In Column 73, Line 61, delete "dim ethylformamidine" and insert --dimethylformamidine--.

In Column 73, Line 61, delete "LNA-G^IBu" and insert --LNA-G^iBu--.

In Column 74, Line 20, delete "(O—CO$_6$-" and insert --(O—C$_{1-6}$- --.

In Column 74, Line 31, delete "—OC$_4$H$_5$," and insert -- —OC$_4$H$_9$,--.

In Column 74, Line 33, delete "cycl" and insert --cyclo--.

In Column 74, Line 33, delete "GOGH" and insert --COCH--.

In Column 74, Line 35, delete "cycl" and insert --cyclo--.

In Column 75, Line 7, delete "—O—P(O) (OCH$_2$CH$_2$S-C$_{1-6}$-alkyl)$_2$," and insert -- —O—P(O)(OCH$_2$CH$_2$S-C$_{1-6}$-alkyl)$_2$,--.

In Column 81, Line 30 (Approx.), delete "No.s" and insert --Nos.--.

In Column 81, Line 63, delete "No.s" and insert --Nos.--.

In Column 84, Lines 62-63, delete "and or" and insert --and/or--.

In Columns 93-94, TABLE 2-continued, Line 6, delete "AbsGbCsd" and insert --AbsGbsd--.

In Column 96, Line 63, delete "anti sense" and insert --antisense--.

In Column 101, Line 45, delete "(=X$^-$)" and insert --(=X')--.

In Column 104, Line 19, delete "N$_4$" and insert --N$^4$--.

In Column 104, Line 27, delete "N$_4$" and insert --N$^4$--.

In Column 106, Line 38, delete "ba," and insert --b$^8$,--.

In Column 106, Line 55, delete "(=X$^-$)" and insert --(=X')--.

In Column 106, Line 62, delete "(BH$_3$)" and insert --(BH$_3^-$)--.

In Column 107, Line 40, delete "-D-oxy-LNA" and insert --β-D-oxy-LNA--.

In Column 107, Line 43, delete "(b$^6$)" and insert --(b$^8$)--.

In Column 108, Line 3, delete "N$_4$" and insert --N$^4$--.

In Column 108, Line 22, delete "N$_4$" and insert --N$^4$--.

In Column 108, Line 31, delete "N$_4$" and insert --N$^4$--.

In Column 108, Line 34, delete "N$_4$" and insert --N$^4$--.

In Column 108, Line 61, delete "(b4)," and insert --($b^4$),--.

In Column 111, Line 66, delete "(=X$^-$)" and insert --(=X')--.

In Column 112, Line 42, delete "TATITGGTAG-," and insert --TATTTGGTAG-,--.

In Column 116, Line 57, delete "(ba)" and insert --($b^8$)--.

In Column 117, Line 9, delete "(=X$^-$)(X'')" and insert --(=X')(X$^-$)--.

In Column 117, Line 65, delete "(b9);" and insert --($b^9$);--.

In Column 118, Line 47, delete "11))," and insert --11),--.

In Column 122, Line 3, delete "(be)," and insert --($b^6$),--.

In Column 122, Line 6, delete "$b^1$," and insert --$b^7$,--.

In Column 122, Line 24, delete "(=X$^-$)(X'')" and insert --(=X')(X$^-$)--.

In Column 127, Line 35, delete "(=X$^-$)" and insert --(=X')--.

In Column 128, Line 24, delete "($b^6$)" and insert --($b^8$)--.

In Columns 141-142, TABLE 5-continued, Line 27 (Approx.), delete "C*$b^1$G$b^1$" and insert --C*$b^1$T$b^1$--.

In Columns 143-144, TABLE 6-continued, Line 29, delete "/s3SpC3/" and insert --/3SpC3s/--.

In Columns 157-158, TABLE 8-continued, Line 7, delete "C*bs$^1$" and insert --C*$b^1$s--.

In Column 167, Line 53, delete "nasopharyngial" and insert --nasopharyngeal--.

In Column 167, Line 63, delete "administratable" and insert --administrable--.

In Column 168, Line 67, after "preferably from" insert --5--.

In Column 169, Line 10, delete "cryoprotectent" and insert --cryoprotectant--.

In Column 171, Line 41, delete "dodecandiol" and insert --dodecanediol--.

In Column 173, Line 52, delete "KlOver-Bucy" and insert --Klüver-Bucy--.

In Column 174, Line 20, delete "parmyotonia" and insert --paramyotonia--.

In Column 174, Line 36, delete "siezure" and insert --seizure--.

In Column 175, Line 1, delete "Werdnig-Hoffinan" and insert --Werdnig-Hoffmann--.

In Column 175, Line 22, delete "Binswanger'" and insert --Binswanger's--.

In Column 175, Line 63, delete "TGF-P." and insert --TGF-β.--.

In Column 176, Line 24, delete "erythematodes" and insert --erythematosus--.

In Column 176, Lines 35-36, delete "erythematodes." and insert --erythematosus.--.

In Column 177, Line 10, delete "ovarial" and insert --ovarian--.

In Column 177, Line 11, delete "plasmocytoma," and insert --plasmacytoma,--.

In Column 179, Lines 13-14 (Approx.), delete "Corel DRAW® X7" and insert --CorelDRAW® X7--.

In Column 181, Line 51, delete "TGF β1." and insert --TGF-β1.--.

In Column 181, Line 63, delete "=SEM," and insert --±=SEM,--.

In Column 182, Line 15, delete "21 A," and insert --21A,--.

In Column 182, Line 15, delete "21 B," and insert --21B,--.

In Column 184, Line 10, delete "Tb's)" and insert --Tb$^1$s)--.

In Column 184, Line 55, delete "Ref.0" and insert --Ref. 0--.

In Column 185, Line 3, delete "Ref. 4=;" and insert --Ref. 4=--.

In Columns 185-186, TABLE 10, Line 5 (Approx.), delete "water" and insert --water)--.

In Columns 185-186, TABLE 10, Line 16 (Approx.), delete "15" and insert --15%--.

In Column 187, Line 53, delete "Universial" and insert --Universal--.

In Column 190, Line 8, delete "TGF-R$_{II}$" and insert --TGF-βR$_{II}$--.

In Column 190, Line 30, delete "SPGT" and insert --SGPT--.

In Column 190, Line 32, delete "SPGT" and insert --SGPT--.

In Column 190, Line 35, delete "Ficoll-Histopague®" and insert --Ficoll-Histopaque®--.

In Column 190, Line 46, delete "#BMS2161NSTCE)" and insert --#BMS216INSTCE)--.

In Column 190, Line 49, delete "#BMS2231NSTCE)" and insert --#BMS223INSTCE)--.

In Column 190, Line 54, delete "Panomics/Affimetrix)." and insert --Panomics/Affymetrix).--.

In Column 191, Line 2, delete "#ZU0025" and insert --#ZUC025--.

In Column 191, Line 30, delete "xylacin" and insert --xylazine--.

In Column 192, Line 2, delete "µm" and insert --pm--.

In Column 194, Line 10, delete "TGF-Ru" and insert --TGF-R$_{II}$--.

In Column 194, Line 50, delete "Panel" and insert --Panc1--.

In Column 196, Line 48-49, delete "Universial" and insert --Universal--.

In Column 203, Line 8, delete "decapentaphlegic" and insert --decapentaplegic--.

In Column 203, Line 23, delete "(Seq.ID" and insert --(Seq. ID--.

In Column 203, Line 33, delete "Seq.ID No.218b" and insert --Seq. ID No. 218b--.

In Column 203, Line 40, delete "Seq.ID No.218b" and insert --Seq. ID No. 218b--.

In Column 204, Line 57, delete "TGF-D" and insert --TGF-β--.

In Column 204, Line 60, delete "Seq.ID" and insert --Seq. ID--.

In Column 205, Line 23 (Approx.), delete "TGF-(3" and insert --TGF-β--.

In Column 206, Line 10, delete "TGF-P1," and insert --TGF-β1,--.

In Column 212, Line 3, delete "decapentaphlegic" and insert --decapentaplegic--.

In Column 212, Line 54, delete "MRNA" and insert --mRNA--.

In Column 213, Line 4, delete "MRNA" and insert --mRNA--.

In Column 214, Line 34 (Approx.), after "Table" insert --30--.

In Column 215, Line 67, delete "Factor-31" and insert --Factor-β1--.

In Column 217, Line 45, delete "decapentaphlegic" and insert --decapentaplegic--.

In Column 218, Line 15 (Approx.), delete "18 A)" and insert --18A)--.

In Column 218, Line 16 (Approx.), delete "18 B)." and insert --18B).--.

In Column 219, Line 10, delete "SPGT" and insert --SGPT--.

In Column 219, Line 11, delete "SPGT" and insert --SGPT--.

In Column 219, Line 15, delete "Ficoll-Histopague®" and insert --Ficoll-Histopaque®--.

In Column 219, Line 30, delete "#BMS2231NSTCE)" and insert --#BMS223INSTCE)--.

In Column 219, Line 40, delete "#tirl-pic)" and insert --#tlrl-pic)--.

In Column 220, Lines 64-65, delete "Panomics/Affimetrix)." and insert --Panomics/Affymetrix).--.

In Columns 221-222, TABLE 36, Line 2, delete "C57/BI6N" and insert --C57/Bl6N--.

In Column 221, Line 29, delete "C57/BI6N" and insert --C57/Bl6N--.

In Column 221, Line 54 (Approx.), delete "C57/BI6N" and insert --C57/Bl6N--.

In Column 222, Line 27 (Approx.), delete "C57/BI6N" and insert --C57/Bl6N--.

In Column 222, Line 54, delete "C57/B16N" and insert --C57/Bl6N--.

In Column 222, Line 56, delete "TGF-B" and insert --TGF-β--.

In Column 223, Line 16, delete "TGF-§ 1" and insert --TGF-β1--.

In Column 223, Line 28, delete "sagital" and insert --sagittal--.

In Column 223, Line 59, delete "TGF-B31" and insert --TGF-β1--.

In Column 226, Line 66, delete "(8 d)" and insert --(8d)--.

In Column 229, Line 18, after "markers" insert --.--.

In Column 229, Line 29, delete "7 d" and insert --7 days--.

In Column 230, Line 45, delete "Examples" and insert --Example--.

In Column 230, Line 60, delete "xylacin" and insert --xylazine--.

In Column 231-232, TABLE 46, Line 1, delete "TABLE 46" and insert --TABLE 45--.

In Column 232, Line 3, delete "CaCl$_2$)," and insert --CaCl$_2$,--.

CERTIFICATE OF CORRECTION (continued)

U.S. Pat. No. 11,213,541 B2

In Column 233, Line 20, delete "xylacin" and insert --xylazine--.

In Column 236, Line 46, delete "L3.6 µl," and insert --L3.6 pl,--.

In Column 236, Line 51, delete "L3.6 µl," and insert --L3.6 pl,--.

In Column 236, Line 66, delete "No.s" and insert --Nos.--.

In Column 242, Line 20, delete "(Table 56) In" and insert --(Table 56). In--.

In Column 242, Line 31, delete "No.s" and insert --Nos.--.

In Column 244, Line 67, after "comparisons" insert --.--.

In Column 245, Line 59, delete "TGF-s" and insert --TGF-β--.

In Column 245, Line 67, delete "aktin-cytoskeleton." and insert --actin-cytoskeleton.--.

In Column 246, Line 9, delete "aktin-cytoskeleton." and insert --actin-cytoskeleton.--.

In Column 246, Line 16, delete "aktin-cytoskeleton" and insert --actin-cytoskeleton--.

In Column 246, Line 39 (Approx.), delete "Seq.ID No." and insert --Seq. ID No.--.

In Column 249, Line 44 (Approx.), delete "level" and insert --levels--.

In Column 250, Line 34, delete "#$C_{63499}$)" and insert --#C63499)--.

In Column 250, Line 39, delete "Seq.ID" and insert --Seq. ID--.

In Column 251, Line 29, delete "TGF-f" and insert --TGF-β--.

In Column 251, Line 38 (Approx.), delete "(FIG. 260A)." and insert --(FIG. 26A).--.

In Column 255, Line 13, delete "L3.6 µl" and insert --L3.6 pl--.

In Column 255, Line 15, delete "L3.6 µl" and insert --L3.6 pl--.

In Column 259, Line 23, delete "xylacin" and insert --xylazine--.

In Column 260, Line 18, delete "xylacin" and insert --xylazine--.

In Column 260, Line 20, delete "Icy" and insert --Icv--.

In Column 260, Line 23, delete "(coordinates" and insert --coordinates--.

CERTIFICATE OF CORRECTION (continued)  Page 11 of 18
U.S. Pat. No. 11,213,541 B2

In Column 261, Line 19, delete "(once daily, bod" and insert --(once daily), body--.

In Column 261, Line 44, delete "(once daily, bod" and insert --(once daily), body--.

In Column 262, Line 6, delete "xylacin" and insert --xylazine--.

In Columns 263-264, TABLE 81, Line 5, delete "NaCL" and insert --NaCl--.

In Columns 265-266, TABLE 81-continued, Line 5, delete "NaCL" and insert --NaCl--.

In Columns 267-268, TABLE 83-continued, Line 18 (Approx.), delete "port," and insert --port),--.

In Columns 267-268, TABLE 83-continued, Line 19 (Approx.), after "AS)" insert --.--.

In Column 267, Line 37 (Approx.), after "AS)" insert --.--.

In Column 267, Line 52, delete "hexafluorophosphat" and insert --hexafluorophosphate--.

In Column 267, Line 58, delete "aminomethan" and insert --aminomethane--.

In Column 267, Line 59, delete "aminomethan" and insert --aminomethane--.

In Column 268, Line 32, delete "2'-0," and insert --2'-O,--.

In Column 268, Line 45, delete "O—4'-" and insert --O,4'- --.

In Column 268, Line 48, delete "(Vebaek," and insert --(Vedbaek,--.

In Column 269, Line 7, delete "dimethyformamidineguanosine" and insert --dimethylformamidineguanosine--.

In Column 269, Line 20, delete "dimethyformamidineguanosine" and insert --dimethylformamidineguanosine--.

In Column 269, Line 30, delete "dimethyformamidineguanosine" and insert --dimethylformamidineguanosine--.

In Column 269, Line 41, delete "dimethyformamidineguanosine" and insert --dimethylformamidineguanosine--.

In Column 270, Line 16, after "and" insert --35--.

In Column 270, Line 34, delete "1S)" and insert --(1S)--.

In Column 270, Line 36, delete "phosphorthioate" and insert --phosphorothioate--.

CERTIFICATE OF CORRECTION (continued)
U.S. Pat. No. 11,213,541 B2

In Column 270, Line 42, delete "usind" and insert --by using--.

In Column 270, Line 50, delete "phosphordithioate" and insert --phosphorodithioate--.

In Column 271, Lines 28-36, delete "The solid supported oligonucleotide was treated with 3% trichloroacetic acid in dichloromethane (w/v) to completely remove the 5'-DMT protection group. Further, the compound was converted with an appropriate terminal group with cyanoethyl-N,N-diisopropyl)phosphoramidite-moiety., after the oxidation of the phosphorus(III) to phosphorus(V), the deprotection, detachment from the solid support and deprotection sequence were performed as described above." and insert the same on Column 271, Line 29 as a new paragraph.

In Columns 271-272, Lines 65-67, delete "5'-O-DMT-2'-O,4'-C-methylene-5-methyl-$N^{4'}$-benzoxylcytidine-3'-O-succinoyl-linked LCAA CPG (0.2 μmol) was treated with 1400 μl 3% trichloroacetic acid in dichloromethane for 60 s to completely remove the 5'-DMT protection group., after several washes with a total amount of 800 μl acetonitrile, the coupling reaction was carried out with 80 μl 5'-O-DMT-2'-O,4'-C-methylene-$N^2$-dimethyformamidineguanosine-3'-[(2-c- yanoethyl)-(N,N-diisopropyl)]-phosphoramidite (0.07 M) and 236 μl DCI in acetonitrile (0.25 M). The coupling reaction was allowed to take place for 250 sec., and excess reagents were flashed out with 800 μl acetonitrile, and 640 μl of Beaucage (0.2 M) were inserted to the column for 180 s The system was flushed with 320 μl acetonitrile. For the capping step, 448 μl of acetic anhydride in THF (1:9 v/v) and 448 μl N-methylimidazol (NMI)/THF/pyridine (1:8:1) were added and allowed to react for 45 sec. At the end of this cycle, the system was washed with 480 μl acetonitrile. The compound was treated with 1400 μl 3% trichloroacetic acid in dichloromethane for 60 s to completely remove the 5'-DMT protection group." and insert the same on Column 271, Line 66 as a new paragraph.

In Column 272, Line 5, delete "dimethyformamidineguanosine" and insert --dimethylformamidineguanosine--.

In Column 272, Line 11, after "s" insert --.--.

In Column 272, Line 25, after "180 s" insert --.--.

In Column 272, Line 40, after "180 s" insert --.--.

In Column 272, Line 42, delete "THE" and insert --THF--.

In Column 273, Line 19, after "180 s" insert --.--.

In Column 275, Line 10, delete "dimethyformamidineguanosine" and insert --dimethylformamidineguanosine--.

In Column 275, Line 17, after "s" insert --.--.

In Column 276, Line 42, after "s" insert --.--.

In Column 276, Line 52, delete "ESI-sMS:" and insert --ESI-MS:--.

In Column 277, Line 2-3, delete "dimethyformamidineguanosine" and insert --dimethylformamidineguanosine--.

In Column 277, Line 3, delete "3'-[(p-" and insert --3'-[(β- --.

In Column 277, Line 9, after "240 s" insert --.--.

In Column 277, Line 18, delete "3'-[(p-" and insert --3'-[(β- --.

In Column 277, Line 25, after "240 s" insert --.--.

In Column 278, Line 30, delete "pocedure" and insert --procedure--.

In Column 279, Line 30, after "180 s" insert --.--.

In Column 279, Line 40, delete "dimethyformamidineguanosine" and insert --dimethylformamidineguanosine--.

In Column 279, Line 46, after "s" insert --.--.

In Column 279, Line 60, after "180 s" insert --.--.

In Column 279, Line 62, delete "THE" and insert --THF--.

In Column 280, Line 7, after "180 s" insert --.--.

In Column 280, Line 22, after "180 s" insert --.--.

In Column 280, Line 24, delete "THE" and insert --THF--.

In Column 281, Line 55, after "180 s" insert --.--.

In Column 282, Line 3, after "180 s" insert --.--.

In Column 282, Line 18, after "180 s" insert --.--.

In Column 282, Line 22, after "react for" insert --45--.

In Column 282, Line 28, delete "dimethyformamidineguanosine" and insert --dimethylformamidineguanosine--.

In Column 282, Line 34, after "s" insert --.--.

In Column 283, Line 57, after "180 s" insert --.--.

In Column 284, Line 42, delete "3'-[(R-" and insert --3'-[(β- --.

In Column 284, Line 49, after "240 s" insert --.--.

In Column 284, Line 58, delete "dimethyformamidineguanosine" and insert --dimethylformamidineguanosine--.

In Column 284, Line 58, delete "3'-[(3-" and insert --3'-[(β- --.

In Column 284, Line 65, after "240 s" insert --.--.

In Column 285, Line 20, delete "Example 140-233" and insert --Examples 140-233--.

In Column 286, Line 10, after "180 s" insert --.--.

In Column 286, Line 20, delete "dimethyformamidineguanosine" and insert --dimethylformamidineguanosine--.

In Column 286, Line 25, after "180 s" insert --.--.

In Column 287, Line 16, after "180 s" insert --.--.

In Column 287, Line 60, after "180 s" insert --.--.

In Column 288, Line 50, after "180 s" insert --.--.

In Column 288, Line 52, delete "THE" and insert --THF--.

In Column 289, Line 14, after "180 s" insert --.--.

In Column 289, Line 16, delete "THE" and insert --THF--.

In Column 289, Line 18, after "for" insert --45--.

In Column 290, Line 41, after "180 s" insert --.--.

In Column 291, Line 1, delete "3'-[(p-" and insert --3'-[(β- --.

In Column 291, Line 8, after "240 s" insert --.--.

In Column 291, Line 17, delete "dimethyformamidineguanosine" and insert --dimethylformamidineguanosine--.

In Column 291, Line 17, delete "3'-[(R-" and insert --3'-[(β- --.

In Column 291, Line 24, after "240 s" insert --.--.

In Column 291, Line 26, delete "THE" and insert --THF--.

In Column 293, Line 26, after "5673.5 Da" insert --.--.

In Column 293, Line 28 (Approx.), delete "Example 247-335" and insert --Examples 247-335--.

In Column 293, Line 57, after "180 s" insert --.--.

In Column 293, Line 59, delete "THE" and insert --THF--.

In Column 294, Line 48, after "180 s" insert --.--.

In Column 295, Line 53, after "180 s" insert --.--.

In Column 295, Line 67, after "180 s" insert --.--.

In Column 296, Line 25, delete "dimethyformamidineguanosine" and insert --dimethylformamidineguanosine--.

In Column 296, Line 31, after "s" insert --.--.

In Column 296, Line 32, delete "THE" and insert --THF--.

In Column 296, Line 45, after "180 s" insert --.--.

In Column 296, Line 47, delete "THE" and insert --THF--.

In Column 297, Line 66, after "180 s" insert --.--.

In Column 298, Line 25 (Approx.), delete "3'-[(p-" and insert --3'-[(β- --.

In Column 298, Line 33 (Approx.), after "240 s" insert --.--.

In Column 298, Line 35, delete "THE" and insert --THF--.

In Column 298, Line 49, after "240 s" insert --.--.

In Column 298, Line 50, delete "THE" and insert --THF--.

In Column 299, Line 3 (Approx.), delete "Example 341-433" and insert --Examples 341-433--.

In Column 299, Lines 21-22 (Approx.), delete "dimethyformamidineguanosine -3'-" and insert --dimethylformamidineguanosine-3'- --.

In Column 299, Line 33, after "180 s" insert --.--.

In Column 300, Line 9, after "180 s" insert --.--.

CERTIFICATE OF CORRECTION (continued)
U.S. Pat. No. 11,213,541 B2

In Column 301, Line 56, after "180 s" insert --.--.

In Column 302, Line 66, delete "C₃" and insert --C3--.

In Column 303, Line 20, delete "dimethyformamidineguanosine" and insert --dimethylformamidineguanosine--.

In Column 303, Line 26, after "s" insert --.--.

In Column 303, Lines 46-47, delete "dimethyformamidineguanosine" and insert --dimethylformamidineguanosine--.

In Column 303, Line 53, delete "3'-[(p-" and insert --3'-[(β- --.

In Column 303, Line 59, after "240 s" insert --.--.

In Column 304, Line 2, delete "3'-[(p-" and insert --3'-[(β- --.

In Column 304, Line 9, after "240 s" insert --.--.

In Column 304, Line 32 (Approx.), delete "Example 439-534" and insert --Examples 439-534--.

In Column 304, Lines 51-52, delete "dimethyformamidineguanosine" and insert --dimethylformamidineguanosine--.

In Column 304, Line 63, after "s" insert --.--.

In Column 304, Line 64, delete "THE" and insert --THF--.

In Column 305, Line 67, after "180 s" insert --.--.

In Column 307, Line 18, after "180 s" insert --.--.

In Column 307, Line 32, after "180 s" insert --.--.

In Column 307, Line 64, delete "THE" and insert --THF--.

In Column 308, Line 10, after "180 s" insert --.--.

In Column 308, Line 15, after "for" insert --45--.

In Column 308, Line 33, delete "015" and insert --Q15--.

In Column 308, Line 52, delete "ccapping" and insert --capping--.

In Column 309, Line 27, delete "dimethyformamidineguanosine" and insert

CERTIFICATE OF CORRECTION (continued)
U.S. Pat. No. 11,213,541 B2

--dimethylformamidineguanosine--.

In Column 309, Line 33, after "s" insert --.--.

In Column 309, Lines 53-54, delete "dimethyformamidineguanosine" and insert --dimethylformamidineguanosine--.

In Column 310, Lines 3-4, delete "3'-[(p-" and insert --3'-[(β- --.

In Column 310, Line 10, after "240 s" insert --.--.

In Column 310, Line 19, delete "dimethyformamidineguanosine" and insert --dimethylformamidineguanosine--.

In Column 310, Line 26, after "240 s" insert --.--.

In the Claims

In Column 618, Claim 1, Line 20, delete "Gb$^1$ ssAb$^1$" and insert --Gb$^1$ssAb$^1$--.

In Column 618, Claim 1, Line 38 (Approx.), delete "Gb4" and insert --Gb$^4$--.

In Column 619, Claim 1, Line 21, delete "Ab$^1$ sGb$^1$" and insert --Ab$^1$sGb$^1$--.

In Column 621, Claim 1, Line 31, delete "b$^1$ sAb$^1$" and insert --b$^1$sAb$^1$--.

In Column 621, Claim 1, Line 34 (Approx.), delete "Ab$^1$ /3" and insert --Ab$^1$/3--.

In Column 622, Claim 1, Line 61, delete "Gs Gb$^7$" and insert --GsGb$^7$--.

In Column 625, Claim 1, Line 7, delete "Gb$^1$ ssC*b$^1$" and insert --Gb$^1$ssC*b$^1$--.

In Column 625, Claim 1, Line 18 (Approx.), delete "/s3SpC3/" and insert --/3SpC3s/--.

In Column 625, Claim 1, Line 60, delete "Gb$^1$sTb$^1$sAb$^1$sGb$^1$sTb$^1$sdGsdTsdTsdTsdA*sdGsdGsdGs" and insert --Gb$^1$sTb$^1$sAb$^1$sGb$^1$sTb$^1$sdGsdTsdTsdTsdA*sdGsdGsdGsAb$^1$sGb$^1$sC*b$^1$--.

In Column 625, Claim 1, Lines 61-62, delete "Gb$^1$sGb$^1$sAb$^1$sGb$^1$sC*b$^1$Ab$^1$sGb$^1$sC*b$^1$" and insert --Gb$^1$sGb$^1$sAb$^1$sGb$^1$sC*b$^1$--.

In Column 626, Claim 1, Line 54 (Approx.), delete "s C*b$^1$" and insert --sC*b$^1$--.

In Column 626, Claim 1, Line 56 (Approx.), delete "s C*b$^1$" and insert --sC*b$^1$--.

In Column 627, Claim 1, Line 55, delete "Tb$^1$ C*b$^1$Tb$^1$" and insert --Tb$^1$C*b$^1$Tb$^1$--.

CERTIFICATE OF CORRECTION (continued)
U.S. Pat. No. 11,213,541 B2

In Column 632, Claim 1, Lines 24-25 (Approx.), delete "$Gb^1sTb^1sTb^1$" and insert --$Gb^1sTb^1$--.

In Column 632, Claim 1, Lines 26-27 (Approx.), delete "$Ab^1sGb^1$" and insert --$Ab^1sGb^1sTb^1$--.

In Column 634, Claim 1, Line 50, delete "290 g" and insert --290g--.

In Column 635, Claim 1, Line 35, delete "$Ab^1$ $Ab^1$" and insert --$Ab^1Ab^1$--.

In Column 636, Claim 4, Line 38, delete "Binswanger'" and insert --Binswanger's--.

In Column 636, Claim 4, Line 56, delete "erythematodes." and insert --erythematosus.--.